US012774274B2

(12) United States Patent
Levinson et al.

(10) Patent No.: US 12,774,274 B2
(45) Date of Patent: Oct. 27, 2026

(54) HETEROCYCLIC COMPOUNDS AND METHODS OF USE

(71) Applicant: Schrödinger, Inc., New York, NY (US)

(72) Inventors: Adam Marc Levinson, Astoria, NY (US); Evelyne Houang, Astoria, NY (US); Abba Elias Leffler, Bronx, NY (US); Andrew Placzek, Portland, OR (US); Anatoly Ruvinsky, Lexington, MA (US); Jeremy Robert Greenwood, Brooklyn, NY (US); Zef Konst, New York, NY (US); Leah Frye, Portland, OR (US)

(73) Assignee: Schrödinger, Inc.

( * ) Notice: Subject to any disclaimer, the term of this patent is extended or adjusted under 35 U.S.C. 154(b) by 177 days.

(21) Appl. No.: 18/164,346

(22) Filed: Feb. 3, 2023

(65) Prior Publication Data

US 2023/0348424 A1 Nov. 2, 2023

Related U.S. Application Data

(60) Provisional application No. 63/376,595, filed on Sep. 21, 2022, provisional application No. 63/306,784, filed on Feb. 4, 2022.

(51) Int. Cl.

| | |
|---|---|
| ***C07D 401/12*** | (2006.01) |
| ***C07D 213/82*** | (2006.01) |
| ***C07D 401/14*** | (2006.01) |
| ***C07D 405/04*** | (2006.01) |
| ***C07D 405/14*** | (2006.01) |
| ***C07D 471/04*** | (2006.01) |
| ***C07D 487/04*** | (2006.01) |

(52) U.S. Cl.

CPC ......... *C07D 401/12* (2013.01); *C07D 213/82* (2013.01); *C07D 401/14* (2013.01); *C07D 405/04* (2013.01); *C07D 405/14* (2013.01); *C07D 471/04* (2013.01); *C07D 487/04* (2013.01); *C07B 2200/13* (2013.01)

(58) Field of Classification Search

CPC .. C07D 401/12; C07D 213/82; C07D 401/14; C07D 405/04; C07D 405/14; C07D 471/04; C07D 487/04; C07B 2200/13

See application file for complete search history.

(56) References Cited

U.S. PATENT DOCUMENTS

| | | | |
|---|---|---|---|
| 5,272,158 | A | 12/1993 | Hartman et al. |
| 5,654,307 | A | 8/1997 | Bridges et al. |
| 5,808,015 | A | 9/1998 | Hamprecht |
| 5,955,615 | A | 9/1999 | Hamprecht |
| 6,413,971 | B1 | 7/2002 | Arnold et al. |
| 6,528,508 | B2 | 3/2003 | Salituro et al. |
| 6,534,510 | B2 | 3/2003 | Barrow et al. |
| 6,800,626 | B2 | 10/2004 | Salituro et al. |
| 6,867,201 | B2 | 3/2005 | Kath et al. |
| 6,921,821 | B2 | 7/2005 | Blackburn et al. |
| 6,977,266 | B2 | 12/2005 | Tada et al. |
| 7,151,101 | B2 | 12/2006 | Salituro et al. |
| 7,211,572 | B2 | 5/2007 | Miyazaki et al. |
| 7,223,776 | B2 | 5/2007 | Surivet et al. |
| 7,297,700 | B2 | 11/2007 | Kelly et al. |
| 7,402,596 | B2 | 7/2008 | Kelly et al. |
| 7,485,643 | B2 | 2/2009 | Wallace et al. |
| 7,491,713 | B2 | 2/2009 | Burgey et al. |
| 7,521,455 | B2 | 4/2009 | Nagase et al. |
| 7,576,072 | B2 | 8/2009 | Wallace et al. |
| 7,579,486 | B2 | 8/2009 | Puerta et al. |
| 7,652,141 | B2 | 1/2010 | Tada et al. |
| 7,705,164 | B2 | 4/2010 | Puerta et al. |
| 7,772,234 | B2 | 8/2010 | Wallace et al. |
| 7,786,316 | B2 | 8/2010 | Puerta et al. |
| 7,816,371 | B2 | 10/2010 | Kelly et al. |
| 7,880,004 | B2 | 2/2011 | Borzilleri et al. |
| 7,928,111 | B2 | 4/2011 | Tachdjian et al. |
| 7,998,978 | B2 | 8/2011 | Huang et al. |
| 8,008,510 | B2 | 8/2011 | Puerta et al. |
| 8,030,318 | B2 | 10/2011 | Simmen et al. |
| 8,084,471 | B2 | 12/2011 | Hamilton et al. |
| 8,088,924 | B2 | 1/2012 | Tada et al. |
| 8,207,347 | B2 | 6/2012 | Khanzhin et al. |
| 8,314,087 | B2 | 11/2012 | Albrecht et al. |

(Continued)

FOREIGN PATENT DOCUMENTS

| | | | |
|---|---|---|---|
| AR | 079457 | A1 | 1/2012 |
| CN | 104230952 | B | 2/2017 |

(Continued)

OTHER PUBLICATIONS

Ramharter et al. (Mar. 15, 2021) "One Atom Makes All the Difference: Getting a Foot in the Door Between SOS1 and KRAS", Journal of Medicinal Chemistry, 64(10):6569-6580.

(Continued)

*Primary Examiner* — Clinton A Brooks

*Assistant Examiner* — Josmalen M. Ramos-Lewis

(74) *Attorney, Agent, or Firm* — Barnes & Thornburg LLP

(57) ABSTRACT

The present application relates to compounds of Formula (I), as defined herein, and pharmaceutically acceptable salts thereof. The present application also describes pharmaceutical composition comprising a compound of Formula (I), and pharmaceutically acceptable salts thereof, and methods of using the compounds and compositions for inhibiting certain protein-protein interactions, and for treating cancer.

26 Claims, No Drawings

(56) References Cited

U.S. PATENT DOCUMENTS

| | | | |
|---|---|---|---|
| 8,318,945 | B2 | 11/2012 | Puerta et al. |
| 8,334,288 | B2 | 12/2012 | Epple et al. |
| 8,541,421 | B2 | 9/2013 | Tachdjian et al. |
| 8,546,579 | B2 | 10/2013 | Kelly et al. |
| 8,568,998 | B2 | 10/2013 | Mani et al. |
| 8,633,186 | B2 | 1/2014 | Tachdjian et al. |
| 8,889,638 | B2 | 11/2014 | Cohen et al. |
| 8,940,740 | B2 | 1/2015 | Pathak et al. |
| 9,073,878 | B2 | 7/2015 | Fairfax et al. |
| 9,181,276 | B2 | 11/2015 | Tachdjian et al. |
| 9,242,958 | B2 | 1/2016 | Liang |
| 9,273,068 | B2 | 3/2016 | Geneste et al. |
| 9,278,940 | B2 | 3/2016 | Fairfax et al. |
| 9,408,826 | B2 | 8/2016 | Iadonato et al. |
| 9,469,631 | B2 | 10/2016 | Nosse et al. |
| 9,493,503 | B2 | 11/2016 | Qian |
| 9,540,352 | B2 | 1/2017 | Gray et al. |
| 9,580,409 | B2 | 2/2017 | Malcolm et al. |
| 9,595,683 | B2 | 3/2017 | Choi et al. |
| 9,603,848 | B2 | 3/2017 | Servant et al. |
| 9,657,034 | B2 | 5/2017 | Geneste et al. |
| 9,810,690 | B2 | 11/2017 | Patricelli et al. |
| 9,850,232 | B2 | 12/2017 | Gray et al. |
| 9,896,446 | B2 | 2/2018 | Breslin et al. |
| 9,914,730 | B2 | 3/2018 | Breslin et al. |
| 10,155,764 | B2 | 12/2018 | Albrecht et al. |
| 10,188,649 | B2 | 1/2019 | Bagdanoff et al. |
| 10,238,650 | B2 | 3/2019 | Huang |
| 10,344,048 | B2 | 7/2019 | Qian |
| 10,668,063 | B2 | 6/2020 | Huang |
| 10,722,484 | B2 | 7/2020 | Chen et al. |
| 10,766,920 | B2 | 9/2020 | Qian |
| 10,894,788 | B2 | 1/2021 | Kanouni et al. |
| 11,390,618 | B2 | 7/2022 | Kanouni et al. |
| 11,414,444 | B2 | 8/2022 | Zhao et al. |
| 2002/0006923 | A1 | 1/2002 | Barrow et al. |
| 2002/0045630 | A1 | 4/2002 | Arnold et al. |
| 2002/0149037 | A1 | 10/2002 | Shimoda et al. |
| 2003/0055049 | A1 | 3/2003 | Kath et al. |
| 2004/0025044 | A1 | 2/2004 | Day |
| 2004/0082619 | A1 | 4/2004 | Tada et al. |
| 2004/0087577 | A1 | 5/2004 | Pratt et al. |
| 2004/0097492 | A1 | 5/2004 | Pratt et al. |
| 2004/0106645 | A1 | 6/2004 | Blackburn et al. |
| 2005/0016927 | A1 | 1/2005 | Rohrbach et al. |
| 2005/0049251 | A1 | 3/2005 | Salituro et al. |
| 2005/0054645 | A1 | 3/2005 | Miyazaki et al. |
| 2005/0065144 | A1 | 3/2005 | Feng et al. |
| 2005/0101590 | A1 | 5/2005 | Yasui et al. |
| 2005/0130943 | A1 | 6/2005 | Wallace et al. |
| 2005/0130976 | A1 | 6/2005 | Wallace et al. |
| 2005/0153942 | A1 | 7/2005 | Wallace et al. |
| 2005/0182045 | A1 | 8/2005 | Nagase et al. |
| 2005/0256123 | A1 | 11/2005 | Marlow et al. |
| 2006/0040949 | A1 | 2/2006 | Surivet et al. |
| 2006/0052361 | A1 | 3/2006 | Miyazaki et al. |
| 2006/0052411 | A1 | 3/2006 | Tada et al. |
| 2006/0069110 | A1 | 3/2006 | Andersen et al. |
| 2006/0217448 | A1 | 9/2006 | Kelly et al. |
| 2007/0066632 | A1 | 3/2007 | Hart et al. |
| 2007/0117802 | A1 | 5/2007 | Borzilleri et al. |
| 2007/0117848 | A1 | 5/2007 | Puerta et al. |
| 2007/0161670 | A1 | 7/2007 | Staab et al. |
| 2007/0197565 | A1 | 8/2007 | Kelly et al. |
| 2007/0225324 | A1 | 9/2007 | Kelly et al. |
| 2007/0244103 | A1 | 10/2007 | Pierau et al. |
| 2007/0287696 | A1 | 12/2007 | Burgey et al. |
| 2008/0039478 | A1 | 2/2008 | Kelly et al. |
| 2008/0161311 | A1 | 7/2008 | Miyazaki et al. |
| 2008/0161362 | A1 | 7/2008 | Puerta et al. |
| 2008/0182863 | A1 | 7/2008 | Simmen et al. |
| 2008/0280917 | A1 | 11/2008 | Albrecht et al. |
| 2008/0306053 | A1 | 12/2008 | Tachdjian et al. |
| 2008/0306093 | A1 | 12/2008 | Servant et al. |
| 2008/0312292 | A1 | 12/2008 | Yasui et al. |
| 2009/0048276 | A1 | 2/2009 | Goulet et al. |
| 2009/0053455 | A1 | 2/2009 | Miyazawa et al. |
| 2009/0068255 | A1 | 3/2009 | Yu et al. |
| 2009/0105225 | A1 | 4/2009 | Gore et al. |
| 2009/0170838 | A1 | 7/2009 | Kelly et al. |
| 2009/0220586 | A1 | 9/2009 | Hamilton et al. |
| 2009/0246198 | A1 | 10/2009 | Dong et al. |
| 2009/0286987 | A1 | 11/2009 | Puerta et al. |
| 2009/0298825 | A1 | 12/2009 | Kelly et al. |
| 2010/0022531 | A1 | 1/2010 | Kincaid et al. |
| 2010/0056506 | A1 | 3/2010 | Huang et al. |
| 2010/0081686 | A1 | 4/2010 | Tada et al. |
| 2010/0089284 | A1 | 4/2010 | Tanaka et al. |
| 2010/0173952 | A1 | 7/2010 | Puerta et al. |
| 2010/0184802 | A1 | 7/2010 | Kelly et al. |
| 2010/0227778 | A1 | 9/2010 | Neel et al. |
| 2010/0292235 | A1 | 11/2010 | Kelly et al. |
| 2011/0092476 | A1 | 4/2011 | Kelly et al. |
| 2011/0144164 | A1 | 6/2011 | Khanzhin et al. |
| 2011/0190298 | A1 | 8/2011 | Epple et al. |
| 2011/0224155 | A1 | 9/2011 | Tachdjian et al. |
| 2011/0230502 | A1 | 9/2011 | Tachdjian et al. |
| 2011/0262482 | A1 | 10/2011 | Iadonato et al. |
| 2011/0312905 | A1 | 12/2011 | Cohen et al. |
| 2012/0035194 | A1 | 2/2012 | Huang et al. |
| 2012/0041032 | A1 | 2/2012 | Puerta et al. |
| 2012/0108615 | A1 | 5/2012 | Pathak et al. |
| 2012/0196842 | A1 | 8/2012 | Qian |
| 2013/0012485 | A1 | 1/2013 | Kaspar et al. |
| 2013/0029925 | A1 | 1/2013 | Vandier et al. |
| 2013/0116233 | A1 | 5/2013 | Geneste et al. |
| 2013/0116241 | A1 | 5/2013 | Geneste et al. |
| 2013/0203763 | A1 | 8/2013 | Liang |
| 2013/0245016 | A1 | 9/2013 | Knight et al. |
| 2013/0317037 | A1 | 11/2013 | Bachman et al. |
| 2014/0113882 | A1 | 4/2014 | Breslin et al. |
| 2014/0117318 | A1 | 5/2014 | Choi et al. |
| 2014/0142102 | A1 | 5/2014 | Fairfax et al. |
| 2014/0199405 | A1 | 7/2014 | Pierce et al. |
| 2014/0235623 | A1 | 8/2014 | Tachdjian et al. |
| 2014/0275179 | A1 | 9/2014 | Sui et al. |
| 2014/0344442 | A1 | 11/2014 | Crawford et al. |
| 2015/0225390 | A1 | 8/2015 | Nosse et al. |
| 2015/0307494 | A1 | 10/2015 | Gray et al. |
| 2016/0102094 | A1 | 4/2016 | Breslin et al. |
| 2016/0137668 | A1 | 5/2016 | Geneste et al. |
| 2016/0200711 | A1 | 7/2016 | Gray et al. |
| 2017/0051356 | A1 | 2/2017 | Gualberto et al. |
| 2017/0088580 | A1 | 3/2017 | Qian |
| 2017/0130271 | A1 | 5/2017 | Wong |
| 2017/0275289 | A1 | 9/2017 | Albrecht et al. |
| 2019/0194192 | A1 | 6/2019 | Ramharter et al. |
| 2019/0358230 | A1 | 11/2019 | Gmachl et al. |
| 2020/0131132 | A1 | 4/2020 | Smith et al. |
| 2021/0179648 | A1 | 6/2021 | Zhao et al. |
| 2021/0317127 | A1 | 10/2021 | Li et al. |
| 2022/0211703 | A1 | 7/2022 | Zhao et al. |
| 2022/0249478 | A1 | 8/2022 | Zhao et al. |
| 2023/0002422 | A1 | 1/2023 | Yamamoto et al. |
| 2023/0238599 | A1 | 7/2023 | Hong et al. |

FOREIGN PATENT DOCUMENTS

| | | | |
|---|---|---|---|
| EP | 0521664 | A1 | 1/1993 |
| EP | 0542059 | A1 | 5/1993 |
| EP | 0624583 | A1 | 11/1994 |
| EP | 0767220 | B1 | 4/1999 |
| EP | 1755586 | A2 | 2/2007 |
| EP | 1357111 | B1 | 8/2009 |
| EP | 1477186 | B1 | 11/2009 |
| EP | 1682138 | B1 | 1/2011 |
| EP | 2331503 | B1 | 8/2013 |
| EP | 1765805 | B1 | 11/2013 |
| EP | 2251327 | B1 | 2/2014 |
| EP | 2062050 | B1 | 5/2016 |
| EP | 2892888 | B1 | 4/2018 |
| EP | 2670763 | B1 | 8/2018 |
| EP | 2776437 | B1 | 9/2018 |
| EP | 3712144 | A1 | 9/2020 |

(56) References Cited

FOREIGN PATENT DOCUMENTS

| | | | | |
|---|---|---|---|---|
| EP | 3453714 | B1 | 11/2020 | |
| JP | H03274045 | A | 12/1991 | |
| JP | H04198930 | A | 7/1992 | |
| JP | H05204071 | A | 8/1993 | |
| JP | H107572 | A | 1/1998 | |
| JP | 2006071822 | A | 3/2006 | |
| JP | 2021181432 | A | 11/2021 | |
| WO | 1995019774 | A1 | 7/1995 | |
| WO | 1999064400 | A1 | 12/1999 | |
| WO | 2001070229 | A1 | 9/2001 | |
| WO | 2002053543 | A1 | 7/2002 | |
| WO | 2003059871 | A1 | 7/2003 | |
| WO | 2003070277 | A1 | 8/2003 | |
| WO | 2003106452 | A2 | 12/2003 | |
| WO | 2004035569 | A2 | 4/2004 | |
| WO | 2005000818 | A1 | 1/2005 | |
| WO | 2005030751 | A2 | 4/2005 | |
| WO | 2005051301 | A2 | 6/2005 | |
| WO | 2005072308 | A2 | 8/2005 | |
| WO | 2005077905 | A1 | 8/2005 | |
| WO | 2005110399 | A2 | 11/2005 | |
| WO | 2005118571 | A1 | 12/2005 | |
| WO | 2006021448 | A1 | 3/2006 | |
| WO | 2006028523 | A2 | 3/2006 | |
| WO | 2006037117 | A1 | 4/2006 | |
| WO | 2006089150 | A2 | 8/2006 | |
| WO | 2006100310 | A1 | 9/2006 | |
| WO | 2006102588 | A1 | 9/2006 | |
| WO | 2006102610 | A2 | 9/2006 | |
| WO | 2006104196 | A1 | 10/2006 | |
| WO | 2006105063 | A1 | 10/2006 | |
| WO | 2006108107 | A1 | 10/2006 | |
| WO | 2007028022 | A2 | 3/2007 | |
| WO | 2007035428 | A1 | 3/2007 | |
| WO | 2007082131 | A1 | 7/2007 | |
| WO | 2007089634 | A2 | 8/2007 | |
| WO | 2007109154 | A2 | 9/2007 | |
| WO | 2007109172 | A2 | 9/2007 | |
| WO | 2007109192 | A2 | 9/2007 | |
| WO | 2007109201 | A2 | 9/2007 | |
| WO | 2007125405 | A2 | 11/2007 | |
| WO | 2008030408 | A2 | 3/2008 | |
| WO | 2008060476 | A2 | 5/2008 | |
| WO | 2008074803 | A2 | 6/2008 | |
| WO | 2008077597 | A1 | 7/2008 | |
| WO | 2008103277 | A2 | 8/2008 | |
| WO | 2008103353 | A1 | 8/2008 | |
| WO | 2008134712 | A2 | 11/2008 | |
| WO | 2008154221 | A2 | 12/2008 | |
| WO | 2009052467 | A1 | 4/2009 | |
| WO | 2009140634 | A2 | 11/2009 | |
| WO | 2009146034 | A2 | 12/2009 | |
| WO | 2010006191 | A1 | 1/2010 | |
| WO | 2010/019637 | A1 | 2/2010 | |
| WO | 2010056758 | A1 | 5/2010 | |
| WO | 2010131147 | A1 | 11/2010 | |
| WO | 2011133728 | A2 | 10/2011 | |
| WO | 2012011707 | A2 | 1/2012 | |
| WO | 2012016050 | A2 | 2/2012 | |
| WO | 2012048258 | A2 | 4/2012 | |
| WO | 2012058601 | A1 | 5/2012 | |
| WO | 2012103810 | A1 | 8/2012 | |
| WO | 2013020062 | A1 | 2/2013 | |
| WO | 2013033981 | A1 | 3/2013 | |
| WO | 2013068470 | A1 | 5/2013 | |
| WO | 2013070659 | A1 | 5/2013 | |
| WO | 2013113942 | A2 | 8/2013 | |
| WO | 2013/130976 | A1 | 9/2013 | |
| WO | 2014037327 | A1 | 3/2014 | |
| WO | 2014052699 | A1 | 4/2014 | |
| WO | 2014080290 | A2 | 5/2014 | |
| WO | 2014083567 | A2 | 6/2014 | |
| WO | 2014160185 | A2 | 10/2014 | |
| WO | 2014169843 | A1 | 10/2014 | |
| WO | 2015081813 | A1 | 6/2015 | |
| WO | 2015162516 | A1 | 10/2015 | |
| WO | 2016031833 | A1 | 3/2016 | |
| WO | 2016036954 | A1 | 3/2016 | |
| WO | 2016077793 | A1 | 5/2016 | |
| WO | 2018020242 | A1 | 2/2018 | |
| WO | 2018046933 | A1 | 3/2018 | |
| WO | 2018115380 | A1 | 6/2018 | |
| WO | 2018170167 | A1 | 9/2018 | |
| WO | 2018172250 | A1 | 9/2018 | |
| WO | 2018192250 | A1 | 10/2018 | |
| WO | 2018204765 | A1 | 11/2018 | |
| WO | 2018215798 | A1 | 11/2018 | |
| WO | 2019085916 | A1 | 5/2019 | |
| WO | WO-2019122129 | A1 * | 6/2019 | ........... A61K 31/519 |
| WO | 2019201848 | A1 | 10/2019 | |
| WO | 2019241850 | A1 | 12/2019 | |
| WO | 2020/023657 | A1 | 1/2020 | |
| WO | 2020006497 | A1 | 1/2020 | |
| WO | 2020012068 | A1 | 1/2020 | |
| WO | 2020028706 | A1 | 2/2020 | |
| WO | 2020115500 | A1 | 6/2020 | |
| WO | 2020180768 | A1 | 9/2020 | |
| WO | 2020180770 | A1 | 9/2020 | |
| WO | 2020192562 | A1 | 10/2020 | |
| WO | 2020221274 | A1 | 11/2020 | |
| WO | 2020221277 | A1 | 11/2020 | |
| WO | 2020254451 | A1 | 12/2020 | |
| WO | 2021074227 | A1 | 4/2021 | |
| WO | 2021085636 | A1 | 5/2021 | |
| WO | 2021092115 | A1 | 5/2021 | |
| WO | 2021105960 | A1 | 6/2021 | |
| WO | 2021127429 | A1 | 6/2021 | |
| WO | 2021130731 | A1 | 7/2021 | |
| WO | 2021173524 | A1 | 9/2021 | |
| WO | 2021203768 | A1 | 10/2021 | |
| WO | 2021228028 | A1 | 11/2021 | |
| WO | 2022026465 | A1 | 2/2022 | |
| WO | 2022058344 | A1 | 3/2022 | |
| WO | 2022060583 | A1 | 3/2022 | |
| WO | 2022/140427 | A1 | 6/2022 | |
| WO | 2022/146698 | A1 | 7/2022 | |
| WO | 2022/156972 | A1 | 7/2022 | |
| WO | 2022146699 | A1 | 7/2022 | |
| WO | 2022187266 | A1 | 9/2022 | |
| WO | 2022224924 | A1 | 10/2022 | |
| WO | 2022/262691 | A1 | 12/2022 | |
| WO | 2022251497 | A1 | 12/2022 | |
| WO | 2023022497 | A1 | 2/2023 | |
| WO | 2023116902 | A1 | 6/2023 | |
| WO | 2023143147 | A1 | 8/2023 | |
| WO | 2023245015 | A2 | 12/2023 | |
| WO | 2024/062360 | A1 | 3/2024 | |
| WO | 2024/064178 | A1 | 3/2024 | |

OTHER PUBLICATIONS

Pubchem (Oct. 30, 2019) “3-Pyridinecarboxamide,2,4-diamino-1,6-dihydro-6-oxo-n,1-bis(phenylmethyl)-”, SID_386428103, 5 pages.

European Search Report for Application No. 22812161.2, dated Mar. 3, 2025.

Adjei AA. Blocking oncogenic Ras signaling for cancer therapy. J Natl Cancer Inst. Jul. 18, 2001;93(14):1062-74.

Andreucci E, Francica P, Fearns A, Martin LA, Chiarugi P, Isacke CM, Morandi A. Targeting the receptor tyrosine kinase RET in combination with aromatase inhibitors in ER positive breast cancer xenografts. Oncotarget. Dec. 6, 2016;7(49):80543-80553.

Bagchi S, Chhibber T, Lahooti B, Verma A, Borse V, Jayant RD. In-vitro blood-brain barrier models for drug screening and permeation studies: an overview. Drug Des Devel Ther. Oct. 18, 2019;13:3591-3605.

Baker NM, Der CJ. Cancer: Drug for an ‘undruggable’ protein. Nature. May 30, 2013;497(7451):577-8.

Bandaru P, Kondo Y, Kuriyan J. The Interdependent Activation of Son-of-Sevenless and Ras. Cold Spring Harb Perspect Med. Feb. 1, 2019;9(2):a031534.

Baruch EN, Nagarajan P, Gleber-Netto FO, Rao X, Xie T, Akhter S, Adewale A, Shajedul I, Mattson BJ, Ferrarotto R, Wong MK,

(56) References Cited

OTHER PUBLICATIONS

Davies MA, Jindal S, Basu S, Harwood C, Leigh I, Ajami N, Futreal A, Castillo M, Gunaratne P, Goepfert RP, Khushalani N, Wang J, Watowich S, Calin GA, Migden MR, Vermeer P, D'Silva N, Yaniv D, Burks JK, Gomez J, Dougherty PM, Tsai KY, Allison JP, Sharma P, Wargo J, Myers JN, Gross ND, Amit M. Inflammation induced by tumor-associated nerves promotes resistance to anti-PD-1 therapy in cancer patients and is targetable by interleukin-6.
Bhinge K, Yang L, Terra S, Nasir A, Muppa P, Aubry MC, Yi J, Janaki N, Kovtun IV, Murphy SJ, Halling G, Rahi H, Mansfield A, de Andrade M, Yang P, Vasmatzis G, Peikert T, Kosari F. EGFR mediates activation of RET in lung adenocarcinoma with neuroendocrine differentiation characterized by ASCL1 expression. Oncotarget. Apr. 18, 2017;8 (16):27155-27165.
Blom KF, Glass B, Sparks R, Combs AP. Preparative LC-MS purification: improved compound-specific method optimization. J Comb Chem. Nov.-Dec. 2004;6(6):874-83.
Burns MC, Sun Q, Daniels RN, Camper D, Kennedy JP, Phan J, Olejniczak ET, Lee T, Waterson AG, Rossanese OW, Fesik SW. Approach for targeting Ras with small molecules that activate SOS-mediated nucleotide exchange. Proc Natl Acad Sci U S A. Mar. 4, 2014;111(9):3401-6.
Cai D, Choi PS, Gelbard M, Meyerson M. Identification and Characterization of Oncogenic SOS1 Mutations in Lung Adenocarcinoma. Mol Cancer Res. Apr. 2019;17(4):1002-1012.
Chang H, Sung JH, Moon SU, Kim HS, Kim JW, Lee JS. EGF Induced RET Inhibitor Resistance in CCDC6-RET Lung Cancer Cells. Yonsei Med J. Jan. 2017;58(1):9-18.
Chappell WH, Steelman LS, Long JM, Kempf RC, Abrams SL, Franklin RA, Bäsecke J, Stivala F, Donia M, Fagone P, Malaponte G, Mazzarino MC, Nicoletti F, Libra M, Maksimovic-Ivanic D, Mijatovic S, Montalto G, Cervello M, Laidler P, Milella M, Tafuri A, Bonati A, Evangelisti C, Cocco L, Martelli AM, McCubrey JA. Ras/Raf/MEK/ERK and PI3K/PTEN/Akt/mTOR inhibitors: rationale and importance to inhibiting these pathways in human health. Oncotarget. Mar. 2011;2 (3): 135-64.
Cho CF, Wolfe JM, Fadzen CM, Calligaris D, Hornburg K, Chiocca EA, Agar NYR, Pentelute BL, Lawler SE. Blood-brain-barrier spheroids as an in vitro screening platform for brain-penetrating agents. Nat Commun. Jun. 6, 2017;8:15623.
Cox AD, Fesik SW, Kimmelman AC, Luo J, Der CJ. Drugging the undruggable RAS: Mission possible? Nat Rev Drug Discov. Nov. 2014;13(11):828-51.
Dang CV, Reddy EP, Shokat KM, Soucek L. Drugging the 'undruggable' cancer targets. Nat Rev Cancer. Aug. 2017;17 (8):502-508.
Denayer E, Devriendt K, de Ravel T, Van Buggenhout G, Smeets E, Francois I, Sznajer Y, Craen M, Leventopoulos G, Mutesa L, Vandecasseye W, Massa G, Kayserili H, Sciot R, Fryns JP, Legius E. Tumor spectrum in children with Noonan syndrome and SOS1 or RAF1 mutations. Genes Chromosomes Cancer. Mar. 2010;49(3):242-52.
Ding K, Banerjee A, Tan S, Zhao J, Zhuang Q, Li R, Qian P, Liu S, Wu ZS, Lobie PE, Zhu T. Artemin, a member of the glial cell line-derived neurotrophic factor family of ligands, is HER2-regulated and mediates acquired trastuzumab resistance by promoting cancer stem cell-like behavior in mammary carcinoma cells. J Biol Chem. Jun. 6, 2014;289 (23):16057-71.
Downward J. Targeting RAS signalling pathways in cancer therapy. Nat Rev Cancer. Jan. 2003;3(1):11-22.
Evelyn CR, Duan X, Biesiada J, Seibel WL, Meller J, Zheng Y. Rational design of small molecule inhibitors targeting the RAS GEF, SOS1. Chem Biol. Dec. 18, 2014;21(12):1618-28.
Fernández-Medarde A, Santos E. Ras in cancer and developmental diseases. Genes Cancer. Mar. 2011;2(3):344-58.
Freedman TS, Sondermann H, Friedland GD, Kortemme T, Bar-Sagi D, Marqusee S, Kuriyan J. A Ras-induced conformational switch in the Ras activator Son of sevenless. Proc Natl Acad Sci U S A. Nov. 7, 2006;103(45):16692-7.
Fresno Vara JA, Casado E, de Castro J, Cejas P, Belda-Iniesta C, González-Barón M. PI3K/Akt signalling pathway and cancer. Cancer Treat Rev. Apr. 2004;30(2): 193-204.
Gao L, Bo H, Wang Y, Zhang J, Zhu M. Neurotrophic Factor Artemin Promotes Invasiveness and Neurotrophic Function of Pancreatic Adenocarcinoma In Vivo and In Vitro. Pancreas. Jan. 2015;44(1):134-43.
Gastfriend BD, Palecek SP, Shusta EV. Modeling the blood-brain barrier: Beyond the endothelial cells. Curr Opin Biomed Eng. Mar. 2018;5:6-12.
Gurung AB, Bhattacharjee A. Oncology & Hematology Review, 2015;11(2):147-52.
Hennessy BT, Smith DL, Ram PT, Lu Y, Mills GB. Exploiting the PI3K/AKT pathway for cancer drug discovery. Nat Rev Drug Discov. Dec. 2005;4(12):988-1004.
Hezam K, Jiang J, Sun F, Zhang X, Zhang J. Artemin promotes oncogenicity, metastasis and drug resistance in cancer cells. Rev Neurosci. Jan. 26, 2018;29(1):93-98.
Hillig RC, Sautier B, Schroeder J, Moosmayer D, Hilpmann A, Stegmann CM, Werbeck ND, Briem H, Boemer U, Weiske J, Badock V, Mastouri J, Petersen K, Siemeister G, Kahmann JD, Wegener D, Böhnke N, Eis K, Graham K, Wortmann L, von Nussbaum F, Bader B. Discovery of potent SOS1 inhibitors that block RAS activation via disruption of the RAS-SOS1 interaction. Proc Natl Acad Sci U S A. Feb. 12, 2019;116(7):2551-2560.
IPRP issued in PCT/US2022/03113, dated Dec. 7, 2023.
IPRP issued in PCT/US2023/012307, dated Aug. 6, 2024.
ISR/WO issued in PCT/US2022/031133, dated Aug. 15, 2022.
ISR/WO issued in PCT/US2023/012307, dated Jul. 3, 2023.
ISR/WO issued in PCT/US2023/68371, dated Dec. 15, 2023.
Ian A. Prior, Paul D. Lewis, Carla Mattos; A Comprehensive Survey of Ras Mutations in Cancer. Cancer Res May 15, 2012; 72 (10): 2457-2467.
Jiro Abe, Nobuhiro Tanuma, Miyuki Nomura, Shin Ito, Isao Kasugai, Ikuro Sato, Keiichi Tamai, Mai Mochizuki, Kazunori Yamaguchi, Hiroshi Shima, Yoshinori Okada, Jun Yasuda, Novel activating KRAS mutation candidates in lung adenocarcinoma, Biochemical and Biophysical Research Communications, vol. 522, Issue 3, 2020, pp. 690-696.
Karachaliou N, Mayo-de-Las-Casas C, Molina-Vila MA, Rosell R. Real-time liquid biopsies become a reality in cancer treatment. Ann Transl Med. Mar. 2015;3(3):36.
Kato S, Subbiah V, Marchlik E, Elkin SK, Carter JL, Kurzrock R. RET Aberrations in Diverse Cancers: Next-Generation Sequencing of 4,871 Patients. Clin Cancer Res. Apr. 15, 2017;23(8):1988-1997.
Kessler D, Gmachl M, Mantoulidis A, Martin LJ, Zoephel A, Mayer M, Gollner A, Covini D, Fischer S, Gerstberger T, Gmaschitz T, Goodwin C, Greb P, Häring D, Hela W, Hoffmann J, Karolyi-Oezguer J, Knesl P, Kornigg S, Koegl M, Kousek R, Lamarre L, Moser F, Munico-Martinez S, Peinsipp C, Phan J, Rinnenthal J, Sai J, Salamon C, Scherbantin Y, Schipany K, Schnitzer R, Schrenk A, Sharps B, Siszler G, Sun Q, Waterson A, Wolkerstorfer B, Zeeb M, Pearson M, Fesik SW, McConnell DB. Drugging an undruggable pocket on KRAS. Proc Natl Acad Sci U S A. Aug. 6, 2019;116.
Khan I, Rhett JM, O'Bryan JP. Therapeutic targeting of RAS: New hope for drugging the "undruggable". Biochim Biophys Acta Mol Cell Res. Feb. 2020;1867(2):118570.
Kinsey, CG., Camolotto, S.A., Boespflug, A.M. et al. Protective autophagy elicited by RAF→MEK→ERK inhibition suggests a treatment strategy for RAS-driven cancers. Nat Med 25, 620-627 (2019).
Koumaki D, Kostakis G, Koumaki V, Papadogeorgakis N, Makris M, Katoulis A, Kamakari S, Koutsodontis G, Perisanidis C, Lambadiari V, Chrysomali E, Stavrianeas N, Alexandridis C, Rigopoulos D. Novel mutations of the HRAS gene and absence of hotspot mutations of the BRAF genes in oral squamous cell carcinoma in a Greek population. Oncol Rep. May 2012;27(5): 1555-60.
Labadie, Sharada; Barrett, Kathy; Blair, Wade S.; Chang, Christine; Deshmukh, Gauri; Eigenbrot, Charles; Gibbons, Paul; Johnson, Adam; Kenny, Jane R.; Kohli, Pawan Bir; Liimatta, Marya; Lupardus, Patrick J.; Shia, Steven; Steffek, Micah; Ubhayakar, Savita; Abbema, Anne van; Zak, Mark. Design and evaluation of novel 8-oxo-

(56) References Cited

OTHER PUBLICATIONS pyridopyrimidine Jak1/2 inhibitors. Bioorganic & Medicinal Chemistry Letters (2013), 23(21), 5923-5930.

Levterov VV, Panasyuk Y, Pivnytska VO, Mykhailiuk PK. Water-Soluble Non-Classical Benzene Mimetics. Angew Chem Int Ed Engl. Apr. 27, 2020;59(18):7161-7167.

Lopez-Delisle L, Pierre-Eugène C, Louis-Brennetot C, Surdez D, Raynal V, Baulande S, Boeva V, Grossetête-Lalami S, Combaret V, Peuchmaur M, Delattre O, Janoueix-Lerosey I. Activated ALK signals through the ERK-ETV5-RET pathway to drive neuroblastoma oncogenesis. Oncogene. Mar. 2018;37(11):1417-1429.

Louis DN, Perry A, Reifenberger G, von Deimling A, Figarella-Branger D, Cavenee WK, Ohgaki H, Wiestler OD, Kleihues P, Ellison DW. The 2016 World Health Organization Classification of Tumors of the Central Nervous System: a summary. Acta Neuropathol. Jun. 2016;131(6):803-20.

Lu T, Markotan T, Ballentine SK, Giardino EC, Spurlino J, Crysler CS, Brown K, Maryanoff BE, Tomczuk BE, Damiano BP, Shukla U, End D, Andrade-Gordon P. Bone RF, Player MR. Discovery and clinical evaluation of 1-{N-[2-(amidinoaminooxy)ethyl]amino}carbonylmethyl-6-methyl-3-[2,2-difluoro-2-phenylethylamino]pyrazinone (RWJ-671818), a thrombin inhibitor with an oxyguanidine P1 motif. J Med Chem. Feb. 25, 2010;53(4):1843-56.

Luo J, Manning BD, Cantley LC. Targeting the PI3K-Akt pathway in human cancer: rationale and promise. Cancer Cell. Oct. 2003;4(4):257-62.

Mahar Doan KM, Humphreys JE, Webster LO, Wring SA, Shampine LJ, Serabjit-Singh CJ, Adkison KK, Polli JW. Passive permeability and P-glycoprotein-mediated efflux differentiate central nervous system (CNS) and non-CNS marketed drugs. J Pharmacol Exp Ther. Dec. 2002;303(3):1029-37.

Margarit SM, Sondermann H, Hall BE, Nagar B, Hoelz A, Pirruccello M, Bar-Sagi D, Kuriyan J. Structural evidence for feedback activation by Ras.GTP of the Ras-specific nucleotide exchange factor SOS. Cell. Mar. 7, 2003;112(5):685-95.

Maria Luisa Villahermosa et al. NRAS and KRAS testing by a new diagnostic method to detect point mutations in colorectal cancer specimens: Clart-NRAS iKRAS . . JCO 32, e22159-e22159 (2014).

Marin-Acevedo JA, Dholaria B, Soyano AE, Knutson KL, Chumsri S, Lou Y. Next generation of immune checkpoint therapy in cancer: new developments and challenges. J Hematol Oncol. Mar. 15, 2018;11(1):39.

Maurer T, Garrenton LS, Oh A, Pitts K, Anderson DJ, Skelton NJ, Fauber BP, Pan B, Malek S, Stokoe D, Ludlam MJ, Bowman KK, Wu J, Giannetti AM, Starovasnik MA, Mellman I, Jackson PK, Rudolph J, Wang W, Fang G. Small-molecule ligands bind to a distinct pocket in Ras and inhibit SOS-mediated nucleotide exchange activity. Proc Natl Acad Sci U S A. Apr. 3, 2012;109(14):5299-304.

Mehrdad Payandeh, Masoud Sadeghi, Edris Sadeghi and Faezeh Gholami. Analysis of KRAS, BRAF and NRAS in Patients with Colorectal Cancer: the First Report of Western Iran. American Journal of Cancer Prevention. 2015; 3 (1):19-22.

Nelson-Taylor SK, Le AT, Yoo M, Schubert L, Mishall KM, Doak A, Varella-Garcia M, Tan AC, Doebele RC. Resistance to RET-Inhibition in RET-Rearranged NSCLC Is Mediated By Reactivation of RAS/MAPK Signaling. Mol Cancer Ther. Aug. 2017;16(8):1623-1633.

Osaki M, Oshimura M, Ito H. PI3K-Akt pathway: its functions and alterations in human cancer. Apoptosis. Nov. 2004;9 (6):667-76.

Pubchem, 132377612 deposited on Jan. 24, 2012 (Jan. 24, 2012) pp. 1-5, p. 2.

Pubchem, Substance Record for SID 376512364, Modify Date: Sep. 11, 2019 (retrieved on Jul. 13, 2022). Retrieved from the internet: <URL:https://pubchem.ncbi.nlm.gov/substance/376512364>, entire document.

Pubchem, Substance Record for SID 386428103, Modify Date: Oct. 30, 2019 (retrieved on May 16, 2023). Retrieved from the Internet: <URL:https://pubchem.ncbi.nlm.nih.gov/substance/386428103>, entire document.

Park, et al Design, synthesis, and biological evaluation of a series of resorcinol based N-benzyl benzamide derivatives as potent Hsp90 inhibitors in European Journal of Medicinal Chemistry, 2018, vol. 143, pp. 390-401. Entire Document.

Patgiri A, Yadav KK, Arora PS, Bar-Sagi D. An orthosteric inhibitor of the Ras-Sos interaction. Nat Chem Biol. Jul. 17, 2011;7(9):585-7.

Peng X, Liu X, Liu Y-L, Kim JY, Chen Y-I, Ang P, et al. Brain-Penetrating Peptide Shuttles Across the Blood-Brain Barrier and Extracellular-like Space. ChemRxiv. 2019.

Pierre S, Bats A, Coumoul X. Understanding SOS (Son of Sevenless), Biochem. Pharmacol. 2011, 82(9), 1049-1056.

R.L. Kortum,C.L. Sommers,C.P. Alexander,J.M. Pinski,W. Li,A. Grinberg,J. Lee,P.E. Love, & L.E. Samelson, Targeted Sos1 deletion reveals its critical role in early T-cell development, Proc. Natl. Acad. Sci. U.S.A. 108 (30) 12407-12412, (2011).

Roberts PJ, Der CJ. Targeting the Raf-MEK-ERK mitogen-activated protein kinase cascade for the treatment of cancer. Oncogene. May 14, 2007;26(22):3291-310.

Santarpia L, Lippman SM, El-Naggar AK. Targeting the MAPK-RAS-RAF signaling pathway in cancer therapy. Expert Opin Ther Targets. Jan. 2012;16(1):103-19.

Scheffzek K, Ahmadian MR, Kabsch W, Wiesmüller L, Lautwein A, Schmitz F, Wittinghofer A. The Ras-RasGAP complex: structural basis for GTPase activation and its loss in oncogenic Ras mutants. Science. Jul. 18,1997;277(5324):333-8.

Shen Y, Wang J, Han X, Yang H, Wang S, et al. (2013) Effectors of Epidermal Growth Factor Receptor Pathway: The Genetic Profiling of KRAS, BRAF, PIK3CA, NRAS Mutations in Colorectal Cancer Characteristics and Personalized Medicine. PLOS One 8(12): e81628.

Swanson KD, Winter JM, Reis M, Bentires-Alj M, Greulich H, Grewal R, Hruban RH, Yeo CJ, Yassin Y, Iartchouk O, Montgomery K, Whitman SP, Caligiuri MA, Loh ML, Gilliland DG, Look AT, Kucherlapati R, Kern SE, Meyerson M, Neel BG. SOS1 mutations are rare in human malignancies: implications for Noonan Syndrome patients. Genes Chromosomes Cancer. Mar. 2008;47(3):253-9.

Tang Z, Zhang J, Lu X, Wang W, Chen H, Robinson MK, Cheng J, Tang G, Medeiros LJ. Coexistent genetic alterations involving ALK, RET, ROS1 or MET in 15 cases of lung adenocarcinoma. Mod Pathol. Feb. 2018;31 (2):307-312.

Tanizaki R, Katsumi A, Kiyoi H, Kunishima S, Iwasaki T, Ishikawa Y, Kobayashi M, Abe A, Matsushita T, Watanabe T, Kojima T, Kaibuchi K, Kojima S, Naoe T. Mutational analysis of SOS1 gene in acute myeloid leukemia. Int J Hematol. Nov. 2008;88(4):460-462.

Tyner, J. W., Erickson, H., Deininger, M. W. N., Willis, S. G., Eide, C. A., Levine, R. L., Heinrich, M. C., Gattermann, N., Gilliland, D. G., Druker, B. J., & Loriaux, M. M. (2009). High-throughput sequencing screen reveals novel, transforming RAS mutations in myeloid leukemia patients. Blood, 113(8), 1749-1755.

Urano M, Nakaguro M, Yamamoto Y, Hirai H, Tanigawa M, Saigusa N, Shimizu A, Tsukahara K, Tada Y, Sakurai K, Isomura M, Okumura Y, Yamaguchi H, Matsubayashi J, Nagao T. Diagnostic Significance of HRAS Mutations in Epithelial-Myoepithelial Carcinomas Exhibiting a Broad Histopathologic Spectrum. Am J Surg Pathol. Jul. 2019;43 (7):984-994.

Vetter IR, Wittinghofer A. The guanine nucleotide-binding switch in three dimensions. Science. Nov. 9, 2001;294 (5545):1299-304.

Wang YI, Abaci HE, Shuler ML. Microfluidic blood-brain barrier model provides in vivo-like barrier properties for drug permeability screening. Biotechnol Bioeng. Jan. 2017;114(1):184-194.

Wang, X. S., Shankar, S., Dhanasekaran, S. M., Ateeq, B., Sasaki, A. T., Jing, X., Robinson, D., Cao, Q., Prensner, J. R., Yocum, A. K., Wang, R., Fries, D. F., Han, B., Asangani, I. A., Cao, X., Li, Y., Omenn, G. S., Pflueger, D., Gopalan, A., . . . Chinnaiyan, A. M. Cancer Discov. Jun. 2011;1(1):35-43.

Waters AM, Bagni R, Portugal F, Hartley JL (2016) Single Synonymous Mutations in KRAS Cause Transformed Phenotypes in NIH3T3 Cells. PLoS One 11(9): e0163272.

Wei, Linyi; Malhotra, Sanjay V. Synthesis and cytotoxicity evaluation of novel pyrido[3,4-d]pyrimidine derivatives as potential anticancer agents. MedChemComm (2012), 3(10), 1250-1257.

Winter JJ, Anderson M, Blades K, Brassington C, Breeze AL, Chresta C, Embrey K, Fairley G, Faulder P, Finlay MR, Kettle JG,

(56) References Cited

OTHER PUBLICATIONS

Nowak T, Overman R, Patel SJ, Perkins P, Spadola L, Tart J, Tucker JA, Wrigley G. Small molecule binding sites on the Ras:SOS complex can be exploited for inhibition of Ras activation. J Med Chem. Mar. 12, 2015;58(5):2265-74.
X. Xu, X. Wen, A. Moosa, S. Bhimani, & T. Jin, Ras inhibitor CAPRI enables neutrophil-like cells to chemotax through a higher-concentration range of gradients, Proc. Natl. Acad. Sci. U.S.A. 118 (43) e2002162118.
Zhu, et al. Discovery of novel N-benzylbenzamide derivatives as tubulin polymerization inhibitorsactivities in European Ournal Of Medicinal Chemistry, 2021, vol. 216(113316), pp. 1-26.

* cited by examiner

HETEROCYCLIC COMPOUNDS AND METHODS OF USE

CROSS-REFERENCE TO RELATED APPLICATIONS

This application claims priority to U.S. Provisional Patent Application No. 63/306,784, filed Feb. 4, 2022, and U.S. Provisional Patent Application No. 63/376,595, filed Sep. 21, 2022, the disclosure of each of which is incorporated by reference in its entirety.

TECHNICAL FIELD

This present application relates to heterocyclic compounds that are useful for treating proliferative disorders such as cancer.

BACKGROUND

Cancer is characterized by aberrant cell growth and proliferation. Ras proteins are critical components of signaling networks responsible for controlling cellular proliferation, differentiation, and survival. See, e.g., Fernandes-Medarde and Santos, Genes Cancer, Vol. 2, No. 3, pp. 344-358 (2011). Ras is a GTPase that acts as a molecular switch between an active GTP-bound state and an inactive GDP-bound state. GTP-bound Ras can activate several downstream signaling pathways involved in cell cycle progression, survival, and apoptosis.

Guanine nucleotide exchange factors (GEFs), such as SOS1, are required to activate Ras by facilitating the exchange of GDP (inactive Ras) for GTP (active Ras). SOS1 is itself activated by Ras via an allosteric interaction, which strongly activates the GEF function of SOS1, thus creating a positive feedback loop between SOS1 and Ras. See, e.g., Bandaru, et al., Cold Spring Harb. Perspect Med., Vol. 9, No. 2, a031534 (2019). Mutations in Ras occur in many human cancers, but currently no drug targeting Ras proteins has been approved. See Hillig, et al., Proc. Nat. Acad. Sci., Vol. 117, No. 7, pp. 2551-2560 (2019). Thus, there remains a need for novel therapeutics to disrupt Ras signaling.

SUMMARY

It has now been found that certain heterocyclic compounds are inhibitors of SOS1 activity, and are useful for treating various diseases and disorders, such as cancers.

Accordingly, provided herein is a compound of the Formula (I):

(I)

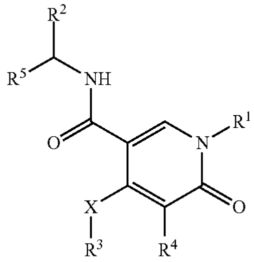

or a pharmaceutically acceptable salt thereof, wherein $R^1$, $R^2$, $R^3$, $R^4$, $R^5$, and X are as defined herein.

Also provided herein is a pharmaceutical composition comprising a compound of Formula (I), or a pharmaceutically acceptable salt thereof, and at least one pharmaceutically acceptable excipient.

Also provided herein is a method of inhibiting mammalian cell proliferation, in vitro or in vivo, comprising contacting a cell with an effective amount of a compound of Formula (I) or a pharmaceutically acceptable salt thereof, or a pharmaceutical composition thereof as defined herein.

Also provided herein is a method of treating cancer in a subject in need of such treatment, comprising administering to the subject an effective amount of a compound of Formula (I), or a pharmaceutically acceptable salt thereof, or a pharmaceutical composition thereof as defined herein.

Also provided herein is a method of treating a SOS1-associated cancer in a subject in need of such treatment, comprising administering to the subject an effective amount of a compound of Formula (I), or a pharmaceutically acceptable salt thereof, or a pharmaceutical composition thereof as defined herein.

Also provided herein is a method of treating a Ras pathway-associated disease or disorder in a subject, comprising administering to a subject identified or diagnosed as having a Ras pathway-associated disease or disorder an effective amount of a compound of Formula (I), or a pharmaceutically acceptable salt thereof, or a pharmaceutical composition thereof as defined herein, to the subject.

Also provided herein is a method of treating a Ras pathway-associated cancer in a subject, comprising administering to a subject identified or diagnosed as having a Ras pathway-associated cancer an effective amount of a compound of Formula (I), or a pharmaceutically acceptable salt thereof, or a pharmaceutical composition thereof as defined herein, to the subject.

Also provided herein is a method of treating a Ras-associated disease or disorder in a subject, comprising administering to a subject identified or diagnosed as having a Ras-associated disease or disorder an effective amount of a compound of Formula (I), or a pharmaceutically acceptable salt thereof, or a pharmaceutical composition thereof as defined herein, to the subject.

Also provided herein is a method of treating a Ras-associated cancer in a subject, comprising administering to a subject identified or diagnosed as having a Ras-associated cancer an effective amount of a compound of Formula (I), or a pharmaceutically acceptable salt thereof, or a pharmaceutical composition thereof as defined herein, to the subject.

Also provided herein is a method of treating a SOS1-associated cancer in a subject, comprising administering to a subject identified or diagnosed as having a SOS1-associated cancer an effective amount of a compound of Formula (I), or a pharmaceutically acceptable salt thereof, or a pharmaceutical composition thereof as defined herein, to the subject.

Also provided herein is a method for treating cancer in a subject in need thereof, comprising:

(a) determining that the cancer is associated with a dysregulation of a Ras pathway gene, a Ras pathway protein, or expression or activity or level of any of the same; and (b) administering to the subject an effective amount of a compound of Formula (I), or a pharmaceutically acceptable salt thereof, or a pharmaceutical composition thereof as defined herein, to the subject.

Also provided herein is a method for treating cancer in a subject in need thereof, comprising administering to the subject an effective amount of a compound of Formula (I), or a pharmaceutically acceptable salt thereof, or a pharmaceutical composition thereof as defined herein to a subject determined to have a cancer is associated with a dysregulation of a Ras pathway gene, a Ras pathway protein, or expression or activity or level of any of the same.

Also provided herein is a method for treating cancer in a subject in need thereof, comprising:

(a) determining that the cancer is associated with a dysregulation of a Ras gene, a Ras protein, or expression or activity or level of any of the same; and
(b) administering to the subject an effective amount of a compound of Formula (I), or a pharmaceutically acceptable salt thereof, or a pharmaceutical composition thereof as defined herein, to the subject.

Also provided herein is a method for treating cancer in a subject in need thereof, comprising administering to the subject an effective amount of a compound of Formula (I), or a pharmaceutically acceptable salt thereof, or a pharmaceutical composition thereof as defined herein to a subject determined to have a cancer is associated with a dysregulation of a Ras gene, a Ras protein, or expression or activity or level of any of the same.

Also provided herein is a method for treating cancer in a subject in need thereof, comprising administering to the subject an effective amount of a compound of Formula (I), or a pharmaceutically acceptable salt thereof, or a pharmaceutical composition thereof as defined herein to a subject determined to have a cancer is associated with a dysregulation of a SOS1 gene, a SOS1 protein, or expression or activity or level of any of the same.

Also provided herein is a method for treating cancer in a subject in need thereof, comprising:

(a) determining that the cancer is associated with a dysregulation of a SOS1 gene, a SOS1 protein, or expression or activity or level of any of the same; and
(b) administering to the subject an effective amount of a compound of Formula (I), or a pharmaceutically acceptable salt thereof, or a pharmaceutical composition thereof as defined herein, to the subject.

Also provided herein is a method for inhibiting mammalian cell proliferation, comprising contacting the mammalian cell with a compound of Formula (I), or a pharmaceutically acceptable salt thereof.

Also provided herein is a method for inhibiting Ras pathway activity in a mammalian cell, comprising contacting the mammalian cell with a compound of Formula (I), or a pharmaceutically acceptable salt thereof.

Also provided herein is a method for inhibiting SOS1 activity in a mammalian cell, comprising contacting the mammalian cell with a compound of Formula (I), or a pharmaceutically acceptable salt thereof.

Also provided herein is a method for inhibiting Ras activity in a mammalian cell, comprising contacting the mammalian cell with a compound of Formula (I), or a pharmaceutically acceptable salt thereof.

Also provided herein is a method for inhibiting a SOS1-Ras protein-protein interaction in a mammalian cell, comprising contacting the mammalian cell with a compound of Formula (I), or a pharmaceutically acceptable salt thereof.

Also provided herein is a method for inhibiting metastasis in a subject having a particular cancer in need of such treatment, comprising administering to the subject an effective amount of a compound of Formula (I), or a pharmaceutically acceptable salt thereof, or a pharmaceutical composition comprising a compound of Formula (I), or a pharmaceutically acceptable salt thereof.

Also provided herein is a compound of Formula (I), or a pharmaceutically acceptable salt thereof, or a pharmaceutical composition thereof as defined herein for use in the treatment of cancer.

Also provided herein is a compound of Formula (I), or a pharmaceutically acceptable salt thereof, or a pharmaceutical composition thereof as defined herein for use in the treatment of a Ras pathway-associated disease or disorder.

Also provided herein is a compound of Formula (I), or a pharmaceutically acceptable salt thereof, or a pharmaceutical composition thereof as defined herein for use in the treatment of a Ras pathway-associated cancer.

Also provided herein is a compound of Formula (I), or a pharmaceutically acceptable salt thereof or a pharmaceutical composition thereof as defined herein for use in the treatment of cancer and/or inhibiting metastasis associated with a particular cancer.

Also provided herein is a compound of Formula (I), or a pharmaceutically acceptable salt thereof for use in the inhibition of a SOS1-Ras protein-protein interaction in a mammalian cell.

Also provided herein is a compound of Formula (I), or a pharmaceutically acceptable salt thereof, defined herein in the manufacture of a medicament for the inhibition of a SOS1-Ras protein-protein interaction in a mammalian cell.

Also provided herein is a compound of Formula (I), or a pharmaceutically acceptable salt thereof, as defined herein, in the manufacture of a medicament for the treatment of a Ras pathway-associated disease or disorder.

Also provided herein is a compound of Formula (I), or a pharmaceutically acceptable salt thereof, as defined herein, in the manufacture of a medicament for the treatment of a Ras pathway-associated cancer.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

Other features and advantages of the invention will be apparent from the following detailed description and FIGURES, and from the claims.

DETAILED DESCRIPTION

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "tautomer," as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. An example of a tautomeric forms includes the following example:

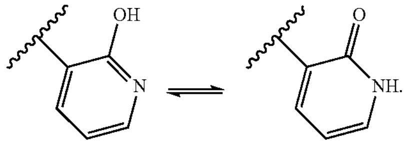 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

The term "halo" refers to one of the halogens, group 17 of the periodic table. In particular the term refers to fluorine, chlorine, bromine and iodine. Preferably, the term refers to fluorine or chlorine.

The term "$C_1$-$C_6$ alkyl" refers to a linear or branched saturated hydrocarbon chain containing 1, 2, 3, 4, 5 or 6 carbon atoms, for example, methyl, ethyl, n-propyl, iso-propyl, n-butyl, sec-butyl, tert-butyl, n-pentyl and n-hexyl.

The term "$C_1$-$C_6$ alkylene" refers to a straight or branched divalent hydrocarbon (alkyl) chain linking the rest of the molecule to a radical group, consisting solely of carbon and hydrogen, respectively, containing 1, 2, 3, 4, 5 or 6 carbon atoms. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain.

The term "$C_1$-$C_6$ haloalkyl" refers to a $C_1$-$C_6$ alkyl group, as defined herein, substituted with at least one halogen atom independently chosen at each occurrence, for example fluorine, chlorine, bromine, and iodine. The halogen atom(s) may be present at any position on the alkyl group. For example, $C_1$-$C_6$ haloalkyl may refer to chloromethyl, fluoromethyl, diflouoromethyl, trifluoromethyl, chloroethyl e.g., 1-chloroethyl and 2-chloroethyl, trichloroethyl e.g., 1,2,2-trichloroethyl, 2,2,2-trichloroethyl, fluoroethyl e.g. 1-fluoromethyl and 2-fluoroethyl, difluoroethyl e.g. 1,1-difluoroethyl, 2,2-difluoroethyl, 1,2-difluoroethyl, trifluoroethyl e.g. 1,2,2-trifluoroethyl and 2,2,2-trifluoroethyl, chloropropyl, trichloropropyl, fluoropropyl, trifluoropropyl.

As used herein, the term "heteroaryl" refers to a 5 to 10-membered mono- or bicyclic group wherein at least one ring in the system is aromatic; and wherein one or more carbon atoms in at least one ring in the system is/are replaced with an heteroatom independently selected from N, O, and S. Non-limiting examples of heteroaryl groups include furanyl, furazanyl, thiofuranyl, benzothiophenyl, phthalazinyl, pyrrolyl, oxazolyl, benzoxazolyl, 1,2,3-oxadiazolyl, 1,2,4-oxadiazole, thiazolyl, 1,2,3-thiadiazolyl, 1,2,4-thiadiazolyl, benzothiazolyl, imidazolyl, benzimidazolyl, indolyl, indazole, pyrazolyl, benzopyrazolyl, isoxazolyl, benzoisoxazole, isothiazolyl, triazolyl, benzotriazolyl, thiadiazolyl, tetrazolyl, pyridinyl, pyridazinyl, pyrimidinyl, pyrazinyl, purinyl, pteridinyl, quinolinyl, isoquinolinyl, quinazolinyl, quinoxalinyl, cinnolinyl, triazinyl, 2,3-dihydrobenzofuranyl, and 5,6,7,8-tetrahydroimidazo[1,5]pyridinyl.

As used herein, the term "cycloalkyl" refers to a saturated or partially unsaturated mono- or bicyclic carbon group having 3 to 10 carbon atoms, such as $C_3$-$C_{10}$ cycloalkyl groups and $C_3$-$C_6$ cycloalkyl groups. Bicyclic cycloalkyl groups include fused, spiro, and bridged ring systems. Non-limiting examples of cycloalkyl groups include phenyl, 2,3-dihydro-1H-indene, cyclopropyl, cyclobutyl, cyclopentyl, cyclohexyl, spiro[2.3]hexyl, spiro[3.3]heptanyl, and bicyclo[1.1.1]pentyl, bicyclo[2.2.1]heptyl, and spiro[2.5]octyl.

The term "heterocyclyl" refers to a saturated or partially unsaturated hydrocarbon monocyclic or bicyclic ring system, having 3 to 10 ring atoms, that is not aromatic, having at least one heteroatom within the ring selected from N, O and S. Bicyclic heterocyclyl groups include fused, spiro, and bridged ring systems. The heterocyclyl group may be denoted as, for example, a "5 to 10-membered heterocyclyl group," which is a ring system containing 5, 6, 7, 8, 9 or 10 atoms at least one being a heteroatom. Heterocyclyl groups can, for example, have 1, 2, 3, or more, heteroatoms. In some embodiments, a heterocyclyl group has one or two independently selected heteroatoms. A heterocycle may further contain one or more carbonyl or thiocarbonyl functionalities, so as to make the definition include oxo-systems and thio-systems such as lactams, lactones, cyclic imides, cyclic thioimides and cyclic carbamates. The heterocyclyl group may be bonded to the rest of the molecule through any carbon atom or through a heteroatom such as nitrogen. Exemplary heterocyclyl groups include, but are not limited to azepanyl, 1,3-dioxolane, 1,4-dioxolanyl, maleimidyl, succinimidyl, dioxopiperazinyl, hydantoinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, quinuclidineyl, 4H-pyranyl, azetidinyl, oxetanyl, octahydrocyclopenta[c]pyrrole, 2-azaspiro[3.3]heptanyl, 3-oxabicyclo[3.1.0]hexanyl, 3-azabicyclo[3.1.0]hexanyl, 3-azabicyclo[3.1.1]heptanyl, 4-azaspiro[2.5]octanyl, 6-azaspiro[3.5]nonanyl, 2,6-diazaspiro[3.3]heptanyl, 7-azabicyclo[2.2.1]heptanyl, 2-azabicyclo[2.2.1]heptanyl, 2,5-diazabicyclo[2.2.2]octanyl, 2,5-diazabicyclo[2.2.1]heptanyl, 2-oxabicyclo[2.1.1]hexanyl, 3-azabicyclo[3.2.1]octanyl, hexahydro-1H-cyclopenta[c]pyrrolyl, 3-oxa-9-azabicyclo[3.3.1]nonanyl, and hexahydro-1H-pyrrolizinyl.

As used herein, when a ring is described as being "partially unsaturated", it means said ring has one or more additional degrees of unsaturation (in addition to the degree of unsaturation attributed to the ring itself; e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

The compounds of Formula (I) include pharmaceutically acceptable salts thereof. In addition, the compounds of Formula (I) also include other salts of such compounds which are not necessarily pharmaceutically acceptable salts, and which may be useful as intermediates for preparing and/or purifying compounds of Formula (I) and/or for separating enantiomers of compounds of Formula (I).

It will further be appreciated that the compounds of Formula (I) or their salts may be isolated in the form of solvates, and accordingly that any such solvate is included within the scope of the present invention. For example, compounds of Formula (I) and salts thereof can exist in unsolvated as well as solvated forms with pharmaceutically acceptable solvents such as water, ethanol, and the like.

In some embodiments, the compounds of Formula (I) include the compounds of Examples 1-313 and stereoisomers and pharmaceutically acceptable salts and solvates thereof. In some embodiments, the compounds of Examples 1-313 are in the free base form. In some embodiments, the compounds of Examples 1-313 are in the form of a pharmaceutically acceptable salt.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some embodiments, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salts not specifically limited as far as it can be used in medicaments. Examples of a salt that the compounds described herein with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, for example addition salts with mineral acids such as hydrochloric acid, hydrobromic acid, hydroiodic acid, sulfuric acid, nitric acid, and phosphoric acid: organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Compounds provided herein may also contain unnatural proportions of atomic isotopes at one or more of the atoms that constitute such compounds. That is, an atom, in particular when mentioned in relation to a compound according to Formula (I), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

The ability of test compounds to act as inhibitors of the SOS1-Ras (e.g., KRas (e.g., KRas G12C)) interaction may be demonstrated by the biological assays described herein. $IC_{50}$ values for inhibiting the SOS1-Ras interaction are shown in Table A. hSOS1 $K_D$ values in a Surface Plasmon Resonance (SPR) SOS1 binding assay are shown in Table B.

In some embodiments, the compounds provided herein exhibit brain and/or central nervous system (CNS) penetrance. Such compounds are capable of crossing the blood brain barrier and inhibiting SOS1 activity in the brain and/or other CNS structures. In some embodiments, the compounds provided herein are capable of crossing the blood brain barrier in an effective amount. For example, treatment of a subject with cancer (e.g., a Ras pathway-associated cancer (e.g., a SOS1-associated cancer, a Ras-associated cancer (e.g., a KRas-associated cancer, a HRas-associated cancer, and/or a NRas-associated cancer), an EGFR-associated cancer, an ErbB2-associated cancer, an ErbB3-associated cancer, an ErbB4-associated cancer, a NF1-associated cancer, a PDGFR-A-associated cancer, a PDGFR-B-associated cancer, a FGFR1-associated cancer, FGFR2-associated cancer, FGFR3-associated cancer, a IGF1 R-associated cancer, a INSR-associated cancer, a ALK-associated cancer, a ROS-associated cancer, a TrkA-associated cancer, a TrkB-associated cancer, a TrkC-associated cancer, a RET-associated cancer, a c-MET-associated cancer, a VEGFR1-associated cancer, a VEGFR2-associated cancer, a VEGFR3-associated cancer, an AXL-associated cancer, a SHP2-associated cancer, a RAF-associated cancer (e.g., a BRAF-associated cancer), a PI3K-associated cancer, an AKT-associated cancer, an mTOR-associated cancer, a MEK-associated cancer, an ERK-associated cancer, or a combination thereof) such as a Ras pathway-associated brain or CNS cancer) can include administration (e.g., oral administration) of the compound to the subject. In some such embodiments, the compounds provided herein are useful for treating a primary brain tumor or metastatic brain tumor. For example, a Ras pathway-associated primary brain tumor or metastatic brain tumor.

Compounds of Formula (I), or a pharmaceutically acceptable salt thereof, are useful for treating diseases and disorders which can be treated with a SOS1 inhibitor, such as a Ras pathway-associated disease or disorder (e.g., a SOS1-associated disease or disorder, a Ras-associated disease or disorder (e.g., a KRas-associated disease or disorder, a HRas-associated disease or disorder, and/or a NRas-associated disease or disorder), an EGFR-associated disease or disorder, an ErbB2-associated disease or disorder, an ErbB3-associated disease or disorder, an ErbB4-associated disease or disorder, a NF1-associated disease or disorder, a PDGFR-A-associated disease or disorder, a PDGFR-B-associated disease or disorder, a FGFR1-associated disease or disorder, FGFR2-associated disease or disorder, FGFR3-associated disease or disorder, a IGF1 R-associated disease or disorder, a INSR-associated disease or disorder, a ALK-associated disease or disorder, a ROS-associated disease or disorder, a TrkA-associated disease or disorder, a TrkB-associated disease or disorder, a TrkC-associated disease or disorder, a RET-associated disease or disorder, a c-MET-associated disease or disorder, a VEGFR1-associated disease or disorder, a VEGFR2-associated disease or disorder, a VEGFR3-associated disease or disorder, an AXL-associated disease or disorder, a SHP2-associated disease or disorder, a RAF-associated disease or disorder (e.g., a BRAF-associated disease or disorder), a PI3K-associated disease or disorder, an AKT-associated disease or disorder, an mTOR-associated disease or disorder, a MEK-associated disease or disorder, an ERK-associated disease or disorder, or a combination thereof), including hematological cancers, solid tumors, Neurofibromatosis type 1 (NF1), Noonan Syndrome (NS), LEOPARD syndrome, Capillary Malformation-Arteriovenous Malformation Syndrome (CM-AVM), Costello Syndrome (CS), Cardio-Facio-Cutaneous Syndrome (CFC), Legius Syndrome, and Hereditary gingival fibromatosis.

Compounds of Formula (I) or a pharmaceutically acceptable salt thereof are useful for treating diseases and disorders which can be treated with a SOS1 inhibitor, such as a Ras pathway-associated cancer, including hematological cancers and solid tumors.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

In some embodiments, the subject has been identified or diagnosed as having a cancer with a dysregulation of a Ras pathway gene (e.g., SOS1, Ras (e.g., KRas, HRas, and/or NRas), EGFR, ErbB2, ErbB3, ErbB4, NF1, PDGFR-A, PDGFR-B, FGFR1, FGFR2, FGFR3, IGF1 R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof), a Ras pathway protein (e.g., SOS1, Ras (e.g., KRas, HRas, and/or NRas), EGFR, ErbB2, ErbB3, ErbB4, NF1, PDGFR-A, PDGFR-B, FGFR1, FGFR2, FGFR3, IGF1 R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof), or expression or activity, or level of any of the same (a Ras pathway-associated cancer) (e.g., as determined using a regulatory agency-approved, e.g., FDA-approved, assay or kit). In some embodiments, the subject has a tumor that is positive for a dysregulation of a Ras pathway gene, a Ras pathway protein, or expression or activity, or level of any of the same (e.g., as determined using a regulatory agency-approved assay or kit). The subject can be a subject with a tumor(s) that is positive for a dysregulation of a Ras pathway gene, a Ras pathway protein, or expression or activity, or level of any of the same (e.g., identified as positive using a regulatory agency-approved, e.g., FDA-approved, assay or kit). The subject can be a subject whose tumors have a dysregulation of a Ras pathway gene, a Ras pathway protein, or expression or activity, or a level of the same (e.g., where the tumor is identified as such using a regulatory agency-approved, e.g., FDA-approved, kit or assay). In some embodiments, the subject is suspected of having a Ras pathway-associated cancer. In some embodiments, the subject has a clinical record indicating that the subject has a tumor that has a dysregulation of a Ras pathway gene, a Ras pathway protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a Ras pathway gene, a Ras pathway protein, or expression or activity, or level of any of the same (a Ras pathway-associated cancer).

In some embodiments, the subject has been identified or diagnosed as having a cancer with a dysregulation of a Ras gene, a Ras protein, or expression or activity, or level of any of the same (a Ras-associated cancer) (e.g., as determined using a regulatory agency-approved, e.g., FDA-approved, assay or kit). In some embodiments, the subject has a tumor that is positive for a dysregulation of a Ras gene, a Ras protein, or expression or activity, or level of any of the same (e.g., as determined using a regulatory agency-approved assay or kit). The subject can be a subject with a tumor(s) that is positive for a dysregulation of a Ras gene, a Ras protein, or expression or activity, or level of any of the same (e.g., identified as positive using a regulatory agency-approved, e.g., FDA-approved, assay or kit). The subject can be a subject whose tumors have a dysregulation of a Ras gene, a Ras protein, or expression or activity, or a level of the same (e.g., where the tumor is identified as such using a regulatory agency-approved, e.g., FDA-approved, kit or assay). In some embodiments, the subject is suspected of having a Ras-associated cancer. In some embodiments, the subject has a clinical record indicating that the subject has a tumor that has a dysregulation of a Ras gene, a Ras protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a Ras gene, a Ras protein, or expression or activity, or level of any of the same (a Ras-associated cancer).

In some embodiments, the subject has been identified or diagnosed as having a cancer with a dysregulation of a KRas gene, a KRas protein, or expression or activity, or level of any of the same (a KRas-associated cancer) (e.g., as determined using a regulatory agency-approved, e.g., FDA-approved, assay or kit). In some embodiments, the subject has a tumor that is positive for a dysregulation of a KRas gene, a KRas protein, or expression or activity, or level of any of the same (e.g., as determined using a regulatory agency-approved assay or kit). The subject can be a subject with a tumor(s) that is positive for a dysregulation of a KRas gene, a KRas protein, or expression or activity, or level of any of the same (e.g., identified as positive using a regulatory agency-approved, e.g., FDA-approved, assay or kit). The subject can be a subject whose tumors have a dysregulation of a KRas gene, a KRas protein, or expression or activity, or a level of the same (e.g., where the tumor is identified as such using a regulatory agency-approved, e.g., FDA-approved, kit or assay). In some embodiments, the subject is suspected of having a KRas-associated cancer. In some embodiments, the subject has a clinical record indicating that the subject has a tumor that has a dysregulation of a KRas gene, a KRas protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a KRas gene, a KRas protein, or expression or activity, or level of any of the same (a KRas-associated cancer).

In some embodiments, the subject has been identified or diagnosed as having a cancer with a dysregulation of a HRas gene, a HRas protein, or expression or activity, or level of any of the same (a HRas-associated cancer) (e.g., as determined using a regulatory agency-approved, e.g., FDA-approved, assay or kit). In some embodiments, the subject has a tumor that is positive for a dysregulation of a HRas gene, a HRas protein, or expression or activity, or level of any of the same (e.g., as determined using a regulatory agency-approved assay or kit). The subject can be a subject with a tumor(s) that is positive for a dysregulation of a HRas gene, a HRas protein, or expression or activity, or level of any of the same (e.g., identified as positive using a regulatory agency-approved, e.g., FDA-approved, assay or kit). The subject can be a subject whose tumors have a dysregulation of a HRas gene, a HRas protein, or expression or activity, or a level of the same (e.g., where the tumor is identified as such using a regulatory agency-approved, e.g., FDA-approved, kit or assay). In some embodiments, the subject is suspected of having a HRas-associated cancer. In some embodiments, the subject has a clinical record indicating that the subject has a tumor that has a dysregulation of a HRas gene, a HRas protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a HRas gene, a HRas protein, or expression or activity, or level of any of the same (a HRas-associated cancer).

In some embodiments, the subject has been identified or diagnosed as having a cancer with a dysregulation of a NRas gene, a NRas protein, or expression or activity, or level of any of the same (a NRas-associated cancer) (e.g., as determined using a regulatory agency-approved, e.g., FDA-approved, assay or kit). In some embodiments, the subject has a tumor that is positive for a dysregulation of a NRas gene, a NRas protein, or expression or activity, or level of any of the same (e.g., as determined using a regulatory agency-approved assay or kit). The subject can be a subject with a tumor(s) that is positive for a dysregulation of a NRas gene, a NRas protein, or expression or activity, or level of any of the same (e.g., identified as positive using a regulatory agency-approved, e.g., FDA-approved, assay or kit). The subject can be a subject whose tumors have a dysregulation of a NRas gene, a NRas protein, or expression or activity, or a level of the same (e.g., where the tumor is identified as such using a regulatory agency-approved, e.g., FDA-approved, kit or assay). In some embodiments, the subject is suspected of having a NRas-associated cancer. In some embodiments, the subject has a clinical record indicating that the subject has a tumor that has a dysregulation of a NRas gene, a NRas protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a NRas gene, a NRas protein, or expression or activity, or level of any of the same (a NRas-associated cancer).

In some embodiments, the subject has been identified or diagnosed as having a cancer with a dysregulation of a SOS1 gene, a SOS1 protein, or expression or activity, or level of any of the same (a SOS1-associated cancer) (e.g., as determined using a regulatory agency-approved, e.g., FDA-approved, assay or kit). In some embodiments, the subject has a tumor that is positive for a dysregulation of a SOS1 gene, a SOS1 protein, or expression or activity, or level of any of the same (e.g., as determined using a regulatory agency-approved assay or kit). The subject can be a subject with a tumor(s) that is positive for a dysregulation of a SOS1 gene, a SOS1 protein, or expression or activity, or level of any of the same (e.g., identified as positive using a regulatory agency-approved, e.g., FDA-approved, assay or kit). The subject can be a subject whose tumors have a dysregulation of a SOS1 gene, a SOS1 protein, or expression or activity, or a level of the same (e.g., where the tumor is identified as such using a regulatory agency-approved, e.g., FDA-approved, kit or assay). In some embodiments, the subject is suspected of having a SOS1-associated cancer. In some embodiments, the subject has a clinical record indicating that the subject has a tumor that has a dysregulation of a SOS1 gene, a SOS1 protein, or expression or activity, or level of any of the same (and optionally the clinical record indicates that the subject should be treated with any of the compositions provided herein). In some embodiments, the subject is a pediatric subject. In some embodiments, the subject has been identified or diagnosed as having a cancer that, based on histological examination, is determined to be associated with a dysregulation of a SOS1 gene, a SOS1 protein, or expression or activity, or level of any of the same (a SOS1-associated cancer).

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21 st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday).

In certain embodiments, compounds of Formula (I), or a pharmaceutically acceptable salt thereof are useful for preventing diseases and disorders as defined herein (for example, autoimmune diseases, inflammatory diseases, and cancer). The term “preventing” as used herein means the prevention of the onset, recurrence or spread, in whole or in part, of the disease or condition as described herein, or a symptom thereof.

In certain embodiments, compounds of Formula (I), or a pharmaceutically acceptable salt thereof are useful for preventing diseases and disorders as defined herein (for example, Ras pathway-associated diseases or disorders (e.g., autoimmune diseases, inflammatory diseases, and cancer) as described herein. The term “preventing” as used herein means the prevention of the onset, recurrence or spread, in whole or in part, of the disease or condition as described herein, or a symptom thereof.

Aberrant cell growth and proliferation is a hallmark of cancer. One such pathway through which such aberrant cell growth can occur is through Ras family protein signaling. The human Ras proteins (e.g., KRas (V-Ki-Ras2 Kirsten Rat Sarcoma 2 Viral Oncogene Homolog), HRas (V-Ha-Ras Harvey Rat Sarcoma Viral Oncogene Homolog), and/or NRas (Neuroblastoma RAS Viral (V-Ras) Oncogene Homolog); sometimes also called KRAS, HRAS, and NRAS, or K-Ras H-Ras, and N-Ras, respectively) are membrane-bound guanosine triphosphate (GTP)/guanosine diphosphate (GDP)-binding (G) proteins that are implicated in many oncogenic signaling cascades. Each of these proteins is approximately 21 kD in size. KRas has two common isoforms known as KRas4A and KRas4B.

Mature Ras proteins are typically associated with the cellular membrane via post-translational modification, such as prenylation (e.g., farnesylation of a “CAAX box”, where C represents cysteine, A represents an aliphatic amino acid, and X is methionine, serine, leucine, or glutamine). In the inactive state, Ras proteins are bound to GDP. See, e.g., Adjei, *J. Nat'l. Cancer Inst.* 93.14 (2001): 1062-1074.

Activation of Ras proteins can be initiated via multiple types of cell-surface receptors including receptor tyrosine kinases (TKIs) (e.g., EGFR, ErbB2, ErbB3, ErbB4, PDGFR-A/B, FGFR1/2/3, IGF1 R, INSR, ALK, ROS, TrkA, TrkB, TrkC, RET, c-MET, VEGFR1/2/3, AXL), T-cell receptors, B-cell receptors, monocyte colony-stimulating factor receptor, G-protein coupled receptors (GPCRs), and integrin family proteins. Activation of one of these types of cell-surface receptors generally leads, directly or indirectly, to activation of one or more guanine nucleotide exchange factors (GEFs), which promote Ras proteins to release GDP, allowing GTP to bind. Non-limiting examples of GEFs include the SOS (Son of Sevenless Homolog) proteins and RASGRF1 (Ras protein specific guanine nucleotide releasing factor 1; also sometimes called Cdc25). For example, upon activation, dimerization, and auto-phosphorylation of EGFR, the receptor can bind to the SH2 domain of the adaptor protein growth-factor-receptor-bound protein 2 (GRB2), which can then bind to a SOS protein (e.g., SOS1 or SOS2, sometimes also called SOS-1 and SOS-2, respectively), thereby co-localizing the SOS protein with the Ras family protein at the cellular membrane. See, e.g., Xuehua et al., *Proc. Nat. Acad. Sci. November* 2017, 114 (47) E10092-E10101; Vetter and Wittinghofer, *Science* 294.5545 (2001): 1299-1304*; Downward, Nat. Rev. Cancer* 3.1 (2003): 11-22; Pierre and Coumoul, *Biochem. Pharmacol.* 82.9 (2011): 1049-1056. Kortum, et al. *Proc. Nat. Acad. Sci.* 108.30 (2011): 12407-12412; U.S. Appl. Publ. Nos. 2019/0358230 and 2019/0194192; and PCT Publication Nos. WO 2018/172250 and WO 2019/201848.

Once activated by binding GTP, the Ras proteins can bind to and activate a number of downstream effectors, including the RAF family proteins, phosphatidyl inositol 3-kinases (PI3Ks), and RAL family proteins. See, e.g., Gurung and Bhattacharjee. *Oncology & Hematology Review,* 2015; 11(2):147-52(2015). For instance, signaling through the Ras-RAF-MAPK pathway has been implicated in many cancers, including, but not limited to, pancreatic cancer, thyroid cancer (e.g., papillary thyroid cancer), colon cancer, lung cancer (e.g., non-small cell lung cancer), melanoma, biliary tract cancer, small intestinal cancer, endometrial cancer, ovarian cancer, cervical cancer, prostate cancer, soft tissue cancers, peritoneal cancer, stomach cancer, liver cancer, urinary tract cancer, breast cancer, and combinations thereof. See, e.g., Kinsey, et al. *Nat. Medicine* 25.4 (2019): 620-627; Roberts and Der. *Oncogene* 26.22 (2007): 3291-3310; Santarpia, et al. *Expert Opinion on Therapeutic Targets* 16.1 (2012): 103-119. As another example, signaling through the Ras-PI3K/AKT/mammalian target of rapamycin (mTOR) pathway has been shown to play a role in many cancers, including, but not limited to, melanoma, ovarian cancer, cervical cancer, endometrial cancer, breast cancer, prostate cancer, brain cancer (e.g., glioblastoma), lung cancer (e.g., non-small cell lung cancer), pancreatic cancer, bladder cancer, colon cancer, head and neck cancer, leukemia, thyroid cancer, lymphoma, bowel cancer, gastric cancer, and combinations thereof. See, e.g., Chappell, et al. *Oncotarget* 2.3 (2011): 135; Vara, et al. *Cancer Treatment Reviews* 30.2 (2004): 193-204; Hennessy, et al. *Nat. Rev. Drug Disc.* 4.12 (2005): 988-1004; Osaki, et al. *Apoptosis* 9.6 (2004): 667-676; Luo, et al. *Cancer Cell* 4.4 (2003): 257-262.

Though Ras proteins have intrinsic GTPase activity, it is typically not physiologically relevant. Instead, hydrolysis of the bound GTP is enhanced (e.g., by up to about 5 orders of magnitude) by the binding of a GTPase-activating protein (GAP), such as neurofibromatosis type 1 (NF1) or $p120^{GAP}$. See, e.g., Adjei, *Journal of the National Cancer Institute* 93.14 (2001): 1062-1074; Downward, Nature Reviews *Cancer* 3.1 (2003): 11-22; Scheffzek, et al. *Science* 277.5324 (1997): 333-339.

Activating mutations (especially, e.g., at residues G12, G13, and/or Q61) in Ras family proteins are estimated to be present in up to about 30% of all human cancers. Commonly, activating mutations in Ras family proteins render the Ras protein insensitive to the activity of GAPs. See, e.g., Santarpia, et al. *Expert Opinion on Therapeutic Targets* 16.1 (2012): 103-119. Exemplary, non-limiting examples of Ras mutations are presented in Tables 1 (KRas mutations), 2 (HRas mutations), and 3 (NRas mutations).

The term “Ras pathway-associated disease or disorder” as used herein refers to diseases or disorders associated with or having a dysregulation of a gene in a Ras pathway, a protein in a Ras pathway, or the expression or activity or level of any (e.g., one or more) of the same (e.g., any of the types of dysregulation of a gene in a Ras pathway, a protein in a Ras pathway, or the expression or activity or level of any of the same, as described herein). Non-limiting examples of a Ras pathway-associated diseases or disorders include, for example, Neurofibromatosis type 1 (NF1), Noonan Syndrome (NS), LEOPARD syndrome, Capillary Malformation-Arteriovenous Malformation Syndrome (CM-AVM), Costello Syndrome (CS), Cardio-Facio-Cutaneous Syndrome (CFC), Legius Syndrome, Hereditary gingival fibromatosis, and cancers.

In some embodiments, a Ras pathway-associated disease or disorder is a Ras pathway-associated cancer. The term "Ras pathway-associated cancer" as used herein refers to cancers associated with or having a dysregulation of a gene in a Ras pathway, a protein in a Ras pathway, or the expression or activity or level of any (e.g., one or more) of the same (e.g., any of the types of dysregulation of a gene in a Ras pathway, a protein in a Ras pathway, or the expression or activity or level of any of the same, as described herein). Non-limiting examples of a Ras pathway-associated cancer are described herein. In some embodiments, a Ras pathway-associated cancer can be a KRas-associated cancer, a HRas-associated cancer, a NRas-associated cancer, a SOS1-associated cancer, an EGFR-associated cancer, an ErbB2-associated cancer, an ErbB3-associated cancer, an ErbB4-associated cancer, a NF1-associated cancer, a PDGFR-A-associated cancer, a PDGFR-B-associated cancer, a FGFR1-associated cancer, FGFR2-associated cancer, FGFR3-associated cancer, a IGF1 R-associated cancer, a INSR-associated cancer, a ALK-associated cancer, a ROS-associated cancer, a TrkA-associated cancer, a TrkB-associated cancer, a TrkC-associated cancer, a RET-associated cancer, a c-MET-associated cancer, a VEGFR1-associated cancer, a VEGFR2-associated cancer, a VEGFR3-associated cancer, an AXL-associated cancer, a SHP2-associated cancer, a RAF-associated cancer (e.g., a BRAF-associated cancer), a PI3K-associated cancer, an AKT-associated cancer, an mTOR-associated cancer, a MEK-associated cancer, an ERK-associated cancer, or a combination thereof.

The term "Ras-associated cancer" as used herein refers to cancers associated with or having a dysregulation of a Ras gene, a Ras protein, or the expression or activity or level of any (e.g., one or more) of the same (e.g., any of the types of dysregulation of a Ras gene, a Ras protein, or the expression or activity or level of any of the same, as described herein). Non-limiting examples of a Ras-associated cancer are described herein. In some embodiments, a Ras-associated cancer can be a KRas-associated cancer, a HRas-associated cancer, a NRas-associated cancer, or a combination thereof.

The phrase "dysregulation of a Ras gene, a Ras protein, or the expression or activity or level of any of the same" refers to a genetic mutation (e.g., a Ras (e.g., KRas, NRas, or HRas) gene translocation that results in the expression of a fusion protein, a mutation in a Ras gene that results in the expression of a Ras protein that includes a deletion of at least one amino acid as compared to a wild type Ras protein, a mutation in a Ras gene that results in the expression of a Ras protein with one or more point mutations as compared to a wild type Ras protein, a mutation in a Ras gene that results in the expression of a Ras protein with at least one inserted amino acid as compared to a wild type Ras protein, a gene duplication that results in an increased level of Ras protein in a cell, or a mutation in a regulatory sequence (e.g., a promoter and/or enhancer) that results in an increased level of Ras protein in a cell), an alternative spliced version of a Ras mRNA (e.g., that results in a Ras protein having a deletion of at least one amino acid in the Ras protein as compared to the wild type Ras protein or that results in a Ras protein having an insertion of at least one amino acid in the Ras protein as compared to the wild type Ras protein), or increased expression (e.g., increased levels) of a wild type Ras protein in a mammalian cell due to aberrant cell signaling and/or dysregulated autocrine/paracrine signaling (e.g., as compared to a control non-cancerous cell). As another example, a dysregulation of a Ras gene, a Ras protein, or expression or activity, or level of any of the same, can be a mutation in a Ras gene that encodes a Ras protein that is constitutively active or has increased activity as compared to a protein encoded by a Ras gene that does not include the mutation. In some embodiments of any of the methods described herein, a dysregulation of a Ras gene, a Ras protein, or the expression or activity or level of any of the same can be selected from the group consisting of a G12 mutation, a G13 mutation, a Q61 mutation, and a combination thereof.

Table 1 lists some non-limiting exemplary KRas mutations. Table 1A lists a non-limiting exemplary KRas fusion. In some embodiments of any of the methods described herein, a dysregulation of a KRas gene, a KRas protein, or the expression or activity or level of any of the same can be selected from the group consisting of a G12 mutation (e.g., G12I, G12A, G12C, G12D, G12E, G12F, G12L, G12N, G12R, G12S, G12T, G12V, G12W, or G12Y), a G13 mutation (e.g., G13A, G13C, G13D, G13E, G13F, G13I, G13M, G13N, G13P, G13R, G13S, G13V, or G13Y), a Q61 mutation (e.g., Q61D, Q61E, Q61H, Q61K, Q61L, Q61P, Q61R), and a combination thereof.

Table 2 lists some non-limiting exemplary HRas mutations. In some embodiments of any of the methods described herein, a dysregulation of a HRas gene, a HRas protein, or the expression or activity or level of any of the same can be selected from the group consisting of a G12 mutation (e.g., G12A, G12C, G12D, G12R, G12S, G12V), a G13 mutation (e.g., G13A, G13C, G13D, G13R, G13S, G13V), a Q61 mutation (e.g., Q61H, Q61K, Q61L, Q61P, Q61R, Q61*), and a combination thereof.

Table 3 lists some non-limiting exemplary HRas mutations. In some embodiments of any of the methods described herein, a dysregulation of a HRas gene, a HRas protein, or the expression or activity or level of any of the same can be selected from the group consisting of a G12 mutation (e.g., G12A, G12C, G12D, G12R, G12S, G12V, G12W, G12N), a G13 mutation (e.g., G13A, G13C, G13D, G13R, G13S, G13V), a Q61 mutation (e.g., Q61E, Q61H, Q61K, Q61L, Q61P, Q61R, Q61E, Q61N), and a combination thereof.

TABLE 1

| KRAS Protein Amino Acid Substitutions/Insertions/Deletions[4] | | |
|---|---|---|
| Amino Acid Position(s) | Non-Limiting Exemplary Mutations | Non-Limiting Exemplary RAS-Associated Cancers |
| 5 | K5E[2], K5N[2], K5R[1] | |
| 6 | L6F[1] | |
| 7 | V7E[1], V7M[1] | |
| 8 | V8A[1], V8V[1†] | |
| 9 | V9I[1], V9V[1†] | |
| 10 | G10E[1], G10G[1†], G10R[1] | |
| 11 | A11A[1†], A11P[1], A11T[1], A11V[2] | |

TABLE 1-continued

| KRAS Protein Amino Acid Substitutions/Insertions/Deletions[A] | | |
|---|---|---|
| Amino Acid Position(s) | Non-Limiting Exemplary Mutations | Non-Limiting Exemplary RAS-Associated Cancers |
| 12 | G12I[1], G12A[2], G12C[2], G12D[2], G12E[1], G12F[2], G12G*[1†], G12L[2], G12N[2], G12R[2], G12S[2], G12T[1], G12V[2], G12W[1], G12Y[1] | Bile duct carcinoma[11], gall bladder carcinoma[11], colorectal cancer[11], haematopoietic neoplasm[11], lymphoid neoplasm[11], lung adenocarcinoma[11], NSCLC[11], pancreatic ductal carcinoma[11] prostate cancer[11], melanoma[11], gastric adenocarcinoma[11] |
| 13 | G13A[2], G13C[1], G13D[2], G13E[1], G13F[1], G13G[1†], G13I[1], G13M[1], G13N[2], G13P[1], G13R[2], G13S[2], G13V[2], G13Y[1] | colorectal cancer11, haematopoietic neoplasm11, lymphoid neoplasm11, gastric adenocarcinoma11 |
| 14 | V14A[1], V14G[1], V14I[2], V14L[1] | |
| 15 | G15D[2], G15G[1†], G15S[1], G15W[9] | |
| 16 | K16R[1] | |
| 17 | S17G[2], S17N[1] | |
| 18 | A18D[2], A18T[1] , A18V[1] | |
| 19 | L19F[2] | |
| 20 | T20A[1] | |
| 20 | T20A[1], T20M[1], T20R[2], T20S[1], T20T[1†] | |
| 21 | I21R[1] | |
| 22 | Q22*[1], Q22K[1], Q22Q[1†], Q22R[2] | |
| 23 | L23I[1], L23R[2] | |
| 24 | I24F[1], I24N[2], I24V[2] | |
| 27 | H27H[1†], H27L[2], H27N[2] | |
| 28 | F28S[1] | |
| 30 | D30E[1] | |
| 31 | E31K[1], E31Q[1], E37G[5], E31Q[1] | |
| 33 | D33E[1] | |
| 34 | P34L[1], P34S[2] | |
| 35 | T35A[1], T35I[2], T35S[5], T35T[1†] | |
| 36 | I36L[1], I36M[1] | |
| 37 | E37G[5], E37K[1] | |
| 40 | Y40C[5] | |
| 45 | V45V[1†] | |
| 49 | E49*[1], E49K[1] | |
| 51 | C51C[1†] | |
| 52 | L52F[1] | |
| 57 | D57N[1] | |
| 58 | T58I[2], T58T[1†] | |
| 59 | A59A[1†], A59D[4], A59del[1], A59E[2], A59G[2], A59S[1], A59T[1] | |
| 60 | G60A[1], G60D[2], G60E[8], G60G[1†], G60R[1], G60V[1], G61H[2] | |
| 61 | Q61D[1], Q61E[2], Q61H[2], Q61K[2], Q61L[2], Q61P[2], Q61R[1] | Lung adenocarcinoma[11], NSCLC[11], colorectal cancer[11] |
| 62 | E62D[2], E62G[1], E62K[1] | |
| 63 | E63del[1], E62E[1†], E63K[2] | |
| 64 | Y64D[1], Y64H[1], Y64N[1] | |
| 65 | S65I[1] | |
| 67 | M67L[2] | |
| 66 | A66T[10], A66V[10], | |
| 68 | R68G[1], R68M[1], R68S[1] | |
| 69 | D69G[1] | |
| 70 | Q70P[1] | |
| 71 | Y71C[1] | |
| 72 | M72I[2], M72T[1], M72V[1] | |
| 73 | R73M[1] | |
| 74 | T74P[2], T74T[1†] | |
| 75 | G75E[10] | |
| 76 | E76G[6], E76K[6], E76Q[6] | |
| 77 | G77A[1] | |
| 80 | C80S[1], C80Y[1] | |
| 86 | N86K[1] | |
| 88 | K88*[1], K88K[1†] | |
| 91 | E91K[1] | |
| 92 | D92G[1], D92Y[1] | |
| 95 | H95L[1] | |
| 97 | R97I[1] | |
| 98 | E98*[1] | |

TABLE 1-continued

KRAS Protein Amino Acid Substitutions/Insertions/Deletions[A]

| Amino Acid Position(s) | Non-Limiting Exemplary Mutations | Non-Limiting Exemplary RAS-Associated Cancers |
|---|---|---|
| 102 | R102fs*2[1] | |
| 110 | P110S[1] | |
| 117 | K117E[1], K117N[2], K117R[1] | |
| 118 | C118S[1] | |
| 120 | L120V[7] | |
| 121 | P121H[1], P121S[1] | |
| 127 | T127I[1] | |
| 130 | A130V[1] | |
| 134 | A134T[1] | |
| 134 | S136N[1] | |
| 135 | R135T[1†] | |
| 138 | G138E[1], G138R[1] | |
| 140 | P140S[1] | |
| 145 | S145T[7] | |
| 146 | A146A[1†], A146G[1], A146P[2], A146T[2], A146V[2] | |
| 147 | A147T[3], K147N[1] | |
| 153 | D153N[1], D153V[1] | |
| 154 | D154delD[1] | |
| 156 | F156L[2] | |
| 161 | R161*[1] | |
| 164 | R164L[1], R164Q[1], R164R[1†] | |
| 173 | D173D[1] | |
| 183 | T183_K184delTK[1] | |
| 185 | C185R[1], C185S[1] | |
| 188 | M188L[1] | |
| Insertions and Deletions | | |
| | A11_G12insGA[1] | |
| | V14_G15insG[2] | |
| | A66_M67insEEYSA[1] | |
| | D69fs*4[1] | |
| | E3fs*3[1] | |
| | E62 S65 > D[2] (c.186 194del9) | |
| | G10 A11insG[2] (c.30 31insGGA) | |
| | G12 G13insA[2] (c.37 37insGCG) | |
| | G12 G13insG[2] (c.36 37insGGT) | |
| | G12fs*3[1] | |
| | G12V9F[1] | |
| | G13 V14 > DI[1] | |
| | G13 V14insG[2] (c.39 40insGGC) | |
| | G60fs*27[1] | |
| | K16_S17insW[1] | |
| | L19_T20 > FA[1] | |
| | M72_R73ins15[1] | |
| | S65_A66ins15[1] | |
| | T183_K184delTK[1] | |
| | T58_A59insVA[1] | |
| | D154delD[1] | |
| | V9 G10insG[2] (c.27 28insGTA) | |
| | V9 G10insV[1] | |

[A]The KRAS mutations shown may be activating mutations and/or confer increased resistance of KRAS to a KRAS modulator (e.g., a KRAS inhibitor), e.g., as compared to a wild type KRAS.
*Indicates a synonymous mutation which may affect KRAS protein expression. See, e.g., Waters et al.. PLOS One 2016; 11(9). doi: 10.1371/journal.pone.0163272.
[1]U.S. Pat. No. 9,810,690
[2]U.S. Publication No. 2014/0199405
[3]P.C.T. Publication No. WO 2012/016050
[4]U.S. Pat. No. 10,238,650
[5]P.C.T. Publication No. WO 2009/052467
[6]U.S. Publication No. 2013/0317037
[7]P.C.T. Publication No. WO 2020/012068
[8]U.S. Publication No. 2017/0130271
[9]U.S. Publication No. 2017/0051356
[10]Abe et al. *Biochemical and Biophysical Research Communications.* 2020:522(3): P.360-696.
[11]Prior et al. *Cancer Res.* 2012 May 15; 72(10): 2457-2467.

TABLE 1A

| Exemplary KRAS Fusion Proteins and Cancers | |
|---|---|
| Non-limiting Exemplary KRAS Fusions | Non-limiting Exemplary KRAS-associated Cancer(s) |
| UBE2L3-KRAS[1] | Metastatic Prostate Cancer |

[1]Wang et al. Cancer Discovery. 2011; 9(1): 35-43. doi: 10.1158-2159-8274.CD-10-0022.

TABLE 2

| HRAS Protein Amino Acid Substitutions/Insertions/Deletions[A] | | |
|---|---|---|
| Amino Acid Position(s) | Non-Limiting Exemplary Mutations | Non-Limiting Exemplary HRAS-Associated Cancers |
| 12 | G12A, G12C, G12D, G12R, G12S, G12V[1] | Salivary gland adenocarcinoma, prostate cancer, melanoma, gastric adenocarcinoma[1], Epithelial-Myoepithelial Carcinoma[3] |
| 13 | G13A, G13C, G13D, G13R, G13S, G13V[1] | |
| 18 | A18V[2] | Oral squamous cell carcinoma[2] |
| 61 | Q61H, Q61K, Q61L, Q61P, Q61R, Q61E, Q61*[1,3,4] | Epithelial-Myoepithelial Carcinoma[3] |

[A]The HRAS mutations shown may be activating mutations and/or confer increased resistance of HRAS to a HRAS modulator (e.g., a HRAS inhibitor), e.g., as compared to a wild type HRAS.
[1]Prior et al. *Cancer Res.* 2012 May 15; 72(10): 2457-2467.
[2]Koumaki, Dimitra, et al. *Oncology Reports* 27 (2012): 1555-1560.
[3]Urano, Makoto, et al. *The American journal of surgical pathology* 43.7 (2019): 984-994.
[4]U.S. Pat. No. 10,722,484

TABLE 3

| NRAS Protein Amino Acid Substitutions/Insertions/Deletions[A] | | |
|---|---|---|
| Amino Acid Position(s) | Non-Limiting Exemplary Mutations | Non-Limiting Exemplary NRAS-Associated Cancers |
| 12 | G12A, G12C, G12D, G12R, G12S, G12V, G12W, G12N[1,2,4] | Myeloid leukemia[2], colorectal cancer[4] |
| 13 | G13A, G13C, G13D, G13R, G13S, G13V[1,2] | Myeloid leukemia[2] |
| 15 | G15W[6] | Colorectal cancer[6] |
| 60 | G60E[2,6] | Myeloid leukemia[2] |
| 61 | Q61E, Q61H, Q61K, Q61L, Q61P, Q61R, Q61E, Q61N[1,2,4,5] | Myeloid leukemia[2], colorectal cancer[4,5] |
| 117 | K117N[4] | Colorectal cancer[4] |
| 146 | A146T, A146P, A146V[3,4] | Colorectal cancer[4] |

[A]The NRAS mutations shown may be activating mutations and/or confer increased resistance of NRAS to a NRAS modulator (e.g., a NRAS inhibitor), e.g., as compared to a wild type NRAS.
[1]Prior et al. *Cancer Res.* 2012 May 15; 72(10): 2457-2467.
[2]Tyner, Jeffrey W., et al. *Blood, The Journal of the American Society of Hematology* 113.8 (2009): 1749-1755.
[3]U.S. Pat. No. 10,668,063
[4]Payandeh, et al. *American Journal of Cancer Prevention* 3.1 (2015): 19-22.
[5]Villahermosa, et al. *Journal of Clinical Oncology* 2014 32:15_suppl, e22159-e22159
[6]Shen, et al. *PloS One* 8.12 (2013): e81628.

However, the Ras proteins have often been considered to be "undruggable", and no direct Ras inhibitor has been approved by the United States Food and Drug Administration. Accordingly, other targets in Ras signaling pathways have been targeted in order to curb aberrant signaling through these pathways, including targets both upstream and downstream of the Ras family proteins. See, e.g., Cox, et al. *Nat. Rev. Drug Disc.* 13.11 (2014): 828-851; Khan, et al. *Biochimica et Biophysica Acta (BBA)-Molecular Cell Research* 1867.2 (2020): 118570; Kessler, et al. *Proc. Nat. Acad. Sci.* 116.32 (2019): 15823-15829; Dang, et al. *Nat. Rev. Cancer* 17.8 (2017): 502; Baker and Der, *Nature* 497.7451 (2013): 577-578.

Guanine nucleotide exchange factors, which promote the exchange of GDP for GTP bound by Ras family proteins, can be suitable targets to reduce signaling through Ras pathways. Inhibition of a GEF may promote the inactive (GDP bound) state of Ras family proteins and therefore decreased signaling through the pathway. See, e.g., Evelyn, et al. *Chemistry & Biology* 21.12 (2014): 1618-1628; Hillig, et al. *Proc. Nat. Acad. Sci.* 116.7 (2019): 2551-2560; Patgiri, et al. *Nat. Chem. Bio.* 7.9 (2011): 585-587: Maurer, et al. *Proc. Nat. Acad. Sci.* 109.14 (2012): 5299-5304; Winter, et al. *J. Med. Chem.* 58.5 (2015): 2265-2274. One such GEF is SOS1.

SOS1 has a central "catalytic" core (SOScat) of about 500 residues, which is sufficient for Ras-activating activity. SOS1 has a primary (sometimes also called the "catalytic" site) Ras binding site (e.g., including a Cdc25 homology domain) that can bind to and distort the nucleotide binding site of a Ras protein, thereby promoting the release of the bound nucleotide (e.g., GDP), allowing another nucleotide (e.g., GTP). SOS1 can bind two Ras molecules in a ternary complex, wherein binding of a Ras GTP complex to a second (sometimes also called the "allosteric" site) site on SOS1, further activating the catalytic activity of SOS1 in a positive feedback-type mechanism. See, e.g., Margarit, et al. *Cell* 112.5 (2003): 685-695; Freedman, et al. *Proc. Nat. Acad. Sci.* 103.45 (2006): 16692-16697. Further, it has been shown that small-molecule binders of SOS1 can modulate its GEF activity. See, e.g., Burns, et al. *Proc. Nat. Acad. Sci.* 111.9 (2014): 3401-3406. In some cases, small-molecule binders of SOS1 can negatively modulate its GEF activity with Ras proteins; such molecules can also be called herein "SOS1 inhibitors" and referred to as inhibiting "SOS1 activity." Some SOS1 inhibitors have been shown to bind proximal to the primary Ras binding site, for example, causing a movement in the sidechain of Tyr884 and reducing favorable stacking interactions with Arg73 of KRas. Further, antiproliferative activity of some such SOS1 inhibitors has been demonstrated. See, e.g., Hillig, et al., *Proc. Nat. Acad. Sci.* 116.7 (2019): 2551-2560; U.S. Patent Appl. Publ. Nos. 2019/0358230 and 2019/0194192; and PCT Publication Nos WO 2018/172250 and WO 2019/201848

The term "SOS1-associated cancer" as used herein refers to cancers associated with or having a dysregulation of a SOS1 gene, a SOS1-GEF (also called herein SOS1 protein), or the expression or activity or level of any (e.g., one or more) of the same (e.g., any of the types of dysregulation of a SOS1 gene, a SOS1 protein, or the expression or activity or level of any of the same, as described herein). Non-limiting examples of a SOS1-associated cancer are described herein.

The phrase "dysregulation of a SOS1 gene, a SOS1 protein, or the expression or activity or level of any of the same" refers to a genetic mutation (e.g., a SOS1 gene translocation that results in the expression of a fusion protein, a mutation in a SOS1 gene that results in the expression of a SOS1 protein that includes a deletion of at least one amino acid as compared to a wild type SOS1 protein, a mutation in a SOS1 gene that results in the expression of a SOS1 protein with one or more point mutations as compared to a wild type SOS1 protein, a mutation in a SOS1 gene that results in the expression of a SOS1 protein with at least one inserted amino acid as compared to a wild type SOS1 protein, a gene duplication that results in an increased level of SOS1 protein in a cell, or a mutation in a regulatory sequence (e.g., a promoter and/or enhancer) that results in an increased level of SOS1 protein in a cell), an alternative spliced version of a SOS1 mRNA (e.g., that results in a SOS1 protein having a deletion of at least one amino acid in the SOS1 protein as compared to the wild type SOS1 protein or that results in a SOS1 protein having an insertion of at least one amino acid in the SOS1 protein as compared to the wild type SOS1 protein), or increased expression (e.g., increased levels) of a wild type SOS1 protein in a mammalian cell due to aberrant cell signaling and/or dysregulated autocrine/paracrine signaling (e.g., as compared to a control non-cancerous cell). As another example, a dysregulation of a SOS1 gene, a SOS1 protein, or expression or activity, or level of any of the same, can be a mutation in a SOS1 gene that encodes a SOS1 protein that is constitutively active or has increased activity as compared to a protein encoded by a SOS1 gene that does not include the mutation. Non-limiting examples of SOS1 protein point mutations/insertions/deletions are described in Table 4. Table 4A lists a non-limiting exemplary SOS1 fusion.

TABLE 4

SOS1 Protein Amino Acid Substitutions/Insertions/Deletions[A]

| Amino Acid Position(s) | Non-Limiting Exemplary Mutations | Non-Limiting Exemplary SOS1-Associated Cancers |
|---|---|---|
| 65 | R65R[1†] | Colon cancer[1] |
| 102 | P102R[3] | Rhabdomyoscarcoma[3] |
| 248 | R248H[2] | T-ALL[2] |
| 233 | N233Y[4] | Lung adenocarcinoma[4] |
| 265 | D265N[4] | Lung adenocarcinoma[4] |
| 316 | S316L[1] | Colon cancer[1] |
| 327 | I327T[4] | Lung adenocarcinoma[4] |
| 340 | P340S[1] | Colon cancer[1] |
| 378 | T378A[3] | Sertoli cell tumor[3] |
| 410 | Q410Q[2†] | Lung adenocarcinoma[2] |
| 414 | G414G[1†] | Colon cancer[1] |
| 477 | Q477*[1] | Colon cancer[1] |
| 478 | P478L[4] | Lung adenocarcinoma[4] |
| 494 | F494L[5] | AML[5] |
| 535 | N535S[4] | Lung adenocarcinoma[4] |
| 552 | R552G[3] | Granular cell tumors of the skin[3] |
| 604 | G604V[4] | Lung adenocarcinoma[4] |
| 610 | I610T[5] | AML[5] |
| 684 | P684S[1] | Colon cancer[1] |
| 688 | R688Q[2] | Pancreatic cancer[2] |
| 733 | I733V, I733F[4] | Lung adenocarcinoma[4] |
| 806 | G806R[1] | Colon cancer[1] |
| 861 | V861I[1] | Colon cancer[1] |
| 888 | H888Q[2] | Lung adenocarcinoma[2] |
| 938 | L938F[4] | Lung adenocarcinoma[4] |
| 1019 | R1019Q[1] | Colon cancer[1] |
| 1051 | R1051G[4] | Lung adenocarcinoma[4] |
| 1236 | P1236P[1†] | Colon cancer[1] |
| Insertions, Deletions, and UTRs | | |
| | SOS1 − 116G > T[1] | Colon cancer[1] |
| | IVS8 + 5G > C[1] | Colon cancer[1] |

[A]The SOS1 mutations shown may be activating mutations and/or confer increased resistance of SOS1 to a SOS1 modulator (e.g., a SOS1 inhibitor), e.g., as compared to a wild type SOS1.

[†]Indicates a synonymous mutation, which may or may not affect SOS1 protein expression or other aspects of SOS1 regulation or function.

[1]U.S. Patent Application Publication No. 2010/0227778

[2]Swanson, et al. *Genes, Chromosomes and Cancer* 47.3 (2008): 253-259. doi: 10.1002/gcc.20527

[3]Denayer, et al. *Genes, Chromosomes and Cancer* 49.3 (2010): 242-252. doi: 10.1002/gcc.20735

[4]Cai, et al. *Mol. Cancer Res*, 17.4 (2019): 1002-1012. doi: 10.1158/1541-7786.MCR-18-0316

[5]Tanizaki, et al. *International Journal of Hematology* 88.4 (2008): 460-462.

TABLE 4A

| Exemplary SOS1 Fusion Proteins and Cancers | |
|---|---|
| Non-limiting Exemplary SOS1 Fusion Partners | Non-limiting Exemplary SOS1-associated Cancer(s) |
| ADCY3[1] | Lung adenocarcinoma[1] |

[1]P.C.T. Publication No. WO 2013/113942

The term "wild type" describes a nucleic acid (e.g., a SOS1 gene or mRNA) or protein (e.g., a SOS1 protein) that is found in a subject that does not have a disease or disorder associated with that nucleic acid or protein (e.g., a SOS1-related disease or disorder), e.g., a cancer associated with that nucleic acid or protein (and optionally also does not have an increased risk of developing a disease or disorder associated with that nucleic acid or protein and/or is not suspected of having a disease or disorder associated with that nucleic acid or protein), or is found in a cell or tissue from a subject that does not have a disease associated with that nucleic acid or protein, e.g., a cancer associated with that nucleic acid or protein (and optionally also does not have an increased risk of developing a disease or disorder associated with that nucleic acid or protein and/or is not suspected of having a disease or disorder associated with that nucleic acid or protein).

The term "regulatory agency" refers to a country's agency for the approval of the medical use of pharmaceutical agents with the country. For example, a non-limiting example of a regulatory agency is the U.S. Food and Drug Administration (FDA).

Compounds

Provided herein are compounds of Formula (I):

(I)

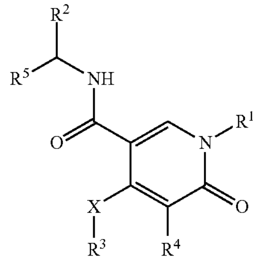

or a pharmaceutically acceptable salt thereof, wherein:

$R^1$ is a $C_1$-$C_6$ alkyl, 4 to 10-membered heterocyclyl or $C_3$-$C_{10}$ cycloalkyl, wherein each alkyl, heterocyclyl, and cycloalkyl is optionally substituted with one or more $R^a$;

$R^a$ is each independently $C_1$-$C_3$ alkyl, $C_1$-$C_3$ haloalkyl, $C_3$-$C_6$ cycloalkyl, halogen, —C(O)$C_1$-$C_3$ alkyl, or —C(O)—$C_3$-$C_6$ cycloalkyl, wherein each cycloalkyl is optionally substituted with one or more halogens;

$R^2$ is a $C_6$ aryl or 5 to 10-membered heteroaryl, wherein each aryl and heteroaryl is optionally substituted with one or more $R^b$;

$R^b$ is each independently halogen, $C_1$-$C_3$ haloalkyl, $C_1$-$C_3$ alkyl, or $C_3$ cycloalkyl;

$R^3$ is —H, a 4 to 10-membered heterocyclyl, $C_1$-$C_6$ alkyl, $C_1$-$C_6$ alkylene-O—NH—C(NH)($NH_2$), $C_3$-$C_{10}$ cycloalkyl, $C_1$-$C_6$ alkylene-5 to 10-membered heteroaryl, $C_1$-$C_6$ alkylene-4 to 10-membered heterocyclyl, $C_1$-$C_6$ alkylene-($C_3$-$C_{10}$ cycloalkyl), or $C_3$-$C_{10}$ cycloalkyl, wherein each alkyl heterocyclyl, cycloalkyl, and heteroaryl is optionally substituted with one or more $R^c$;

$R^c$ is each independently $C_1$-$C_6$ alkyl, —OH, —O—($C_1$-$C_6$ alkyl), $C_1$-$C_6$ alkylene-O—$CH_3$, halogen, $C_1$-$C_6$ alkylene-5 to 10-membered heterocyclyl, —N($CH_3$)($CH_3$), $C_3$-$C_{10}$ cycloalkyl, $C_1$-$C_6$ haloalkyl, wherein each heterocyclyl, cycloalkyl, and alkyl is optionally substituted with one or more deuterium, $C_1$-$C_6$ alkyl, —OH, halogen, —CN, or $C_1$-$C_6$ haloalkyl;

$R^4$ is —H, —$CH_3$, —CN, -OMe, or halogen;

$R^5$ is $C_1$-$C_3$ alkyl or $C_1$-$C_3$ haloalkyl; and

X is NH or S.

In some embodiments, $R^1$ is a 4 to 10-membered heterocyclyl. In some embodiments, $R^1$ is a 4 to 10-membered heterocyclyl, optionally substituted with one or more $R^a$. In some embodiments, $R^1$ is a 4 to 10-membered heterocyclyl, substituted with one $R^a$.

In some embodiments, $R^1$ is a 4 to 6-membered heterocyclyl. In some embodiments, $R^1$ is a 4 to 6-membered heterocyclyl, optionally substituted with one or more $R^a$. In some embodiments, $R^1$ is a 4 to 6-membered heterocyclyl, substituted with one $R^a$.

In some embodiments, $R^1$ is azepanyl, 1,3-dioxolanyl, 1,4-dioxolanyl, maleimidyl, succinimidyl, dioxopiperazinyl, hydantoinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, quinuclidinyl, 4H-pyran, azetidinyl, oxetanyl, octahydrocyclopenta[c]pyrrole, 2-azaspiro[3.3]heptanyl, 3-oxabicyclo[3.1.0]hexanyl, 3-azabicyclo[3.1.0]hexanyl, 3-azabicyclo[3.1.1]heptanyl, 4-azaspiro[2.5]octanyl, 6-azaspiro[3.5]nonanyl, 2,6-diazaspiro[3.3]heptanyl, 7-azabicyclo[2.2.1]heptanyl, 2-azabicyclo[2.2.1]heptanyl, 2,5-diazabicyclo[2.2.2]octanyl, 2,5-diazabicyclo[2.2.1]heptanyl, 2-oxabicyclo[2.1.1]hexanyl, 3-azabicyclo[3.2.1]octanyl, hexahydro-1H-cyclopenta[c]pyrrolyl, 3-oxa-9-azabicyclo[3.3.1]nonanyl, or hexahydro-1H-pyrrolizinyl, optionally substituted with one or more $R^a$.

In some embodiments, $R^1$ is tetrahydrofuranyl, tetrahydropyranyl, azetidinyl, pyrrolidinyl, or piperidinyl. In some embodiments, $R^1$ is tetrahydrofuranyl, tetrahydropyranyl, azetidinyl, pyrrolidinyl, or piperidinyl, optionally substituted with one or more $R^a$. In some embodiments, $R^1$ is tetrahydrofuranyl, tetrahydropyranyl, azetidinyl, pyrrolidinyl, or piperidinyl, substituted with one $R^a$.

In some embodiments, $R^1$ is tetrahydrofuranyl, tetrahydropyranyl, or azetidinyl.

In some embodiments, $R^1$ is a $C_3$-$C_{10}$ cycloalkyl. In some embodiments, $R^1$ is a $C_3$-$C_{10}$ cycloalkyl, optionally substituted with one or more $R^a$. In some embodiments, $R^1$ is a $C_3$-$C_{10}$ cycloalkyl, substituted with one $R^a$.

In some embodiments, $R^1$ is a $C_3$ or $C_4$ cycloalkyl. In some embodiments, $R^1$ is a $C_3$ or $C_4$ cycloalkyl, optionally substituted with one or more $R^a$. In some embodiments, $R^1$ is a $C_3$ or $C_4$ cycloalkyl, substituted with one $R^a$.

In some embodiments, $R^1$ is cyclopropyl. In some embodiments, $R^1$ is cyclopropyl, optionally substituted with one or more $R^a$. In some embodiments, $R^1$ is cyclopropyl, substituted with one $R^a$.

In some embodiments, $R^a$ is $C_1$-$C_3$ alkyl. In some embodiments, $R^a$ is methyl, ethyl, n-propyl, or isopropyl. In some embodiments, $R^a$ is methyl.

In some embodiments, $R^a$ is halogen. In some embodiments, $R^a$ is Cl, F, or Br. In some embodiments, $R^a$ is F.

In some embodiments, $R^a$ is $C_1$-$C_3$ haloalkyl. In some embodiments, $R^a$ is fluoromethyl. In some embodiments, $R^a$ is difluoromethyl. In some embodiments, $R^a$ is trifluoromethyl.

In some embodiments, $R^a$ is $C_3$-$C_6$ cycloalkyl, optionally substituted with one or more halogen. In some embodiments, $R^a$ is $C_3$ cycloalkyl, optionally substituted with one or more halogen. In some embodiments, $R^a$ is $C_4$ cycloalkyl, optionally substituted with one or more halogen. In some embodiments, $R^a$ is $C_5$ cycloalkyl, optionally substituted with one or more halogen. In some embodiments, $R^a$ is $C_6$ cycloalkyl, optionally substituted with one or more halogen.

In some embodiments, $R^a$ is —C(O)$C_1$-$C_3$ alkyl. In some embodiments, $R^a$ is —C(O)$CH_3$.

In some embodiments, $R^a$ is —C(O)—$C_3$-$C_6$ cycloalkyl, optionally substituted with one or more halogen. In some embodiments $R^a$ is —C(O)-cyclopropyl, optionally substituted with one or more halogen.

In some embodiments, $R^1$ is selected from:

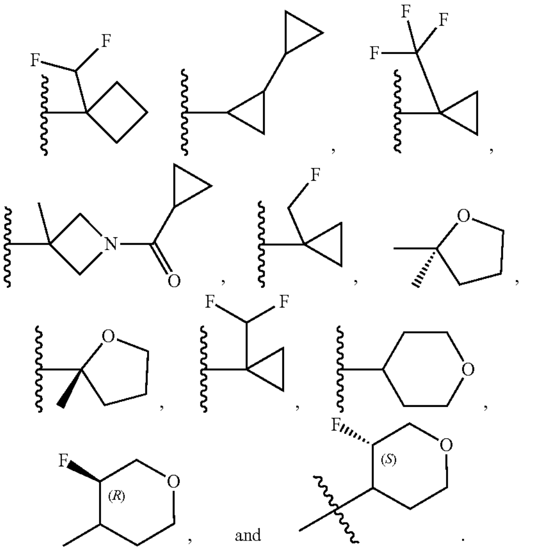

, , , , , , , , and .

In some embodiments, $R^1$ is a $C_1$-$C_6$ alkyl, optionally substituted with one or more $R^a$. In some embodiments, $R^1$ is a $C_3$ alkyl, optionally substituted with a $C_3$-$C_6$ cycloalkyl. In some embodiments, $R^1$ is isopropyl. In some embodiments, $R^1$ is cyclopropylpropan-2-yl.

In some embodiments, $R^2$ is $C_6$ aryl, optionally substituted with one or more $R^b$. In some embodiments $R^2$ is phenyl, optionally substituted with one or more $R^b$. The $R^b$ group(s) can be at any of the five available positions in the phenyl ring.

In some embodiments, $R^2$ is phenyl substituted by one $R^b$. The one $R^b$ group can be in the ortho, meta, or para position, relative to the bond connecting $R^2$ to the remainder of the molecule. In some embodiments, $R^2$ is phenyl substituted by two independently selected $R^b$. The two independently selected $R^b$ groups can be in the ortho, meta, or para position relative to one another. In some embodiments, $R^2$ is phenyl substituted by three independently selected $R^b$. The three independently selected $R^b$ groups can be located at any combination of the five available positions on the phenyl ring. In some embodiments, $R^2$ is an unsubstituted phenyl.

In some embodiments, $R^2$ is selected from

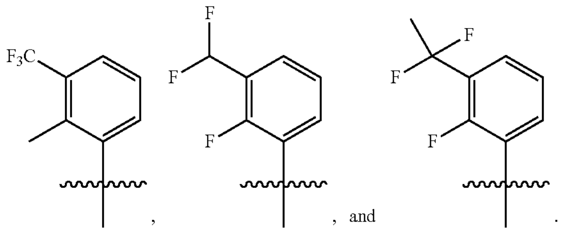

, , and .

In some embodiments, $R^2$ is a 5 to 10-membered heteroaryl, optionally substituted one or more $R^b$. In some embodiments, $R^2$ is a 9-membered heteroaryl, optionally substituted by one or more $R^b$.

In some embodiments, $R^2$ is

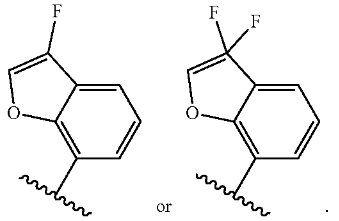

or .

In some embodiments, $R^b$ is halogen. In some embodiments, $R^b$ is F, Cl, Br, or I. In some embodiments, $R^b$ is F.

In some embodiments, $R^b$ is $C_1$-$C_3$ haloalkyl. In some embodiments $R^b$ is chloromethyl, fluoromethyl, diflouoromethyl, trifluoromethyl, chloroethyl e.g., 1-chloroethyl and 2-chloroethyl, trichloroethyl e.g., 1,2,2-trichloroethyl, 2,2,2-trichloroethyl, fluoroethyl e.g. 1-fluoromethyl and 2-fluoroethyl, difluoroethyl e.g. 1,1-difluoroethyl, 2,2-difluoroethyl, 1,2-difluoroethyl, trifluoroethyl e.g. 1,2,2-trifluoroethyl and 2,2,2-trifluoroethyl, chloropropyl, trichloropropyl, fluoropropyl, or trifluoropropyl. In some embodiments, $R^b$ is trifluoromethyl, diflouoromethyl, or 1,1-difluoroethyl.

In some embodiments, $R^b$ is $C_1$-$C_3$ alkyl. In some embodiments, $R^b$ is methyl, ethyl, n-propyl, or isopropyl. In some embodiments, $R^b$ is methyl.

In some embodiments, $R^b$ is $C_3$ cycloalkyl.

In some embodiments, $R^3$ is —H.

In some embodiments, $R^3$ is 4 to 10-membered heterocyclyl. In some embodiments, $R^3$ is a 4 to 10-membered heterocyclyl, optionally substituted with one or more $R^c$. In some embodiments, $R^3$ is a 4 to 10-membered heterocyclyl, substituted with one $R^c$.

In some embodiments, $R^3$ is a 4 to 6-membered heterocyclyl. In some embodiments, $R^3$ is a 4 to 6-membered heterocyclyl, optionally substituted with one or more $R^c$. In some embodiments, $R^3$ is a 4 to 6-membered heterocyclyl, substituted with one $R^c$.

In some embodiments, $R^3$ is azepanyl, 1,3-dioxolane, 1,4-dioxolanyl, maleimidyl, succinimidyl, dioxopiperazinyl, hydantoinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, quinuclidineyl, 4H-pyranyl, azetidinyl, oxetanyl, octahydrocyclopenta[c]

pyrrole, 2-azaspiro[3.3]heptanyl, 3-oxabicyclo[3.1.0]hexanyl, 3-azabicyclo[3.1.0]hexanyl, 3-azabicyclo[3.1.1]heptanyl, 4-azaspiro[2.5]octanyl, 6-azaspiro[3.5]nonanyl, 2,6-diazaspiro[3.3]heptanyl, 7-azabicyclo[2.2.1]heptanyl, 2-azabicyclo[2.2.1]heptanyl, 2,5-diazabicyclo[2.2.2]octanyl, 2,5-diazabicyclo[2.2.1]heptanyl, 2-oxabicyclo[2.1.1]hexanyl, 3-azabicyclo[3.2.1]octanyl, hexahydro-1H-cyclopenta[c]pyrrolyl, 3-oxa-9-azabicyclo[3.3.1]nonanyl, or hexahydro-1H-pyrrolizinyl, optionally substituted with one or more $R^c$.

In some embodiments, $R^3$ is tetrahydropyranyl, azepanyl, azetidinyl, pyrrolidinyl, piperidinyl, 4-azaspiro[2.5]octanyl, 7-azabicyclo[2.2.1]heptanyl, 3-azabicyclo[3.2.1]octanyl, 3-azabicyclo[3.1.0]hexanyl, 3-azabicyclo[3.1.1]heptanyl, 2-azaspiro[3.3]heptanyl, or hexahydro-1H-cyclopenta[c]pyrrolyl, optionally substituted with one or more $R^c$.

In some embodiments, $R^3$ is piperidinyl, optionally substituted with one or more $R^c$. In some embodiments, $R^3$ is piperidinyl, substituted with one $R^c$. In some embodiments, $R^3$ is piperidinyl.

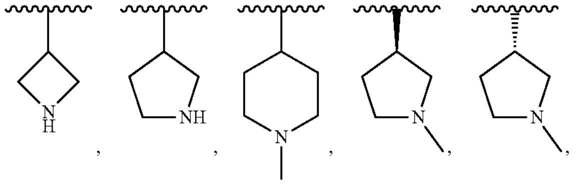

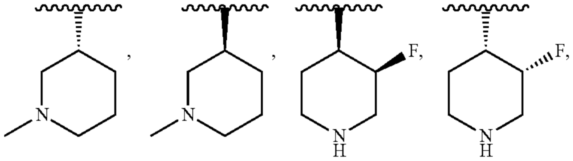

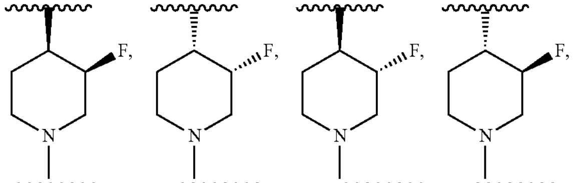

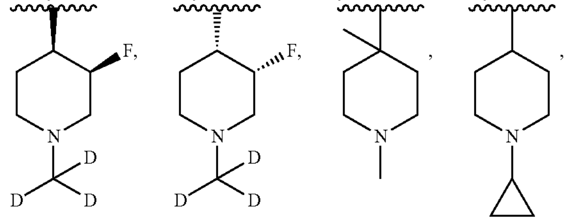

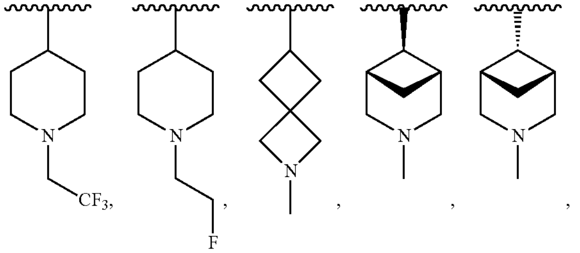

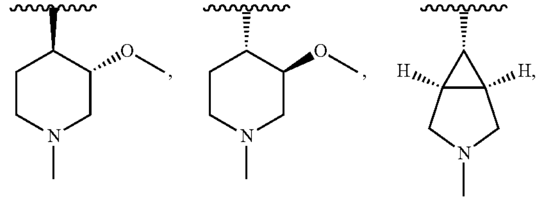

-continued

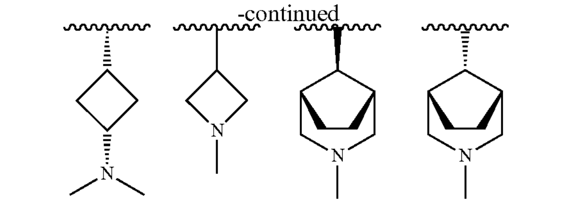

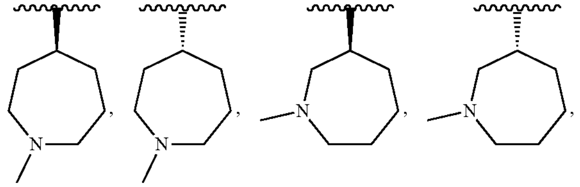

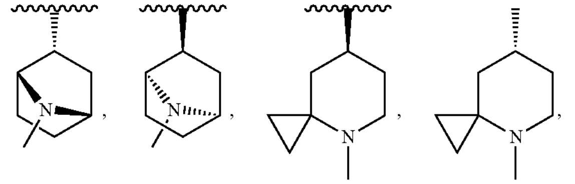

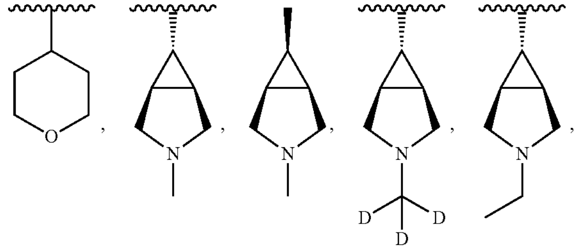

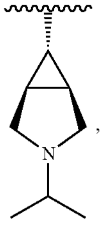

and

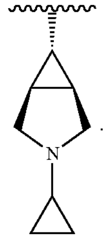

In some embodiments, $R^3$ is selected from:

In some embodiments, $R^3$ is $C_1$-$C_6$ alkyl, optionally substituted with one or more $R^c$. In some embodiments, $R^3$ is $C_1$-$C_3$ alkyl, optionally substituted with one or more $R^c$. In some embodiments, $R^3$ is methyl, optionally substituted with one or more $R^c$. In some embodiments, $R^3$ is ethyl, optionally substituted with one or more $R^c$. In some embodiments, $R^3$ is n-propyl, optionally substituted with one or more $R^c$. In some embodiments, $R^3$ is isopropyl, optionally substituted with one or more $R^c$.

In some embodiments, $R^3$ is selected from:

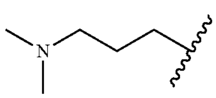

and

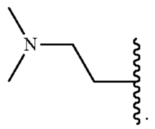

In some embodiments, $R^3$ is $C_1$-$C_6$ alkylene-O—NH—C(NH)($NH_2$). In some embodiments, $R^3$ is —$CH_2$—O—NH—C(NH)($NH_2$).

In some embodiments, $R^3$ is $C_3$-$C_{10}$ cycloalkyl, optionally substituted with one or more $R^c$. In some embodiments, $R^3$ is $C_3$-$C_6$ cycloalkyl, optionally substituted with one or more $R^c$. In some embodiments, $R^3$ is $C_3$ cycloalkyl, optionally substituted with one or more $R^c$. In some embodiments, $R^3$ is $C_4$ cycloalkyl, optionally substituted with one or more $R^c$. In some embodiments, $R^3$ is $C_5$ cycloalkyl, optionally substituted with one or more $R^c$. In some embodiments, $R^3$ is $C_6$ cycloalkyl, optionally substituted with one or more $R^c$.

In some embodiments, $R^3$ is selected from phenyl, 2,3-dihydro-1H-indene, cyclopropyl, cyclobutyl, cyclopentyl, cyclohexyl, spiro[2.3]hexyl, spiro[3.3]heptane, and bicyclo[1.1.1]pentyl, bicyclo[2.2.1]heptyl, and spiro[2.5]octyl, optionally substituted with one or more $R^c$.

In some embodiments, $R^3$ is cyclobutyl or cyclopentyl, optionally substituted with one or more $R^c$.

In some embodiments, $R^3$ is selected from:

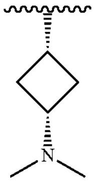 , 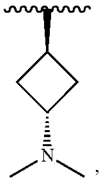 , 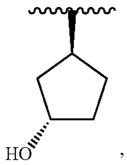 , and 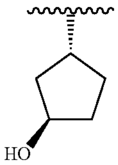 .

In some embodiments, $R^3$ is $C_1$-$C_6$ alkylene-5 to 10-membered heteroaryl, optionally substituted with at least one $R^c$. In some embodiments, $R^3$ is —$CH_2$-5 to 10-membered heteroaryl, optionally substituted with at least one $R^c$. In some embodiments, $R^3$ is $CH_2$-5-membered heteroaryl, optionally substituted with at least one $R^c$.

In some embodiments, $R^3$ is

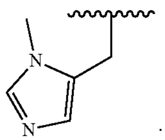 [SMILES: *Cc1cncn1C] .

In some embodiments, $R^3$ is $C_1$-$C_6$ alkylene-4 to 10-membered heterocyclyl, optionally substituted with at least one $R^c$. In some embodiments, $R^3$ is —$CH_2$-5 to 10-membered heterocyclyl, optionally substituted with at least one $R^c$. In some embodiments, $R^3$ is $CH_2$-6-membered heterocyclyl, optionally substituted with at least one $R^c$.

In some embodiments, $R^3$ is selected from:

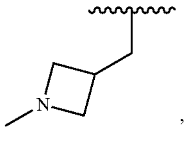 , 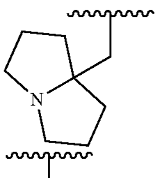 , and 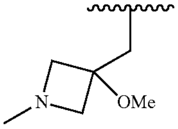

In some embodiments, $R^3$ is $C_1$-$C_6$ alkylene-($C_3$-$C_{10}$ cycloalkyl) optionally substituted with at least one $R^c$. In some embodiments, $R^3$ is —$CH_2$-5 to 10-membered cycloalkyl optionally substituted with at least one $R^c$. In some embodiments, $R^3$ is $CH_2$-6-membered cycloalkyl optionally substituted with at least one $R^c$.

In some embodiments, $R^c$ is $C_1$-$C_6$ alkyl, optionally substituted with one or more $C_1$-$C_6$ alkyl, —OH, halogen, CN, or $C_1$-$C_6$ haloalkyl. In some embodiments, Re is methyl, ethyl, n-propyl, or isopropyl, optionally substituted with one or more $C_1$-$C_6$ alkyl, —OH, halogen, CN, or $C_1$-$C_6$ haloalkyl. In some embodiments, $R^c$ is methyl.

In some embodiments, $R^c$ is —OH.

In some embodiments, Re is —O—($C_1$-$C_6$ alkyl), optionally substituted with one or more $C_1$-$C_6$ alkyl, —OH, halogen, CN, or $C_1$-$C_6$ haloalkyl. In some embodiments, Re is —O—($C_1$-$C_3$ alkyl), optionally substituted with one or more $C_1$-$C_6$ alkyl, —OH, halogen, CN, or $C_1$-$C_6$ haloalkyl. In some embodiments, $R^c$ is —O—$CH_3$.

In some embodiments, $R^c$ is $C_1$-$C_6$ alkylene-O—$CH_3$, optionally substituted with one or more $C_1$-$C_6$ alkyl, —OH, halogen, CN, or $C_1$-$C_6$ haloalkyl. In some embodiments, Re is $C_1$-$C_3$ alkylene-O—$CH_3$, optionally substituted with one or more $C_1$-$C_6$ alkyl, —OH, halogen, CN, or $C_1$-$C_6$ haloalkyl. In some embodiments, $R^c$ is —$CH_2CH_2$—O—$CH_3$.

In some embodiments, $R^c$ is halogen. In some embodiments, $R^c$ is Cl, F, Br, or I. In some embodiments, $R^c$ is F.

In some embodiments, Re is $C_1$-$C_6$ alkylene-5 to 10-membered heterocyclyl, optionally substituted with one or more $C_1$-$C_6$ alkyl, —OH, halogen, CN, or $C_1$-$C_6$ haloalkyl. In some embodiments, $R^c$ is —$CH_2$—$CH_2$-5 to 10-membered heterocyclyl, optionally substituted with one or more $C_1$-$C_6$ alkyl, —OH, halogen, CN, or $C_1$-$C_6$ haloalkyl. In some embodiments, $R^c$ is —$CH_2$—$CH_2$-5-membered heterocyclyl, optionally substituted with one or more $C_1$-$C_6$ alkyl, —OH, halogen, CN, or $C_1$-$C_6$ haloalkyl.

In some embodiments, $R^c$ is —N($CH_3$)($CH_3$),

In some embodiments, $R^c$ is $C_3$-$C_{10}$ cycloalkyl, optionally substituted with one or more $C_1$-$C_6$ alkyl, —OH, halogen, CN, or $C_1$-$C_6$ haloalkyl. In some embodiments, Re is $C_3$-$C_6$ cycloalkyl, optionally substituted with one or more $C_1$-$C_6$ alkyl, —OH, halogen, CN, or $C_1$-$C_6$ haloalkyl. In some embodiments, $R^c$ is $C_3$ cycloalkyl, optionally substituted with one or more $C_1$-$C_6$ alkyl, —OH, halogen, CN, or $C_1$-$C_6$ haloalkyl.

In some embodiments, $R^c$ is $C_1$-$C_6$ haloalkyl. In some embodiments, $R^c$ is $C_1$-$C_3$ haloalkyl. In some embodiments $R^c$ is chloromethyl, fluoromethyl, difluoromethyl, trifluoromethyl, chloroethyl e.g., 1-chloroethyl and 2-chloroethyl, trichloroethyl e.g., 1,2,2-trichloroethyl, 2,2,2-trichloroethyl, fluoroethyl e.g. 1-fluoromethyl and 2-fluoroethyl, difluoroethyl e.g. 1,1-difluoroethyl, 2,2-difluoroethyl, 1,2-difluoroethyl, trifluoroethyl e.g. 1,2,2-trifluoroethyl and 2,2,2-trifluoroethyl, chloropropyl, trichloropropyl, fluoropropyl, or trifluoropropyl. In some embodiments, Re is trifluoromethyl, diflouoromethyl, or 1,1-difluoroethyl.

In some embodiments, $R^4$ is —H. In some embodiments, $R^4$ is —$CH_3$. In some embodiments, $R^4$ is CN. In some embodiments, $R^4$ is -OMe. In some embodiments, $R^4$ is halogen.

In some embodiments, $R^5$ is $C_1$-$C_3$ alkyl. In some embodiments, $R^5$ is methyl, ethyl, n-propyl, or isopropyl. In some embodiments, $R^5$ is methyl. In some embodiments, $R^5$ is deuterated $C_1$-$C_3$ alkyl.

In some embodiments, $R^5$ is $C_1$-$C_3$ haloalkyl. In some embodiments, $R^5$ is fluoromethyl, diflouoromethyl, trifluoromethyl, trichloroethyl e.g., 1,2,2-trichloroethyl, 2,2,2-trichloroethyl, fluoroethyl e.g. 1-fluoromethyl and 2-fluoroethyl, difluoroethyl e.g. 1,1-difluoroethyl, 2,2-difluoroethyl, 1,2-difluoroethyl, trifluoroethyl e.g. 1,2,2-trifluoroethyl and 2,2,2-trifluoroethyl, fluoropropyl, or trifluoropropyl. In some embodiments, $R^5$ is trifluoromethyl, diflouoromethyl, or 1,1-difluoroethyl.

In some embodiments, X is NH. In some embodiments, X is S.

In some embodiments, in Formula (I)

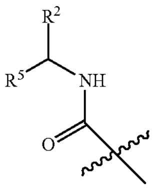

is

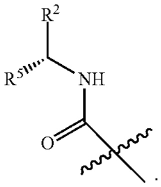

.

In some embodiments, the compound is a compound selected from Examples 1-313.

Methods of Treatment

Provided herein is a method of treating cancer (e.g., a Ras pathway-associated cancer) in a subject in need of such treatment, the method comprising administering to the subject an effective amount of a compound of Formula (I), or a pharmaceutically acceptable salt thereof or a pharmaceutical composition thereof. In some embodiments, a cancer is a Ras pathway-associated cancer. In some embodiments, a cancer is a Ras-associated cancer. In some embodiments, a cancer is a KRas-associated cancer. In some embodiments, a cancer is a HRas-associated cancer. In some embodiments, a cancer is a NRas-associated cancer. In some embodiments, a cancer is a SOS1-associated cancer.

For example, provided herein are methods for treating a Ras pathway-associated cancer (e.g., a SOS1-associated cancer, a Ras-associated cancer (e.g., a KRas-associated cancer, a HRas-associated cancer, and/or a NRas-associated cancer), an EGFR-associated cancer, an ErbB2-associated cancer, an ErbB3-associated cancer, an ErbB4-associated cancer, a NF1-associated cancer, a PDGFR-A-associated cancer, a PDGFR-B-associated cancer, a FGFR1-associated cancer, FGFR2-associated cancer, FGFR3-associated cancer, a IGF1 R-associated cancer, a INSR-associated cancer, a ALK-associated cancer, a ROS-associated cancer, a TrkA-associated cancer, a TrkB-associated cancer, a TrkC-associated cancer, a RET-associated cancer, a c-MET-associated cancer, a VEGFR1-associated cancer, a VEGFR2-associated cancer, a VEGFR3-associated cancer, an AXL-associated cancer, a SHP2-associated cancer, a RAF-associated cancer (e.g., a BRAF-associated cancer), a PI3K-associated cancer, an AKT-associated cancer, an mTOR-associated cancer, a MEK-associated cancer, an ERK-associated cancer, or a combination thereof) in a subject in need of such treatment, the method comprising a) detecting a dysregulation of a Ras pathway gene, a Ras pathway protein, or the expression or activity or level of any of the same in a sample from the subject; and b) administering a effective amount of a compound of Formula (I), or a pharmaceutically acceptable salt thereof. In some embodiments, the dysregulation of a Ras pathway gene, a Ras pathway protein, or the expression or activity or level of any of the same includes one or more fusion proteins.

For example, provided herein are methods for treating a Ras-associated cancer in a subject in need of such treatment, the method comprising a) detecting a dysregulation of a Ras gene, a Ras protein, or the expression or activity or level of any of the same in a sample from the subject; and b) administering a effective amount of a compound of Formula (I), or a pharmaceutically acceptable salt thereof. In some embodiments, the dysregulation of a Ras gene, a Ras protein, or the expression or activity or level of any of the same includes one or more fusion proteins.

For example, provided herein are methods for treating a KRas-associated cancer in a subject in need of such treatment, the method comprising a) detecting a dysregulation of a KRas gene, a KRas protein, or the expression or activity or level of any of the same in a sample from the subject; and b) administering a effective amount of a compound of Formula (I), or a pharmaceutically acceptable salt thereof. In some embodiments, the dysregulation of a KRas gene, a KRas protein, or the expression or activity or level of any of the same includes one or more fusion proteins.

For example, provided herein are methods for treating a HRas-associated cancer in a subject in need of such treatment, the method comprising a) detecting a dysregulation of a HRas gene, a HRas protein, or the expression or activity or level of any of the same in a sample from the subject; and b) administering a effective amount of a compound of Formula (I), or a pharmaceutically acceptable salt thereof. In some embodiments, the dysregulation of a HRas gene, a HRas protein, or the expression or activity or level of any of the same includes one or more fusion proteins.

For example, provided herein are methods for treating a NRas-associated cancer in a subject in need of such treatment, the method comprising a) detecting a dysregulation of a NRas gene, a NRas protein, or the expression or activity or level of any of the same in a sample from the subject; and b) administering a effective amount of a compound of Formula (I), or a pharmaceutically acceptable salt thereof. In some embodiments, the dysregulation of a NRas gene, a NRas protein, or the expression or activity or level of any of the same includes one or more fusion proteins.

For example, provided herein are methods for treating a SOS1-associated cancer in a subject in need of such treatment, the method comprising a) detecting a dysregulation of a SOS1 gene, a SOS1 protein, or the expression or activity or level of any of the same in a sample from the subject; and b) administering a effective amount of a compound of Formula (I), or a pharmaceutically acceptable salt thereof. In some embodiments, the dysregulation of a SOS1 gene, a SOS1 protein, or the expression or activity or level of any of the same includes one or more fusion proteins.

Also provided are methods for treating cancer in a subject in need thereof, the method comprising: (a) detecting a Ras pathway-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a Ras pathway-associated cancer through the use of a regulatory agency-approved, e.g., FDA-approved test or assay for identifying dysregulation of a Ras pathway gene, a Ras pathway protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a Ras-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a Ras-associated cancer through the use of a regulatory agency-approved, e.g., FDA-approved test or assay for identifying dysregulation of a Ras gene, a Ras protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a KRas-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a KRas-associated cancer through the use of a regulatory agency-approved, e.g., FDA-approved test or assay for identifying dysregulation of a KRas gene, a KRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a HRas-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a HRas-associated cancer through the use of a regulatory agency-approved, e.g., FDA-approved test or assay for identifying dysregulation of a HRas gene, a HRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a NRas-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a NRas-associated cancer through the use of a regulatory agency-approved, e.g., FDA-approved test or assay for identifying dysregulation of a NRas gene, a NRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a SOS1-associated cancer in the subject; and (b) administering to the subject an effective amount of a compound of Formula (I), or a pharmaceutically acceptable salt thereof, or a pharmaceutical composition thereof. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a SOS1-associated cancer through the use of a regulatory agency-approved, e.g., FDA-approved test or assay for identifying dysregulation of a SOS1 gene, a SOS1 protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a Ras pathway gene, a Ras pathway protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a Ras pathway-associated cancer through the use of a regulatory agency-approved, e.g., FDA-approved test or assay for identifying dysregulation of a Ras pathway gene, a Ras pathway protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a Ras gene, a Ras protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a Ras-associated cancer through the use of a regulatory agency-approved, e.g., FDA-approved test or assay for identifying dysregulation of a Ras gene, a Ras protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a KRas gene, a KRas protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a KRas-associated cancer through the use of a regulatory agency-approved, e.g., FDA-approved test or assay for identifying dysregulation of a KRas gene, a KRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a HRas gene, a HRas protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a HRas-associated cancer through the use of a regulatory agency-approved, e.g., FDA-approved test or assay for identifying dysregulation of a HRas gene, a HRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a NRas gene, a NRas protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a NRas-associated cancer through the use of a regulatory agency-approved, e.g., FDA-approved test or assay for identifying dysregulation of a NRas gene, a NRas protein, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: administering an effective amount of a compound of Formula (I), or a pharmaceutically acceptable salt thereof, or a pharmaceutical composition thereof to a subject determined to have a cancer associated with a dysregulation of a SOS1 gene, a SOS1 protein, or expression or activity or level of any of the same. Some embodiments of these methods further include administering to the subject another anticancer agent (e.g., a small molecule or an immunotherapy). In some embodiments, the subject was previously treated with another anticancer treatment, e.g., at least partial resection of the tumor or radiation therapy. In some embodiments, the subject is determined to have a SOS1-associated cancer through the use of a regulatory agency-approved, e.g., FDA-approved test or assay for identifying dysregulation of a SOS1 gene, a SOS1 protein, or expression or activity or level of any of the same, in a subject or a biopsy sample from the subject or by performing any of the non-limiting examples of assays described herein. In some embodiments, the test or assay is provided as a kit.

Also provided are methods of treating a subject that include performing an assay on a sample obtained from the subject to determine whether the subject has a dysregulation of a Ras pathway gene, a Ras pathway protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a Ras pathway gene, a Ras pathway protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a Ras pathway-associated cancer, a subject presenting with one or more symptoms of a Ras pathway-associated cancer, or a subject having an elevated risk of developing a Ras pathway-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided are methods of treating a subject that include performing an assay on a sample obtained from the subject to determine whether the subject has a dysregulation of a Ras gene, a Ras protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a Ras gene, a Ras protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a Ras-associated cancer, a subject presenting with one or more symptoms of a Ras-associated cancer, or a subject having an elevated risk of developing a Ras-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided are methods of treating a subject that include performing an assay on a sample obtained from the subject to determine whether the subject has a dysregulation of a KRas gene, a KRas protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a KRas gene, a KRas protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a KRas-associated cancer, a subject presenting with one or more symptoms of a KRas-associated cancer, or a subject having an elevated risk of developing a KRas-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided are methods of treating a subject that include performing an assay on a sample obtained from the subject to determine whether the subject has a dysregulation of a HRas gene, a HRas protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a HRas gene, a HRas protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a HRas-associated cancer, a subject presenting with one or more symptoms of an HRas-associated cancer, or a subject having an elevated risk of developing a HRas-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided are methods of treating a subject that include performing an assay on a sample obtained from the subject to determine whether the subject has a dysregulation of a NRas gene, a NRas protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a NRas gene, a NRas protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a NRas-associated cancer, a subject presenting with one or more symptoms of an NRas-associated cancer, or a subject having an elevated risk of developing a NRas-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided are methods of treating a subject that include performing an assay on a sample obtained from the subject to determine whether the subject has a dysregulation of a SOS1 gene, a SOS1 protein, or expression or activity or level of any of the same, and administering (e.g., specifically or selectively administering) an effective amount of a compound of Formula (I), or a pharmaceutically acceptable salt thereof, or a pharmaceutical composition thereof, to the subject determined to have a dysregulation of a SOS1 gene, a SOS1 protein, or expression or activity or level of any of the same. Some embodiments of these methods further include administering to the subject another anticancer agent (e.g., a small molecule or immunotherapy). In some embodiments of these methods, the subject was previously treated with another anticancer treatment, e.g., at least partial resection of a tumor or radiation therapy. In some embodiments, the subject is a subject suspected of having a SOS1-associated cancer, a subject presenting with one or more symptoms of a SOS1-associated cancer, or a subject having an elevated risk of developing a SOS1-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art.

Also provided is a compound of Formula (I), or a pharmaceutically acceptable salt thereof, or a pharmaceutical composition thereof, for use in treating a Ras pathway-associated cancer in a subject identified or diagnosed as having a Ras pathway-associated cancer through a step of performing an assay (e.g., an in vitro assay) on a sample obtained from the subject to determine whether the subject has a dysregulation of a Ras pathway protein, a Ras pathway protein, or expression or activity or level of any of the same, where the presence of a dysregulation of a Ras pathway gene, a Ras pathway protein, or expression or activity or level of any of the same, identifies that the subject has a Ras pathway-associated cancer. Also provided is the use of a compound of Formula (I), or a pharmaceutically acceptable salt thereof, for the manufacture of a medicament for treating a Ras pathway-associated cancer in a subject identified or diagnosed as having a Ras pathway-associated cancer through a step of performing an assay on a sample obtained from the subject to determine whether the subject has a dysregulation of a Ras pathway gene, a Ras pathway protein, or expression or activity or level of any of the same where the presence of dysregulation of a Ras pathway gene, a Ras pathway protein, or expression or activity or level of any of the same, identifies that the subject has a Ras pathway-associated cancer. Some embodiments of any of the methods or uses described herein further include recording in the subject's clinical record (e.g., a computer readable medium) that the subject is determined to have a dysregulation of a Ras pathway gene, a Ras pathway protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, or a pharmaceutical composition thereof, for use in treating a Ras-associated cancer in a subject identified or diagnosed as having a Ras-associated cancer through a step of performing an assay (e.g., an in vitro assay) on a sample obtained from the subject to determine whether the subject has a dysregulation of a Ras gene, a Ras protein, or expression or activity or level of any of the same, where the presence of a dysregulation of a Ras gene, a Ras protein, or expression or activity or level of any of the same, identifies that the subject has a Ras-associated cancer. Also provided is the use of a compound of Formula (I), or a pharmaceutically acceptable salt thereof, for the manufacture of a medicament for treating a Ras-associated cancer in a subject identified or diagnosed as having a Ras-associated cancer through a step of performing an assay on a sample obtained from the subject to determine whether the subject has a dysregulation of a Ras gene, a Ras protein, or expression or activity or level of any of the same where the presence of dysregulation of a Ras gene, a Ras protein, or expression or activity or level of any of the same, identifies that the subject has a Ras-associated cancer. Some embodiments of any of the methods or uses described herein further include recording in the subject's clinical record (e.g., a computer readable medium) that the subject is determined to have a dysregulation of a Ras gene, a Ras protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, or a pharmaceutical composition thereof, for use in treating a KRas-associated cancer in a subject identified or diagnosed as having a KRas-associated cancer through a step of performing an assay (e.g., an in vitro assay) on a sample obtained from the subject to determine whether the subject has a dysregulation of a KRas gene, a KRas protein, or expression or activity or level of any of the same, where the presence of a dysregulation of a KRas gene, a KRas protein, or expression or activity or level of any of the same, identifies that the subject has a KRas-associated cancer. Also provided is the use of a compound of Formula (I), or a pharmaceutically acceptable salt thereof, for the manufacture of a medicament for treating a KRas-associated cancer in a subject identified or diagnosed as having a KRas-associated cancer through a step of performing an assay on a sample obtained from the subject to determine whether the subject has a dysregulation of a KRas gene, a KRas protein, or expression or activity or level of any of the same where the presence of dysregulation of a KRas gene, a KRas protein, or expression or activity or level of any of the same, identifies that the subject has a KRas-associated cancer. Some embodiments of any of the methods or uses described herein further include recording in the subject's clinical record (e.g., a computer readable medium) that the subject is determined to have a dysregulation of a KRas gene, a KRas protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, or a pharmaceutical composition thereof, for use in treating a HRas-associated cancer in a subject identified or diagnosed as having a HRas-associated cancer through a step of performing an assay (e.g., an in vitro assay) on a sample obtained from the subject to determine whether the subject has a dysregulation of a HRas gene, a HRas protein, or expression or activity or level of any of the same, where the presence of a dysregulation of a HRas gene, a HRas protein, or expression or activity or level of any of the same, identifies that the subject has a HRas-associated cancer. Also provided is the use of a compound of Formula (I), or a pharmaceutically acceptable salt thereof, for the manufacture of a medicament for treating a HRas-associated cancer in a subject identified or diagnosed as having a HRas-associated cancer through a step of performing an assay on a sample obtained from the subject to determine whether the subject has a dysregulation of a HRas gene, a HRas protein, or expression or activity or level of any of the same where the presence of dysregulation of a HRas gene, a HRas protein, or expression or activity or level of any of the same, identifies that the subject has a HRas-associated cancer. Some embodiments of any of the methods or uses described herein further include recording in the subject's clinical record (e.g., a computer readable medium) that the subject is determined to have a dysregulation of a HRas gene, a HRas protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, or a pharmaceutical composition thereof, for use in treating a NRas-associated cancer in a subject identified or diagnosed as having a NRas-associated cancer through a step of performing an assay (e.g., an in vitro assay) on a sample obtained from the subject to determine whether the subject has a dysregulation of a NRas gene, a NRas protein, or expression or activity or level of any of the same, where the presence of a dysregulation of a NRas gene, a NRas protein, or expression or activity or level of any of the same, identifies that the subject has a NRas-associated cancer. Also provided is the use of a compound of Formula (I), or a pharmaceutically acceptable salt thereof, for the manufacture of a medicament for treating a NRas-associated cancer in a subject identified or diagnosed as having a NRas-associated cancer through a step of performing an assay on a sample obtained from the subject to determine whether the subject has a dysregulation of a NRas gene, a NRas protein, or expression or activity or level of any of the same where the presence of dysregulation of a NRas gene, a NRas protein, or expression or activity or level of any of the same, identifies that the subject has a NRas-associated cancer. Some embodiments of any of the methods or uses described herein further include recording in the subject's clinical record (e.g., a computer readable medium) that the subject is determined to have a dysregulation of a NRas gene, a NRas protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula (I), or a pharmaceutically acceptable salt thereof, or a pharmaceutical composition thereof, for use in treating a SOS1-associated cancer in a subject identified or diagnosed as having a SOS1-associated cancer through a step of performing an assay (e.g., an in vitro assay) on a sample obtained from the subject to determine whether the subject has a dysregulation of a SOS1 gene, a SOS1 protein, or expression or activity or level of any of the same, where the presence of a dysregulation of a SOS1 gene, a SOS1 protein, or expression or activity or level of any of the same, identifies that the subject has a SOS1-associated cancer. Also provided is the use of a compound of Formula (I), or a pharmaceutically acceptable salt thereof, for the manufacture of a medicament for treating a SOS1-associated cancer in a subject identified or diagnosed as having a SOS1-associated cancer through a step of performing an assay on a sample obtained from the subject to determine whether the subject has a dysregulation of a SOS1 gene, a SOS1 protein, or expression or activity or level of any of the same where the presence of dysregulation of a SOS1 gene, a SOS1 protein, or expression or activity or level of any of the same, identifies that the subject has a SOS1-associated cancer. Some embodiments of any of the methods or uses described herein further include recording in the subject's clinical record (e.g., a computer readable medium) that the subject is determined to have a dysregulation of a SOS1 gene, a SOS1 protein, or expression or activity or level of any of the same, through the performance of the assay, should be administered a compound of Formula (I), or a pharmaceutically acceptable salt thereof, or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

In some embodiments of any of the methods or uses described herein, the subject has been identified or diagnosed as having a cancer with a dysregulation of a Ras pathway gene, a Ras pathway protein, or expression or activity or level of any of the same. In some embodiments of any of the methods or uses described herein, the subject has a tumor that is positive for a dysregulation of a Ras pathway gene, a Ras pathway protein, or expression or activity or level of any of the same. In some embodiments of any of the methods or uses described herein, the subject can be a subject with a tumor(s) that is positive for a dysregulation of a Ras pathway gene, a Ras pathway protein, or expression or activity or level of any of the same. In some embodiments of any of the methods or uses described herein, the subject can be a subject whose tumors have a dysregulation of a Ras pathway gene, a Ras pathway protein, or expression or activity or level of any of the same. In some embodiments of any of the methods or uses described herein, the subject is suspected of having a Ras pathway-associated cancer. In some embodiments, provided herein are methods for treating a Ras pathway-associated cancer in a subject in need of such treatment, the method comprising a) detecting a dysregulation of a Ras pathway gene, a Ras pathway protein, or the expression or activity or level of any of the same in a sample from the subject; and b) administering an effective amount of a compound of Formula (I), or a pharmaceutically acceptable salt thereof. In some embodiments, the dysregulation of a Ras pathway gene, a Ras pathway protein, or the expression or activity or level of any of the same includes one or more Ras pathway protein point mutations/insertions/deletions.

In some embodiments of any of the methods or uses described herein, the subject has been identified or diagnosed as having a cancer with a dysregulation of a Ras gene, a Ras protein, or expression or activity or level of any of the same. In some embodiments of any of the methods or uses described herein, the subject has a tumor that is positive for a dysregulation of a Ras gene, a Ras protein, or expression or activity or level of any of the same. In some embodiments of any of the methods or uses described herein, the subject can be a subject with a tumor(s) that is positive for a dysregulation of a Ras gene, a Ras protein, or expression or activity or level of any of the same. In some embodiments of any of the methods or uses described herein, the subject can be a subject whose tumors have a dysregulation of a Ras gene, a Ras protein, or expression or activity or level of any of the same. In some embodiments of any of the methods or uses described herein, the subject is suspected of having a Ras-associated cancer. In some embodiments, provided herein are methods for treating a Ras-associated cancer in a subject in need of such treatment, the method comprising a) detecting a dysregulation of a Ras gene, a Ras protein, or the expression or activity or level of any of the same in a sample from the subject; and b) administering an effective amount of a compound of Formula (I), or a pharmaceutically acceptable salt thereof. In some embodiments, the dysregulation of a Ras gene, a Ras protein, or the expression or activity or level of any of the same includes one or more Ras protein point mutations/insertions/deletions.

In some embodiments of any of the methods or uses described herein, the subject has been identified or diagnosed as having a cancer with a dysregulation of a KRas gene, a KRas protein, or expression or activity or level of any of the same. In some embodiments of any of the methods or uses described herein, the subject has a tumor that is positive for a dysregulation of a KRas gene, a KRas protein, or expression or activity or level of any of the same.

In some embodiments of any of the methods or uses described herein, the subject can be a subject with a tumor(s) that is positive for a dysregulation of a KRas gene, a KRas protein, or expression or activity or level of any of the same. In some embodiments of any of the methods or uses described herein, the subject can be a subject whose tumors have a dysregulation of a KRas gene, a KRas protein, or expression or activity or level of any of the same. In some embodiments of any of the methods or uses described herein, the subject is suspected of having a KRas-associated cancer. In some embodiments, provided herein are methods for treating a KRas-associated cancer in a subject in need of such treatment, the method comprising a) detecting a dysregulation of a KRas gene, a KRas protein, or the expression or activity or level of any of the same in a sample from the subject; and b) administering an effective amount of a compound of Formula (I), or a pharmaceutically acceptable salt thereof. In some embodiments, the dysregulation of a KRas gene, a KRas protein, or the expression or activity or level of any of the same includes one or more KRas protein point mutations/insertions/deletions. Non-limiting examples of KRas protein point mutations/insertions/deletions are described in Table 1.

In some embodiments of any of the methods or uses described herein, the subject has been identified or diagnosed as having a cancer with a dysregulation of a HRas gene, a HRas protein, or expression or activity or level of any of the same. In some embodiments of any of the methods or uses described herein, the subject has a tumor that is positive for a dysregulation of a HRas gene, a HRas protein, or expression or activity or level of any of the same. In some embodiments of any of the methods or uses described herein, the subject can be a subject with a tumor(s) that is positive for a dysregulation of a HRas gene, a HRas protein, or expression or activity or level of any of the same. In some embodiments of any of the methods or uses described herein, the subject can be a subject whose tumors have a dysregulation of a HRas gene, a HRas protein, or expression or activity or level of any of the same. In some embodiments of any of the methods or uses described herein, the subject is suspected of having a HRas-associated cancer. In some embodiments, provided herein are methods for treating a HRas-associated cancer in a subject in need of such treatment, the method comprising a) detecting a dysregulation of a HRas gene, a HRas protein, or the expression or activity or level of any of the same in a sample from the subject; and b) administering an effective amount of a compound of Formula (I), or a pharmaceutically acceptable salt thereof. In some embodiments, the dysregulation of a HRas gene, a HRas protein, or the expression or activity or level of any of the same includes one or more HRas protein point mutations/insertions/deletions. Non-limiting examples of HRas protein point mutations/insertions/deletions are described in Table 2.

In some embodiments of any of the methods or uses described herein, the subject has been identified or diagnosed as having a cancer with a dysregulation of a NRas gene, a NRas protein, or expression or activity or level of any of the same. In some embodiments of any of the methods or uses described herein, the subject has a tumor that is positive for a dysregulation of a NRas gene, a NRas protein, or expression or activity or level of any of the same. In some embodiments of any of the methods or uses described herein, the subject can be a subject with a tumor(s) that is positive for a dysregulation of a NRas gene, a NRas protein, or expression or activity or level of any of the same. In some embodiments of any of the methods or uses described herein, the subject can be a subject whose tumors have a dysregulation of a NRas gene, a NRas protein, or expression or activity or level of any of the same. In some embodiments of any of the methods or uses described herein, the subject is suspected of having a NRas-associated cancer. In some embodiments, provided herein are methods for treating a NRas-associated cancer in a subject in need of such treatment, the method comprising a) detecting a dysregulation of a NRas gene, a NRas protein, or the expression or activity or level of any of the same in a sample from the subject; and b) administering an effective amount of a compound of Formula (I), or a pharmaceutically acceptable salt thereof. In some embodiments, the dysregulation of a NRas gene, a NRas protein, or the expression or activity or level of any of the same includes one or more NRas protein point mutations/insertions/deletions. Non-limiting examples of NRas protein point mutations/insertions/deletions are described in Table 3.

In some embodiments of any of the methods or uses described herein, the subject has been identified or diagnosed as having a cancer with a dysregulation of a SOS1 gene, a SOS1 protein, or expression or activity or level of any of the same. In some embodiments of any of the methods or uses described herein, the subject has a tumor that is positive for a dysregulation of a SOS1 gene, a SOS1 protein, or expression or activity or level of any of the same. In some embodiments of any of the methods or uses described herein, the subject can be a subject with a tumor(s) that is positive for a dysregulation of a SOS1 gene, a SOS1 protein, or expression or activity or level of any of the same. In some embodiments of any of the methods or uses described herein, the subject can be a subject whose tumors have a dysregulation of a SOS1 gene, a SOS1 protein, or expression or activity or level of any of the same. In some embodiments of any of the methods or uses described herein, the subject is suspected of having a SOS1-associated cancer. In some embodiments, provided herein are methods for treating a SOS1-associated cancer in a subject in need of such treatment, the method comprising a) detecting a dysregulation of a SOS1 gene, a SOS1 protein, or the expression or activity or level of any of the same in a sample from the subject; and b) administering an effective amount of a compound of Formula (I), or a pharmaceutically acceptable salt thereof. In some embodiments, the dysregulation of a SOS1 gene, a SOS1 protein, or the expression or activity or level of any of the same includes one or more SOS1 protein point mutations/insertions/deletions. Non-limiting examples of SOS1 protein point mutations/insertions/deletions are described in Table 4.

In some embodiments, the cancer with a dysregulation of a Ras pathway gene, a Ras pathway protein, or expression or activity or level of any of the same is determined using a regulatory agency-approved, e.g., FDA-approved, assay or kit. In some embodiments, the tumor with a dysregulation of a Ras pathway gene, a Ras pathway protein, or expression or activity or level of any of the same is determined using a regulatory agency-approved, e.g., FDA-approved, assay or kit.

In some embodiments, the cancer with a dysregulation of a Ras gene, a Ras protein, or expression or activity or level of any of the same is determined using a regulatory agency-approved, e.g., FDA-approved, assay or kit. In some embodiments, the tumor with a dysregulation of a Ras gene, a Ras protein, or expression or activity or level of any of the same is determined using a regulatory agency-approved, e.g., FDA-approved, assay or kit.

In some embodiments, the cancer with a dysregulation of a KRas gene, a KRas protein, or expression or activity or level of any of the same is determined using a regulatory agency-approved, e.g., FDA-approved, assay or kit. In some embodiments, the tumor with a dysregulation of a KRas gene, a KRas protein, or expression or activity or level of any of the same is determined using a regulatory agency-approved, e.g., FDA-approved, assay or kit.

In some embodiments, the cancer with a dysregulation of a HRas gene, a HRas protein, or expression or activity or level of any of the same is determined using a regulatory agency-approved, e.g., FDA-approved, assay or kit. In some embodiments, the tumor with a dysregulation of a HRas gene, a HRas protein, or expression or activity or level of any of the same is determined using a regulatory agency-approved, e.g., FDA-approved, assay or kit.

In some embodiments, the cancer with a dysregulation of a NRas gene, a NRas protein, or expression or activity or level of any of the same is determined using a regulatory agency-approved, e.g., FDA-approved, assay or kit. In some embodiments, the tumor with a dysregulation of a NRas gene, a NRas protein, or expression or activity or level of any of the same is determined using a regulatory agency-approved, e.g., FDA-approved, assay or kit.

In some embodiments, the cancer with a dysregulation of a SOS1 gene, a SOS1 protein, or expression or activity or level of any of the same is determined using a regulatory agency-approved, e.g., FDA-approved, assay or kit. In some embodiments, the tumor with a dysregulation of a SOS1 gene, a SOS1 protein, or expression or activity or level of any of the same is determined using a regulatory agency-approved, e.g., FDA-approved, assay or kit.

In some embodiments of any of the methods or uses described herein, the subject has a clinical record indicating that the subject has a tumor that has a dysregulation of a Ras pathway gene, a Ras pathway protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a Ras pathway gene, a Ras pathway protein, or expression or activity or level of any of the same.

In some embodiments of any of the methods or uses described herein, the subject has a clinical record indicating that the subject has a tumor that has a dysregulation of a Ras gene, a Ras protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a Ras gene, a Ras protein, or expression or activity or level of any of the same.

In some embodiments of any of the methods or uses described herein, the subject has a clinical record indicating that the subject has a tumor that has a dysregulation of a KRas gene, a KRas protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a KRas gene, a KRas protein, or expression or activity or level of any of the same.

In some embodiments of any of the methods or uses described herein, the subject has a clinical record indicating that the subject has a tumor that has a dysregulation of a HRas gene, a HRas protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a HRas gene, a HRas protein, or expression or activity or level of any of the same.

In some embodiments of any of the methods or uses described herein, the subject has a clinical record indicating that the subject has a tumor that has a dysregulation of a NRas gene, a NRas protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a NRas gene, a NRas protein, or expression or activity or level of any of the same.

In some embodiments of any of the methods or uses described herein, the subject has a clinical record indicating that the subject has a tumor that has a dysregulation of a SOS1 gene, a SOS1 protein, or expression or activity or level of any of the same. Also provided are methods of treating a subject that include administering an effective amount of a compound of Formula (I), or a pharmaceutically acceptable salt thereof, to a subject having a clinical record that indicates that the subject has a dysregulation of a SOS1 gene, a SOS1 protein, or expression or activity or level of any of the same.

In some embodiments, the methods provided herein include performing an assay on a sample obtained from the subject to determine whether the subject has a dysregulation of a Ras pathway gene, a Ras pathway protein, or expression or level of any of the same. In some such embodiments, the method also includes administering to a subject determined to have a dysregulation of a Ras pathway gene, a Ras pathway protein, or expression or activity, or level of any of the same an effective amount of a compound of Formula (I), or a pharmaceutically acceptable salt thereof. In some embodiments, the method includes determining that a subject has a dysregulation of a Ras pathway gene, a Ras pathway protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments, the methods provided herein include performing an assay on a sample obtained from the subject to determine whether the subject has a dysregulation of a Ras gene, a Ras protein, or expression or level of any of the same. In some such embodiments, the method also includes administering to a subject determined to have a dysregulation of a Ras gene, a Ras protein, or expression or activity, or level of any of the same an effective amount of a compound of Formula (I), or a pharmaceutically acceptable salt thereof. In some embodiments, the method includes determining that a subject has a dysregulation of a Ras gene, a Ras protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments, the methods provided herein include performing an assay on a sample obtained from the subject to determine whether the subject has a dysregulation of a KRas gene, a KRas protein, or expression or level of any of the same. In some such embodiments, the method also includes administering to a subject determined to have a dysregulation of a KRas gene, a KRas protein, or expression or activity, or level of any of the same an effective amount of a compound of Formula (I), or a pharmaceutically acceptable salt thereof. In some embodiments, the method includes determining that a subject has a dysregulation of a KRas gene, a KRas protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments, the methods provided herein include performing an assay on a sample obtained from the subject to determine whether the subject has a dysregulation of a HRas gene, a HRas protein, or expression or level of any of the same. In some such embodiments, the method also includes administering to a subject determined to have a dysregulation of a HRas gene, a HRas protein, or expression or activity, or level of any of the same an effective amount of a compound of Formula (I), or a pharmaceutically acceptable salt thereof. In some embodiments, the method includes determining that a subject has a dysregulation of a HRas gene, a HRas protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments, the methods provided herein include performing an assay on a sample obtained from the subject to determine whether the subject has a dysregulation of a NRas gene, a NRas protein, or expression or level of any of the same. In some such embodiments, the method also includes administering to a subject determined to have a dysregulation of a NRas gene, a NRas protein, or expression or activity, or level of any of the same an effective amount of a compound of Formula (I), or a pharmaceutically acceptable salt thereof. In some embodiments, the method includes determining that a subject has a dysregulation of a NRas gene, a NRas protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments, the methods provided herein include performing an assay on a sample obtained from the subject to determine whether the subject has a dysregulation of a SOS1 gene, a SOS1 protein, or expression or level of any of the same. In some such embodiments, the method also includes administering to a subject determined to have a dysregulation of a SOS1 gene, a SOS1 protein, or expression or activity, or level of any of the same an effective amount of a compound of Formula (I), or a pharmaceutically acceptable salt thereof. In some embodiments, the method includes determining that a subject has a dysregulation of a SOS1 gene, a SOS1 protein, or expression or level of any of the same via an assay performed on a sample obtained from the subject. In such embodiments, the method also includes administering to a subject an effective amount of a compound of Formula (I), or a pharmaceutically acceptable salt thereof.

In some embodiments of any of the methods or uses described herein, the cancer is a hematological cancer. Examples of hematological cancers (e.g., hematological cancers that are Ras pathway-associated cancers) include, for example, leukemias (e.g., acute myeloid leukemia, acute lymphoblastic leukemia, chronic lymphocytic leukemia, chronic myelogenous leukemia, specify juvenile myelomonocytic leukemia (JMML), and hairy cell leukemia) and lymphomas (e.g., non-Hodgkin's lymphoma, Hodgkin's disease cutaneous T-cell lymphoma, and Burkitt lymphoma).

In some embodiments of any of the methods or uses described herein, the cancer is a solid tumor. Examples of solid tumors (e.g., solid tumors that are Ras pathway-associated cancers) include, for example, thyroid cancer (e.g., papillary thyroid carcinoma, medullary thyroid carcinoma), lung cancer (e.g., non-small cell lung cancer, small-cell lung carcinoma, bronchial adenoma, and pleuropulmonary blastoma), pancreatic cancer, pancreatic ductal carcinoma, biliary tract cancer, breast cancer (e.g., invasive ductal carcinoma, invasive lobular carcinoma, ductal carcinoma in situ, and lobular carcinoma in situ), stomach cancer, small intestinal cancer, colon cancer, colorectal cancer, peritoneal cancer, ovarian cancer, uterine cancer, liver cancer, endometrial cancer, prostate cancer (including benign prostatic hyperplasia), testicular cancer, bladder cancer, urinary tract cancer, cervical cancer, head and neck cancer, brain cancer (e.g., glioblastoma, brain stem and hypophtalmic glioma, cerebellar and cerebral astrocytoma, medulloblastoma, and ependymoma), squamous cell carcinoma, and melanoma.

In some embodiments, the subject is a human.

Compounds of Formula (I) and pharmaceutically acceptable salts and solvates thereof are also useful for treating a Ras pathway-associated cancer.

Accordingly, also provided herein is a method for treating a subject diagnosed with or identified as having a Ras pathway-associated cancer, e.g., any of the exemplary Ras pathway-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Accordingly, also provided herein is a method for treating a subject diagnosed with or identified as having a Ras pathway-associated cancer, e.g., any of the exemplary Ras pathway-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Compounds of Formula (I) and pharmaceutically acceptable salts and solvates thereof are also useful for treating a Ras-associated cancer.

Accordingly, also provided herein is a method for treating a subject diagnosed with or identified as having a Ras-associated cancer, e.g., any of the exemplary Ras-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Accordingly, also provided herein is a method for treating a subject diagnosed with or identified as having a Ras-associated cancer, e.g., any of the exemplary Ras-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Compounds of Formula (I) and pharmaceutically acceptable salts and solvates thereof are also useful for treating a KRas-associated cancer.

Accordingly, also provided herein is a method for treating a subject diagnosed with or identified as having a KRas-associated cancer, e.g., any of the exemplary KRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Accordingly, also provided herein is a method for treating a subject diagnosed with or identified as having a KRas-associated cancer, e.g., any of the exemplary KRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Compounds of Formula (I) and pharmaceutically acceptable salts and solvates thereof are also useful for treating a HRas-associated cancer.

Accordingly, also provided herein is a method for treating a subject diagnosed with or identified as having a HRas-associated cancer, e.g., any of the exemplary HRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Accordingly, also provided herein is a method for treating a subject diagnosed with or identified as having a HRas-associated cancer, e.g., any of the exemplary HRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Compounds of Formula (I) and pharmaceutically acceptable salts and solvates thereof are also useful for treating a NRas-associated cancer.

Accordingly, also provided herein is a method for treating a subject diagnosed with or identified as having a NRas-associated cancer, e.g., any of the exemplary NRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Accordingly, also provided herein is a method for treating a subject diagnosed with or identified as having a NRas-associated cancer, e.g., any of the exemplary NRas-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Compounds of Formula (I) and pharmaceutically acceptable salts and solvates thereof are also useful for treating a SOS1-associated cancer.

Accordingly, also provided herein is a method for treating a subject diagnosed with or identified as having a SOS1-associated cancer, e.g., any of the exemplary SOS1-associated cancers disclosed herein, comprising administering to the subject an effective amount of a compound of Formula (I), or a pharmaceutically acceptable salt thereof, or a pharmaceutical composition thereof as defined herein. In some embodiments, the compound of Formula (I) is selected from Examples 1-313, or a pharmaceutically acceptable salt thereof.

Dysregulation of a Ras pathway protein, a Ras pathway gene, or the expression or activity or level of any (e.g., one or more) of the same can contribute to tumorigenesis. For example, a fusion protein can have increased activity as compared to a wild type Ras pathway protein (e.g., for SOS1, increased Ras activation through more advantageous binding and/or increased GEF activity), increased expression (e.g., increased levels) of a wild type Ras pathway protein in a mammalian cell can occur due to aberrant cell signaling and/or dysregulated autocrine/paracrine signaling (e.g., as compared to a control non-cancerous cell), Ras pathway mRNA splice variants may also result in dysregulation of Ras pathway.

In some embodiments, the compounds provided herein exhibit brain and/or central nervous system (CNS) penetrance. Such compounds are capable of crossing the blood brain barrier and inhibiting Ras pathway (e.g., SOS1, Ras (e.g., KRas, HRas, and/or NRas), EGFR, ErbB2, ErbB3, ErbB4, NF1, PDGFR-A, PDGFR-B, FGFR1, FGFR2, FGFR3, IGF1 R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof)) activity in the brain and/or other CNS structures. In some embodiments, the compounds provided herein are capable of crossing the blood brain barrier in an effective amount. For example, treatment of a subject with cancer (e.g., a Ras pathway-associated cancer such as a Ras pathway-associated brain or CNS cancer) can include administration (e.g., oral administration) of the compound to the subject. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the subject has previously been treated with another anticancer agent, e.g., another Ras pathway inhibitor (e.g., a compound that is not a compound of General Formula (I), or an inhibitor of another Ras pathway gene or protein (e.g., Ras (e.g., KRas, HRas, and/or NRas), EGFR, ErbB2, ErbB3, ErbB4, NF1, PDGFR-A, PDGFR-B, FGFR1, FGFR2, FGFR3, IGF1 R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof), or a combination thereof). In some embodiments, the brain tumor is a metastatic brain tumor. In some embodiments, the subject has previously been treated with another anticancer agent, e.g., another Ras pathway inhibitor (e.g., a compound that is not a compound of Formula (I), or an inhibitor of another Ras pathway gene or protein.

The ability of the compounds described herein, to cross the BBB can be demonstrated by assays known in the art. Such assays include BBB models such as the transwell system, the hollow fiber (dynamic in vitro BBB) model, other microfluidic BBB systems, the BBB spheroid platform, and other cell aggregate-based BBB models. See, e.g., Cho et al. Nat Commun. 2017; 8: 15623; Bagchi, et al. Drug Des Devel Ther. 2019; 13: 3591-3605; Gastfriend, et al. Curr Opin Biomed Eng. 2018 March; 5: 6-12; and Wang et al. Biotechnol Bioeng. 2017 January; 114(1): 184-194. In some embodiments, the compounds described herein, are fluorescently labeled, and the fluorescent label can be detected using microscopy (e.g., confocal microscopy). In some such embodiments, the ability of the compound to penetrate the surface barrier of the model can be represented by the fluorescence intensity at a given depth below the surface. In some assays, such as a calcein-AM-based assay, the fluorescent label is non-fluorescent until it permeates live cells and is hydrolyzed by intracellular esterases to produce a fluorescent compound that is retained in the cell and can be quantified with a spectrophotometer. Non-limiting examples of fluorescent labels that can be used in the assays described herein include Cy5, rhodamine, infrared IRDye® CW-800 (LICOR #929-71012), far-red IRDye® 650 (LICOR #929-70020), sodium fluorescein (Na—F), lucifer yellow (LY), 5'carboxyfluorescein, and calcein-acetoxymethylester (calcein-AM). In some embodiments, the BBB model (e.g., the tissue or cell aggregate) can be sectioned, and a compound described herein can be detected in one or more sections using mass spectrometry (e.g., MALDI-MSI analyses). In some embodiments, the ability of a compound described herein to cross the BBB through a transcellular transport system, such as receptor-mediated transport (RMT), carrier-mediated transport (CMT), or active efflux transport (AET), can be demonstrated by assays known in the art. See, e.g., Wang, et al. Drug Deliv. 2019; 26(1): 551-565. In some embodiments, assays to determine if compounds can be effluxed by the P-glycoprotein (Pgp) include monolayer efflux assays in which movement of compounds through Pgp is quantified by measuring movement of digoxin, a model Pgp substrate (see, e.g., Doan et al. 2002. J Pharmacol Exp Ther. 303(3):1029-1037). Alternative in vivo assays to identify compounds that pass through the blood-brain barriers include phage-based systems (see, e.g., Peng et al. 2019. ChemRxiv. Preprint doi.org/10.26434/chemrxiv.8242871.v1). In some embodiments, binding of the compounds described herein to brain tissue is quantified. For example, a brain tissue binding assay can be performed using equilibrium dialysis, and the fraction of a compound described herein unbound to brain tissue can be detected using LC-MS/MS (Cyprotex: Brain Tissue Binding Assay www.cyprotex.com/admepk/protein binding/brain-tissue-binding/).

In some embodiments, the subject has been identified or diagnosed as having a cancer with a dysregulation of a Ras pathway gene, a Ras pathway protein, or expression or activity, or level of any of the same (a Ras pathway-associated cancer) (e.g., as determined using a regulatory agency-approved, e.g., FDA-approved, assay or kit). In some embodiments, the subject has a tumor that is positive for a dysregulation of a Ras pathway gene, a Ras pathway protein, or expression or activity, or level of any of the same (e.g., as determined using a regulatory agency-approved assay or kit). The subject can be a subject with a tumor(s) that is positive for a dysregulation of a Ras pathway gene, a Ras pathway protein, or expression or activity, or level of any of the same (e.g., identified as positive using a regulatory agency-approved, e.g., FDA-approved, assay or kit). The subject can be a subject whose tumors have a dysregulation of a Ras pathway gene, a Ras pathway protein, or expression or activity, or a level of the same (e.g., where the tumor is identified as such using a regulatory agency-approved, e.g., FDA-approved, kit or assay). In some embodiments, the subject is suspected of having a Ras pathway-associated cancer. In some embodiments, the subject has a clinical record indicating that the subject has a tumor that has a dysregulation of a Ras pathway gene, a Ras pathway protein, or expression or activity, or level of any of the same (and optionally the clinical record indicates that the subject should be treated with any of the compositions provided herein).

In some embodiments, the subject has been identified or diagnosed as having a cancer with a dysregulation of a Ras gene, a Ras protein, or expression or activity, or level of any of the same (a Ras-associated cancer) (e.g., as determined using a regulatory agency-approved, e.g., FDA-approved, assay or kit). In some embodiments, the subject has a tumor that is positive for a dysregulation of a Ras gene, a Ras protein, or expression or activity, or level of any of the same (e.g., as determined using a regulatory agency-approved assay or kit). The subject can be a subject with a tumor(s) that is positive for a dysregulation of a Ras gene, a Ras protein, or expression or activity, or level of any of the same (e.g., identified as positive using a regulatory agency-approved, e.g., FDA-approved, assay or kit). The subject can be a subject whose tumors have a dysregulation of a Ras gene, a Ras protein, or expression or activity, or a level of the same (e.g., where the tumor is identified as such using a regulatory agency-approved, e.g., FDA-approved, kit or assay). In some embodiments, the subject is suspected of having a Ras-associated cancer. In some embodiments, the subject has a clinical record indicating that the subject has a tumor that has a dysregulation of a Ras gene, a Ras protein, or expression or activity, or level of any of the same (and optionally the clinical record indicates that the subject should be treated with any of the compositions provided herein).

In some embodiments, the subject has been identified or diagnosed as having a cancer with a dysregulation of a KRas gene, a KRas protein, or expression or activity, or level of any of the same (a KRas-associated cancer) (e.g., as determined using a regulatory agency-approved, e.g., FDA-approved, assay or kit). In some embodiments, the subject has a tumor that is positive for a dysregulation of a KRas gene, a KRas protein, or expression or activity, or level of any of the same (e.g., as determined using a regulatory agency-approved assay or kit). For example, the subject has a tumor that is positive for a mutation as described in Table 1. The subject can be a subject with a tumor(s) that is positive for a dysregulation of a KRas gene, a KRas protein, or expression or activity, or level of any of the same (e.g., identified as positive using a regulatory agency-approved, e.g., FDA-approved, assay or kit). The subject can be a subject whose tumors have a dysregulation of a KRas gene, a KRas protein, or expression or activity, or a level of the same (e.g., where the tumor is identified as such using a regulatory agency-approved, e.g., FDA-approved, kit or assay). In some embodiments, the subject is suspected of having a KRas-associated cancer. In some embodiments, the subject has a clinical record indicating that the subject has a tumor that has a dysregulation of a KRas gene, a KRas protein, or expression or activity, or level of any of the same (and optionally the clinical record indicates that the subject should be treated with any of the compositions provided herein).

In some embodiments, the subject has been identified or diagnosed as having a cancer with a dysregulation of a HRas gene, a HRas protein, or expression or activity, or level of any of the same (a HRas-associated cancer) (e.g., as determined using a regulatory agency-approved, e.g., FDA-approved, assay or kit). In some embodiments, the subject has a tumor that is positive for a dysregulation of a HRas gene, a HRas protein, or expression or activity, or level of any of the same (e.g., as determined using a regulatory agency-approved assay or kit). For example, the subject has a tumor that is positive for a mutation as described in Table 2. The subject can be a subject with a tumor(s) that is positive for a dysregulation of a HRas gene, a HRas protein, or expression or activity, or level of any of the same (e.g., identified as positive using a regulatory agency-approved, e.g., FDA-approved, assay or kit). The subject can be a subject whose tumors have a dysregulation of a HRas gene, a HRas protein, or expression or activity, or a level of the same (e.g., where the tumor is identified as such using a regulatory agency-approved, e.g., FDA-approved, kit or assay). In some embodiments, the subject is suspected of having a HRas-associated cancer. In some embodiments, the subject has a clinical record indicating that the subject has a tumor that has a dysregulation of a HRas gene, a HRas protein, or expression or activity, or level of any of the same (and optionally the clinical record indicates that the subject should be treated with any of the compositions provided herein).

In some embodiments, the subject has been identified or diagnosed as having a cancer with a dysregulation of a NRas gene, a NRas protein, or expression or activity, or level of any of the same (a NRas-associated cancer) (e.g., as determined using a regulatory agency-approved, e.g., FDA-approved, assay or kit). In some embodiments, the subject has a tumor that is positive for a dysregulation of a NRas gene, a NRas protein, or expression or activity, or level of any of the same (e.g., as determined using a regulatory agency-approved assay or kit). For example, the subject has a tumor that is positive for a mutation as described in Table 3. The subject can be a subject with a tumor(s) that is positive for a dysregulation of a NRas gene, a NRas protein, or expression or activity, or level of any of the same (e.g., identified as positive using a regulatory agency-approved, e.g., FDA-approved, assay or kit). The subject can be a subject whose tumors have a dysregulation of a NRas gene, a NRas protein, or expression or activity, or a level of the same (e.g., where the tumor is identified as such using a regulatory agency-approved, e.g., FDA-approved, kit or assay). In some embodiments, the subject is suspected of having a NRas-associated cancer. In some embodiments, the subject has a clinical record indicating that the subject has a tumor that has a dysregulation of a NRas gene, a NRas protein, or expression or activity, or level of any of the same (and optionally the clinical record indicates that the subject should be treated with any of the compositions provided herein).

In some embodiments, the subject has been identified or diagnosed as having a cancer with a dysregulation of a SOS1 gene, a SOS1 protein, or expression or activity, or level of any of the same (a SOS1-associated cancer) (e.g., as determined using a regulatory agency-approved, e.g., FDA-approved, assay or kit). In some embodiments, the subject has a tumor that is positive for a dysregulation of a SOS1 gene, a SOS1 protein, or expression or activity, or level of any of the same (e.g., as determined using a regulatory agency-approved assay or kit). For example, the subject has a tumor that is positive for a mutation as described in Table 4. The subject can be a subject with a tumor(s) that is positive for a dysregulation of a SOS1 gene, a SOS1 protein, or expression or activity, or level of any of the same (e.g., identified as positive using a regulatory agency-approved, e.g., FDA-approved, assay or kit). The subject can be a subject whose tumors have a dysregulation of a SOS1 gene, a SOS1 protein, or expression or activity, or a level of the same (e.g., where the tumor is identified as such using a regulatory agency-approved, e.g., FDA-approved, kit or assay). In some embodiments, the subject is suspected of having a SOS1-associated cancer. In some embodiments, the subject has a clinical record indicating that the subject has a tumor that has a dysregulation of a SOS1 gene, a SOS1 protein, or expression or activity, or level of any of the same (and optionally the clinical record indicates that the subject should be treated with any of the compositions provided herein).

In some embodiments of any of the methods or uses described herein, an assay used to determine whether the subject has a dysregulation of a Ras pathway gene, or a Ras pathway protein, or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a Ras pathway gene, a Ras pathway protein, or expression or activity or levels of any of the same. In some embodiments, the sample is a biological sample or a biopsy sample (e.g., a paraffin-embedded biopsy sample) from the subject. In some embodiments, the subject is a subject suspected of having a Ras pathway-associated cancer, a subject having one or more symptoms of a Ras pathway-associated cancer, and/or a subject that has an increased risk of developing a Ras pathway-associated cancer).

In some embodiments, dysregulation of a Ras pathway gene, a Ras pathway protein, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.,* 3(3):36, 2016. Liquid biopsy methods can be used to detect total tumor burden and/or the dysregulation of a Ras pathway gene, a Ras pathway protein, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a Ras pathway gene, a Ras pathway protein, or the expression or activity or level of any of the same. In some embodiments, liquid biopsies can be used to detect the presence of dysregulation of a Ras pathway gene, a Ras pathway protein, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a Ras pathway gene, a Ras pathway protein, or the expression or activity or level of any of the same.

In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a Ras pathway gene, a Ras pathway protein, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a Ras pathway gene, a Ras pathway protein, or the expression or activity or level of any of the same). Liquid biopsies can be used to detect dysregulation of a Ras pathway gene, a Ras pathway protein, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a dysregulation of a Ras pathway gene, a Ras pathway protein, or the expression or activity or level of any of the same identified using a liquid biopsy is also present in a cancer cell that is present in the subject (e.g., in a tumor). In some embodiments, any of the types of dysregulation of a Ras pathway gene, a Ras pathway protein, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a Ras pathway gene, a Ras pathway protein, or the expression or activity or level of any of the same in the subject can indicate that the subject will be responsive to a treatment that includes administration of a compound of Formula (I), or a pharmaceutically acceptable salt thereof.

Some embodiments of these methods can further include administering to the subject at least one dose of the compound of Formula (I), or a pharmaceutically acceptable salt thereof, between the first and second time points. For example, a reduction (e.g., a 1% to about a 99% reduction, a 1% reduction to about a 50% reduction, a 1% reduction to about a 10% reduction, about a 50% to about a 99% reduction, or about a 75% to about a 95% reduction,) in the allele frequency (AF) of the dysregulation of a Ras pathway gene in the cfDNA obtained from the subject at the second time point as compared to the allele frequency (AF) of the dysregulation of a Ras pathway gene in the cfDNA obtained from the subject at the first time point indicates that the compound of Formula (I), or a pharmaceutically acceptable salt thereof, was effective in the subject. In some embodiments, the AF is reduced such that the level is below the detection limit of the instrument. Alternatively, an increase in the allele frequency (AF) of the dysregulation of a Ras pathway gene in the cfDNA obtained from the subject at the second time point as compared to the allele frequency (AF) of the dysregulation of a Ras pathway gene in the cfDNA obtained from the subject at the first time point indicates that the compound of Formula (I), or a pharmaceutically acceptable salt thereof, was not effective in the subject. Some embodiments of these methods can further include, administering additional doses of a compound of Formula (I), or a pharmaceutically acceptable salt thereof, to a subject in which a compound of Formula (I), or a pharmaceutically acceptable salt thereof, was determined to be effective. Some embodiments of these methods can further include, administering a different treatment (e.g., a treatment that does not include the administration of a compound of Formula (I), or a pharmaceutically acceptable salt thereof, as a monotherapy) to a subject in which a compound of Formula (I), or a pharmaceutically acceptable salt thereof, was determined not to be effective.

In some examples of these methods, the time difference between the first and second time points can be about 1 day to about 1 year, about 1 day to about 1 month, about 1 day to about 5 days, about 1 month to about 3 months, about 3 months to about 6 months, or about 7 months to about 9 months. In some embodiments of these methods, the subject can be previously identified as having a cancer having a dysregulated Ras pathway gene (e.g., any of the examples of a dysregulated Ras pathway gene described herein). In some embodiments of these methods, a subject can have been previously diagnosed as having any of the types of cancer described herein. In some embodiments of these methods, the subject can have one or more metastases (e.g., one or more brain metastases).

In some of the above embodiments, the cfDNA comprises ctDNA such as Ras pathway-associated ((e.g., SOS1, Ras (e.g., KRas, HRas, and/or NRas), EGFR, ErbB2, ErbB3, ErbB4, NF1, PDGFR-A, PDGFR-B, FGFR1, FGFR2, FGFR3, IGF1 R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof)-associated) ctDNA. For example, the cfDNA is ctDNA such as Ras pathway-associated ctDNA. In some embodiments, at least some portion of cfDNA is determined to be Ras pathway-associated ctDNA, for example, a sequenced and/or quantified amount of the total cfDNA is determined to have a Ras pathway fusion and/or overexpression of Ras pathway.

Combinations

In the field of medical oncology it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other Ras pathway inhibitors, kinase inhibitors, signal transduction inhibitors, and/or monoclonal antibodies. For example, a surgery may be open surgery or minimally invasive surgery. Compounds of Formula (I), or a pharmaceutically acceptable salt thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I), or a pharmaceutically acceptable salt thereof, can be used prior to administration of an additional therapeutic agent or additional therapy. For example, a subject in need thereof can be administered one or more doses of a compound of Formula (I), or a pharmaceutically acceptable salt thereof for a period of time and then undergo at least partial resection of the tumor. In some embodiments, the treatment with one or more doses of a compound of Formula (I), or a pharmaceutically acceptable salt thereof reduces the size of the tumor (e.g., the tumor burden) prior to the at least partial resection of the tumor. In some embodiments, a subject in need thereof can be administered one or more doses of a compound of Formula (I), or a pharmaceutically acceptable salt thereof for a period of time and under one or more rounds of radiation therapy. In some embodiments, the treatment with one or more doses of a compound of Formula (I), or a pharmaceutically acceptable salt thereof reduces the size of the tumor (e.g., the tumor burden) prior to the one or more rounds of radiation therapy.

A "Ras pathway targeted therapeutic agent" as used herein includes any compound exhibiting inactivation activity (e.g., active site (e.g., competitive) inhibition, allosteric inhibition, inhibition of dimerization, inhibition of expression, inhibition of protein-protein interaction, and induction of degradation) of any protein in a Ras pathway. Non-limiting examples of a protein in a Ras pathway include any one of the proteins in the Ras-RAF-MAPK pathway or PI3K/AKT pathway such as Ras (e.g., KRas, HRas, and/or NRas), EGFR, ErbB2, ErbB3, ErbB4, NF1, PDGFR-A, PDGFR-B, FGFR1, FGFR2, FGFR3, IGF1R, INSR, ALK, ROS, TrkA, TrkB, TrkC, RET, c-MET, VEGFR1, VEGFR2, VEGFR3, AXL, SHP2, RAF (e.g., BRAF), PI3K, AKT, mTOR, MEK, ERK, or a combination thereof. In some embodiments, a Ras pathway targeted therapeutic agent can be selective for a protein in a Ras pathway. For example, the Ras pathway targeted therapeutic agent can be selective for a Ras protein (e.g., KRas, HRas, and/or NRas, or mutated forms of any thereof); such an agent can also be called a "Ras modulator"). In some embodiments, a Ras modulator is a covalent inhibitor. In some embodiments, a Ras pathway targeted therapeutic agent can be selective for a particular Ras protein (e.g., KRas, HRas, or NRas), or a mutated form thereof (e.g., a G12 mutant, a G13 mutant, or a Q61 mutant). Non-limiting examples of KRas-targeted therapeutic agents (e.g., KRas inhibitors (such as KRas G12C inhibitors)) include AMG 510, ARS-3248, ARS1620, SML-8-73-1, SML-10-70-1, VSA9, AA12, MRTX-849, MRTX849, LY3499446, JNJ-74699157, ARS853, AZD4785, and JNJ-74699157.

Compounds of Formula (I), or pharmaceutically acceptable salts or thereof, can be used in combination with one or more additional therapies or therapeutic agents, for example, a chemotherapeutic agent that works by the same or by a different mechanism of action. In some embodiments, a compound of Formula (I), or a pharmaceutically acceptable salt thereof, can be used prior to administration of an additional therapeutic agent or additional therapy. For example, a subject in need thereof can be administered one or more doses of a compound of Formula (I), or a pharmaceutically acceptable salt thereof, for a period of time and then undergo at least partial resection of the tumor. In some embodiments, the treatment with one or more doses of a compound of Formula (I), or a pharmaceutically acceptable salt thereof, reduces the size of the tumor (e.g., the tumor burden) prior to the at least partial resection of the tumor. In some embodiments, a subject in need thereof can be administered one or more doses of a compound of Formula (I), or a pharmaceutically acceptable salt thereof, for a period of time and under one or more rounds of radiation therapy. In some embodiments, the treatment with one or more doses of a compound of Formula (I), or a pharmaceutically acceptable salt thereof, reduces the size of the tumor (e.g., the tumor burden) prior to the one or more rounds of radiation therapy.

In some embodiments, the one or more additional therapies or therapeutic agents are independently selected from: EGFR inhibitors (e.g., afatinib, erlotinib, gefitinib, lapatinib, cetuximab, panitumumab, osimertinib, and olmutinib), ErbB2/Her2 inhibitors (e.g., afatinib, lapatinib, trastuzumab, and pertuzumab), ALK inhibitors (e.g., crizotinib, alectinib, entrectinib, brigatinib), ROS1 inhibitors (e.g., crizotinib, entrectinib, lorlatinib, ceritinib, and merestinib), MEK inhibitors (e.g., trametinib, cobimetinib, binimetinib, selumetinib, refametinib), RAS (KRas, HRas, and/or NRas) inhibitors (e.g., MRTX849, LY3499446, JNJ-74699157, AMG 510, and AZD4785), Bcr-Abl inhibitors (e.g., imatinib, dasatinib, nilotinib), FGFR1, 2, or 3 inhibitors (e.g., nintedanib), MET inhibitors (e.g., capmatinib), AXL inhibitors (e.g., sitravatinib), RET inhibitors (e.g., sunitinib and selpercatinib), ERK inhibitors (e.g., ulixertinib), Shp2 inhibitors (e.g., RLY-1971, RMC-4630, TNO155, and JAB-3068), Bcl-2 inhibitors (e.g., ABT-263, obatoclax, ABT-737, and navitoclax), mTOR inhibitors (e.g., everolimus and tacrolimus), Trk inhibitors (e.g., larotrectinib and entrectinib), checkpoint inhibitors (e.g., ipilimumab, nivolumab, pembrolizumab, atezolizumab, avelumab, durvalumab, and pidilizumab) or other immunotherapies (e.g., monoclonal antibodies), PARP inhibitors (e.g., olaparib), PI3K inhibitors (e.g., buparlisib), BET inhibitors (e.g., GSK1210151A), Raf inhibitors (e.g., encorafenib), MCL-1 inhibitors (e.g., AZD5991), AKT inhibitors (e.g., miltefosine), PDK1 inhibitors (e.g., GSK 2334470), and other chemotherapeutic agents such as taxanes (e.g., paclitaxel and docetaxel), platinum-based agents (e.g., cisplatin and carboplatin), cytoxic agents (e.g., 5-fluorouracil, capecitabine, floxuridine, cytarabine, and gemcitabine), farnesyltransferase inhibitors, topoisomerase inhibitors (e.g., topotecan and irinotecan), DNA synthesis inhibitors (e.g., capecitabine (Xeloda®) and gemcitabine hydrochloride (Gemzar®)), alkylating agents (e.g., temozolomide (Temodar® and Temodal®), dactinomycin (also known as actinomycin-D, Cosmegen®), carmustine (BiCNU®), bendamustine (Treanda®), and lomustine (CeeNU®)), and cytotoxic agents (e.g., vincristine, cytarabine, and pemetrexed).

Epidermal growth factor receptor (EGFR) inhibitors such as osimertinib (AZD9291, merelectinib, TAGRISSO®), erlotinib (TARCEVA®), gefitinib (IRESSA®), cetuximab (ERBITUX®), necitumumab (PORTRAZZA®, IMC-11F8), neratinib (HKI-272, NERLYNX®), lapatinib (TYKERB®), panitumumab (ABX-EGF, VECTIBIX®), vandetanib (CAPRELSA®), rociletinib (CO-1686), olmutinib (OLITA®, HM61713, BI-1482694), naquotinib (ASP8273), nazartinib (EGF816, NVS-816), PF-06747775, icotinib (BPI-2009H), afatinib (BIBW 2992, GILOTRIF®), dacomitinib (PF-00299804, PF-804, PF-299, PF-299804), avitinib (AC0010), AC0010MA EAI045, matuzumab (EMD-7200), nimotuzumab (h-R3, BIOMAb EGFR®), zalutumab, MDX447, depatuxizumab (humanized mAb 806, ABT-806), depatuxizumab mafodotin (ABT-414), ABT-806, mAb 806, canertinib (CI-1033), shikonin, shikonin derivatives (e.g., deoxyshikonin, isobutyrylshikonin, acetylshikonin, β,β-dimethylacrylshikonin and acetylalkannin), poziotinib (NOV120101, HM781-36B), AV-412, ibrutinib, WZ4002, brigatinib (AP26113, ALUNBRIG®), pelitinib (EKB-569), tarloxotinib (TH-4000, PR610), BPI-15086, Hemay022, ZN-e4, tesevatinib (KD019, XL647), YH25448, epitinib (HMPL-813), CK-101, MM-151, AZD3759, ZD6474, PF-06459988, varlintinib (ASLAN001, ARRY-334543), AP32788, HLX07, D-0316, AEE788, HS-10296, avitinib, GW572016, pyrotinib (SHR1258), SCT200, CPGJ602, Sym004, MAb-425, Modotuximab (TAB-H49), futuximab (992 DS), zalutumumab, KL-140, RO5083945, IMGN289, JNJ-61186372, LY3164530, Sym013, AMG 595, BDTX-189, avatinib, Disruptin, CL-387785, EGFRBi-Armed Autologous T Cells, and EGFR CAR-T Therapy. In some embodiments, the EGFR-targeted therapeutic agent is selected from osimertinib, gefitinib, erlotinib, afatinib, lapatinib, neratinib, AZD-9291, CL-387785, CO-1686, or WZ4002.

Human Epidermal Growth Factor Receptor 2 (HER2 receptor) (also known as Neu, ErbB-2, CD340, or p185) inhibitors such as trastuzumab (e.g., TRAZIMERA™, HERCEPTIN®), pertuzumab (e.g., PERJETA®), trastuzumab emtansine (T-DM1 or ado-trastuzumab emtansine, e.g., KADCYLAR), lapatinib, KU004, neratinib (e.g., NERLYNX®), dacomitinib (e.g., VIZIMPRO®), afatinib (GILOTRIF®), tucatinib (e.g., TUKYSA™), erlotinib (e.g., TARCEVA®), pyrotinib, poziotinib, CP-724714, CUDC-101, sapitinib (AZD8931), tanespimycin (17-AAG), IPI-504, PF299, pelitinib, S-22261 1, and AEE-788.

In some embodiments, the FGFR inhibitor is selected from infigratinib, AZD4547, erdafitinib (JNJ-42756493), nintedanib dovitinib, ponatinib, and TAS120.

In some embodiments, the ALK inhibitor is selected from alectinib, crizotinib (XALKORI®), ceritinib, AP26113, ASP3026, TSR-011, PF-06463922, X-396, and CEP-37440.

In some embodiments, the ROS1 inhibitor is selected from crizotinib (XALKORI®), ceritinib, lorlatinib, brigatinib, cabozantinib, and repotrectinib.

In some embodiments, the mTOR inhibitor is selecte from everolimus, tacrolimus rapamycin, perifosine, and temsirolimus.

In some embodiments, the Trk inhibitor is selected from larotrectinib, lestaurtinib, and entrectinib.

In some embodiments, the RET inhibitors is selected from sunitinib (Sutent®), selpercatinib (RETEVMO®), vandetanib (Caprelsa®), motesanib (AMG706), sorafenib, regorafenib, and danusertib.

In some embodiments, the MET inhibitor is selected from capmatinib, tepotinib, savolitinib, crizotinib, cabozantinib, tivantinib, bozitinib, merestinib, glesatinib, sitravatinib, onartuzumab, and emibetuzumab.

In some embodiments, the AXL inhibitor is selected from sitravatinib, bemcentinib, dubermatinib, DS-1205, SLC-391, INCB081776, ONO-7475, and BA3011.

In some embodiments, the Shp2 inhibitor is selected from TNO155, BBP-398, JAB-3068, RMC-4360, and RLY-1971.

In some embodiments, the RAF inhibitor is a BRAF inhibitor, such as vemurafenib (ZELBORAF®), dabrafenib (TAFINLAR®), encorafenib (BRAFTOVI®), BMS-908662, sorafenib, LGX818, PLX3603, RAF265, RO5185426, GSK2118436, ARQ 736, GDC-0879, PLX-4720, AZ304, PLX-8394, HM95573, RO5126766, and LXH254.

In some embodiments, the PI3K inhibitor is selected from buparlisib (BKM120), alpelisib (BYL719), WX-037, copanlisib (ALIQOPAR, BAY80-6946), dactolisib (NVP-BEZ235, BEZ-235), taselisib (GDC-0032, RG7604), sonolisib (PX-866), CUDC-907, PQR309, ZSTK474, SF1126, AZD8835, GDC-0077, ASN003, pictilisib (GDC-0941), pilaralisib (XL147, SAR245408), gedatolisib (PF-05212384, PKI-587), serabelisib (TAK-117, MLN1117, INK 1117), BGT-226 (NVP-BGT226), PF-04691502, apitolisib (GDC-0980), omipalisib (GSK2126458, GSK458), voxtalisib (XL756, SAR245409), AMG 511, $CH_{5132799}$, GSK1059615, GDC-0084 (RG7666), VS-5584 (SB2343), PKI-402, wortmannin, LY294002, PI-103, rigosertib, XL-765, LY2023414, SAR260301, KIN-193 (AZD-6428), GS-9820, AMG319, and GSK2636771.

In some embodiments, the AKT inhibitor is selected from miltefosine (IMPADIVO®), wortmannin, NL-71-101, H-89, GSK690693, CCT128930, AZD5363, ipatasertib (GDC-0068, RG7440), A-674563, A-443654, AT7867, AT13148, uprosertib, afuresertib, DC120, MK-2206, edelfosine, miltefosine, perifosine, erucylphophocholine, erufosine, SR13668, OSU-A9, PH-316, PHT-427, PIT-1, DM-PIT-1, triciribine, API-1, ARQ092, BAY 1125976, 3-oxo-tirucallic acid, lactoquinomycin, GSK2141795, ONC201, tricirbine, A674563, and AT7867.

In some embodiments, the MEK inhibitor is selected from trametinib (MEKINIST®), cobimetinib (COTELLIC®), binimetinib (MEKTOVI®), selumetinib (AZD6244), PD0325901, MSC1936369B, SHR7390, TAK-733, RO5126766, CS3006, WX-554, PD98059, CI1040 (PD184352), and hypothemycin.

In some embodiments, the ERK inhibitor is selected from FRI-20 (ON-01060), VTX-11e, 25-OH-D3-3-BE (B3CD, bromoacetoxycalcidiol), FR-180204, AEZ-131 (AEZS-131), AEZS-136, AZ-13767370, BL-EI-001, LY-3214996, LTT-462, KO-947, MK-8353 (SCH900353), SCH772984, ulixertinib (BVD-523), CC-90003, GDC-0994 (RG-7482), ASN007, FR148083, 5-7-Oxozeaenol, 5-iodotubercidin, GDC0994, and ONC201.

In some embodiments, the PARP inhibitors include olaparib (LYNPARZA®), talazoparib, rucaparib, niraparib, veliparib, BGB-290 (pamiparib), CEP 9722, E7016, iniparib, IMP4297 NOV1401, 2X-121, ABT-767, RBN-2397, BMN 673, KU-0059436 (AZD2281), BSI-201, PF-01367338, INO-1001, and JPI-289.

In some embodiments, the RAS inhibitor is MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849.

In some embodiments, the PDK-1 inhibitor is selected from GSK 2334470, JX06, SNS-510, and AR-12.

In some embodiments, the BET inhibitor is selected from GSK1210151A, GSK525762, OTX-015, TEN-010, CPI-203, CPI-0610, olinone, RVX-208, ABBV-744, LY294002, AZD5153, MT-1, and MS645.

In some embodiments, the MCL-1 inhibitor is AZD5991.

In some embodiments, the Bcl-2 protein family inhibitor is selected from ABT-263, Tetrocarcin A, Antimycin, Gossypol ((−) BL-193), obatoclax, HA14-1, oblimersen (Genasense®); (−)-Gossypol acetic acid (AT-101); ABT-737, and navitoclax.

In some embodiments, the Bcr/Abl kinase inhibitor is selected from imatinib (Gleevec®), inilotinib, nilotinib (Tasigna®), dasatinib (BMS-345825), bosutinib (SKI-606), ponatinib (AP24534), bafetinib (INNO406), danusertib (PHA-739358), AT9283, saracatinib (AZD0530), and PF-03814735.

In some embodiments, the checkpoint inhibitor is selected from ipilimumab (YERVOY®), pembrolizumab (KEYTRUDA®), nivolumab (OPDIVO®), cemiplimab (LIBTAYO®), atezolizumab (TECENTRIQ®), avelumab (BAVENCIO®), durvalumab (IMFINZI®), IMP701 (LAG525), CPI-444, MBG453, enoblituzumab, JNJ-61610588, and indoximod. See, e.g., Marin-Acevedo, et. al., *J Hematol Oncol.* 11: 39 (2018).

In some embodiments, the other immunotherapy is an antibody therapy (e.g., a monoclonal antibody). In some embodiments, the antibody therapy is selected from bevacizumab (Mvasti™, Avastin®), trastuzumab (Herceptin®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, and amatuximab.

In some embodiments, the other chemotherapeutic agents are selected from an anthracycline, an alkylating agent, a taxane, a platinum-based agent, eribulin (HALAVEN™), a farnesyl transferase inhibitor, a topoisomerase inhibitor, a DNA synthesis inhibitor, and cytotoxic agents.

In some embodiments, the taxane is selected from paclitaxel, docetaxel, cabazitaxel, abraxane, and taxotere.

In some embodiments, the anthracycline is selected from daunorubicin, doxorubicin, epirubicin, idarubicin, and combinations thereof.

In some embodiments, the platinum-based agent is selected from carboplatin, cisplatin, oxaliplatin, nedplatin, triplatin tetranitrate, phenanthriplatin, picoplatin, and satraplatin.

In some embodiments, the farnesyl transferase inhibitor is selected from lonafarnib, tipifarnib, BMS-214662, L778123, L744832, and FTI-277.

In some embodiments, the topoisomerase inhibitor is a topoisomerase I inhibitor (e.g., irinotecan (Camptosar®), topotecan (Hycamtin®), and 7-Ethyl-10-hydroxycampothecin (SN38)) or a topoisomerase II inhibitor (e.g., etoposide (Toposar®, VePesid®, and Etopophos®), teniposide (VM-26, Vumon®), and tafluposide.

In some embodiments, the DNA synthesis inhibitor is selected from capecitabine (Xeloda®), gemcitabine hydrochloride (Gemzar®), nelarabine (Arranon® and Atriance®), and sapacitabine.

In some embodiments, the alkylating agent is selected from temozolomide (Temodar® and Temodal®), dactinomycin (also known as actinomycin-D, Cosmegen®), melphalan (Alkeran®), altretamine (Hexalen®), carmustine (BiCNU®), bendamustine (Treanda®), busulfan (Busulfex® and Myleran®), lomustine (CeeNU®), chlorambucil (Leukeran®), cyclophosphamide (Cytoxan® and Neosar®), dacarbazine (DTIC-Dome®), altretamine (Hexalen®), ifosfamide (Ifex®), prednumustine, procarbazine (Matulane®), mechlorethamine (Mustargen®), streptozocin (Zanosar®), and thiotepa (Thioplex®).

In some embodiments, the cytotoxic agent is selected from bleomycin, cytarabine, dacarbazine, methotrexate, mitomycin C, pemetrexed, and vincristine.

Also provided herein is (i) a pharmaceutical combination for treating a cancer in a subject in need thereof, which comprises (a) a compound of Formula (I), or a pharmaceutically acceptable salt thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula (I), or pharmaceutically acceptable salt thereof, and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a subject in need thereof. In some embodiments, the cancer is a Ras pathway-associated cancer.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula (I), or a pharmaceutically acceptable salt thereof, and at least one additional therapeutic agent (e.g., a chemotherapeutic agent), are both administered to a subject simultaneously in the form of a single composition or dosage. The term "non-fixed combination" means that a compound of Formula (I), or a pharmaceutically acceptable salt thereof, and at least one additional therapeutic agent (e.g., chemotherapeutic agent) are formulated as separate compositions or dosages such that they may be administered to a subject in need thereof simultaneously, concurrently or sequentially with variable intervening time limits, wherein such administration provides effective levels of the two or more compounds in the body of the subject. These also apply to cocktail therapies, e.g., the administration of three or more active ingredients.

Accordingly, also provided herein is a method of treating a cancer, comprising administering to a subject in need thereof a pharmaceutical combination for treating cancer which comprises (a) a compound of Formula (I), or pharmaceutically acceptable salt thereof, and (b) an additional therapeutic agent, wherein the compound of Formula (I) and the additional therapeutic agent are administered simultaneously, separately or sequentially, wherein the amounts of the compound of Formula (I), or pharmaceutically acceptable salt thereof, and the additional therapeutic agent are together effective in treating the cancer. In some embodiments, the compound of Formula (I), or pharmaceutically acceptable salt thereof, and the additional therapeutic agent are administered simultaneously as separate dosages. In some embodiments, the compound of Formula (I), or pharmaceutically acceptable salt thereof, and the additional therapeutic agent are administered as separate dosages sequentially in any order, in jointly effective amounts, e.g., in daily or intermittently dosages. In some embodiments, the compound of Formula (I), or pharmaceutically acceptable salt thereof, and the additional therapeutic agent are administered simultaneously as a combined dosage. In some embodiments, the cancer is a Ras pathway-associated cancer.

Accordingly, also provided herein are methods for inhibiting, preventing, aiding in the prevention, or decreasing the symptoms of metastasis of a cancer in a subject in need thereof, the method comprising administering to the subject an effective amount of a compound of Formula (I), or a pharmaceutically acceptable salt thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a Ras pathway-associated cancer. In some embodiments, the compound of Formula (I), or a pharmaceutically acceptable salt thereof is used in combination with an additional therapy or another therapeutic agent, such as those described herein.

The term "metastasis" is an art known term and means the formation of an additional tumor (e.g., a solid tumor) at a site distant from a primary tumor in a subject, where the additional tumor includes the same or similar cancer cells as the primary tumor.

Also provided are methods of decreasing the risk of developing a metastasis or an additional metastasis in a subject having a Ras pathway-associated cancer that include: selecting, identifying, or diagnosing a subject as having a Ras pathway-associated cancer, and administering an effective amount of a compound of Formula (I), or a pharmaceutically acceptable salt thereof to the subject selected, identified, or diagnosed as having a Ras pathway-associated cancer. Also provided are methods of decreasing the risk of developing a metastasis or an additional metastasis in a subject having a Ras pathway-associated cancer that includes administering an effective amount of a compound of Formula (I), or a pharmaceutically acceptable salt thereof to a subject having a Ras pathway-associated cancer. The decrease in the risk of developing a metastasis or an additional metastasis in a subject having a Ras pathway-associated cancer can be compared to the risk of developing a metastasis or an additional metastasis in the subject prior to treatment, or as compared to a subject or a population of subjects having a similar or the same Ras pathway-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

Also provided are methods of decreasing the risk of developing a metastasis or an additional metastasis in a subject having a Ras-associated cancer that include: selecting, identifying, or diagnosing a subject as having a Ras-associated cancer, and administering an effective amount of a compound of Formula (I), or a pharmaceutically acceptable salt thereof to the subject selected, identified, or diagnosed as having a Ras-associated cancer. Also provided are methods of decreasing the risk of developing a metastasis or an additional metastasis in a subject having a Ras-associated cancer that includes administering an effective amount of a compound of Formula (I), or a pharmaceutically acceptable salt thereof to a subject having a Ras-associated cancer. The decrease in the risk of developing a metastasis or an additional metastasis in a subject having a Ras-associated cancer can be compared to the risk of developing a metastasis or an additional metastasis in the subject prior to treatment, or as compared to a subject or a population of subjects having a similar or the same Ras-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

Also provided are methods of decreasing the risk of developing a metastasis or an additional metastasis in a subject having a KRas-associated cancer that include: selecting, identifying, or diagnosing a subject as having a KRas-associated cancer, and administering an effective amount of a compound of Formula (I), or a pharmaceutically acceptable salt thereof to the subject selected, identified, or diagnosed as having a KRas-associated cancer. Also provided are methods of decreasing the risk of developing a metastasis or an additional metastasis in a subject having a KRas-associated cancer that includes administering an effective amount of a compound of Formula (I), or a pharmaceutically acceptable salt thereof to a subject having a KRas-associated cancer. The decrease in the risk of developing a metastasis or an additional metastasis in a subject having a KRas-associated cancer can be compared to the risk of developing a metastasis or an additional metastasis in the subject prior to treatment, or as compared to a subject or a population of subjects having a similar or the same KRas-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

Also provided are methods of decreasing the risk of developing a metastasis or an additional metastasis in a subject having a HRas-associated cancer that include: selecting, identifying, or diagnosing a subject as having a HRas-associated cancer, and administering an effective amount of a compound of Formula (I), or a pharmaceutically acceptable salt thereof to the subject selected, identified, or diagnosed as having a HRas-associated cancer. Also provided are methods of decreasing the risk of developing a metastasis or an additional metastasis in a subject having a HRas-associated cancer that includes administering an effective amount of a compound of Formula (I), or a pharmaceutically acceptable salt thereof to a subject having a HRas-associated cancer. The decrease in the risk of developing a metastasis or an additional metastasis in a subject having a HRas-associated cancer can be compared to the risk of developing a metastasis or an additional metastasis in the subject prior to treatment, or as compared to a subject or a population of subjects having a similar or the same HRas-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

Also provided are methods of decreasing the risk of developing a metastasis or an additional metastasis in a subject having a NRas-associated cancer that include: selecting, identifying, or diagnosing a subject as having a NRas-associated cancer, and administering an effective amount of a compound of Formula (I), or a pharmaceutically acceptable salt thereof to the subject selected, identified, or diagnosed as having a NRas-associated cancer. Also provided are methods of decreasing the risk of developing a metastasis or an additional metastasis in a subject having a NRas-associated cancer that includes administering an effective amount of a compound of Formula (I), or a pharmaceutically acceptable salt thereof to a subject having a NRas-associated cancer. The decrease in the risk of developing a metastasis or an additional metastasis in a subject having a NRas-associated cancer can be compared to the risk of developing a metastasis or an additional metastasis in the subject prior to treatment, or as compared to a subject or a population of subjects having a similar or the same NRas-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

Also provided are methods of decreasing the risk of developing a metastasis or an additional metastasis in a subject having a SOS1-associated cancer that include: selecting, identifying, or diagnosing a subject as having a SOS1-associated cancer, and administering an effective amount of a compound of Formula (I), or a pharmaceutically acceptable salt thereof to the subject selected, identified, or diagnosed as having a SOS1-associated cancer. Also provided are methods of decreasing the risk of developing a metastasis or an additional metastasis in a subject having a SOS1-associated cancer that includes administering an effective amount of a compound of Formula (I), or a pharmaceutically acceptable salt thereof to a subject having a SOS1-associated cancer. The decrease in the risk of developing a metastasis or an additional metastasis in a subject having a SOS1-associated cancer can be compared to the risk of developing a metastasis or an additional metastasis in the subject prior to treatment, or as compared to a subject or a population of subjects having a similar or the same SOS1-associated cancer that has received no treatment or a different treatment. In some embodiments, the additional therapeutic agent is selected from MRTX849, LY3499446, JNJ-74699157, AMG 510, ARS3248, ARS853, ARS1620, AZD4785, JNJ-74699157, SML-8-73-1, SML-10-70-1, VSA9, AA12, and MRTX-849. In some embodiments, the subject has been administered one or more doses of a compound of Formula (I), or a pharmaceutically acceptable salt thereof, prior to administration of the pharmaceutical composition.

The phrase "risk of developing a metastasis" means the risk that a subject having a primary tumor will develop an additional tumor (e.g., a solid tumor) at a site distant from a primary tumor in a subject over a set period of time, where the additional tumor includes the same or similar cancer cells as the primary tumor. Methods for reducing the risk of developing a metastasis in a subject having a cancer are described herein.

The phrase "risk of developing additional metastases" means the risk that a subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Treatment of a subject having a cancer with a multi-kinase inhibitor (MKI) or target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can result in dysregulation of a Ras pathway gene, a Ras pathway protein, or the expression or activity or level of the same in the cancer. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, *Oncogene* 2018.

Treatment of a subject having a cancer with a SOS1 inhibitor in combination with a multi-kinase inhibitor or a target-specific kinase inhibitor (e.g., a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) can have increased therapeutic efficacy as compared to treatment of the same subject or a similar subject with the SOS1 inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a subject having a cancer (e.g., any of the cancers described herein) and previously administered a multi-kinase inhibitor (MKI) or a target-specific kinase inhibitor (e.g., a Ras inhibitor, a BRAF inhibitor, an EGFR inhibitor, a MEK inhibitor, an ALK inhibitor, a ROS1 inhibitor, a MET inhibitor, an aromatase inhibitor, a RAF inhibitor, a RET inhibitor, or a RAS inhibitor) (e.g., as a monotherapy) that include: administering to the subject (i) an effective dose of a compound of Formula (I), or a pharmaceutically acceptable salt thereof as a monotherapy, or (ii) an effective dose of a compound of Formula (I), or a pharmaceutically acceptable salt thereof, and an effective dose of the previously administered MKI or the previously administered target-specific kinase inhibitor.

Also provided is a method for inhibiting SOS1 activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having SOS1 activity. In some embodiments, the mammalian cell is a mammalian cancer cell. In some embodiments, the mammalian cancer cell is any cancer as described herein. In some embodiments, the mammalian cancer cell is a Ras pathway-associated cancer cell.

Also provided is a method for inhibiting Ras activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having Ras activity. In some embodiments, the mammalian cell is a mammalian cancer cell. In some embodiments, the mammalian cancer cell is any cancer as described herein. In some embodiments, the mammalian cancer cell is a Ras pathway-associated cancer cell.

Also provided is a method for inhibiting a SOS1-Ras (e.g., KRas, HRas, and/or NRas) protein-protein interaction in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having a SOS1-Ras (e.g., KRas, HRAs, and/or NRas) protein-protein interaction. In some embodiments, the mammalian cell is a mammalian cancer cell. In some embodiments, the mammalian cancer cell is any cancer as described herein. In some embodiments, the mammalian cancer cell is a Ras pathway-associated cancer cell.

Also provided is a method for inhibiting Ras pathway activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having Ras pathway activity. In some embodiments, the mammalian cell is a mammalian cancer cell. In some embodiments, the mammalian cancer cell is any cancer as described herein. In some embodiments, the mammalian cancer cell is a Ras pathway-associated cancer cell.

As used herein, the term "contacting" refers to the bringing together of indicated moieties in an in vitro system or an in vivo system. For example, "contacting" a SOS1 protein with a compound provided herein includes the administration of a compound provided herein to a subject, such as a human, having a SOS1 protein, as well as, for example, introducing a compound provided herein into a sample containing a mammalian cellular or purified preparation containing the SOS1 protein.

Also provided herein is a method of inhibiting mammalian cell proliferation, in vitro or in vivo, the method comprising contacting a mammalian cell with an effective amount of a compound of Formula (I), or a pharmaceutically acceptable salt thereof, or a pharmaceutical composition thereof as defined herein.

The phrase "effective amount" means an amount of compound that, when administered to a subject in need of such treatment, is sufficient to (i) treat a Ras pathway-associated disease or disorder (such as a Ras pathway-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula (I), or a pharmaceutically acceptable salt thereof that will correspond to such an amount will vary depending upon factors such as the particular compound, disease condition and its severity, the identity (e.g., weight) of the subject in need of treatment, but can nevertheless be routinely determined by one skilled in the art.

Pharmaceutical Compositions

When employed as pharmaceuticals, compounds of Formula (I), including pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I) or pharmaceutically acceptable salt thereof, in combination with one or more pharmaceutically acceptable excipients. For example, a pharmaceutical composition prepared using a compound of Formula (I) or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I) or a pharmaceutically acceptable salt thereof with a pharmaceutically acceptable carrier. Pharmaceutical compositions containing a compound of Formula (I) or a pharmaceutically acceptable salt thereof as the active ingredient can be prepared by intimately mixing the compound of Formula (I), or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula (I) or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula (I) or a pharmaceutically acceptable salt thereof) calculated to produce the desired therapeutic effect, in association with a suitable pharmaceutical excipient.

In some embodiments, the compositions provided herein contain from about 5 mg to about 50 mg of the active ingredient.

In some embodiments, the compositions provided herein contain from about 50 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient.

The daily dosage of the compound of Formula (I) or a pharmaceutically acceptable salt thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula (I) or a pharmaceutically acceptable salt thereof can be administered on a regimen of 1 to 4 times per day or in a single daily dose.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. In some embodiments, such administration can be once-daily or twice-daily (BID) administration.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of Ras pathway-associated diseases or disorders, such as cancer, which include one or more containers containing a pharmaceutical composition comprising an effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Examples

Abbreviations

° C.=degrees Celsius
$^1$H NMR=proton nuclear magnetic resonance spectrum
ACN or MeCN=acetonitrile
AcOH=acetic acid
Boc=tert-butoxycarbonyl
con.=concentrated
d=doublet
DAST=Diethylaminosulful trifluoride
DCM=dichloromethane
DIPEA or DIEA=N,N-diisopropylethylamine
DMF=N,N-dimethylformamide
DMF-DMA=dimethylformamide dimethyl acetal
DMSO=dimethylsulfoxide
DPPA=diphenylphosphoryl azide
EDCI=1-Ethyl-3-(3-dimethylaminopropyl)carbodiimide
Et=ethyl
EtOAc or EA=ethyl acetate
EtOH=ethanol
ESI=electrospray ionization
g=gram(s)
HATU=(1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium
hr=hour(s)
HOBt=1-hydroxybenzotriazole
HPLC=high-performance liquid chromatography
IPA=2-propanol
LCMS=liquid chromatograph-mass spectrum
M=mass
MTBA=methyl tert-butyl ether
m/z=mass-to-charge ratio
Me=methyl
MeCN=acetonitrile
MeOH=methanol
MeONa=sodium methoxide
mg=milligram(s)
mL=milliliter
mmol=millimole(s)
mol=mole(s)
MS=mass spectrum
NBS=N-bromosuccinimide
obsd.=observed
$Pd(OAc)_2$=palladium(II) acetate
$Pd(dppf)Cl_2$=(1,1'-Bis(diphenylphosphino)ferrocene)palladium(II) dichloride
PE=petroleum ether
ppm=parts per million
rt=room temperature
s=singlet
SPhos-Pd-G3=(2-Dicyclohexylphosphino-2',6'-dimethoxybiphenyl) [2-(2'-amino-1,1'-biphenyl)]palladium (II) methanesulfonate
Tf=trifluoromethanesulfonyl
T3P=Propylphosphonic anhydride
t=triplet
TBAF=tetrabutylammonium fluoride
TEA=triethylamine
TFA=trifluoroacetic acid
THF=tetrahydrofuran
TLC=thin-layer chromatography
UPCC=Ultra Performance Convergence Chromatography

Materials and Methods

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry,* 1st Ed., Oxford University Press, 2000; *March's Advanced Organic Chemistry: Reactions, Mechanisms, and Structure,* 5th Ed., Wiley-Interscience Publication, 2001; and Petursson, S. et al., "*Protecting Groups in Carbohydrate Chemistry,*" *J. Chem. Educ.,* 74(11), 1297 (1997).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874

(2004), normal phase silica chromatography, and supercritical fluid chromatography (SFC).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), normal phase silica chromatography, and supercritical fluid chromatography (SFC).

All solvents and reagents were obtained from commercial sources and used without further purification unless indicated otherwise. Anhydrous solvents were purchased and used as supplied. Reactions were monitored by thin-layer chromatography (TLC), visualizing with a UV lamp (254 nm) and $KMnO_4$ stain. NMR spectra were obtained on a Bruker Neo 400M spectrometer operating at 400 MHz. Chemical shifts are reported in parts per million (δ) from the tetramethysilane resonance in the indicated solvent. LC-Mass spectra were taken with Agilent 1260-6125B single quadrupole mass spectrometer using a Welch Biomate column (C18, 2.7 μm, 4.6*50 mm) or waters H-Class SQD2 system. The detection was by DAD (254 nm and 210 nm and 280 nm). Chiral HPLC was performed on the Waters acquity UPC2 system under base-containing on Daicel chiralpak AD-H (5 μm, 4.6*250 mm), Daicel chiralpak OD-H (5 μm, 4.6*250 mm), Daicel chiralpak IG-3 (3 μm, 4.6*150 mm), Chiral Technologies Europe AD-3 (3 μm, 3.0*150 mm) and Trefoil™ Technology Trefoil™ AMY1 (2.5 μm, 3.0*150 mm) or other specified columns. The detection was by DAD (254 nm). Preparative HPLC was performed on GILSON Trilution LC system using a Welch XB-C18 column (5 um, 21.2*150 mm). Flash chromatography was carried out on Biotage Isolera Prime system using Welch WelFlash flash columns (40-63 μm). The compounds synthesized are all with purity ≥95% unless otherwise specified.

Example 1: (R)—N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide

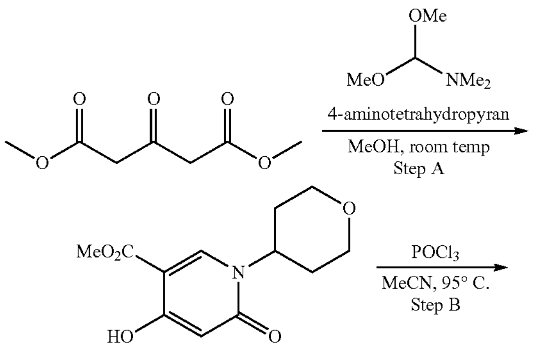

-continued

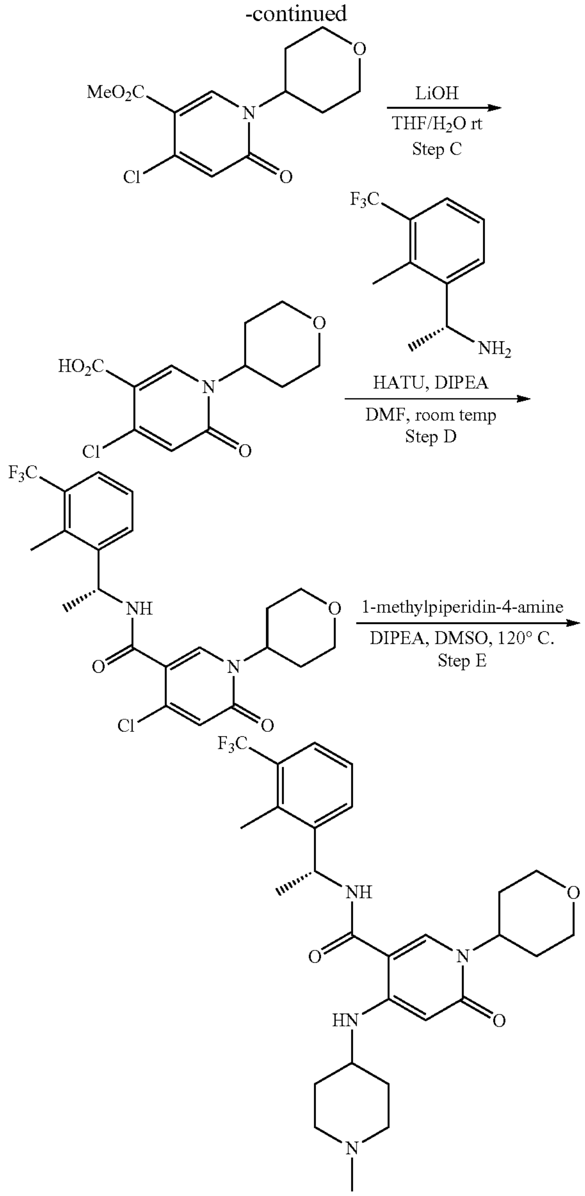

example 1

Step A: methyl 4-hydroxy-6-oxo-1-tetrahydropyran-4-yl-pyridine-3-carboxylate To a solution of dimethyl 3-oxopentanedioate (7.83 g, 44.9 mmol, 6.6 mL) in MeOH (30 mL) was added N,N-dimethylformamide dimethyl acetal (6.43 g, 53.9 mmol, 7.2 mL). The mixture was stirred at ambient temperature for 2 hr. 4-aminotetrahydropyran (5.00 g, 49.4 mmol) was added and the resulting mixture was stirred for 24 hr. The solvent was removed in vacuo and the residue was purified by silica gel chromatography (PE:EtOAc=1:1) to afford the title compound (3.6 g, 31% yield). MS obsd. (ESI+) 254.1 $[M+H]^+$.

Step B: methyl 4-chloro-6-oxo-1-tetrahydropyran-4-yl-pyridine-3-carboxylate To a solution of methyl 4-hydroxy-6-oxo-1-tetrahydropyran-4-yl-pyridine-3-carboxylate (2.0 g, 7.9 mmol) in acetonitrile (15 mL) was added phosphorus oxychloride (32.7 g, 213 mmol) at room temperature. The resulting mixture was stirred at 95° C. for 6 hr. The mixture was then concentrated under vacuum. The residue was treated with aqueous $Na_2CO_3$ and extracted with EtOAc (3×40 mL). The combined organic layers were washed with brine, dried over anhydrous sodium sulfate, filtered and concentrated under vacuum. The residue was purified by silica gel chromatography to afford the title compound (960 mg, 45% yield). MS obsd. (ESI+) $^{35}Cl/^{37}Cl$ 272.1/274.1 $[M+H]^+$.

Step C: 4-chloro-6-oxo-1-(tetrahydro-2H-pyran-4-yl)-1,6-dihydropyridine-3-carboxylic acid A solution of methyl 4-chloro-6-oxo-1-tetrahydropyran-4-yl-pyridine-3-carboxylate (2.0 g, 7.36 mmol) and LiOH (264 mg, 11.0 mmol) in THF (15.0 mL) and $H_2O$ (5.0 mL) was stirred at room temperature for 2 hr. The mixture was then concentrated under vacuum. The residue was dissolved in $H_2O$ (100 mL) and pH was adjusted to ~3. The mixture was extracted with EtOAc, dried over $Na_2SO_4$ and filtered. The filtrate was concentrated under vacuum to afford the title compound (1.82 g, crude). This material is used in subsequent steps without further purification. MS obsd. (ESI+) 258.1 $[M+H]^+$.

Step D: (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide To a solution of 4-chloro-6-oxo-1-(tetrahydro-2H-pyran-4-yl)-1,6-dihydropyridine-3-carboxylic acid (1.80 g, crude, assumed 7.0 mmol) in DMF (50 mL) was added HATU (4.0 g, 10.5 mmol) and the mixture was stirred for 30 minutes. Then (R)-1-(2-methyl-3-(trifluoromethyl)phenyl)ethan-1-amine (2.10 g, 10.5 mmol) and DIPEA (2.70 g, 20.9 mmol) were added and the mixture was stirred for 1 hr. The reaction was quenched with $H_2O$ and extracted with EtOAc. The combined organic layers were dried over anhydrous $Na_2SO_4$, filtered and concentrated. The residue was purified by silica gel chromatography (eluting with 0-6% MeOH in DCM) to afford the title compound (3.0 g). MS obsd. (ESI+) $^{35}Cl/^{37}Cl$ 443.5/445.2 $[M+H]^+$.

Step E: (R)—N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide (Example 1)

To a solution of (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (206 mg, 0.47 mmol) and 1-methylpiperidin-4-amine (80 mg, 0.70 mmol) in DMSO (4.2 mL) was added triethylamine (142 mg, 1.4 mmol). The reaction was stirred in a sealed vial in a microwave reactor at 120° C. for 10 hr. The mixture was then diluted with water and extracted with EtOAc (4×30 mL). The combined organic layers were dried over anhydrous $Na_2SO_4$, filtered and concentrated. The residue was purified by silica gel chromatography (eluting with 20-30% MeOH in DCM) to afford the title compound (150 mg, 61% yield). MS obsd. (ESI+) 521.6 $[M+H]^+$. $^1H$ NMR (400 MHz, DMSO-d6) δ: 8.75 (1H), 8.12 (2H), 7.71 (1H), 7.59 (1H), 7.43 (1H), 5.34 (1H), 5.26 (1H), 4.86 (1H), 4.02 (2H), 3.47 (2H), 3.22 (1H), 2.56 (2H), 2.46 (3H), 2.13 (3H), 2.05 (4H), 1.83 (2H), 1.66 (2H), 1.45 (3H), 1.41-1.27 (2H).

Example 2: (R)-4-((2-(dimethylamino)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

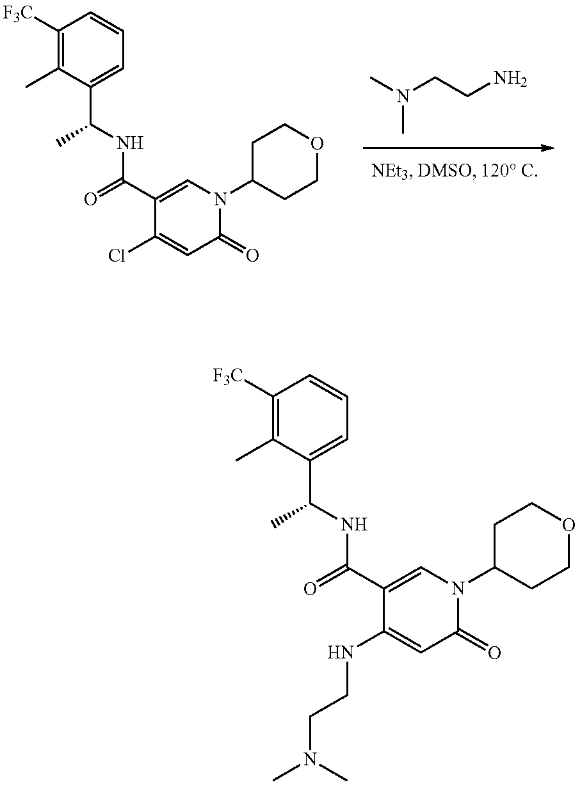

example 2

To a solution of (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (67 mg, 0.15 mmol) and N',N'-dimethylethane-1,2-diamine (20 mg, 0.23 mmol) in DMSO (1.5 mL) was added triethylamine (46 mg, 0.45 mmol). The reaction was stirred in a sealed tube in a microwave reactor for 6 hr at 120° C. The mixture was then diluted with $H_2O$ and extracted with EtOAc (4*30 mL). The combined organic layers were dried over $Na_2SO_4$, filtered and concentrated. The residue was purified by silica gel chromatography (eluting with 5-10% MeOH in DCM) followed by preparative HPLC (MeCN/0.1% aqueous $NH_4HCO_3$) to afford (R)-4-((2-(dimethylamino)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide (19.7 mg, 26% yield). MS obsd. (ESI+) 495.2 $(M+H)^+$. $^1H$ NMR (400 MHz, DMSO-d6) δ: 8.71 (1H), 8.07 (2H), 7.71 (1H), 7.58 (1H), 7.43 (1H), 5.32 (1H), 5.21 (1H), 4.86 (1H), 4.02 (2H), 3.47 (2H), 3.04 (2H), 2.46 (3H), 2.38 (2H), 2.11 (6H), 2.05 (2H), 1.65 (2H), 1.45 (3H).

The following examples can be synthesized in an analogous fashion to example 2 starting with (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide and varying the amine reagent used.

| Example number | Compound Structure | Name | Amine reagent used | MS obsd (ESI+) $[M + H]^+$ |
|---|---|---|---|---|
| 3 | 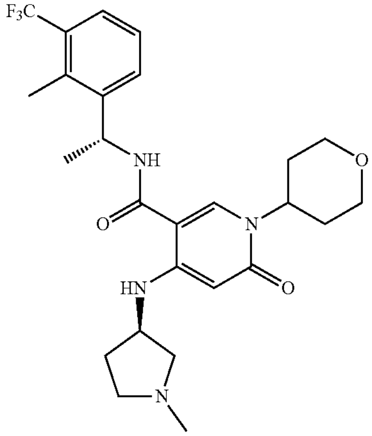 [SMILES: Cc1c([C@@H](C)NC(=O)c2cn(C3CCOCC3)c(=O)cc2N[C@@H]2CCN(C)C2)cccc1C(F)(F)F] | N-((R)-1-(2-methyl-3-(trifluoromethyl)phenyl)ethyl)-4-(((R)-1-methylpyrrolidin-3-yl)amino)-6-oxo-1-(tetrahydro-2H-pyran-4-yl)-1,6-dihydropyridine-3-carboxamide | 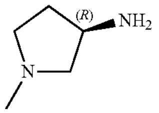 | 507.2 |
| 4 | 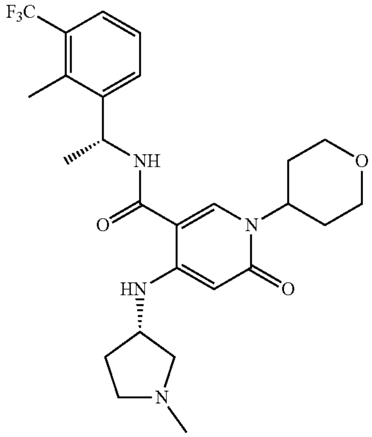 [SMILES: Cc1c([C@@H](C)NC(=O)c2cn(C3CCOCC3)c(=O)cc2N[C@H]2CCN(C)C2)cccc1C(F)(F)F] | N-((R)-1-(2-methyl-3-(trifluoromethyl)phenyl)ethyl)-4-(((S)-1-methylpyrrolidin-3-yl)amino)-6-oxo-1-(tetrahydro-2H-pyran-4-yl)-1,6-dihydropyridine-3-carboxamide | 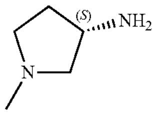 | 507.2 |
| 5 | 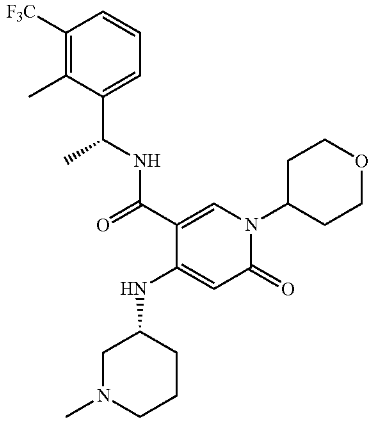 [SMILES: Cc1c([C@@H](C)NC(=O)c2cn(C3CCOCC3)c(=O)cc2N[C@@H]2CCCN(C)C2)cccc1C(F)(F)F] | N-((R)-1-(2-methyl-3-(trifluoromethyl)phenyl)ethyl)-4-(((R)-1-methylpiperidin-3-yl)amino)-6-oxo-1-(tetrahydro-2H-pyran-4-yl)-1,6-dihydropyridine-3-carboxamide | 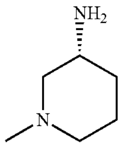 | 521.2 |

-continued

| Example number | Compound Structure | Name | Amine reagent used | MS obsd (ESI+) $[M + H]^+$ |
|---|---|---|---|---|
| 6 | 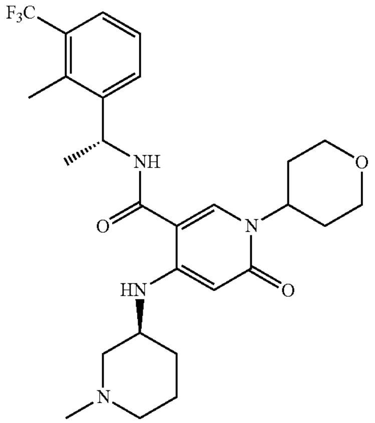 [SMILES: Cc1c([C@@H](C)NC(=O)c2cn(C3CCOCC3)c(=O)cc2N[C@H]2CCCN(C)C2)cccc1C(F)(F)F] | N-((R)-1-(2-methyl-3-(trifluoromethyl)phenyl)ethyl)-4-(((S)-1-methylpiperidin-3-yl)amino)-6-oxo-1-(tetrahydro-2H-pyran-4-yl)-1,6-dihydropyridine-3-carboxamide | 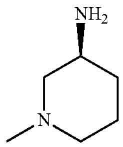 | 521.2 |
| 7 | 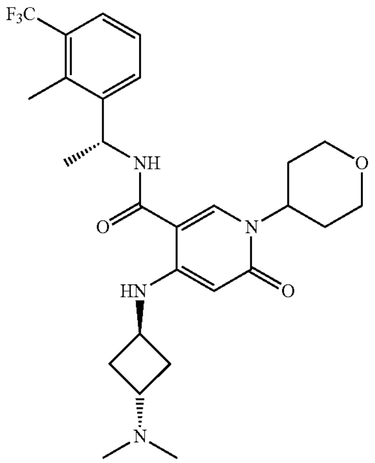 | 4-(((1r,3R)-3-(dimethylamino)cyclobutyl)amino)-N-((R)-1-(2-methyl-3-(trifluoromethyl)phenyl)ethyl)-6-oxo-1-(tetrahydro-2H-pyran-4-yl)-1,6-dihydropyridine-3-carboxamide | 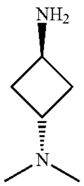 | 521.2 |
| 8 | 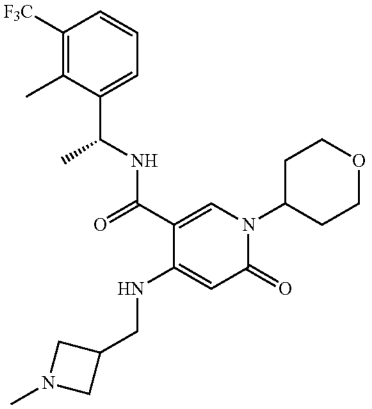 [SMILES: Cc1c([C@@H](C)NC(=O)c2cn(C3CCOCC3)c(=O)cc2NCC2CN(C)C2)cccc1C(F)(F)F] | (R)-N-(1-(2-methyl-3-(trifluoromethyl)phenyl)ethyl)-4-(((1-methylazetidin-3-yl)methyl)amino)-6-oxo-1-(tetrahydro-2H-pyran-4-yl)-1,6-dihydropyridine-3-carboxamide | 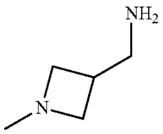 | 507.5 |

-continued

| Example number | Compound Structure | Name | Amine reagent used | MS obsd (ESI+) [M + H]+ |
|---|---|---|---|---|
| 9 | 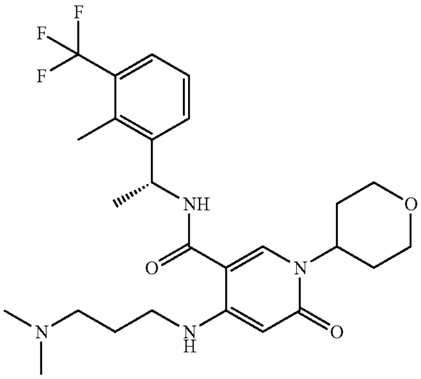 [SMILES: Cc1c([C@@H](C)NC(=O)c2cn(C3CCOCC3)c(=O)cc2NCCCN(C)C)cccc1C(F)(F)F] | (R)-4-((3-(dimethylamino)propyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide | 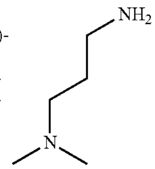 | 509.6 |
| 10 | 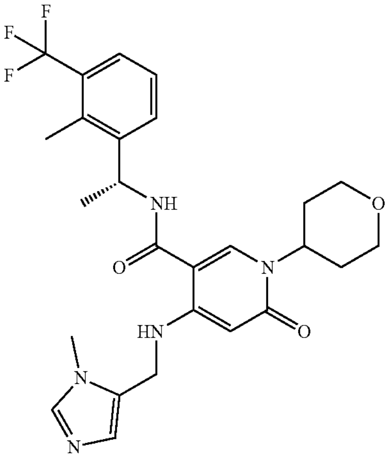 [SMILES: Cc1c([C@@H](C)NC(=O)c2cn(C3CCOCC3)c(=O)cc2NCc2cncn2C)cccc1C(F)(F)F] | (R)-4-(((1-methyl-1H-imidazol-5-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide | 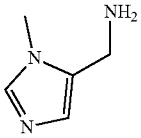 | 518.2 |
| 11 | 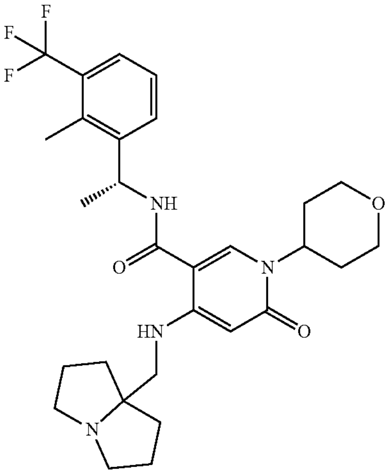 [SMILES: Cc1c([C@@H](C)NC(=O)c2cn(C3CCOCC3)c(=O)cc2NCC23CCCN2CCC3)cccc1C(F)(F)F] | (R)-N-(1-(2-methyl-3-(trifluoromethyl)phenyl)ethyl)-6-oxo-4-(((tetrahydro-1H-pyrrolizin-7a(5H)-yl)methyl)amino)-1-(tetrahydro-2H-pyran-4-yl)-1,6-dihydropyridine-3-carboxamide | 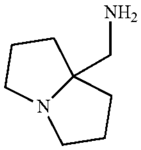 | 547.3 |

Example 12: (R)—N-(1-(2-methyl-3-(trifluoromethyl)phenyl)ethyl)-4-(methylamino)-6-oxo-1-(tetrahydro-2H-pyran-4-yl)-1,6-dihydropyridine-3-carboxamide

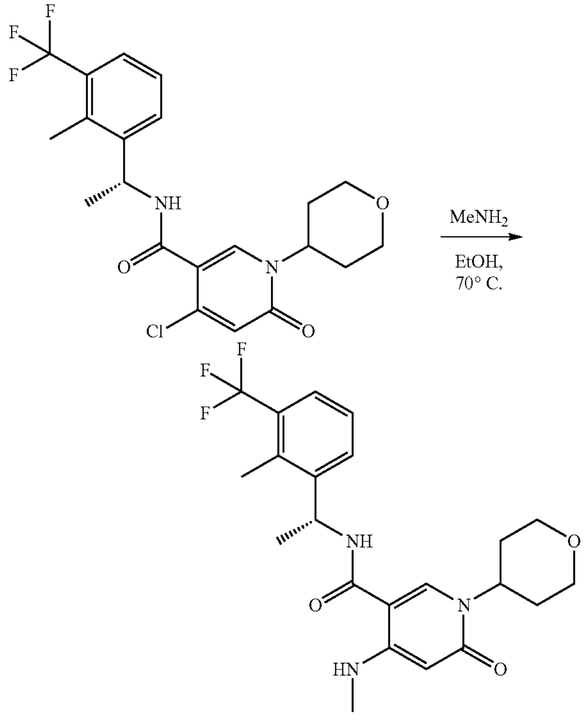

Example 12

To a round bottom flask, (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (35 mg, 0.079 mmol) and methylamine (33% in EtOH, 1 mL) were added and the mixture was stirred at 70° C. for 2 hr. The solvent was evaporated and the residue was purified by preparative HPLC (ACN/water/0.1% $NH_4CO_3$) to afford the title compound (20.3 mg, 58% yield). MS obsd. (ESI+) 438.5 $[M+H]^+$.

Example 13: 4-(((1S,3S)-3-hydroxycyclopentyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide

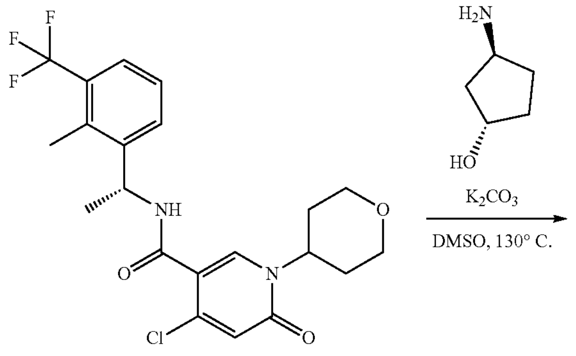

-continued

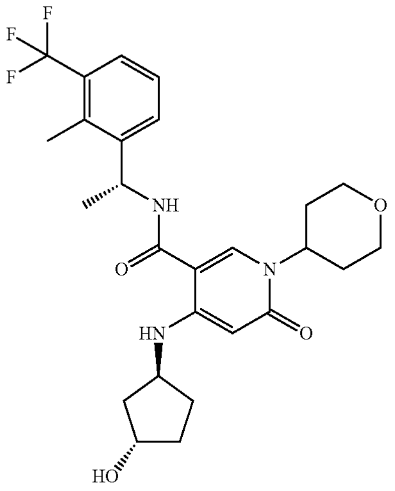

Example 13

To a mixture of (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (50 mg, 0.11 mmol) in DMSO (2 mL) was added (1S,3S)-3-aminocyclopentanol (11.4 mg, 0.11 mmol), and potassium carbonate (46.8 mg, 0.34 mmol). The mixture was stirred at 130° C. for 1 hr under microwave heating. The mixture was cooled to rt and diluted with EtOAc (6 mL). The organic mixture was washed with $H_2O$ (4 mL×3) and brine (4 mL×3), dried over sodium sulfate, filtered and concentrated. The residue was purified by Preparative HPLC (acetonitrile: 0.1% $NH_4HCO_3$ in water=10% to 95%) to provide the title compound (15.8 mg, 28% yield). MS obsd. (ESI+) 508.5 $[M+H]^+$. $^1H$ NMR (400 MHz, DMSO-$d_6$) δ 8.75 (1H), 8.12 (2H), 7.70 (1H), 7.58 (1H), 7.43 (1H), 5.31 (1H), 5.19 (1H), 4.87 (1H), 4.56 (1H), 4.16 (1H), 4.02 (2H), 3.78 (1H), 3.48 (2H), 2.45 (3H), 2.17-1.98 (3H), 1.93 (1H), 1.87-1.74 (1H), 1.66 (2H), 1.50 (1H), 1.44 (3H), 1.33-1.25 (1H).

Example 14: 4-(((1R,3R)-3-hydroxycyclopentyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide

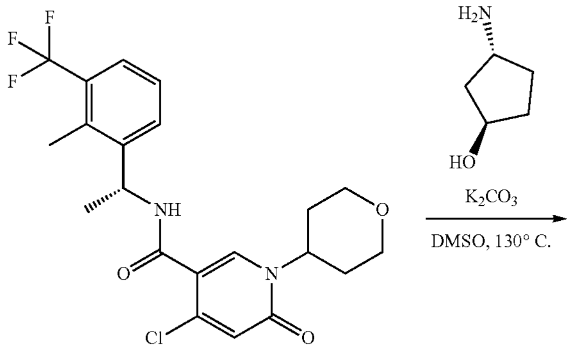

-continued

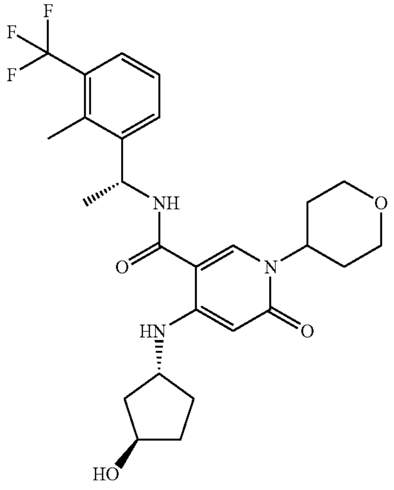

Example 14

Prepared according to an analogous procedure to example 13 using (1R,3R)-3-aminocyclopentanol in place of (1S,3S)-3-aminocyclopentanol. MS obsd. (ESI+) 508.4 $[M+H]^+$.

Example 15: (R)—N-(1-(2-methyl-3-(trifluoromethyl)phenyl)ethyl)-6-oxo-1-(tetrahydro-2H-pyran-4-yl)-4-((1-(2,2,2-trifluoroethyl)piperidin-4-yl)amino)-1,6-dihydropyridine-3-carboxamide

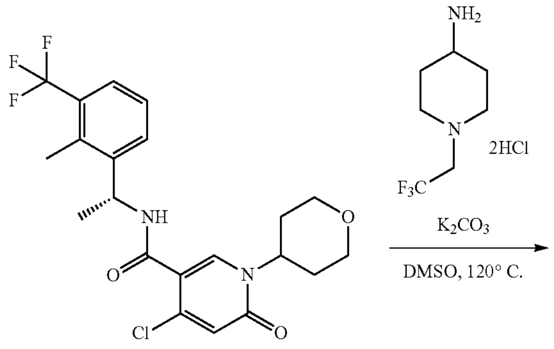

-continued

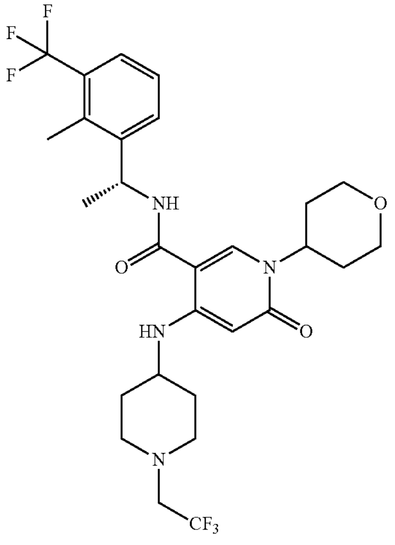

Example 15

1-(2,2,2-trifluoroethyl)piperidin-4-amine; dihydrochloride (57.60 mg, 0.23 mmol) and potassium carbonate (62.4 mg, 0.45 mmol) were dissolved in DMSO (5 mL) at room temperature, and the mixture was stirred at this temperature for 5 minutes. Then (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (50 mg, 0.11 mmol) was added to the mixture. The resulting solution was stirred at 120° C. for 24 hr. Then the mixture was poured into water (50 mL) and extracted with EtOAc (30 mL×3). The combined organic layers were dried over sodium sulfate, filtered and concentrated. The residue was purified by column chromatography (0%-10% MeOH in DCM) to afford the title compound (6.30 mg, 4% yield). MS obsd. (ESI+) 589.6 $[M+H]^+$.

Example 16: (R)-4-((1-(2-fluoroethyl)piperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

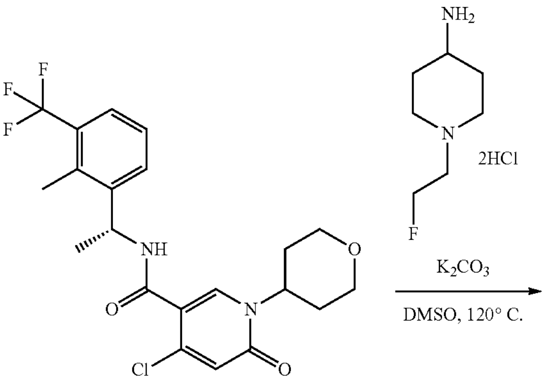

-continued

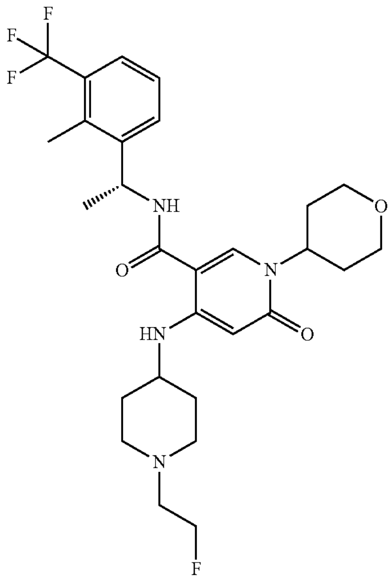

Example 16

Prepared according to an analogous procedure as example 15 using 1-(2-fluoroethyl)piperidin-4-amine dihydrochloride. MS obsd. (ESI+) 553.7 $[M+H]^+$.

Example 17: (R)-5-bromo-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide -continued

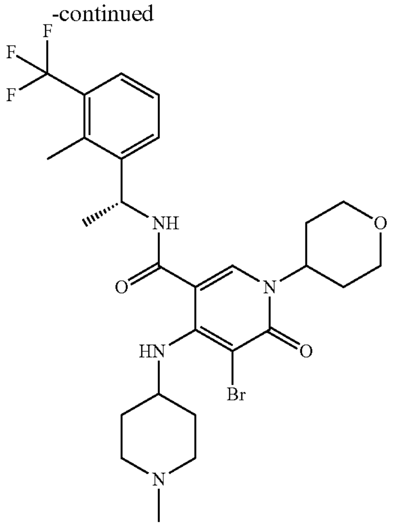

Example 17

To a solution of (R)—N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide (200 mg, 0.38 mmol) in AcOH (5 mL) was added molecular bromine (92 mg, 0.57 mmol) and potassium acetate (57 mg, 0.57 mmol). The mixture was stirred at rt for 1 hr. The reaction mixture was then concentrated in vacuo. The residue was purified by preparative TLC (eluted with 10:1 DCM:MeOH) to afford the title compound (120 mg, 53% yield). MS obsd. (ESI+) $^{79}Br/^{81}Br$ 599.2/601.2 $[M+H]^+$.

Example 18: (R)-5-methoxy-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide

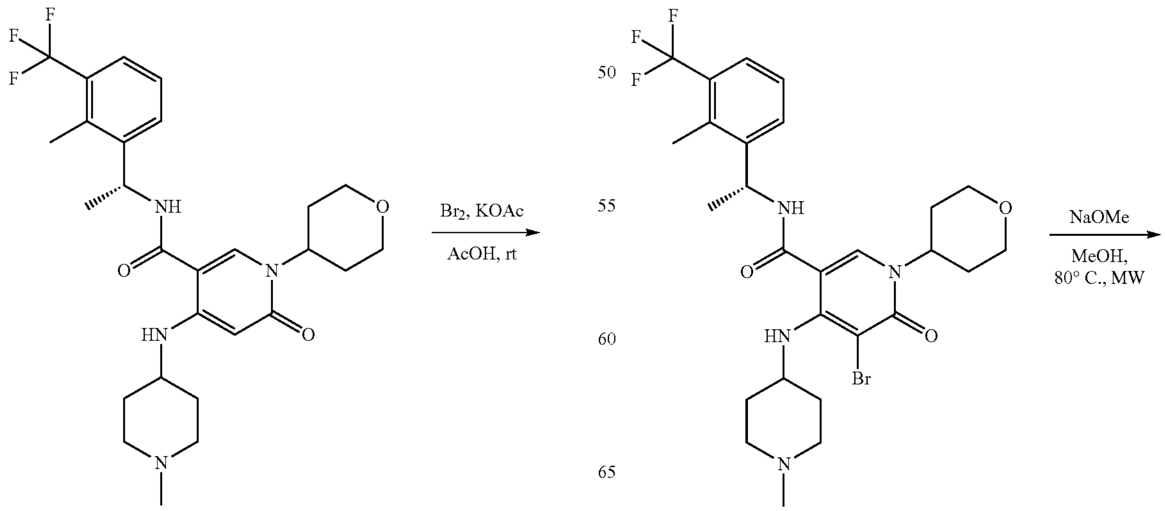

-continued

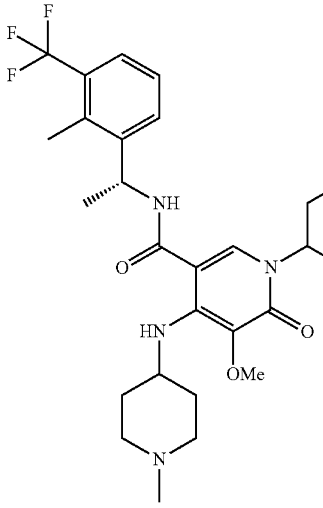

example 18

To a solution of (R)-5-bromo-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide (40 mg, 0.066 mmol) in MeOH (3.0 mL) was added sodium methoxide (72 mg, 1.33 mmol) at room temperature. The reaction was heated in a sealed tube in a microwave reactor at 80° C. for 2 hr. The mixture was then quenched with saturated aqueous $NH_4Cl$ and extracted with EtOAc. The organic layer was dried over anhydrous $Na_2SO_4$, filtered and concentrated. The residue was purified by silica gel chromatography (eluting with 2% MeOH in DCM) to afford the title compound (7.0 mg, 18% yield). MS obsd. (ESI+) 551.3 $[M+H]^+$.

Example 19: (R)-5-methyl-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide

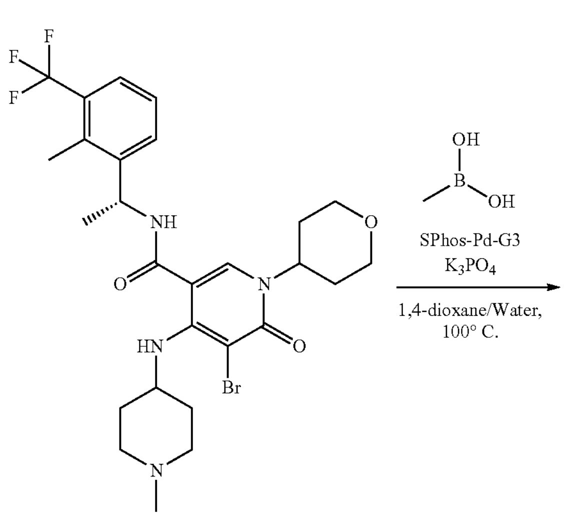

-continued

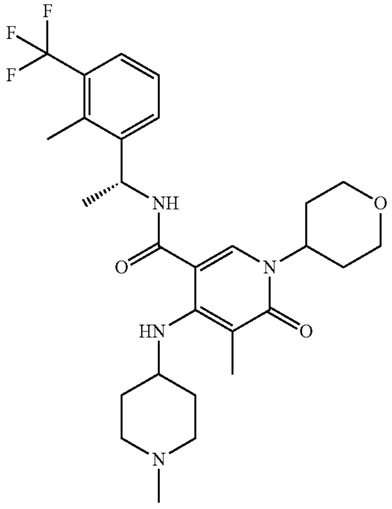

example 19

To a solution of (R)-5-bromo-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide (40 mg, 0.066 mmol) in water (0.2 mL) and 1,4-dioxane (0.8 mL) was added SPhos-Pd-G3 (10.4 mg, 0.013 mmol) and methylboronic acid (12 mg, 0.2 mmol) at rt. The mixture was stirred at 100° C. for 16 hr in a sealed tube. The reaction mixture was concentrated to dryness, and the residue was purified by preparative TLC (10% MeOH in DCM) followed by preparative HPLC (ACN/water/0.1% NH4HCO3) to afford the title compound (2.25 mg, 6% yield). MS obsd. (ESI+) 535.6 $[M+H]^+$.

Example 20: (R)-5-cyano-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide

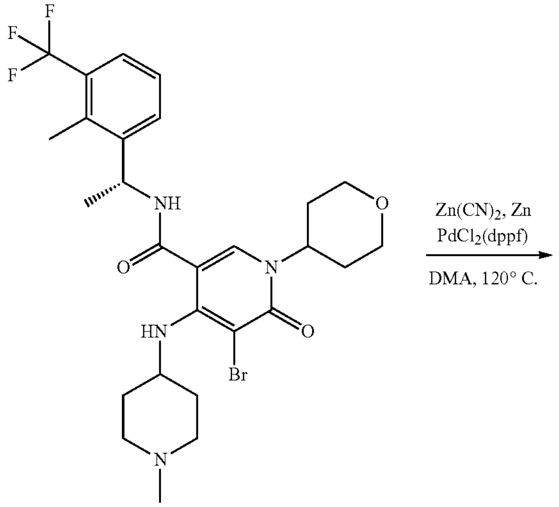

-continued

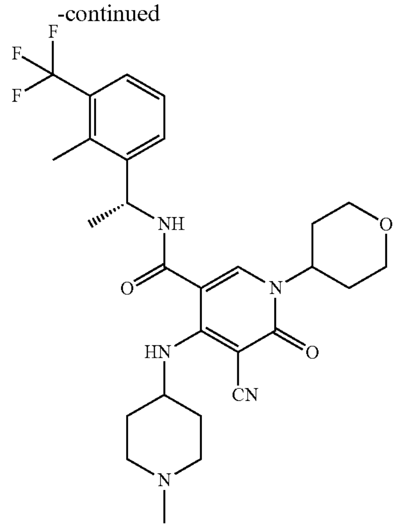

example 20

To a solution of (R)-5-bromo-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide (50 mg, 0.08 mmol) in N,N-dimethylacetamide (0.99 mL) was added zinc cyanide (29.3 mg, 0.25 mmol), zinc powder (0.5 mg, 0.08 mmol) and Pd(dppf)$Cl_2$ (18 mg, 0.025 mmol) at rt. The reaction mixture was then stirred at 120° C. for 4 hr under $N_2$ atmosphere. The mixture was diluted with water and extracted with DCM (50 mL×3). The combined organic layers were dried over $Na_2SO_4$ filtered and concentrated. The residue was purified by preparative TLC (DCM/MeOH=10/1) followed by preparative HPLC (ACN/water/0.1% $NH_4HCO_3$) to afford the title compound (4 mg, 9% yield). MS obsd. (ESI+) 546.2 $[M+H]^+$.

Example 21: (R)-4-((2-methyl-2-azaspiro[3.3]heptan-6-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

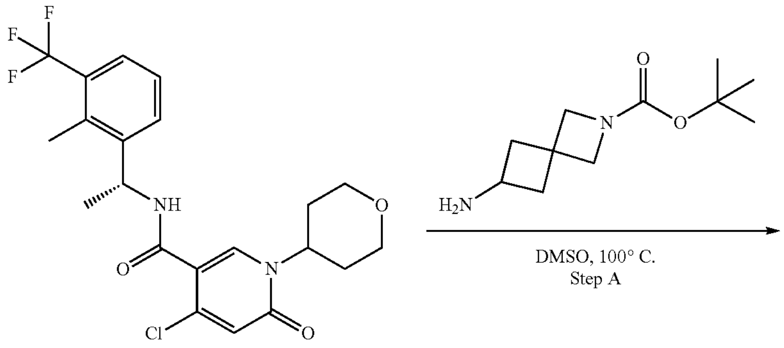

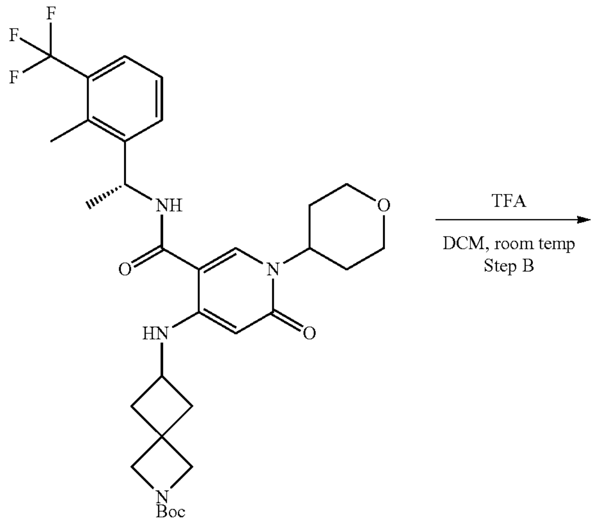

-continued

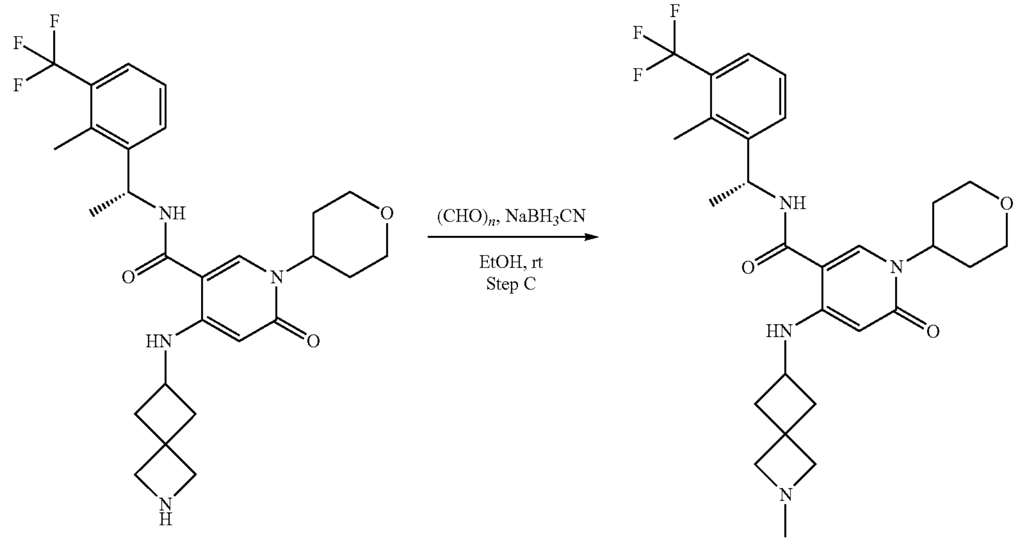

example 21

Step A: tert-butyl (R)-6-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)amino)-2-azaspiro[3.3]heptane-2-carboxylate A mixture of (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (50 mg, 0.11 mmol) and tert-butyl 6-amino-2-azaspiro[3.3]heptane-2-carboxylate (71 mg, 0.34 mmol) in DMSO (1 mL) was sealed in a microwave tube and heated to 100° C. for 16 hours. The mixture was diluted with water (80 mL) and extracted with EtOAc (50 mL×3). The combined organic layers were concentrated in vacuo and the residue was purified by silica gel chromatography (eluting with 0-20% MeOH in DCM) to afford the title compound (65 mg, 93% yield). MS obsd. (ESI+) 619.7 $(M+H)^+$.

Step B: (R)-4-((2-azaspiro[3.3]heptan-6-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide A mixture of tert-butyl (R)-6-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)amino)-2-azaspiro[3.3]heptane-2-carboxylate (65 mg, 0.11 mmol) in TFA (5.0 mL) and DCM (5.0 mL) was stirred for 30 minutes at room temperature. The reaction mixture was then concentrated in vacuo. The residue was diluted with water (50 mL) and the resulting mixture was adjusted to pH~10 with aqueous sodium bicarbonate. The aqueous phase was extracted with EtOAc (50 mL×3). The combined organic layers were washed with brine, dried over $Na_2SO_4$ and concentrated under vacuum to afford the title compound (48 mg, crude). This material was used without further purification. MS obsd. (ESI+) 519.6 $(M+H)^+$.

Step C: (R)-4-((2-methyl-2-azaspiro[3.3]heptan-6-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide A mixture of (R)-4-((2-azaspiro[3.3]heptan-6-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide (48 mg, crude, assumed 0.09 mmol), paraformaldehyde (27 mg) and sodium cyanoborohydride (29 mg, 0.46 mmol) in EtOH (5 mL) was stirred for 16 hours at room temperature. The resulting mixture was then poured into water and extracted with EtOAc (100 mL×3). The organic layers were washed with brine, dried over $Na_2SO_4$ and concentrated under vacuum. The residue was purified by preparative TLC (10% MeOH in DCM) to afford the title compound (24 mg, 50% yield). MS obsd. (ESI+) 533.2 $(M+H)^+$. $^1H$ NMR (400 MHz, DMSO-d6) δ 8.80 (1H), 8.21 (1H), 8.15 (1H), 7.70 (1H), 7.58 (1H), 7.43 (1H), 5.36-5.24 (1H), 5.13 (1H), 4.85 (1H), 4.02 (4H), 3.86 (2H), 3.76-3.66 (1H), 3.47 (2H), 2.74-2.57 (5H), 2.46 (3H), 2.03 (4H), 1.65 (2H), 1.45 (3H).

The following examples can be synthesized in an analogous fashion to example 21 (steps A-C) starting with (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide and modifying the amine reagent used in step A.

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 22 | 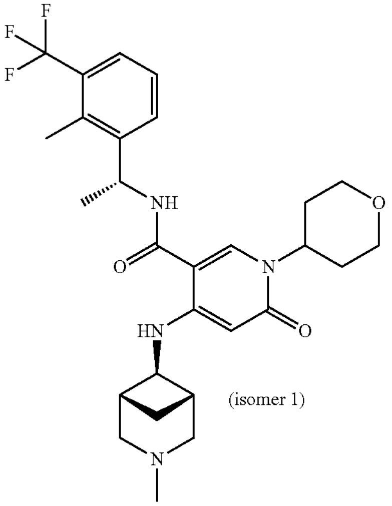 [SMILES: Cc1c([C@@H](C)NC(=O)c2cn(C3CCOCC3)c(=O)cc2N[C@@H]2[C@@H]3C[C@H]2CN(C)C3)cccc1C(F)(F)F] (isomer 1) | N-((R)-1-(2-methyl-3-(trifluoromethyl)phenyl)ethyl)-4-(((1R,5S,6s)-3-methyl-3-azabicyclo[3.1.1]heptan-6-yl)amino)-6-oxo-1-(tetrahydro-2H-pyran-4-yl)-1,6-dihydropyridine-3-carboxamide (arbitrarily assigned diastereomer 1) Analytical chiral UPCC: (Column: OD-3, 4.6 * 100 mm 3 um, Flow rate: 3.0 mL/min, Co-solvent:EtOH (1% 7M NH3 in MeOH), Temp 40° C.) Retention time = 1.7 min. | 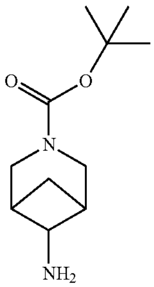 | 533.2 |
| 23 | 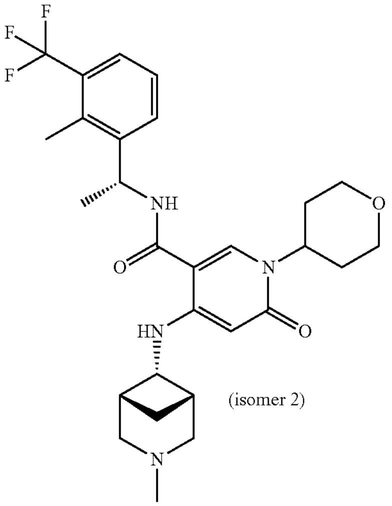 [SMILES: Cc1c([C@@H](C)NC(=O)c2cn(C3CCOCC3)c(=O)cc2N[C@H]2[C@@H]3C[C@H]2CN(C)C3)cccc1C(F)(F)F] (isomer 2) | N-((R)-1-(2-methyl-3-(trifluoromethyl)phenyl)ethyl)-4-(((1R,5S,6r)-3-methyl-3-azabicyclo[3.1.1]heptan-6-yl)amino)-6-oxo-1-(tetrahydro-2H-pyran-4-yl)-1,6-dihydropyridine-3-carboxamide (arbitrarily assigned diastereomer 2) Analytical chiral UPCC: (Column: OD-3, 4.6 * 100 mm 3 um, Flow rate: 3.0 mL/min, Co-solvent:EtOH (1% 7M NH3 in MeOH), Temp 40° C.) Retention time = 2.4 min. | 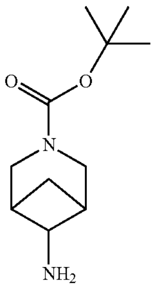 | 533.2 |
| 24 | 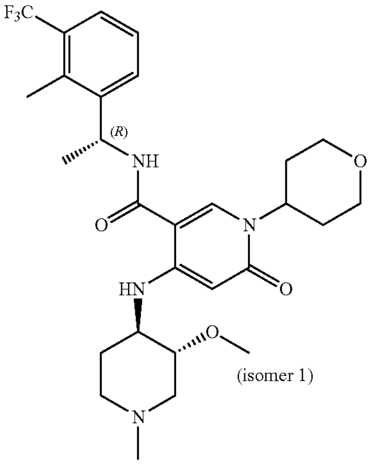 (isomer 1) | 4-(((3R,4R)-3-methoxy-1-methylpiperidin-4-yl)amino)-N-((R)-1-(2-methyl-3-(trifluoromethyl)phenyl)ethyl)-6-oxo-1-(tetrahydro-2H-pyran-4-yl)-1,6-dihydropyridine-3-carboxamide (arbitrarily assigned isomer 1) Analytical chiral UPCC: (Column: OD-3, 4.6 * 100 mm 3 um, Flow rate: 3.0 mL/min, Co-solvent: EtOH (1% 7M NH3 in MeOH), Temp 40° C.) Retention time = 1.3 min. | 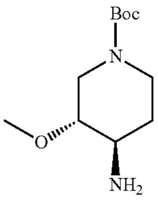 trans (racemate) | 551.2 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 25 | 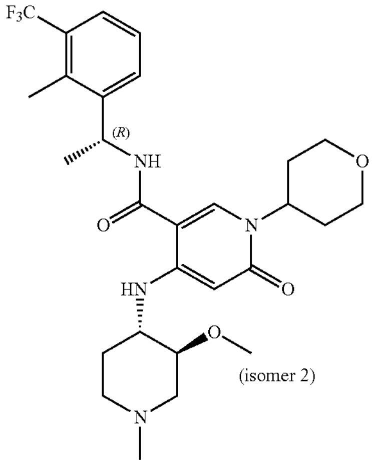 (isomer 2) | 4-(((3S,4S)-3-methoxy-1-methylpiperidin-4-yl)amino)-N-((R)-1-(2-methyl-3-(trifluoromethyl)phenyl)ethyl)-6-oxo-1-(tetrahydro-2H-pyran-4-yl)-1,6-dihydropyridine-3-carboxamide (arbitrarily assigned isomer 2) Analytical chiral UPCC: (Column: OD-3, 4.6 * 100 mm 3 um, Flow rate: 3.0 mL/min, Co-solvent: EtOH (1% 7M NH3 in MeOH), Temp 40° C.) Retention time = 2.9 min. | 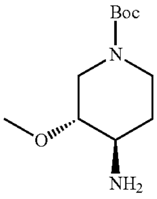 trans (racemate) | 551.2 |
| 26 | 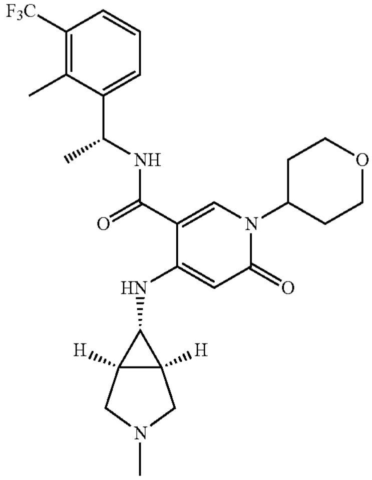 [SMILES: Cc1c([C@@H](C)NC(=O)c2cn(C3CCOCC3)c(=O)cc2N[C@H]2[C@@H]3CN(C)C[C@@H]32)cccc1C(F)(F)F] | N-((R)-1-(2-methyl-3-(trifluoromethyl)phenyl)ethyl)-4-(((1R,5S,6s)-3-methyl-3-azabicyclo[3.1.0]hexan-6-yl)amino)-6-oxo-1-(tetrahydro-2H-pyran-4-yl)-1,6-dihydropyridine-3-carboxamide | 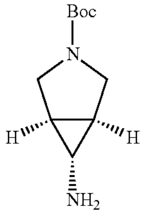 | 519.6 |
| 27 | 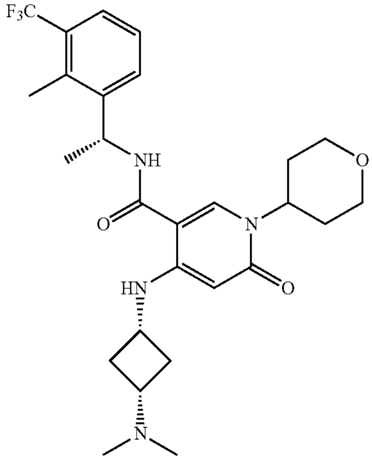 [SMILES: Cc1c([C@@H](C)NC(=O)c2cn(C3CCOCC3)c(=O)cc2N[C@H]2C[C@@H](N(C)C)C2)cccc1C(F)(F)F] | 4-(((1s,3S)-3-(dimethylamino)cyclobutyl)amino)-N-((R)-1-(2-methyl-3-(trifluoromethyl)phenyl)ethyl)-6-oxo-1-(tetrahydro-2H-pyran-4-yl)-1,6-dihydropyridine-3-carboxamide | 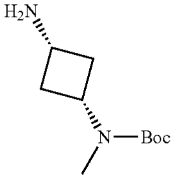 | 521.2 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 28 | 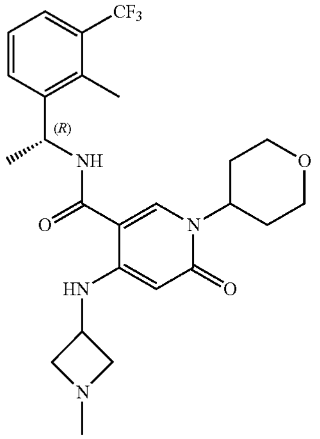 | (R)-N-(1-(2-methyl-3-(trifluoromethyl)phenyl)ethyl)-4-((1-methylazetidin-3-yl)amino)-6-oxo-1-(tetrahydro-2H-pyran-4-yl)-1,6-dihydropyridine-3-carboxamide | 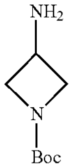 | 493.5 |
| 29 | 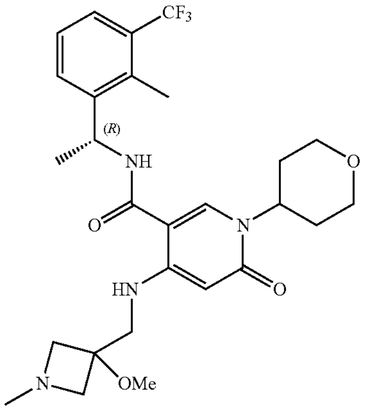 | (R)-4-(((3-methoxy-1-methylazetidin-3-yl)methyl)amino)-N-(1-(2-methyl-3-(trifluoromethyl)phenyl) ethyl)-6-oxo-1-(tetrahydro-2H-pyran-4-yl)-1,6-dihydropyridine-3-carboxamide | 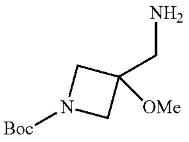 [SMILES: COC1(CN)CN(C(=O)OC(C)(C)C)C1] | 537.7 |
| 30 | 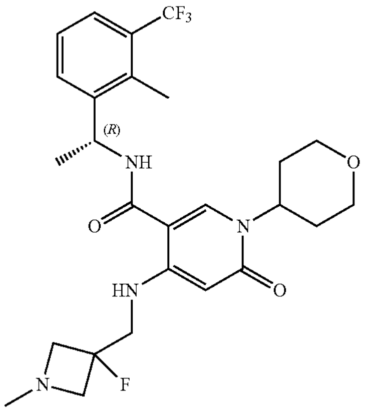 | (R)-4-(((3-fluoro-1-methylazetidin-3-yl)methyl)amino)-N-(1-(2-methyl-3-(trifluoromethyl)phenyl) ethyl)-6-oxo-1-(tetrahydro-2H-pyran-4-yl)-1,6-dihydropyridine-3-carboxamide | 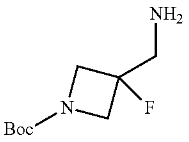 [SMILES: CC(C)(C)OC(=O)N1CC(F)(CN)C1] | 525.7 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 31 | 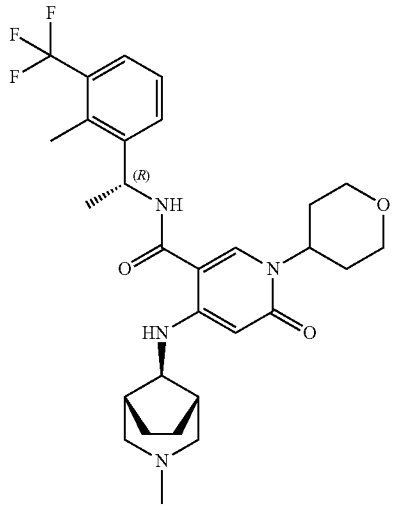 (isomer 1) | N-((R)-1-(2-methyl-3-(trifluoromethyl)phenyl)ethyl)-4-(((1R,5S,8s)-3-methyl-3-azabicyclo[3.2.1]octan-8-yl)amino)-6-oxo-1-(tetrahydro-2H-pyran-4-yl)-1,6-dihydropyridine-3-carboxamide (arbitrarily assigned diastereomer 1) Analytical chiral UPCC: (Column: Cellulose-SC, 4.6 * 100 mm 3 um, Flow rate: 3.0 mL/min, Co-solvent:EtOH (0.2% 7M NH3 in MeOH), Temp 40° C.) Retention time = 1.1 min. | 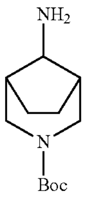 [SMILES: CC(C)(C)OC(=O)N1CC2CCC(C1)C2N] | 547.5 |
| 32 | 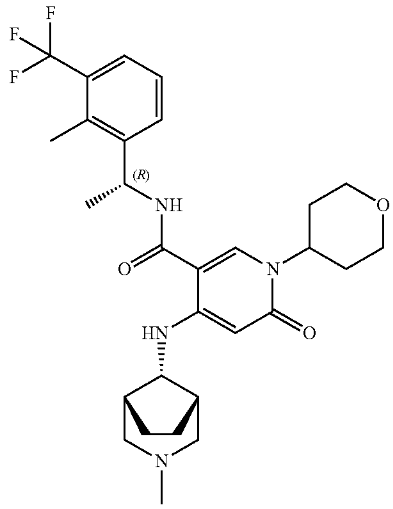 (isomer 2) | N-((R)-1-(2-methyl-3-(trifluoromethyl)phenyl)ethyl)-4-(((1R,5S,8r)-3-methyl-3-azabicyclo[3.2.1]octan-8-yl)amino)-6-oxo-1-(tetrahydro-2H-pyran-4-yl)-1,6-dihydropyridine-3-carboxamide (arbitrarily assigned diastereomer 2) Analytical chiral UPCC: (Column: Cellulose-SC, 4.6 * 100 mm 3 um, Flow rate: 3.0 mL/min, Co-solvent: EtOH (0.2% 7M NH3 in MeOH), Temp 40° C.) Retention time = 1.5 min. | 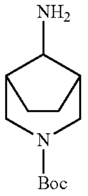 [SMILES: CC(C)(C)OC(=O)N1CC2CCC(C1)C2N] | 547.5 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 33 | 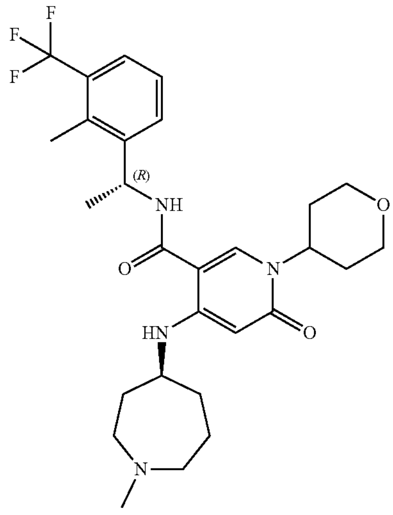 (diastereomer 1) | N-((R)-1-(2-methyl-3-(trifluoromethyl)phenyl)ethyl)-4-(((S)-1-methylazepan-4-yl)amino)-6-oxo-1-(tetrahydro-2H-pyran-4-yl)-1,6-dihydropyridine-3-carboxamide (arbitrarily assigned diastereomer 1) Analytical chiral UPCC: (Column: Cellulose-SC, 4.6 * 100 mm 3 um, Flow rate: 3.0 mL/min, Co-solvent:EtOH (1% 7M NH3 in MeOH), Temp 40° C.) Retention time = 2.8 min. | 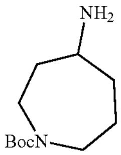 [SMILES: CC(C)(C)OC(=O)N1CCCC(N)CC1] | 535.5 |
| 34 | 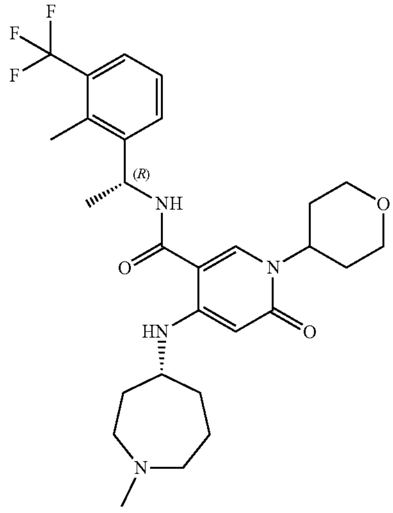 (diastereomer 2) | N-((R)-1-(2-methyl-3-(trifluoromethyl)phenyl)ethyl)-4-(((R)-1-methylazepan-4-yl)amino)-6-oxo-1-(tetrahydro-2H-pyran-4-yl)-1,6-dihydropyridine-3-carboxamide (arbitrarily assigned diastereomer 2) Analytical chiralUPCC: (Column: Cellulose-SC, 4.6 * 100 mm 3 um, Flow rate: 3.0 mL/min, Co-solvent: EtOH (1% 7M NH3 in MeOH), Temp 40° C.) Retention time = 3.2 min. | 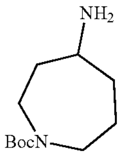 [SMILES: CC(C)(C)OC(=O)N1CCCC(N)CC1] | 535.6 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 35 | 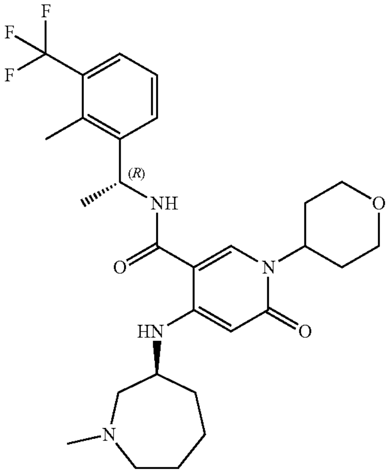 | N-((R)-1-(2-methyl-3-(trifluoromethyl)phenyl)ethyl)-4-(((S)-1-methylazepan-3-yl)amino)-6-oxo-1-(tetrahydro-2H-pyran-4-yl)-1,6-dihydropyridine-3-carboxamide | 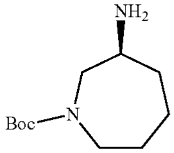 [SMILES: CC(C)(C)OC(=O)N1CCCC[C@H](N)C1] | 535.7 |
| 36 | 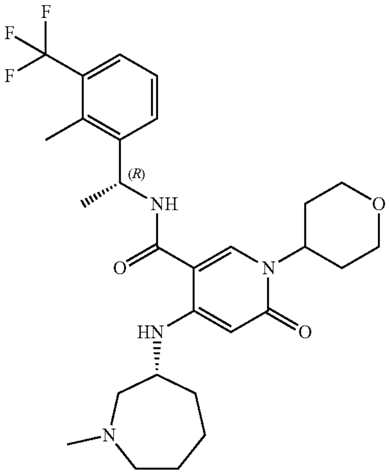 | N-((R)-1-(2-methyl-3-(trifluoromethyl)phenyl)ethyl)-4-(((R)-1-methylazepan-3-yl)amino)-6-oxo-1-(tetrahydro-2H-pyran-4-yl)-1,6-dihydropyridine-3-carboxamide | 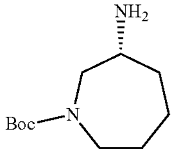 [SMILES: CC(C)(C)OC(=O)N1CCCC[C@@H](N)C1] | 535.7 |
| 37 | 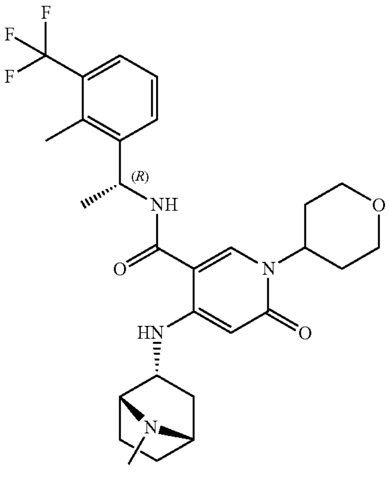 (Isomer 1) | N-((R)-1-(2-methyl-3-(trifluoromethyl)phenyl)ethyl)-4-(((1R,2R,4S)-7-methyl-7-azabicyclo[2.2.1]heptan-2-yl)amino)-6-oxo-1-(tetrahydro-2H-pyran-4-yl)-1,6-dihydropyridine-3-carboxamide (arbitrarily assigned diastereomer 1) Analytical chiral UPCC: (Column: AS-3, 4.6 * 100 mm 3 um, Flow rate: 3.0 mL/min, Co-solvent: EtOH (1% 7M NH3 in MeOH), Temp 40° C.) Retention time = 2.6 min. | 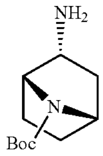 (Racemate) | 533.6 |

-continued

| Example number | Compound Structure | Compound Name (Analytical chiral UPCC retention time for cases where diastereomers are obtained and separated) | Amine reagent used | MS obsd (ESI+) $[M + H]^+$ |
|---|---|---|---|---|
| 38 | 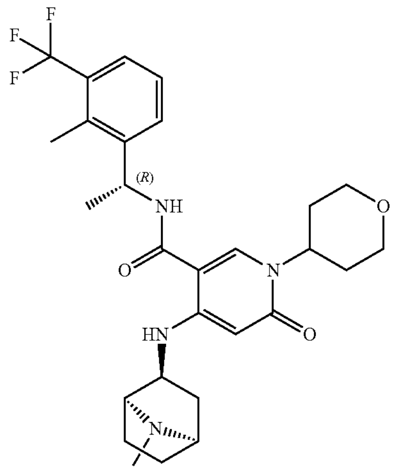 (isomer 2) | N-((R)-1-(2-methyl-3-(trifluoromethyl)phenyl)ethyl)-4-(((1S,2S,4R)-7-methyl-7-azabicyclo[2.2.1]heptan-2-yl)amino)-6-oxo-1-(tetrahydro-2H-pyran-4-yl)-1,6-dihydropyridine-3-carboxamide (arbitrarily assigned diastereomer 2) Analytical chiral UPCC: (Column: AS-3, 4.6 * 100 mm 3 um, Flow rate: 3.0 mL/min, Co-solvent:EtOH (1% 7M NH3 in MeOH), Temp 40° C.) Retention time = 0.9 min. | 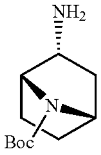 (Racemate) | 533.6 |
| 39 | 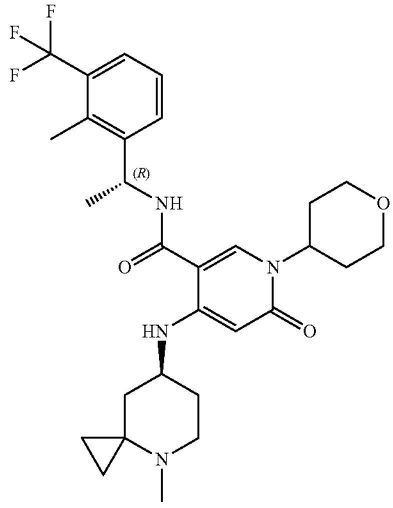 (isomer 1) | N-((R)-1-(2-methyl-3-(trifluoromethyl)phenyl)ethyl)-4-(((S)-4-methyl-4-azaspiro[2.5]octan-7-yl)amino)-6-oxo-1-(tetrahydro-2H-pyran-4-yl)-1,6-dihydropyridine-3-carboxamide (arbitrarily assigned diastereomer 1) Analytical chiral UPCC: (Column: (R,R)Whelk-O1, 4.6 * 100 mm 3 um, Flow rate: 3.0 mL/min, Co-solvent:MeOH (0.2% 7M NH3 in MeOH), Temp 40° C.) Retention time = 1.8 min. | 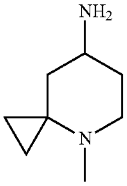 | 547.5 |

-continued

| Example number | Compound Structure | Compound Name (Analytical chiral UPCC retention time for cases where diastereomers are obtained and separated) | Amine reagent used | MS obsd (ESI+) [M + H]+ |
|---|---|---|---|---|
| 40 | 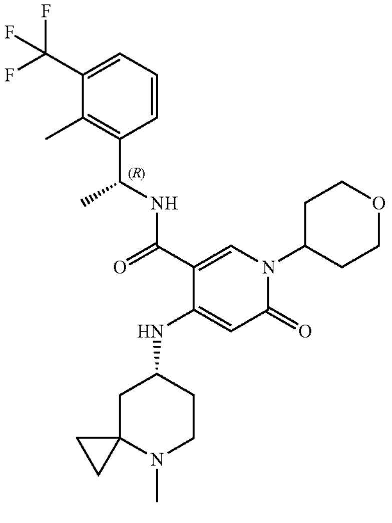 (isomer 2) | N-((R)-1-(2-methyl-3-(trifluoromethyl)phenyl)ethyl)-4-(((R)-4-methyl-4-azaspiro[2.5]octan-7-yl)amino)-6-oxo-1-(tetrahydro-2H-pyran-4-yl)-1,6-dihydropyridine-3-carboxamide (arbitrarily assigned diastereomer 2) Analytical chiral UPCC: (Column: (R,R)Whelk-O1, 4.6 * 100 mm 3 um, Flow rate: 3.0 mL/min, Co-solvent: MeOH (0.2% 7M NH3 in MeOH), Temp 40° C.) Retention time = 2.1 min. | 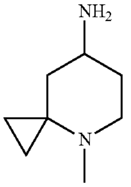 | 547.5 |

Example 41: (R)—N-(1-(3-(difluoromethyl)-2-fluorophenyl)ethyl)-4-((1-methylpiperidin-4-yl)amino)-6-oxo-1-(tetrahydro-2H-pyran-4-yl)-1,6-dihydropyridine-3-carboxamide

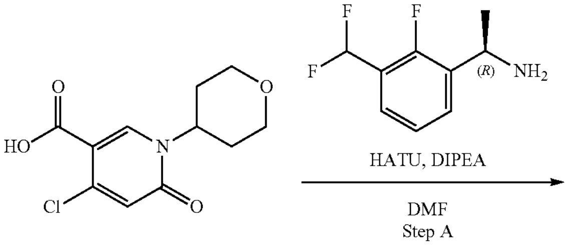

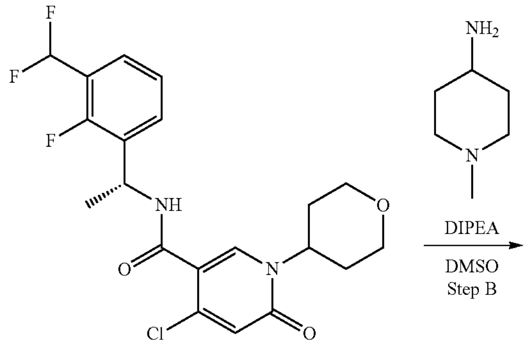

-continued

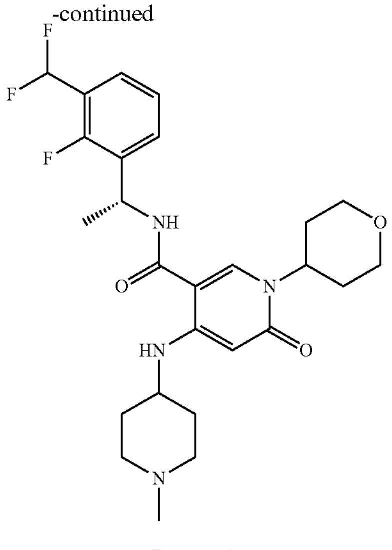

Example 41

Step A: (R)-4-chloro-N-(1-(3-(difluoromethyl)-2-fluorophenyl)ethyl)-6-oxo-1-(tetrahydro-2H-pyran-4-yl)-1,6-dihydropyridine-3-carboxamide To a solution of (R)-1-(3-(difluoromethyl)-2-fluorophenyl)ethan-1-amine (531 mg, 2.81 mmol) in DMF (10.0 mL) was added HATU (1.1 g, 2.81 mmol) and the mixture was stirred at rt for 30 minutes. Then 4-chloro-6-oxo-1-(tetrahydro-2H-pyran-4-yl)-1,6-dihydropyridine-3-carboxylic acid (482 mg, 1.87 mmol) and DIPEA (725 mg, 5.61 mmol) was added to the mixture and stirred at rt for 1 h. The crude reaction mixture was combined with a mixture from a separate reaction run under identical conditions on 0.097 mmol scale. The combined reaction mixture was quenched with water and extracted with EtOAc. Then the organic layer was washed with water, dried over anhydrous $Na_2SO_4$, filtered and concentrated in vacuo to afford the title compound (840 mg, crude) which is used without further purification.

MS obsd. (ESI+) $^{35}Cl/^{37}Cl$ 429.5/431.2 $[M+H]^+$.

Step B: (R)—N-(1-(3-(difluoromethyl)-2-fluorophenyl)ethyl)-4-((1-methylpiperidin-4-yl)amino)-6-oxo-1-(tetrahydro-2H-pyran-4-yl)-1,6-dihydropyridine-3-carboxamide Example 41

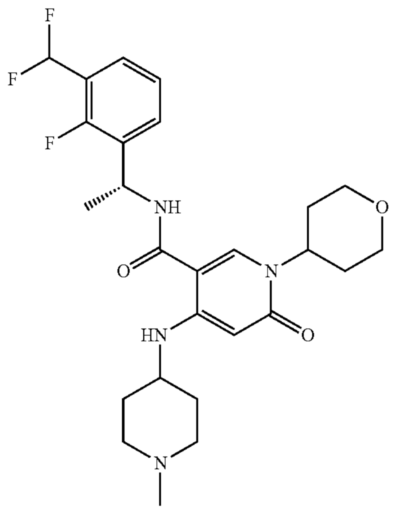

A solution of 1-methylpiperidin-4-amine (107 mg, 0.93 mmol) in DMSO (4.0 mL) was added DIPEA (121 mg, 0.93 mmol) and (R)-4-chloro-N-(1-(3-(difluoromethyl)-2-fluorophenyl)ethyl)-6-oxo-1-(tetrahydro-2H-pyran-4-yl)-1,6-dihydropyridine-3-carboxamide (100 mg, crude, assumed 0.23 mmol). The reaction was stirred at 80° C. for 1 hr. The reaction mixture was combined with crude material from a separate reaction run under identical conditions on 0.058 mmol scale. The combined reaction mixture was quenched with saturated aqueous $NH_4Cl$ solution and extracted with EtOAc. The organic layer was dried over anhydrous $Na_2SO_4$, filtered and concentrated. Purification by silica gel chromatography (eluting with 10% MeOH in DCM) afforded the title compound (31 mg, 20% yield). MS obsd. (ESI+) 507.3 $[M+H]^+$. $^1H$ NMR (400 MHz, DMSO-$d_6$) δ: 8.77 (1H), 8.14-8.10 (2H), 7.63 (1H), 7.53 (1H), 7.37-7.10 (2H), 5.35-5.27 (2H), 4.87 (1H), 4.02 (2H), 3.47 (2H), 3.23 (1H), 2.59 (2H), 2.16 (3H), 2.10-1.99 (4H), 1.84 (2H), 1.66 (2H), 1.49 (3H), 1.40-1.30 (2H).

Example 42: (R)—N-(1-(2-methyl-3-(trifluoromethyl)phenyl)ethyl)-6-oxo-1-(tetrahydro-2H-pyran-4-yl)-4-((tetrahydro-2H-pyran-4-yl)amino)-1,6-dihydropyridine-3-carboxamide

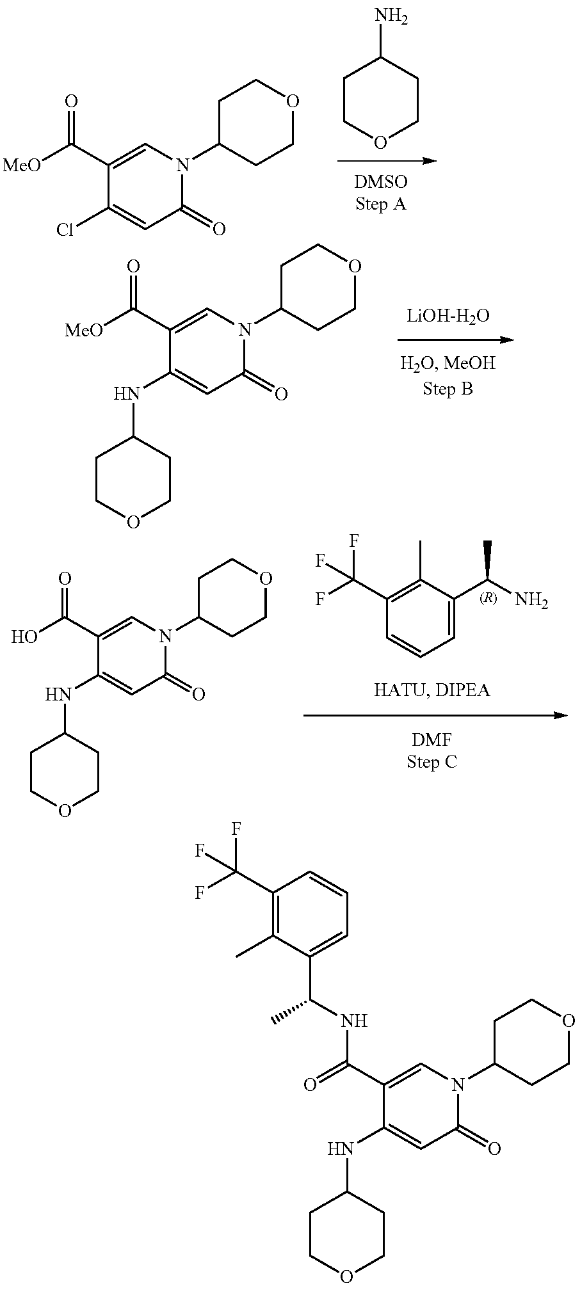

example 42

Step A: methyl 6-oxo-1-(tetrahydro-2H-pyran-4-yl)-4-((tetrahydro-2H-pyran-4-yl)amino)-1,6-dihydropyridine-3-carboxylate To a solution of methyl 4-chloro-6-oxo-1-(tetrahydro-2H-pyran-4-yl)-1,6-dihydropyridine-3-carboxylate (100 mg, 0.37 mmol) in DMSO (2 mL) was added tetrahydropyran-4-amine (186 mg, 1.84 mmol). The reaction was stirred for 2 hours at 105° C. The mixture was diluted with water and extracted with DCM (3*30 mL). The combined organic layers were dried over $Na_2SO_4$. The mixture was filtered concentrated in vacuo. The residue was purified by preparative TLC (DCM/MeOH=15/1) to afford methyl 6-oxo-1-(tetrahydro-2H-pyran-4-yl)-4-((tetrahydro-2H-pyran-4-yl)amino)-1,6-dihydropyridine-3-carboxylate (120 mg, 96% yield). MS obsd. (ESI+) 337.3 $[M+H]^+$.

Step B: 6-oxo-1-(tetrahydro-2H-pyran-4-yl)-4-((tetrahydro-2H-pyran-4-yl)amino)-1,6-dihydropyridine-3-carboxylic acid To a solution of methyl 6-oxo-1-(tetrahydro-2H-pyran-4-yl)-4-((tetrahydro-2H-pyran-4-yl)amino)-1,6-dihydropyridine-3-carboxylate (126 mg, 0.37 mmol) in MeOH (4 mL) and water (1 mL) was added $LiOH \cdot H_2O$ (30.6 mg, 0.74 mmol) at rt. The reaction mixture was stirred for 2 hr at rt. The mixture was acidified with 1M aq. HCl and extracted with DCM (3*30 mL). The combined organic layers were dried over $Na_2SO_4$. The mixture was filtered and concentrated in vacuo to afford 6-oxo-1-(tetrahydro-2H-pyran-4-yl)-4-((tetrahydro-2H-pyran-4-yl)amino)-1,6-dihydropyridine-3-carboxylic acid (115 mg, crude), which was used without further purification. MS obsd. (ESI+) 323.3 $[M+H]^+$.

Step C: (R)—N-(1-(2-methyl-3-(trifluoromethyl)phenyl)ethyl)-6-oxo-1-(tetrahydro-2H-pyran-4-yl)-4-((tetrahydro-2H-pyran-4-yl)amino)-1,6-dihydropyridine-3-carboxamide (Example 42)

Example 42

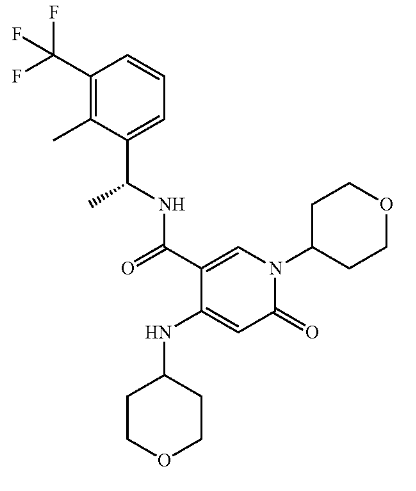

To a solution of 6-oxo-1-(tetrahydro-2H-pyran-4-yl)-4-((tetrahydro-2H-pyran-4-yl)amino)-1,6-dihydropyridine-3-carboxylic acid (115 mg, crude, assumed 0.35 mmol) and HATU (176 mg, 0.46 mmol) in DMF (5 mL) was added DIPEA (138 mg, 1.07 mmol) at rt. The reaction was stirred for 10 min at room temperature. To the reaction mixture was added (R)-1-(2-methyl-3-(trifluoromethyl)phenyl)ethan-1-amine (94 mg, 0.46 mmol) and the reaction was stirred for 1 hr at rt. To this mixture was then added water, and the mixture was extracted into DCM. The organic layers were dried over sodium sulfate, filtered and concentrated to dryness. The residue was purified by silica gel chromatography (eluting with 0%-15% MeOH in DCM) followed by preparative HPLC (ACN/water/0.1% $NH_4HCO_3$) to afford (R)—N-(1-(2-methyl-3-(trifluoromethyl)phenyl)ethyl)-6-oxo-1-(tetrahydro-2H-pyran-4-yl)-4-((tetrahydro-2H-pyran-4-yl)amino)-1,6-dihydropyridine-3-carboxamide (79.4 mg). MS obsd. (ESI+) 508.5 $[(M+H)^+]$.

Example 43: (R)-4-(azetidin-3-ylamino)-N-(1-(2-methyl-3-(trifluoromethyl)phenyl)ethyl)-6-oxo-1-(tetrahydro-2H-pyran-4-yl)-1,6-dihydropyridine-3-carboxamide

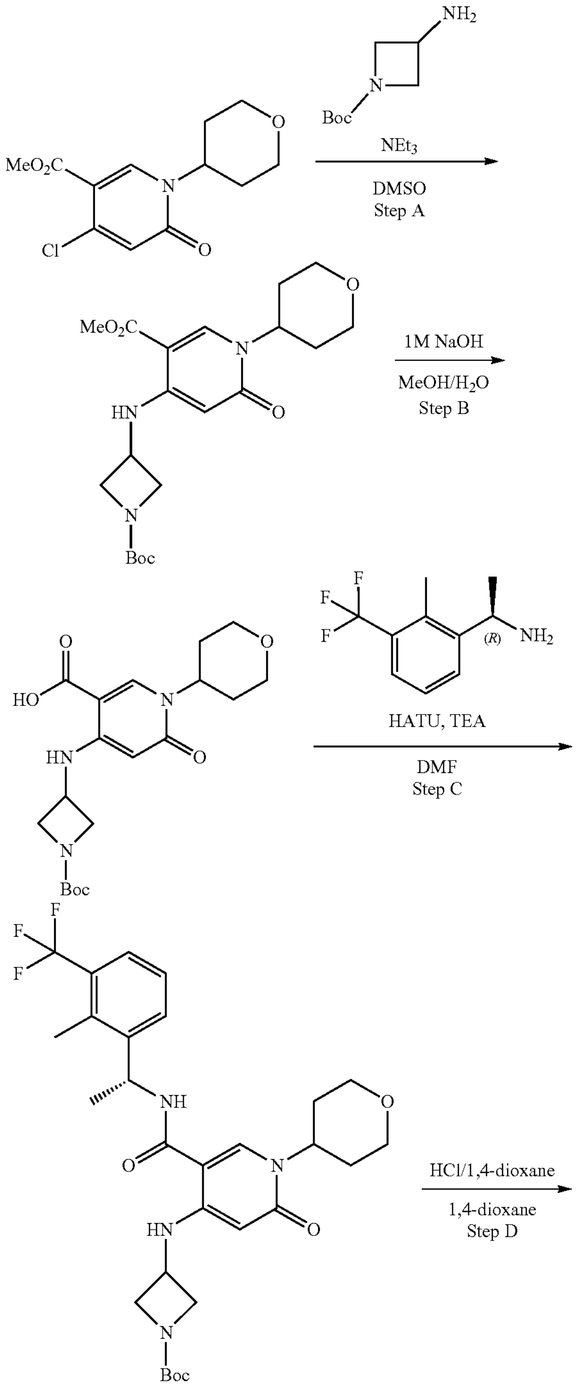

-continued

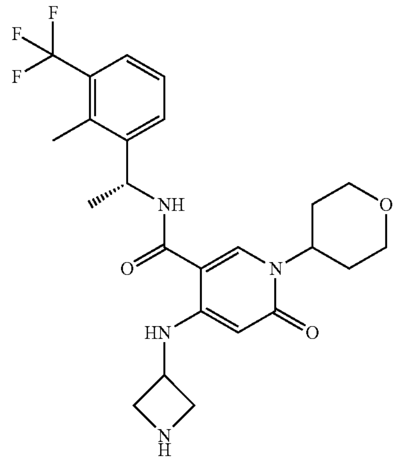

example 43

Step A: methyl 4-((1-(tert-butoxycarbonyl) azetidin-3-yl)amino)-6-oxo-1-(tetrahydro-2H-pyran-4-yl)-1,6-dihydropyridine-3-carboxylate A mixture of tert-butyl 3-aminoazetidine-1-carboxylate (475 mg, 2.76 mmol), methyl 4-chloro-6-oxo-1-tetrahydro-pyran-4-yl-pyridine-3-carboxylate (250 mg, 0.92 mmol) and triethylamine (279 mg, 2.76 mmol) in DMSO (3 mL) was sealed in microwave tube. The resulting mixture was heated to 120° C. in a microwave reactor for 2 hours. The mixture was then diluted with water and extracted with EtOAc (80 mL×3). The organic layers were concentrated in vacuo. The residue was purified by silica gel chromatography (eluting with 30-100% EA in PE) to afford the title compound (260 mg, 69% yield). MS obsd. (ESI+) 408.5 [$(M+H)^+$].

Step B: 4-((1-(tert-butoxycarbonyl) azetidin-3-yl) amino)-6-oxo-1-(tetrahydro-2H-pyran-4-yl)-1,6-dihydropyridine-3-carboxylic acid To a mixture of methyl 4-((1-(tert-butoxycarbonyl) azetidin-3-yl)amino)-6-oxo-1-(tetrahydro-2H-pyran-4-yl)-1,6-dihydropyridine-3-carboxylate (260 mg, 0.64 mmol) in MeOH (5 mL) and THF (5 mL) was added 1M NaOH (1.0 M, 6.38 mL). The resulting mixture was stirred for 2 hr at room temperature. The mixture was then diluted with water (50 mL) and adjusted to pH~3 with 1M aqueous HCl. The resulting mixture was extracted with EtOAc (80 mL×3). The combined organic layers were dried over sodium sulfate, filtered and concentrated in vacuo to afford the title compound (220 mg, crude). This material was used in subsequent steps without further purification. MS obsd. (ESI+) 394.5 [$(M+H)^+$].

Step C: tert-butyl (R)-3-((5-((1-(2-methyl-3-(trifluoromethyl)phenyl)ethyl)carbamoyl)-2-oxo-1-(tetrahydro-2H-pyran-4-yl)-1,2-dihydropyridin-4-yl) amino) azetidine-1-carboxylate To a mixture of (R)-1-(2-methyl-3-(trifluoromethyl)phenyl)ethan-1-amine (112 mg, 0.55 mmol), 4-((1-(tert-butoxycarbonyl) azetidin-3-yl)amino)-6-oxo-1-(tetrahydro-2H-pyran-4-yl)-1,6-dihydropyridine-3-carboxylic acid (180 mg, crude, assumed 0.45 mmol) and triethylamine (93 mg, 0.91 mmol) in DMF (8.0 mL) was added HATU (261 mg, 0.69 mmol) portion-wise. The resulting mixture was stirred for 1.5 hr at room temperature. The mixture was diluted with water (100 mL) and extracted with EtOAc (50 mL×3). The combined organic layers were washed with brine followed by water and dried over $Na_2SO_4$. The mixture was filtered and concentrated in vacuo. The residue was purified by preparative TLC (10% MeOH in DCM) to afford the title compound (100 mg, 37% yield). MS obsd. (ESI+) 579.7 [$(M+H)^+$].

Step D: (R)-4-(azetidin-3-ylamino)-N-(1-(2-methyl-3-(trifluoromethyl)phenyl)ethyl)-6-oxo-1-(tetrahydro-2H-pyran-4-yl)-1,6-dihydropyridine-3-carboxamide (Example 43)

example 43

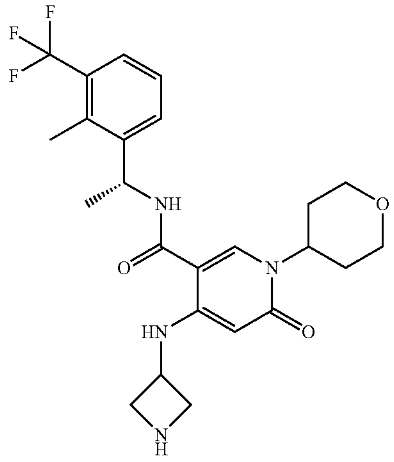

To a mixture of tert-butyl (R)-3-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)amino) azetidine-1-carboxylate (100 mg, 0.17 mmol) in 1,4-Dioxane (0.5 mL) was added HCl/1,4-dioxane (4 M, 0.43 mL). The resulting mixture was stirred at room temperature for 1.5 hr. The mixture was concentrated in vacuo and the residue was neutralized with 7M Ammonia/methanol solution. The mixture was again concentrated in vacuo. The residue was purified by preparative HPLC (ACN/water/0.1% $NH_4HCO_3$) to afford the title compound (13.1 mg, 15% yield). MS obsd. (ESI+) 479.5 [$(M+H)^+$]. $^1H$ NMR (400 MHz, DMSO-d6) δ 8.80 (1H), 8.40 (1H), 8.15 (1H), 7.71 (1H), 7.58 (1H), 7.43 (1H), 5.36-5.29 (1H), 5.00 (1H), 4.86 (1H), 4.10 (1H), 4.02 (2H), 3.67 (2H), 3.47 (2H), 3.28-3.19 (2H), 2.47 (3H), 2.09-1.99 (2H), 1.66 (2H), 1.46 (3H).

Example 44: N—((R)-1-(2-methyl-3-(trifluoromethyl)phenyl)ethyl)-6-oxo-4-(pyrrolidin-3-ylamino)-1-(tetrahydro-2H-pyran-4-yl)-1,6-dihydropyridine-3-carboxamide example 44

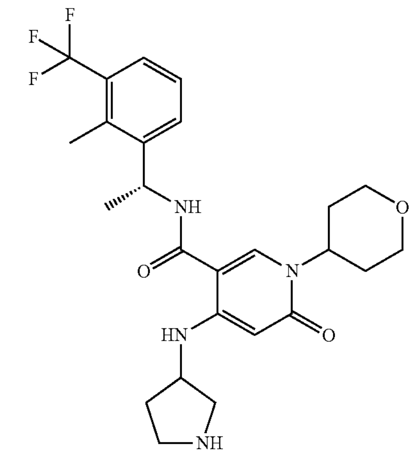

Prepared in an analogous manner to example 43 using tert-butyl 3-aminopyrrolidine-1-carboxylate in step A. MS obsd. (ESI+) 493.5 [$(M+H)^+$].

Example 45: (R)-4-((1,4-dimethylpiperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

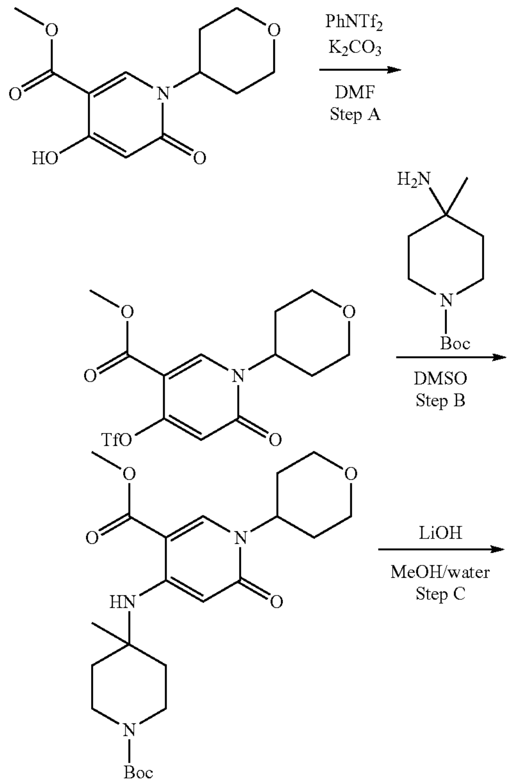

-continued

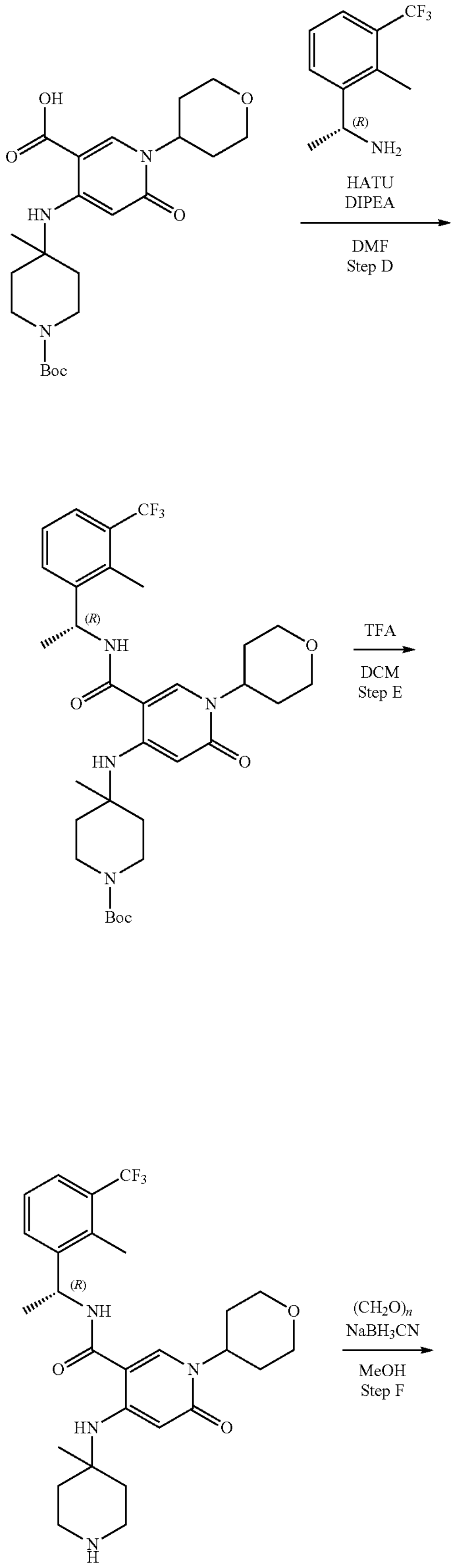

-continued

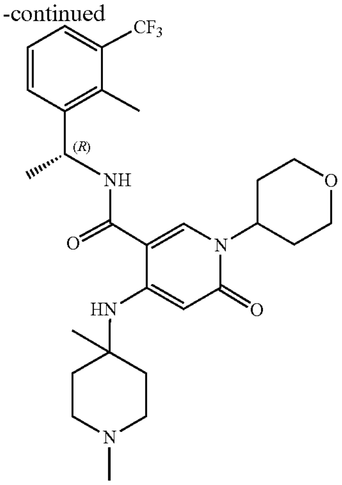

example 45

Step A: methyl 6-oxo-1-(tetrahydro-2H-pyran-4-yl)-4-(((trifluoromethyl)sulfonyl)oxy)-1,6-dihydropyridine-3-carboxylate To a solution of methyl 4-hydroxy-6-oxo-1-(tetrahydro-2H-pyran-4-yl)-1,6-dihydropyridine-3-carboxylate (850 mg, 3.36 mmol) and 1,1,1-trifluoro-N-phenyl-N-(trifluoromethylsulfonyl)methanesulfonamide (1.80 g, 5.04 mmol.) in dry DMF (50 mL) was added potassium carbonate (1.39 g, 10.08 mmol). The reaction mixture was stirred at rt for 3 hr. The reaction mixture was quenched with water and the mixture was extracted with three portions of 100 mL of DCM. The combined organic layers were washed with water (4×100 mL), dried over $Na_2SO_4$, filtered and concentrated. The residue was purified by flash chromatography on a silica gel column (eluting with 0-40% EA in PE) to afford the title compound (1.01 g, ~71% purity), which was used without further purification. MS obsd. (ESI+) 386.5 [$(M+H)^+$].

Step B: methyl 4-((1-(tert-butoxycarbonyl)-4-methylpiperidin-4-yl)amino)-6-oxo-1-(tetrahydro-2H-pyran-4-yl)-1,6-dihydropyridine-3-carboxylate To a solution of methyl 6-oxo-1-(tetrahydro-2H-pyran-4-yl)-4-(((trifluoromethyl)sulfonyl)oxy)-1,6-dihydropyridine-3-carboxylate (200 mg, approximately 71% purity, assumed 0.36 mmol) in DMSO (1 mL) was added tert-butyl 4-amino-4-methyl-piperidine-1-carboxylate (334 mg, 1.56 mmol). The mixture was stirred for 3.5 hr at 120° C. in a microwave reactor. The mixture was then quenched with water and extracted with DCM (3*80 mL). The combined organic layers were washed with water (3×50 mL), dried over $Na_2SO_4$, concentrated in vacuo and purified by silica gel chromatography (eluted with 0-10% MeOH in DCM) to afford impure title compound (125 mg, approximately 46% purity), which was used without further purification. MS obsd. (ESI+) 450.5 [$(M+H)^+$].

Step C: lithium 4-((1-(tert-butoxycarbonyl)-4-methylpiperidin-4-yl)amino)-6-oxo-1-(tetrahydro-2H-pyran-4-yl)-1,6-dihydropyridine-3-carboxylate To a solution of methyl 4-((1-(tert-butoxycarbonyl)-4-methylpiperidin-4-yl)amino)-6-oxo-1-(tetrahydro-2H-pyran-4-yl)-1,6-dihydropyridine-3-carboxylate (125 mg, approximately 46% purity, assumed 0.27 mmol) in MeOH (5 mL) and water (1 mL) was added lithium hydroxide (10 mg, 0.42 mmol). The mixture was stirred for 3 hr at rt. The solvent was removed in vacuo to afford the crude title compound (120 mg, crude). The crude product was used in the next step without further purification. MS obsd. (ESI+) 436.5 [$(M+H)^+$].

Step D: tert-butyl (R)-4-methyl-4-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)amino)piperidine-1-carboxylate To a solution of lithium 4-((1-(tert-butoxycarbonyl)-4-methylpiperidin-4-yl)amino)-6-oxo-1-(tetrahydro-2H-pyran-4-yl)-1,6-dihydropyridine-3-carboxylate (120 mg, crude) in DMF (5 mL) was added HATU (157 mg, 0.41 mmol). The mixture was stirred for 20 min at rt. Then ((R)-1-(2-methyl-3-(trifluoromethyl)phenyl)ethan-1-amine (84 mg, 0.41 mmol) and N,N-diisopropylethylamine (107 mg, 0.82 mmol) were added and the mixture was stirred for 1 hr at rt. The mixture was quenched with water and extracted with DCM (3*80 mL). The combined organic layers were washed with water (3*50 mL), dried over $Na_2SO_4$, filtered and concentrated. Purification by silica gel chromatography (eluted with 0-10% MeOH in DCM) afforded the impure title compound (155 mg, approximately 67% purity). This material was used without further purification. MS obsd. (ESI+) 621.7 [$(M+H)^+$].

Step E: (R)—N-(1-(2-methyl-3-(trifluoromethyl)phenyl)ethyl)-4-((4-methylpiperidin-4-yl)amino)-6-oxo-1-(tetrahydro-2H-pyran-4-yl)-1,6-dihydropyridine-3-carboxamide trifluoroacetate salt To a solution of tert-butyl (R)-4-methyl-4-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)amino)piperidine-1-carboxylate (155 mg, ~67% purity) in DCM (5 mL) was added TFA (5 mL). The mixture was stirred for 1 h at rt. The solvent was removed in vacuo to afford the crude title compound (130 mg, crude). The crude product was used in the next step without further purification. MS obsd. (ESI+) 521.6 [$(M+H)^+$].

Step F: (R)-4-((1,4-dimethylpiperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide (Example 45)

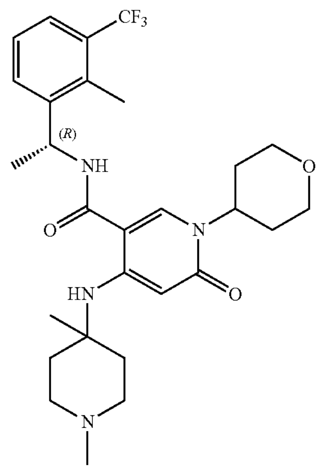

Example 45

To a solution of crude (R)—N-(1-(2-methyl-3-(trifluoromethyl)phenyl)ethyl)-4-((4-methylpiperidin-4-yl)amino)-6-oxo-1-(tetrahydro-2H-pyran-4-yl)-1,6-dihydropyridine-3-carboxamide trifluoroacetate salt (130 mg, crude) in MeOH (10 mL) was added paraformaldehyde (75 mg). The mixture was stirred for 15 min at rt. Then sodium cyanoborohydride (94 mg, 1.50 mmol) was added and the mixture was stirred for 16 hr. The reaction was quenched with water and extracted with DCM (3×50 mL). The combined organic layers were dried over $Na_2SO_4$, filtered and concentrated. The residue was purified by silica gel chromatography (eluted with 0-20% MeOH in DCM) followed by preparative HPLC (ACN/water/0.05% $NH_4HCO_3$) to afford the title compound (53 mg) as a white solid. MS obsd. (ESI+) 535.6 $[(M+H)^+]$. $^1$H NMR (400 MHz, DMSO-d6) δ: 8.75 (1H), 8.18 (1H), 8.00 (1H), 7.72 (1H), 7.59 (1H), 7.44 (1H), 5.34 (1H), 5.31 (1H), 4.81 (1H), 4.01 (2H), 3.47 (2H), 2.46 (3H), 2.38 (2H), 2.05-1.87 (9H), 1.66 (2H), 1.59- 1.50 (2H), 1.47 (3H), 1.27 (3H).

Example 46: (R)-4-((2-(guanidinooxy)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

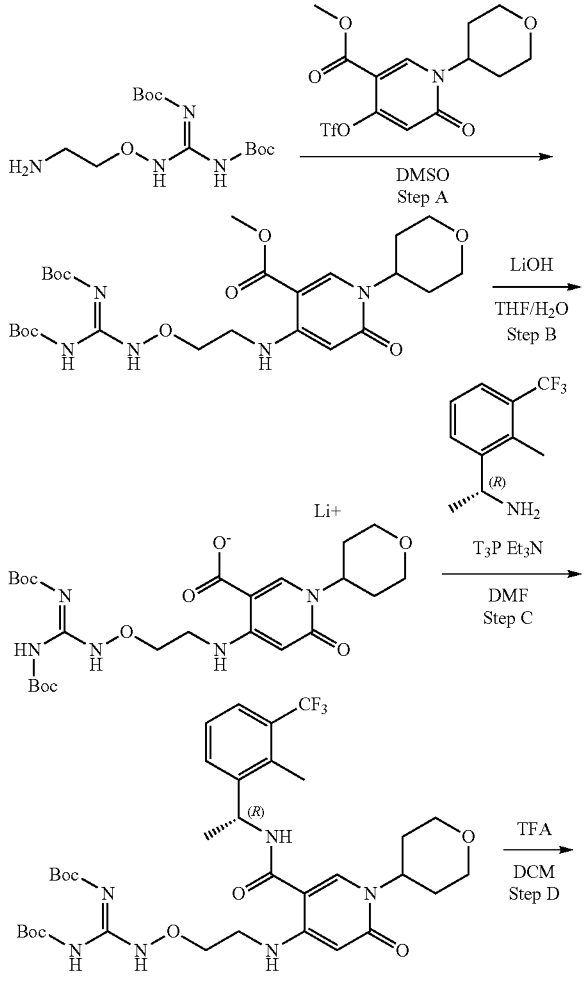

-continued

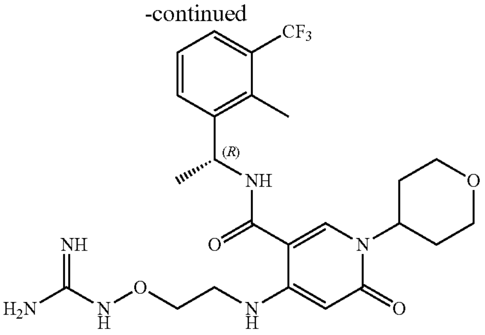

Example 46

Step A: methyl 4-((5-((tert-butoxycarbonyl)amino)-9,9-dimethyl-7-oxo-3,8-dioxa-4,6-diazadec-5-en-1-yl)amino)-6-oxo-1-(tetrahydro-2H-pyran-4-yl)-1,6-dihydropyridine-3-carboxylate To a solution of methyl 6-oxo-1-tetrahydropyran-4-yl-4-(trifluoromethylsulfonyloxy)pyridine-3-carboxylate (60 mg, 0.16 mmol) in DMSO (2 mL) was added [N,N'-Di-(tert-butoxycarbonyl)]-2-aminoethoxyguanidine (100 mg, 0.31 mmol, prepared according to the procedure described in *J. Med. Chem.* 2010, 53, 1843-1856) at rt. The reaction was stirred for 2 hr at 80° C. The mixture was extracted with DCM (3×15 mL) and the combined organic layers were dried over $Na_2SO_4$, filtered and concentrated. The residue was combined with crude material from a reaction performed on 0.2 mmol scale and the combined mixture was purified via silica gel chromatography (eluting with 0%-10% MeOH in DCM), to afford the title compound (206 mg). MS obsd. (ESI+) 554.5 $[(M+H)^+]$.

Step B: lithium 4-((5-((tert-butoxycarbonyl)amino)-9,9-dimethyl-7-oxo-3,8-dioxa-4,6-diazadec-5-en-1-yl)amino)-6-oxo-1-(tetrahydro-2H-pyran-4-yl)-1,6-dihydropyridine-3-carboxylate To a solution of methyl 4-((5-((tert-butoxycarbonyl)amino)-9,9-dimethyl-7-oxo-3,8-dioxa-4,6-diazadec-5-en-1-yl)amino)-6-oxo-1-(tetrahydro-2H-pyran-4-yl)-1,6-dihydropyridine-3-carboxylate (200 mg, 0.36 mmol) in THF/$H_2O$ (4:1, 2.5 mL) was added $LiOH{\cdot}H_2O$ (29.6 mg, 0.72 mmol). The reaction was stirred for 10 hr at rt. The mixture was then concentrated in vacuo to afford crude title compound (190 mg) which was used in the next step without further purification. MS obsd. (ESI+) 540.5 $[(M+H)^+]$.

Step C: tert-butyl N-[(tert-butoxycarbonylamino)-[2-[[5-[[(1R)-1-[2-methyl-3-(trifluoromethyl)phenyl]ethyl]carbamoyl]-2-oxo-1-tetrahydropyran-4-yl-4-pyridyl]amino]ethoxyamino]methylene]carbamate To a solution of lithium 4-((5-((tert-butoxycarbonyl)amino)-9,9-dimethyl-7-oxo-3,8-dioxa-4,6-diazadec-5-en-1-yl)amino)-6-oxo-1-(tetrahydro-2H-pyran-4-yl)-1,6-dihydropyridine-3-carboxylate (190 mg, crude) in DMF (3 mL) was added triethylamine (143 mg, 1.41 mmol), (R)-1-(2-methyl-3-(trifluoromethyl)phenyl)ethan-1-amine (85 mg, 0.42 mmol) and 2,4,6-tripropyl-1,3,5,2,4,6-trioxatriphosphorinane-2,4,6-trioxide (50 wt % in ethyl acetate, 443 mg, 0.70 mmol). The reaction was stirred for 1 hr at rt. To this mixture was added water (30 mL) and the mixture was extracted with DCM (3×20 mL). The organic layers were dried over sodium sulfate, filtered and concentrated to dryness. The residue was purified by flash column chromatography (eluting with 0%-10% MeOH in DCM) to afford the title compound (136 mg). MS obsd. ($ESI^+$): 725.5 $[(M+H)^+]$ Step D: (R)-4-((2-(guanidinooxy)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide (Example 46)

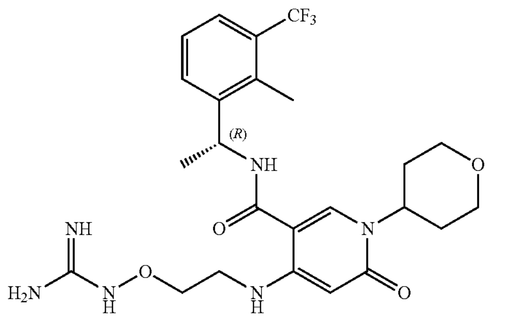

Example 46

To a solution of tert-butyl N-[(tert-butoxycarbonylamino)-[2-[[5-[[(1R)-1-[2-methyl-3-(trifluoromethyl)phenyl]ethyl]carbamoyl]-2-oxo-1-tetrahydropyran-4-yl-4-pyridyl]amino]ethoxyamino]methylene]carbamate (126 mg, 0.17 mmol, 1.0 eq.) in DCM (4.5 mL) was added TFA (1.5 mL) at rt. The reaction was stirred for 1 hr at rt. The mixture was concentrated in vacuo and the residue was purified by preparative HPLC (ACN/water/0.1% $NH_4HCO_3$) to afford the title compound (46 mg, 50% yield). MS obsd. ($ESI^+$): 525.6 $[(M+H)^+]$. $^1H$ NMR (400 MHz, DMSO-d6) δ ppm 8.75 (1H), 8.25 (1H), 8.07 (1H), 7.71 (1H), 7.58 (1H), 7.43 (1H), 5.32 (1H), 5.24 (1H), 4.98 (2H), 4.86 (1H), 4.34 (2H), 4.02 (2H), 3.72 (2H), 3.47 (2H), 3.15 (2H), 2.46 (3H), 2.12-1.96 (2H), 1.66 (2H), 1.45 (3H).

Examples 47 and 48: N—((R)-1-(3-(difluoromethyl)-2-fluorophenyl)ethyl)-4-((1-methylpiperidin-4-yl)amino)-1-((S)-3-methyltetrahydrofuran-3-yl)-6-oxo-1,6-dihydropyridine-3-carboxamide and N—((R)-1-(3-(difluoromethyl)-2-fluorophenyl)ethyl)-4-((1-methylpiperidin-4-yl)amino)-1-((R)-3-methyltetrahydrofuran-3-yl)-6-oxo-1,6-dihydropyridine-3-carboxamide (Diastereomers Unassigned)

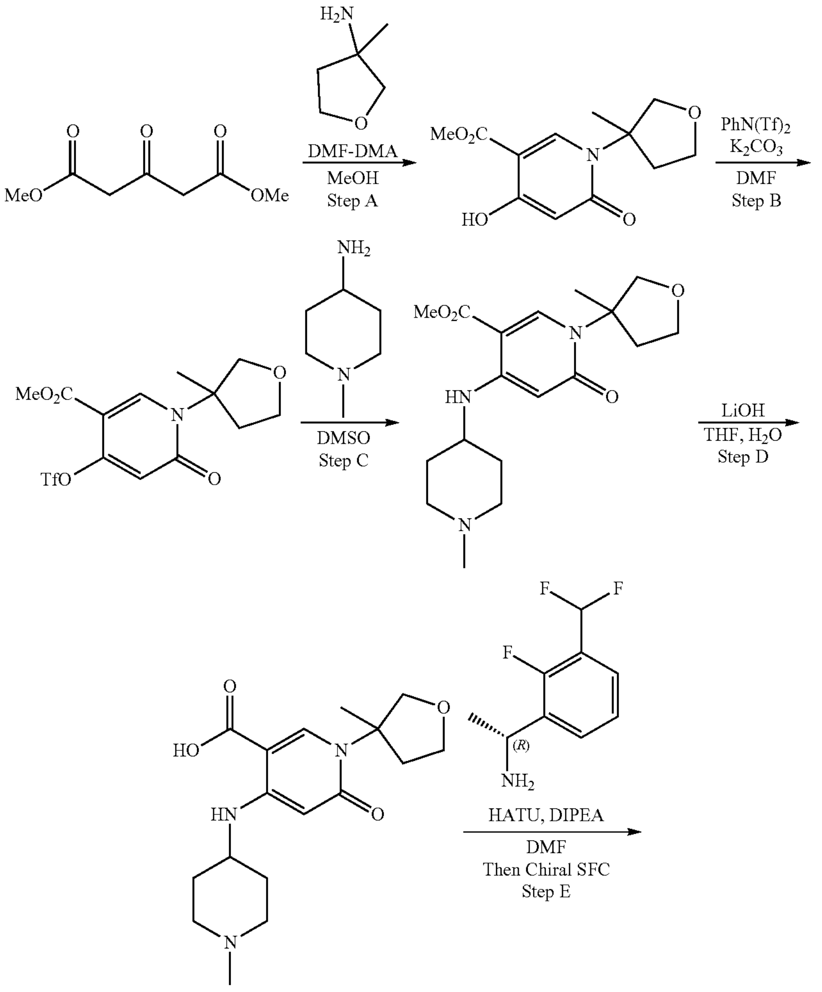

-continued

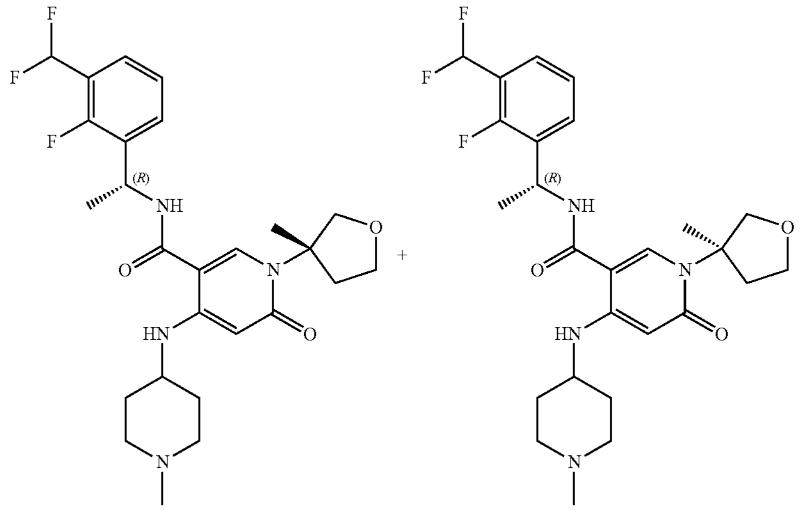

Examples 47 and 48

Step A: methyl 4-hydroxy-1-(3-methyltetrahydrofuran-3-yl)-6-oxo-1,6-dihydropyridine-3-carboxylate To a solution of dimethyl 3-oxopentanedioate (500 mg, 2.87 mmol) in MeOH (10.0 mL) was added DMF-DMA (411 mg, 3.45 mmol). The mixture was stirred at rt for 2 h. Then 3-methyltetrahydrofuran-3-amine (334 mg, 3.30 mmol) was added. The mixture was stirred at rt for 16 hr. Volatiles were removed under reduced pressure. To the residue was added water, and the suspension was adjusted to pH=11. The solution was washed with EtOAc. The aqueous phase was collected and acidified with saturated citric acid to pH=4. Then it was extracted with DCM. The organic layers were dried over anhydrous $Na_2SO_4$, filtered and concentrated to afford the title compound (238 mg, crude). The crude material was used without further purification in the following steps. MS obsd. (ESI+) 254.4 $[M+H]^+$.

Step B: methyl 1-(3-methyltetrahydrofuran-3-yl)-6-oxo-4-(((trifluoromethyl)sulfonyl)oxy)-1,6-dihydropyridine-3-carboxylate To a solution of methyl 4-hydroxy-1-(3-methyltetrahydrofuran-3-yl)-6-oxo-1,6-dihydropyridine-3-carboxylate (188 mg, crude, assumed 0.74 mmol) and $PhN(Tf)_2$ (398 mg, 1.11 mmol) in dry DMF (7.5 mL) was added $K_2CO_3$ (308 mg, 2.23 mmol). The reaction mixture was stirred at rt for 0.5 hr. The reaction mixture was quenched by adding 5 mL of aqueous saturated ammonium chloride. The reaction mixture was extracted with ethyl acetate (3×5 mL). The organic layer was washed with brine and dried over anhydrous $Na_2SO_4$. The crude material was combined with crude material from a separate reaction run under identical conditions on 0.099 mmol scale. The solvent was removed and the residue was purified by silica gel chromatography (eluting with 0-20% EtOAc in PE) to afford the title compound (271 mg). MS obsd. (ESI+) 386.5 $[M+H]^+$.

Step C: methyl 4-((1-methylpiperidin-4-yl)amino)-1-(3-methyltetrahydrofuran-3-yl)-6-oxo-1,6-dihydropyridine-3-carboxylate To a solution of methyl 1-(3-methyltetrahydrofuran-3-yl)-6-oxo-4-(((trifluoromethyl)sulfonyl)oxy)-1,6-dihydropyridine-3-carboxylate (221 mg, 0.57 mmol) in DMSO (5.0 mL) was added 1-methylpiperidin-4-amine (262 mg, 2.29 mmol). The reaction was stirred at 80° C. for 1 hr. The crude material was combined with crude material from a separate reaction run under identical conditions on 0.065 mmol scale. The combined reaction mixture was quenched with saturated aqueous $NH_4Cl$ solution and extracted with EtOAc. The organic layers were dried over anhydrous $Na_2SO_4$. The mixture was filtered and concentrated to afford the title compound (264 mg, crude) as a white solid. MS obsd. (ESI+) 350.6 $[M+H]^+$.

Step D: 4-((1-methylpiperidin-4-yl)amino)-1-(3-methyltetrahydrofuran-3-yl)-6-oxo-1,6-dihydropyridine-3-carboxylic acid A solution of methyl 1-(3-methyltetrahydrofuran-3-yl)-6-oxo-4-(((trifluoromethyl)sulfonyl)oxy)-1,6-dihydropyridine-3-carboxylate (239 mg, crude, assumed 0.68 mmol) in $H_2O$ (1.0 mL) and THF (3.0 mL) was added LiOH (25 mg, 1.03 mmol), and the reaction mixture was stirred at rt for 2 hr. The mixture was directly concentrated under vacuum. The crude residue was combined with crude material from a separate reaction run under identical conditions on 0.071 mmol scale. The residue was dissolved in $H_2O$, the solution was adjusted to pH~3 with aq HCl and the mixture was extracted with EtOAc. The aqueous phase was then concentrated in vacuum to afford the title compound (250 mg, crude) as a white solid. MS obsd. (ESI+) 336.2 $[M+H]^+$.

Step E: N—((R)-1-(3-(difluoromethyl)-2-fluorophenyl)ethyl)-4-((1-methylpiperidin-4-yl)amino)-1-((S)-3-methyltetrahydrofuran-3-yl)-6-oxo-1,6-dihydropyridine-3-carboxamide and N—((R)-1-(3-(difluoromethyl)-2-fluorophenyl)ethyl)-4-((1-methylpiperidin-4-yl)amino)-1-((R)-3-methyltetrahydrofuran-3-yl)-6-oxo-1,6-dihydropyridine-3-carboxamide (Examples 47 and 48, Diastereomers are Unassigned)

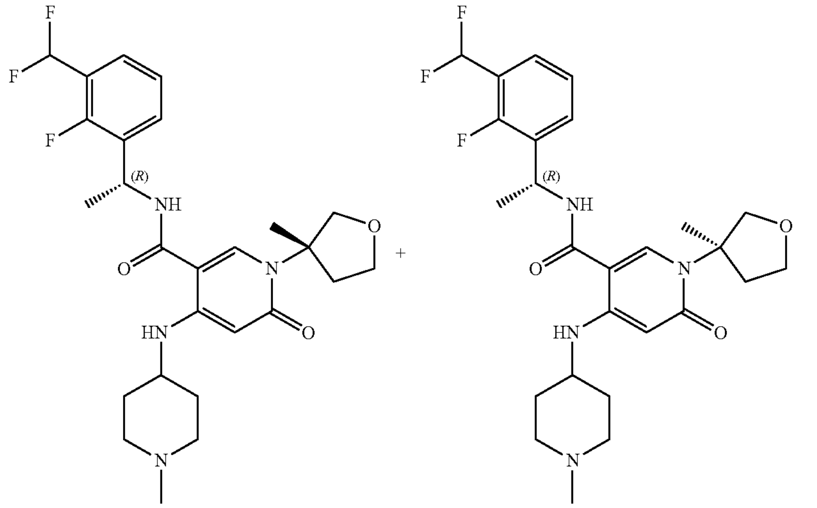

Examples 47 and 48

To a solution of (R)-1-(3-(difluoromethyl)-2-fluorophenyl)ethan-1-amine (190 mg, 1.01 mmol) in DMF (5.0 mL) was added HATU (383 mg, 1.01 mmol) and the mixture was stirred at rt for 0.5 hr. Then 4-((1-methylpiperidin-4-yl)amino)-1-(3-methyltetrahydrofuran-3-yl)-6-oxo-1,6-dihydropyridine-3-carboxylic acid (225 mg, crude, assumed 0.67 mmol) and DIPEA (347 mg, 2.68 mmol) were added and the mixture was stirred for an additional 2 hr. The mixture was quenched with water and extracted with EtOAc. Then the organic layer was washed with water, dried over anhydrous $Na_2SO_4$, filtered and concentrated in vacuo. Purification via silica gel chromatography (eluting with 0-10% MeOH in DCM) afforded the title compound (47 mg, 0.09 mmol). MS obsd. (ESI+) 507.8 $[M+H]^+$.

Individual diastereomers were purified via chiral SFC: (Column: Daicel IG (25*250 mm, 10 um), Mobile phase: $CO_2$/EtOH [0.5% $NH_3$ (7M in MeOH)]=75/25. Absolute structures were not determined.

Example 47: MS obsd. (ESI+) 507.6 $[M+H]^+$. Analytical chiral UPCC: (Column: IG-3, 4.6*100 mm 3 um, Flow rate: 3.0 mL/min, Co-solvent:EtOH (1% 7M NH3 in MeOH), Temp 40° C.) Retention time=1.5 min.

Example 48: MS obsd. (ESI+) 507.6 $[M+H]^+$. Analytical chiral UPCC: (Column: IG-3, 4.6*100 mm 3 um, Flow rate: 3.0 mL/min, Co-solvent:EtOH (1% 7M NH3 in MeOH), Temp 40° C.) Retention time=2.1 min.

Example 49: (R)—N-(1-(3-(difluoromethyl)-2-fluorophenyl)ethyl)-1-(1-(difluoromethyl)cyclopropyl)-4-((1-methylpiperidin-4-yl)amino)-6-oxo-1,6-dihydropyridine-3-carboxamide

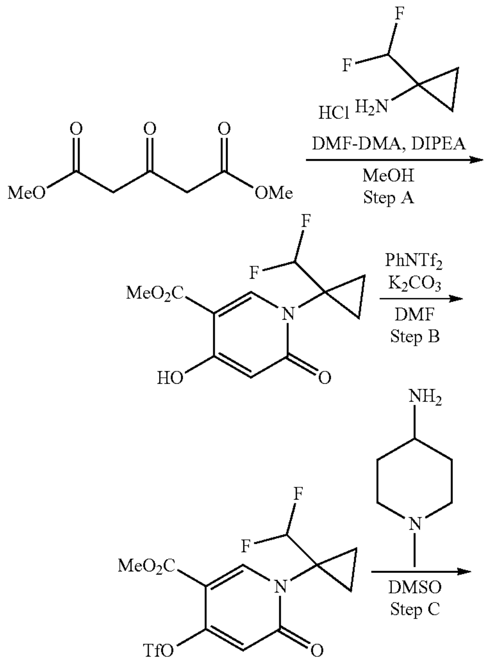

-continued

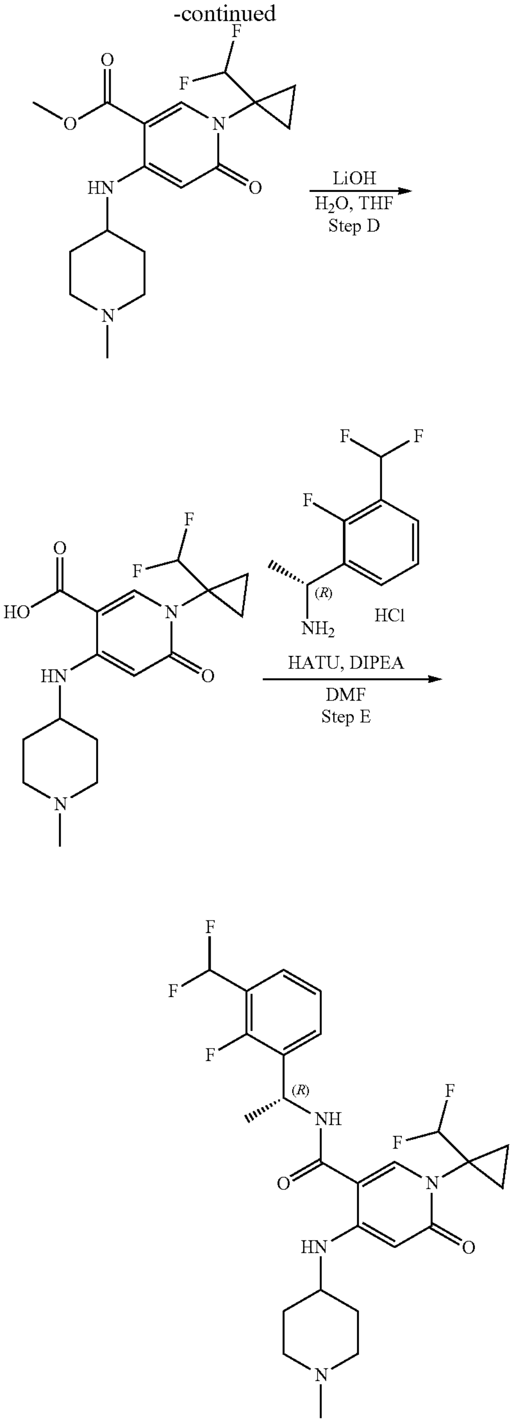

example 49

Step A: methyl 1-(1-(difluoromethyl)cyclopropyl)-4-hydroxy-6-oxo-1,6-dihydropyridine-3-carboxylate To a solution of dimethyl 3-oxopentanedioate (6 g, 34.45 mmol, 5.06 mL) in MeOH (89 mL) was added 1,1-dimethoxy-N,N-dimethyl-methanamine (4.93 g, 41.34 mmol, 5.54 mL) at room temperature, and the mixture was stirred for 2 hr. In a separate flask, a solution of 1-(difluoromethyl)cyclopropan-1-amine hydrochloride (4.95 g, 34.45 mmol) and DIPEA (9.80 g, 75.80 mmol, 13.20 mL) in 3 mL MeOH was stirred at room temperature for 2 hr. At this time, the freebased amine solution was added to the reaction mixture, and the combined mixture was stirred for 2 hr. The solvent was removed under reduced pressure. To the residue was added water, and the suspension was adjusted pH~11 with $K_2CO_3$ (aq.). The solution was extracted with EtOAc and the organic layer was discarded. The water layer was collected, and acidified with saturated citric acid to pH~4. The aqueous phase was then extracted with DCM. The organic layer was dried over anhydrous $Na_2SO_4$, filtered and concentrated to afford the title compound (6.6 g, crude). The material is used without further purification. MS obsd. (ESI+) 260.0 [(M+H)$^+$].

Step B: methyl 1-(1-(difluoromethyl)cyclopropyl)-6-oxo-4-(((trifluoromethyl)sulfonyl)oxy)-1,6-dihydropyridine-3-carboxylate To a solution of methyl 1-(1-(difluoromethyl)cyclopropyl)-4-hydroxy-6-oxo-1,6-dihydropyridine-3-carboxylate and 1,1,1-trifluoro-N-phenyl-N-((trifluoromethyl)sulfonyl)methanesulfonamide (2.07 g, crude, assumed 5.79 mmol) in dry DMF (25 mL) was added potassium carbonate (1.60 g, 11.57 mmol). The reaction mixture was stirred at rt for 30 minutes. The reaction mixture was quenched with aqueous saturated ammonium chloride and extracted with ethyl acetate. The organic layer was dried over sodium sulfate, filtered and concentrated under vacuum. The residue was purified by silica gel chromatography (eluted with 0-30% EtOAc in PE) to afford the title compound (1.4 g, 62% yield). MS obsd. (ESI+) 392.0 [(M+H)$^+$].

Step C: methyl 1-(1-(difluoromethyl)cyclopropyl)-4-((1-methylpiperidin-4-yl)amino)-6-oxo-1,6-dihydropyridine-3-carboxylate To a solution of methyl 1-(1-(difluoromethyl)cyclopropyl)-6-oxo-4-(((trifluoromethyl)sulfonyl)oxy)-1,6-dihydropyridine-3-carboxylate (350 mg, 0.90 mmol) in DMSO (0.5 mL) was added 1-methyl-piperidin-4-amine (408 mg, 3.58 mmol). The mixture was stirred at 80° C. for 1 h. The mixture was then cooled to rt, diluted with water and extracted with EtOAc. The organic layer was washed with brine, dried over anhydrous $Na_2SO_4$ and concentrated to afford crude title compound (260 mg, crude). This material was used in subsequent steps without further purification. MS obsd. (ESI$^+$) 356.6 [M+H]$^+$.

Step D: 1-(1-(difluoromethyl)cyclopropyl)-4-((1-methylpiperidin-4-yl)amino)-6-oxo-1,6-dihydropyridine-3-carboxylic acid To a suspension of methyl 1-(1-(difluoromethyl)cyclopropyl)-4-((1-methylpiperidin-4-yl)amino)-6-oxo-1,6-dihydropyridine-3-carboxylate (130 mg, crude, assumed 0.36 mmol) in $H_2O$ (0.75 mL) was added LiOH (17 mg, 0.73 mmol) and THF (0.75 mL). The mixture was stirred at rt for 2 hr. The reaction mixture was acidified with 4 M aq HCl solution to pH=1. The solvent was removed to afford crude title compound (120 mg, crude), which was used without further purification. MS obsd. (ESI+) 342.4 [M+H]$^+$.

Step E: (R)—N-(1-(3-(difluoromethyl)-2-fluorophenyl)ethyl)-1-(1-(difluoromethyl)cyclopropyl)-4-((1-methylpiperidin-4-yl)amino)-6-oxo-1,6-dihydropyridine-3-carboxamide (Example 49)

Example 49

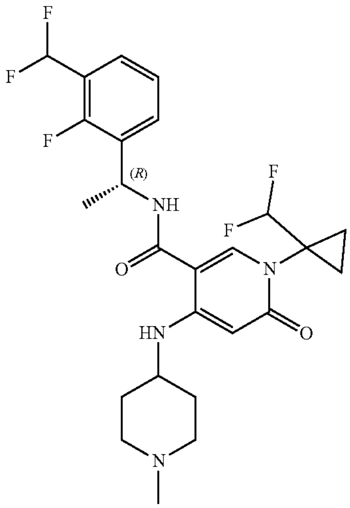

To a solution of 1-(1-(difluoromethyl)cyclopropyl)-4-((1-methylpiperidin-4-yl)amino)-6-oxo-1,6-dihydropyridine-3-carboxylic acid (100 mg, crude, assumed 0.29 mmol) and (R)-1-(3-(difluoromethyl)-2-fluorophenyl)ethan-1-amine hydrochloride (79 mg, 0.35 mmol) in DMF (5.0 mL) was added HATU (167 mg, 0.44 mmol) and DIPEA (151 mg, 1.17 mmol). The mixture was stirred at rt for 1 hr. The solvent was removed and the residue was purified by silica gel chromatography (0-20% MeOH in DCM) to afford the title compound (Example 49, 47 mg). MS obsd. (ESI+) 513.6 $(M+H)^+$. $^1$H NMR (400 MHz, $CD_3OD$) δ ppm: 8.02 (1H), 7.57-7.49 (2H), 7.29 (1H), 7.14-6.86 (1H), 6.29-6.00 (1H), 5.44 (1H), 5.37 (1H), 3.40 (1H), 2.83-2.72 (2H), 2.42-2.32 (2H), 2.33 (3H), 2.03 (2H), 1.61-1.49 (5H), 1.45 (2H), 1.31 (2H).

Example 50: (R)-1-(1-(difluoromethyl)cyclopropyl)-N-(1-(2-methyl-3-(trifluoromethyl)phenyl)ethyl)-4-((1-methylpiperidin-4-yl)amino)-6-oxo-1,6-dihydropyridine-3-carboxamide

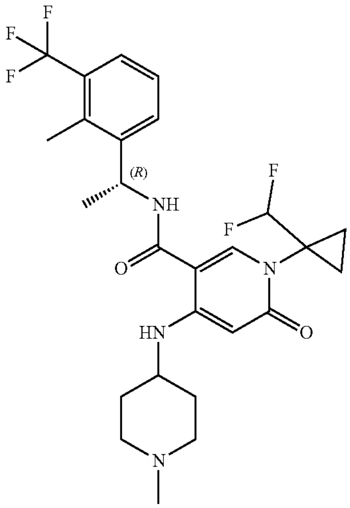

Example 50

To a solution of 1-(1-(difluoromethyl)cyclopropyl)-4-((1-methylpiperidin-4-yl)amino)-6-oxo-1,6-dihydropyridine-3-carboxylic acid (96 mg, crude, assumed 0.28 mmol) and (R)-1-(2-methyl-3-(trifluoromethyl)phenyl)ethan-1-amine (68 mg, 0.34 mmol) in DMF (5.0 mL) was added HATU (160 mg, 0.42 mmol) and DIPEA (145 mg, 1.12 mmol). The mixture was stirred at rt for 1 h. The solvent was removed and the residue was purified by reverse phase HPLC ($MeCN/H_2O/NH_3H_2O$) to afford the title compound (58 mg). MS obsd. (ESI+) 527.3 $[M+H]^+$. $^1$H NMR (400 MHz, DMSO-$d_6$) δ ppm: 8.80 (1H), 8.02 (2H), 7.69 (1H), 7.58 (1H), 7.42 (1H), 6.37-6.08 (1H), 5.32 (1H), 5.21 (1H), 3.22 (1H), 2.56 (2H), 2.44 (3H), 2.12 (3H), 2.05 (2H), 1.85- 1.77 (2H), 1.44 (3H), 1.34-1.26 (6H).

Example 51: (R)—N-(1-(3-(1,1-difluoroethyl)-2-fluorophenyl)ethyl)-1-(1-(difluoromethyl)cyclopropyl)-4-((1-methylpiperidin-4-yl)amino)-6-oxo-1,6-dihydropyridine-3-carboxamide

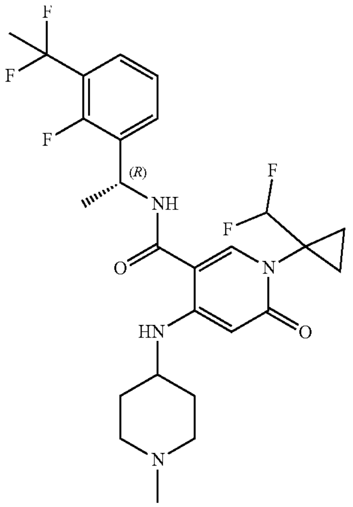

Example 51

To a solution of 1-(1-(difluoromethyl)cyclopropyl)-4-((1-methylpiperidin-4-yl)amino)-6-oxo-1,6-dihydropyridine-3-carboxylic acid (100 mg, 0.29 mmol) in DMF (4.95 mL) was added HATU (222.7 mg, 0.56 mmol) and DIPEA (76 mg, 0.59 mmol). The mixture was stirred for 15-20 min at rt. Then (R)-1-(3-(1,1-difluoroethyl)-2-fluorophenyl)ethan-1-amine (71.4 mg, 0.35 mmol, prepared according to the procedure described in WO/2019/122129) was added and the reaction mixture was stirred at rt for 16 hrs. The mixture was diluted with DCM (100 mL), and the organic mixture was washed with water (100 mL×3), and dried over Na2SO4, filtered and concentrated. The residue was purified by flash chromatography (MeOH/DCM, 0-25%) followed by preparative HPLC (MeCN/0.1% HCOOH-Water=20-40%) to afford the title compound (63.9 mg, 41% yield, 0.6 eq formic acid). MS obsd. (ESI+) 527.4 $[M+H]^+$. $^1H$ NMR (400 MHz, DMSO-$d_6$) δ: 8.81 (1H), 8.18 (1H), 8.02 (2H), 7.57 (1H), 7.47 (1H), 7.30 (1H), 6.23 (1H), 5.36-5.26 (1H), 5.24 (1H), 3.42 (1H), 3.26 (2H), 2.60 (2H), 2.17 (3H), 2.15 (2H), 2.02 (3H), 1.84 (2H), 1.48 (3H), 1.44-1.32 (4H).

Example 52: (R)-1-(1-(difluoromethyl)cyclopropyl)-N-(1-(2-fluoro-3-(trifluoromethyl)phenyl)ethyl)-4-((1-methylpiperidin-4-yl)amino)-6-oxo-1,6-dihydropyridine-3-carboxamide

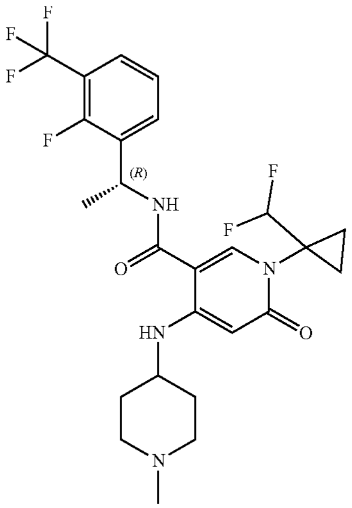

Example 52

To a mixture of 1-(1-(difluoromethyl)cyclopropyl)-4-((1-methylpiperidin-4-yl)amino)-6-oxo-1,6-dihydropyridine-3-carboxylic acid (49.0 mg, 0.14 mmol) in DMF (4 mL) were sequentially added HATU (81.9 mg, 0.22 mmol), DIPEA (55.7 mg, 0.43 mmol) and (R)-1-(2-fluoro-3-(trifluoromethyl)phenyl)ethan-1-amine hydrochloride (35 mg, 0.14 mmol, prepared according to the procedure described in WO/2019/122129). The mixture was stirred at rt for 4 hr. The mixture was diluted with EtOAc (10 mL), and the organic mixture was washed with $H_2O$ (8 mL×3) and brine (8 mL×3). The organic layer was dried ($Na_2SO_4$), filtered and concentrated. The residue was purified by preparative TLC (DCM:MeOH=10:1) followed by preparative HPLC (acetonitrile: 0.1% FA in water=10% to 95%) to provide the title compound (33.9 mg, 44% yield, 0.54 eq formic acid). MS obsd. (ESI+) 531.3 $[M+H]^+$. $^1H$ NMR (400 MHz, DMSO-$d_6$) δ 8.85 (1H), 8.18 (1H), 8.05 (1H), 7.99 (1H), 7.76 (1H), 7.68 (1H), 7.42 (1H), 6.24 (1H), 5.31 (1H), 5.23 (1H), 3.28-3.21 (1H), 2.57 (2H), 2.16 (3H), 2.13 (1H), 1.83 (2H), 1.50 (3H), 1.36 (6H).

Example 53: (R)—N-(1-(3,3-difluoro-2,3-dihydrobenzofuran-7-yl)ethyl)-1-(1-(difluoromethyl)cyclopropyl)-4-((1-methylpiperidin-4-yl)amino)-6-oxo-1,6-dihydropyridine-3-carboxamide

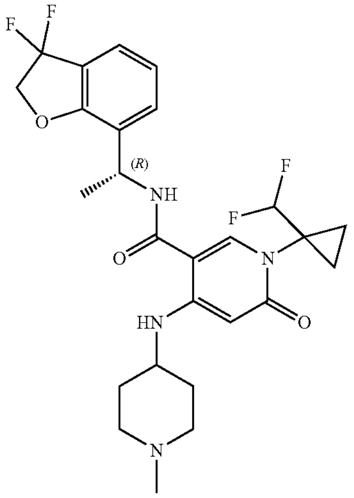

Example 53

Prepared according to an analogous procedure as example 52 using (R)-1-(3,3-difluoro-2,3-dihydrobenzofuran-7-yl)ethan-1-amine hydrochloride (prepared according to the procedure described in WO/2019/122129). MS obsd. (ESI+) 523.2 $[M+H]^+$. $^1H$ NMR (400 MHz, DMSO-$d_6$) δ: 8.76 (1H), 8.01 (2H), 7.53-7.48 (2H), 7.14 (1H), 6.37 (1H), 5.22 (1H), 5.22 (1H), 4.89-4.80 (2H), 3.29-3.19 (3H), 2.60-2.50 (2H), 2.14-2.08 (5H), 1.82 (2H), 1.47 (3H), 1.47-1.24 (4H).

Example 54: (R)-1-(1-(difluoromethyl)cyclopropyl)-N-(1-(3-fluorobenzofuran-7-yl)ethyl)-4-((1-methylpiperidin-4-yl)amino)-6-oxo-1,6-dihydropyridine-3-carboxamide

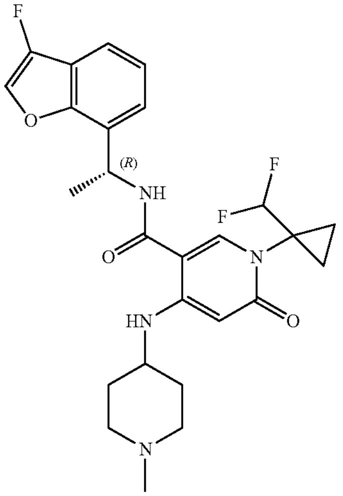

Example 54

Prepared according to an analogous procedure as example 52 using (R)-1-(3-fluorobenzofuran-7-yl)ethan-1-amine hydrochloride (prepared according to the procedure described in WO/2019/122129). MS obsd. (ESI+) 503.2 $[M+H]^+$. $^1$H NMR (400 MHz, DMSO-$d_6$) δ:8.89 (1H), 8.30 (1H), 8.03 (2H), 7.59 (1H), 7.38-7.32 (2H), 6.37 (1H), 5.55-5.48 (1H), 5.22 (1H), 3.25-3.18 (1H), 2.59-2.53 (2H), 2.12 (3H), 2.11-2.02 (2H), 1.85 (2H), 1.57 (3H), 1.40-1.24 (6H).

Example 55: N—((R)-1-(3-(difluoromethyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide

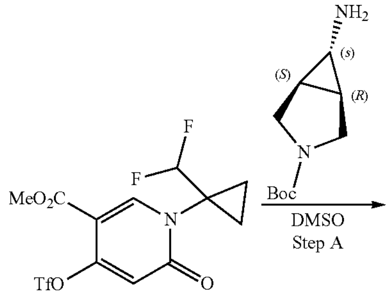

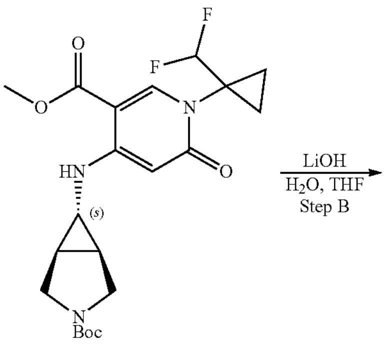

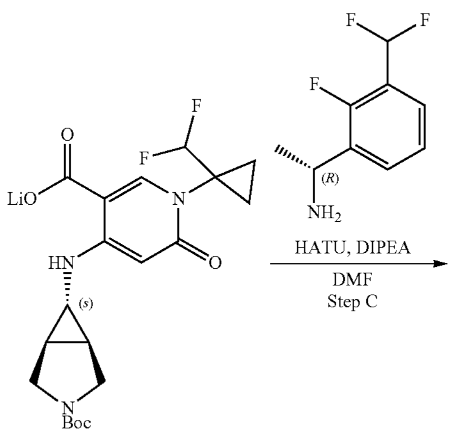

-continued

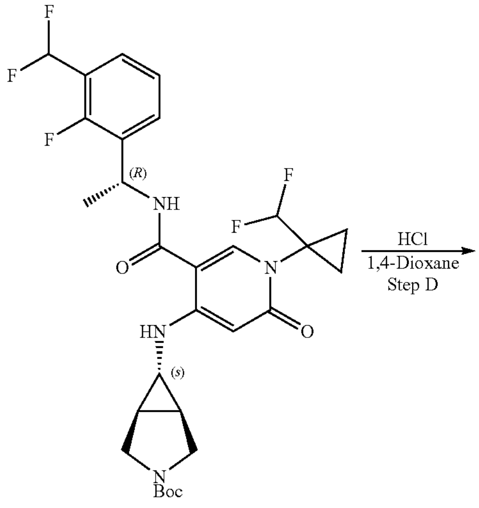

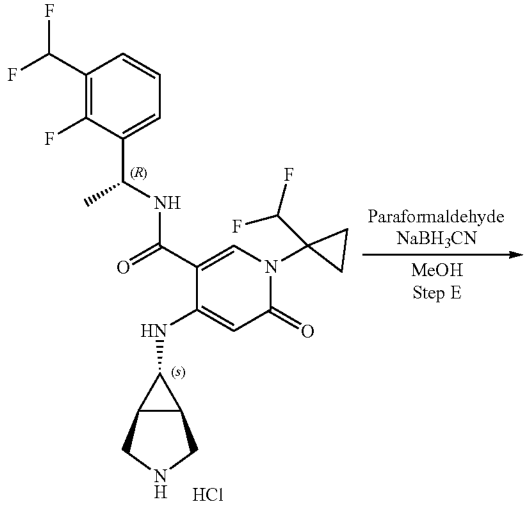

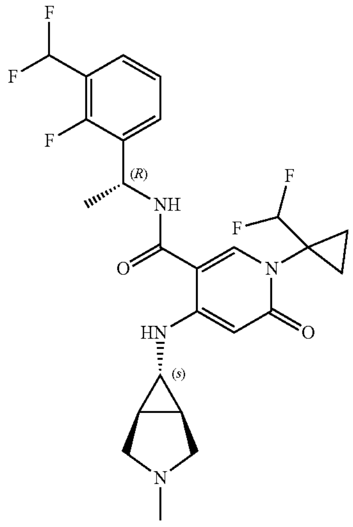

example 55

Step A: tert-butyl (1R,5S,6s)-6-((1-(1-(difluoromethyl)cyclopropyl)-5-(methoxycarbonyl)-2-oxo-1,2-dihydropyridin-4-yl)amino)-3-azabicyclo[3.1.0]hexane-3-carboxylate To a solution of methyl 1-(1-(difluoromethyl)cyclopropyl)-6-oxo-4-(((trifluoromethyl)sulfonyl)oxy)-1,6-dihydropyridine-3-carboxylate (1.5 g, 3.83 mmol) in DMSO (8 mL) was added tert-butyl (1R,5S,6s)-6-amino-3-azabicyclo[3.1.0]hexane-3-carboxylate (1.52 g, 7.67 mmol) at rt. The reaction mixture was stirred for 1 hr at 80° C. The reaction mixture cooled to room temperature and was filtered to afford the title compound (1.3 g, 77% yield). MS obsd. (ESI+) 440.3 $[M+H]^+$.

Step B: lithium 4-(((1R,5S,6s)-3-(tert-butoxycarbonyl)-3-azabicyclo[3.1.0]hexan-6-yl)amino)-1-(1-(difluoromethyl)cyclopropyl)-6-oxo-1,6-dihydropyridine-3-carboxylate To a solution of tert-butyl (1R,5S,6s)-6-((1-(1-(difluoromethyl)cyclopropyl)-5-(methoxycarbonyl)-2-oxo-1,2-dihydropyridin-4-yl)amino)-3-azabicyclo[3.1.0]hexane-3-carboxylate (200 mg, 0.46 mmol) in water (3 mL) and MeOH (12 mL) was added LiOH (22 mg, 0.92 mmol) at rt. The reaction mixture was stirred for 6 hr at ambient temperature. The reaction mixture was directly concentrated to afford the title compound (200 mg, crude) as a white solid, which was used without further purification. MS obsd. 426.2 (ESI+) $[M+H]^+$ for free acid.

Step C: tert-butyl (1R,5S,6s)-6-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-azabicyclo[3.1.0]hexane-3-carboxylate To a solution of lithium 4-(((1R,5S,6s)-3-(tert-butoxycarbonyl)-3-azabicyclo[3.1.0]hexan-6-yl)amino)-1-(1-(difluoromethyl)cyclopropyl)-6-oxo-1,6-dihydropyridine-3-carboxylate (1.3 g, crude) in DMF (2.55 mL) was added HATU (1.38 g, 3.62 mmol), DIPEA (1.17 g, 9.04 mmol), and (R)-1-(3-(difluoromethyl)-2-fluorophenyl)ethan-1-amine (684 mg, 3.6 mmol) at rt. The reaction mixture was stirred for 2 hr at rt. To the reaction mixture was added water and the mixture was extracted with DCM. The organic layer was dried over sodium sulfate, filtered and concentrated to dryness. The residue was purified by silica gel chromatography eluting 0-4% MeOH in DCM to afford the title compound (1.50 g) MS obsd. (ESI+) 597.4 $[M+H]^+$.

Step D: 4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide hydrochloride To a solution of tert-butyl (1R,5S,6s)-6-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-azabicyclo[3.1.0]hexane-3-carboxylate (1.50 g, 2.51 mmol) in 1,4-dioxane (10 mL) was added HCl (4 M in 1,4-Dioxane, 30 mL) at rt. The mixture was stirred at rt for 1 hr. The reaction mixture was concentrated to the title compound (1.50 g, crude), which is used without further purification. MS obsd. (ESI+) 497.2 $[M+H]^+$.

Step E: N—((R)-1-(3-(difluoromethyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide To a solution of 4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide hydrochloride (120 mg, crude, assumed 0.23 mmol) in MeOH (5 mL) was added paraformaldehyde (102.2 mg) at rt. The reaction mixture was stirred for 15 min at rt. To the mixture was added sodium cyanoborohydride (71 mg, 1.13 mmol) at rt. The reaction mixture was stirred for 16 hr at rt. The reaction mixture was concentrated to dryness. The residue was purified by preparative TLC (MeOH:DCM=1:10) followed by preparative HPLC to afford (14.7 mg, 13% yield). MS obsd. (ESI+) 511.8 $[M+H]^+$. $^1H$ NMR (400 MHz, DMSO-d6) δ 8.81 (1H), 8.06 (1H), 7.98 (1H), 7.59 (1H), 7.52 (1H), 7.35 (1H), 7.21 (1H), 6.24 (1H), 5.35 (1H), 5.27 (1H), 3.00 (2H), 2.48 (1H), 2.27 (2H), 2.20 (3H), 1.54-1.49 (2H), 1.47 (3H), 1.29-1.23 (4H).

Example 56: N—((R)-1-(3-(difluoromethyl)-2-fluorophenyl)ethyl)-1-(1-(difluoromethyl)cyclopropyl)-4-(((1R,5S,6r)-3-methyl-3-azabicyclo[3.1.0]hexan-6-yl)amino)-6-oxo-1,6-dihydropyridine-3-carboxamide example 56

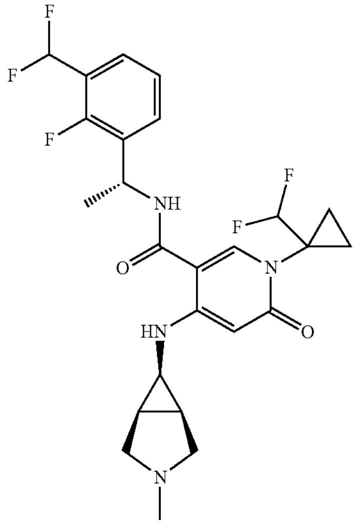

Example 56 was synthesized according to analogous procedures described in example 55 using tert-butyl (1R,5S,6r)-6-amino-3-azabicyclo[3.1.0]hexane-3-carboxylate in step A. MS obsd. (ESI+) 511.2 $[M+H]^+$.

Example 57: N—((R)-1-(3-(difluoromethyl)-2-fluorophenyl)ethyl)-1-(1-(difluoromethyl)cyclopropyl)-4-(((1R,5S,6s)-3-(methyl-d3)-3-azabicyclo[3.1.0]hexan-6-yl)amino)-6-oxo-1,6-dihydropyridine-3-carboxamide

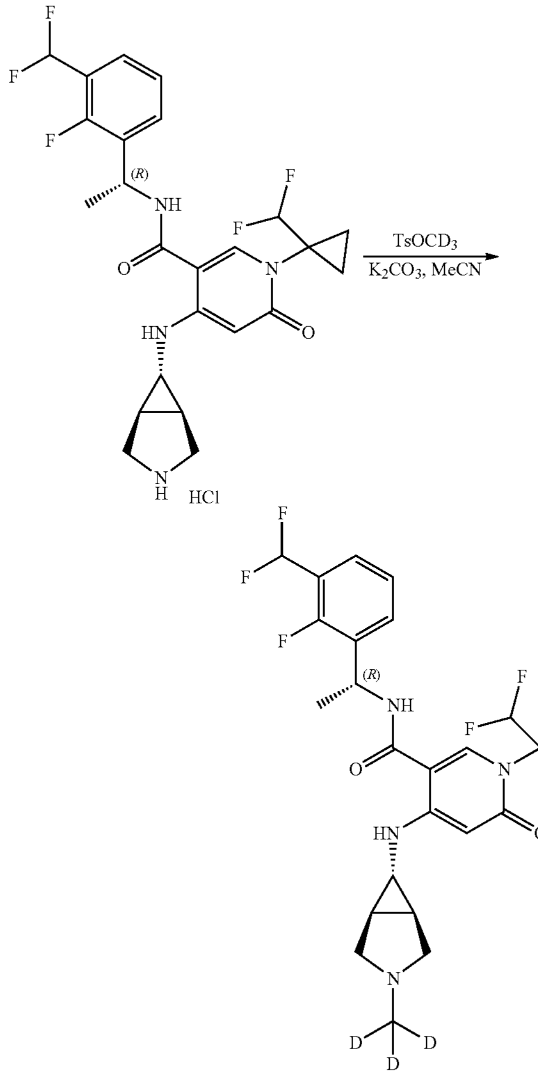

example 57

To a solution of 4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide hydrochloride (50 mg, crude, assumed 0.09 mmol) in acetonitrile (10 mL) was added potassium carbonate (38.9 mg, 0.28 mmol) at rt. The reaction mixture was stirred for 20 min. To the reaction mixture was added trideuteriomethyl 4-methylbenzenesulfonate (19.53 mg, 0.1 mmol) at rt. The reaction mixture was stirred for 2 hr at 80° C. After cooling to room temperature, the reaction was poured into water (5 mL) and extracted with DCM (10 mL×3). The combined organic layers were washed with brine, dried over anhydrous $Na_2SO_4$, filtered, and concentrated in vacuo. The crude product was combined with the crude product from a reaction performed on identical scale, and purified by silica gel chromatography (0-50% MeOH in DCM) followed by preparative HPLC (ACN/water/0.1% NH4HCO3) to the title compound (16.6 mg) as a white solid. MS obsd. (ESI+) 514.4 $[M+H]^+$. $^1H$ NMR (400 MHz, DMSO-$d_6$) δ 8.82 (1H), 8.06 (s, 1H), 7.98 (1H), 7.60 (1H), 7.52 (1H), 7.35 (1H), 7.21 (1H), 6.24 (1H), 5.36 (1H), 5.30-5.23 (1H), 3.00 (2H), 2.47 (1H), 2.27 (2H), 1.49 (5H), 1.39-1.19 (4H).

Example 58: N—((R)-1-(3-(difluoromethyl)-2-fluorophenyl)ethyl)-1-(1-(difluoromethyl)cyclopropyl)-4-(((1R,5S,6s)-3-ethyl-3-azabicyclo[3.1.0]hexan-6-yl)amino)-6-oxo-1,6-dihydropyridine-3-carboxamide

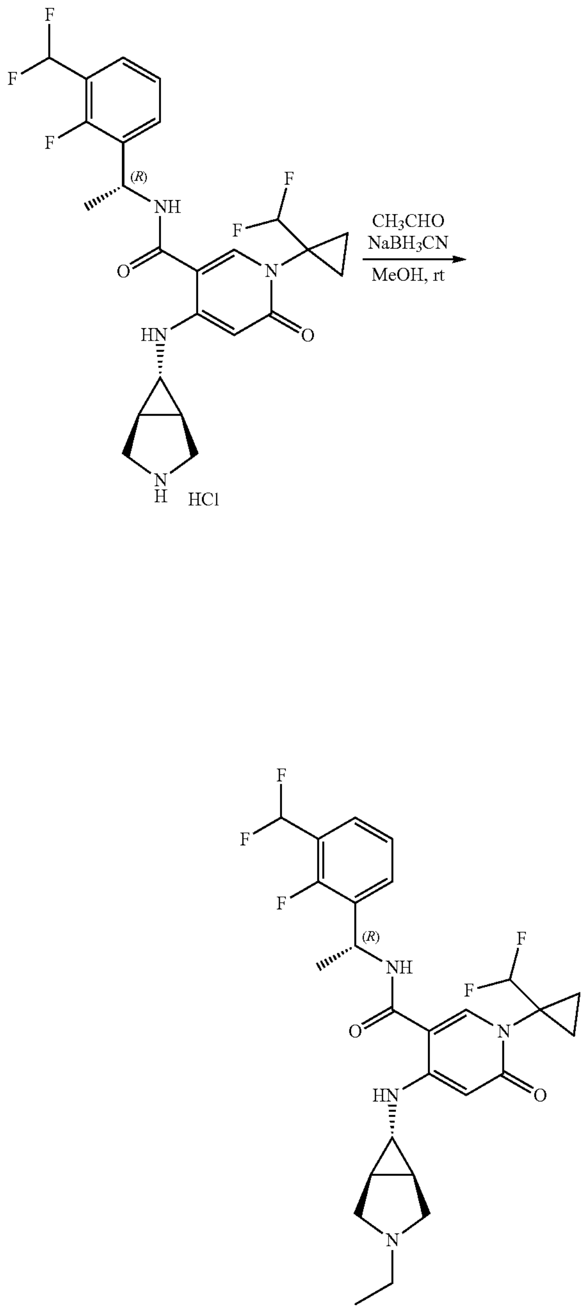

example 58

To a solution of 4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide hydrochloride (50 mg, crude, assumed 0.09 mmol) in MeOH (5 mL) was added acetaldehyde (83 mg, 1.88 mmol) at rt. The reaction mixture was stirred for 15 min at rt. To the mixture was then added sodium cyanoborohydride (59 mg, 0.9 mmol). The reaction mixture was stirred for 2 hr at rt. The reaction was poured into water (5 mL) and extracted with DCM (10 mL×3). The combined organic layers were washed with brine, dried over anhydrous sodium sulfate, filtered and concentrated. This crude product was combined with crude material from a reaction run under identical conditions and purified by preparative HPLC (ACN/water/0.1% NH4HCO3) to afford the title compound (34.2 mg). MS obsd. (ESI+) 525.3 $[M+H]^+$. $^1H$ NMR (400 MHz, DMSO-$d_6$) δ 8.81 (1H), 8.06 (1H), 7.99 (1H), 7.59 (1H), 7.52 (1H), 7.35 (1H), 7.21 (1H), 6.24 (1H), 5.36 (1H), 5.26 (1H), 3.06 (2H), 2.45 (1H), 2.38 (2H), 2.26 (2H), 1.52 (2H), 1.47 (3H), 1.35-1.30 (4H), 0.97 (3H).

Example 59: N—((R)-1-(3-(difluoromethyl)-2-fluorophenyl)ethyl)-1-(1-(difluoromethyl)cyclopropyl)-4-(((1R,5S,6s)-3-isopropyl-3-azabicyclo[3.1.0]hexan-6-yl)amino)-6-oxo-1,6-dihydropyridine-3-carboxamide example 59

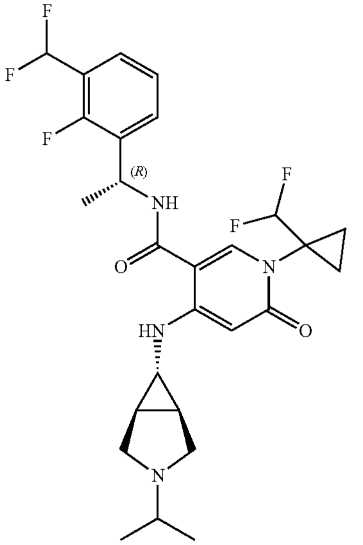

Example 59 was prepared according to an analogous procedure as described in Example 58, using acetone in place of acetaldehyde. MS obsd. (ESI+) 539.4 $[M+H]^+$. $^1H$ NMR (400 MHz, DMSO-d6) δ 8.80 (1H), 8.06 (1H), 7.99 (1H), 7.60 (1H), 7.52 (1H), 7.34 (1H), 7.21 (1H), 6.24 (1H), 5.36 (1H), 5.26 (1H), 3.05 (2H), 2.42 (1H), 2.39-2.32 (3H), 1.51 (2H), 1.47 (3H), 1.35-1.30 (4H), 0.96 (6H).

Example 60: 4-(((1R,5S,6s)-3-cyclopropyl-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide example 60

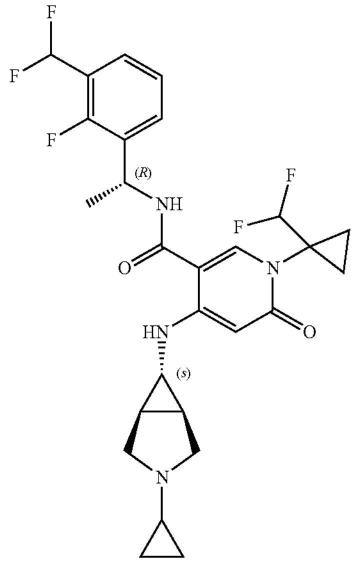

To a solution of 4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide hydrochloride (50 mg, crude, assumed 0.09 mmol) in MeOH (5 mL) was added HOAc (23 mg, 0.38 mmol), (1-ethoxycyclopropoxy)trimethylsilane (98 mg, 0.56 mmol) and sodium cyanoborohydride (29.5 mg, 0.47 mmol) at rt. The reaction mixture was stirred for 3 hr at 65° C. After cooling to room temperature, the reaction was poured into water (5 mL) and extracted with DCM (10 mL×3). The combined organic layers were washed with brine, dried over anhydrous sodium sulfate, filtered and concentrated. This crude product was combined crude material from a reaction performed under identical conditions and purified by preparative HPLC (ACN/water/0.1% NH4HCO3) to afford the title compound (40.6 mg). MS obsd. (ESI+) 537.4 $[M+H]^+$. $^1H$ NMR (400 MHz, DMSO-d6) δ 8.80 (1H), 8.05 (1H), 7.97 (1H), 7.59 (1H), 7.52 (1H), 7.34 (1H), 7.20 (1H), 6.23 (1H), 5.33 (1H), 5.26 (1H), 3.02 (2H), 2.56 (2H), 2.34 (1H), 1.61 (1H), 1.51 (2H), 1.47 (3H), 1.35-1.30 (4H), 0.34 (2H), 0.24 (2H).

Example 61: (R)—N-(1-(3-(difluoromethyl)-2-fluorophenyl)ethyl)-1-(1-(difluoromethyl)cyclopropyl)-4-((2-(dimethylamino)ethyl)amino)-6-oxo-1,6-dihydropyridine-3-carboxamide

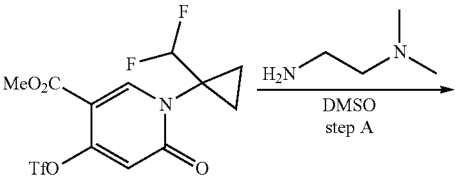

-continued

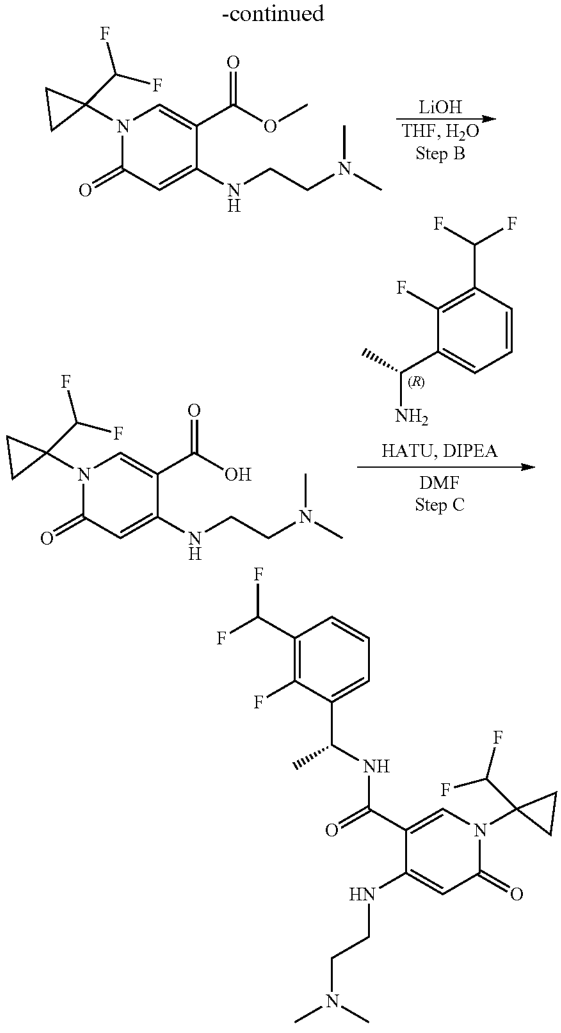

Example 61

Step A: methyl 1-(1-(difluoromethyl)cyclopropyl)-4-((2-(dimethylamino)ethyl)amino)-6-oxo-1,6-dihydropyridine-3-carboxylate To a solution of N',N'-dimethylethane-1,2-diamine (379 mg, 4.29 mmol) in DMSO (8.0 mL) was added methyl 1-(1-(difluoromethyl)cyclopropyl)-6-oxo-4-(((trifluoromethyl)sulfonyl)oxy)-1,6-dihydropyridine-3-carboxylate (525 mg, 1.07 mmol). The mixture was stirred at room temperature for 2 hr. The mixture was then diluted with water and extracted with EtOAc. The organic layer was dried over anhydrous $Na_2SO_4$, filtered and concentrated. The residue was purified by flash chromatography (eluted with 3% MeOH in DCM) to afford the title compound (244 mg, 69% yield). MS obsd. (ESI+) 330.2 $[M+H]^+$.

Step B: 1-(1-(difluoromethyl)cyclopropyl)-4-((2-(dimethylamino)ethyl)amino)-6-oxo-1,6-dihydropyridine-3-carboxylic acid To a solution of methyl 1-(1-(difluoromethyl)cyclopropyl)-4-((2-(dimethylamino)ethyl)amino)-6-oxo-1,6-dihydropyridine-3-carboxylate (244 mg, 0.74 mmol) in THF (3.0 mL) and $H_2O$ (1.0 mL) was added lithium hydroxide (36 mg, 1.5 mmol) and the mixture was stirred at room temperature for 2 hr. The mixture was then directly concentrated under vacuum. The residue was dissolved in $H_2O$, adjusted to PH~1 with aqueous 1M HCl, and concentrated under vacuum to afford the title compound (340 mg, crude). This crude material was used in following steps without further purification. MS obsd. (ESI+) 316.1 $[M+H]^+$.

Step C: (R)—N-(1-(3-(difluoromethyl)-2-fluorophenyl)ethyl)-1-(1-(difluoromethyl)cyclopropyl)-4-((2-(dimethylamino)ethyl)amino)-6-oxo-1,6-dihydropyridine-3-carboxamide Example 61

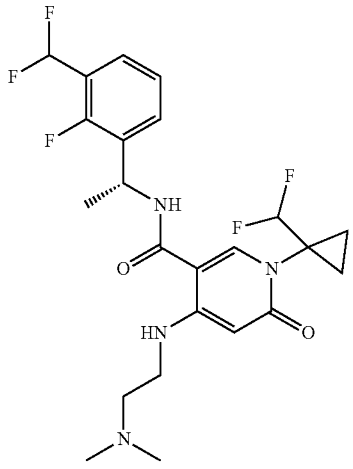

A solution of ((R)-1-(3-(difluoromethyl)-2-fluorophenyl) ethan-1-amine (164 mg, 0.87 mmol), 1-(1-(difluoromethyl) cyclopropyl)-4-((2-(dimethylamino)ethyl)amino)-6-oxo-1, 6-dihydropyridine-3-carboxylic acid (330 mg, crude from previous step), HATU (412 mg, 1.08 mmol) and DIPEA (280 mg, 2.17 mmol) in DMF (5.0 mL) was stirred at room temperature for 2 hr. The mixture was then diluted with water and extracted with EtOAc. The organic layers were dried over sodium sulfate, filtered and concentrated. The residue was purified by flash chromatography (eluted with 10% MeOH in DCM) followed by preparative HPLC ($MeCN/H_2O/10\%\ NH_4CO_3$) to afford the title compound (39 mg) as a white solid. MS obsd. (ESI+) 487.2 $[M+H]^+$. $^1H$ NMR (400 MHz, DMSO-d6) δ: 8.86 (1H), 8.14 (1H), 8.06 (1H), 7.63 (1H), 7.54 (1H), 7.36-7.08 (2H), 6.36 (1H), 5.39 (1H), 5.29 (1H), 3.42 (2H), 3.13 (2H), 2.74 (6H), 1.49 (3H), 1.37-1.14 (4H).

Example 62: (R)-4-((1-cyclopropylpiperidin-4-yl) amino)-N-(1-(3-(difluoromethyl)-2-fluorophenyl) ethyl)-1-(1-(difluoromethyl)cyclopropyl)-6-oxo-1,6-dihydropyridine-3-carboxamide

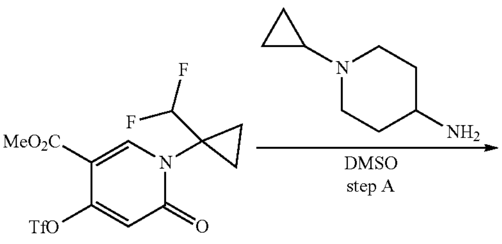

-continued

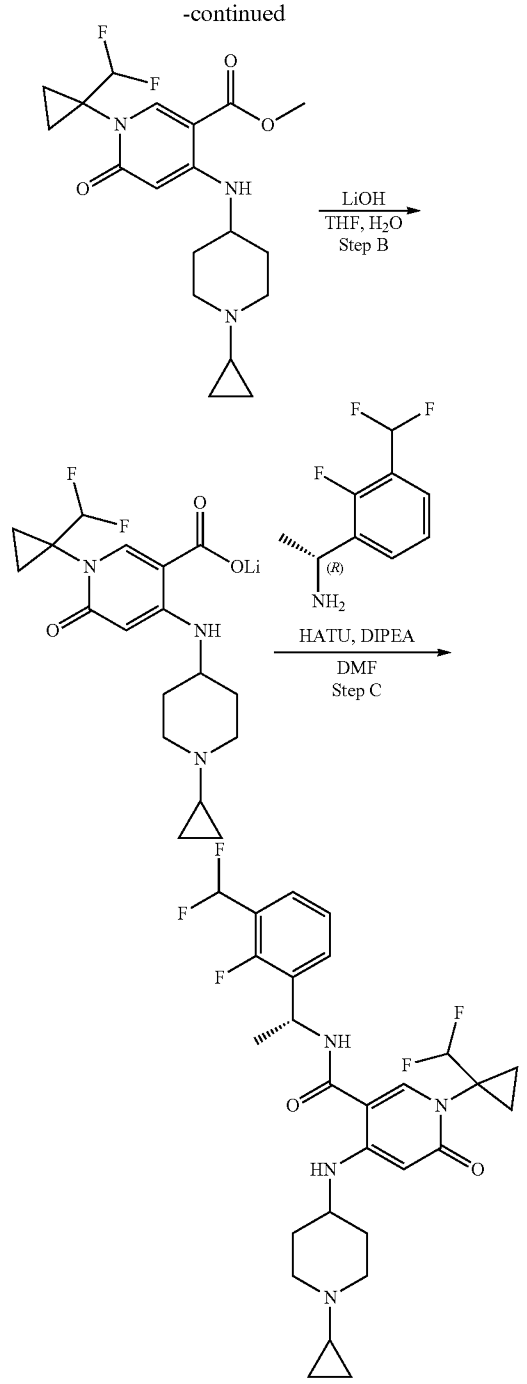

Example 62

Step A: methyl 4-((1-cyclopropylpiperidin-4-yl)amino)-1-(1-(difluoromethyl)cyclopropyl)-6-oxo-1,6-dihydropyridine-3-carboxylate To a solution of methyl 1-(1-(difluoromethyl)cyclopropyl)-6-oxo-4-(((trifluoromethyl)sulfonyl)oxy)-1,6-dihydropyridine-3-carboxylate (80 mg, 0.20 mmol) in DMSO (2 mL) was added 1-cyclopropylpiperidin-4-amine (86 mg, 0.61 mmol). The mixture was stirred at 80° C. for 2 hr. Then mixture was diluted with DCM (5 mL) and washed with water (5 mL×3). The organic layer was dried over sodium sulfate, filtered and concentrated. The residue was purified via silica gel chromatography (eluting with 0 to 10% MeOH in DCM) to afford the title compound (46 mg, 59% yield). MS obsd. (ESI+) 382.7 $[M+H]^+$.

Step B: lithium 4-((1-cyclopropylpiperidin-4-yl)amino)-1-(1-(difluoromethyl)cyclopropyl)-6-oxo-1,6-dihydropyridine-3-carboxylate To a solution of methyl 4-((1-cyclopropylpiperidin-4-yl)amino)-1-(1-(difluoromethyl)cyclopropyl)-6-oxo-1,6-dihydropyridine-3-carboxylate (46 mg, 0.12 mmol) in methanol (5 mL) was added LiOH (6 mg, 0.24 mmol) dissolved in water (1 mL), and the mixture was stirred at rt for 2 hr. The mixture was then concentrated to afford the crude title compound (45 mg, crude), which was used in next step reaction without further purification. MS obsd. (ESI+) 368.4 $[M+H]^+$ for free acid.

Step C: (R)-4-((1-cyclopropylpiperidin-4-yl)amino)-N-(1-(3-(difluoromethyl)-2-fluorophenyl)ethyl)-1-(1-(difluoromethyl)cyclopropyl)-6-oxo-1,6-dihydropyridine-3-carboxamide (Example 62)

Example 62

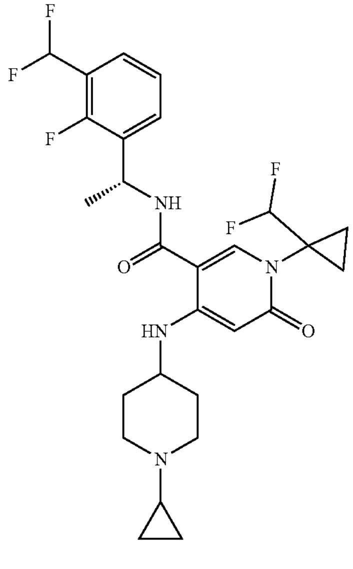

To a solution of lithium 4-((1-cyclopropylpiperidin-4-yl)amino)-1-(1-(difluoromethyl)-cyclopropyl)-6-oxo-1,6-dihydropyridine-3-carboxylate (45 mg, crude from previous step) in DMF (2 mL) was added triethylamine (36 mg, 0.36 mmol), HATU (91 mg, 0.24 mmol) and (R)-1-(3-(difluoromethyl)-2-fluorophenyl)ethan-1-amine (25 mg, 0.13 mmol). The mixture was stirred at rt for 16 hr. Then the mixture was diluted with DCM (6 mL) and washed with water (4 mL×3). The organic layer was dried over $Na_2SO_4$, filtered and concentrated. The residue was purified by preparative HPLC (ACN/water/0.1% $NH_4HCO_3$) to afford the title compound (27 mg, 42% yield). MS obsd. (ESI+) 539.4 $[M+H]^+$. $^1H$ NMR (400 MHz, DMSO) δ8.80 (1H), 8.04 (2H), 7.61 (1H), 7.52 (1H), 7.35 (1H), 7.21 (1H), 6.24 (1H), 5.30 (1H), 5.22 (1H), 3.29-3.17 (1H), 2.73 (2H), 2.34 (2H), 1.80 (2H), 1.56 (1H), 1.48 (3H), 1.38-1.20 (6H), 0.42-0.35 (2H), 0.30-0.22 (2H).

Examples 63 and 64: N—((R)-1-(3-(difluoromethyl)-2-fluorophenyl)ethyl)-1-(1-(difluoromethyl)cyclopropyl)-4-(((3S,4R)-3-fluoro-1-methylpiperidin-4-yl)amino)-6-oxo-1,6-dihydropyridine-3-carboxamide and N—((R)-1-(3-(difluoromethyl)-2-fluorophenyl)ethyl)-1-(1-(difluoromethyl)cyclopropyl)-4-(((3R,4S)-3-fluoro-1-methylpiperidin-4-yl)amino)-6-oxo-1,6-dihydropyridine-3-carboxamide (Diastereomers are Unassigned)
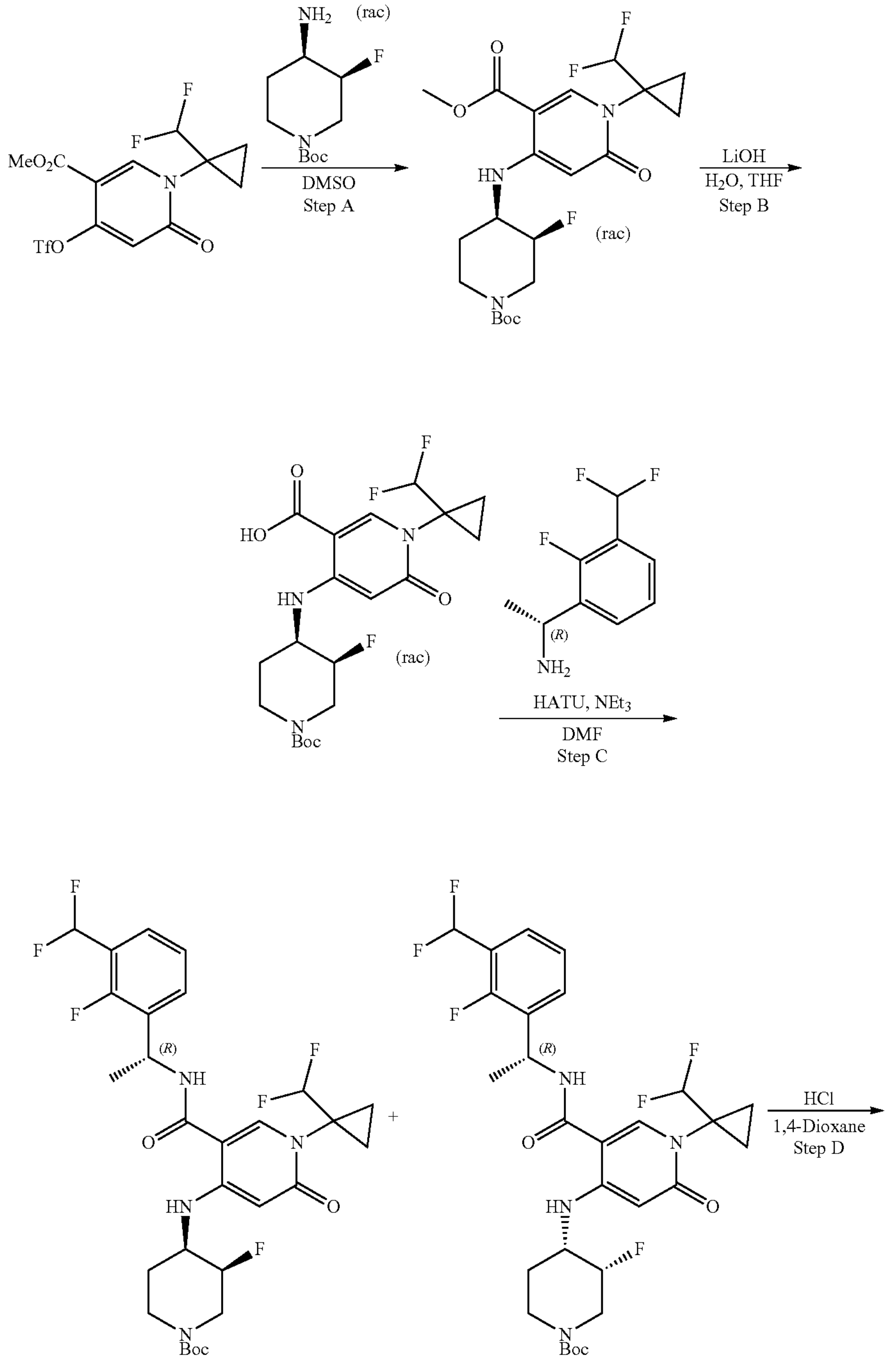
(mixture)

-continued

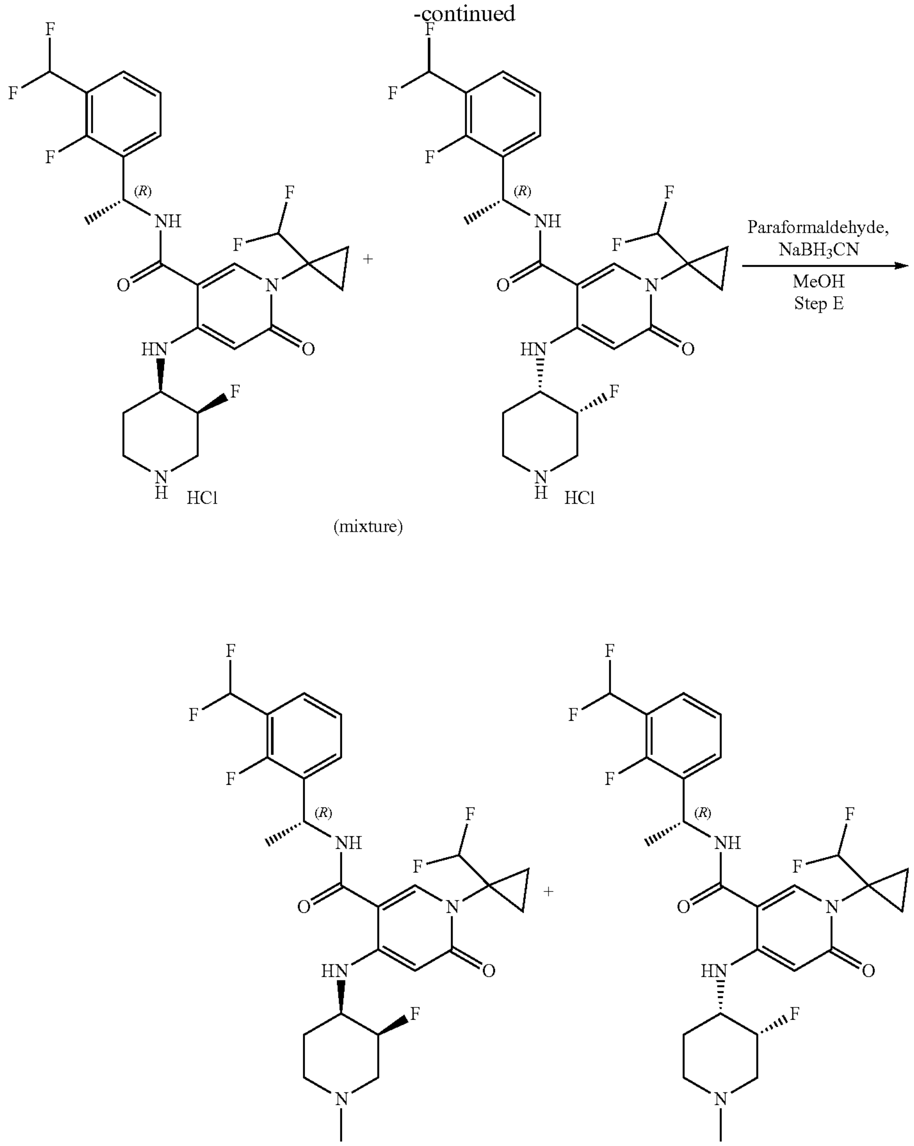

(mixture)

example 63 and 64

Step A: methyl 4-(((cis)-1-(tert-butoxycarbonyl)-3-fluoropiperidin-4-yl)amino)-1-(1-(difluoromethyl)cyclopropyl)-6-oxo-1,6-dihydropyridine-3-carboxylate To a mixture of methyl 1-[1-(difluoromethyl)cyclopropyl]-6-oxo-4-(trifluoromethylsulfonyloxy)pyridine-3-carboxylate (150 mg, 0.38 mmol) in DMSO (3 mL) was added cis-tert-butyl 4-amino-3-fluoro-piperidine-1-carboxylate (251 mg, 1.15 mmol). The mixture was stirred at 90° C. for 6 hr in a sealed tube. The mixture was cooled to rt and diluted with EtOAc (10 mL). The mixture was washed with water (10 mL×3) and brine (10 mL×3). The organic layer was dried over sodium sulfate, filtered and concentrated. The residue was purified by silica gel chromatography column (DCM:MeOH=30:1) to provide impure title compound (150 mg, approximately 88% purity), which was used without further purification. MS obsd. (ESI+) 460.4 $[M+H]^+$.

Step B: 4-(((cis)-1-(tert-butoxycarbonyl)-3-fluoropiperidin-4-yl)amino)-1-(1-(difluoromethyl)cyclopropyl)-6-oxo-1,6-dihydropyridine-3-carboxylic acid To a mixture of methyl 4-(((cis)-1-(tert-butoxycarbonyl)-3-fluoropiperidin-4-yl)amino)-1-(1-(difluoromethyl)cyclopropyl)-6-oxo-1,6-dihydropyridine-3-carboxylate (130 mg, approximately 88% purity, approximately 0.25 mmol) in MeOH (2 mL) at 0° C. was added a solution of lithium hydroxide monohydrate (23 mg, 0.56 mmol) in water (0.4 mL). The mixture was stirred at rt for 16 hr. The mixture was cooled down to 0° C., adjusted pH=5 with 1 N HCl, and extracted with EtOAc (3 mL×3). The combined organic layers were washed with water (4 mL×3) and brine (4 mL×3), then dried over sodium sulfate, filtered and concentrated to provide the crude title compound (126 mg, crude). This material is used in subsequent steps without further purification. MS obsd. (ESI+) 446.4 $[M+H]^+$.

Step C: tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate and tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate To a mixture of 4-(((cis)-1-(tert-butoxycarbonyl)-3-fluoropiperidin-4-yl)amino)-1-(1-(difluoromethyl)cyclopropyl)-6-oxo-1,6-dihydropyridine-3-carboxylic acid (126 mg, crude) in DMF (5 mL) was added HATU (161 mg, 0.42 mmol), triethylamine (86 mg, 0.85 mmol) and (R)-1-(3-(difluoromethyl)-2-fluorophenyl)ethan-1-amine hydrochloride (76 mg, 0.34 mmol). The mixture was stirred at rt for 3 h. The mixture was diluted with EtOAc (20 mL), washed with $H_2O$ (12 mL*3) and brine (12 mL*3). The combined organic layers were dried over $Na_2SO_4$, filtered, and concentrated. The residue was purified by silica gel chromatography (7% MeOH in DCM) to provide a diastereomeric mixture of the title compounds (151 mg, 86% yield). MS obsd. (ESI+) 617.6 $[M+H]^+$.

Step D: N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide hydrochloride and N—((R)-1-(3-(difluoromethyl)-2-fluorophenyl)ethyl)-1-(1-(difluoromethyl)cyclopropyl)-4-(((34,4S)-3-fluoropiperidin-4-yl)amino)-6-oxo-1,6-dihydropyridine-3-carboxamide hydrochloride To a mixture of tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate and tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate (131 mg, 0.21 mmol) in 1,4-dioxane (2 mL) was added HCl (4M in 1,4-dioxane, 2 mL). The mixture was stirred at rt for 3 hr. The mixture was concentrated to provide a diastereomeric mixture of the crude title compounds (117 mg, crude). MS obsd. (ESI+) 517.5 $[M+H]^+$.

Step E: N—((R)-1-(3-(difluoromethyl)-2-fluorophenyl)ethyl)-1-(1-(difluoromethyl)cyclopropyl)-4-(((3S,4R)-3-fluoro-1-methylpiperidin-4-yl)amino)-6-oxo-1,6-dihydropyridine-3-carboxamide and N—((R)-1-(3-(difluoromethyl)-2-fluorophenyl)ethyl)-1-(1-(difluoromethyl)cyclopropyl)-4-(((3R,4S)-3-fluoro-1-methylpiperidin-4-yl)amino)-6-oxo-1,6-dihydropyridine-3-carboxamide (Diastereomers are Unassigned)

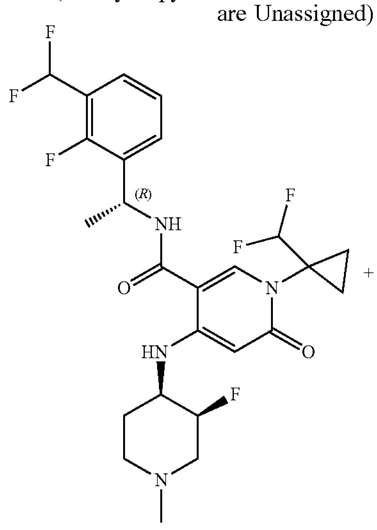

+

-continued

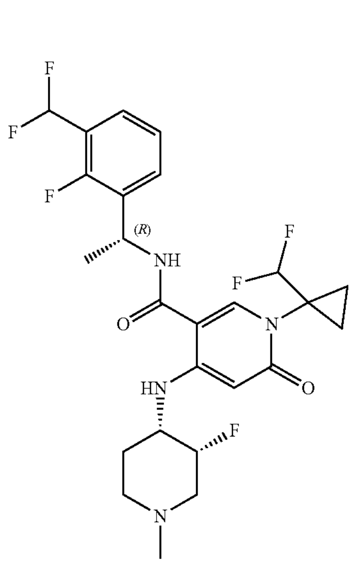

Examples 63 and 64

To a diastereomeric mixture of N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide hydrochloride and N—((R)-1-(3-(difluoromethyl)-2-fluorophenyl)ethyl)-1-(1-(difluoromethyl)cyclopropyl)-4-(((34,4S)-3-fluoropiperidin-4-yl)amino)-6-oxo-1,6-dihydropyridine-3-carboxamide hydrochloride (117 mg, crude, assumed 0.21 mmol) in MeOH (4 mL) was added paraformaldehyde (32 mg). The mixture was stirred at rt for 30 min, then sodium cyanoborohydride (66.5 mg, 1.06 mmol) was added to the mixture, and the resultant mixture was stirred at rt for another 15.5 hr. The reaction was quenched with $H_2O$ (10 mL) and extracted with DCM (10 mL×3). The combined organic layers were washed with $H_2O$ (15 mL×3) and brine (15 mL×3), dried ($Na_2SO_4$), filtered and concentrated. The residue was purified by preparative TLC (DCM:MeOH=10:1) to provide a diastereomeric mixture of the title compounds (105 mg, 93% yield). Individual diastereomers were separated via chiral SFC.

Example 63: MS obsd. (ESI+) 531.2 $[M+H]^+$. Analytical chiral UPCC: (Column: IG-3, 4.6*100 mm 3 um, Flow rate: 3.0 mL/min, Co-solvent: IPA (1% 7M NH3 in MeOH), Temp 40° C.) Retention time=1.9 min.

Example 64: MS obsd. (ESI+) 531.2 $[M+H]^+$. Analytical chiral UPCC: (Column: IG-3, 4.6*100 mm 3 um, Flow rate: 3.0 mL/min, Co-solvent: IPA (1% 7M NH3 in MeOH), Temp 40° C.). Retention time=2.4 min.

Examples 65 and 66: N—((R)-1-(3-(difluoromethyl)-2-fluorophenyl)ethyl)-1-(1-(difluoromethyl)cyclopropyl)-4-(((3R,4R)-3-fluoro-1-methylpiperidin-4-yl)amino)-6-oxo-1,6-dihydropyridine-3-carboxamide and N—((R)-1-(3-(difluoromethyl)-2-fluorophenyl)ethyl)-1-(1-(difluoromethyl)cyclopropyl)-4-(((3S,4S)-3-fluoro-1-methylpiperidin-4-yl)amino)-6-oxo-1,6-dihydropyridine-3-carboxamide (Diastereomers are Unassigned)

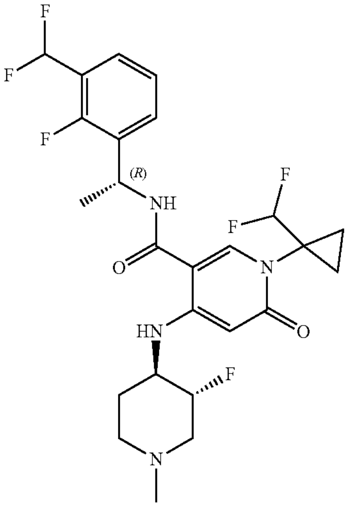

+

-continued

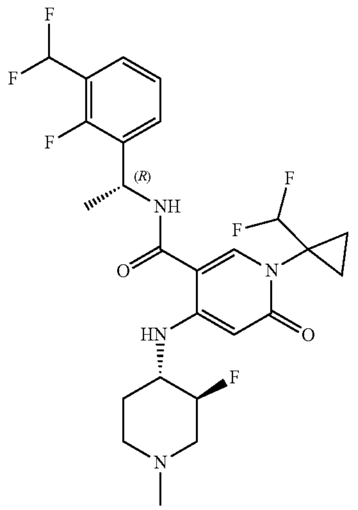

Examples 65 and 66

Examples 65 and 66 were synthesized according to analogous procedures described in Examples 63 and 64 using trans-tert-butyl 4-amino-3-fluoro-piperidine-1-carboxylate in step A.

Example 65: MS obsd. (ESI+) 531.4 $[M+H]^+$. Analytical chiral UPCC: (Column: AS-3, 4.6*100 mm 3 um, Flow rate: 3.0 mL/min, Co-solvent:EtOH (1% 7M NH3 in MeOH, Temp 40° C.). Retention time=1.3 min.

Example 66: MS obsd. (ESI+) 531.4 $[M+H]^+$. Analytical chiral UPCC: (Column: AS-3, 4.6*100 mm 3 um, Flow rate: 3.0 mL/min, Co-solvent:EtOH (1% 7M NH3 in MeOH, Temp 40° C.). Retention time=2.4 min.

Examples 67 and 68: N—((R)-1-(3-(difluoromethyl)-2-fluorophenyl)ethyl)-1-(1-(difluoromethyl)cyclopropyl)-4-(((3S,4R)-3-fluoro-1-(methyl-d3)piperidin-4-yl)amino)-6-oxo-1,6-dihydropyridine-3-carboxamide and N—((R)-1-(3-(difluoromethyl)-2-fluorophenyl)ethyl)-1-(1-(difluoromethyl)cyclopropyl)-4-(((3R,4S)-3-fluoro-1-(methyl-d3)piperidin-4-yl)amino)-6-oxo-1,6-dihydropyridine-3-carboxamide (Unassigned Diastereomers)

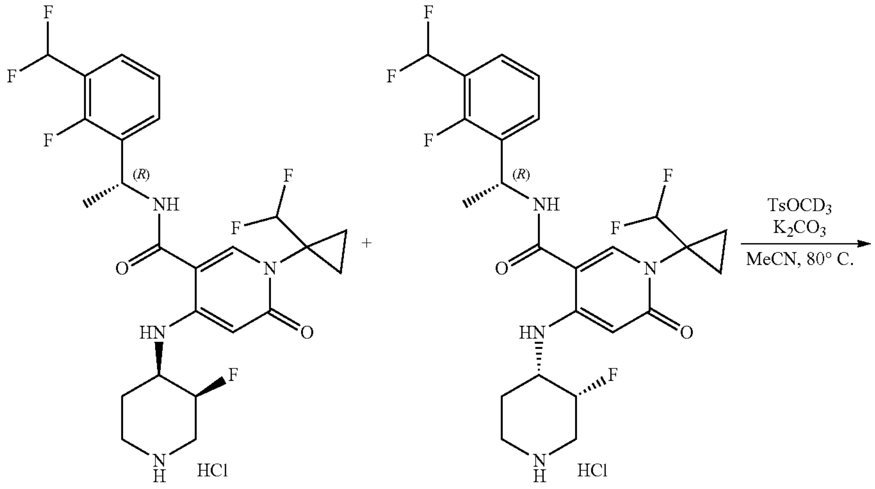

(mixture)

-continued

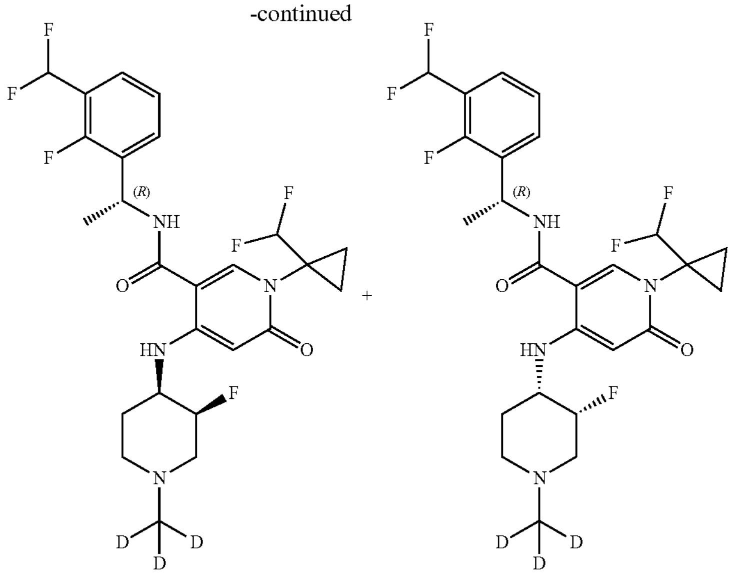

Examples 67 and 68

To a mixture of N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide hydrochloride and N—((R)-1-(3-(difluoromethyl)-2-fluorophenyl)ethyl)-1-(1-(difluoromethyl)cyclopropyl)-4-(((34,4S)-3-fluoropiperidin-4-yl)amino)-6-oxo-1,6-dihydropyridine-3-carboxamide hydrochloride (370 mg, crude, assumed 0.67 mmol) in $CH_3CN$ (10 mL) was added potassium carbonate (277 mg, 2.01 mmol) and trideuteriomethyl 4-methylbenzenesulfonate (126.6 mg, 0.67 mmol). The mixture was stirred at 80° C. for 2 h under $N_2$ atmosphere. The mixture was filtered through a celite pad and the filtrate was concentrated. The residue was purified by silica gel chromatography (DCM:MeOH=10:1) to provide a diastereomeric mixture of the title compounds (101 mg, 28% yield). Individual diastereomers were further separated via chiral SFC, and are arbitrarily assigned.

Example 67: MS obsd. (ESI+) 534.2 $[M+H]^+$. Analytical chiral UPCC: (Column: IG-3, 4.6*100 mm 3 um, Flow rate: 3.0 mL/min, Co-solvent: IPA (1% 7M NH3 in MeOH, Temp 40° C.). Retention time=1.3 min.

Example 68: MS obsd. (ESI+) 534.2 $[M+H]^+$. Analytical chiral UPCC: (Column: IG-3, 4.6*100 mm 3 um, Flow rate: 3.0 mL/min, Co-solvent: IPA (1% 7M NH3 in MeOH, Temp 40° C.). Retention time=1.5 min.

Examples 69 and 70: N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide (Example 69, absolute stereochemistry on piperidine ring is arbitrarily defined) and N—((R)-1-(3-(difluoromethyl)-2-fluorophenyl)ethyl)-1-(1-(difluoromethyl)cyclopropyl)-4-(((3R,4S)-3-fluoropiperidin-4-yl)amino)-6-oxo-1,6-dihydropyridine-3-carboxamide (Example 70, Absolute Stereochemistry on Piperidine Ring is Arbitrarily Defined)

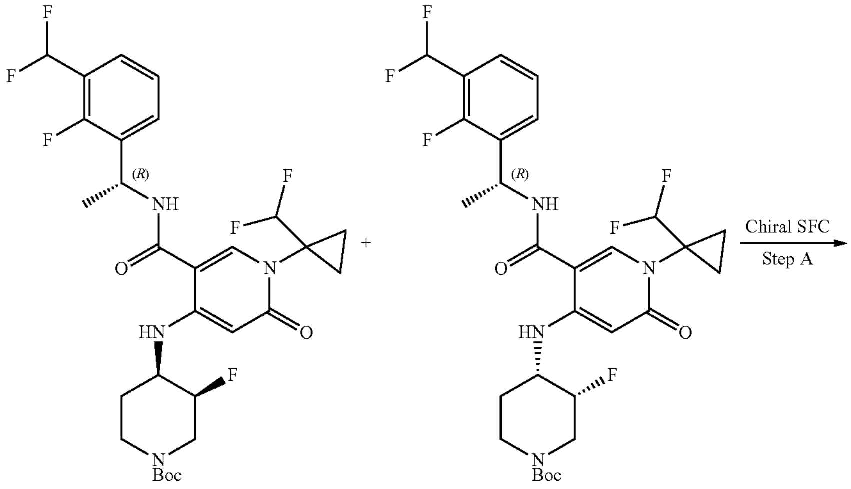

Mixture

-continued
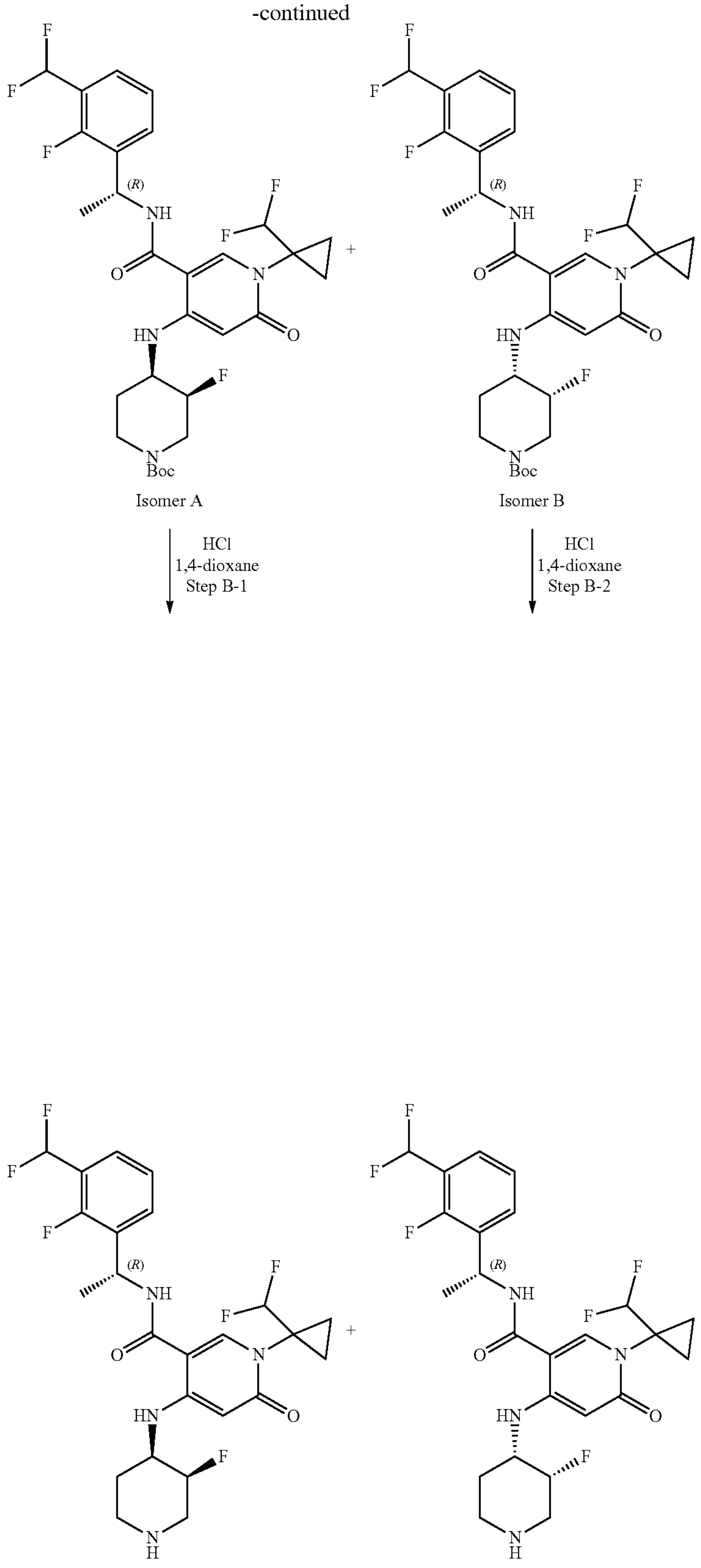

Example 69 Example 70

Step A: tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate [Isomer A, Arbitrarily Defined] and tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate [Isomer B, Arbitrarily Defined]

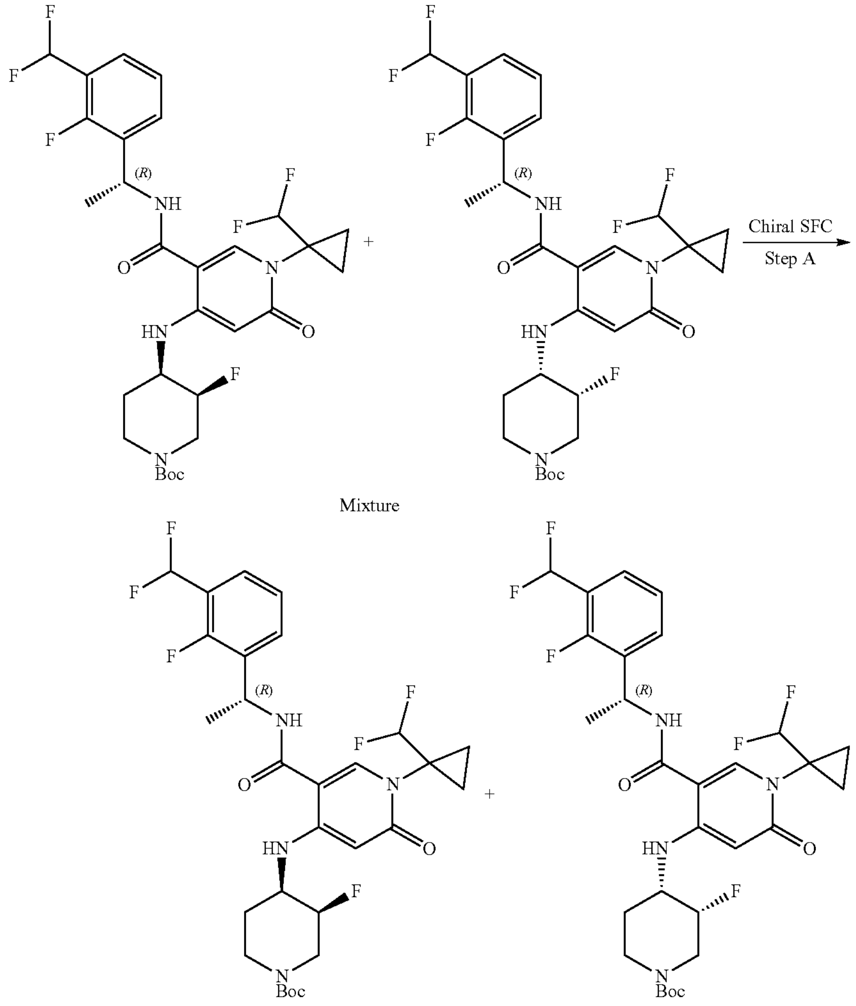

Mixture

Isomer A

Isomer B

A diastereomeric mixture of tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate and tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate (80 mg, 0.13 mmol) was separated by chiral separation (Daicel IG-3 (4.6*100 mm 3 um), $CO_2$/EtOH [1% NH3 (7M in MeOH)]=75/25) to provide the title compounds. Stereochemistry on the piperidine ring is cis, and diastereomers are arbitrarily assigned.

tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate (Isomer A, arbitrarily assigned): (36 mg, 45% yield). MS obsd. (ESI+) 617.4 $[M+H]^+$. Analytical chiral UPCC: (Column: IG-3, 4.6*100 mm 3 um, Flow rate: 3.0 mL/min, Co-solvent:EtOH (1% 7M NH3 in MeOH, Temp 40° C.). Retention time=1.3 min.

tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate (Isomer B, arbitrarily assigned) (31 mg, 39% yield). MS obsd. (ESI+) 617.4 [M+H]+. Analytical chiral UPCC: (Column: IG-3, 4.6*100 mm 3 um, Flow rate: 3.0 mL/min, Co-solvent:EtOH (1% 7M NH3 in MeOH, Temp 40° C.). Retention time=1.8 min.

Step B-1: N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide (Example 69, Absolute Stereochemistry on Piperidine Ring is Arbitrarily Defined)

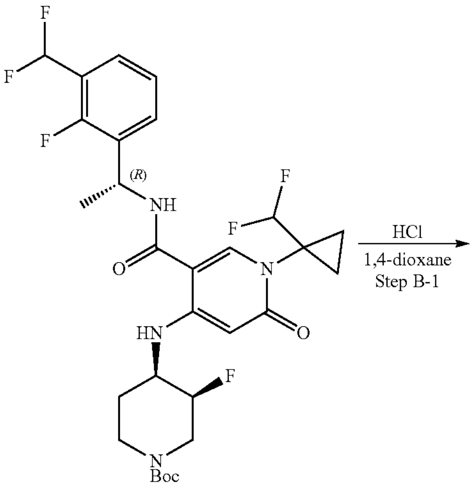

Isomer A

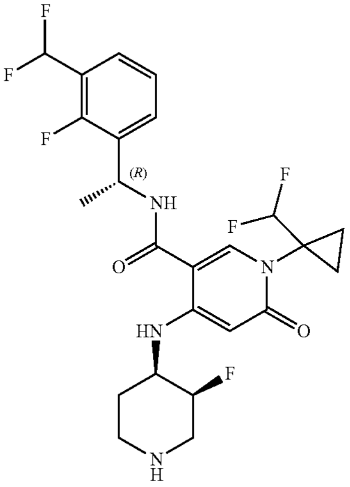
Example 69

To a mixture of tert-butyl (3S,4R)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate [Isomer A] (36 mg, 0.06 mmol) in 1,4-Dioxane (2 mL) was added HCl (4M in 1,4-dioxane, 2 mL). The mixture was stirred at rt for 2 hr. The mixture was concentrated, and the residue was basified by dissolving in 2 mL 7 M $NH_3$ in MeOH. The crude material was purified by preparative HPLC (ACN/water/0.1$NH_4HCO_3$) to provide the title compound (15.9 mg, 53% yield). MS obsd. (ESI+) 517.3 $[M+H]^+$. Analytical chiral UPCC: (Column: IG-3, 4.6*100 mm 3 um, Flow rate: 3.0 mL/min, Co-solvent:EtOH (1% 7M NH3 in MeOH, Temp 40° C.). Retention time=2.0 min.

Step B-2: N—((R)-1-(3-(difluoromethyl)-2-fluorophenyl)ethyl)-1-(1-(difluoromethyl)cyclopropyl)-4-(((3R,4S)-3-fluoropiperidin-4-yl)amino)-6-oxo-1,6-dihydropyridine-3-carboxamide (Example 70, Absolute Stereochemistry on Piperidine Ring is Arbitrarily Defined)

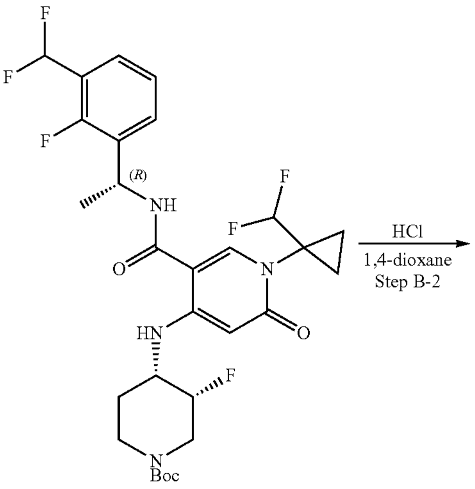

Isomer B

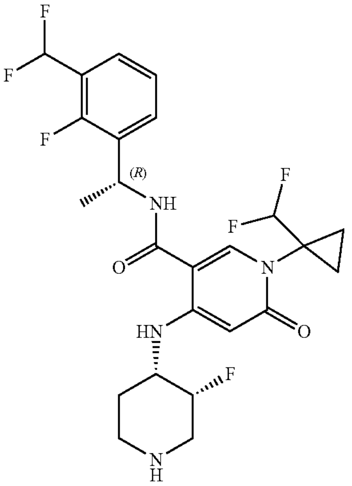
Example 70

To a mixture of tert-butyl (3R,4S)-4-((5-(((R)-1-(3-(difluoromethyl)-2-fluorophenyl)ethyl)carbamoyl)-1-(1-(difluoromethyl)cyclopropyl)-2-oxo-1,2-dihydropyridin-4-yl)amino)-3-fluoropiperidine-1-carboxylate [Isomer B] (31 mg, 0.05 mmol) in 1,4-dioxane (2 mL) was added HCl (4M in dioxane, 2 mL). The mixture was stirred at rt for 2 hr. The mixture was concentrated and the residue was basified by dissolving it in 2 mL 7 M $NH_3$ in MeOH and concentrating again. The crude material was purified by preparative HPLC (ACN/water/0.1% $NH_4HCO_3$) to provide the title compound (17 mg, 65% yield). MS obsd. (ESI+) 517.3 [M+H]+. Analytical chiral UPCC: (Column: IG-3, 4.6*100 mm 3 um, Flow rate: 3.0 mL/min, Co-solvent:EtOH (1% 7M NH3 in MeOH, Temp 40° C.). Retention time=1.5 min.

Examples 71 and 72: 1-((1S,2R)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Example 71) and 1-((1R,2S)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Example 72)(Unassigned Diastereomers)
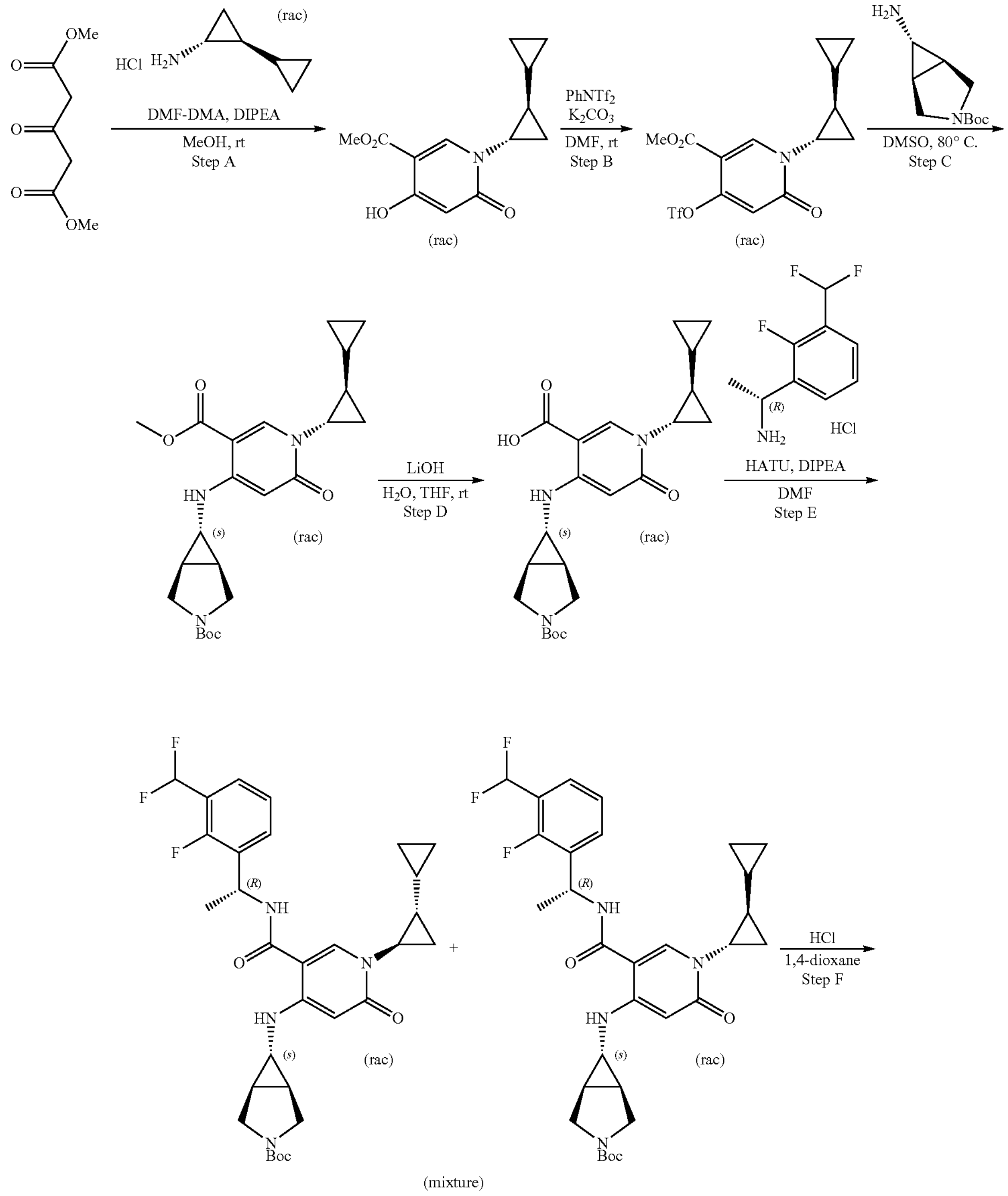

-continued

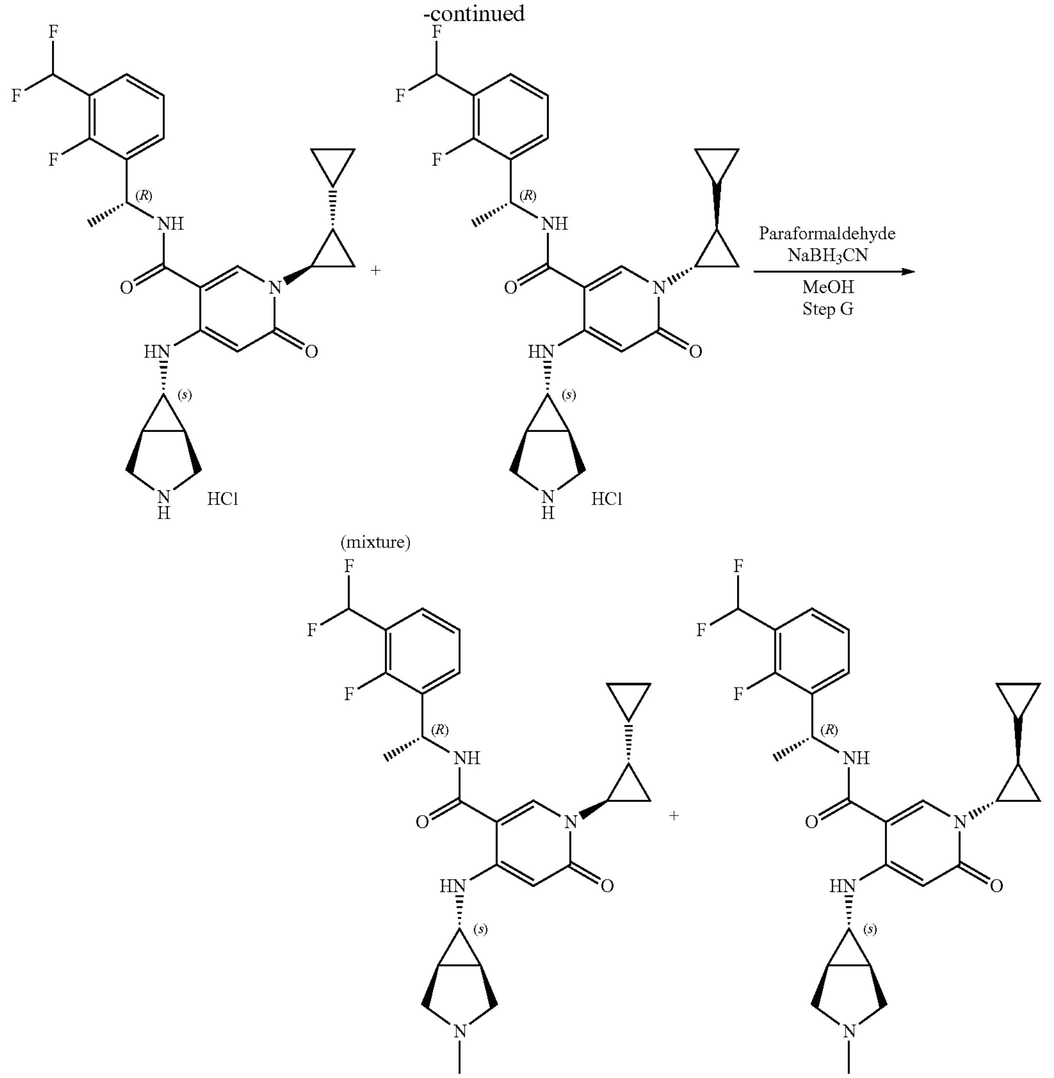

Example 71 Example 72

Step A: methyl 1-((trans)-[1,1'-bi(cyclopropan)]-2-yl)-4-hydroxy-6-oxo-1,6-dihydropyridine-3-carboxylate

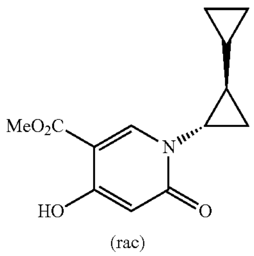 [SMILES: COC(=O)c1cn([C@H]2C[C@@H]2C2CC2)c(=O)cc1O]

(rac)

To a solution of dimethyl 3-oxopentanedioate (500 mg, 2.87 mmol) in methanol (7 mL) was added 1,1-dimethoxy-N,N-dimethyl-methanamine (410 mg, 3.45 mmol), and the mixture was stirred at rt for 16 hr. To the reaction mixture was added ((trans)-[1,1'-bi(cyclopropan)]-2-amine hydrochloride (403 mg, 3.01 mmol) and DIPEA (742 mg, 5.74 mmol). The reaction mixture was stirred at rt for 24 hr. The solvent was removed under reduced pressure. To the residue was added water (20 mL) and DCM (30 mL), and the mixture was acidified with saturated citric acid to pH~4. Then it was extracted with DCM (50 mL×3). The combined organic layers were dried over $Na_2SO_4$, filtered and concentrated. Purification by silica gel chromatography (50%-60% EtOAc in PE) afforded the title compound (317 mg, 44% yield). (ESI+) 250.2 $[M+H]^+$.

Step B: methyl 1-((trans)-[1,1'-bi(cyclopropan)]-2-yl)-6-oxo-4-(((trifluoromethyl)sulfonyl)oxy)-1,6-dihydropyridine-3-carboxylate

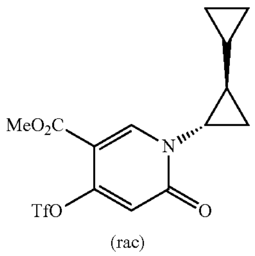 [SMILES: COC(=O)c1cn([C@H]2C[C@@H]2C2CC2)c(=O)cc1OS(=O)(=O)C(F)(F)F]

(rac)

To a solution of methyl 1-((trans)-[1,1'-bi(cyclopropan)]-2-yl)-4-hydroxy-6-oxo-1,6-dihydropyridine-3-carboxylate (317 mg, 1.27 mmol) in DMF (5 mL) was added N,N-bis (trifluoromethylsulfonyl) aniline (681.50 mg, 1.91 mmol) and potassium carbonate (527.31 mg, 3.82 mmol). The reaction mixture was stirred for 1.5 hr then quenched by adding 5 mL of aqueous saturated ammonium chloride. The reaction mixture was extracted with DCM (5 mL×3). The combined organic layers were washed with brine and dried ($Na_2SO_4$), filtered and concentrated. The residue was purified by silica gel chromatography (20%-30% EtOAc in PE) to afford the title compound (360 mg, 74% yield). MS obsd. (ESI+) 382.0 $[M+H]^+$.

Step C: tert-butyl (1R,5S,6s)-6-((1-((trans)-[1,1'-bi (cyclopropan)]-2-yl)-5-(methoxycarbonyl)-2-oxo-1,2-dihydropyridin-4-yl)amino)-3-azabicyclo[3.1.0] hexane-3-carboxylate

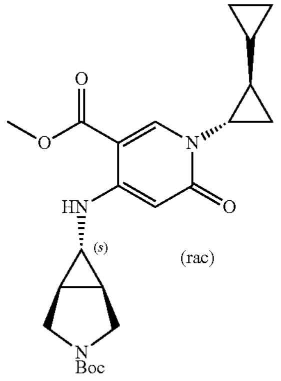 [SMILES: COC(=O)c1cn([C@H]2C[C@@H]2C2CC2)c(=O)cc1N[C@H]1[C@@H]2CN(C(=O)OC(C)(C)C)C[C@@H]21]

(rac)

To a solution of methyl 1-((trans)-[1,1'-bi(cyclopropan)]-2-yl)-6-oxo-4-(((trifluoromethyl)sulfonyl)oxy)-1,6-dihydropyridine-3-carboxylate (5.5 g, 14.42 mmol) in DMSO (20 mL) was added tert-butyl (1R,5S,6s)-6-amino-3-azabicyclo[3.1.0]hexane-3-carboxylate (5.72 g, 28.85 mmol) and the mixture was stirred at 80° C. for 3 h. After cooling to room temperature, the reaction was poured into water (100 mL) and extracted with EtOAc (150 mL×3). The combined organic layers were washed with brine, dried over anhydrous $Na_2SO_4$, filtered, and concentrated in vacuo. The residue was purified by silica gel chromatography (eluting with 50% to 60% EA in PE) to afford the title compound (5.0 g, 80% yield). MS obsd. (ESI+) 430.2 $[M+H]^+$.

Step D: 1-((trans)-[1,1'-bi(cyclopropan)]-2-yl)-4-(((1R,5S,6s)-3-(tert-butoxycarbonyl)-3-azabicyclo [3.1.0]hexan-6-yl)amino)-6-oxo-1,6-dihydropyridine-3-carboxylic acid

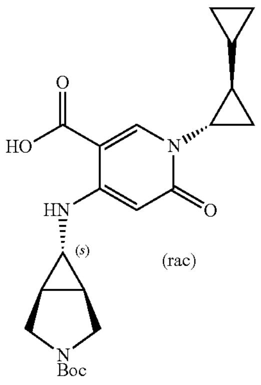 [SMILES: CC(C)(C)OC(=O)N1C[C@@H]2[C@H](C1)[C@H]2Nc1cc(=O)n([C@H]2C[C@@H]2C2CC2)cc1C(=O)O]

(rac)

To a solution of tert-butyl (1R,5S,6s)-6-((1-((trans)-[1,1'-bi(cyclopropan)]-2-yl)-5-(methoxycarbonyl)-2-oxo-1,2-dihydropyridin-4-yl)amino)-3-azabicyclo[3.1.0]hexane-3-carboxylate (5.0 g, 11.64 mmol) in THF (20 mL) and water (5 mL) was added LiOH (557 mg, 23.28 mmol) at room temperature. The reaction mixture was stirred for 16 hr. The mixture was then concentrated to dryness. To the residue was added water (10 mL) and DCM (10 mL), and the aqueous phase was acidified with 1 N HCl to pH~4. The mixture was extracted with DCM (30 mL×3). The combined organic layers were washed with brine, dried over anhydrous sodium sulfate, filtered and concentrated to afford crude title compound (5.0 g, crude), which was used without further purification. MS obsd. (ESI+) 416.3 $[M+H]^+$.

Step E: tert-butyl (1R,5S,6s)-6-((1-((1S,2R)-[1,1'-bi (cyclopropan)]-2-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate and tert-butyl (1R,5S,6s)-6-((1-((1R, 2S)-[1,1'-bi(cyclopropan)]-2-yl)-5-(((R)-1-(3-(difluoromethyl)-2-fluorophenyl)ethyl)carbamoyl)-2-oxo-1,2-dihydropyridin-4-yl)amino)-3-azabicyclo [3.1.0]hexane-3-carboxylate (mixture)

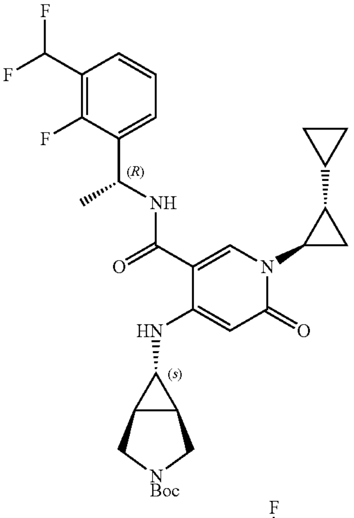

+

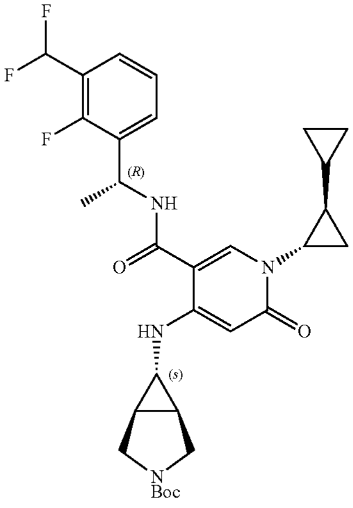

To a solution of 1-((trans)-[1,1'-bi(cyclopropan)]-2-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (5.0 g, crude) in DMF (50 mL) was added HATU (5.95 g, 15.64 mmol) and DIPEA (4.67 g, 36.10 mmol) at rt. The reaction was stirred for 30 min at rt. To the reaction mixture was (R)-1-(3-(difluoromethyl)-2-fluorophenyl)ethan-1-amine hydrochloride (3.53 g, 15.64 mmol) and the mixture was stirred for 1 hr at room temperature. The reaction mixture was poured into water (150 mL) and extracted with DCM (200 mL×3). The combined organic layers were washed with brine, dried over anhydrous $Na_2SO_4$, filtered and concentrated in vacuo. The residue was purified by silica gel chromatography (eluting with 5% to 10% MeOH in DCM) to afford a diastereomeric mixture of the title compounds (6.50 g, 95% yield over two steps). MS obsd. (ESI+) 587.4 $[M+H]^+$.

Step F: 4-(((1R,5S,6s)-3-azabicyclo[3.1.0]hexan-6-yl)amino)-1-((1S,2R)-[1,1'-bi(cyclopropan)]-2-yl)-N—((R)-1-(3-(difluoromethyl)-2-fluorophenyl)ethyl)-6-oxo-1,6-dihydropyridine-3-carboxamide hydrochloride and 4-(((1R,5S,6s)-3-azabicyclo[3.1.0]hexan-6-yl)amino)-1-((1R,2S)-[1,1'-bi(cyclopropan)]-2-yl)-N—((R)-1-(3-(difluoromethyl)-2-fluorophenyl)ethyl)-6-oxo-1,6-dihydropyridine-3-carboxamide hydrochloride (mixture)

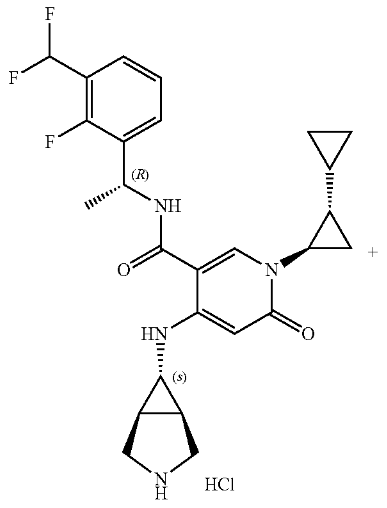

-continued

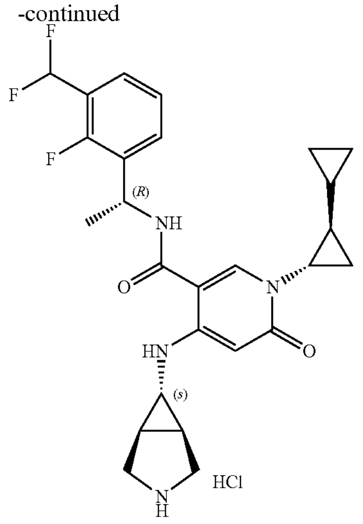

A mixture of tert-butyl (1R,5S,6s)-6-((1-((1S,2R)-[1,1'-bi(cyclopropan)]-2-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate and tert-butyl (1R,5S,6s)-6-((1-((1R,2S)-[1,1'-bi(cyclopropan)]-2-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate (6.5 g, 11.08 mmol) in HCl (4M in 1,4-dioxane, 30 mL) was stirred for 1 hr at rt. The mixture was concentrated to dryness to afford the title compounds as a diastereomeric mixture (6 g, crude). This material was used in subsequent steps without further purification. MS obsd. (ESI+) 487.2 $[M+H]^+$ Step G: 1-((1S,2R)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((1R,2S)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Examples 71 and 72, unassigned Diastereomers)

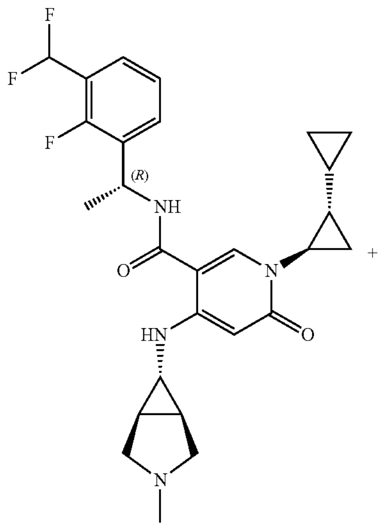

-continued

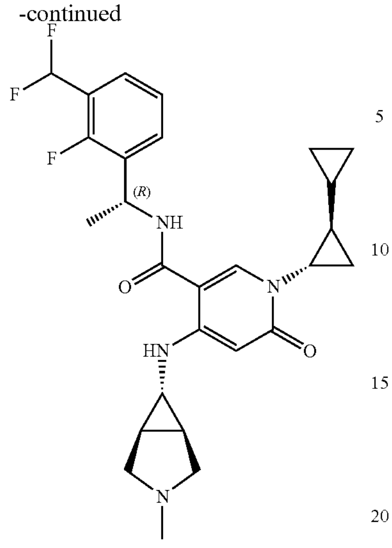

Examples 71 and 72

To a solution 4-(((1R,5S,6s)-3-azabicyclo[3.1.0]hexan-6-yl)amino)-1-((1S,2R)-[1,1'-bi(cyclopropan)]-2-yl)-N—((R)-1-(3-(difluoromethyl)-2-fluorophenyl)ethyl)-6-oxo-1,6-dihydropyridine-3-carboxamide hydrochloride and 4-(((1R,5S,6s)-3-azabicyclo[3.1.0]hexan-6-yl)amino)-1-((1R,2S)-[1,1'-bi(cyclopropan)]-2-yl)-N—((R)-1-(3-(difluoromethyl)-2-fluorophenyl)ethyl)-6-oxo-1,6-dihydropyridine-3-carboxamide hydrochloride (220 mg, 0.42 mmol) in MeOH (5 mL) was added paraformaldehyde (63.2 mg) at rt. The reaction was stirred for 15 min at rt. To the reaction mixture was added sodium cyanoborohydride (132 mg, 2.10 mmol) and the mixture was stirred for 16 hr at room temperature. The reaction was quenched with water and stirred for 30 min. The mixture was extracted with DCM (30 mL×3). The combined organic layers were washed with brine, dried over anhydrous sodium sulfate, filtered, and concentrated in vacuo. The residue was purified by preparative TLC (MeOH:DCM=1:10) followed by preparative HPLC (ACN/water/0.08% $NH_4HCO_3$) to obtain 80 mg of the title compounds as a diastereomeric mixture.

Diastereomers were further separated by chiral SFC (Daicel AD (25*250 mm, 10 um), CO2/MeOH [0.2% NH3 (7M in MeOH)]=75/25) to afford the title compounds.

Example 71: MS obsd. (ESI+) 501.2 [M+H]+. Analytical chiral UPCC: (Column: AD-3, 4.6*100 mm 3 um, Flow rate: 3.0 mL/min, Co-solvent: MeOH (0.2% 7M NH3 in MeOH), Temp 40° C.) Retention time=1.0 min.

Example 72: MS obsd. (ESI+) 501.2 [M+H]+. Analytical chiral UPCC: (Column: AD-3, 4.6*100 mm 3 um, Flow rate: 3.0 mL/min, Co-solvent: MeOH (0.2% 7M NH3 in MeOH), Temp 40° C.) Retention time=2.0 min.

Examples 73 and 74: 1-((1R,2S)-[1,1'-bi(cyclopropan)]-2-yl)-N—((R)-1-(3-(difluoromethyl)-2-fluorophenyl)ethyl)-4-((1-methylpiperidin-4-yl)amino)-6-oxo-1,6-dihydropyridine-3-carboxamide and 1-((1S,2R)-[1,1'-bi(cyclopropan)]-2-yl)-N—((R)-1-(3-(difluoromethyl)-2-fluorophenyl)ethyl)-4-((1-methylpiperidin-4-yl)amino)-6-oxo-1,6-dihydropyridine-3-carboxamide [Unassigned Diastereomers]

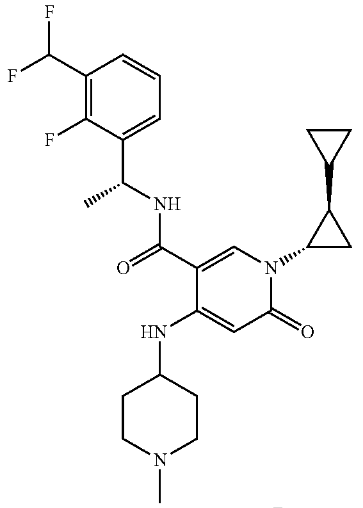

+

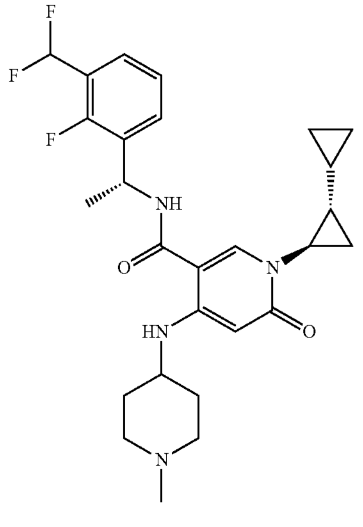

Examples 73 and 74

Examples 73 and 74 were synthesized according to analogous procedures described in examples 71 and 72 steps A-E, substituting 1-methylpiperidin-4-amine in place of tert-butyl (1R,5S,6s)-6-amino-3-azabicyclo[3.1.0]hexane-3-carboxylate in step C.

Example 73: MS obsd. (ESI+) 503.5 $[M+H]^+$. Analytical chiral UPCC: (Column: AD-3, 4.6*100 mm 3 um, Flow rate: 3.0 mL/min, Co-solvent:EtOH (1% 7M NH3 in MeOH), Temp 40° C.) Retention time=0.8 min.

Example 74: MS obsd. (ESI+) 503.5 $[M+H]^+$. Analytical chiral UPCC: (Column: AD-3, 4.6*100 mm 3 um, Flow rate: 3.0 mL/min, Co-solvent:EtOH (1% 7M NH3 in MeOH), Temp 40° C.) Retention time=1.1 min.

Example 75: (R)—N-(1-(3-(difluoromethyl)-2-fluorophenyl)ethyl)-4-((1-methylpiperidin-4-yl)amino)-6-oxo-1-(1-(trifluoromethyl)cyclopropyl)-1,6-dihydropyridine-3-carboxamide

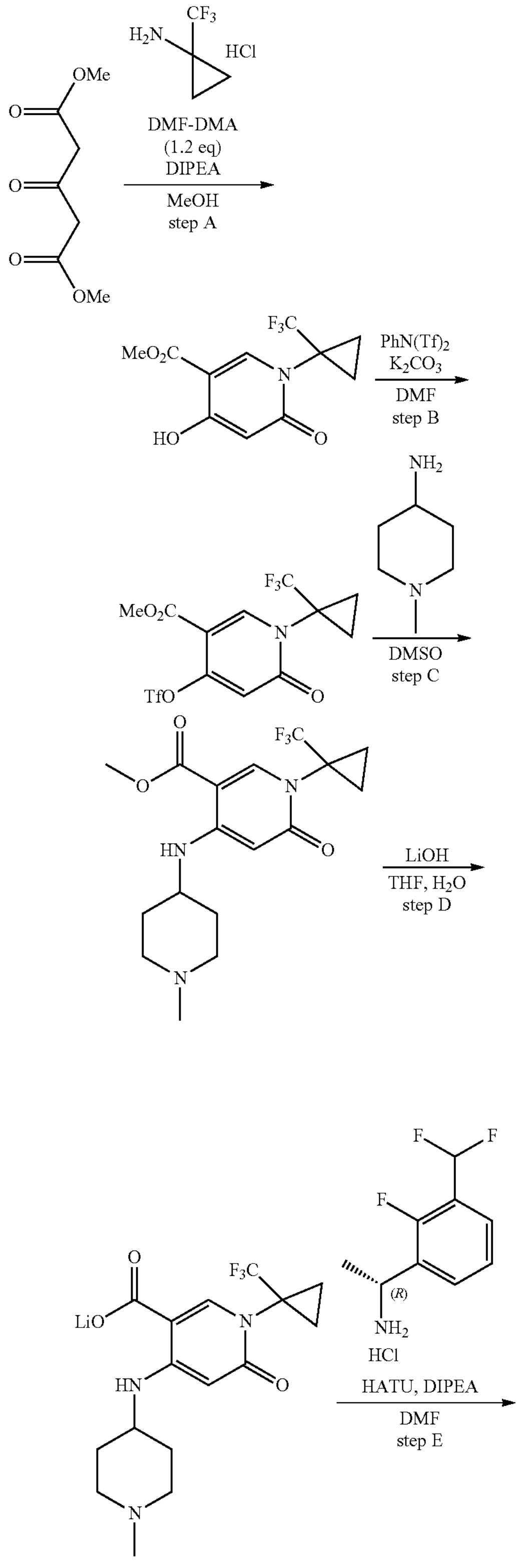

-continued

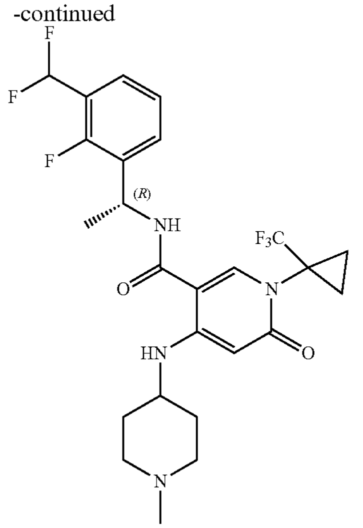

example 75

Step A: methyl 4-hydroxy-6-oxo-1-(1-(trifluoromethyl)cyclopropyl)-1,6-dihydropyridine-3-carboxylate To a solution of 1,1-dimethoxy-N,N-dimethyl-methanamine (804 mg, 6.75 mmol) in MeOH (20.0 mL) was added dimethyl 3-oxopentanedioate (979 mg, 5.63 mmol). The mixture was stirred at rt for 4 hr. 1-(trifluoromethyl)cyclopropanamine hydrochloride (1.0 g, 6.20 mmol) and DIPEA (1.25 g, 12.40 mmol) were added and stirred for 16 hr. The reaction mixture was concentrated under reduced pressure. To the residue was added water (25 mL), and the suspension was adjusted to pH~11. The solution was extracted with EtOAc. The aqueous phase was collected, and acidified with saturated citric acid to pH~4. Then the aqueous mixture was extracted with DCM. The organic layers were dried over anhydrous $Na_2SO_4$, filtered and concentrated to afford crude title compound (1.1 g, crude). This material was used without further purification. MS obsd. (ESI+) 278.0 $[M+H]^+$.

Step B: methyl 6-oxo-1-(1-(trifluoromethyl)cyclopropyl)-4-(((trifluoromethyl)sulfonyl)oxy)-1,6-dihydropyridine-3-carboxylate To a solution methyl 4-hydroxy-6-oxo-1-(1-(trifluoromethyl)cyclopropyl)-1,6-dihydropyridine-3-carboxylate (1.1 g, crude, assumed 3.97 mmol) and 1,1,1-trifluoro-N-phenyl-N-((trifluoromethyl)sulfonyl)methanesulfonamide (2.13 g, 5.95 mmol) in dry DMF (14.8 mL) was added potassium carbonate (1.65 g, 11.90 mmol). The reaction mixture was stirred at rt for 2 hr. Then the reaction mixture was quenched with aqueous saturated ammonium chloride and the mixture was extracted with ethyl acetate. The organic layer was washed with brine, dried over $Na_2SO_4$ and filtered. The solvent was removed and the residue was purified by silica gel column (eluting with 0-40% EtOAc in PE) to afford the title compound (600 mg, 37% yield). MS obsd. (ESI+) 410.0 $[M+H]^+$.

Step C: methyl 4-((1-methylpiperidin-4-yl)amino)-6-oxo-1-(1-(trifluoromethyl)cyclopropyl)-1,6-dihydropyridine-3-carboxylate To a solution of methyl 6-oxo-1-(1-(trifluoromethyl)cyclopropyl)-4-(((trifluoromethyl)sulfonyl)oxy)-1,6-dihydropyridine-3-carboxylate (300 mg, 0.73 mmol) in DMSO (5.0 mL) was added 1-methylpiperidin-4-amine (334 mg, 2.93 mmol). The mixture was stirred at rt for 1 hr. The reaction was partitioned between EtOAc and water. The organic layer was dried over sodium sulfate, filtered and concentrated to afford the title compound (170 mg, crude). This material was used without further purification. MS obsd. (ESI+) 374.1 $[M+H]^+$.

Step D: lithium 4-((1-methylpiperidin-4-yl)amino)-6-oxo-1-(1-(trifluoromethyl)cyclopropyl)-1,6-dihydropyridine-3-carboxylate To a suspension of methyl 4-((1-methylpiperidin-4-yl)amino)-6-oxo-1-(1-(trifluoromethyl)cyclopropyl)-1,6-dihydropyridine-3-carboxylate (200 mg, crude, assumed 0.53 mmol) in $H_2O$ (0.75 mL) was added LiOH (26 mg, 1.07 mmol) and THF (1.5 mL). The mixture was stirred at rt for 2 hr. The solvent was removed to afford the title compound (200 mg, crude), which was used directly in the next step. MS obsd. (ESI+) 360.1 $[M+H]^+$.

Step E: (R)—N-(1-(3-(difluoromethyl)-2-fluorophenyl)ethyl)-4-((1-methylpiperidin-4-yl)amino)-6-oxo-1-(1-(trifluoromethyl)cyclopropyl)-1,6-dihydropyridine-3-carboxamide (Example 75)

example 75

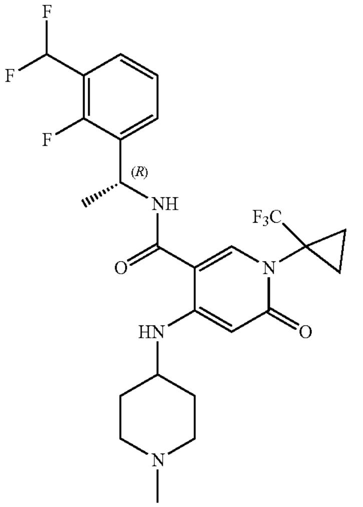

To a solution of lithium 4-((1-methylpiperidin-4-yl)amino)-6-oxo-1-(1-(trifluoromethyl)cyclopropyl)-1,6-dihydropyridine-3-carboxylate (105 mg, crude, assumed 0.29 mmol) and (R)-1-(3-(difluoromethyl)-2-fluorophenyl)ethan-1-amine hydrochloride (79 mg, 0.35 mmol) in DMF (5.0 mL) was added HATU (167 mg, 0.44 mmol) and DIPEA (151 mg, 1.17 mmol). The mixture was stirred at rt for 1 hr. The mixture was diluted with water and extracted with EtOAc. The organic layer was dried over sodium sulfate, filtered and concentrated. The residue was purified by reverse phase HPLC ($MeOH/H_2O/0.1\%$ $NH_3H_2O$) to afford the title compound (63.6 mg). MS obsd. (ESI+) 531.2 $[M+H]^+$.

Example 76: (R)—N-(1-(3-(difluoromethyl)-2-fluorophenyl)ethyl)-1-(1-(difluoromethyl)cyclobutyl)-4-((1-methylpiperidin-4-yl)amino)-6-oxo-1,6-dihydropyridine-3-carboxamide

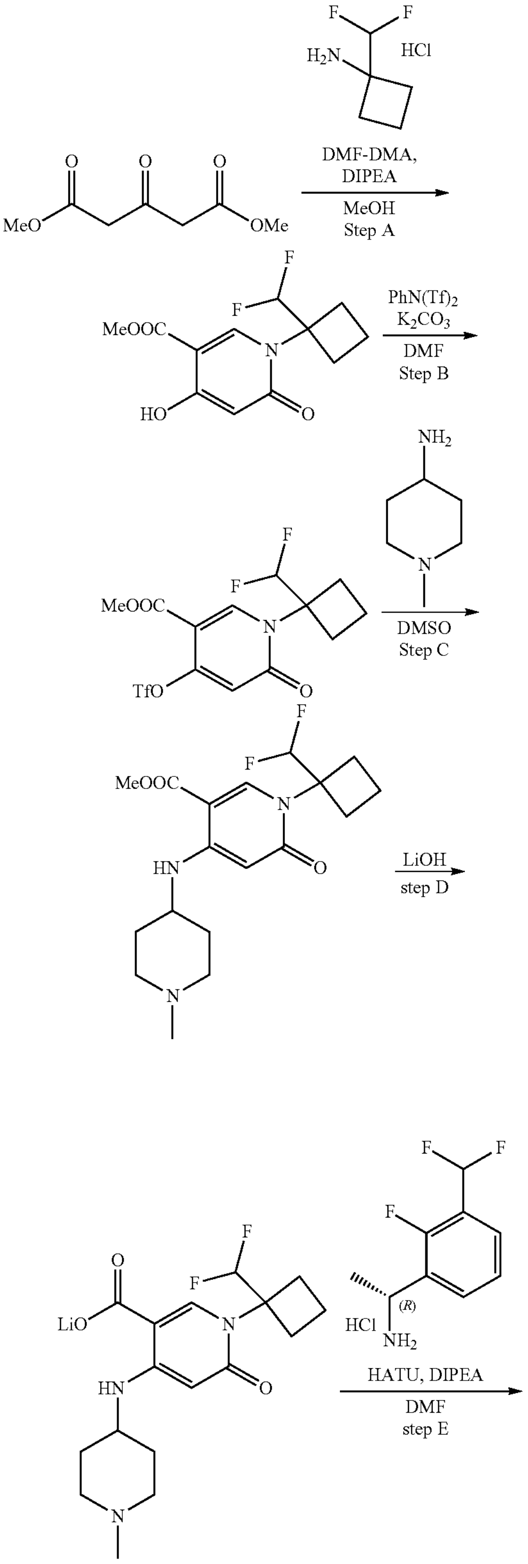

-continued

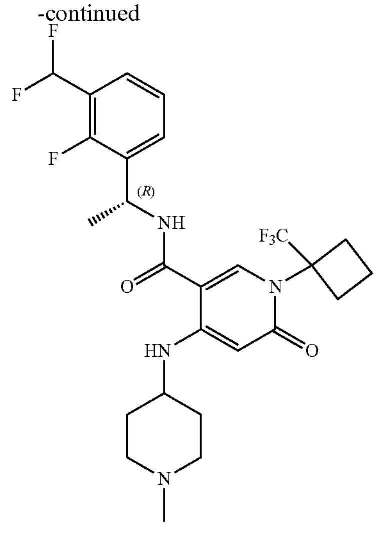

example 76

Step A: methyl 1-(1-(difluoromethyl)cyclobutyl)-4-hydroxy-6-oxo-1,6-dihydropyridine-3-carboxylate Prepared according to an analogous procedure as example 75, step A, using 1-(difluoromethyl)cyclobutan-1-amine hydrochloride in of place 1-(trifluoromethyl)cyclopropan-amine hydrochloride. MS obsd. (ESI+) 274.3 $[M+H]^+$.

Step B: methyl 1-(1-(difluoromethyl)cyclobutyl)-6-oxo-4-(((trifluoromethyl)sulfonyl)oxy)-1,6-dihydropyridine-3-carboxylate Prepared according to an analogous procedure as example 75, step B, starting with methyl 1-(1-(difluoromethyl)cyclobutyl)-4-hydroxy-6-oxo-1,6-dihydropyridine-3-carboxylate. MS obsd. (ESI+) 406.4 $[M+H]^+$.

Step C: methyl 1-(1-(difluoromethyl)cyclobutyl)-4-((1-methylpiperidin-4-yl)amino)-6-oxo-1,6-dihydropyridine-3-carboxylate To a solution of methyl 3-(1-(difluoromethyl)cyclobutyl)-4-oxo-6-(((trifluoromethyl)sulfonyl)oxy)cyclohexa-1,5-diene-1-carboxylate (151 mg, 0.37 mmol) in DMSO (2 mL) was added 1-methylpiperidin-4-amine (128 mg, 1.12 mmol), and the mixture was stirred at 80° C. for 3 hr. The mixture was diluted with DCM, and the organic phase was washed with water, dried over $Na_2SO_4$, filtered and concentrated. The residue was purified by silica gel chromatography on (eluting with 0% to 20% MeOH in DCM) to afford the title compound (123 mg, 89% yield). MS obsd. (ESI+) 370.5 $[M+H]^+$.

Step D: lithium 1-(1-(difluoromethyl)cyclobutyl)-4-((1-methylpiperidin-4-yl)amino)-6-oxo-1,6-dihydropyridine-3-carboxylate Prepared according to an analogous procedure as example 75, step D, starting with methyl 1-(1-(difluoromethyl)cyclobutyl)-4-((1-methylpiperidin-4-yl)amino)-6-oxo-1,6-dihydropyridine-3-carboxylate. Material was used crude in next step. MS obsd. (ESI+) 356.4 $[M+H]^+$.

Step E: (R)—N-(1-(3-(difluoromethyl)-2-fluorophenyl)ethyl)-1-(1-(difluoromethyl)cyclobutyl)-4-((1-methylpiperidin-4-yl)amino)-6-oxo-1,6-dihydropyridine-3-carboxamide (Example 76)

example 76

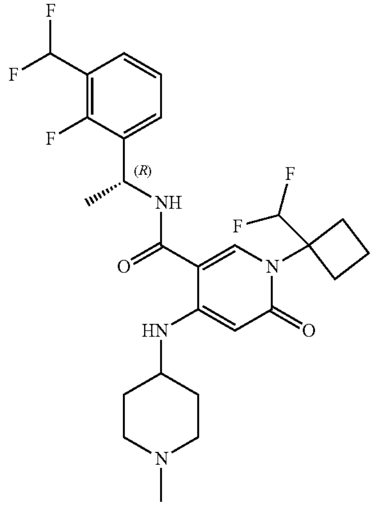

(R)—N-(1-(3-(difluoromethyl)-2-fluorophenyl)ethyl)-1-(1-(difluoromethyl)cyclobutyl)-4-((1-methylpiperidin-4-yl)amino)-6-oxo-1,6-dihydropyridine-3-carboxamide was prepared according to an analogous procedure as example 75, step E, starting with crude lithium 1-(1-(difluoromethyl)cyclobutyl)-4-((1-methylpiperidin-4-yl)amino)-6-oxo-1,6-dihydropyridine-3-carboxylate. MS obsd. (ESI+) 527.6 $[M+H]^+$. $^1H$ NMR (400 MHz, DMSO-$d_6$) δ 8.88 (1H), 7.90 (1H), 7.74 (1H), 7.60 (1H), 7.53 (1H), 7.35 (1H), 7.21 (1H), 6.36 (1H), 5.30 (1H), 5.20 (1H), 3.23 (1H), 2.64 (4H), 2.54 (2H), 2.12 (3H), 2.07 (2H), 1.97-1.75 (4H), 1.48 (3H), 1.42-1.26 (2H).

Example 77: (R)—N-(1-(3-(difluoromethyl)-2-fluorophenyl)ethyl)-1-(1-(fluoromethyl)cyclopropyl)-4-((1-methylpiperidin-4-yl)amino)-6-oxo-1,6-dihydropyridine-3-carboxamide

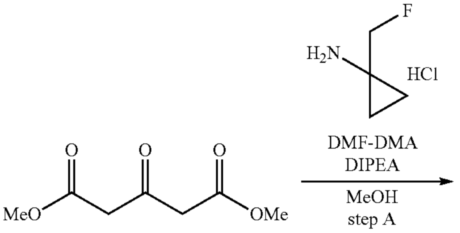

-continued

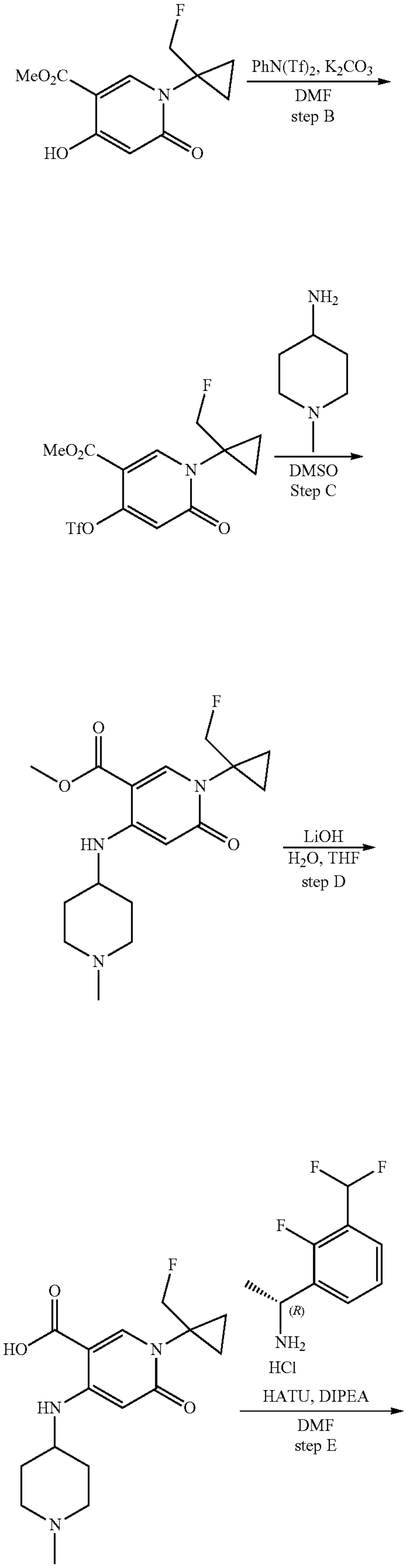

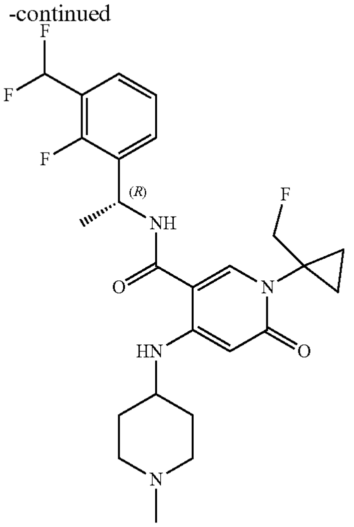

example 77

Step A: methyl 1-(1-(fluoromethyl)cyclopropyl)-4-hydroxy-6-oxo-1,6-dihydropyridine-3-carboxylate Methyl 1-(1-(fluoromethyl)cyclopropyl)-4-hydroxy-6-oxo-1,6-dihydropyridine-3-carboxylate was prepared according to an analogous procedure as example 75, step A, starting with 1-(fluoromethyl)cyclopropan-1-amine hydrochloride 1-in place of (trifluoromethyl)cyclopropanamine hydrochloride. MS obsd. (ESI+) 242.3 $[M+H]^+$.

Step B: methyl 1-(1-(fluoromethyl)cyclopropyl)-6-oxo-4-(((trifluoromethyl)sulfonyl)oxy)-1,6-dihydropyridine-3-carboxylate Methyl 1-(1-(fluoromethyl)cyclopropyl)-6-oxo-4-(((trifluoromethyl)sulfonyl)oxy)-1,6-dihydropyridine-3-carboxylate was prepared according to an analogous procedure as example 75, step B, starting with methyl 1-(1-(fluoromethyl)cyclopropyl)-4-hydroxy-6-oxo-1,6-dihydropyridine-3-carboxylate. MS obsd. (ESI+) 374.3 $[M+H]^+$.

Step C: methyl 1-(1-(fluoromethyl)cyclopropyl)-4-((1-methylpiperidin-4-yl)amino)-6-oxo-1,6-dihydropyridine-3-carboxylate Methyl 1-(1-(fluoromethyl)cyclopropyl)-4-((1-methylpiperidin-4-yl)amino)-6-oxo-1,6-dihydropyridine-3-carboxylate was prepared according to an analogous procedure as example 75, step C, starting with methyl 1-(1-(fluoromethyl)cyclopropyl)-6-oxo-4-(((trifluoromethyl)sulfonyl)oxy)-1,6-dihydropyridine-3-carboxylate. MS obsd. (ESI+) 338.4 $[M+H]^+$.

Step D: 1-(1-(fluoromethyl)cyclopropyl)-4-((1-methylpiperidin-4-yl)amino)-6-oxo-1,6-dihydropyridine-3-carboxylic acid To a suspension of methyl 1-(1-(fluoromethyl)cyclopropyl)-4-((1-methylpiperidin-4-yl)amino)-6-oxo-1,6-dihydropyridine-3-carboxylate (95 mg, 0.28 mmol) in $H_2O$ (0.5 mL) and THF (1.5 mL) was added LiOH (10 mg, 0.42 mmol) at room temperature. The mixture was stirred at room temperature for 2 hr. The reaction mixture was adjusted to pH=4 with HCl (3M), then the mixture was concentrated under vacuum to afford the crude title compound (91 mg, crude). The crude material was directly used in the next step without further purification. MS obsd. (ESI+) 324.3 $[M+H]^+$.

Step E: (R)—N-(1-(3-(difluoromethyl)-2-fluorophenyl)ethyl)-1-(1-(fluoromethyl)cyclopropyl)-4-((1-methylpiperidin-4-yl)amino)-6-oxo-1,6-dihydropyridine-3-carboxamide (Example 77)

example 77

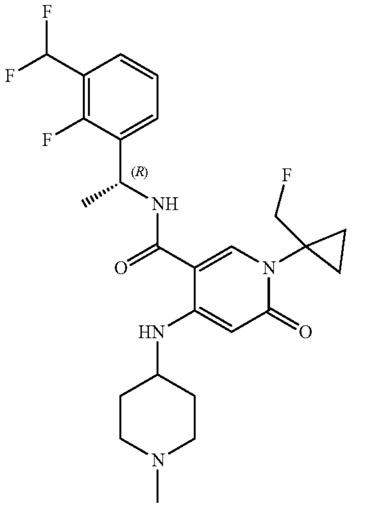

To a solution of 1-(1-(fluoromethyl)cyclopropyl)-4-((1-methylpiperidin-4-yl)amino)-6-oxo-1,6-dihydropyridine-3-carboxylic acid (91 mg, crude) and (R)-1-(3-(difluoromethyl)-2-fluorophenyl)ethan-1-amine hydrochloride (76 mg, 0.33 mmol) in DMF (5.0 mL) was added HATU (161 mg, 0.42 mmol) and DIPEA (146 mg, 1.13 mmol). The mixture was stirred at room temperature for 1 hr. The mixture was concentrated directly. The residue was purified by silica gel chromatography (eluted with 0-10% MeOH in DCM) followed by reverse phase column (C18, MeCN/water) to afford the target compound (21 mg) as a white solid. MS obsd. (ESI+) 495.2 $[M+H]^+$. $^1H$ NMR (400 MHz, $CD_3OD$) δ ppm: 8.05 (1H), 7.57-7.49 (2H), 7.30 (1H), 7.14 (1H), 5.45 (1H), 5.41 (1H), 4.58 (2H), 5.38 (1H), 2.81-2.70 (2H), 2.39-2.31 (5H), 2.00 (2H), 1.60-1.52 (5H), 1.32-1.23 (4H).

Example 78: (R)-1-(1-(cyclopropanecarbonyl)-3-methylazetidin-3-yl)-N-(1-(3-(difluoromethyl)-2-fluorophenyl)ethyl)-4-((1-methylpiperidin-4-yl)amino)-6-oxo-1,6-dihydropyridine-3-carboxamide

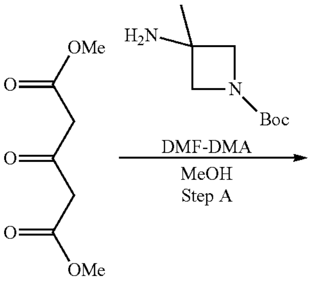

-continued

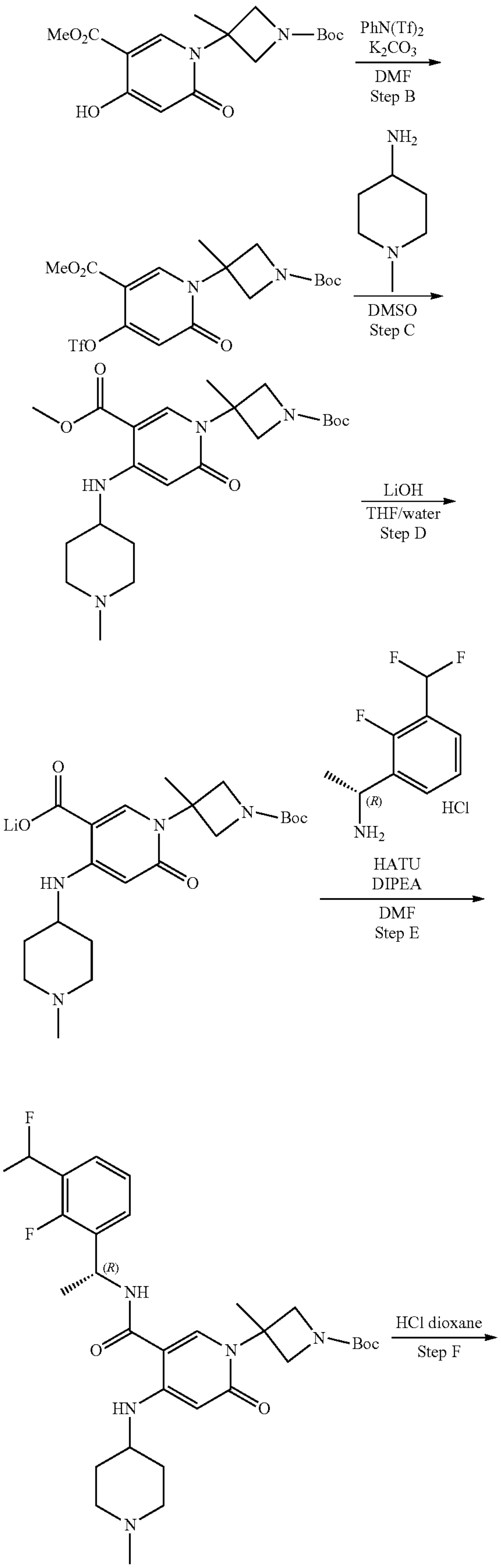

-continued

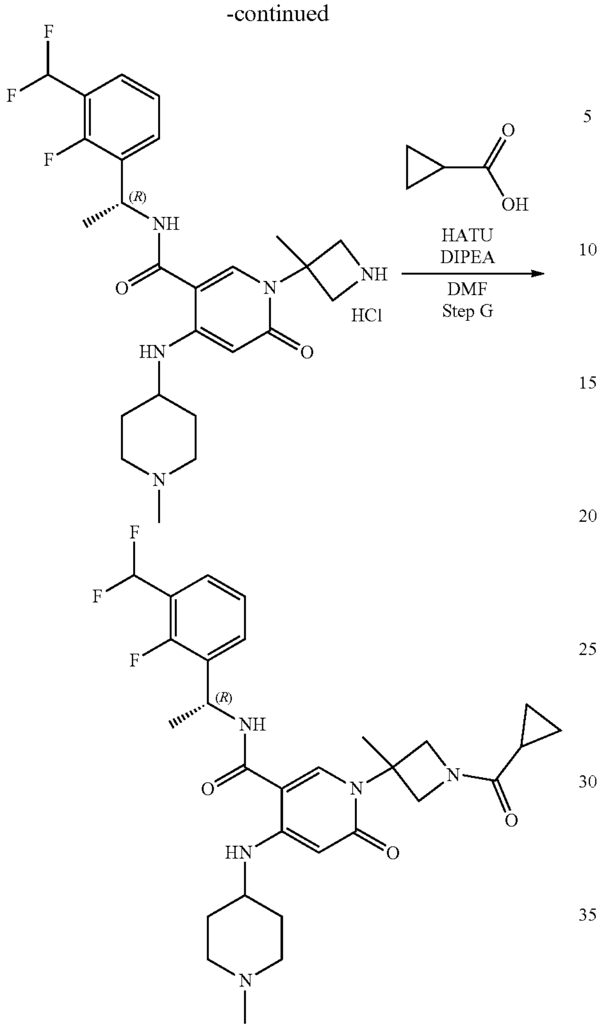

Example 78

Step A: methyl 1-(1-(tert-butoxycarbonyl)-3-methylazetidin-3-yl)-4-hydroxy-6-oxo-1,6-dihydropyridine-3-carboxylate To a solution of dimethyl 3-oxopentanedioate (100 mg, 0.57 mmol) in MeOH (10 mL) was added 1,1-dimethoxy-N,N-dimethyl-methanamine (82 mg, 0.69 mmol). The mixture was stirred for 6 hr at rt. Then tert-butyl 3-amino-3-methyl-azetidine-1-carboxylate (118 mg, 0.63 mmol) was added to the mixture. The mixture was stirred for 14 hr at rt. The solvent was removed in vacuo. The residue was purified by silica gel chromatography (eluted with 0% to 30% EtOAc in PE) to afford the title compound (92 mg, 47% yield). MS obsd. (ESI+) 339.4 $[M+H]^+$.

Step B: methyl 1-(1-(tert-butoxycarbonyl)-3-methylazetidin-3-yl)-6-oxo-4-(((trifluoromethyl)sulfonyl)oxy)-1,6-dihydropyridine-3-carboxylate To a solution of methyl 1-(1-(tert-butoxycarbonyl)-3-methylazetidin-3-yl)-4-hydroxy-6-oxo-1,6-dihydropyridine-3-carboxylate (92 mg, 0.27 mmol) and 1,1,1-trifluoro-N-phenyl-N-(trifluoromethylsulfonyl)methanesulfonamide (146 mg, 0.41 mmol) in dry DMF (5 mL) was added potassium carbonate (113 mg, 0.82 mmol). The reaction mixture was stirred at rt for 3 hr. The reaction mixture was quenched with water and the pH was adjusted to ~4 with saturated aqueous citric acid. The reaction mixture was extracted with DCM (3×50 mL). The combined organic layers were washed with water (3×50 mL) and dried over $Na_2SO_4$, filtered and concentrated. The residue was purified by silica gel chromatography (eluted with 0% to 50% EtOAc in PE) to afford the title compound (113 mg, 88% yield). MS obsd. (ESI+) 471.3 $[M+H]^+$.

Step C: methyl 1-(1-(tert-butoxycarbonyl)-3-methylazetidin-3-yl)-4-((1-methylpiperidin-4-yl)amino)-6-oxo-1,6-dihydropyridine-3-carboxylate A solution of methyl 1-(1-(tert-butoxycarbonyl)-3-methylazetidin-3-yl)-6-oxo-4-(((trifluoromethyl)sulfonyl)oxy)-1,6-dihydropyridine-3-carboxylate (113 mg, 0.24 mmol) and 1-methylpiperidin-4-amine (82 mg, 0.72 mmol) in DMSO (1 mL) was stirred for 3 hr at 80° C. The mixture was quenched with water and extracted with DCM (3×80 mL). The combined organic layers were washed with water (3×50 mL), dried over $Na_2SO_4$, filtered and concentrated. The residue was purified by silica gel chromatography (eluted with 0% to 20% EtOAc in PE) to afford the title compound (37 mg, 35% yield). MS obsd. (ESI+) 435.3 $[M+H]^+$.

Step D: lithium 1-(1-(tert-butoxycarbonyl)-3-methylazetidin-3-yl)-4-((1-methylpiperidin-4-yl)amino)-6-oxo-1,6-dihydropyridine-3-carboxylate To a solution of methyl 1-(1-(tert-butoxycarbonyl)-3-methylazetidin-3-yl)-4-((1-methylpiperidin-4-yl)amino)-6-oxo-1,6-dihydropyridine-3-carboxylate (37 mg, 0.09 mmol) in THF (4 mL) and water (1 mL) was added lithium hydroxide (4 mg, 0.18 mmol). The mixture was stirred for 14 h at rt. The solvent was removed in vacuo to afford the crude title compound (36 mg, crude). The crude product was used in the next step directly without further purification. MS obsd. (ESI+) 421.4 $[M+H]^+$.

Step E: tert-butyl (R)-3-(5-((1-(3-(difluoromethyl)-2-fluorophenyl)ethyl)carbamoyl)-4-((1-methylpiperidin-4-yl)amino)-2-oxopyridin-1 (2H)-yl)-3-methylazetidine-1-carboxylate To a solution of lithium 1-(1-(tert-butoxycarbonyl)-3-methylazetidin-3-yl)-4-((1-methylpiperidin-4-yl)amino)-6-oxo-1,6-dihydropyridine-3-carboxylate (36 mg, crude) in DMF (5 mL) was added HATU (47 mg, 0.12 mmol) and N,N-Diisopropylethylamine (32 mg, 0.24 mmol) and the mixture was stirred for 30 min at rt. Then (R)-1-(3-(difluoromethyl)-2-fluorophenyl)ethan-1-amine hydrochloride (28 mg, 0.12 mmol) was added and stirred for 1 hr. The mixture was quenched with water and extracted with DCM (3×80 mL). The combined organic layers were washed with water (3×50 mL), dried over $Na_2SO_4$, filtered and concentrated in vacuo. The residue was purified by silica gel chromatography (eluted with 0% to 10% MeOH in DCM) to afford the title compound (43 mg, 87% yield). MS obsd. (ESI+) 592.5 $[M+H]^+$.

Step F: (R)—N-(1-(3-(difluoromethyl)-2-fluorophenyl)ethyl)-1-(3-methylazetidin-3-yl)-4-((1-methylpiperidin-4-yl)amino)-6-oxo-1,6-dihydropyridine-3-carboxamide hydrochloride A solution of tert-butyl (R)-3-(5-((1-(3-(difluoromethyl)-2-fluorophenyl)ethyl)carbamoyl)-4-((1-methylpiperidin-4-yl)amino)-2-oxopyridin-1 (2H)-yl)-3-methylazetidine-1-carboxylate (43 mg, 0.07 mmol) in HCl (4M in 1,4-dioxane, 5 mL) was stirred for 1 hr at rt. The solvent was removed in vacuo to afford crude title compound (38 mg, crude). The crude product was used in the next step directly without further purification. MS obsd. (ESI+) 492.6 $[M+H]^+$.

Step G: (R)-1-(1-(cyclopropanecarbonyl)-3-methylazetidin-3-yl)-N-(1-(3-(difluoromethyl)-2-fluorophenyl)ethyl)-4-((1-methylpiperidin-4-yl)amino)-6-oxo-1,6-dihydropyridine-3-carboxamide (Example 78)

Example 78

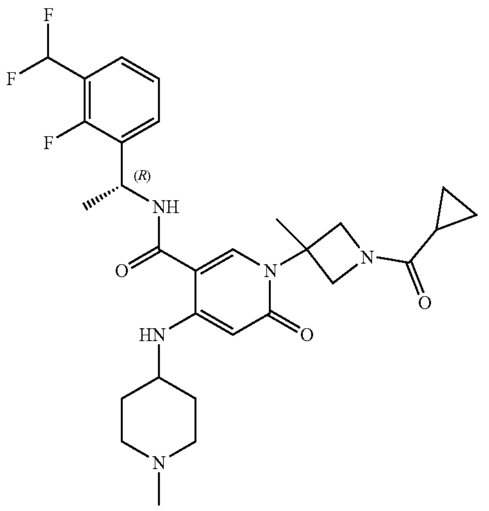

To a solution of cyclopropanecarboxylic acid (4 mg, 0.05 mmol) in DMF (5 mL) was added HATU (27 mg, 0.07 mmol) and N,N-Diisopropylethylamine (19 mg, 0.14 mmol) and the mixture was stirred for 30 min at rt. Then (R)—N-(1-(3-(difluoromethyl)-2-fluorophenyl)ethyl)-1-(3-methylazetidin-3-yl)-4-((1-methylpiperidin-4-yl)amino)-6-oxo-1,6-dihydropyridine-3-carboxamide hydrochloride (38 mg, crude) was added and the mixture was stirred for 1 hr at rt. The mixture was quenched with water and extracted with DCM (3×80 mL). The combined organic layers were washed with water (3×50 mL), dried over $Na_2SO_4$, filtered and concentrated. The residue was purified by silica gel chromatography (eluted with 0% to 20% MeOH in DCM) followed by preparative HPLC (MeCN/water/0.1% $NH_4HCO_3$) to afford the title compound (9.26 mg) as a white solid. MS obsd. (ESI+) 560.5 $[M+H]^+$. $^1H$ NMR (400 MHz, DMSO-d6) δ: 8.72 (1H), 7.87-7.83 (2H), 7.64 (1H), 7.53 (1H), 7.36-7.09 (2H), 5.28 (1H), 5.22 (1H), 4.58 (1H), 4.40 (1H), 4.32 (1H), 3.91 (1H), 3.22 (1H), 2.60-2.48 (2H), 2.13 (3H), 2.07 (2H), 1.84-1.79 (2H), 1.70 (3H), 1.59 (1H), 1.48 (3H), 1.41-1.28 (2H), 0.74-0.67 (4H).

Example 79: N—((R)-1-(3-(difluoromethyl)-2-fluorophenyl)ethyl)-1-((3S,4R)-3-fluorotetrahydro-2H-pyran-4-yl)-4-((1-methylpiperidin-4-yl)amino)-6-oxo-1,6-dihydropyridine-3-carboxamide

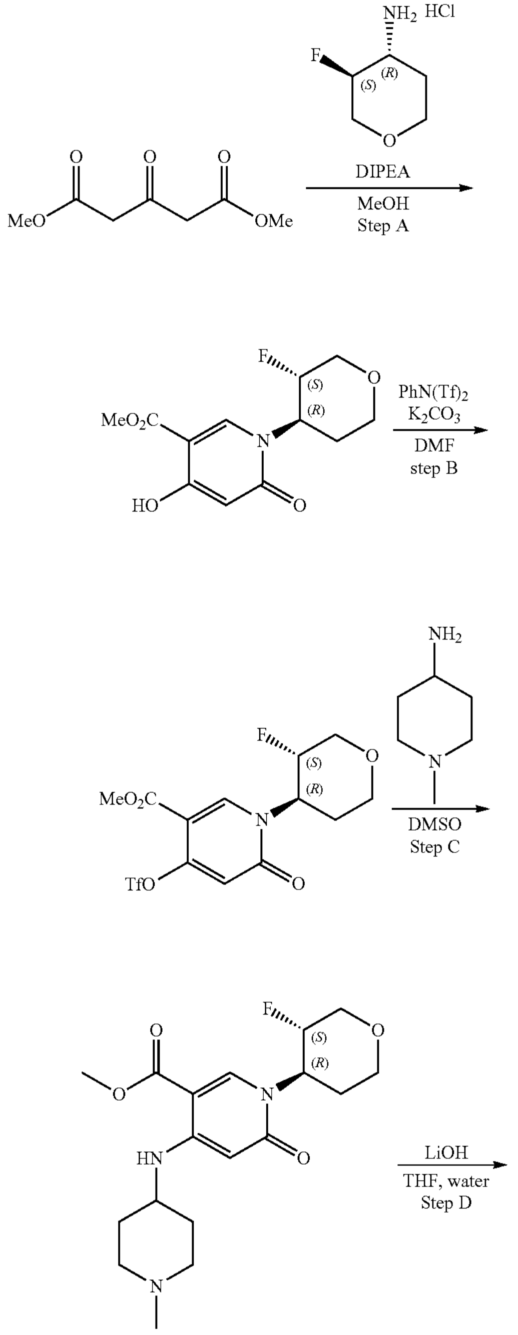

-continued

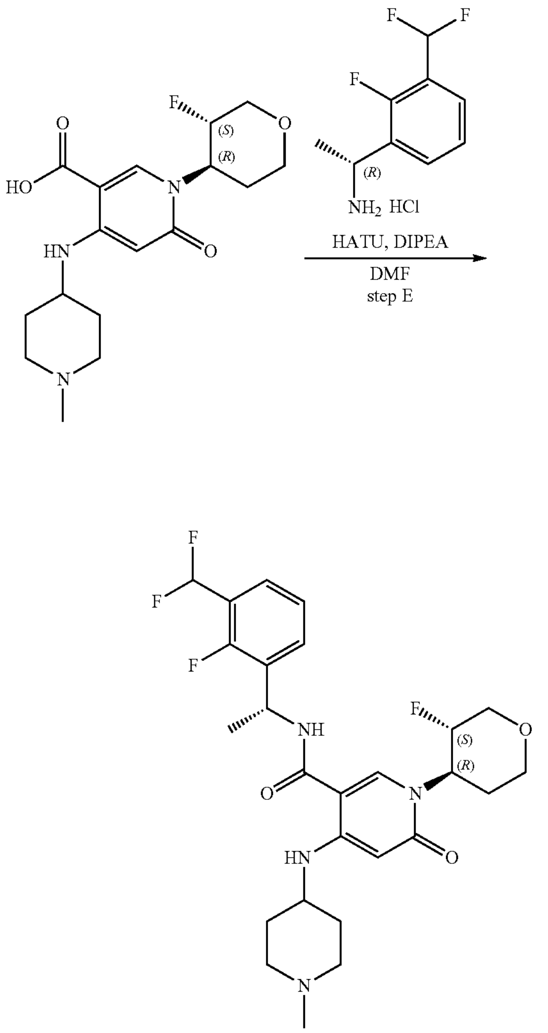

example 79

Step A: methyl 1-((3S,4R)-3-fluorotetrahydro-2H-pyran-4-yl)-4-hydroxy-6-oxo-1,6-dihydropyridine-3-carboxylate To a solution of dimethyl 3-oxopentanedioate (259 mg, 1.48 mmol) in methanol (2 mL) was added 1,1-dimethoxy-N,N-dimethyl-methanamine (193 mg, 1.62 mmol), and the mixture was stirred at rt for 8 hr. To the reaction mixture was added (3S,4R)-3-fluorotetrahydropyran-4-amine; hydrochloride (210 mg, 1.35 mmol) and DIPEA (349 mg, 2.70 mmol). The reaction mixture was stirred at rt for 24 hr. The solvent was removed under reduced pressure. To the residue was added water (20 mL) and DCM (30 mL), and the mixture was acidified with saturated citric acid to pH~4. Then it was extracted with DCM (50 mL×3). The combined organic layers were washed with brine, dried over anhydrous $Na_2SO_4$, filtered and concentrated in vacuo. The residue was purified by silica gel chromatography (eluting with 50% to 60% EtOAc in PE) to afford the title compound (184 mg, 50% yield) as a white solid. MS obsd. (ESI+) 272.1 $[M+H]^+$.

Step B: methyl 1-((3S,4R)-3-fluorotetrahydro-2H-pyran-4-yl)-6-oxo-4-(((trifluoromethyl)sulfonyl)oxy)-1,6-dihydropyridine-3-carboxylate To a solution of methyl 1-((3S,4R)-3-fluorotetrahydro-2H-pyran-4-yl)-4-hydroxy-6-oxo-1,6-dihydropyridine-3-carboxylate (184 mg, 0.68 mmol) in dry DMF (5 mL) was added N,N-bis(trifluoromethylsulfonyl) aniline (364 mg, 1.02 mmol) and potassium carbonate (281 mg, 2.04 mmol), and the mixture was stirred at rt for 2 hr. The reaction was poured into cold water (20 mL) and acidified with saturated citric acid to pH~4. Then it was extracted with DCM (50 mL×3). The combined organic layers were washed with brine, dried over anhydrous $Na_2SO_4$, filtered, and concentrated in vacuo. The residue was purified by silica gel chromatography (eluting with 20% to 30% EA in PE) to afford the title compound (250 mg, 91% yield). MS obsd. (ESI+) 404.2 $[M+H]^+$.

Step C: methyl 1-((3S,4R)-3-fluorotetrahydro-2H-pyran-4-yl)-4-((1-methylpiperidin-4-yl)amino)-6-oxo-1,6-dihydropyridine-3-carboxylate To a solution of methyl 1-((3S,4R)-3-fluorotetrahydro-2H-pyran-4-yl)-6-oxo-4-(((trifluoromethyl)sulfonyl)oxy)-1,6-dihydropyridine-3-carboxylate (250 mg, 0.62 mmol) in DMSO (2 mL) was added 1-methylpiperidin-4-amine (212 mg, 1.86 mmol), and the mixture was stirred at 80° C. for 3 hr. After cooling to room temperature, the reaction was poured into water (30 mL) and extracted with DCM (50 mL×3). The combined organic layers were washed with brine, dried over anhydrous $Na_2SO_4$, filtered and concentrated in vacuo. The residue was purified by silica gel chromatography (eluting with 10-20% MeOH in DCM) to afford the title compound (180 mg, 79% yield, approx 85% purity). This material was used without further purification. MS obsd. (ESI+) 368.2 $[M+H]^+$.

Step D: 1-((3S,4R)-3-fluorotetrahydro-2H-pyran-4-yl)-4-((1-methylpiperidin-4-yl)amino)-6-oxo-1,6-dihydropyridine-3-carboxylic acid To a solution of methyl 1-((3S,4R)-3-fluorotetrahydro-2H-pyran-4-yl)-4-((1-methylpiperidin-4-yl)amino)-6-oxo-1,6-dihydropyridine-3-carboxylate (80 mg, approximately 85% purity, 0.18 mmol) in THF (2 mL) and $H_2O$ (0.5 mL) was added LiOH (11 mg, 0.44 mmol). The reaction mixture was stirred for 2 hr at rt. The mixture was then directly concentrated to dryness. To the residue was added water (20 mL) and DCM (20 mL). The mixture was acidified with 1 N HCl to pH~4 and was extracted with DCM (30 mL×3). The combined organic layers were washed with brine, dried over anhydrous $Na_2SO_4$, filtered and concentrated to afford the title compound (80 mg, crude). This material was used without further purification. MS obsd. (ESI+) 354.2 $[M+H]^+$.

Step E: N—((R)-1-(3-(difluoromethyl)-2-fluorophenyl)ethyl)-1-((3S,4R)-3-fluorotetrahydro-2H-pyran-4-yl)-4-((1-methylpiperidin-4-yl)amino)-6-oxo-1,6-dihydropyridine-3-carboxamide (Example 79)

Example 79

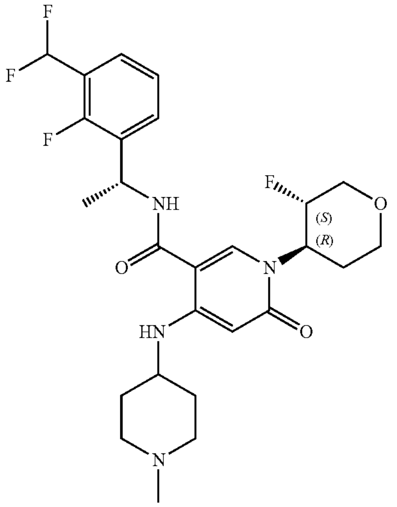

To a solution of 1-((3S,4R)-3-fluorotetrahydro-2H-pyran-4-yl)-4-((1-methylpiperidin-4-yl)amino)-6-oxo-1,6-dihydropyridine-3-carboxylic acid (80 mg, crude, assumed 0.22 mmol) in DMF (3 mL) was added HATU (112 mg, 0.29 mmol) and DIPEA (88 mg, 0.68 mmol) at rt. The reaction was stirred for 30 min at rt. To the reaction mixture was added (R)-1-(3-(difluoromethyl)-2-fluorophenyl)ethan-1-amine hydrochloride (66 mg, 0.29 mmol) and the mixture was stirred for 1 hr at rt. The reaction was poured into water (30 mL) and extracted with DCM (50 mL×3). The combined organic layers were washed with brine, dried over anhydrous $Na_2SO_4$, filtered, and concentrated in vacuo. The residue was purified by silica gel chromatography (eluting with 30% to 40% MeOH in DCM) followed by preparative HPLC (MeCN/water/0.1% $NH_4HCO_3$) to afford the title compound (13 mg). MS obsd. (ESI+) 525.2 $[M+H]^+$. $^1$H NMR (400 MHz, DMSO-$d_6$) δ: 8.73 (1H), 8.24 (1H), 8.12 (1H), 7.65 (1H), 7.53 (1H), 7.36 (1H), 7.22 (1H), 5.32 (1H), 5.27 (1H), 5.25-4.99 (2H), 4.22 (1H), 3.96 (1H), 3.51 (1H), 3.38 (1H), 3.23 (1H), 2.56 (2H), 2.22-2.11 (4H), 2.07 (2H), 1.84 (3H), 1.50 (3H), 1.43- 1.27 (2H).

Example 80: N—((R)-1-(3-(difluoromethyl)-2-fluorophenyl)ethyl)-1-((3R,4S)-3-fluorotetrahydro-2H-pyran-4-yl)-4-((1-methylpiperidin-4-yl)amino)-6-oxo-1,6-dihydropyridine-3-carboxamide Example 80

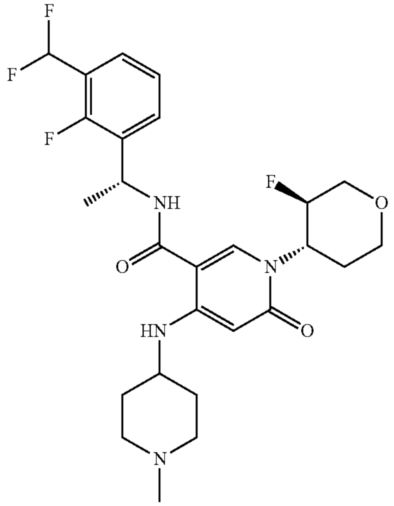

Example 80 was synthesized according to analogous procedures described in example 79, steps A-E using (3R,4S)-3-fluorotetrahydropyran-4-amine hydrochloride in step A in place of (3S,4R)-3-fluorotetrahydropyran-4-amine hydrochloride. MS obsd. (ESI+) 525.4 $[M+H]^+$. $^1$H NMR (400 MHz, DMSO-$d_6$) δ 8.73 ppm (1H), 8.25 (1H), 8.13 (1H), 7.66 (1H), 7.53 (1H), 7.39-7.08 (2H), 5.32 (1H), 5.27 (1H), 5.25-4.96 (2H), 4.22 (1H), 3.95 (1H), 3.51 (1H), 3.38 (1H), 3.22 (1H), 2.55 (2H), 2.27-2.04 (6H), 1.89-1.77 (3H), 1.49 (3H), 1.34 (2H).

The following examples can be synthesized via an analogous procedure to example 62:

| Example No. | Compound Structure | Compound Name | Characterization |
|---|---|---|---|
| 81 | 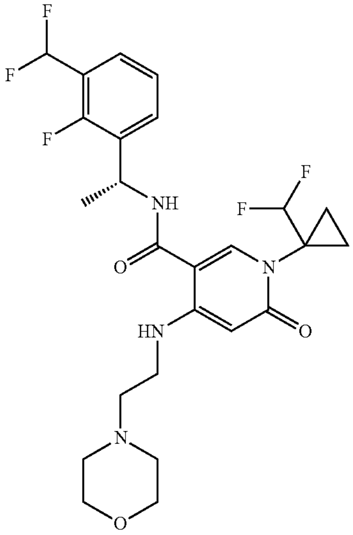 [SMILES: C[C@@H](NC(=O)c1cn(C2(C(F)F)CC2)c(=O)cc1NCCN1CCOCC1)c1cccc(C(F)F)c1F] | (R)-N-(1-(3-(difluoromethyl)-2-fluorophenyl)ethyl)-1-(1-(difluoromethyl)cyclopropyl)-4-((2-morpholinoethyl)amino)-6-ox0-1,6-dihydropyridine-3-carboxamide | MS obsd (ESI+) 529.5 $[M + H]^+$ $^1$H NMR (400 MHz, DMSO-$d_6$) δ: 8.77 (1H), 8.01 (1H), 7.94 (1H), 7.61 (1H), 7.52 (1H), 7.39 -7.03 (2H), 6.23 (1H), 5.29 (1H), 5.17 (1H), 3.56-3.40 (4H), 3.08 (2H), 2.45 (2H), 2.33 (4H), 1.48 (3H), 1.38-1.27 (4H). |

-continued

| Example No. | Compound Structure | Compound Name | Characterization |
|---|---|---|---|
| 82 | 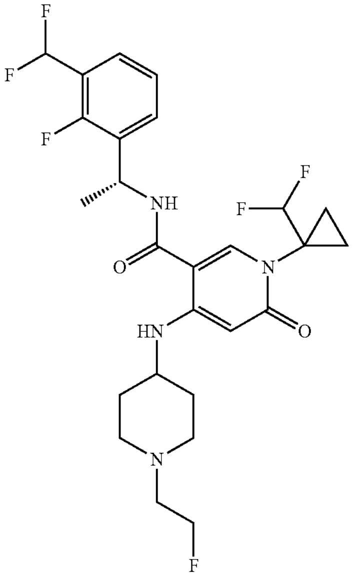 [SMILES: C[C@@H](NC(=O)c1cn(C2(C(F)F)CC2)c(=O)cc1NC1CCN(CCF)CC1)c1cccc(C(F)F)c1F] | (R)-N-(1-(3-(difluoromethyl)-2-fluorophenyl)ethyl)-1-(1-(difluoromethyl)cyclopropyl)-4-((1-(2-fluoroethyl)piperidin-4-yl)amino)-6-oxo-1,6-dihydropyridine-3-carboxamide | MS obsd (ESI+) 545.5 $[M + H]^+$ $^1H$ NMR (400 MHz, DMSO-$d_6$) δ 8.81 (1H), 8.04 (2H), 7.61 (1H), 7.53 (1H), 7.35 (1H), 7.22 (1H), 6.24 (1H), 5.37-5.26 (1H), 5.23 (1H), 4.55 (1H), 4.43 (1H), 3.25 (1H), 2.68 (2H), 2.63 - 2.52 (2H), 2.22 (2H), 1.84 (2H), 1.48 (3H), 1.42 - 1.12 (6H). |
| 83 | 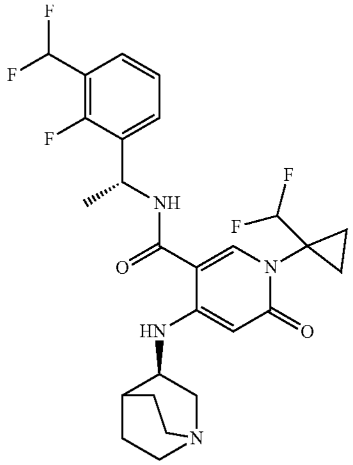 [SMILES: C[C@@H](NC(=O)c1cn(C2(C(F)F)CC2)c(=O)cc1N[C@H]1CN2CCC1CC2)c1cccc(C(F)F)c1F] | N-((R)-1-(3-(difluoromethyl)-2-fluorophenyl)ethyl)-1-(1-(difluoromethyl)cyclopropyl)-6-oxo-4-(((R)-quinuclidin-3-yl)amino)-1,6-dihydropyridine-3-carboxamide | MS obsd (ESI+) 525.4 $[M + H]^+$ $^1H$ NMR (400 MHz, DMSO-$d_6$) δ 8.83 (1H), 8.36 (1H), 8.06 (1H), 7.62 (1H), 7.53 (1H), 7.36 (1H), 7.22 (1H), 6.24 (1H), 5.32 (1H), 5.13 (1H), 3.39 (1H), 3.19 (1H), 2.65 (4H), 2.34-2.22 (1H), 1.84 (1H), 1.62-1.53 (2H), 1.49 (4H), 1.40-1.23 (5H). |
| 84 | 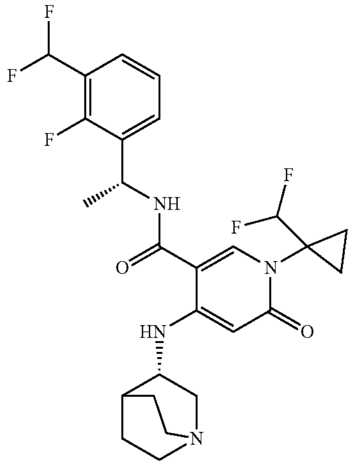 [SMILES: C[C@@H](NC(=O)c1cn(C2(C(F)F)CC2)c(=O)cc1N[C@@H]1CN2CCC1CC2)c1cccc(C(F)F)c1F] | N-((R)-1-(3-(difluoromethyl)-2-fluorophenyl)ethyl)-1-(1-(difluoromethyl)cyclopropyl)-6-oxo-4-(((S)-quinuclidin-3-yl)amino)-1,6-dihydropyridine-3-carboxamide | MS obsd (ESI+) 525.2 $[M + H]^+$ $^1H$ NMR (400 MHz, DMSO-$d_6$) δ: 8.88 (1H), 8.41 (1H), 8.09 (1H), 7.62 (1H), 7.53 (1H), 7.36 (1H), 7.23 (1H), 6.24 (1H), 5.33 (1H), 5.16 (1H), 3.50 (1H), 3.32 (1H), 2.77 (4H), 2.44 (1H), 1.88 (1H), 1.63 (2H), 1.57 - 1.42 (5H), 1.35 (4H). |

-continued

| Example No. | Compound Structure | Compound Name | Characterization |
|---|---|---|---|
| 85 and 86 | Unassigned Diastereomers 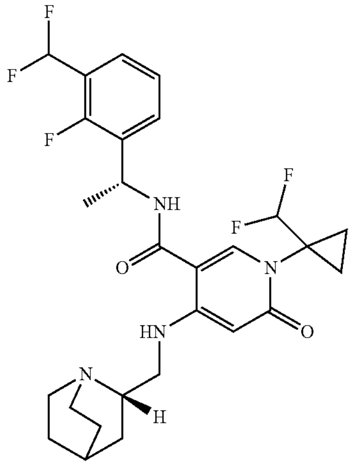 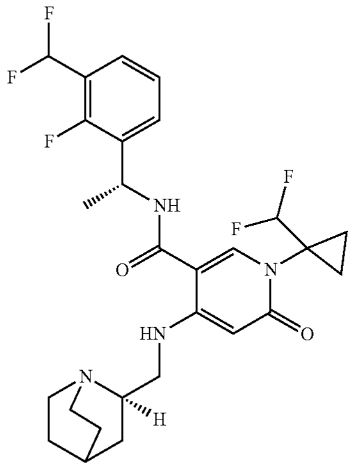 | N-((R)-1-(3-(difluoromethyl)-2-fluorophenyl)ethyl)-1-(1-(difluoromethyl)cyclopropyl)-6-oxo-4-((((S)-quinuclidin-2-yl)methyl)amino)-1,6-dihydropyridine-3-carboxamide and N-((R)-1-(3-(difluoromethyl)-2-fluorophenyl)ethyl)-1-(1-(difluoromethyl)cyclopropyl)-6-oxo-4-((((R)-quinuclidin-2-yl)methyl)amino)-1,6-dihydropyridine-3-carboxamide | Example 85: MS obsd (ESI+) 539.5 $[M + H]^+$ Analytical chiral UPCC: (Column: (R,R)-Whelk-O1, 4.6 * 100 mm 3 um, Flow rate: 3.0 mL/min, Co-solvent:EtOH (1% 7M NH3 in MeOH), Temp 40° C.) Retention time = 1.8 min. Example 86: MS obsd (ESI+) 539.5 $[M + H]^+$ Analytical chiral UPCC: (Column: (R,R)-Whelk-O1, 4.6 * 100 mm 3 um, Flow rate: 3.0 mL/min, Co-solvent:EtOH (1% 7M NH3 in MeOH), Temp 40° C.) Retention time = 1.4 min. |
| 87 and 88 | Unassigned Diastereomers 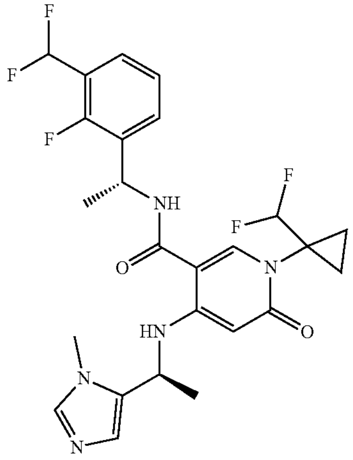 | N-((R)-1-(3-(difluoromethyl)-2-fluorophenyl)ethyl)-1-(1-(difluoromethyl)cyclopropyl)-4-(((S)-1-(1-methyl-1H-imidazol-5-yl)ethyl)amino)-6-oxo-1,6-dihydropyridine-3-carboxamide and N-((R)-1-(3-(difluoromethyl)-2-fluorophenyl)ethyl)-1-(1-(difluoromethyl)cyclopropyl)-4-(((R)-1-(1-methyl-1H-imidazol-5-yl)ethyl)amino)-6-oxo-1,6-dihydropyridine-3-carboxamide | Example 87: MS obsd (ESI+) 524.4 $[M + H]^+$ Analytical chiral UPCC: (Column: OD-3, 4.6 * 100 mm 3 um, Flow rate: 3.0 mL/min, Co-Solvent: MeOH (0.2% 7M NH3 in MeOH), Temp 40° C.) Retention time = 1.2 min. Example 88: MS obsd (ESI+) 524.4 $[M + H]^+$ Analytical chiral UPCC: (Column: OD-3, 4.6 * 100 mm 3 um, Flow rate: 3.0 mL/min, Co-solvent: MeOH (0.2% 7M NH3 in MeOH), Temp 40° C.) Retention time = 1.5 min. |

-continued
| Example No. | Compound Structure | Compound Name | Characterization |
|---|---|---|---|
| | 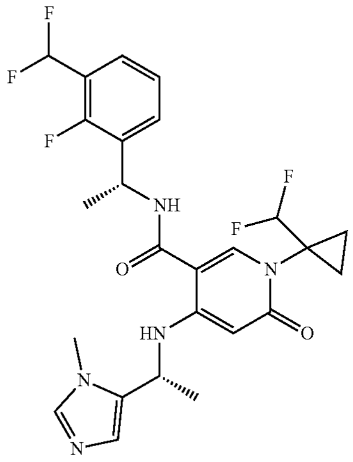 | | |
Example 89: 4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide
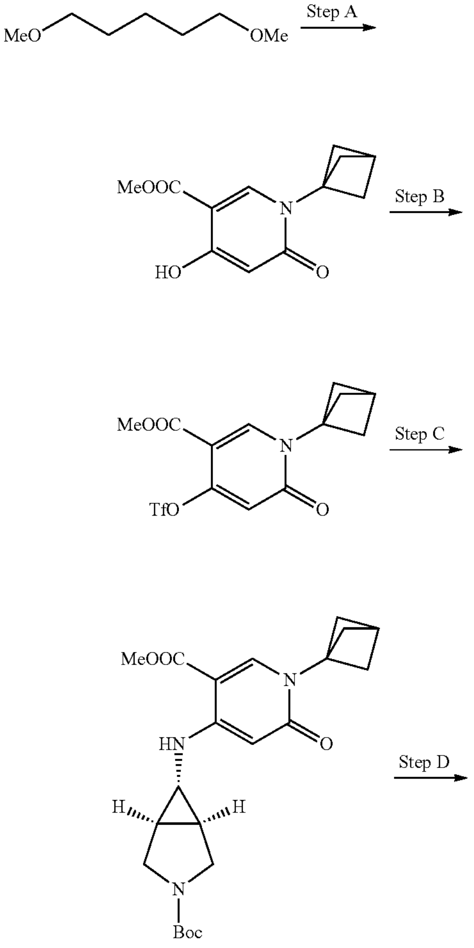
-continued
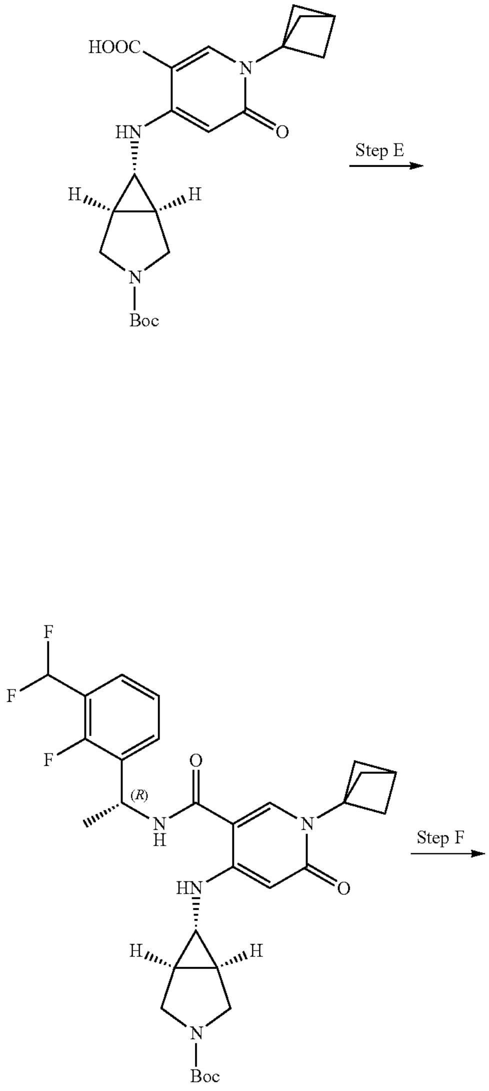

-continued

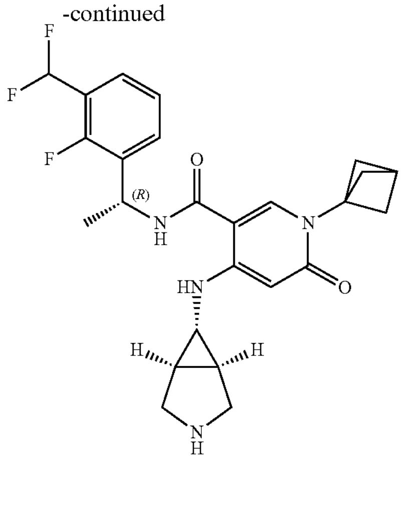

Step A: methyl 1-(bicyclo[1.1.1]pentan-1-yl)-4-hydroxy-6-oxo-1,6-dihydropyridine-3-carboxylate To a solution of dimethyl 3-oxopentanedioate (320 mg, 1.84 mmol) in methanol (5 mL) was added 1,1-dimethoxy-N,N-dimethyl-methanamine (263 mg, 2.20 mmol, 1.2 eq.), and the mixture was stirred at rt for 6 hr. To the mixture was added bicyclo[1.1.1]pentan-1-aminium chloride (200 mg, 1.67 mmol) and DIPEA (648 mg, 5.02 mmol), and the mixture was stirred at rt for 16 hr. The mixture was concentrated and the residue was purified by column chromatography on silica gel (EtOAc/PE, 0-50%) to afford the title compound (225 mg, 57% yield). MS obsd (ESI+) 236.2 ($[M+H]^+$)

Step B: methyl 1-(bicyclo[1.1.1]pentan-1-yl)-6-oxo-4-(((trifluoromethyl)sulfonyl)oxy)-1,6-dihydropyridine-3-carboxylate To a solution of methyl 1-(bicyclo[1.1.1]pentan-1-yl)-4-hydroxy-6-oxo-1,6-dihydropyridine-3-carboxylate (225 mg, 0.96 mmol) in DMF (2 mL) was added 1,1,1-trifluoro-N-phenyl-N-((trifluoromethyl)sulfonyl)methanesulfonamide (513 mg, 1.43 mmol) and potassium carbonate (397 mg, 2.87 mmol). The mixture was stirred at rt for 3 hr, after which the mixture was diluted in DCM (100 mL). The mixture was washed with ice water (100 mL×3) and the organic layer was dried over $Na_2SO_4$, filtered and concentrated. The residue was purified by column chromatography on silica gel (EtOAc/PE, 0-40%) to afford the title compound (262 mg, 74% yield). MS obsd (ESI+) 368.3 ($[M+H]^+$).

Step C: Tert-butyl (1R,5S,6s)-6-((1-(bicyclo[1.1.1]pentan-1-yl)-5-(methoxycarbonyl)-2-oxo-1,2-dihydropyridin-4-yl)amino)-3-azabicyclo[3.1.0]hexane-3-carboxylate To a solution of methyl 1-(bicyclo[1.1.1]pentan-1-yl)-6-oxo-4-(((trifluoromethyl)sulfonyl)oxy)-1,6-dihydropyridine-3-carboxylate (344 mg, 0.94 mmol) in DMSO (3 mL) was added tert-butyl (1R,5S,6s)-6-amino-3-azabicyclo[3.1.0]hexane-3-carboxylate (371 mg, 1.87 mmol), and the mixture was stirred at 80° C. for 3 hr. The mixture was cooled to rt and diluted with DCM (100 mL). The mixture was washed with water (100 mL×3) and the organic layer was dried over $Na_2SO_4$, filtered and concentrated. The residue was purified by column chromatography on silica gel (EtOAc/DCM, 10%-40%) to afford the title compound (364 mg, 93% yield). MS obsd (ESI+) 416.4 ($[M+H]^+$).

Step D: 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid To a solution of tert-butyl (1R,5S,6s)-6-((1-(bicyclo[1.1.1]pentan-1-yl)-5-(methoxycarbonyl)-2-oxo-1,2-dihydropyridin-4-yl)amino)-3-azabicyclo[3.1.0]hexane-3-carboxylate (364 mg, 0.88 mmol) in methanol (5 mL) was added lithium hydroxide (62.94 mg, 2.63 mmol) and water (1 mL). The mixture was stirred at rt for 3 hr, at which time the mixture was directly concentrated. The residue was dissolved in water (10 mL), then the pH was adjusted to 2 with aqueous HCl (1 M) at 0° C. The mixture was extracted with DCM (40 mL×3), the combined organic layers were dried over $Na_2SO_4$, filtered and concentrated to afford the title compound (340 mg, crude) which was used without further purification. MS obsd (ESI+) 402.4 ($[M+H]^+$).

Step E: tert-butyl (1R,5S,6s)-6-((1-(bicyclo[1.1.1]pentan-1-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate To a solution of 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (340 mg, crude, assumed 0.85 mmol) in DMF (2.5 mL) was added HATU (483.04 mg, 1.27 mmol) and triethylamine (257 mg, 2.54 mmol). The mixture was stirred at rt for 30 min, then (R)-1-(3-(difluoromethyl)-2-fluorophenyl)ethan-1-amine (192 mg, 1.02 mmol) was added and the mixture was stirred at rt for 3 hr. The mixture was diluted with DCM (80 mL) and washed with water (80 mL×3). The organic layer was dried over $Na_2SO_4$, filtered and concentrated. The residue was purified by column chromatography on silica gel (EtOAc/DCM, 0-50%) to afford the title compound (350 mg, 72% yield). MS obsd (ESI+) 573.5 ($[M+H]^+$).

Step F: 4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide (Example 89)

A mixture of tert-butyl (1R,5S,6s)-6-((1-(bicyclo[1.1.1]pentan-1-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate (110 mg, 0.19 mmol) in 4M HCl/1,4-dioxane (10 mL) was stirred at rt for 0.5 hr. The reaction mixture was concentrated in vacuo. To the residue was added 7M $NH_3$/MeOH (5 mL). The residue was concentrated in vacuo. The residue was purified by preparative HPLC (ACN/water/10 mM $NH_4HCO_3$) to afford the title compound (12.8 mg, 14% yield) as a white solid. MS obsd (ESI+) 473.5 ($[M+H]^+$). $^1H$ NMR (400 MHz, DMSO-$d_6$) δ 8.83 (1H), 7.74 (1H), 7.68 (1H), 7.60 (1H), 7.52 (1H), 7.35 (1H), 7.21 (1H), 5.30 (1H), 5.25 (1H), 2.97 (2H), 2.69 (1H), 2.62 (1H), 2.29 (6H), 2.17 (1H), 1.46 (5H).

Example 90: 1-(bicyclo[1.1.1]pentan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide

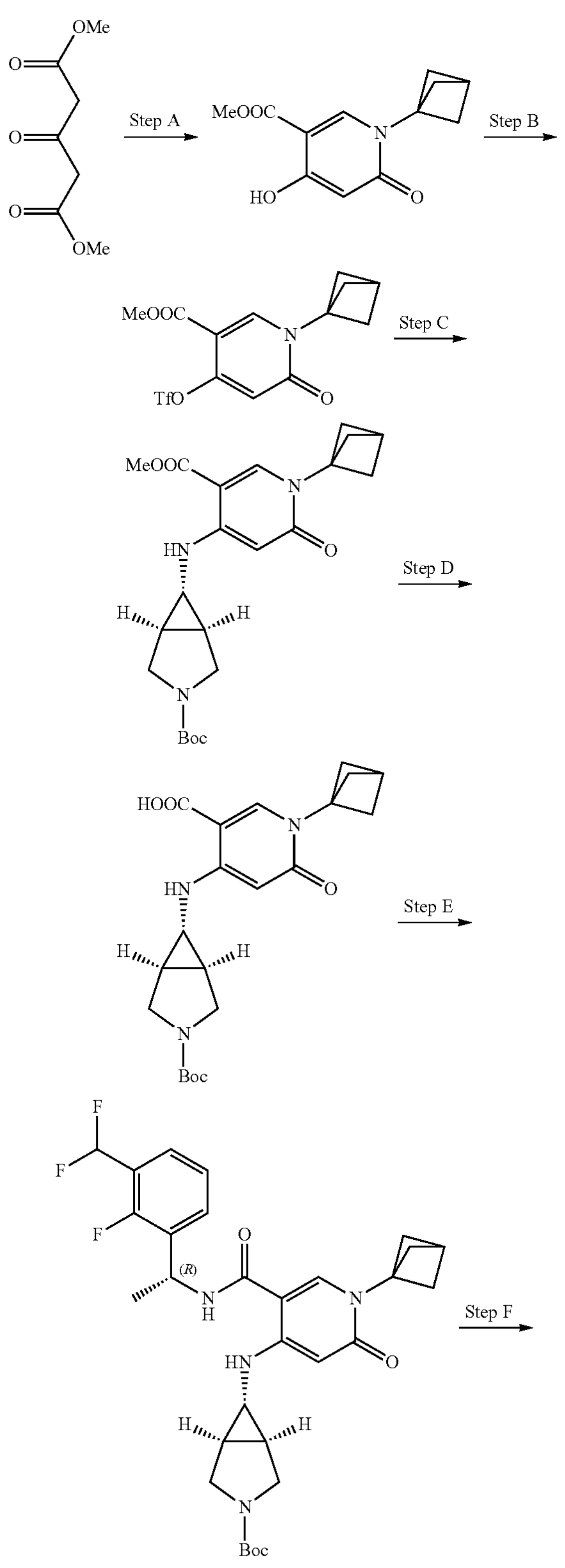

-continued

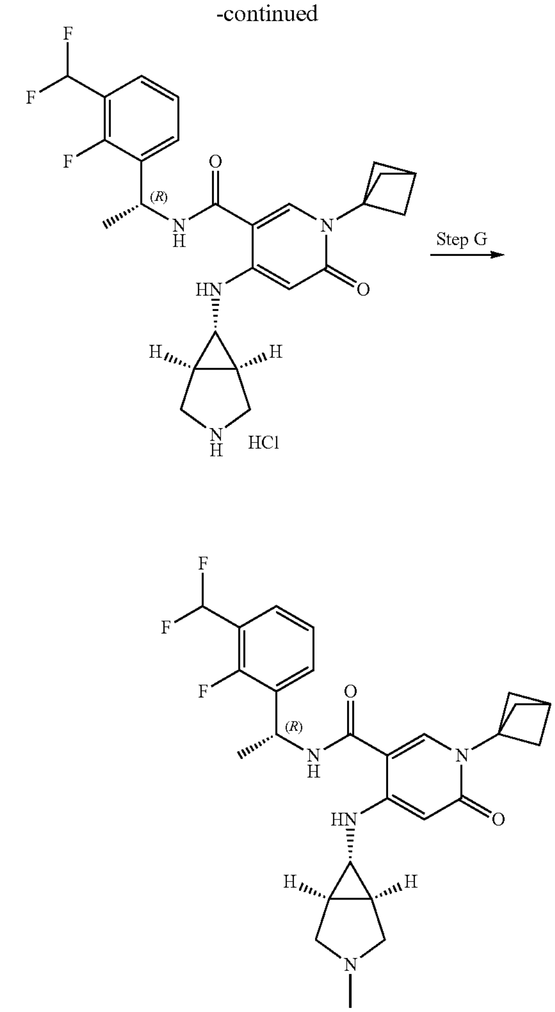

Step A: methyl 1-(bicyclo[1.1.1]pentan-1-yl)-4-hydroxy-6-oxo-1,6-dihydropyridine-3-carboxylate Dimethyl 3-oxopentanedioate (1.11 equiv) was dissolved in AcOH (0.2 equiv) and cooled to 0° C. Dimethylformamide dimethylacetal (1.11 equiv) was added dropwise over 30 minutes. The mixture was stirred for an additional 1 hour, at which point MeOH (2V) was added, followed by bicyclo[1.1.1]pentan-1-aminium chloride (1 eq). N,N-diisopropylethylamine (1.50 equiv) was added dropwise over 30 minutes. The mixture was then stirred at room temperature for 18 hours. The mixture was poured into cooled HCl (1.1 M aqueous, 2.0 equiv), keeping the temperature below 20° C. Solids were filtered, rinsed with water and dried under vacuum to afford the title compound (94% yield). MS obsd (ESI+) 236.2 ([M+H]$^+$) $^1$H NMR (400 MHz, DMSO-$d_6$) δ 10.78 (1H), 7.97 (1H), 5.61 (1H), 3.81 (3H), 2.64 (1H), 2.29 (6H).

Step B: methyl 1-(bicyclo[1.1.1]pentan-1-yl)-6-oxo-4-(((trifluoromethyl)sulfonyl)oxy)-1,6-dihydropyridine-3-carboxylate Methyl 1-(bicyclo[1.1.1]pentan-1-yl)-4-hydroxy-6-oxo-1,6-dihydropyridine-3-carboxylate (1.0 equiv) was dissolved in N,N-dimethylacetamide (7.5 vol) followed by addition of $K_3PO_4$ (1.20 equiv). The mixture was stirred at room temperature for 15 minutes. Then, 1,1,1-trifluoro-N-phenyl-N-((trifluoromethyl)sulfonyl)methanesulfonamide (1.05 equiv) was added and the reaction heated to 45° C. for 1 hour. The reaction mixture was cooled to ambient temperature and ice-water (20 vol) was added over 15 minutes. The mixture was stirred for 1 hour further, and then filtered. The resulting solids were washed with water and dried under vacuum to afford the title compound (95% yield). MS obsd (ESI+) 368.0 ([M+H]$^+$). $^1$H NMR (400 MHz, DMSO-d6, ppm) δ 8.20 (1H), 6.56 (1H), 3.83 (3H), 2.70 (1H), 2.35 (6H).

Step C: Tert-butyl (1R,5S,6s)-6-((1-(bicyclo[1.1.1]pentan-1-yl)-5-(methoxycarbonyl)-2-oxo-1,2-dihydropyridin-4-yl)amino)-3-azabicyclo[3.1.0]hexane-3-carboxylate To a mixture of methyl 1-(bicyclo[1.1.1]pentan-1-yl)-6-oxo-4-(((trifluoromethyl)sulfonyl)oxy)-1,6-dihydropyridine-3-carboxylate (1.00 equiv) in N,N-dimethylacetamide (5 vol) was added N,N-diisopropylethylamine (1.20 equiv) followed by tert-butyl (1R,5S,6s)-6-amino-3-azabicyclo[3.1.0]hexane-3-carboxylate (1.05 equiv). The mixture was heated to 80° C. for 3 hours. Upon completion of the reaction, the mixture was cooled to room temperature and then poured into ice-water (25 vol) over 30 minutes. The mixture was stirred for 1 hour further, then filtered. The solids were rinsed with water, then dried under vacuum until constant weight to afford the title compound (95% yield), which is used without further purification. MS obsd (ESI+) 416.3 ([M+H]$^+$).

Step D: 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid To a suspension of tert-butyl (1R,5S,6s)-6-((1-(bicyclo[1.1.1]pentan-1-yl)-5-(methoxycarbonyl)-2-oxo-1,2-dihydropyridin-4-yl)amino)-3-azabicyclo[3.1.0]hexane-3-carboxylate (1.00 equiv) in THF (2 vol) was added sodium hydroxide (2.0 equiv, dissolved in 8 vol water). The mixture was heated to 50° C. and stirred for 3 hours until the reaction reached completion as judged by HPLC. The mixture was cooled to room temperature, and the solution was slowly poured into ice-water (25 vol). 2M aqueous citric acid was added to the mixture until a pH~4 was reached. The mixture was stirred for 30 minutes, then the solids were filtered and rinsed with water. The solids were dried under vacuum to afford the title compound (96% yield), which is used without further purification. MS obsd (ESI+) 402.2 ([M+H]$^+$).

Step E: tert-butyl (1R,5S,6s)-6-((1-(bicyclo[1.1.1]pentan-1-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate To a solution of 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (1.00 equiv) in N,N-dimethylacetamide (5 vol) was added N,N-diisopropylethylamine (3.0 equiv), HOBt (0.3 equiv), EDCI (1.2 equiv) and (R)-1-(3-(difluoromethyl)-2-fluorophenyl)ethan-1-amine (1.05 equiv). The mixture was heated to 50° C. and stirred for 16 hr until completion of the reaction as judged by HPLC. The mixture was cooled to room temperature and slowly poured into ice water (30 vol), generating a precipitate. The mixture was stirred for 1 hour, and the solids were then filtered and rinsed with water. The solids were dried under vacuum to afford the title compound. This material was used without further purification. MS obsd (ESI+) 573.4 ([M+H]$^+$).

Step F: 4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide hydrochloride Tert-butyl (1R,5S,6s)-6-((1-(bicyclo[1.1.1]pentan-1-yl)-5-(((R)-1-(3-(difluoromethyl)-2-fluorophenyl)ethyl)carbamoyl)-2-oxo-1,2-dihydropyridin-4-yl)amino)-3-azabicyclo[3.1.0]hexane-3-carboxylate (1.00 equiv) was dissolved in HCl (2M in EtOAc, 10 vol), and the mixture stirred at room temperature for 1 hour. Upon completion of the reaction as judged by HPLC, MTBE (10 vol) was added to the mixture and stirred for 1 hour. The solids were filtered, rinsed with MTBE and dried under vacuum to afford the crude title compound. This material was used without further purification. MS obsd (ESI+) 473.4 ([M+H]$^+$).

Step G: 1-(bicyclo[1.1.1]pentan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Example 90)

To a solution of 4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide hydrochloride (1.00 equiv) in EtOH (7 vol) was added $NaBH(OAc)_3$ portionwise while maintaining a reaction temperature of 0-5° C. over 30 minutes. To the mixture was then added formalin (37% in water, 2 equiv) at 0-5° C. over 30 minutes. The mixture was then stirred at this temperature for a further 30 minutes and quenched with water (5 vol). The mixture was stirred at 20° C. for 1 hour. At this time, additional water was added (45 vol) and the mixture basified to pH 9-10 with 2 N NaOH (aqueous). This mixture was stirred at 25° C. for 30 minutes, then filtered. The crude solid was re-suspended in water (40 vol) and HCl (2M aqueous, 2.5 equiv). The mixture was stirred at this temperature for a further hour until all solids were dissolved. Then NaOH (2M in water) was added until pH=9-10 and stirred for 30 minutes, at which time the precipitated solids were collected via centrifugal filtration and then rinsed with water. The solids were dried under vacuum to afford the title compound (87% over 3 steps). MS obsd (ESI+) 487.3 ([M+H]$^+$). $^1$H NMR (400 MHz, DMSO-$d_6$) δ: 8.83 (1H), 7.74 (s, 1H), 7.71 (1H), 7.60 (1H), 7.52 (1H), 7.35 (1H), 7.21 (1H), 5.27 (2H), 2.99 (2H), 2.62 (1H), 2.46 (1H), 2.39-2.22 (8H), 2.19 (3H), 1.53-1.42 (5H).

Example 91: 1-(bicyclo[1.1.1]pentan-1-yl)-N—((R)-1-(3-(difluoromethyl)-2-fluorophenyl)ethyl)-4-(((1R,5S,6s)-3-(methyl-d3)-3-azabicyclo[3.1.0]hexan-6-yl)amino)-6-oxo-1,6-dihydropyridine-3-carboxamide

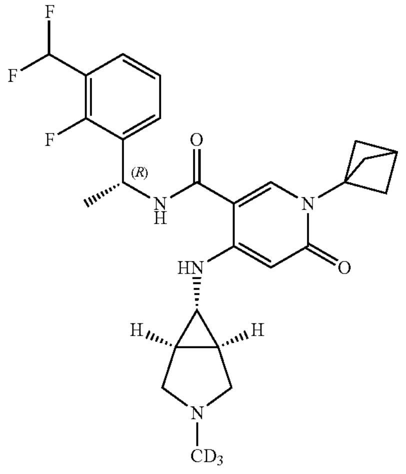

Example 91

To a solution of 4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide (111 mg, 0.23 mmol) acetonitrile (2 mL) was added potassium carbonate (97 mg, 0.7 mmol) and trideuteriomethyl 4-methylbenzenesulfonate (22 mg, 0.12 mmol). The mixture was stirred at rt for 16 hrs. The resulting mixture was poured into water (100 mL) and extracted with EtOAc (50 mL×3). The combined organic layers were washed with brine, dried over $Na_2SO_4$, filtered and concentrated. The residue was purified by preparative HPLC (ACN/water/10 mM $NH_4HCO_3$) to afford the title compound (11.69 mg, 10% yield). MS obsd (ESI+) 490.3 ($[M+H]^+$). $^1H$ NMR (400 MHz, DMSO-$d_6$) δ: 8.83 (1H), 7.74 (s, 1H), 7.71 (1H), 7.60 (1H), 7.52 (1H), 7.35 (1H), 7.21 (1H), 5.30-5.21 (2H), 2.99 (2H), 2.62 (1H), 2.46 (1H), 2.29-2.26 (8H), 1.53-1.42 (5H).

General scheme for target compound synthesis:

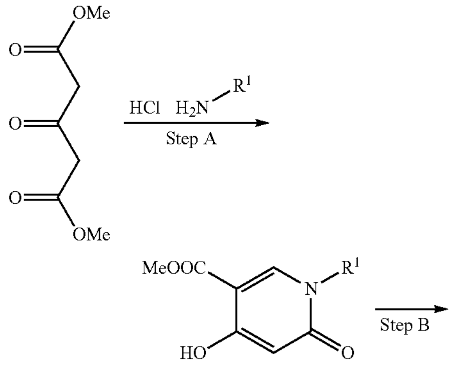

-continued

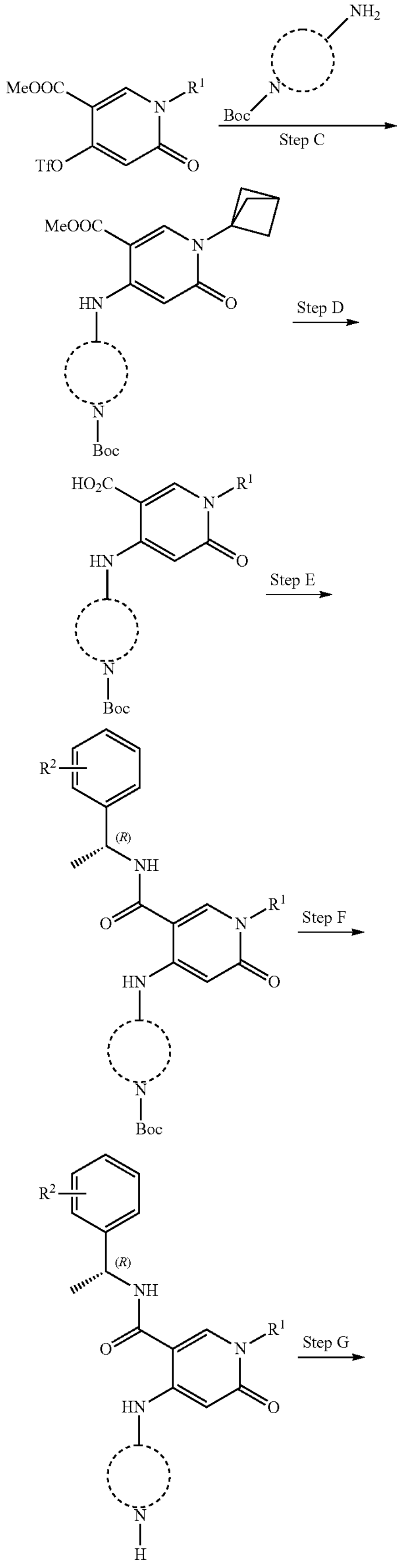

-continued

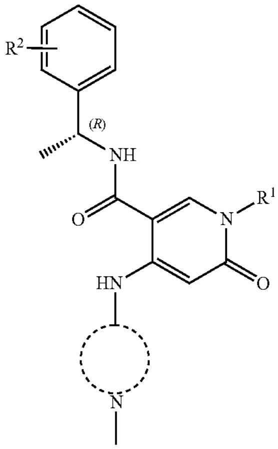

The following examples may be synthesized according to the above generic scheme according to analogous methods described for examples 71 and 72, 90, 45 and 55 using appropriate reagent substitutions in Steps A, C and E in the described general scheme:

| Example Number | Compound Structure | Compound Name | Characterization |
|---|---|---|---|
| 92 and 93 | Unassigned Diastereomers 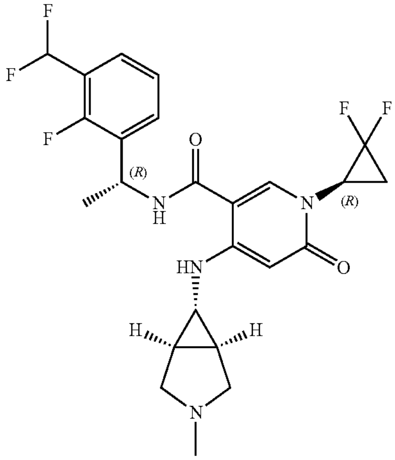 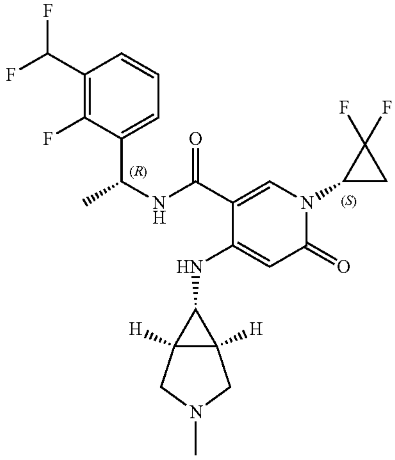 | 1-((R)-2,2-difluorocyclopropyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((S)-2,2-difluorocyclopropyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | Example 92: MS obsd (ESI+) 497.4 ([M + H]$^+$). Analytical chiral UPCC: (Column: CHIRALPAK AD-3, 4.6 * 100mm 3 um, Flow rate: 3.0 mL/min, Co-solvent:EtOH (1% 7M NH3 in MeOH), Temp 40° C.) Retention time = 0.8 min Example 93: MS obsd (ESI+) 497.4 ([M + H]$^+$). Analytical chiral UPCC: (Column: CHIRALPAK AD-3, 4.6 * 100mm 3 um, Flow rate: 3.0 mL/min, Co-solvent: EtOH (1% 7M NH3 in MeOH), Temp 40° C.) Retention time = 1.7 min |

-continued

| Example Number | Compound Structure | Compound Name | Characterization |
|---|---|---|---|
| 94 and 95 | Unassigned Diastereomers 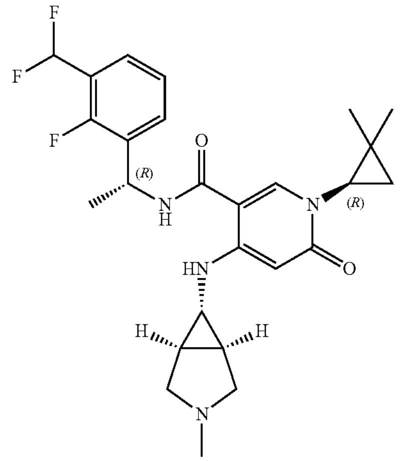 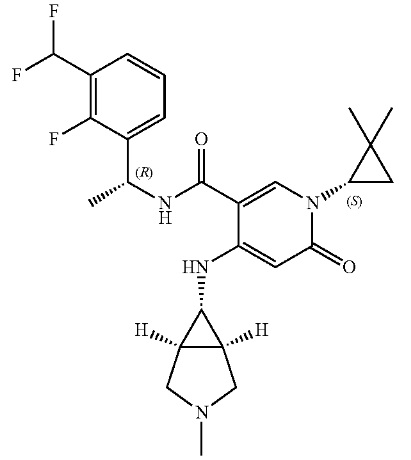 | N-((R)-1-(3-(difluoromethyl)-2-fluorophenyl)ethyl)-1-((R)-2,2-dimethylcyclopropyl)-4-(((1R,5S,6s)-3-methyl-3-azabicyclo[3.1.0]hexan-6-yl)amino)-6-oxo-1,6-dihydropyridine-3-carboxamide and N-((R)-1-(3-(difluoromethyl)-2-fluorophenyl)ethyl)-1-((S)-2,2-dimethylcyclopropyl)-4-(((1R,5S,6s)-3-methyl-3-azabicyclo[3.1.0]hexan-6-yl)amino)-6-oxo-1,6-dihydropyridine-3-carboxamide | Example 94: MS obsd (ESI+) 489.4 ($[M + H]^+$). Analytical chiral UPCC: (Column: CHIRALPAK AD-3, 4.6 * 100mm 3 um, Flow rate: 3.0 mL/min, Co-solvent:MeOH (0.2% 7M NH3 in MeOH), Temp 40° C.) Retention time = 0.6 min Example 95: MS obsd (ESI+) 489.4 ($[M + H]^+$). Analytical chiral UPCC: (Column: CHIRALPAK AD-3, 4.6 * 100mm 3 um, Flow rate: 3.0 mL/min, Co-solvent: MeOH (0.2% 7M NH3 in MeOH), Temp 40° C.) Retention time = 1.6 min |
| 96 | 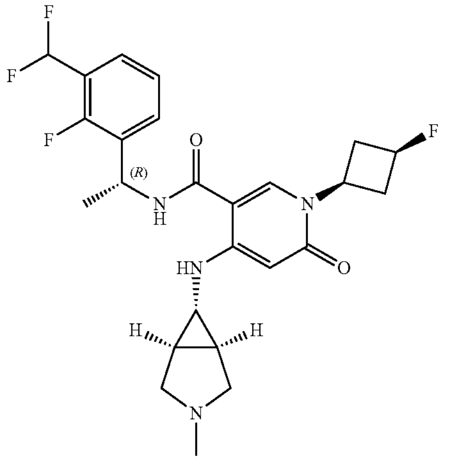 | N-((R)-1-(3-(difluoromethyl)-2-fluorophenyl)ethyl)-1-((1s,3S)-3-fluorocyclobutyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 493.4 ($[M + H]^+$). $^1H$ NMR (400 MHZ, DMSO-$d_6$) δ: 8.88 (1H), 8.02 (1H), 7.84 (1H), 7.63 (1H), 7.52 (1H), 7.40-7.33 (1H), 7.23 (1H), 5.38 (1H), 5.31-5.24 (1H), 5.0 (1H), 4.4 (1H), 3.03 (2H), 2.91-2.78 (2H), 2.69-2.55 (2H), 2.46 (1H), 2.39-2.17 (5H), 1.58-1.51 (2H), 1.48 (3H). MS obsd (ESI+) 493.4 |

-continued

| Example Number | Compound Structure | Compound Name | Characterization |
|---|---|---|---|
| 97 | 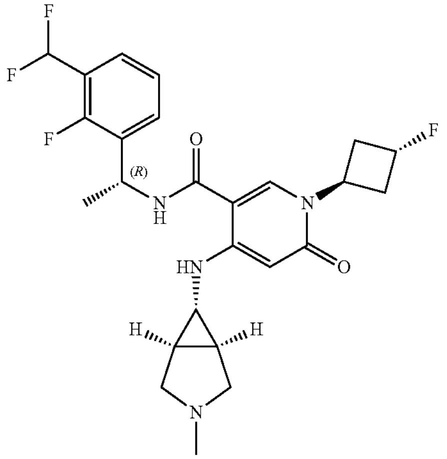 | N-((R)-1-(3-(difluoromethyl)-2-fluorophenyl)ethyl)-1-((1r,3R)-3-fluorocyclobutyl)-4-(((1R,5S,6s)-3-methyl-3-azabicyclo[3.1.0]hexan-6-yl)amino)-6-oxo-1,6-dihydropyridine-3-carboxamide | ($[M + H]^+$). $^1H$ NMR (400 MHZ, DMSO-$d_6$) δ: 8.76 (1H), 8.03 (1H), 7.81 (1H), 7.63 (1H), 7.52 (1H), 7.39-7.33 (1H), 7.21 (1H), 5.46-5.14 (4H), 3.00 (2H), 2.94-2.78 (2H), 2.67-2.53 (2H), 2.47 (1H), 2.27 (2H), 2.19 (3H), 1.49 (2H), 1.47 (3H). |
| 98 | 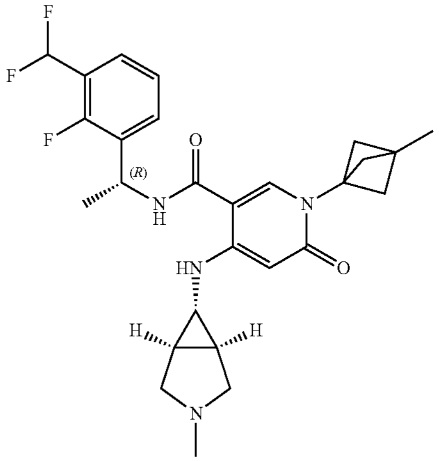 | N-((R)-1-(3-(difluoromethyl)-2-fluorophenyl)ethyl)-4-(((1R,5S,6s)-3-methyl-3-azabicyclo[3.1.0]hexan-6-yl)amino)-1-(3-methylbicyclo[1.1.1]pentan-1-yl)-6-oxo-1,6-dihydropyridine-3-carboxamide | MS obsd (ESI+) 501.4 ($[M + H]^+$). $^1H$ NMR (400 MHz, DMSO-$d_6$) δ ppm 8.82 (1H), 7.72 (1H), 7.67 (1H), 7.59 (1H), 7.52 (1H), 7.35 (1H), 7.21 (1H), 5.32-5.21 (2H), 2.99 (2H), 2.46 (1H), 2.27 (2H), 2.20 (3H), 2.15 (6H), 1.55-1.48 (2H), 1.45 (3H), 1.30 (3H). |
| 99 | 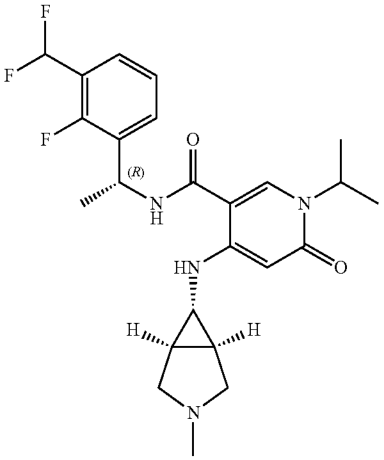 | N-((R)-1-(3-(difluoromethyl)-2-fluorophenyl)ethyl)-1-isopropyl-4-(((1R,5S,6s)-3-methyl-3-azabicyclo[3.1.0]hexan-6-yl)amino)-6-oxo-1,6-dihydropyridine-3-carboxamide | MS obsd (ESI+) 463.2 ($[M + H]^+$). $^1H$ NMR (400 MHZ, DMSO-$d_6$) δ ppm 8.78 (1H), 8.10 (1H), 8.01 (1H), 7.62 (1H), 7.52 (1H), 7.35 (1H), 7.21 (1H), 5.42 (1H), 5.28 (1H), 4.95 (1H), 3.63 (2H), 3.22 (2H), 2.86-2.60 (3H), 2.54 (1H), 1.92 (2H), 1.48 (3H), 1.34 (6H). |

-continued

| Example Number | Compound Structure | Compound Name | Characterization |
|---|---|---|---|
| 100 | 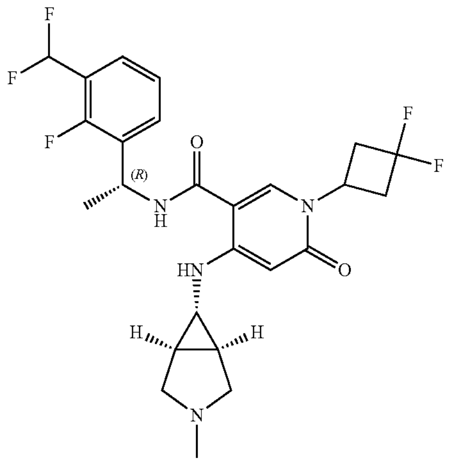 | 1-(3,3-difluorocyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 511.2 ([M + H]+). $^1$H NMR (400 MHZ, DMSO-$d_6$) δ 8.80 (1H), 8.01 (1H), 7.90 (1H), 7.63 (1H), 7.53 (1H), 7.35 (1H), 7.21 (1H), 5.42 (1H), 5.27 (1H), 4.72 (1H), 3.69 (1H) 3.32 (3H), 3.27 (2H), 3.03 (2H), 2.62 (3H), 2.54 (1H), 1.86 (2H), 1.48 (3H). |
| 101 | 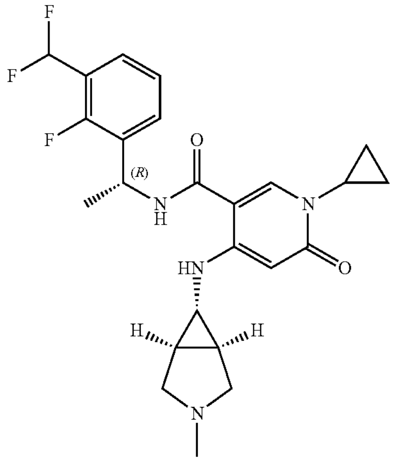 | 1-cyclopropyl-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 461.4 ([M + H]+). $^1$H NMR (400 MHZ, DMSO-$d_6$) δ: 8.76 (1H), 7.97 (1H), 7.84 (1H), 7.61 (1H), 7.52 (1H), 7.35 (1H), 7.15 (1H), 5.36 (1H), 5.25 (1H), 3.21 (1H), 3.00 (2H), 2.46 (1H), 2.27 (2H), 2.20 (3H), 1.49 (2H), 1.45 (3H), 0.97 (2H), 0.89 (2H). |
| 102 | 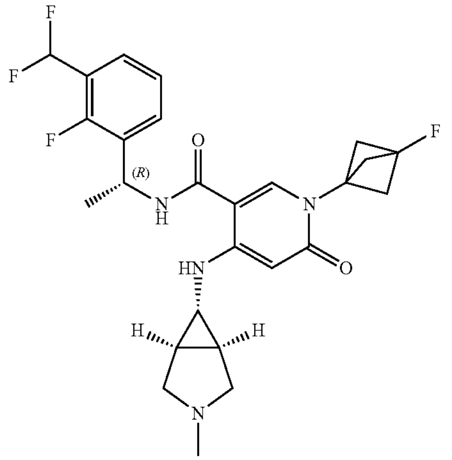 | N-((R)-1-(3-(difluoromethyl)-2-fluorophenyl)ethyl)-1-(3-fluorobicyclo[1.1.1 ]pentan-1-yl)-4-(((1R,5S,6s)-3-methyl-3-azabicyclo[3.1.0]hexan-6-yl)amino)-6-oxo-1,6-dihydropyridine-3-carboxamide | MS obsd (ESI+) 505.4 ([M + H]+). $^1$H NMR (400 MHZ, DMSO-$d_6$) δ ppm 8.82 (1H), 7.75 (2H), 7.60 (1H), 7.53 (1H), 7.35 (1H), 7.21 (1H), 5.32 (1H), 5.26 (1H), 3.00 (1H), 2.98 (1H), 2.65 (6H), 2.48 (1H), 2.26 (2H), 2.19 (3H), 1.51 (2H), 1.46 (3H). |

-continued

| Example Number | Compound Structure | Compound Name | Characterization |
|---|---|---|---|
| 103 and 104 | Unassigned Diastereomers 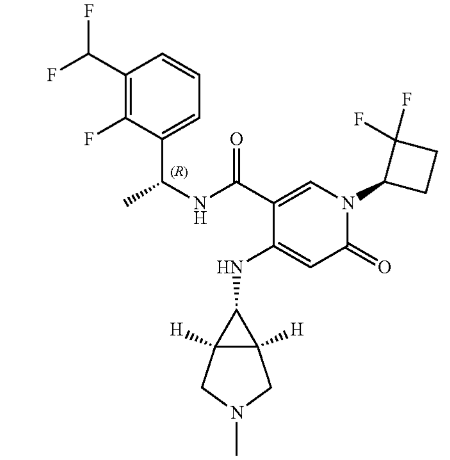 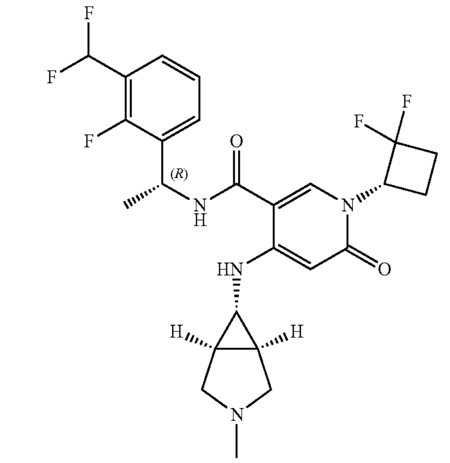 | 1-((R)-2,2-difluorocyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((S)-2,2-difluorocyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | Example 103 MS obsd (ESI+) 511.3 ([M + H]$^+$). Analytical chiral UPCC: (Column: CHIRALPAK AS-3, 4.6 * 100mm 3 um, Flow rate: 3.0 mL/min, Co-solvent: MeOH (0.2% 7M NH3 in MeOH), Temp 40° C.) Retention time = 1.33 min Example 104 MS obsd (ESI+) 511.4 ([M + H]$^+$). Analytical chiral UPCC: (Column: CHIRALPAK AS-3, 4.6 * 100mm 3 um, Flow rate: 3.0 mL/min, Co-solvent:MeOH (0.2% 7M NH3 in MeOH), Temp 40° C.) Retention time = 3.5 min |
| 105 | 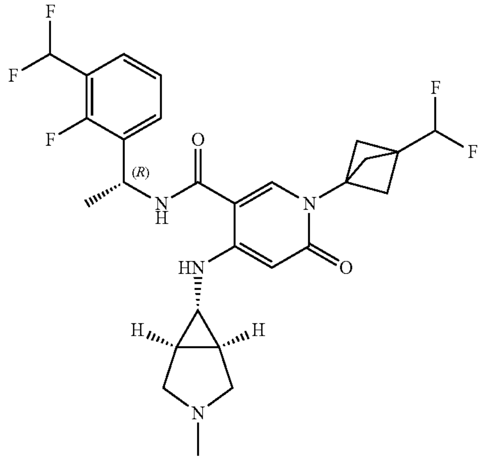 | N-((R)-1-(3-(difluoromethyl)-2-fluorophenyl)ethyl)-1-(3-(difluoromethyl)bicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide | MS obsd (ESI+) 537.3 ([M + H]$^+$). $^1$H NMR (400 MHZ, $CD_3OD$) δ ppm: 7.78 (1H), 7.57-7.45 (2H), 7.28 (1H), 6.99 (1H), 6.04 (1H), 5.62 (1H), 5.34 (1H), 3.18 (2H), 2.62 (2H), 2.57 (1H), 2.46 (6H), 2.37 (3H), 1.66 (2H), 1.54 (3H). |

-continued

| Example Number | Compound Structure | Compound Name | Characterization |
|---|---|---|---|
| 106 | 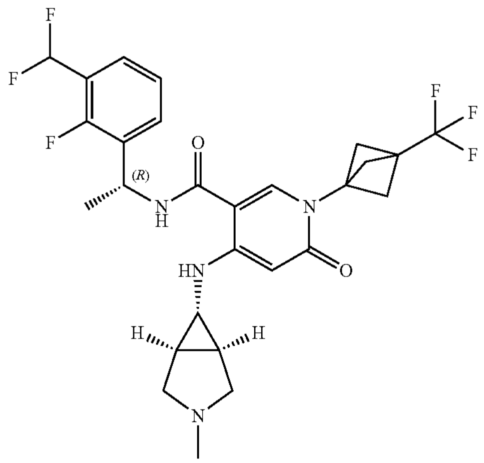 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(3-(trifluoromethyl)bicyclo[1.1.1]pentan-1-yl)-1,6-dihydropyridine-3-carboxamide | MS obsd (ESI+) 555.2 ([M + H]$^+$). $^1$H NMR (400 MHZ, DMSO-$d_6$) δ: 8.86 (1H), 7.83 (1H), 7.79 (1H), 7.63 (1H), 7.53 (1H), 7.35 (1H), 7.21 (1H), 5.32 (1H), 5.26 (1H), 3.10 (2H), 2.58 (6H), 2.53 (2H), 2.32 (4H), 1.80-1.55 (2H), 1.47 (3H). |
| 107 | 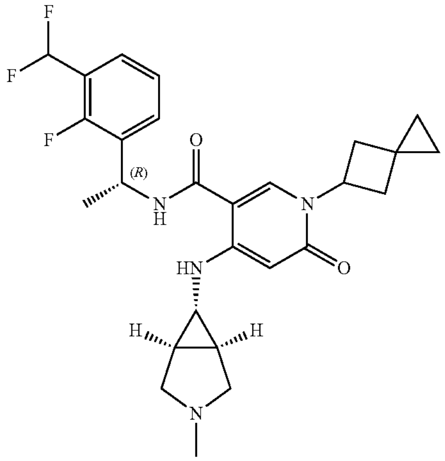 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(spiro[2.3]hexan-5-yl)-1,6-dihydropyridine-3-carboxamide | MS obsd (ESI+) 501.5 ([M + H]$^+$). $^1$H NMR (400 MHz, DMSO-$d_6$) δ: 8.87 (1H), 8.12 (1H), 7.77 (1H), 7.63 (1H), 7.52 (1H), 7.35 (1H), 7.21 (1H), 5.38 (1H), 5.28(1H), 5.16 (1H), 3.00 (2H), 2.69 (2H), 2.47 (1H), 2.33-2.24 (4H), 2.20 (3H), 1.53-1.45 (5H), 0.61-0.47 (4H). |
| 108 | 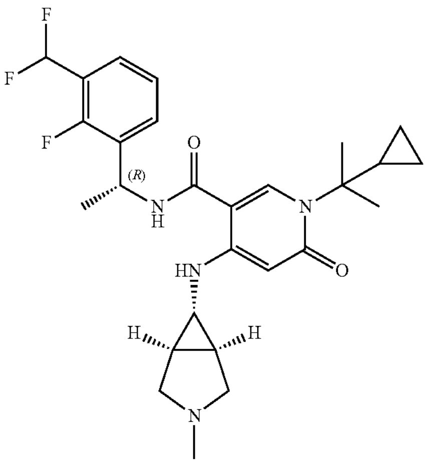 | 1-(2-cyclopropylpropan-2-yl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 503.2 ([M + H]$^+$). $^1$H NMR (400 MHZ, DMSO-$d_6$) δ: 8.72 (1H), 8.29 (1H), 7.58 (1H), 7.52 (1H), 7.37-7.07 (3H), 5.34 (1H), 5.27 (1H), 3.00 (2H), 2.47 (1H), 2.28 (2H), 2.20 (3H), 1.74 (1H), 1.52 (4H), 1.47 (3H), 1.43 (4H), 0.64-0.47 (4H). |

-continued

| Example Number | Compound Structure | Compound Name | Characterization |
|---|---|---|---|
| 109 and 110 | Unassigned Diastereomers 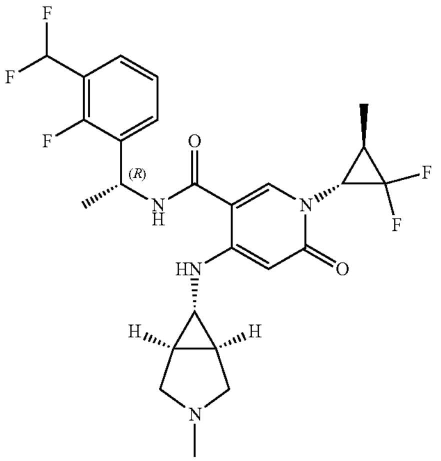 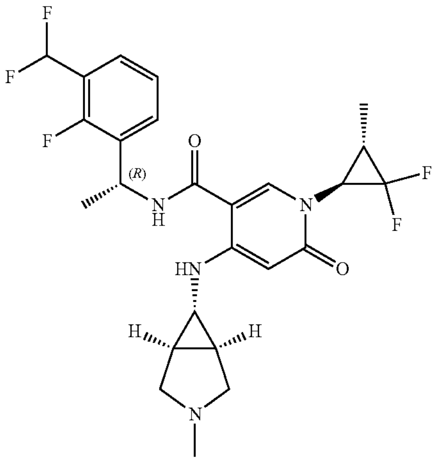 | 1-((1R,3R)-2,2-difluoro-3-methylcyclopropyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((1S,3S)-2,2-difluoro-3-methylcyclopropyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | Example 109: MS obsd (ESI+) 511.4 ($[M + H]^+$). Analytical chiral UPCC: (Column: CHIRALCEL OZ-3, 4.6 * 100mm 3 um, Flow rate: 3.0 mL/min, Co-solvent: MeOH (0.2% 7M NH3 in MeOH), Temp 40° C.) Retention time = 1.5 min Example 110: MS obsd (ESI+) 511.4 ($[M + H]^+$). Analytical chiral UPCC: (Column: CHIRALCEL OZ-3, 4.6 * 100mm 3 um, Flow rate: 3.0 mL/min, Co-solvent:MeOH (0.2% 7M NH3 in MeOH), Temp 40° C.) Retention time = 0.9 min |

-continued

| Example Number | Compound Structure | Compound Name | Characterization |
|---|---|---|---|
| 111 and 112 | Unassigned Diastereomers 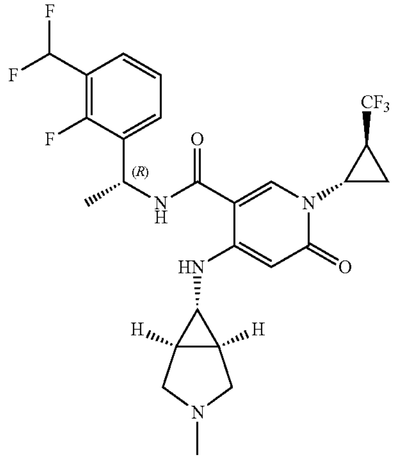 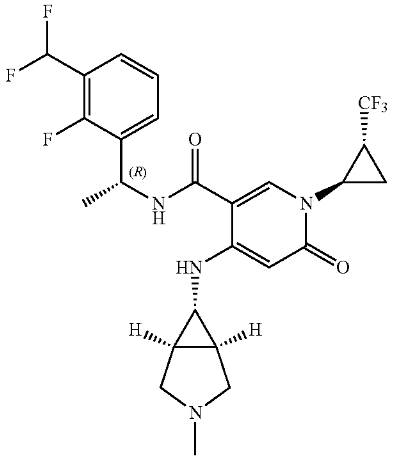 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((1S,2S)-2-(trifluoromethyl)cyclopropyl)-1,6-dihydropyridine-3-carboxamide and N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((1R,2R)-2-(trifluoromethyl)cyclopropyl)-1,6-dihydropyridine-3-carboxamide | Example 111: MS obsd (ESI+) 529.3 ([M + H]$^+$). Analytical chiral UPCC: (Column: Cellulose-SC, 4.6 * 100mm 3 um, Flow rate: 3.0 mL/min, Co-solvent: MeOH (0.2% 7M NH3 in MeOH), Temp 40° C.) Retention time = 1.5 min Example 112: MS obsd (ESI+) 529.3 ([M + H]$^+$). Analytical chiral UPCC: (Column: Cellulose-SC, 4.6 * 100mm 3 um, Flow rate: 3.0 mL/min, Co-solvent: MeOH (0.2% 7M NH3 in MeOH), Temp 40° C.) Retention time = 2.0 min |

-continued

| Example Number | Compound Structure | Compound Name | Characterization |
|---|---|---|---|
| 113 and 114 | Unassigned Diastereomers<br>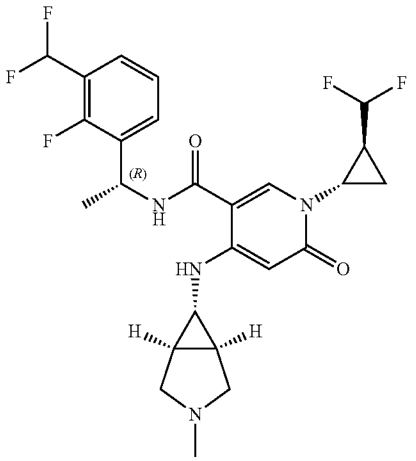<br>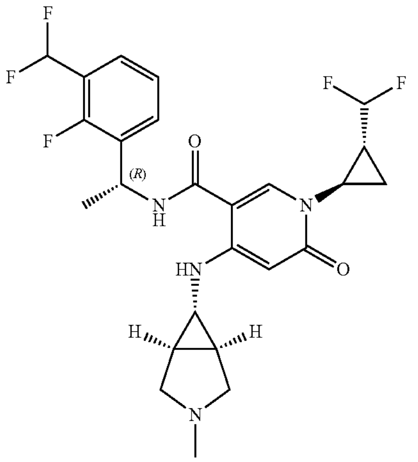 | N-((R)-1-(3-(difluoromethyl)-2-fluorophenyl)ethyl)-1-((1S,2S)-2-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide and N-((R)-1-(3-(difluoromethyl)-2-fluorophenyl)ethyl)-1-((1R,2R)-2-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide | Example 113:<br>MS obsd (ESI+) 511.4 ([M + H]$^+$).<br>Analytical chiral UPCC: (Column: CHIRALPAK AD-3, 4.6 * 100mm 3 um, Flow rate: 3.0 mL/min, Co-solvent:MeOH (0.2% 7M NH3 in MeOH), Temp 40° C.) Retention time = 1.0 min<br>Example 114:<br>MS obsd (ESI+) 511.4 ([M + H]$^+$).<br>Analytical chiral UPCC: (Column: CHIRALPAK AD-3, 4.6 * 100mm 3 um, Flow rate: 3.0 mL/min, Co-solvent:MeOH (0.2% 7M NH3 in MeOH), Temp 40° C.) Retention time = 0.75 min |

-continued

| Example Number | Compound Structure | Compound Name | Characterization |
|---|---|---|---|
| 115 and 116 | Unassigned Diastereomers 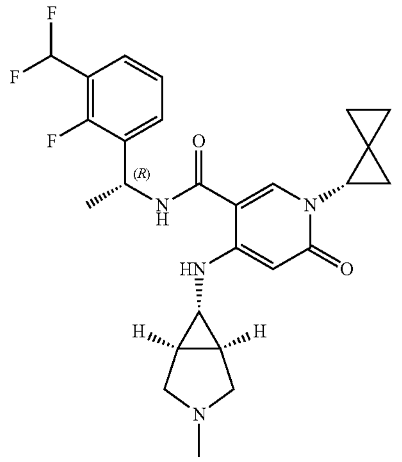 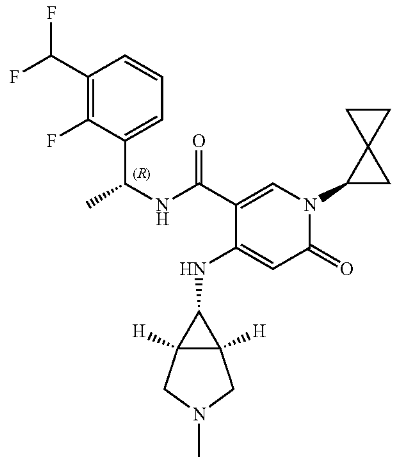 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide and N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide | Example 115: MS obsd (ESI+) 487.4 ([M + H]$^+$). Analytical chiral UPCC: (Column: CHIRALPAK AD-3, 4.6 * 100mm 3 um, Flow rate: 3.0 mL/min, Co-solvent: MeOH (0.2% 7M NH3 in MeOH), Temp 40° C.) Retention time = 0.84 min Example 116: MS obsd (ESI+) 487.4 ([M + H]$^+$). Analytical chiral UPCC: (Column: CHIRALPAK AD-3, 4.6 * 100mm 3 um, Flow rate: 3.0 mL/min, Co-solvent: MeOH (0.2% 7M NH3 in MeOH), Temp 40° C.) Retention time = 1.86 min |

-continued

| Example Number | Compound Structure | Compound Name | Characterization |
|---|---|---|---|
| 117 and 118 | Unassigned Diastereomers 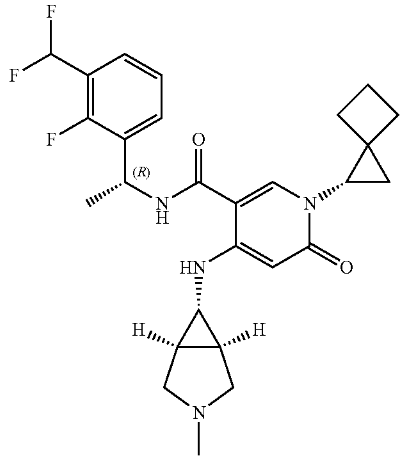 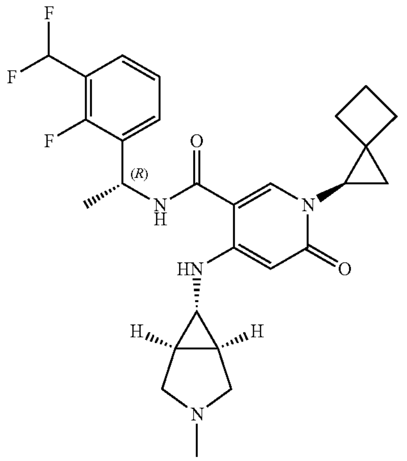 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-spiro[2.3]hexan-1-yl)-1,6-dihydropyridine-3-carboxamide and N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-spiro[2.3]hexan-1-yl)-1,6-dihydropyridine-3-carboxamide | Example 117: MS obsd (ESI+) 501.4 ([M + H]$^+$). Analytical chiral UPCC: (Column: CHIRALPAK AD-3, 4.6 * 100mm 3 um, Flow rate: 3.0 mL/min, Co-solvent:MeOH (0.2% 7M NH3 in MeOH), Temp 40° C.) Retention time = 3.4 min Example 118: MS obsd (ESI+) 501.4 ([M + H]$^+$). Analytical chiral UPCC: (Column: CHIRALPAK AD-3, 4.6 * 100mm 3 um, Flow rate: 3.0 mL/min, Co-solvent:MeOH (0.2% 7M NH3 in MeOH), Temp 40° C.) Retention time = 1.0 min |
| 119 | 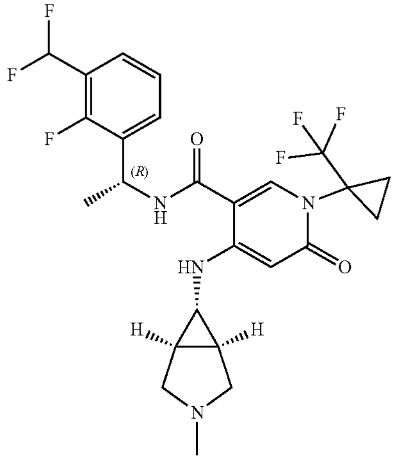 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(1-(trifluoromethyl)cyclopropyl)-1,6-dihydropyridine-3-carboxamide | MS obsd (ESI+) 529.3 ([M + H]$^+$). $^1$H NMR (400 MHz, DMSO-$d_6$) δ 8.82 (1H), 8.12 (1H), 7.97 (1H), 7.60 (1H), 7.52 (1H), 7.35 (1H), 7.21 (1H), 5.34 (1H), 5.25 (1H), 3.00 (2H), 2.47 (1H), 2.27 (2H), 2.19 (3H), 1.76-1.36 (9H) |

-continued

| Example Number | Compound Structure | Compound Name | Characterization |
|---|---|---|---|
| 120 | 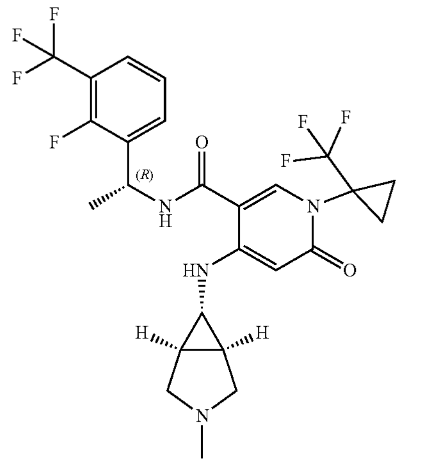 | N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-(1-(trifluoromethyl)cyclopropyl)-1,6-dihydropyridine-3-carboxamide | MS obsd (ESI+) 529.3 ($[M + H]^+$). $^1H$ NMR (400 MHz, $CD_3OD$) δ 8.06 (1H), 7.66 (1H), 7.59 (1H), 7.32 (1H), 5.65 (1H), 5.37 (1H), 3.16 (2H), 2.59 (1H), 2.57-2.49 (2H), 2.34 (3H), 1.81-1.62 (3H), 1.62-1.48 (6H). |
| 121 | 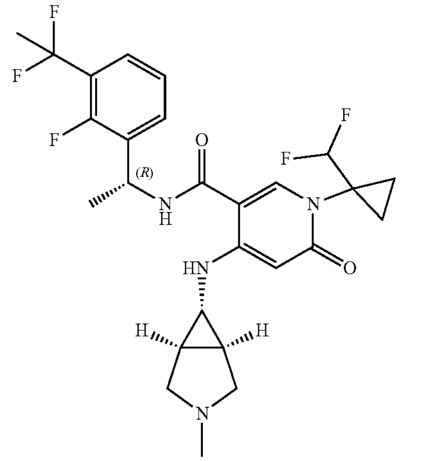 | N-((R)-1-(3-(1,1-difluoroethyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 525.2 ($[M + H]^+$). $^1H$ NMR (400 MHz, $CD_3OD$, formic acid salt) δ: 8.48 (1H), 8.01 (1H), 7.47 (2H), 7.23 (1H), 6.14 (1H), 5.66 (1H), 5.36 (1H), 3.33 (2H), 2.90 (2H), 2.57 (1H), 2.53 (3H), 1.98 (3H), 1.79 (2H), 1.54 (3H), 1.46 (2H), 1.33 (2H). |
| 122 | 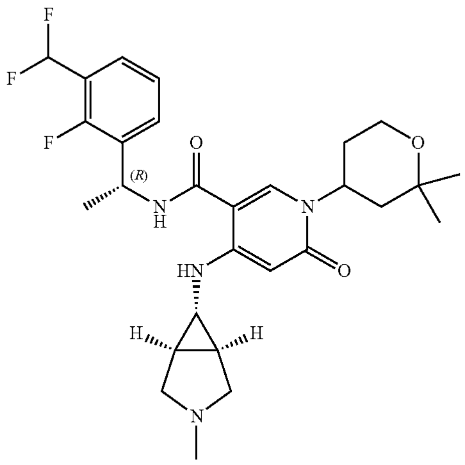 | N-((R)-1-(3-(difluoromethyl)-2-fluorophenyl)ethyl)-1-(2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide | MS obsd (ESI+) 533.3 ($[M + H]^+$). $^1H$ NMR (400 MHZ, DMSO-$d_6$) δ: 8.75 (1H), 8.08 (1H), 8.02 (1H), 7.61 (1H), 7.52 (1H), 7.35 (1H), 7.21 (1H), 5.40 (1H), 5.32-5.21 (1H), 5.09 (1H), 3.81 (1H), 3.74 (1H), 3.00 (2H), 2.47 (1H), 2.27 (2H), 2.19 (3H), 1.99 (1H), 1.76-1.68 (1H), 1.68-1.59 (2H), 1.49 (3H), 1.48 (2H), 1.26 (3H), 1.24 (3H). |

-continued

| Example Number | Compound Structure | Compound Name | Characterization |
|---|---|---|---|
| 123 | 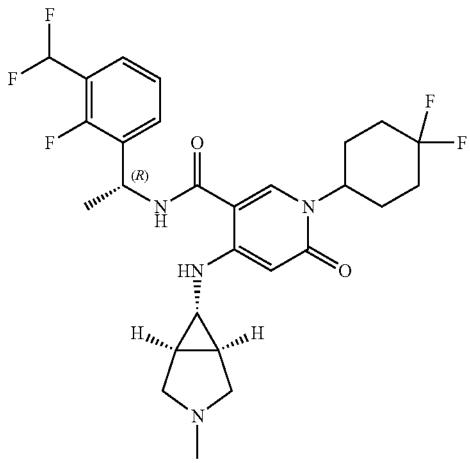 | 1-(4,4-difluorocyclohexyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 539.5 ([M + H]$^+$). $^1$H NMR (400 MHZ, DMSO-$d_6$) δ ppm 8.81 (1H), 7.97 (1H), 7.91 (1H), 7.60 (1H), 7.52 (1H), 7.35 (1H), 7.21 (1H), 5.41 (1H), 5.27 (1H), 4.75 (1H), 3.00 (2H), 2.46 (1H), 2.30-2.24 (2H), 2.19 (3H), 2.14 (3H), 2.08-1.96 (3H), 1.89-1.78 (2H), 1.54-1.43 (5H). |
| 124 and 125 | Unassigned Diastereomers 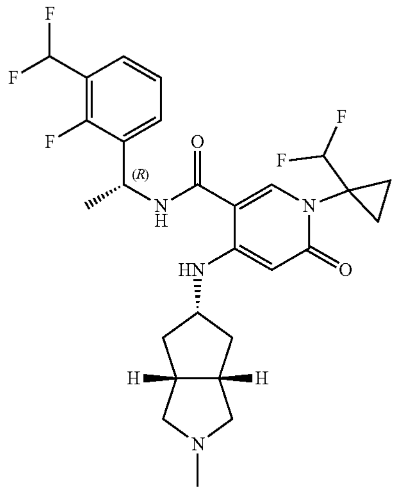 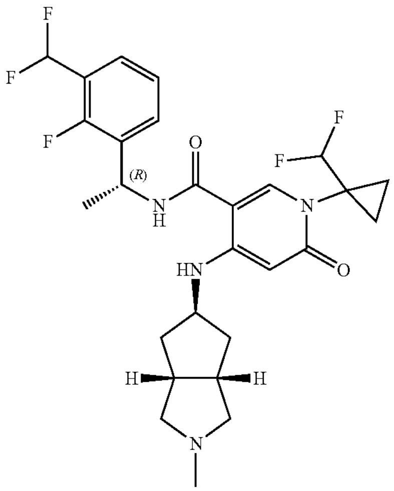 | N-((R)-1-(3-(difluoromethyl)-2-fluorophenyl)ethyl)-1-(1-(difluoromethyl)cyclopropyl)-4-(((3aR,5r,6aS)-2-methyloctahydrocyclopenta[c]pyrrol-5-yl)amino)-6-oxo-1,6-dihydropyridine-3-carboxamide and N-((R)-1-(3-(difluoromethyl)-2-fluorophenyl)ethyl)-1-(1-(difluoromethyl)cyclopropyl)-4-(((3aR,5s,6aS)-2-methyloctahydrocyclopenta[c]pyrrol-5-yl)amino)-6-oxo-1,6-dihydropyridine-3-carboxamide | Example 124: MS obsd (ESI+) 539.4 ([M + H]$^+$). $^1$H NMR (400 MHZ, DMSO-$d_6$) δ 8.80 (1H), 8.06-7.97 (2H), 7.60 (1H), 7.53 (1H), 7.35 (1H), 7.21 (1H), 6.24 (1H), 5.35-5.21 (1H), 5.18 (1H), 3.80 (1H), 2.55 (1H), 2.37-2.23 (5H), 2.18 (3H), 1.78-1.66 (2H), 1.64-1.51 (2H), 1.48 (3H), 1.36-1.21 (4H). Example 125: MS obsd (ESI+) 539.4 ([M + H]$^+$). $^1$H NMR (400 MHZ, DMSO-$d_6$) δ 8.79 (1H), 8.15 (1H), 7.97 (1H), 7.61 (1H), 7.52 (1H), 7.35 (1H), 7.21 (1H), 6.24 (1H), 5.33-5.24 (1H), 5.23 (1H), 3.62-3.48 (1H), 2.43 (4H), 2.25-2.16 (2H), 2.15-2.00 (5H), 1.47 (3H), 1.37-1.23 (4H), 1.22-1.05 (2H). |

-continued

| Example Number | Compound Structure | Compound Name | Characterization |
|---|---|---|---|
| 126 and 127 | Unassigned Diastereomers<br>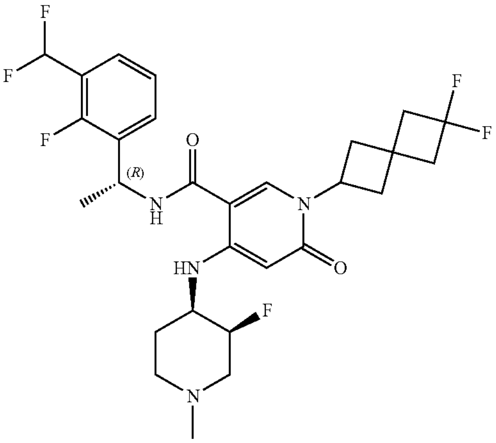<br>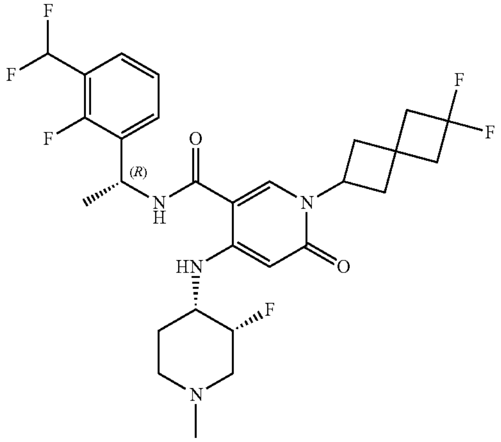 | N-((R)-1-(3-(difluoromethyl)-2-fluorophenyl)ethyl)-1-(6,6-difluorospiro[3.3]heptan-2-yl)-4-(((3S,4R)-3-fluoro-1-methylpiperidin-4-yl)amino)-6-oxo-1,6-dihydropyridine-3-carboxamide and N-((R)-1-(3-(difluoromethyl)-2-fluorophenyl)ethyl)-1-(6,6-difluorospiro[3.3]heptan-2-yl)-4-(((3R,4S)-3-fluoro-1-methylpiperidin-4-yl)amino)-6-oxo-1,6-dihydropyridine-3-carboxamide | Example 126:<br>MS obsd (ESI+) 571.3 ([M + H]$^+$).<br>Analytical chiral UPCC: (Column: CHIRALPAK AD-3, 4.6 * 100mm 3 um, Flow rate: 3.0 mL/min, Co-solvent:iPrOH (1% 7M NH3 in MeOH), Temp 40° C.) Retention time = 2.2 min<br>Example 127:<br>MS obsd (ESI+) 571.3 ([M + H]$^+$).<br>Analytical chiralUPCC: (Column: CHIRALPAK AD-3, 4.6 * 100mm 3 um, Flow rate: 3.0 mL/min, Co-solvent:iPrOH (1% 7M NH3 in MeOH), Temp 40° C.) Retention time = 4.3 min |
| 128 | 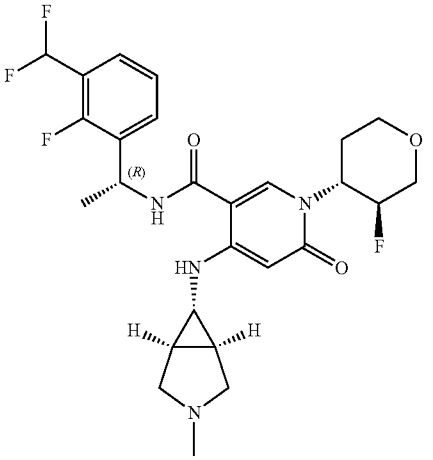 | N-((R)-1-(3-(difluoromethyl)-2-fluorophenyl)ethyl)-1-((3S,4R)-3-fluorotetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide | MS obsd (ESI+) 523.3 ([M + H]$^+$).<br>$^1$H NMR (400 MHZ, $CD_3OD$) δ: 8.11 (1H), 7.57 (1H), 7.50 (1H), 7.28 (1H), 6.99 (1H), 5.73 (1H), 5.37 (1H), 5.20-4.95 (2H), 4.24 (1H), 4.00 (1H), 3.54 (1H), 3.39 (1H), 3.20 (2H), 2.64 (2H), 2.59 (1H), 2.39 (3H), 2.28-2.18 (1H), 1.95 (1H), 1.68 (2H), 1.56 (3H). |

-continued

| Example Number | Compound Structure | Compound Name | Characterization |
|---|---|---|---|
| 129 | 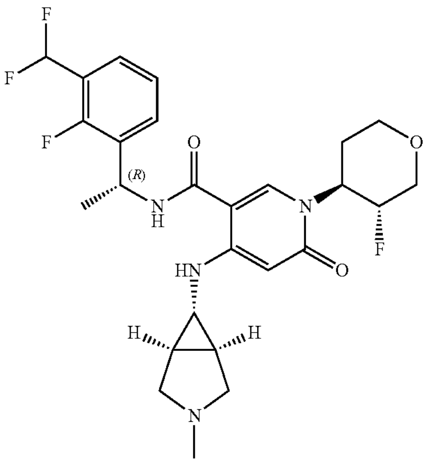 | N-((R)-1-(3-(difluoromethyl)-2-fluorophenyl)ethyl)-1-((3R,4S)-3-fluorotetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide | MS obsd (ESI+) 523.3 ([M + H]$^+$). $^1$H NMR (400 MHZ, DMSO-$d_6$) δ 8.73 (1H), 8.25 (1H), 8.06 (1H), 7.64 (1H), 7.52 (1H), 7.35 (1H), 7.21 (1H), 5.41 (1H), 5.27 (1H), 5.23-4.95 (2H), 4.22 (1H), 3.96 (1H), 3.52 (1H), 3.38 (1H), 3.01 (2H), 2.47 (1H), 2.27 (2H), 2.20 (4H), 1.84 (1H), 1.53-1.44 (5H). |
| 130 | 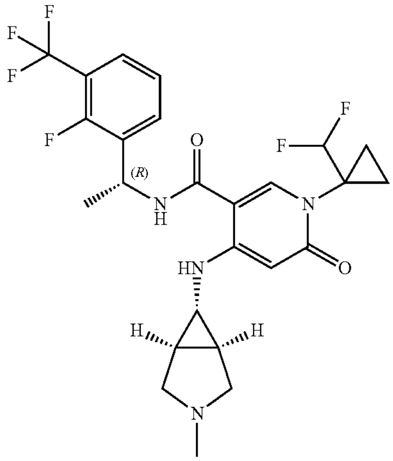 | 1-(1-(difluoromethyl)cyclopropyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 529.3 ([M + H]$^+$). $^1$H NMR (400 MHZ, DMSO-$d_6$) δ 8.84 (1H), 8.06 (1H), 7.95 (1H), 7.74 (1H), 7.67 (1H), 7.42 (1H), 6.24 (1H), 5.36 (1H), 5.28 (1H), 3.00 (2H), 2.48 (1H), 2.27 (2H), 2.20 (3H), 1.56-1.44 (5H), 1.41-1.21 (4H). |
| 131 | 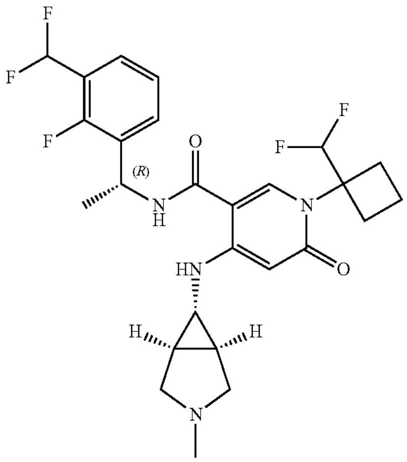 | N-((R)-1-(3-(difluoromethyl)-2-fluorophenyl)ethyl)-1-(1-(difluoromethyl)cyclobutyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 525.2 ([M + H]$^+$). $^1$H NMR (400 MHZ, DMSO-$d_6$) δ 8.87 (1H), 8.16 (1H), 7.86 (1H), 7.75 (1H), 7.55 (2H), 7.28 (2H), 6.36 (1H), 5.34 (1H), 5.26 (1H), 3.00 (2H), 2.65 (4H), 2.29 (2H), 2.20 (3H), 1.97-1.79 (2H), 1.52 (2H), 1.47 (3H). |

-continued

| Example Number | Compound Structure | Compound Name | Characterization |
| --- | --- | --- | --- |
| 132 | 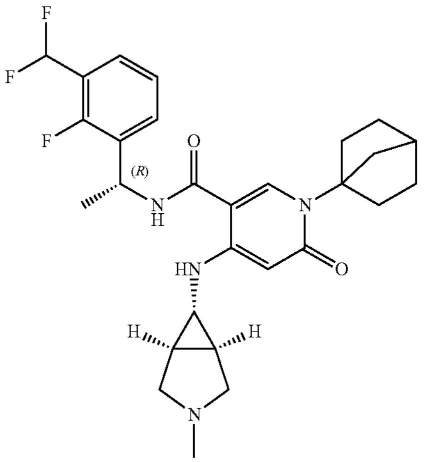 | 1-(bicyclo[2.2.1]heptan-1-yl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 515.2 ([M + H]$^+$).<br>$^1$H NMR (400 MHZ, $CD_3OD$) δ: 7.96 (1H), 7.55 -7.48 (2H), 7.28 (1H), 6.99 (1H), 5.66 (1H), 5.33 (1H), 3.17 (2H), 2.61-2.51 (5H), 2.36 (3H), 2.31 (1H), 2.07 (2H), 1.93-1.82 (2H), 1.74 -1.60 (4H), 1.58-1.47 (5H). |
| 133 | 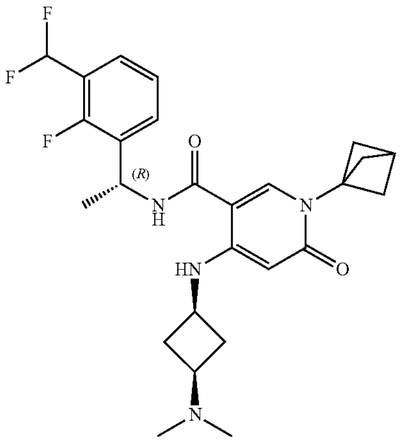 | 1-(bicyclo[1.1.1]pentan-1-yl)-N-((R)-1-(3-(difluoromethyl)-2-fluorophenyl)ethyl)-4-(((1s,3S)-3-(dimethylamino)cyclobutyl)amino)-6-oxo-1,6-dihydropyridine-3-carboxamide | MS obsd (ESI+) 489.4 ([M + H]$^+$).<br>$^1$H NMR (400 MHz, DMSO-$d_6$) δ: 8.83 (1H), 7.78 (1H), 7.74 (1H), 7.61 (1H), 7.53 (1H), 7.35 (1H), 7.22 (1H), 5.28 (1H), 5.00 (1H), 3.46 (1H), 2.61 (1H), 2.52 (1H), 2.47 (1H), 2.38 (1H), 2.28 (6H), 1.99 (6H), 1.48 (5H). |
| 134 and 135 | Unassigned Diastereomers<br>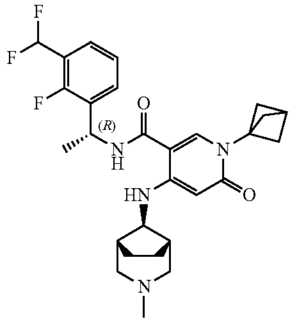<br>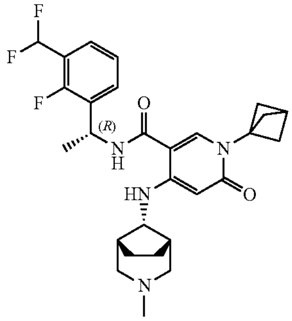 | 1-(bicyclo[1.1.1]pentan-1-yl)-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide and 1-(bicyclo[1.1.1]pentan-1-yl)-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide | Example 134<br>MS obsd (ESI+) 515.4 ([M + H]$^+$).<br>Analytical chiral UPCC: (Column: Cellulose-SC, 4.6 * 100mm 3 um, Flow rate: 3.0 mL/min, Co-solvent: EtOH(1% 7M NH3 in MeOH), Temp 40° C.) Retention time = 1.2 min<br>Example 135<br>MS obsd (ESI+) 515.4 ([M + H]$^+$).<br>Analytical chiral UPCC: (Column: Cellulose-SC, 4.6 * 100mm 3 um, Flow rate: 3.0 mL/min, Co-solvent: EtOH(1% 7M NH3 in MeOH), Temp 40° C.) Retention time = 1.6 min |

-continued

| Example Number | Compound Structure | Compound Name | Characterization |
|---|---|---|---|
| 136 and 137 | Unassigned Diastereomers 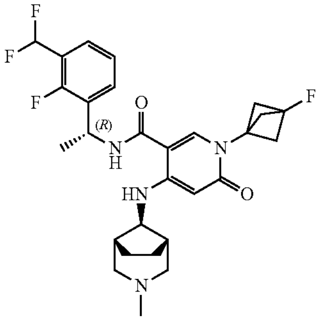 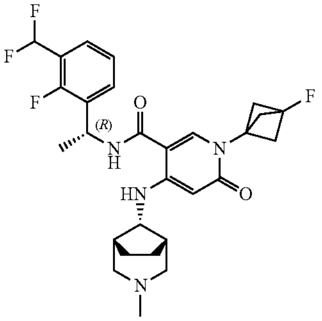 | N-((R)-1-(3-(difluoromethyl)-2-fluorophenyl)ethyl)-1-(3-fluorobicyclo[1.1.1 ]pentan -1-yl)-4-(((1R,5S,8s)-3-methyl-3-azabicyclo[3.2.1]octan-8-yl)amino)-6-oxo-1,6-dihydropyridine-3-carboxamide and N-((R)-1-(3-(difluoromethyl)-2-fluorophenyl)ethyl)-1-(3-fluorobicyclo[1.1.1]pentan -1-yl)-4-(((1R,5S,8r)-3-methyl-3-azabicyclo[3.2.1]octan-8-yl)amino)-6-oxo-1,6-dihydropyridine-3-carboxamide | Example 136 MS obsd (ESI+) 533.4 ([M + H]$^+$). Analytical chiral UPCC: (Column: CHIRALPAK AS-3, 4.6 * 100mm 3 um, Flow rate: 3.0 mL/min, Co-solvent: EtOH(0.2% 7M NH3 in MeOH), Temp 40° C.) Retention time = 1.0 min Example 137: MS obsd (ESI+) 533.4 ([M + H]$^+$). Analytical chiral UPCC: (Column: CHIRALPAK AS-3, 4.6 * 100mm 3 um, Flow rate: 3.0 mL/min, Co-solvent: EtOH(0.2% 7M NH3 in MeOH), Temp 40° C.) Retention time = 2.0 min |
| 138 and 139 | Unassigned Diastereomers 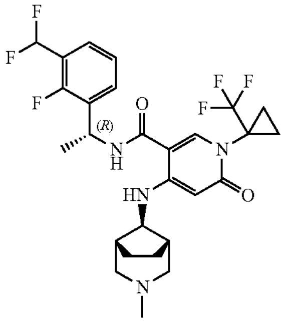 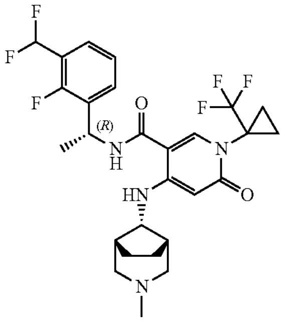 | N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1-(1-(trifluoromethyl)cycloprop yl)-1,6-dihydropyridine-3-carboxamide and N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1-(1-(trifluoromethyl)cycloprop yl)-1,6-dihydropyridine-3-carboxamide | Example 138: MS obsd (ESI+) 557.3 ([M + H]$^+$). Analytical chiral UPCC: (Column: Cellulose-SC, 4.6 * 100mm 3 um, Flow rate: 3.0 mL/min, Co-solvent: MeOH(0.2% 7M NH3 in MeOH), Temp 40° C.) Retention time = 1.0 min Example 139: MS obsd (ESI+) 557.3 ([M + H]$^+$). Analytical chiral UPCC: (Column: Cellulose-SC, 4.6 * 100mm 3 um, Flow rate: 3.0 mL/min, Co-solvent: MeOH(0.2% 7M NH3 in MeOH), Temp 40° C.) Retention time = 1.5 min |

-continued

| Example Number | Compound Structure | Compound Name | Characterization |
| --- | --- | --- | --- |
| 140 and 141 | Unassigned Diastereomers 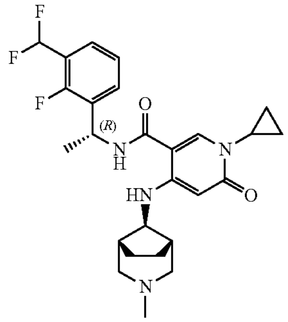 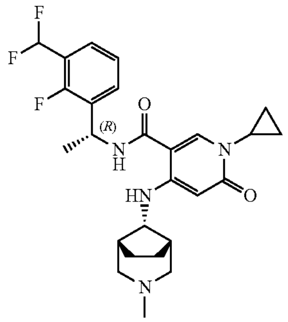 | 1-cyclopropyl-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide and 1-cyclopropyl-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide | Example 140: MS obsd (ESI+) 489.4 ([M + H]$^+$). Analytical chiral UPCC: (Column: Cellulose-SC, 4.6 * 100mm 3 um, Flow rate: 3.0 mL/min, Co-solvent: MeOH(0.2% 7M NH3 in MeOH), Temp 40° C.) Retention time = 1.4 min Example 141: MS obsd (ESI+) 489.4 ([M + H]$^+$). Analytical chiral UPCC: (Column: Cellulose-SC, 4.6 * 100mm 3 um, Flow rate: 3.0 mL/min, Co-solvent: MeOH(0.2% 7M NH3 in MeOH), Temp 40° C.) Retention time = 1.8 min |
| 142 and 143 | Unassigned Diastereomers 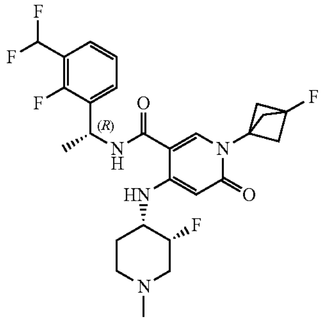 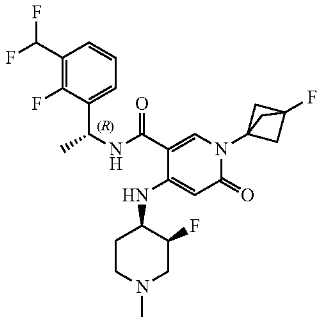 | N-((R)-1-(3-(difluoromethyl)-2-fluorophenyl)ethyl)-4-(((3R,4S)-3-fluoro-1-methylpiperidin-4-yl)amino)-1-(3-fluorobicyclo[1.1.1]pentan-1-yl)-6-oxo-1,6-dihydropyridine-3-carboxamide and N-((R)-1-(3-(difluoromethyl)-2-fluorophenyl)ethyl)-4-(((3S,4R)-3-fluoro-1-methylpiperidin-4-yl)amino)-1-(3-fluorobicyclo[1.1.1 ]pentan-1-yl)-6-oxo-1,6-dihydropyridine-3-carboxamide | Example 142: MS obsd (ESI+) 525.5 ([M + H]$^+$). Analytical chiral UPCC: (Column: CHIRALPAK AD-3, 4.6 * 100mm 3 um, Flow rate: 3.0 mL/min, Co-solvent: EtOH/iPrOH (1:1)(1% 7M NH3 in MeOH), Temp 40° C.) Retention time = 1.5 min Example 143: MS obsd (ESI+) 525.5 ([M + H]$^+$). Analytical chiral UPCC: (Column: CHIRALPAK AD-3, 4.6 * 100mm 3 um, Flow rate: 3.0 mL/min, Co-solvent: EtOH/iPrOH (1:1)(1% 7M NH3 in MeOH), Temp 40° C.) Retention time = 1.8 min |

-continued

| Example Number | Compound Structure | Compound Name | Characterization |
|---|---|---|---|
| 144 and 145 | Unassigned Diastereomers<br>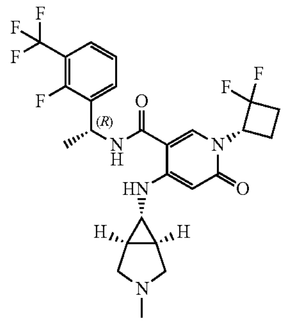<br>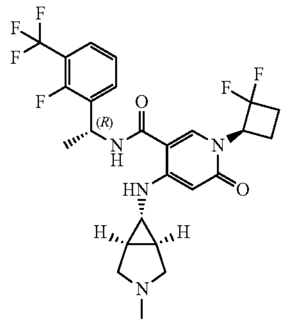 | 1-((S)-2,2-difluorocyclobutyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide and 1-((R)-2,2-difluorocyclobutyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide | Example 144:<br>MS obsd (ESI+) 528.8 ($[M + H]^+$).<br>Analytical chiral UPCC: (Column: CHIRALPAK AS-3, 4.6 * 100mm 3 um, Flow rate: 3.0 mL/min, Co-solvent: MeOH(0.2% 7M NH3 in MeOH), Temp 40° C.) Retention time = 1.1 min<br>Example 145:<br>MS obsd (ESI+) 528.7 ($[M + H]^+$).<br>Analytical chiral UPCC: (Column: CHIRALPAK AS-3, 4.6 * 100mm 3 um, Flow rate: 3.0 mL/min, Co-solvent: MeOH(0.2% 7M NH3 in MeOH), Temp 40° C.) Retention time = 2.9 min |
| 146 and 147 | Unassigned Diastereomers<br>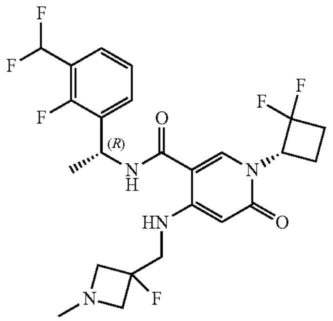<br>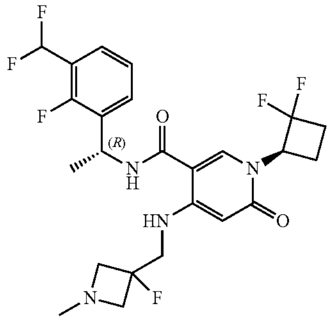 | 1-((S)-2,2-difluorocyclobutyl)-N-((R)-1-(3-(difluoromethyl)-2-fluorophenyl)ethyl)-4-(((3-fluoro-1-methylazetidin-3-yl)methyl)amino)-6-oxo-1,6-dihydropyridine-3-carboxamide and 1-((R)-2,2-difluorocyclobutyl)-N-((R)-1-(3-(difluoromethyl)-2-fluorophenyl)ethyl)-4-(((3-fluoro-1-methylazetidin-3-yl)methyl)amino)-6-oxo-1,6-dihydropyridine-3-carboxamide | Example 146:<br>MS obsd (ESI+) 517.8 ($[M + H]^+$).<br>Analytical chiral UPCC: (Column: CHIRALPAK AD-3, 4.6 * 100mm 3 um, Flow rate: 3.0 mL/min, Co-solvent: MeOH(0.2% 7M NH3 in MeOH), Temp 40° C.) Retention time = 0.7 min<br>Example 147:<br>MS obsd (ESI+) 517.8 ($[M + H]^+$).<br>Analytical chiral UPCC: (Column: CHIRALPAK AD-3, 4.6 * 100mm 3 um, Flow rate: 3.0 mL/min, Co-solvent: MeOH(0.2% 7M NH3 in MeOH), Temp 40° C.) Retention time = 1.0 min |

-continued

| Example Number | Compound Structure | Compound Name | Characterization |
| --- | --- | --- | --- |
| 148 and 149 | Unassigned Diastereomers<br>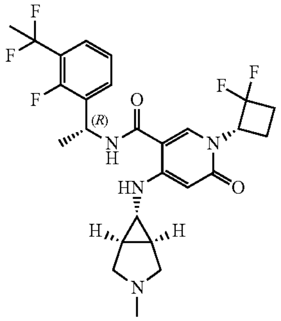<br>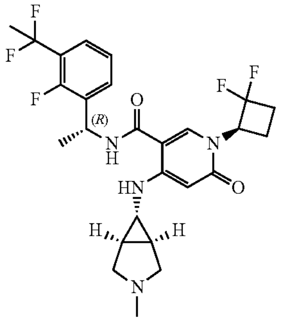 | 1-((S)-2,2-difluorocyclobutyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((R)-2,2-difluorocyclobutyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | Example 148:<br>MS obsd (ESI+) 525.0 ([M + H]$^+$).<br>Analytical chiral UPCC: (Column: Regis (R,R)-Whelk-01, 4.6 * 100mm 3 um, Flow rate: 3.0 mL/min, Co-solvent: MeOH(0.2% 7M NH3 in MeOH), Temp 40° C.) Retention time = 2.0 min<br>Example 149:<br>MS obsd (ESI+) 525.0 ([M + H]$^+$).<br>Analytical chiral UPCC: (Column: Regis (R,R)-Whelk-01, 4.6 * 100mm 3 um, Flow rate: 3.0 mL/min, Co-solvent: MeOH(0.2% 7M NH3 in MeOH), Temp 40° C.) Retention time = 1.5 min |
| 150 | 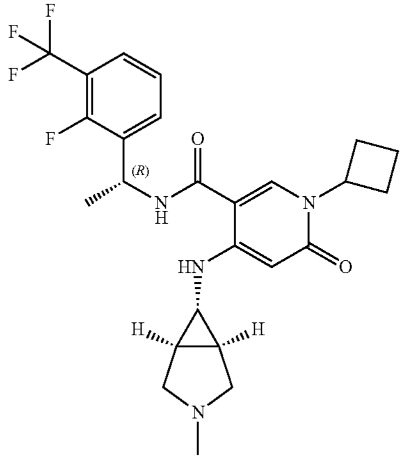 | 1-cyclobutyl-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+) 475.6 ([M + H]$^+$).<br>$^1$H NMR (400 MHz, DMSO-$d_6$) δ: 8.82 (1H), 8.08 (1H), 7.84 (1H), 7.63 (1H), 7.52 (1H), 7.35 (1H), 7.21 (1H), 5.35 (1H), 5.28 (1H), 4.95 (1H), 3.00 (2H), 2.46 (1H), 2.38 (2H), 2.32-2.24 (4H), 2.20 (3H), 1.82-1.72 (2H), 1.50 (5H). |

-continued

| Example Number | Compound Structure | Compound Name | Characterization |
|---|---|---|---|
| 151 and 152 | Unassigned diastereomers 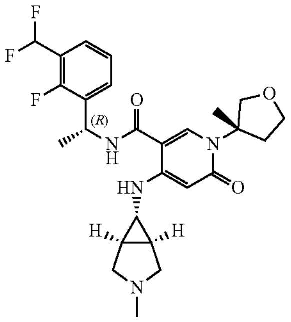 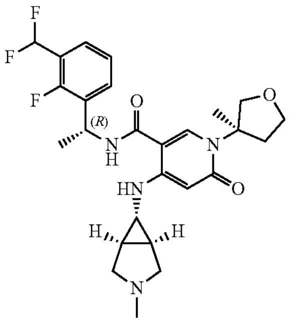 | N-((R)-1-(3-(difluoromethyl)-2-fluorophenyl)ethyl)-4-(((1R,5S,6s)-3-methyl-3-azabicyclo[3.1.0]hexan-6-yl)amino)-1-((S)-3-methyltetrahydrofuran-3-yl)-6-oxo-1,6-dihydropyridine-3-carboxamide and N-((R)-1-(3-(difluoromethyl)-2-fluorophenyl)ethyl)-4-(((1R,5S,6s)-3-methyl-3-azabicyclo[3.1.0]hexan-6-yl)amino)-1-((R)-3-methyltetrahydrofuran-3-yl)-6-oxo-1,6-dihydropyridine-3-carboxamide | Example 151: MS obsd (ESI+) 505.5 ([M + H]+). Analytical chiral UPCC: (Column: CHIRALPAK AS-3 4.6 * 100mm 3 um, Flow rate: 3.0 mL/min, Co-solvent: EtOH(1% 7M NH3 in MeOH), Temp 40° C.) Retention time = 1.3 min Example 152: MS obsd (ESI+) 505.5 ([M + H]+). Analytical chiral UPCC: (Column: CHIRALPAK AS-3 4.6 * 100mm 3 um, Flow rate: 3.0 mL/min, Co-solvent: EtOH(1% 7M NH3 in MeOH), Temp 40° C.) Retention time = 2.1 min |
| 153 and 154 | Unassigned Diastereomers 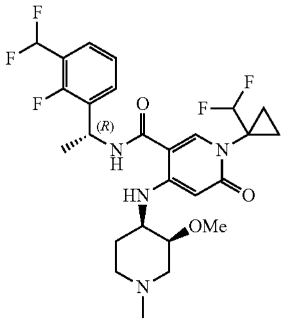 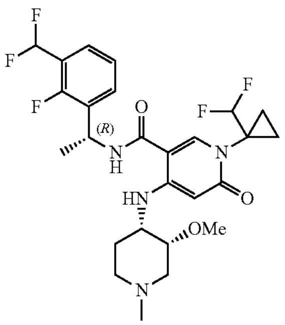 | N-((R)-1-(3-(difluoromethyl)-2-fluorophenyl)ethyl)-1-(1-(difluoromethyl)cyclopropyl)-4-(((3S,4R)-3-methoxy-1-methylpiperidin-4-yl)amino)-6-oxo-1,6-dihydropyridine-3-carboxamide and N-((R)-1-(3-(difluoromethyl)-2-fluorophenyl)ethyl)-1-(1-(difluoromethyl)cyclopropyl)-4-(((3R,4S)-3-methoxy-1-methylpiperidin-4-yl)amino)-6-oxo-1,6-dihydropyridine-3-carboxamide | Example 153: MS obsd (ESI+) 543.3 ([M + H]+). Analytical chiral UPCC: (Column: CHIRALPAK IG-3 4.6 * 100mm 3 um, Flow rate: 3.0 mL/min, Co-solvent: EtOH(1% 7M NH3 in MeOH), Temp 40° C.) Retention time = 1.1 min Example 154: MS obsd (ESI+) 543.3 ([M + H]+). Analytical chiral UPCC: (Column: CHIRALPAK IG-3 4.6 * 100mm 3 um, Flow rate: 3.0 mL/min, Co-solvent: EtOH(1% 7M NH3 in MeOH), Temp 40° C.) Retention time = 0.7 min |

Example 155: 1-(bicyclo[1.1.1]pentan-1-yl)-N—((R)-1-(3-(difluoromethyl)-2-fluorophenyl)ethyl)-6-oxo-4-(((R)-quinuclidin-3-yl)amino)-1,6-dihydropyridine-3-carboxamide

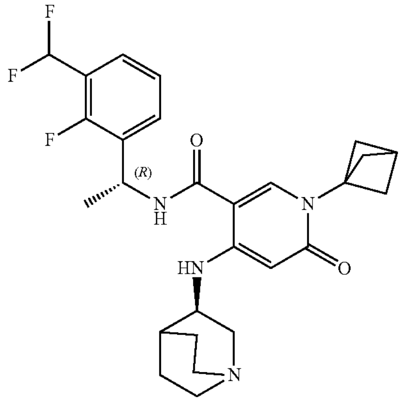

Example 155 was synthesized according to analogous procedures described in example 89 steps A-E, using (R)-quinuclidin-3-amine in step C in place of tert-butyl (1R,5S,6s)-6-amino-3-azabicyclo[3.1.0]hexane-3-carboxylate. MS obsd (ESI+) 501.5 ([M+H]$^+$). $^1$H NMR (400 MHz, DMSO-$d_6$) δ: 8.84 (1H), 8.08 (1H), 7.75 (1H), 7.61 (1H), 7.53 (1H), 7.36 (1H), 7.22 (1H), 5.36-5.24 (1H), 5.06 (1H), 3.40 (1H), 3.20 (1H), 2.67 (4H), 2.61 (1H), 2.33 (1H), 2.29 (6H), 2.24 (1H), 1.83 (1H), 1.63-1.53 (2H), 1.47 (3H), 1.35 (1H).

Example 156: 1-(bicyclo[1.1.1]pentan-1-yl)-N—((R)-1-(3-(difluoromethyl)-2-fluorophenyl)ethyl)-6-oxo-4-(((S)-quinuclidin-3-yl)amino)-1,6-dihydropyridine-3-carboxamide

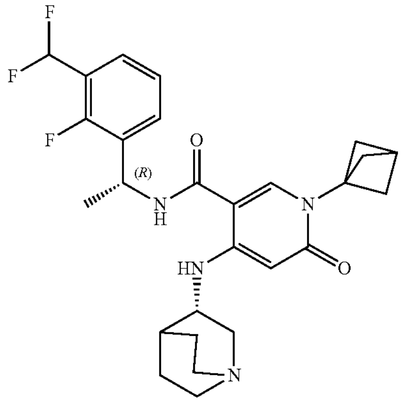

Example 156 was synthesized according to analogous procedures described in example 89 steps A-E, using(S)-quinuclidin-3-amine in step C in place of tert-butyl (1R,5S,6s)-6-amino-3-azabicyclo[3.1.0]hexane-3-carboxylate. MS obsd (ESI+) 501.5 ([M+H]$^+$). $^1$H NMR (400 MHz, DMSO-$d_6$) δ: 8.85 (1H), 8.07 (1H), 7.75 (1H), 7.61 (1H), 7.53 (1H), 7.36 (1H), 7.21 (1H), 5.30 (1H), 5.07 (1H), 3.46-3.37 (1H), 3.27-3.19 (1H), 2.67 (5H), 2.34-2.27 (7H), 1.83 (1H), 1.57 (2H), 1.48 (4H), 1.35 (1H).

Example 157: (R)—N-(1-(2-methyl-3-(trifluoromethyl)phenyl)ethyl)-6-oxo-4-(piperidin-4-ylthio)-1-(tetrahydro-2H-pyran-4-yl)-1,6-dihydropyridine-3-carboxamide

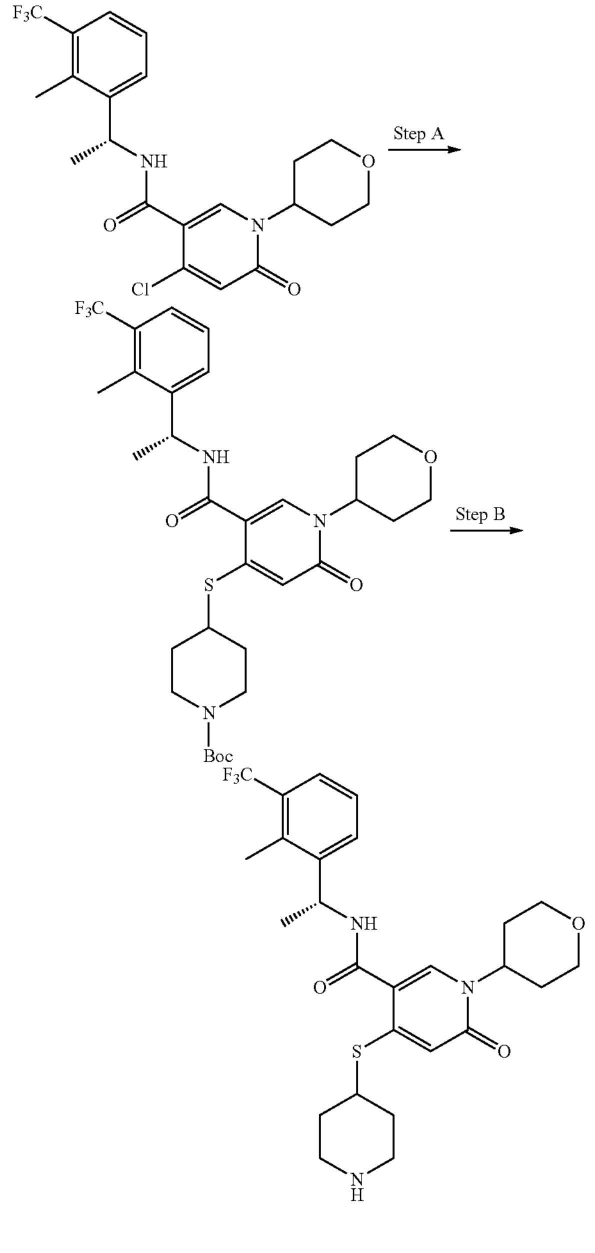

Example 157

Step A: tert-butyl (R)-4-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)thio)piperidine-1-carboxylate To a solution of (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (300 mg, 0.68 mmol) and tert-butyl 4-sulfanylpiperidine-1-carboxylate (442 mg, 2.03 mmol) in DMSO (2 mL) was added DIPEA (263 mg, 2.03 mmol). The mixture was stirred for 16 hr at 120° C. The mixture was quenched with water and extracted with DCM (3×80 mL). The combined organic layers were washed with water (3×50 mL), dried over $Na_2SO_4$, filtered and concentrated. The residue was purified by silica gel chromatography (eluting with 0% to 10% MeOH in DCM) to afford the title compound (377 mg, 89% yield). MS obsd (ESI+) 624.3 ([M+H]$^+$).

Step B: (R)—N-(1-(2-methyl-3-(trifluoromethyl)phenyl)ethyl)-6-oxo-4-(piperidin-4-ylthio)-1-(tetrahydro-2H-pyran-4-yl)-1,6-dihydropyridine-3-carboxamide To a solution of tert-butyl (R)-4-((5-((1-(2-methyl-3-(trifluoromethyl)phenyl)ethyl)carbamoyl)-2-oxo-1-(tetrahydro-2H-pyran-4-yl)-1,2-dihydropyridin-4-yl)thio)piperidine-1-carboxylate (377 mg, 0.60 mmol) in DCM (3 mL) was added TFA (3 mL). The mixture was stirred for 1 hr at rt. The solvent was removed in vacuo. 20 mL of saturated $NaHCO_3$ aqueous solution was added into the mixture and stirred for 5 min. Then the aqueous solution was extracted with DCM (3×50 mL). The combined organic layers were dried over $Na_2SO_4$, filtered and concentrated. The residue was purified by preparative HPLC (ACN/water/0.08% $NH_4HCO_3$) to afford the title compound (55.2 mg, 17% yield). MS obsd (ESI+) 524.3 ([M+H]$^+$). $^1$H NMR (400 MHz, DMSO-$d_6$) δ: 8.76 (1H), 7.85 (1H), 7.72 (1H), 7.58 (1H), 7.42 (1H), 6.24 (1H), 5.25 (1H), 4.82 (1H), 4.01 (2H), 3.48 (2H), 3.42-3.31 (2H), 2.89 (2H), 2.58 (2H), 2.46 (3H), 2.00 (2H), 1.85 (2H), 1.71 (2H), 1.42 (3H), 1.33 (m, 2H).

Examples 158 and 159: N—((S)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Example 158) and N—((R)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Example 159) (Unassigned Diastereomers)

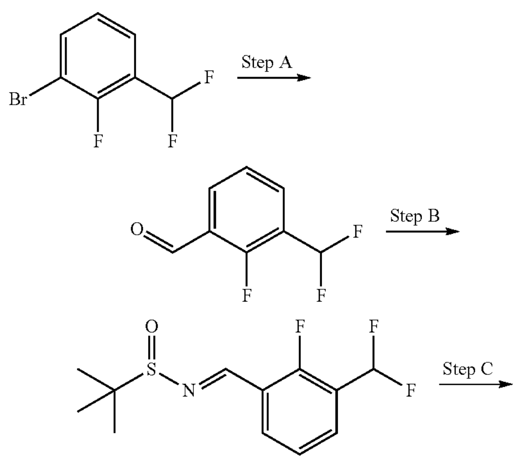

-continued

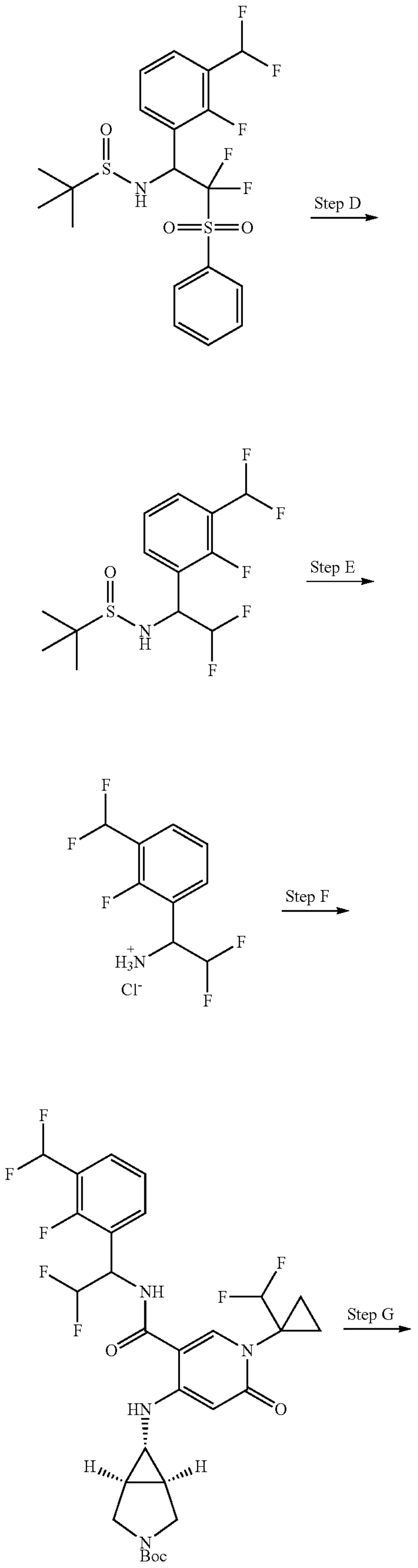

-continued

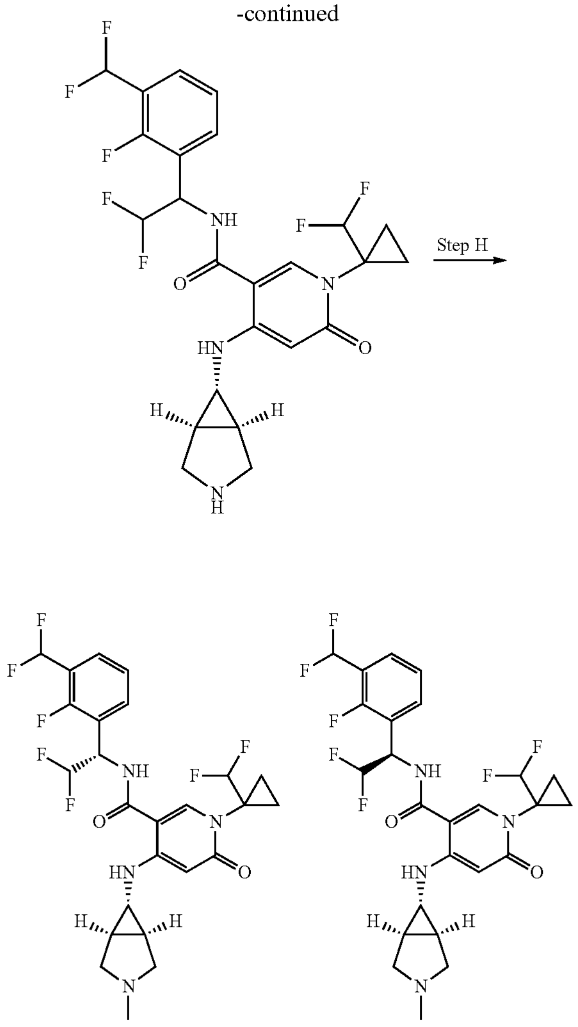

examples 158 and 159
(unassigned diastereomers)

Examples 158 and 159

(Unassigned Diastereomers)

Step A: 3-(difluoromethyl)-2-fluorobenzaldehyde

To a solution of 1-bromo-3-(difluoromethyl)-2-fluorobenzene (1.0 g, 4.44 mmol) in THF (15 mL) was added n-BuLi (2.5 M in hexane, 1.9 mL). The mixture was stirred for 0.5 hr at −78° C., then DMF (944 mg, 12.92 mmol, 1 mL) was added. The reaction was stirred for 1 hr at rt. The reaction mixture was quenched by saturated $NH_4Cl$ and the reaction mixture was extracted with EtOAc (3×10 mL). The combined organic layers were dried over $Na_2SO_4$. The solvent was removed in vacuo and the residue was purified by flash column chromatography (eluted with 0-2% EA in PE) to afford the title compound (248 mg, 32% yield). $^1H$ NMR (400 MHz, DMSO-d6) δ 10.26 (1H), 8.05 (1H), 7.97 (1H), 7.54 (1H), 7.32 (1H).

Step B: N-(3-(difluoromethyl)-2-fluorobenzylidene)-2-methylpropane-2-sulfinamide To a solution of 3-(difluoromethyl)-2-fluoro-benzaldehyde (228 mg, 1.31 mmol) in DCM (13 mL) was added 2-methylpropane-2-sulfinamide (190 mg, 1.57 mmol) and $Ti(OEt)_4$ (140 uL). The reaction was stirred for 16 hrs at rt. The solvent was removed in vacuo and the residue was purified by flash column chromatography (eluted with 0-10% EA in PE) to afford the title compound (320 mg, 88% yield). MS obsd (ESI+) 278.2 [$(M+H)^+$]

Step C: N-(1-(3-(difluoromethyl)-2-fluorophenyl)-2,2-difluoro-2-(phenylsulfonyl)ethyl)-2-methylpropane-2-sulfinamide To a solution of N-(3-(difluoromethyl)-2-fluorobenzylidene)-2-methylpropane-2-sulfinamide (300 mg, 1.08 mmol) in THF (4 mL) was added difluoromethylsulfonylbenzene (208 mg, 1.08 mmol, 157 μL) and LiHMDS (1.0 M in THF, 1.4 mL). The reaction was stirred for 1 hr at −78° C. The reaction mixture was quenched by $NH_4Cl$ (2 mL) and the reaction mixture was extracted with EtOAc (3×10 mL). The combined organic layers were dried over $Na_2SO_4$. The mixture was filtered and concentrated, and the residue was purified by flash column chromatography (eluted with 15% EA in PE) to afford the title compound (430 mg, 84% yield). MS obsd (ESI+) 470.2 [$(M+H)^+$]

Step D: N-(1-(3-(difluoromethyl)-2-fluorophenyl)-2,2-difluoroethyl)-2-methylpropane-2-sulfinamide To a solution of N-(1-(3-(difluoromethyl)-2-fluorophenyl)-2,2-difluoro-2-(phenylsulfonyl)ethyl)-2-methylpropane-2-sulfinamide (430 mg, 0.92 mmol) in DMF (4 mL) and water (1 mL) was added HOAc (1.1 g, 18.32 mmol), NaOAc (1.5 g, 18.32 mmol), and Mg (445 mg, 18.32 mmol). The reaction was stirred for 1 hr at 45° C. The reaction mixture was quenched by $NH_4Cl$ (2 mL) and the reaction mixture was extracted with EtOAc (3×10 mL). The combined organic layers were dried over $Na_2SO_4$ and filtered. The solvent was removed in vacuo and the residue was purified by flash column chromatography (eluted with 0-10% EA in PE) to afford the title compound (340 mg, 83% purity) as a colorless oil. This material is used without further purification. MS obsd (ESI+) 330.1 [$(M+H)^+$]

Step E: 1-(3-(difluoromethyl)-2-fluorophenyl)-2,2-difluoroethan-1-aminium chloride To a solution of N-(1-(3-(difluoromethyl)-2-fluorophenyl)-2,2-difluoroethyl)-2-methylpropane-2-sulfinamide (320 mg, 83% purity from step D) in 1,4-dioxane (2 mL) was added HCl/dioxane (4M, 2 mL). The reaction was stirred for 1 hr at rt. The solvent was removed in vacuo to afford the title compound (243 mg, crude). This material is used without further purification. MS obsd (ESI+) 226.0 [$(M+H)^+$ for freebase]

Step F: tert-butyl (1R,5S,6s)-6-((5-((1-(3-(difluoromethyl)-2-fluorophenyl)-2,2-difluoroethyl)carbamoyl)-1-(1-(difluoromethyl)cyclopropyl)-2-oxo-1,2-dihydropyridin-4-yl)amino)-3-azabicyclo[3.1.0]hexane-3-carboxylate To a solution of crude 1-(3-(difluoromethyl)-2-fluorophenyl)-2,2-difluoroethan-1-aminium chloride (195 mg) in DMF (3 mL) was added HATU (283 mg, 0.74 mmol), 4-(((1R,5S)-3-(tert-butoxycarbonyl)-3-azabicyclo[3.1.0]hexan-6-yl)amino)-1-(1-(difluoromethyl)cyclopropyl)-6-oxo-1,6-dihydropyridine-3-carboxylic acid (211 mg, 0.5 mmol), and DIPEA (192 mg, 1.49 mmol). The reaction was stirred for 2 hrs at rt. The reaction mixture was quenched with water (20 mL) and extracted with EtOAc (3×10 mL). The combined organic layers were dried over $Na_2SO_4$. The solvent was removed in vacuo and the residue was purified by flash column chromatography (eluted with 0-5% MeOH in DCM) to afford the title compound (207 mg). MS obsd (ESI+) 633.7 $[(M+H)^+]$ Step G: 4-(((1R,5S,6s)-3-azabicyclo[3.1.0]hexan-6-yl)amino)-N-(1-(3-(difluoromethyl)-2-fluorophenyl)-2,2-difluoroethyl)-1-(1-(difluoromethyl)cyclopropyl)-6-oxo-1,6-dihydropyridine-3-carboxamide To a solution of tert-butyl (1R,5S,6s)-6-((5-((1-(3-(difluoromethyl)-2-fluorophenyl)-2,2-difluoroethyl)carbamoyl)-1-(1-(difluoromethyl)cyclopropyl)-2-oxo-1,2-dihydropyridin-4-yl)amino)-3-azabicyclo[3.1.0]hexane-3-carboxylate (207 mg, 0.32 mmol) in DCM (6 mL) was added TFA (3 mL). The reaction was stirred for 0.5 hr at rt. The mixture was concentrated in vacuo, and the residue was neutralized with $NH_3$/MeOH (7M, 2 mL). The solvent was removed in vacuo to afford the crude title compound (224 mg, crude), which is used without further purification. MS obsd (ESI+) 533.8 $[(M+H)^+]$ Step H: N—((S)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide and N—((R)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Examples 158 and 159, Unassigned Diastereomers)

To a solution of crude 4-(((1R,5S,6s)-3-azabicyclo[3.1.0]hexan-6-yl)amino)-N-(1-(3-(difluoromethyl)-2-fluorophenyl)-2,2-difluoroethyl)-1-(1-(difluoromethyl)cyclopropyl)-6-oxo-1,6-dihydropyridine-3-carboxamide (178 mg) in MeOH (6 mL) was added paraformaldehyde (100 mg). The mixture was stirred for 30 min, then sodium cyanoborohydride (84 mg, 1.33 mmol) was added. The reaction was stirred for 1 hr at 40° C. The mixture was cooled to room temperature, filtered and concentrated in vacuo. The residue was purified by silica gel column chromatography (eluting with 9% MeOH in DCM) followed by C18 silica gel column chromatography (20% MeCN in $H_2O$) to afford the racemic title compound (88.9 mg). This material is further purified by chiral SFC (Column: Daicel AS (25*250 mm, 10 um), Mobile phase: $CO_2$/EtOH [0.5% NH3 (7M in MeOH)]=90/10) to afford the title compounds.

Example 158: MS obsd (ESI+) 547.5 $[(M+H)^+]$. Analytical chiral UPCC: (Column: CHIRALPAK AS-3, 4.6*100 mm 3 um, Flow rate: 3.0 mL/min, Co-solvent:EtOH (1% 7M NH3 in MeOH), Temp 40° C.) Retention time=0.7 min.

Example 159: MS obsd (ESI+) 547.5 $[(M+H)^+]$. Analytical chiral UPCC: (Column: CHIRALPAK AS-3, 4.6*100 mm 3 um, Flow rate: 3.0 mL/min, Co-solvent:EtOH (1% 7M NH3 in MeOH), Temp 40° C.) Retention time=1.2 min.

Example 160: 1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(trifluoromethyl)phenyl)ethyl)-1,6-dihydropyridine-3-carboxamide

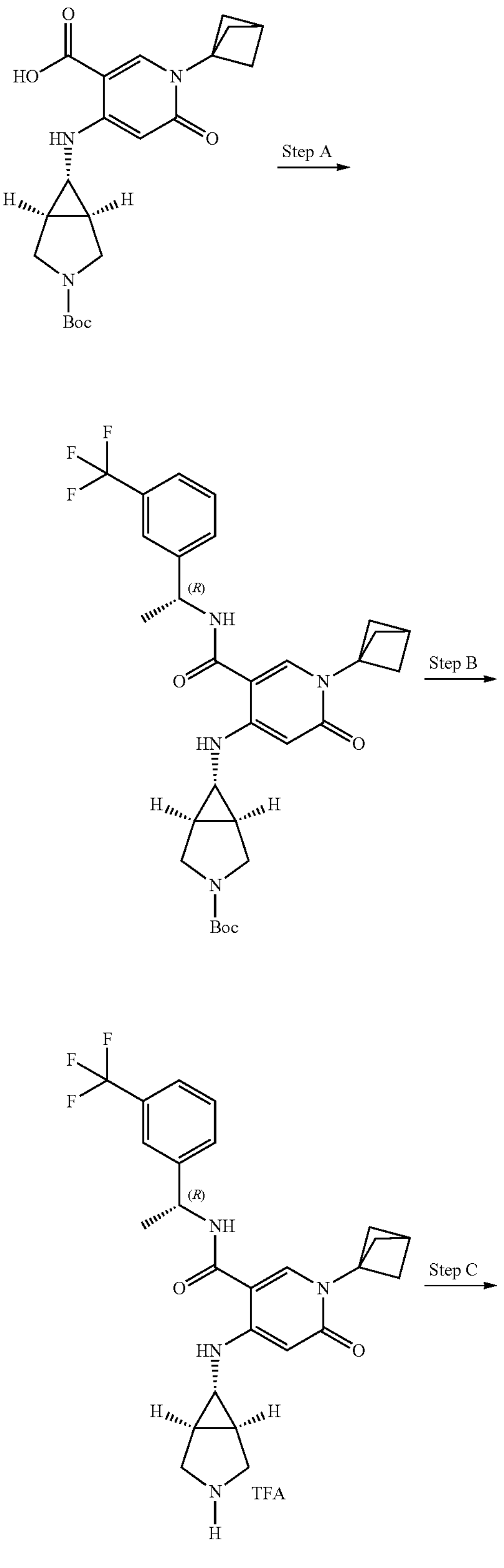

-continued

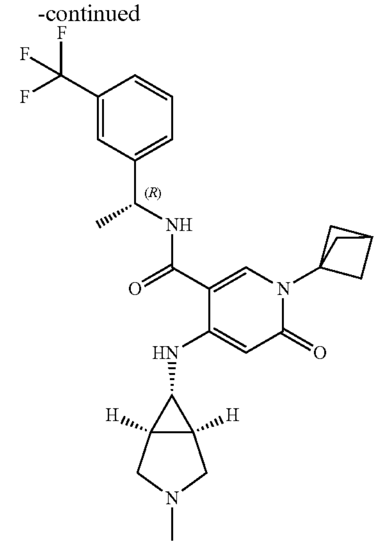

Example 160

Step A: tert-butyl (1R,5S,6s)-6-((1-(bicyclo[1.1.1]pentan-1-yl)-2-oxo-5-(((R)-1-(3-(trifluoromethyl)phenyl)ethyl)carbamoyl)-1,2-dihydropyridin-4-yl)amino)-3-azabicyclo[3.1.0]hexane-3-carboxylate To a solution of 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (100 mg, 0.25 mmol) in DMF (3 mL) was added DIPEA (97 mg, 0.75 mmol) and HATU (123 mg, 0.32 mmol). The mixture was stirred at rt for 30 min, then (1R)-1-[3-(trifluoromethyl)phenyl]ethanamine (61 mg, 0.32 mmol) was added. The mixture was stirred at rt for 1 hr. The mixture was diluted with EtOAc (50 mL) and washed with water (30 mL×3). The organic layer was dried over sodium sulfate, filtered and concentrated. The residue was purified by silica gel chromatography (eluting with 5% to 10% MeOH in DCM) to afford the title compound (120 mg, 84% yield). MS obsd (ESI+) 573.5 [$(M+H)^+$].

Step B: (1R,5S,6s)-6-((1-(bicyclo[1.1.1]pentan-1-yl)-2-oxo-5-(((R)-1-(3-(trifluoromethyl)phenyl)ethyl)carbamoyl)-1,2-dihydropyridin-4-yl)amino)-3-azabicyclo[3.1.0]hexan-3-ium 2,2,2-trifluoroacetate To a solution of tert-butyl (1R,5S,6s)-6-((1-(bicyclo[1.1.1]pentan-1-yl)-2-oxo-5-(((R)-1-(3-(trifluoromethyl)phenyl)ethyl)carbamoyl)-1,2-dihydropyridin-4-yl)amino)-3-azabicyclo[3.1.0]hexane-3-carboxylate (120 mg, 0.21 mmol) in DCM (4 mL) was added TFA (2 mL) at rt. The mixture was stirred for 1 hr. The reaction was concentrated to dryness to afford the title compound (120 mg, crude). MS obsd (ESI+) 473.5 [$(M+H)^+$].

Step C: 1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(trifluoromethyl)phenyl)ethyl)-1,6-dihydropyridine-3-carboxamide (Example 160)

To a solution of (1R,5S,6s)-6-((1-(bicyclo[1.1.1]pentan-1-yl)-2-oxo-5-(((R)-1-(3-(trifluoromethyl)phenyl)ethyl)carbamoyl)-1,2-dihydropyridin-4-yl)amino)-3-azabicyclo[3.1.0]hexan-3-ium 2,2,2-trifluoroacetate (120 mg, crude) in MeOH (10 mL) was added paraformaldehyde (92 mg) at rt. The reaction was stirred for 30 min at rt. To the mixture was added sodium cyanoborohydride (64 mg, 1.02 mmol) and the reaction was stirred for 16 hr at rt. The reaction was quenched with water (20 mL) and stirred for 30 min. The mixture was extracted with DCM (30 mL×3). The combined organic layers were washed with brine, dried over anhydrous $Na_2SO_4$, filtered, and concentrated in vacuo. The residue was first purified by silica gel chromatography (eluting with 15% to 20% MeOH in DCM) followed by preparative HPLC (ACN/water/0.1% FA) to afford the title compound (58 mg). MS obsd (ESI+) 487.3 [$(M+H)^+$]. $^1$H NMR (400 MHz, MeOD-$d_4$) δ: 7.76 (1H), 7.66-7.59 (2H), 7.54 (2H), 5.63 (1H), 5.16 (1H), 3.20 (2H), 2.64 (3H), 2.57 (1H), 2.39 (3H), 2.38 (6H), 1.67 (2H), 1.54 (3H).

Example 161: 1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(pentafluoro-16-sulfaneyl)phenyl)ethyl)-1,6-dihydropyridine-3-carboxamide

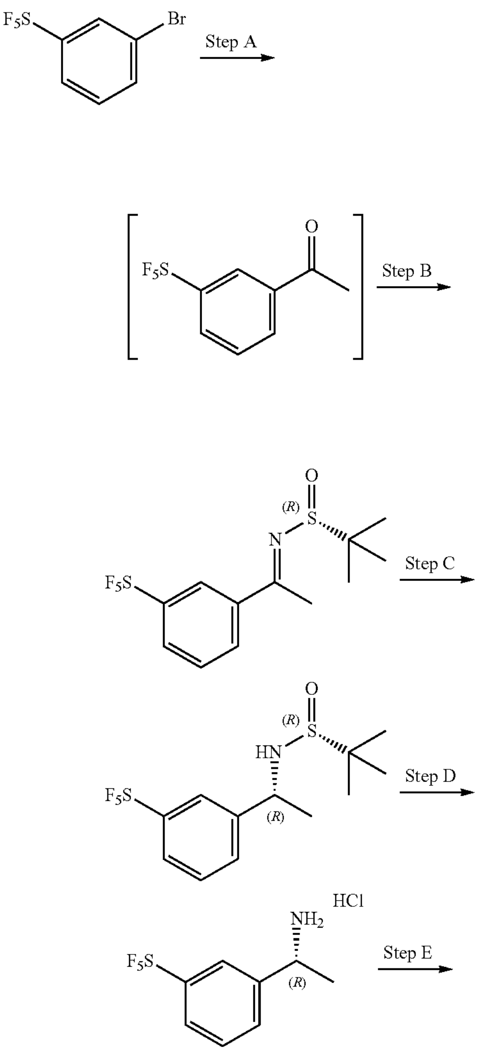

-continued

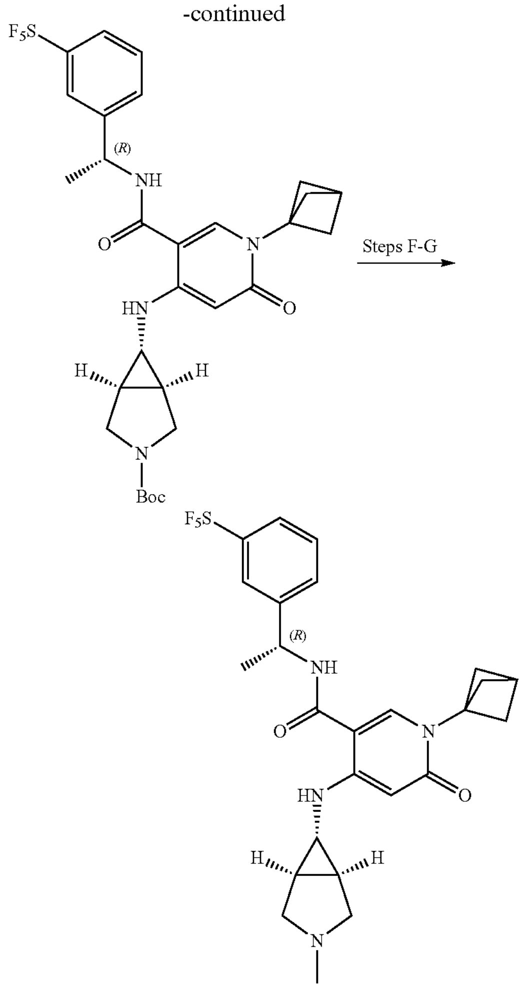

Example 161

Steps A-B: (R)-2-methyl-N-(1-(3-(pentafluoro-16-sulfanyl)phenyl)ethylidene)propane-2-sulfinamide To a solution of (3-bromophenyl) pentafluoro-16-sulfane (10 g, 35.32 mmol) in dioxane (13 mL) was added tributyl (1-ethoxyvinyl) stannane (16 g, 42.40 mmol), triethylamine (11 g, 106 mmol), and $Pd(PPh_3)_2Cl_2$ (2.48 g, 3.54 mmol). The mixture was stirred at 90° C. for 16 h, then to the mixture was added potassium fluoride (sat aq) and the mixture was stirred at rt for 1 h. The mixture was extracted with DCM (50 mL×3), the combined organic layers were dried over $Na_2SO_4$, filtered and concentrated. To the residue was added 1,4-dioxane (20 mL) and HCl (40 mL, 4M in dioxane) and the mixture was stirred at rt for 6 hr. The mixture was diluted with water and extracted with DCM (50 mL×3). The combined organic layers were dried over $Na_2SO_4$, filtered and concentrated to afford a crude residue that was used without further purification or analysis.

The aforementioned residue was dissolved in THF (30 mL). To the mixture was added tetraethyl titanate (22 g, 97.48 mmol) and (R)-2-methylpropane-2-sulfinamide (6 g, 48.74 mmol). The mixture was stirred at 70° C. for 16 hr, then the mixture was quenched with water (100 mL). The suspension was filtered and solids were washed with DCM (20% MeOH). The filtrate was concentrated purified by silica gel chromatography (eluting with 10-20% EtOAc in PE) to afford the title compound (9.8 g, 86% yield overall). MS obsd (ESI+) 350.1 [$(M+H)^+$].

Step C: (R)-2-methyl-N—((R)-1-(3-(pentafluoro-16-sulfanyl)phenyl)ethyl)propane-2-sulfinamide To a solution of (R)-2-methyl-N-(1-(3-(pentafluoro-16-sulfanyl)phenyl)ethylidene)propane-2-sulfinamide (9.8 g, 28.05 mmol) in THF (25 mL) and water (0.5 mL) was added sodium borohydride (3.18 g, 84.15 mmol) portionwise at −20° C. The mixture was stirred at −20° C. for 5 hr, at which time the mixture was quenched with water and extracted with DCM (30 mL×3). The combined organic layers were dried over $Na_2SO_4$, filtered and concentrated. The residue was purified by silica gel chromatography (eluting with 30-40% EtOAc in PE) to afford the title compound (2.0 g, 20% yield). MS obsd (ESI+) 352.2 [$(M+H)^+$].

Step D: (R)-1-(3-(pentafluoro-16-sulfanyl)phenyl)ethan-1-amine hydrochloride (R)-2-methyl-N—((R)-1-(3-(pentafluoro-16-sulfanyl)phenyl)ethyl)propane-2-sulfinamide (1.7 g, 4.84 mmol) was dissolved in HCl (2 M in dioxane, 5 mL). The mixture was stirred at rt for 6 hr and the solution was concentrated. The residue was suspended in methyl tert-butyl ether and the solid was filtered and collected to afford the title compound (1.3 g 94% yield), which was used without further purification. $^1H$ NMR (400 MHz, DMSO-$d_6$) δ: 8.79 (3H), 8.16 (1H), 7.91 (2H), 7.69 (1H), 4.57 (1H), 1.55 (3H).

Step E: tert-butyl (1R,5S,6s)-6-((1-(bicyclo[1.1.1]pentan-1-yl)-2-oxo-5-(((R)-1-(3-(pentafluoro-16-sulfaneyl)phenyl)ethyl)carbamoyl)-1,2-dihydropyridin-4-yl)amino)-3-azabicyclo[3.1.0]hexane-3-carboxylate To a solution of 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (163 mg, 0.4 mmol) in DMF (3 mL) was added DIPEA (157 mg, 1.22 mmol) and HATU (201 mg, 0.53 mmol). The mixture was stirred at rt for 10 min, then (R)-1-(3-(pentafluoro-16-sulfanyl)phenyl)ethan-1-amine hydrochloride (150 mg, 0.53 mmol) was added. The mixture was stirred at rt for 3 hr, at which time DCM (60 mL) was added. The mixture was washed with water (60 mL×3), and the organic layer was dried over sodium sulfate, filtered and concentrated. The residue was purified by silica gel chromatography (eluting with 5% to 10% MeOH in DCM) to afford the title compound (223 mg, 87% yield). MS obsd (ESI+) 631.4 [$(M+H)^+$].

Steps F-G: 1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(pentafluoro-16-sulfaneyl)phenyl)ethyl)-1,6-dihydropyridine-3-carboxamide (Example 161)

Steps F-G were performed according to analogous procedures described for Example 160 steps B-C to afford the title compound. MS obsd (ESI+) 545.3 [$(M+H)^+$]. $^1H$ NMR (400 MHz, DMSO-$d_6$) δ: 9.17 (1H), 7.89 (1H), 7.83 (1H), 7.77 (1H), 7.69 (2H), 7.58 (1H), 5.29 (1H), 5.12 (1H), 3.32 (2H), 3.02 (1H), 2.61 (1H), 2.53 (2H), 2.30 (6H), 2.25 (3H), 1.50 (5H).

Example 162: 1-(bicyclo[1.1.1]pentan-1-yl)-N—((R)-1-(2-fluoro-3-(pentafluoro-16-sulfaneyl)phenyl)ethyl)-4-(((1R,5S,6s)-3-methyl-3-azabicyclo[3.1.0]hexan-6-yl)amino)-6-oxo-1,6-dihydropyridine-3-carboxamide

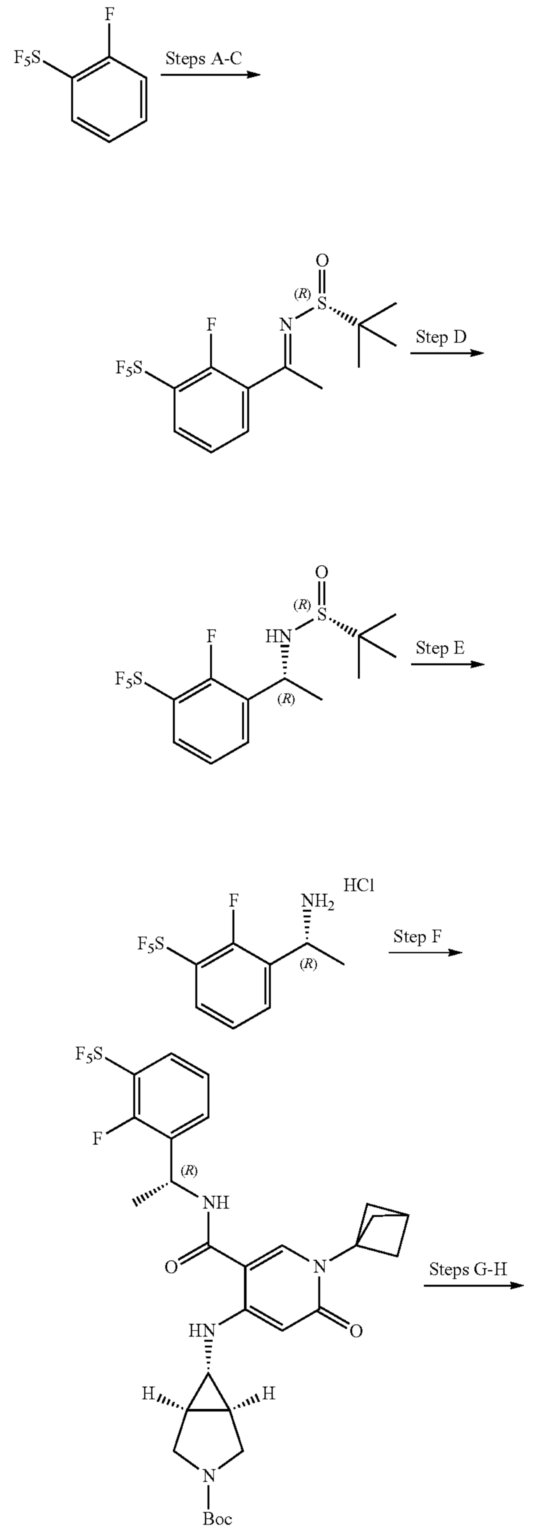

-continued

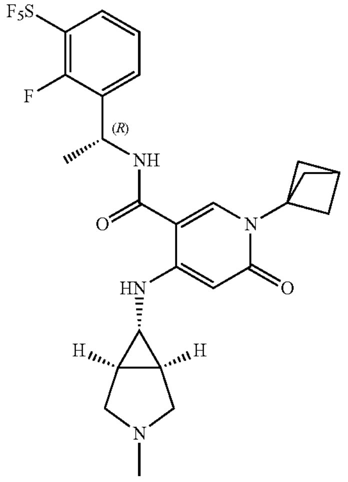

Example 162

Steps A-C: (R)—N-(1-(2-fluoro-3-(pentafluoro-16-sulfaneyl)phenyl)ethylidene)-2-methylpropane-2-sulfinamide To a solution of pentafluoro-(2-fluorophenyl)-sulfane (500 mg, 2.25 mmol) in THF (10 mL) was added 2,2,6,6-tetramethylpiperidinylmagnesium chloride lithium chloride complex (1 M in THF, 4.50 mmol, 4.50 mL) at 0° C. The reaction mixture was stirred for 1 hr at 0° C. Then molecular iodine (1.14 g, 4.50 mmol) in THF (10 mL) was added dropwise to the mixture at 0° C. Then the mixture was warmed to rt. After 1 hr, saturated aqueous sodium thiosulphate solution was added to the reaction and the mixture was extracted with EtOAc (30 mL*3). The combined organic layers were washed with brine, dried over anhydrous $Na_2SO_4$, filtered, concentrated to afford pentafluoro (2-fluoro-3-iodophenyl)-16-sulfane (500 mg, crude), which was used without further purification. Crude $^1H$ NMR (400 MHz, DMSO-$d_6$) δ: 8.22 (m, 1H), 8.04-7.97 (m, 1H), 7.27 (m, 1H).

To a solution of the aforementioned residue in 1,4-dioxane (10 mL) was added tributyl (1-ethoxyvinyl) stannane (623 mg, 1.72 mmol), triethylamine (436 mg, 4.31 mmol) and bis(Triphenylphosphine) palladium(II) chloride (202 mg, 0.29 mmol). The reaction was stirred for 16 hr at 100° C. To the mixture was added 5 mL KF (saturated aq) and stirred for 1 hr at rt. The mixture was extracted with DCM (3×30 mL). The combined organic layers were dried over sodium sulfate, filtered and concentrated. The mixture was treated with 5 mL HCl (2M in dioxane). The reaction was stirred for 1 hr at rt. The mixture was neutralized by $NaHCO_3$ (aq) and extracted with DCM (3*30 mL). The combined organic layers were dried over $Na_2SO_4$. The residue was concentrated to afford crude 1-(2-fluoro-3-(pentafluoro-16-sulfanyl)phenyl)ethan-1-one, which was used without further purification or analysis.

The aforementioned crude residue was dissolved in THF (10 mL), to which was added (R)-2-methylpropane-2-sulfinamide (206 mg, 1.70 mmol) and titanium ethoxide (777 mg, 3.41 mmol). The mixture was stirred at 80° C. for 16 hr. The mixture was poured into cold water (10 mL), filtered and extracted with EtOAc (30 mL*2). The combined organic layers were dried over $Na_2SO_4$ and concentrated under reduced pressure. The residue was purified by silica gel chromatography (eluting with 20-30% EtOAc in PE) to afford the title compound (160 mg). MS obsd (ESI+) 368.2 [(M+H)$^+$].

Step D: (R)—N—((R)-1-(2-fluoro-3-(pentafluoro-16-sulfaneyl)phenyl)ethyl)-2-methylpropane-2-sulfinamide To a solution of (R)—N-(1-(2-fluoro-3-(pentafluoro-16-sulfanyl)phenyl)ethylidene)-2-methylpropane-2-sulfinamide (160 mg, 0.44 mmol) in THF (5 mL) was added sodium borohydride (25 mg, 1.5 eq.) at 0° C. The mixture was stirred for 30 min at 0° C. Cold water was poured into the mixture and it was extracted with DCM. The combined organic layers were dried over $Na_2SO_4$ and concentrated under reduced pressure. The residue was purified by silica gel chromatography (eluting with 50-60% EtOAc in PE) to afford the title compound (60 mg, 37% yield). MS obsd (ESI+) 370.2 [(M+H)$^+$]. $^1$H NMR (400 MHz, DMSO-d$_6$) δ: 7.90 (2H), 7.45 (1H), 5.93 (1H), 4.72 (1H), 1.43 (3H), 1.10 (9H).

Step E: (R)-1-(2-fluoro-3-(pentafluoro-16-sulfaneyl)phenyl)ethan-1-amine hydrochloride To a solution of (R)—N—((R)-1-(2-fluoro-3-(pentafluoro-16-sulfanyl)phenyl)ethyl)-2-methylpropane-2-sulfinamide (60 mg, 162.43 μmol, 1.0 eq.) in dioxane (2 mL) was added HCl (4 M in dioxane, 4 mL) at rt. The mixture was stirred for 1 hr at rt. The mixture was concentrated to dryness to afford the title compound (45 mg, crude). MS obsd (ESI+) 266.1 [(M+H)$^+$].

Step F: tert-butyl (1R,5S,6s)-6-((1-(bicyclo[1.1.1]pentan-1-yl)-5-(((R)-1-(2-fluoro-3-(pentafluoro-16-sulfanyl)phenyl)ethyl)carbamoyl)-2-oxo-1,2-dihydropyridin-4-yl)amino)-3-azabicyclo[3.1.0]hexane-3-carboxylate To a solution of 1-(bicyclo[1.1.1]pentan-1-yl)-4-(((1R,5S,6s)-3-(tert-butoxycarbonyl)-3-azabicyclo[3.1.0]hexan-6-yl)amino)-6-oxo-1,6-dihydropyridine-3-carboxylic acid (66 mg, 0.16 mmol) in DMF (3 mL) was added DIPEA (58 mg, 0.45 mmol) and HATU (74 mg, 0.19 mmol). The mixture was stirred at rt for 30 min, then (R)-1-(2-fluoro-3-(pentafluoro-16-sulfaneyl)phenyl)ethan-1-amine hydrochloride (45 mg, 0.15 mmol) was added. The mixture was stirred at rt for 1 hr. The mixture was diluted with EtOAc (50 mL) and washed with water (30 mL×3). The organic layer was dried over sodium sulfate, filtered and concentrated. The residue was purified by silica gel chromatography (eluting with 60-70% EtOAc in PE) to afford the title compound (70 mg, 73% yield). MS obsd (ESI+) 649.2 [(M+H)$^+$].

Steps G-H: 1-(bicyclo[1.1.1]pentan-1-yl)-N—((R)-1-(2-fluoro-3-(pentafluoro-16-sulfaneyl)phenyl)ethyl)-4-(((1R,5S,6s)-3-methyl-3-azabicyclo[3.1.0]hexan-6-yl)amino)-6-oxo-1,6-dihydropyridine-3-carboxamide (Example 162)

Steps G-H were performed according to analogous procedures described for Example 160 steps B-C to afford the title compound. MS obsd (ESI+) 563.2 [(M+H)$^+$]. $^1$H NMR (400 MHz, DMSO-d$_6$) δ: 8.87 (1H), 7.89 (1H), 7.77-7.72 (2H), 7.67 (1H), 7.44 (1H), 5.29 (1H), 5.25 (1H), 3.00 (2H), 2.62 (1H), 2.46 (1H), 2.32 (2H), 2.29 (6H), 2.21 (3H), 1.54-1.45 (5H).

Example 163: 1-cyclobutyl-4-(((1R,5S,6s)-3-methyl-3-azabicyclo[3.1.0]hexan-6-yl)amino)-6-oxo-N—((R)-1-(3-(pentafluoro-16-sulfaneyl)phenyl)ethyl)-1,6-dihydropyridine-3-carboxamide

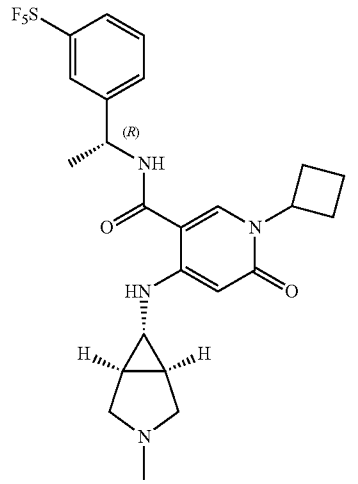

Example 163

Example 163 was synthesized according to analogous procedures described in Example 161. MS obsd (ESI+) 533.2 [(M+H)$^+$]. $^1$H NMR (400 MHz, DMSO-d$_6$) δ 8.82 (1H), 8.03 (1H), 7.88-7.84 (1H), 7.81-7.73 (2H), 7.67 (1H), 7.69 (1H), 5.36 (1H), 5.14 (1H), 5.04-4.92 (1H), 3.01 (dd, J=9.0, 3.6 Hz, 2H), 2.48 (d, J=1.8 Hz, 1H), 2.39-2.24 (m, 6H), 2.20 (s, 3H), 1.83-1.70 (m, 2H), 1.49 (d, J=7.2 Hz, 5H).

Example 164: (R)-1-cyclobutyl-4-((1-methylpiperidin-4-yl)amino)-6-oxo-N-(1-(3-(pentafluoro-16-sulfaneyl)phenyl)ethyl)-1,6-dihydropyridine-3-carboxamide

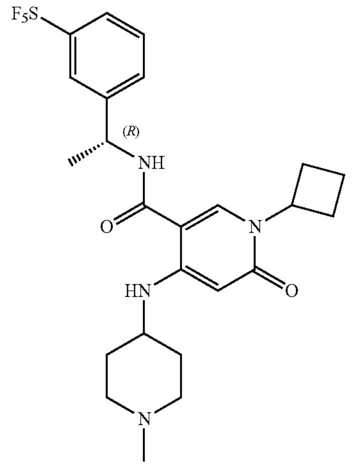

Example 164

Example 164 was synthesized according to analogous procedures described in Example 161. MS obsd (ESI+) 535.4 [(M+H)+]. $^1$HNMR (400 MHz, DMSO) δ 8.83 (1H), 8.03 (1H), 7.88 (1H), 7.80 (2H), 7.69 (1H), 7.60 (1H), 5.25-5.13 (2H), 4.95 (1H), 3.23 (1H), 2.52 (2H), 2.37-2.21 (4H), 2.11 (5H), 1.90-1.67 (4H), 1.51 (3H), 1.44-1.23 (2H).

Examples 165 and 166: (R)-1-(1-(difluoromethyl) cyclopropyl)-N-(1-(2-fluoro-4-methoxy-3-(trifluoromethyl)phenyl)ethyl)-4-((1-methylpiperidin-4-yl) amino)-6-oxo-1,6-dihydropyridine-3-carboxamide (Example 165) and(S)-1-(1-(difluoromethyl)cyclopropyl)-N-(1-(2-fluoro-4-methoxy-3-(trifluoromethyl)phenyl)ethyl)-4-((1-methylpiperidin-4-yl) amino)-6-oxo-1,6-dihydropyridine-3-carboxamide (Example 166) (Unassigned Stereoisomers)

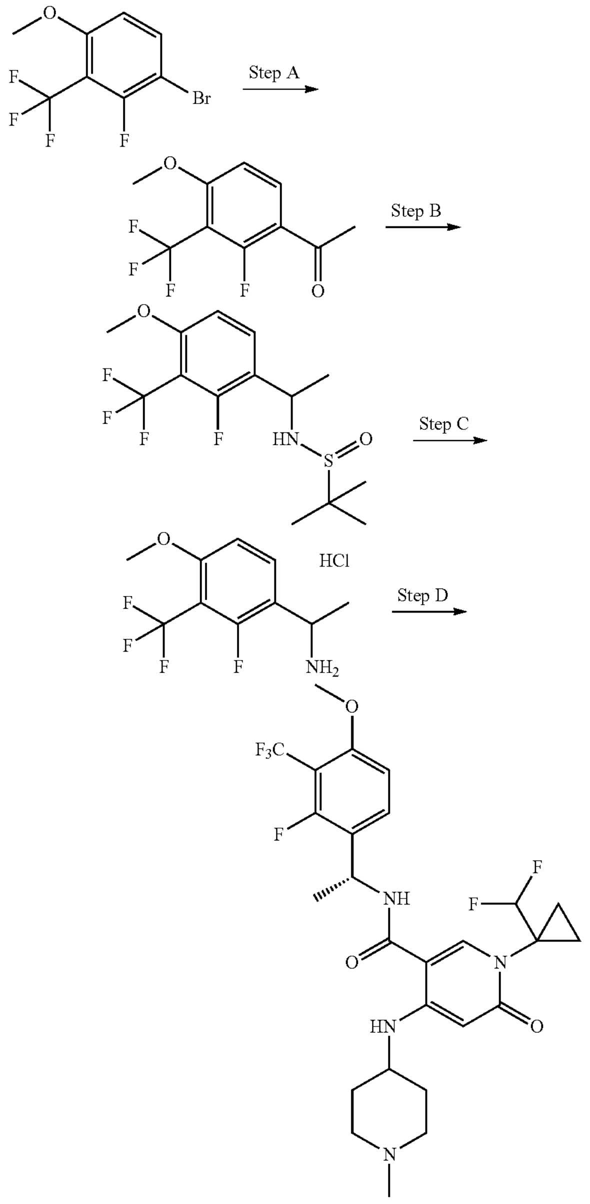

-continued

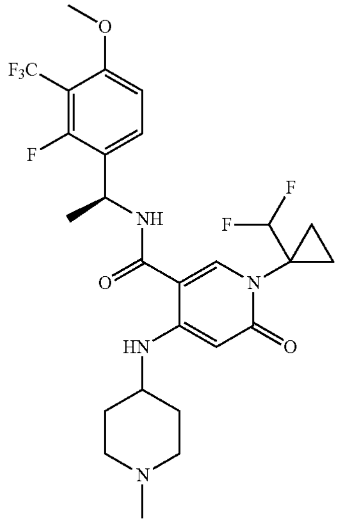

examples 165 and 166

Examples 165 and 166

Step A: 1-(2-fluoro-4-methoxy-3-(trifluoromethyl) phenyl)ethan-1-one 1-bromo-2-fluoro-4-methoxy-3-(trifluoromethyl)benzene (2 g, 7.33 mmol, prepared according to the protocol described in US20140275179A1) and tributyl (1-ethoxyvinyl) stannane (3.97 g, 10.99 mmol) were dissolved in dioxane (20 mL). $Pd(PPh_3)_2Cl_2$ (660.02 mg, 732.54 μmol, 0.1 eq.) and $NEt_3$ (741.26 mg, 7.33 mmol) were added to the mixture and stirred for 2 hr at 100° C. The residue was diluted with water (100 mL), then adjusted to PH~5 with HCl (1M). Then the mixture was extracted with EtOAc (3×100 mL). The combined organic extracts were washed with brine, dried over anhydrous $Na_2SO_4$. After filtration, the filtrate was concentrated under reduced pressure. The residue was purified by silica gel column chromatography (eluting with 1:9 EA/PE) to afford the title compound (1.2 g, 4.47 mmol, 61% yield). MS obsd (ESI+): 237.0 $[M+H]^+$ Step B: N-(1-(2-fluoro-4-methoxy-3-(trifluoromethyl)phenyl)ethyl)-2-methylpropane-2-sulfinamide 1-(2-fluoro-4-methoxy-3-(trifluoromethyl)phenyl)ethan-1-one (200 mg, 0.85 mmol) and 2-methylpropane-2-sulfinamide (154.6 mg, 1.28 mmol) were dissolved in THF (5 mL). $Ti(OEt)_4$ (819.4 mg, 3.59 mmol, 4.0 eq.) was added to the mixture and stirred for 3 h at 80° C. After cooling down to 0° C., $LiBH_4$ (48.22 mg, 1.28 mmol) and MeOH (0.5 mL) were added to the mixture and stirred for 1 h at 0° C. The reaction was quenched with water (30 mL). Then the mixture was extracted with EtOAc (3×100 mL). The combined organic extracts were washed with brine (20 mL), dried over anhydrous $Na_2SO_4$ to afford the title compound (150 mg, 49% yield). MS obsd (ESI+): 342.0 [M+H]+

Step C: 1-(2-fluoro-4-methoxy-3-(trifluoromethyl)phenyl)ethan-1-amine hydrochloride N-(1-(2-fluoro-4-methoxy-3-(trifluoromethyl)phenyl)ethyl)-2-methylpropane-2-sulfinamide (1.2 g, 3.52 mmol) was dissolved in DCM (20 mL). HCl (2 mL, 8 mmol, 4M in dioxane) was added to the mixture and stirred for 1 hr at 20° C. The resulting mixture was concentrated under reduced pressure and solids were washed with EtOAc to afford the title compound (588.2 mg, 60% yield). MS obsd (ESI+): 237.95 [M+H]+.

Step D: (R)-1-(1-(difluoromethyl)cyclopropyl)-N-(1-(2-fluoro-4-methoxy-3-(trifluoromethyl)phenyl)ethyl)-4-((1-methylpiperidin-4-yl)amino)-6-oxo-1,6-dihydropyridine-3-carboxamide and(S)-1-(1-(difluoromethyl)cyclopropyl)-N-(1-(2-fluoro-4-methoxy-3-(trifluoromethyl)phenyl)ethyl)-4-((1-methylpiperidin-4-yl)amino)-6-oxo-1,6-dihydropyridine-3-carboxamide (Examples 165 and 166, Unassigned Stereoisomers)

1-[1-(difluoromethyl)cyclopropyl]-4-[(1-methyl-4-piperidyl)amino]-6-oxo-pyridine-3-carboxylic acid (276 mg) and HATU (234 mg, 0.61 mmol) were dissolved in DMF (10 mL). The mixture was stirred for 0.5 hr at rt. Then DIPEA (106 mg, 0.82 mmol) and 1-(2-fluoro-4-methoxy-3-(trifluoromethyl)phenyl)ethan-1-amine hydrochloride (123 mg, 0.45 mmol) were added. The mixture was stirred for 1.5 hr at this temperature. The mixture was poured into water (100 mL) and extracted with EtOAc (20 mL×3). The organic phase was washed with brine, dried over $Na_2SO_4$, filtered and concentrated to dryness. The residue was purified by column chromatography (eluted with 0-25% MeOH in DCM) to afford the title compound (138 mg, 60% yield) was obtained. MS obsd (ESI+): 561.3 [M+H]+.

The stereoisomeric mixture was purified by SFC (Daicel AD (25*250 mm, 10 um), $CO_2$/EtOH [0.5% $NH_3$ (7M in MeOH)]=85/15).

Example 165: MS obsd (ESI+): 561.2 [M+H]+. Analytical chiral UPCC: (Column: CHIRALPAK AD-3 4.6*100 mm 3 um, Flow rate: 3.0 mL/min, Cosolvent:EtOH (1% 7M NH3 in MeOH), Temp 40° C.) Retention time=0.9 min Example 166: MS obsd (ESI+): 561.2 $[M+H]^+$. Analytical chiral UPCC: (Column: CHIRALPAK AD-3 4.6*100 mm 3 um, Flow rate: 3.0 mL/min, Cosolvent:EtOH (1% 7M NH3 in MeOH), Temp 40° C.) Retention time=1.3 min Examples 167 and 168: (R)-1-(1-(difluoromethyl)cyclopropyl)-N-(1-(4-fluoro-3-(trifluoromethyl)phenyl)ethyl)-4-((1-methylpiperidin-4-yl)amino)-6-oxo-1,6-dihydropyridine-3-carboxamide (Example 167) and(S)-1-(1-(difluoromethyl)cyclopropyl)-N-(1-(4-fluoro-3-(trifluoromethyl)phenyl)ethyl)-4-((1-methylpiperidin-4-yl)amino)-6-oxo-1,6-dihydropyridine-3-carboxamide (Example 168) (Unassigned Stereoisomers)

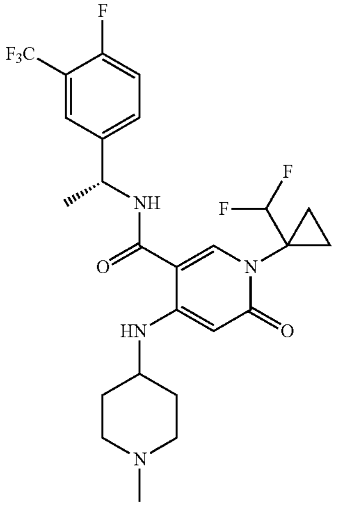

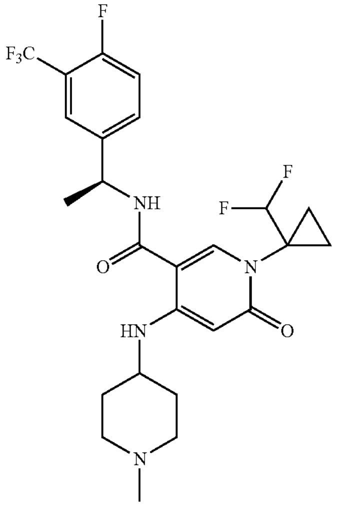

Examples 167 and 168

Examples 167 and 168 were synthesized according to analogous procedures described in Examples 165 and 166, step D using commercially available 1-(4-fluoro-3-(trifluoromethyl)phenyl)ethan-1-amine hydrochloride.

Example 167: MS obsd (ESI+): 531.3 [M+H]+. Analytical chiral UPCC: (Column: (R,R)Whelk-O1 4.6*100 mm 3 um, Flow rate: 3.0 mL/min, Cosolvent: IPA (1% 7M NH3 in MeOH), Temp 40° C.) Retention time=2.0 min Example 168: MS obsd (ESI+): 531.3 [M+H]+. Analytical chiral UPCC: (Column: (R,R)Whelk-O1 4.6*100 mm 3 um, Flow rate: 3.0 mL/min, Cosolvent: IPA (1% 7M NH3 in MeOH), Temp 40° C.) Retention time=2.8 min Example 169: N-(1-(4-cyclopropyl-3-(trifluoromethyl)phenyl)ethyl)-1-(1-(difluoromethyl)cyclopropyl)-4-((1-methylpiperidin-4-yl)amino)-6-oxo-1,6-dihydropyridine-3-carboxamide example 169

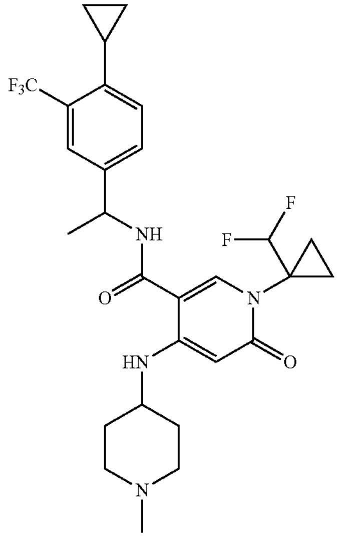

Example 169 was synthesized according to analogous procedures described in examples 165 and 166 steps B-D, starting with known compound 1-(4-cyclopropyl-3-(trifluoromethyl)phenyl)ethan-1-one (prepared as described in WO2016031833). MS obsd. (ESI+): 553.5 [$(M+H)^+$] $^1$H NMR (400 MHz, DMSO-$d_6$) δ ppm 9.16 (1H), 8.80 (1H), 8.05 (2H), 7.60 (1H), 7.51 (1H), 7.14 (1H), 6.20 (1H), 5.37 (1H), 5.18-5.01 (1H), 3.41 (2H), 3.03 (2H), 2.79 (3H), 2.20-2.01 (3H), 1.90 (1H), 1.60-1.39 (5H), 1.38-1.21 (4H), 1.01 (2H), 0.75 (2H).

Example 170: N-(1-(2-chloro-3-(trifluoromethyl)phenyl)ethyl)-1-(1-(difluoromethyl)cyclopropyl)-4-((1-methylpiperidin-4-yl)amino)-6-oxo-1,6-dihydropyridine-3-carboxamide example 170

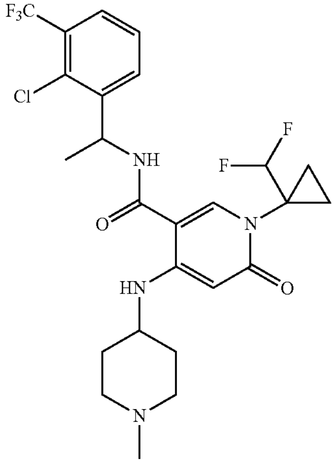

Example 170 was synthesized according to analogous procedures described in Examples 165 and 166, step B-D using commercially available 1-(2-chloro-3-(trifluoromethyl)phenyl)ethan-1-one. MS obsd. ($ESI^+$): 547.3 [$(M+H)^+$]. $^1$H NMR (400 MHz, DMSO-d6) δ ppm 8.88 (1H), 8.11 (1H), 7.97 (1H), 7.78 (2H), 7.58 (1H), 6.25 (1H), 5.41 (1H), 5.22 (1H), 3.21 (1H), 2.63-2.53 (2H), 2.12 (3H), 2.10-1.98 (2H), 1.89-1.72 (2H), 1.47 (3H), 1.40-1.23 (6H).

Examples 171 and 172: (R)-1-(1-(difluoromethyl)cyclopropyl)-N-(1-(2-methyl-6-(trifluoromethyl)pyridin-4-yl)ethyl)-4-((1-methylpiperidin-4-yl)amino)-6-oxo-1,6-dihydropyridine-3-carboxamide (Example 171) and(S)-1-(1-(difluoromethyl)cyclopropyl)-N-(1-(2-methyl-6-(trifluoromethyl)pyridin-4-yl)ethyl)-4-((1-methylpiperidin-4-yl)amino)-6-oxo-1,6-dihydropyridine-3-carboxamide (Example 172) (Stereochemistry not Assigned)

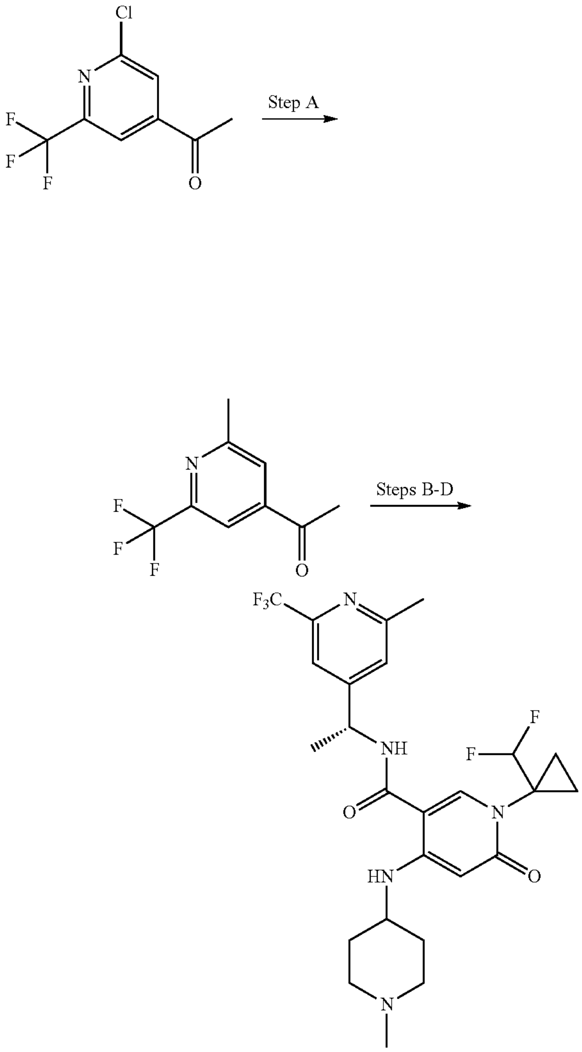

-continued

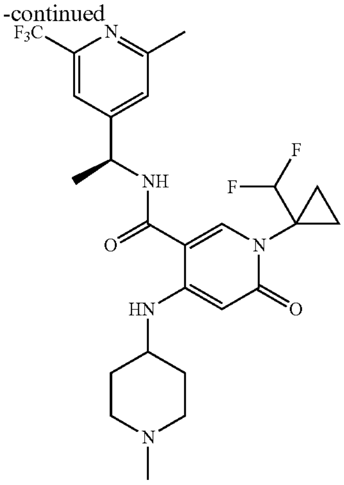

examples 171 and 172

Examples 171 and 172

Step A: 1-(2-methyl-6-(trifluoromethyl)pyridin-4-yl) ethan-1-one

To a solution of 1-(2-chloro-6-(trifluoromethyl)pyridin-4-yl)ethan-1-one (2.5 g, 11.18 mmol), methylboronic acid (2.01 g, 33.55 mmol) and $K_2CO_3$ (4.64 g, 33.55 mmol) in dioxane (50 mL) and $H_2O$ (5 mL) was added $Pd(PPh_3)_4$ (1.29 g, 1.12 mmol). The resulting mixture was stirred for overnight at 100° C. After cooling down to rt, the reaction mixture was then quenched with water (100 mL) and adjusted to pH 6~7 with saturated $NH_4Cl$. The mixture was extracted with DCM (3×100 mL). The organic phase was combined, dried by $Na_2SO_4$ and concentrated in vacuum. The resulting residue was purified by flash chromatography (0-30% EA/PE) to afford 1-(2-methyl-6-(trifluoromethyl) pyridin-4-yl)ethan-1-one (1.5 g, 66% yield). MS obsd. ($ESI^+$): 203.90 $[M+H]^+$.

Steps B-D: (R)-1-(1-(difluoromethyl)cyclopropyl)-N-(1-(2-methyl-6-(trifluoromethyl)pyridin-4-yl) ethyl)-4-((1-methylpiperidin-4-yl)amino)-6-oxo-1,6-dihydropyridine-3-carboxamide and(S)-1-(1-(difluoromethyl)cyclopropyl)-N-(1-(2-methyl-6-(trifluoromethyl)pyridin-4-yl)ethyl)-4-((1-methylpiperidin-4-yl)amino)-6-oxo-1,6-dihydropyridine-3-carboxamide (Examples 171 and 172)

Steps B-D were performed via analogous procedures described in examples 165 and 166.

Example 171: MS obsd (ESI+): 528.3 [M+H]+. Analytical chiral UPCC: (Column: CHIRALPAK IG-3 4.6*100 mm 3 um, Flow rate: 3.0 mL/min, Cosolvent:EtOH (1% 7M NH3 in MeOH), Temp 40° C.) Retention time=0.8 min Example 172: MS obsd (ESI+): 528.3 [M+H]+. Analytical chiral UPCC: (Column: CHIRALPAK IG-3 4.6*100 mm 3 um, Flow rate: 3.0 mL/min, Cosolvent:EtOH (1% 7M NH3 in MeOH), Temp 40° C.) Retention time=1.0 min Example 173: 1-(1-(difluoromethyl)cyclopropyl)-N-(1-(4-methoxy-3-(trifluoromethyl)phenyl)ethyl)-4-((1-methylpiperidin-4-yl)amino)-6-oxo-1,6-dihydropyridine-3-carboxamide example 173

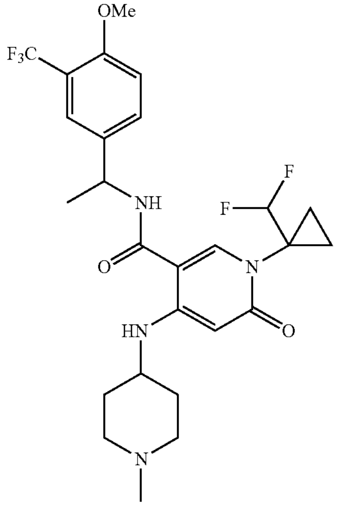

Example 173 was synthesized according to analogous procedures described in Example 165 and 166, steps B-D. MS obsd. ($ESI^+$): 543.3 $[(M+H)^+]$. $^1H$ NMR (400 MHz, DMSO-d6) δ ppm 8.72 (1H), 8.05 (1H), 7.96 (1H), 7.60 (2H), 7.25 (1H), 6.21 (1H), 5.22 (1H), 5.09 (1H), 3.87 (3H), 3.24 (1H), 2.53 (2H), 2.13 (3H), 2.08 (2H), 1.80 (2H), 1.46 (3H), 1.41-1.24 (6H).

Examples 174 and 175: N—((R)-1-(3-(difluoro (pyridin-4-yl)methyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Example 174) and N—((S)-1-(3-(difluoro (pyridin-4-yl) methyl)-2-fluorophenyl)ethyl)-1-(1-(difluoromethyl) cyclopropyl)-4-(((1R,5S,6s)-3-methyl-3-azabicyclo [3.1.0]hexan-6-yl)amino)-6-oxo-1,6-dihydropyridine-3-carboxamide (Example 175) (Stereoisomers are Unassigned)

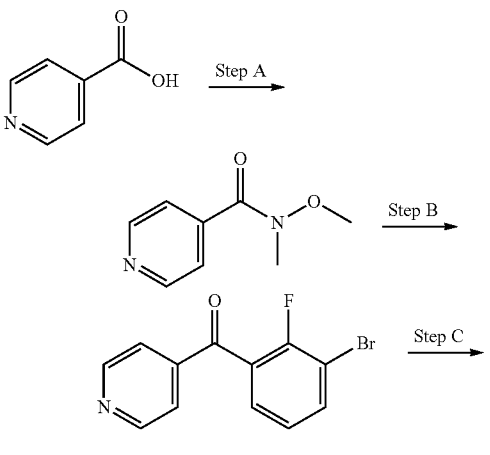

-continued

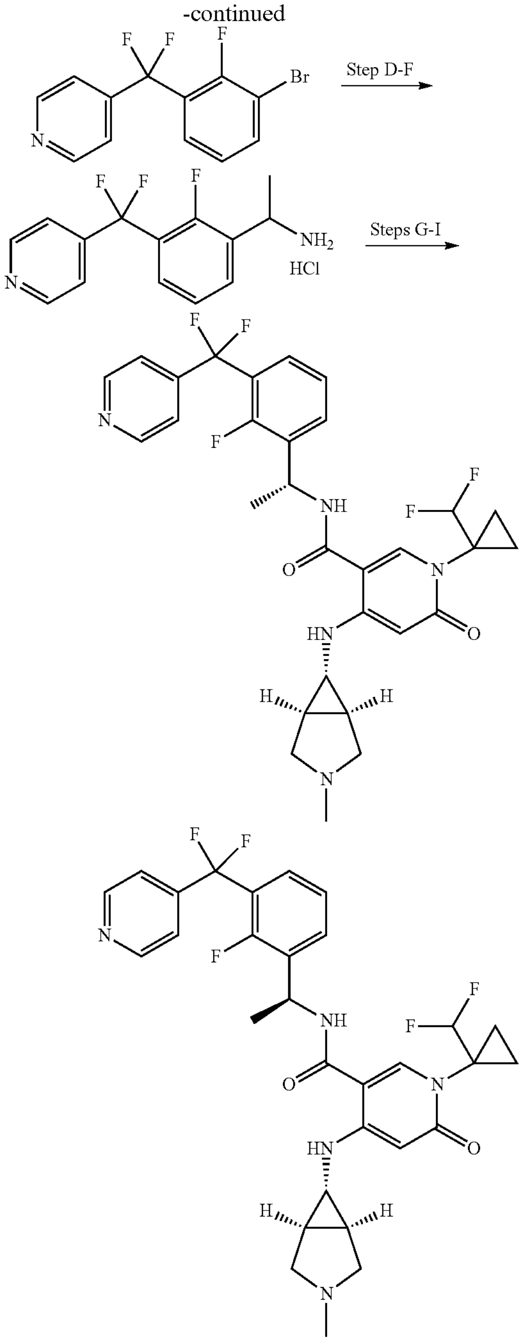

examples 174 and 175

Step A: N-methoxy-N-methylisonicotinamide

To a stirred solution of isonicotinic acid (30 g, 243.69 mmol) and N,O-dimethylhydroxylamine hydrochloride (26.15 g, 268.05 mmol) in DCM (500 mL) was added HATU (101.92 g, 268.05 mmol) and DIPEA (94.48 g, 731.06 mmol) dropwise at 0° C. The resulting mixture was stirred at r.t. overnight. The reaction was quenched with water (500 mL). The resulting mixture was extracted with $CHCl_3$/i-PrOH (3/1, 3×500 mL). The organic layers were combined, dried over anhydrous sodium sulfate, filtered and concentrated. The residue was purified by silica gel chromatography (0-100% EA/PE) to afford the title compound (30 g, 74% yield). MS obsd. (ESI$^+$): 167.10 [M+H]$^+$.

Step B: (3-bromo-2-fluorophenyl)(pyridin-4-yl)methanone

To a stirred solution of 1,3-dibromo-2-fluoro-benzene (38.20 g, 150.44 mmol, 1.0 eq.) in THF (1000 mL) was added n-Butyllithium (60.2 mL, 150.44 mmol, 2.5 M in THF) at −78° C. under $N_2$ atmosphere. The resulting solution was stirred for 15 min at −78° C., and then N-methoxy-N-methylisonicotinamide (25 g, 150.44 mmol) in THF was added dropwise at −78° C. under $N_2$ atmosphere. The resulting solution was stirred for 30 min at −78° C. The reaction was quenched with water (500 mL). The resulting mixture was extracted with ethyl acetate (3×1000 mL). The organic layers were combined, dried over anhydrous sodium sulfate, filtered and concentrated. The residue was purified by silica gel chromatography (0-30% EA/PE) to afford the title compound (25 g, 59% yield). MS obsd. (ESI$^+$): 279.85, 281.85 [M+H]$^+$ Step C: 4-((3-bromo-2-fluorophenyl)difluoromethyl)pyridine To a solution of (3-bromo-2-fluoro-phenyl)-(4-pyridyl) methanone (25 g, 89.26 mmol) in DCM (100 mL) was added DAST (122.00 g, 756.87 mmol) at 0° C. under $N_2$ atmosphere. The resulting mixture was stirred at r.t. for 48 h. The resulting mixture was poured into ice water (500 mL) slowly. The pH of the solution was adjusted to 6~7 with $NaHCO_3$. The resulting mixture was extracted with ethyl acetate (3×1000 mL). The organic layers were combined, dried over anhydrous sodium sulfate, filtered and concentrated. The residue obtained was purified by silica gel chromatography (0-30% EA/PE) to afford the title compound (16 g, 59% yield). MS obsd. (ESI$^+$): 301.85, 303.85 [M+H]$^+$ Steps D-F: 1-(3-(difluoro (pyridin-4-yl)methyl)-2-fluorophenyl)ethan-1-amine hydrochloride Steps D-F were performed via analogous procedures as described in examples 165 and 166 steps A-C starting with 4-((3-bromo-2-fluorophenyl)difluoromethyl)pyridine. MS obsd. (ESI$^+$): 267.15 [M+H]$^+$ Steps G-I: N—((R)-1-(3-(difluoro (pyridin-4-yl) methyl)-2-fluorophenyl)ethyl)-1-(1-(difluoromethyl) cyclopropyl)-4-(((1R,5S,6s)-3-methyl-3-azabicyclo [3.1.0]hexan-6-yl)amino)-6-oxo-1,6-dihydropyridine-3-carboxamide and N—((S)-1-(3-(difluoro (pyridin-4-yl)methyl)-2-fluorophenyl) ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Examples 174 and 175, Enantiomers are Unassigned)

Steps G-I were performed via analogous procedures as described in example 160 steps A-C, starting with 1-(3-(difluoro (pyridin-4-yl)methyl)-2-fluorophenyl)ethan-1-amine hydrochloride. The racemic mixture was purified by SFC Regis (R,R)Whelk-O1 (25*250 mm, 10 um), $CO_2$/EtOH [0.5% $NH_3$ (7M in MeOH)]=70/30 to afford the title compounds.

Example 174: MS obsd (ESI+): 588.4 [M+H]+. Analytical chiral UPCC: (Column: Regis (R,R)Whelk-O1 4.6*100 mm 3 um, Flow rate: 3.0 mL/min, Cosolvent:EtOH (1% 7M NH3 in MeOH), Temp 40° C.) Retention time=1.6 min Example 175: MS obsd (ESI+): 588.2 [M+H]+. Analytical chiral UPCC: (Column: Regis (R,R)Whelk-O1 4.6*100 mm 3 um, Flow rate: 3.0 mL/min, Cosolvent:EtOH (1% 7M NH3 in MeOH), Temp 40° C.) Retention time=1.9 min

Example 176: N-(1-(3-(difluoro (oxazol-4-yl) methyl)-2-fluorophenyl)ethyl)-1-(1-(difluoromethyl) cyclopropyl)-4-(((1R,5S,6s)-3-methyl-3-azabicyclo [3.1.0]hexan-6-yl)amino)-6-oxo-1,6-dihydropyridine-3-carboxamide

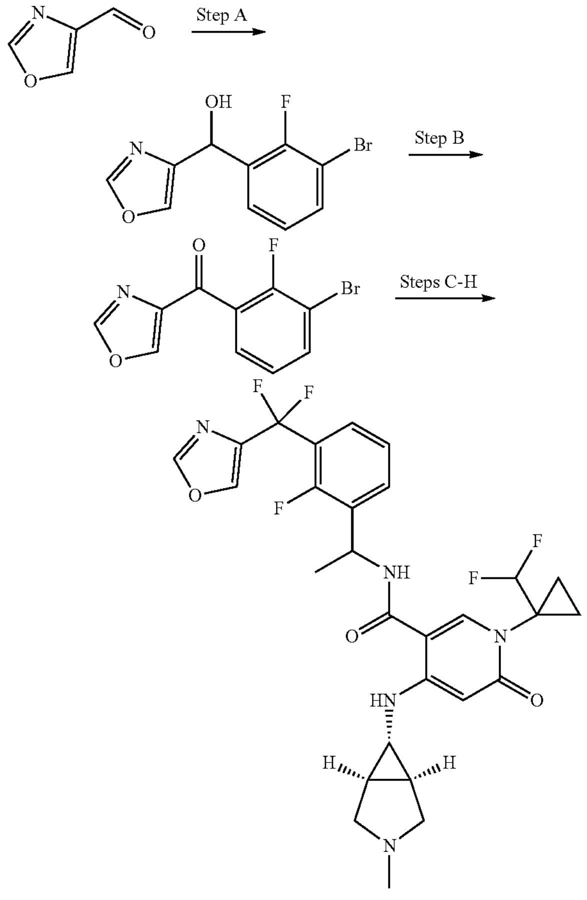

Example 176

Step A: (3-bromo-2-fluorophenyl)(oxazol-4-yl)methanol 1,3-dibromo-2-fluoro-benzene (23.80 g, 93.74 mmol) was dissolved in THF (1.5 mL). Then, n-Butyllithium (37.5 ml, 93.74 mmol, 2.5 M in THF,) was added to the mixture at −78° C. and stirred for 2 h. Oxazole-4-carbaldehyde (7 g, 72.11 mmol) was added to mixture at −78° C. and stirred for 4 h at room temperature. The reaction was quenched with $H_2O$ and then the mixture was extracted with EtOAc (2*150 mL). The combined organic extracts were washed with brine (100 mL) and dried over anhydrous $Na_2SO_4$. The crude product was purified by silica gel column chromatography (eluting with 1:3 EA/PE) to afford the title compound (5.5 g, 26% yield). MS obsd (ESI+): 271.85, 273.85 $[M+H]^+$.

Step B: (3-bromo-2-fluorophenyl)(oxazol-4-yl)methanone (3-bromo-2-fluoro-phenyl)-oxazol-4-yl-methanol (300 mg, 1.10 mmol) was dissolved in DCM (50 ml). Then Dess-Martin periodinane (1.17 g, 2.76 mmol) was added to the mixture and stirred for 24 h at 20° C. The reaction was quenched with water (50 mL) and then the mixture was extracted with EtOAc (2×150 mL). The combined organic extracts were washed with brine (100 mL), dried over anhydrous $Na_2SO_4$, and concentrated under vacuum. The residue was purified by silica gel column (PE:EA=11%) to afford the title compound (250 mg, 71% yield). MS obsd (ESI+): 269.80, 271.80 $[M+H]^+$.

Steps C—H: N-(1-(3-(difluoro (oxazol-4-yl) methyl)-2-fluorophenyl)ethyl)-1-(1-(difluoromethyl) cyclopropyl)-4-(((1R,5S,6s)-3-methyl-3-azabicyclo [3.1.0]hexan-6-yl)amino)-6-oxo-1,6-dihydropyridine-3-carboxamide (Example 176)

Example 176 was synthesized according to analogous procedures described in Examples 174 and 175 steps C-I starting with (3-bromo-2-fluorophenyl)(oxazol-4-yl)methanone. MS obsd (ESI+): 578.3 $[M+H]^+$. $^1$H NMR (400 MHz, DMSO-$d_6$) δ 8.79 (1H), 8.58 (1H), 8.55 (1H), 8.02 (1H), 7.95 (1H), 7.62 (1H), 7.52 (1H), 7.35 (1H), 6.23 (1H), 5.35 (1H), 5.24 (1H), 3.00 (2H), 2.48 (1H), 2.26 (2H), 2.19 (3H), 1.50 (2H), 1.44 (3H), 1.37-1.21 (4H).

Examples 177 and 178: 1-(bicyclo[1.1.1]pentan-1-yl)-N—((R)-1-(2-chloro-3-cyanophenyl)ethyl)-4-(((1R,5S,6s)-3-methyl-3-azabicyclo[3.1.0]hexan-6-yl)amino)-6-oxo-1,6-dihydropyridine-3-carboxamide (Example 177) and 1-(bicyclo[1.1.1]pentan-1-yl)-N—((S)-1-(2-chloro-3-cyanophenyl)ethyl)-4-(((1R, 5S,6s)-3-methyl-3-azabicyclo[3.1.0]hexan-6-yl) amino)-6-oxo-1,6-dihydropyridine-3-carboxamide (Example 178) (Stereoisomers not Assigned)

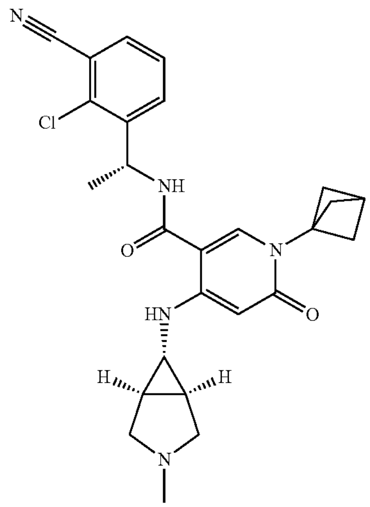

-continued

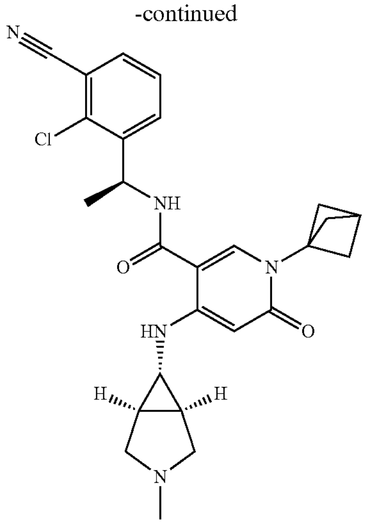

Examples 177 and 178

Examples 177 and 178 were synthesized according to analogous procedures described in example 161 starting with 3-bromo-2-chloro-benzonitrile and using racemic tert-butylsulfinamide. The racemic product was purified by SFC (Regis (R,R)Whelk-O1 (25×250 mm, 10 um), $CO_2$/MeOH [0.2% NH3 (7M in MeOH)]=60/40 to afford the title compounds.

Example 177: MS obsd (ESI+): 478.0 $[M+H]^+$. Analytical chiral UPCC: (Column: Regis (R,R)Whelk-O1 4.6*100 mm 3 um, Flow rate: 3.0 mL/min, Cosolvent: MeOH (0.2% 7M NH3 in MeOH), Temp 40° C.) Retention time=2.3 min Example 178: MS obsd (ESI+): 478.0 $[M+H]^+$. Analytical chiral UPCC: (Column: Regis (R,R)Whelk-O1 4.6*100 mm 3 um, Flow rate: 3.0 mL/min, Cosolvent: MeOH (0.2% 7M $NH_3$ in MeOH), Temp 40° C.) Retention time=1.4 min Example 179: 1-(bicyclo[1.1.1]pentan-1-yl)-N—((R)-1-(3-cyano-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide example 179

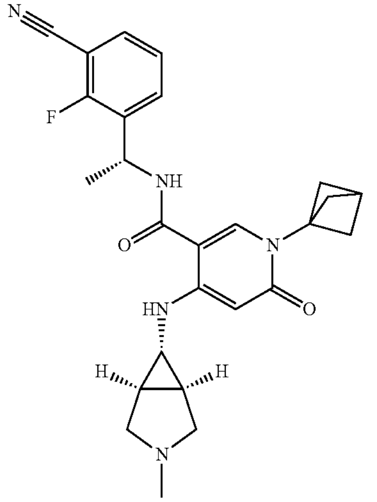

Example 179 was synthesized according to analogous procedures described in example 161 starting with 3-bromo-2-fluoro-benzonitrile. MS obsd (ESI+): 462.5 $[(M+H)^+]$. $^1$H NMR (400 MHz, DMSO-$d_6$) δ 8.94 (1H), 7.91-7.80 (3H), 7.76 (1H), 7.48 (1H), 5.35 (1H), 5.28 (1H), 3.11 (2H), 2.68 (1H), 2.55 (2H), 2.45 (2H), 2.36 (6H), 2.32 (2H), 1.61 (2H), 1.53 (3H).

Example 180: 1-(bicyclo[1.1.1]pentan-1-yl)-N—((R)-1-(2-chloro-3-(difluoromethoxy)phenyl)ethyl)-4-(((1R,5S,6s)-3-methyl-3-azabicyclo[3.1.0]hexan-6-yl)amino)-6-oxo-1,6-dihydropyridine-3-carboxamide example 180

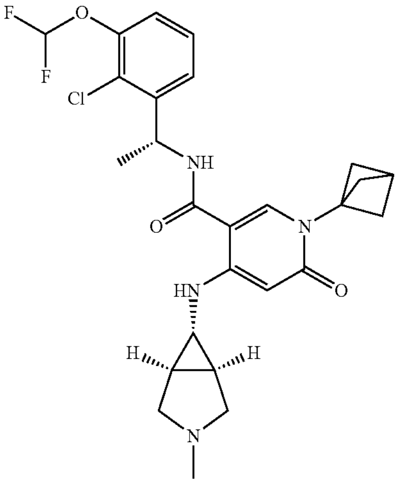

Example 180 was synthesized according to analogous procedures described in example 161 starting with 1-bromo-2-chloro-3-(difluoromethoxy)benzene. MS obsd (ESI+): 519.7, 521.7 $[(M+H)^+]$. $^1$H NMR (400 MHz, DMSO-$d_6$) δ 8.88 (1H), 7.78 (1H), 7.70 (1H), 7.50-7.11 (4H), 5.32 (2H), 3.00 (2H), 2.63 (1H), 2.46 (1H), 2.31 (6H), 2.27 (2H), 2.20 (3H), 1.50 (2H), 1.43 (3H).

Example 181: 1-(bicyclo[1.1.1]pentan-1-yl)-N—((R)-1-(3-cyano-2-methylphenyl)ethyl)-4-(((1R,5S,6s)-3-methyl-3-azabicyclo[3.1.0]hexan-6-yl)amino)-6-oxo-1,6-dihydropyridine-3-carboxamide example 181

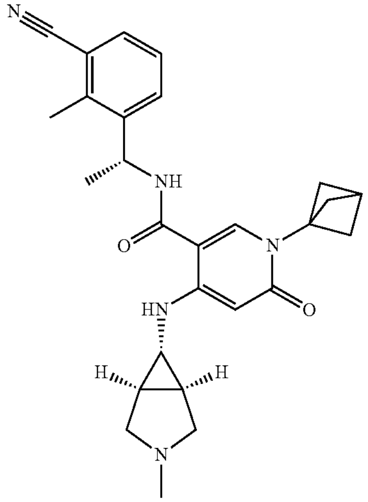

Example 181 was synthesized according to analogous procedures described in example 160 starting with (R)-3-(1-aminoethyl)-2-methylbenzonitrile. MS obsd (ESI+): 458.3 [(M+H)$^+$]. $^1$H NMR (400 MHz, DMSO-$d_6$) δ 8.84 (1H), 7.77 (1H), 7.73 (1H), 7.67 (2H), 7.41 (1H), 5.29 (1H), 5.18 (1H), 3.20 (2H), 2.70 (1H), 2.62 (1H), 2.54 (5H), 2.42 (2H), 2.29 (6H), 1.67 (2H), 1.41 (3H).

Example 182: (R)—N-(1-(3-(difluoromethyl)-2-fluorophenyl)ethyl)-1-(1-(difluoromethyl)cyclopropyl)-4-(((3-hydroxybicyclo[1.1.1]pentan-1-yl)methyl)amino)-6-oxo-1,6-dihydropyridine-3-carboxamide example 182

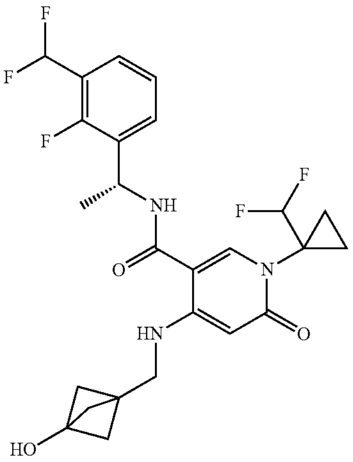

A mixture of (R)-5-((1-(3-(difluoromethyl)-2-fluorophenyl)ethyl)carbamoyl)-1-(1-(difluoromethyl)cyclopropyl)-2-oxo-1,2-dihydropyridin-4-yl trifluoromethanesulfonate (300 mg, 0.55 mmol), 3-(aminomethyl) bicyclo[1.1.1]pentan-1-ol; hydrochloride (122.7 mg, 0.82 mmol) and DIPEA (141 mg, 1.09 mmol) in DMSO (3 mL) was sealed in microwave tube and heated to 90° C. for 3 hours. The mixture was quenched with water, and extracted with EA (30 mL×3). The combined organic layers were washed with brine, dried over anhydrous $Na_2SO_4$ and concentrated in vacuo. The residue was purified by preparative TLC (100% EA) to afford the title compound (18.74 mg, 7% yield). MS obsd. (ESI$^+$): 512.5 [(M+H)$^+$]. $^1$H NMR (400 MHz, DMSO-$d_6$) δ: 8.81 (1H), 8.00 (1H), 7.92 (1H), 7.61 (1H), 7.53 (1H), 7.36 (1H), 7.22 (1H), 6.40-6.07 (2H), 5.31 (1H), 5.16 (1H), 3.18 (2H), 1.66 (6H), 1.49 (3H), 1.32 (4H).

Examples 183 and 184: N—((R)-1-(3-(difluoromethyl)-2-fluorophenyl)ethyl)-1-(1-(difluoromethyl)cyclopropyl)-6-oxo-4-(((S)-5,6,7,8-tetrahydroimidazo[1,5-a]pyridin-8-yl)amino)-1,6-dihydropyridine-3-carboxamide (Example 183) and N—((R)-1-(3-(difluoromethyl)-2-fluorophenyl)ethyl)-1-(1-(difluoromethyl)cyclopropyl)-6-oxo-4-(((R)-5,6,7,8-tetrahydroimidazo[1,5-a]pyridin-8-yl)amino)-1,6-dihydropyridine-3-carboxamide (Example 184) (Diastereomers not Assigned)

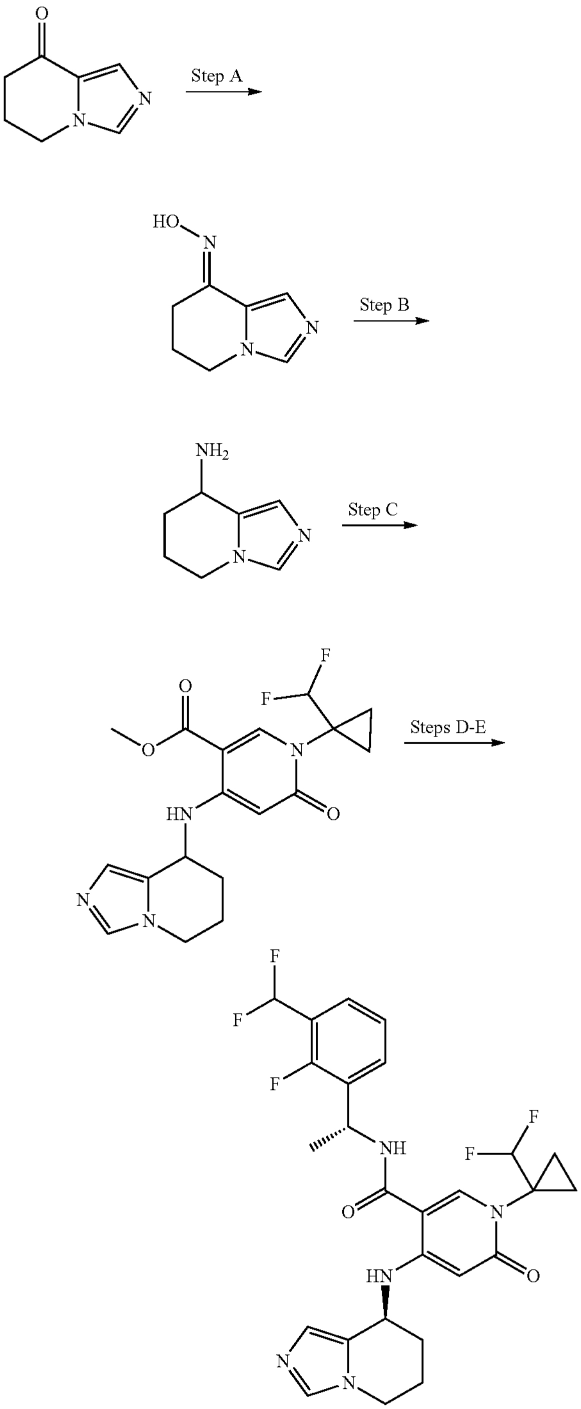

-continued

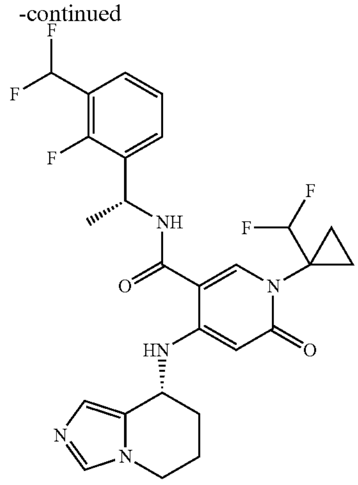

example 183 and 184

Example 183 and 184

Step A: 6,7-dihydroimidazo[1,5-a]pyridin-8 (5H)-one oxime

A mixture of 6,7-dihydro-5H-imidazo[1,5-a]pyridin-8-one (110 mg, 0.8 mmol), Hydroxylamine hydrochloride (62 mg, 0.88 mmol) and pyridine (192 mg, 2.42 mmol) in ethanol (2 mL) was stirred at 70° C. for 16 hr. The reaction mixture was concentrated under vacuum. The residue was purified by silica gel chromatography (0-15% MeOH in DCM) to afford the title compound (80 mg, 65% yield). MS obsd. ($ESI^+$): 152.2 [(M+H)+].

Step B: 5,6,7,8-tetrahydroimidazo[1,5-a]pyridin-8-amine

To a mixture of 6,7-dihydro-5H-imidazo[1,5-a]pyridin-8-one oxime (80 mg, 0.53 mmol) in EtOH (15 mL) was added Raney-Ni (500 mg wet, 0.53 mmol). The resulting mixture was stirred under an $H_2$ atmosphere for 2 hrs at rt. The mixture was filtered and the filtrate was concentrated in vacuo to afford the title compound (100 mg, crude). MS obsd. ($ESI^+$): 138.2 $[M+H]^+$ Step C: methyl 1-(1-(difluoromethyl)cyclopropyl)-6-oxo-4-((5,6,7,8-tetrahydroimidazo[1,5-a]pyridin-8-yl)amino)-1,6-dihydropyridine-3-carboxylate A mixture of methyl 1-(1-(difluoromethyl)cyclopropyl)-6-oxo-4-(((trifluoromethyl)sulfonyl)oxy)-1,6-dihydropyridine-3-carboxylate (160 mg, 0.41 mmol), 5,6,7,8-tetrahydroimidazo[1,5-a]pyridin-8-amine (84 mg, 0.61 mmol) and N,N-Diisopropylethylamine (158 mg, 1.23 mmol) in DMSO (3 mL) was stirred at 90° C. for 3 hr. The mixture was diluted with EtOAc (120 mL) and washed with water (80 mL×3). The organic phase was dried over sodium sulfate, filtered and concentrated. The residue was purified by column chromatography (EA/PE=1:1) to afford the title compound (55 mg, 35% yield). MS obsd. ($ESI^+$): 379.4 $[M+H]^+$ Steps D-E: N—((R)-1-(3-(difluoromethyl)-2-fluorophenyl)ethyl)-1-(1-(difluoromethyl)cyclopropyl)-6-oxo-4-(((S)-5,6,7,8-tetrahydroimidazo[1,5-a]pyridin-8-yl)amino)-1,6-dihydropyridine-3-carboxamide and N—((R)-1-(3-(difluoromethyl)-2-fluorophenyl)ethyl)-1-(1-(difluoromethyl)cyclopropyl)-6-oxo-4-(((R)-5,6,7,8-tetrahydroimidazo[1,5-a]pyridin-8-yl)amino)-1,6-dihydropyridine-3-carboxamide (Diastereomers not Assigned)

Synthesized in an analogous manner to example 49 steps D-E. The diastereomers were further purified by SFC (Regis (R,R)Whelk-O1 (25*250 mm, 10 um), CO2/MeOH [0.2% NH3 (7M in MeOH)]=60/40) to afford the title compounds.

Example 183: MS obsd (ESI+): 536.5 $[M+H]^+$. Analytical chiral UPCC: (Column: Regis (R,R)Whelk-O1 4.6*100 mm 3 um, Flow rate: 3.0 mL/min, Cosolvent: MeOH (0.2% 7M NH3 in MeOH), Temp 40° C.) Retention time=2.7 min Example 184: MS obsd (ESI+): 536.4 $[M+H]^+$. Analytical chiral UPCC: (Column: Regis (R,R)Whelk-O1 4.6*100 mm 3 um, Flow rate: 3.0 mL/min, Cosolvent: MeOH (0.2% 7M NH3 in MeOH), Temp 40° C.) Retention time=1.5 min Example 185: (R)—N-(1-(3-(difluoromethyl)-2-fluorophenyl)ethyl)-1-(1-(difluoromethyl)cyclopropyl)-4-(((3-fluoro-1-methylazetidin-3-yl)methyl)amino)-6-oxo-1,6-dihydropyridine-3-carboxamide example 185

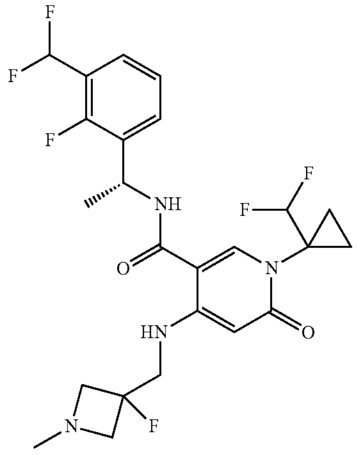

Example 185 was synthesized according to analogous procedures described in example 55. MS obsd. ($ESI^+$): 517.2 $[(M+H)^+]$. $^1H$ NMR (400 MHz, DMSO-$d_6$) δ: 8.84 (1H), 8.24 (1H), 8.06 (1H), 7.61 (1H), 7.53 (1H), 7.35 (1H), 7.21 (1H), 6.24 (1H), 5.36 (1H), 5.30 (1H), 3.51 (1H), 3.45 (1H), 3.36 (2H), 3.08 (1H), 3.02 (1H), 2.27 (3H), 1.48 (3H), 1.35 (4H).

Examples 186 and 187: N—((R)-1-(3-(difluoromethyl)-2-fluorophenyl)ethyl)-1-(1-(difluoromethyl)cyclopropyl)-4-(((S)-4-fluoroquinuclidin-3-yl)amino)-6-oxo-1,6-dihydropyridine-3-carboxamide (Example 186) and N—((R)-1-(3-(difluoromethyl)-2-fluorophenyl)ethyl)-1-(1-(difluoromethyl)cyclopropyl)-4-(((R)-4-fluoroquinuclidin-3-yl)amino)-6-oxo-1,6-dihydropyridine-3-carboxamide (Example 187)

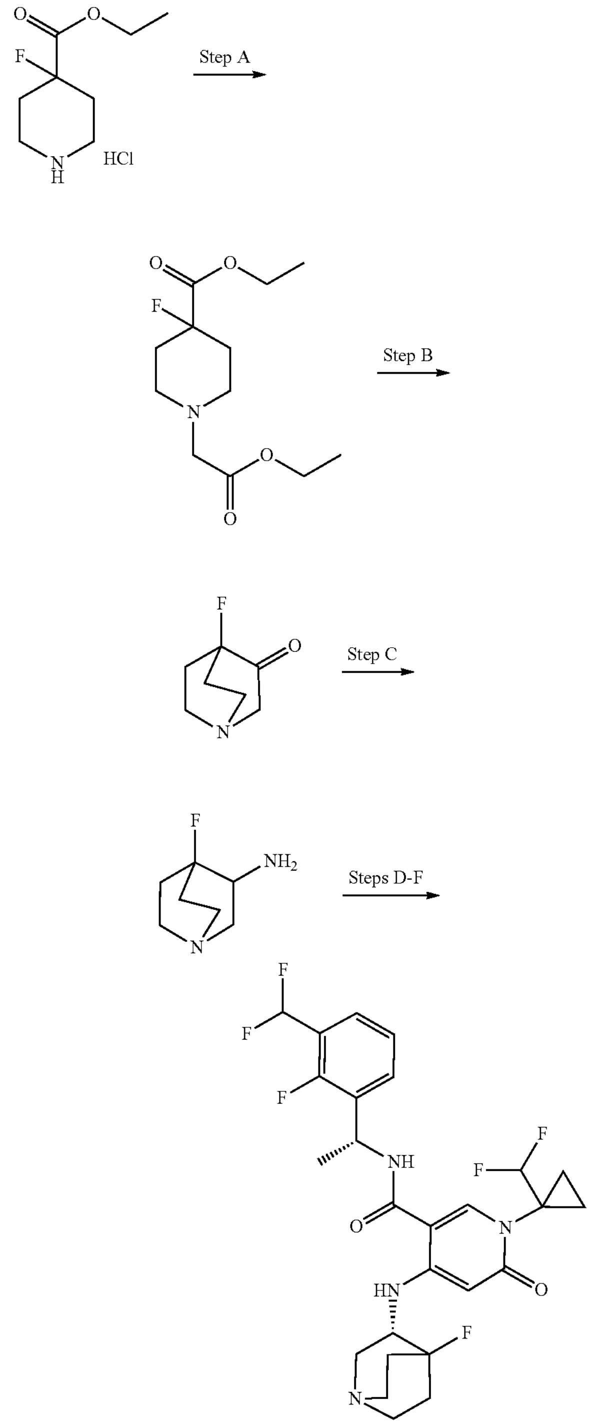

-continued

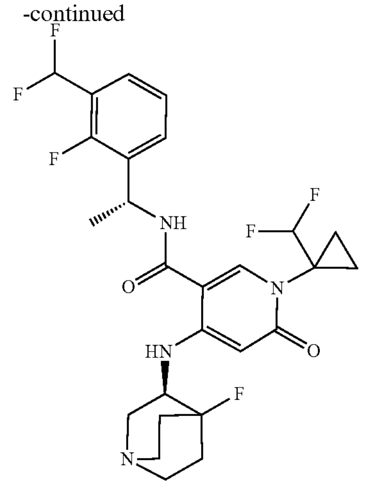

Examples 186 and 187

Step A: Ethyl 1-(2-ethoxy-2-oxoethyl)-4-fluoropiperidine-4-carboxylate

Ethyl 4-fluoropiperidin-1-ium-4-carboxylate; chloride (2 g, 9.45 mmol) and cesium carbonate (9.2 g, 28.35 mmol) were dissolved in THF (30 mL) at rt. Ethyl 2-bromoacetate (2.4 g, 14.17 mmol, 1.6 mL) was added. The mixture was stirred at 70° C. for 16 hrs. The reaction mixture was cooled to room temperature, filtered, and the solvent was concentrated. The crude residue was purified by flash chromatography column (eluted with EA in PE (10-20%)) to obtain the title compound (2.4 g, 97% yield). MS obsd. ($ESI^+$): 262.2 $[(M+H)^+]$.

Step B: 4-Fluoroquinuclidin-3-one

Ethyl 1-(2-ethoxy-2-oxoethyl)-4-fluoropiperidine-4-carboxylate (2.4 g, 9.19 mmol) was dissolved in toluene (50 mL) and potassium t-butoxide (2.6 g, 22.96 mmol) was added. The mixture was stirred at 110° C. for 5 hrs. The mixture was cooled and extracted by concentrated HCl (50 mL). The aqueous extract was heated to 110° C. for 16 hrs to effect decarboxylation. The obtained solution was cooled to room temperature and basified to pH=13, and extracted by $CH_2Cl_2$ (3× 50 mL). The combined organic layers were dried over $Na_2SO_4$, filtered and concentrated to afford the title compound (600 mg, 45% yield). $^1H$ NMR (400 MHz, DMSO-$d_6$) δ:3.38 (2H), 3.08 (4H), 2.17-2.00 (4H).

Step C: 4-Fluoroquinuclidin-3-amine 4-fluoroquinuclidin-3-one (500 mg, 3.49 mmol) was dissolved in ammonia (7 M in MeOH, 15 mL), and the mixture was stirred at 70° C. for 16 hrs. The solution was cooled to room temperature and Pd/C (424 mg, 3.49 mmol) was added. The reaction solution was stirred at RT under $H_2$ atmosphere for 2 hrs. The mixture was cooled to room temperature and filtered. The mixture was diluted with water and extracted into DCM. The organic phase was washed with brine, dried with $Na_2SO_4$, and concentrated under reduced pressure to obtain the title compound (300 mg, crude). $^1H$ NMR (400 MHz, CDC13) δ: 3.38-3.28 (1H), 3.16 (1H), 3.10-2.96 (4H), 2.51 (1H), 2.20 (1H), 1.87 (1H), 1.69-1.53 (4H).

Steps D-F: N—((R)-1-(3-(difluoromethyl)-2-fluorophenyl)ethyl)-1-(1-(difluoromethyl)cyclopropyl)-4-(((S)-4-fluoroquinuclidin-3-yl)amino)-6-oxo-1,6-dihydropyridine-3-carboxamide and N—((R)-1-(3-(difluoromethyl)-2-fluorophenyl)ethyl)-1-(1-(difluoromethyl)cyclopropyl)-4-(((R)-4-fluoroquinuclidin-3-yl)amino)-6-oxo-1,6-dihydropyridine-3-carboxamide Steps D-F were synthesized according to analogous procedures described in example 49 steps C-E. The diastereomeric mixture was purified by chiral SFC: Daicel AD (25*250 mm, 10 um)), $CO_2$/EtOH [0.5% $NH_3$ (7M in MeOH)]=80/20 to afford the unassigned title compounds.

Example 186: MS obsd (ESI+): 543.4 $[M+H]^+$. Analytical chiral UPCC: (Column: CHIRALPAK IG-3 4.6*100 mm 3 um, Flow rate: 3.0 mL/min, Cosolvent:EtOH (1% 7M NH3 in MeOH), Temp 40° C.) Retention time=1.2 min Example 187: MS obsd (ESI+): 543.4 $[M+H]^+$. Analytical chiral UPCC: (Column: CHIRALPAK IG-3 4.6*100 mm 3 um, Flow rate: 3.0 mL/min, Cosolvent:EtOH (1% 7M NH3 in MeOH), Temp 40° C.) Retention time=1.7 min Example 188: N—((R)-1-(3-(difluoromethyl)-2-fluorophenyl)ethyl)-1-(1-(difluoromethyl)cyclopropyl)-4-((((S)-1-methylpyrrolidin-2-yl)methyl)amino)-6-oxo-1,6-dihydropyridine-3-carboxamide example 188

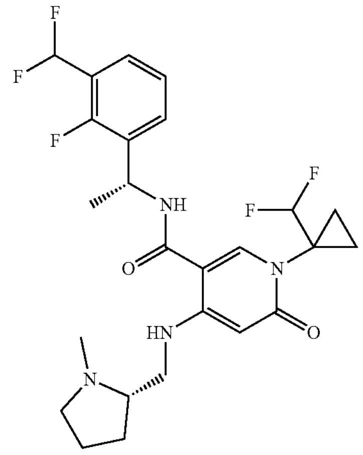

Example 188 was synthesized according to analogous procedures described in example 55. MS obsd. $(ESI^+)$: 513.4. $^1H$ NMR (400 MHz, DMSO-$d_6$) δ 8.76 (1H), 8.15 (1H), 7.98 (2H), 7.61 (1H), 7.53 (1H), 7.35 (1H), 7.15 (1H), 6.23 (1H), 5.30 (1H), 5.20 (1H), 3.09 (1H), 2.99 (2H), 2.42 (1H), 2.22 (3H), 2.15 (1H), 1.85 (1H), 1.69-1.57 (2H), 1.48 (4H), 1.34 (4H).

Example 189: (R)-4-((3-aminobicyclo[1.1.1]pentan-1-yl)amino)-1-(bicyclo[1.1.1]pentan-1-yl)-N-(1-(3-(difluoromethyl)-2-fluorophenyl)ethyl)-6-oxo-1,6-dihydropyridine-3-carboxamide example 189

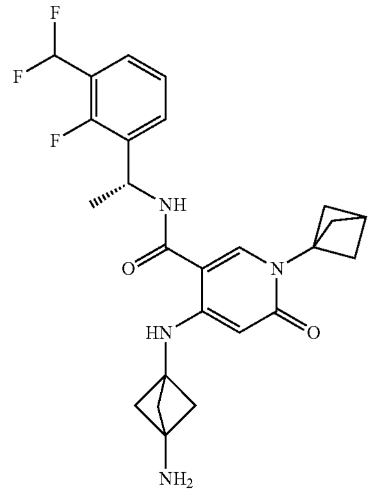

Example 189 was synthesized according to analogous procedures described in example 89. MS obsd. (ESI+): 473.3. $^1H$ NMR (400 MHz, DMSO-$d_6$) δ: 9.21 (1H), 8.24 (1H), 7.90 (1H), 7.70 (1H), 7.52 (1H), 7.36 (1H), 7.21 (1H), 5.34-5.23 (2H), 2.96 (2H), 2.61 (1H), 2.31 (6H), 1.97 (6H), 1.48 (3H).

Example 190: (R)-4-amino-1-(bicyclo[1.1.1]pentan-1-yl)-N-(1-(3-(difluoromethyl)-2-fluorophenyl)ethyl)-6-oxo-1,6-dihydropyridine-3-carboxamide

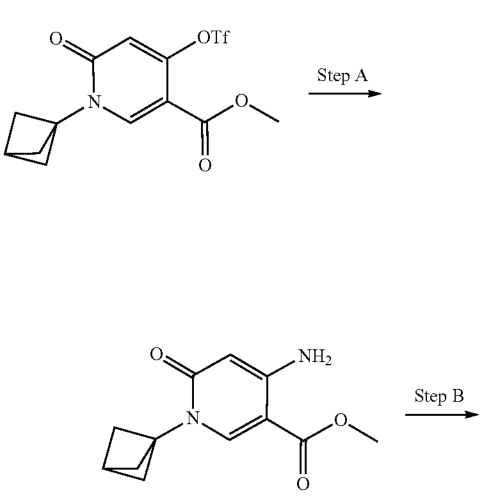

-continued

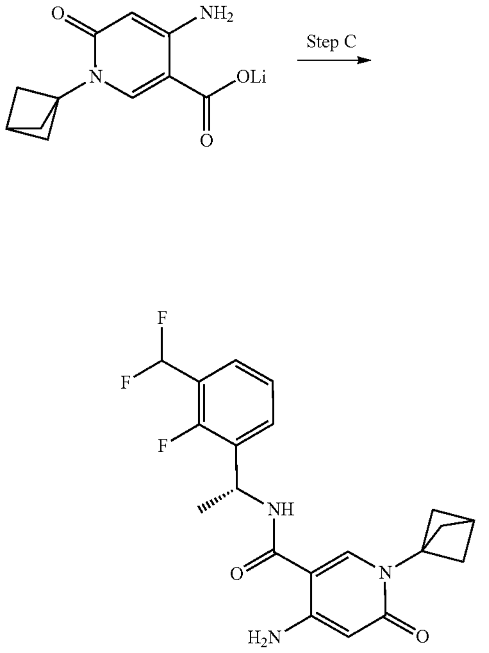

Example 190

Step A: Methyl 4-amino-1-(bicyclo[1.1.1]pentan-1-yl)-6-oxo-1,6-dihydropyridine-3-carboxylate A mixture of (R)—N-(1-(3-(difluoromethyl)-2-fluorophenyl)ethyl)-4-((1-methylpiperidin-4-yl)amino)-6-(1-(tetrahydro-2H-pyran-4-yl)-1H-pyrazol-5-yl) nicotinamide (200 mg, 0.54 mmol) and ammonia (0.4 M in dioxane, 14 mL) was reacted at 90° C. for 30 hrs. The reaction was quenched by water. The mixture was extracted with EtOAc (50 mL×3). The combined organic layers were washed with brine (50 mL×2), dried over sodium sulfate, filtered and concentrated. Purification by flash chromatography (eluting with 0-80% EtOAc in PE) afforded the title compound. MS obsd. (ESI$^+$): 235.3

Step B: lithium 4-amino-1-(bicyclo[1.1.1]pentan-1-yl)-6-oxo-1,6-dihydropyridine-3-carboxylate A mixture of methyl 4-amino-1-(bicyclo[1.1.1]pentan-1-yl)-6-oxo-1,6-dihydropyridine-3-carboxylate (110 mg, 469.58 μmol) and lithium hydroxide (34 mg, 1.41 mmol) was stirred in the mixture of THF (5 mL) and $H_2O$ (5 mL) at rt for 6 hrs. The reaction mixture was concentrated to afford the crude title compound (150 mg, crude), which is used without further purification. MS obsd. (ESI$^+$): 221.3

Step C: (R)-4-amino-1-(bicyclo[1.1.1]pentan-1-yl)-N-(1-(3-(difluoromethyl)-2-fluorophenyl)ethyl)-6-oxo-1,6-dihydropyridine-3-carboxamide To a solution of lithium 4-amino-1-(bicyclo[1.1.1]pentan-1-yl)-6-oxo-1,6-dihydropyridine-3-carboxylate (130 mg, crude), (1R)-1-[3-(difluoromethyl)-2-fluoro-phenyl]ethanamine; hydrochloride (169 mg, 0.74 mmol) and DIPEA (223 mg, 1.72 mmol) in DMF (5 mL) was added HATU (262 mg, 0.69 mmol) at rt. The solution was stirred for 2 hrs at rt. The reaction was quenched by water. The aqueous layer was separated and extracted with EtOAc (50 mL×3). The combined organic layers were washed with brine (50 mL×2), dried over $Na_2SO_4$, filtered and concentrated. The residue was purified by flash chromatography (eluting with 0-10% MeOH in DCM) followed by preparative HPLC (mobile phase: ACN-$H_2O$ (10 mm $NH_4HCO_3$); Gradient: 40-55%) to afford the title compound (184 mg). MS obsd. (ESI$^+$): 392.6 $[M+H]^+$. $^1H$ NMR (400 MHz, DMSO-$d_6$) δ: 8.78 (1H), 7.71 (1H), 7.62 (1H), 7.53 (1H), 7.36 (1H), 7.22 (1H), 6.71 (2H), 5.29 (1H), 5.22 (1H), 2.61 (1H), 2.29 (6H), 1.47 (3H).

Example 191: N—((R)-1-(3-(difluoromethyl)-2-fluorophenyl)ethyl)-1-(1-(difluoromethyl)cyclopropyl)-4-((1-(1-(hydroxymethyl)cyclopropyl)ethyl)amino)-6-oxo-1,6-dihydropyridine-3-carboxamide example 191

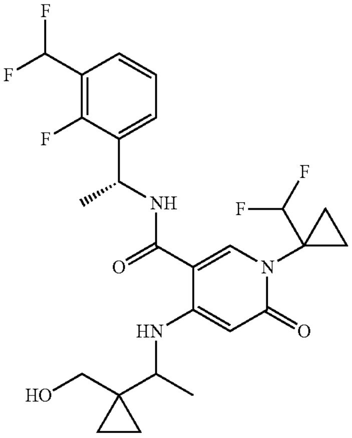

Example 191 was synthesized according to analogous procedures described in example 49. MS obsd. (ESI$^+$): 514.2 $[M+H]^+$. $^1H$ NMR (400 MHz, DMSO-$d_6$) δ 8.76 (1H), 8.08 (1H), 7.99 (1H), 7.61 (1H), 7.53 (1H), 7.36 (1H), 7.22 (1H), 6.24 (1H), 5.30 (1H), 5.23 (1H), 4.70 (1H), 3.48-3.35 (2H), 3.17 (1H), 1.48 (3H), 1.34 (4H), 1.07 (3H), 0.38-0.24 (4H).

The following examples may be synthesized according to analogous methods described for example 49 or examples 92-154 using appropriate reagent substitutions with known or commercial reagents:

| Example number | Compound Structure | Compound Name | Characterization |
|---|---|---|---|
| 192 | 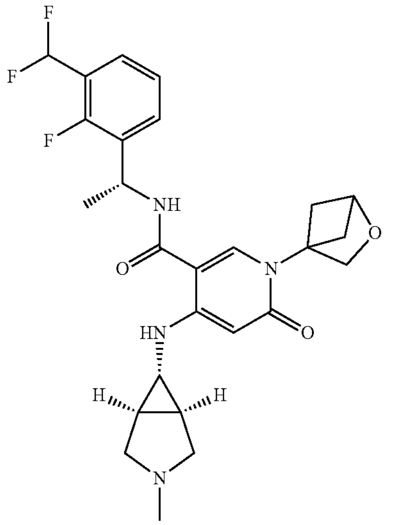 [SMILES: C[C@@H](NC(=O)c1cn(C23COC(C2)C3)c(=O)cc1N[C@H]1[C@@H]2CN(C)C[C@@H]21)c1cccc(C(F)F)c1F] | 1-(2-oxabicyclo[2.1.1]hexan-4-yl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd. ($ESI^+$): 503.3 $[(M + H)^+]$. 1H NMR (400 MHz, DMSO-$d_6$) δ: 8.77 (1H). 7.80 (1H), 7.73 (1H), 7.59 (1H), 7.52 (1H), 7.35 (1H), 7.21 (1H), 5.33 (1H), 5.26 (1H), 4.57 (1H), 3.76 (2H), 3.00 (2H), 2.48 (1H), 2.27 (2H), 2.23 (2H), 2.20 (3H), 2.13 (2H), 1.52 (2H), 1.46 (3H). |
| 193 and 194 | 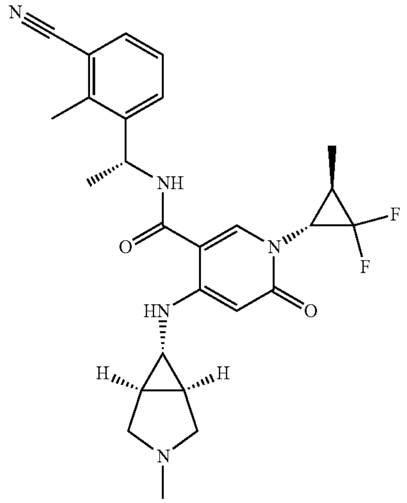 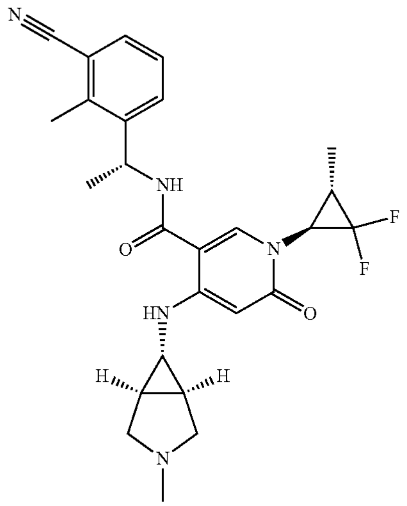 | N-((R)-1-(3-cyano-2-methylphenyl)ethyl)-1-((1R,3R)-2,2-difluoro-3-methyleyclopropyl)-4-(((1R,5S,6s)-3-methyl-3-azabicyclo[3.1.0]hexan-6-yl)amino)-6-oxo-1,6-dihydropyridine-3-carboxamide and N-((R)-1-(3-cyano-2-methylphenyl)ethyl)-1-((1S,3S)-2,2-difluoro-3-methyleyclopropyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 193: MS obsd (ESI+): 482.3 $[M +H]^+$. Analytical UPCC: Cellulose-SC 4.6 * 100 mm 3 um, Flow rate: 3.0 mL/min, Cosolvent: MeOH(0.2% 7M NH3 in MeOH), Temp 40° C.) Retention time = 1.5 min Example 194; MS obsd (ESI+): 482.3 $[M + H]^+$. Analytical UPCC: Cellulose-SC 4.6 * 100 mm 3 um, Flow rate: 3.0 mL/min, Cosolvent: MeOH(0.2% 7M NH3 in MeOH), Temp 40° C.) Retention time = 2.0 min |

-continued

| Example number | Compound Structure | Compound Name | Characterization |
|---|---|---|---|
| 195 and 196 | 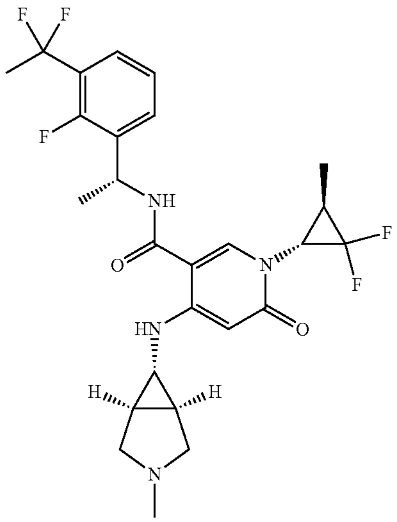 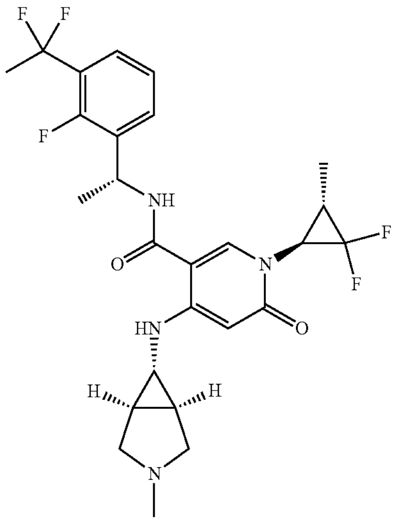 | 1-((1R,3R)-2,2-difluoro-3-methylcyclopropyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((1S,3S)-2,2-difluoro-3-methylcyclopropyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 195: MS obsd (ESI+): 525.8 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.6 min Example 196: MS obsd (ESI+): 525.8 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.0 min |

-continued

| Example number | Compound Structure | Compound Name | Characterization |
| --- | --- | --- | --- |
| 197 and 198 | 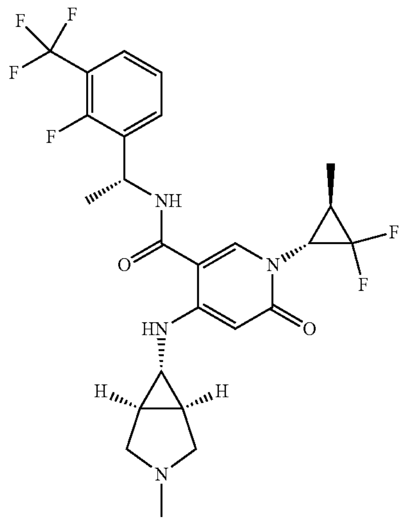 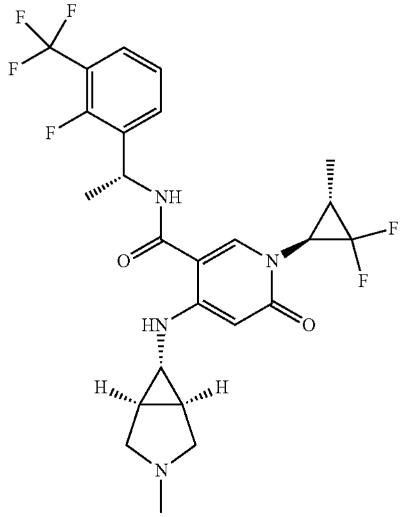 | 1-((1R,3R)-2,2-difluoro-3-methyleyclopropyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide and 1-((1S,3S)-2,2-difluoro-3-methyleyclopropyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 197; MS obsd (ESI+): 529.0 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.0 min Example 198 MS obsd (ESI+): 529.0 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.6 min |

-continued

| Example number | Compound Structure | Compound Name | Characterization |
|---|---|---|---|
| 199 and 200 | 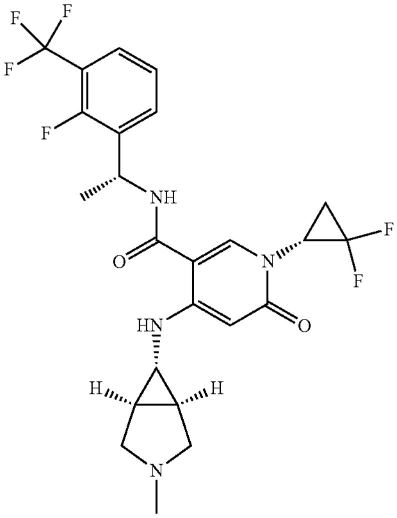 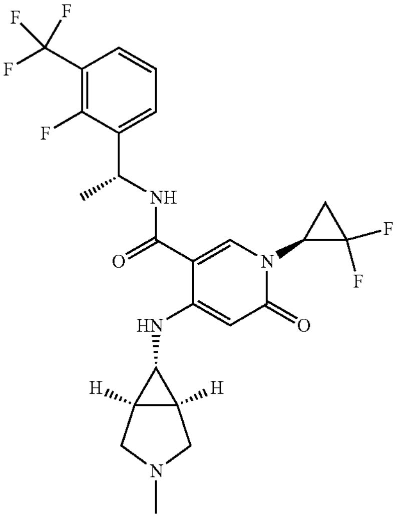 | 1-((R)-2,2-difluorocyclopropyl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide and 1-((S)-2,2-difluorocyclopropyl)-N-((R)-1-(2-fluoro-3-(trifluoromethyl)phenyl) ethyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 199; MS obsd (ESI+): 515.5 $[M + H]^+$. Analytical chiral UPCC: (Column: CHIRALPAK AD-3 4.6 * 100 mm 3 um, Flow rate: 3.0 mL/min, Cosolvent: EtOH(1% 7M NH3 in MeOH), Temp 40° C.) Retention time = 0.7 min Example 200: MS obsd (ESI+): 515.5 $[M + H]^+$. Analytical chiral UPCC: (Column: CHIRALPAK AD-3 4.6 * 100 mm 3 um, Flow rate: 3.0 mL/min, Cosolvent: EtOH(1% 7M NH3 in MeOH), Temp 40° C.) Retention time = 1.3 min |

-continued

| Example number | Compound Structure | Compound Name | Characterization |
| --- | --- | --- | --- |
| 201 and 202 | 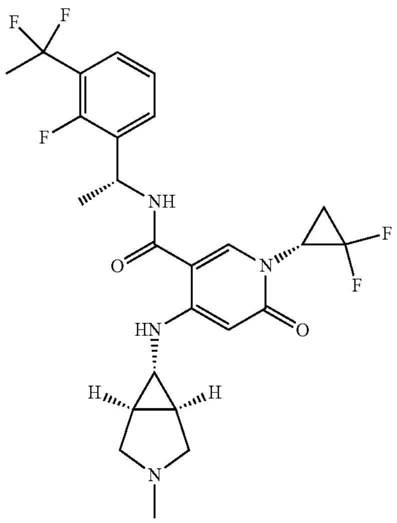 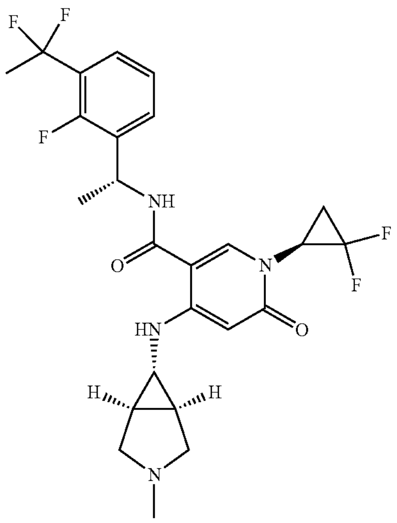 | 1-((R)-2,2-difluorocyclopropyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((S)-2,2-difluorocyclopropyl)-N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 201: MS obsd (ESI+): 511.4 $[M + H]^+$. Analytical chiral UPCC: (Column: CHIRALPAK AD-3 4.6 * 100 mm 3 um, Flow rate: 3.0 mL/min, Cosolvent: EtOH(1% 7M NH3 in MeOH), Temp 40° C.) Retention time = 0.8 min Example 202 MS obsd (ESH+): 511.4 $[M + H]^+$. Analytical chiral UPCC: (Column: CHIRALPAK AD-3 4.6 * 100 mm 3 um, Flow rate: 3.0 mL/min, Cosolvent: EtOH(1% 7M NH3 in MeOH), Temp 40° C.) Retention time = 1.4 min |

-continued

| Example number | Compound Structure | Compound Name | Characterization |
|---|---|---|---|
| 203 and 204 | 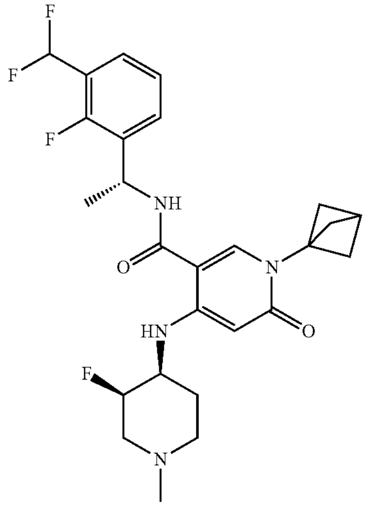 | 1-(bicyclo[1.1.1]pentan-1-yl)-N-((R)-1-(3-(difluoromethyl)-2-fluorophenyl)ethyl)-4-(((3R,4S)-3-fluoro-1-methylpiperidin-4-yl)amino)-6-oxo-1,6-dihydropyridine-3-carboxamide and 1-(bicyclo[1.1.1]pentan-1-yl)-N-((R)-1-(3-(difluoromethyl)-2-fluorophenyl)ethyl)-4-(((3S,4R)-3-fluoro-1-methylpiperidin-4-yl)amino)-6-oxo-1,6-dihydropyridine-3-carboxamide (diastereomers unassigned) | Example 203: MS obsd (ESI+): 507.4 $[M + H]^+$. Analytical chiral UPCC: (Column: CHIRALPAK AS-3 4.6 * 100 mm 3 um, Flow rate: 3.0 mL/min, Cosolvent: EtOH(1% 7M NH3 in MeOH), Temp 40° C.) Retention time = 1.6 min Example 204: MS obsd (ESI+): 507.4 Analytical chiral UPCC: (Column: CHIRALPAK AS-3 4.6 * 100 mm 3 um, Flow rate: 3.0 mL/min, Cosolvent: EtOH(1% 7M NH3 in MeOH), Temp 40° C.) Retention time = 2.3 min |
| | 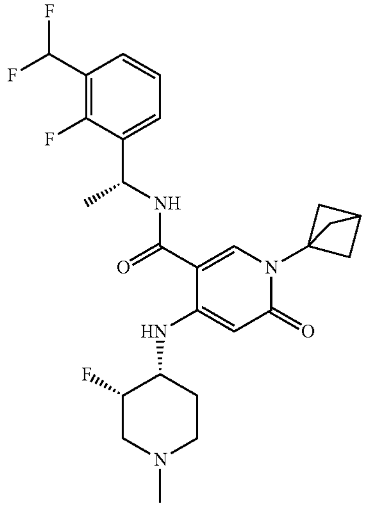 | | |
| 205 | 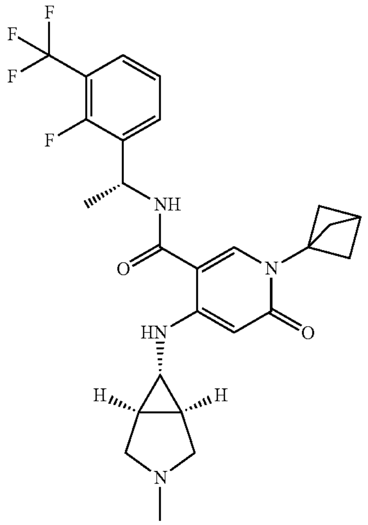 [SMILES: C[C@@H](NC(=O)c1cn(C23CC(C2)C3)c(=O)cc1N[C@H]1[C@@H]2CN(C)C[C@@H]21)c1cccc(C(F)(F)F)c1F] | 1-(bicyclo[1.1.1]pentan-1-yl)-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide | MS obsd. $(ESI^+)$: 505.7 $[(M + H)^+]$. $^1H$ NMR (400 MHz, $DMSO-d_6$) δ 8.95 (1H), 7.82 (2H), 7.74 (2H), 7.48 (1H), 5.33 (2H), 3.09 (2H), 2.69 (1H), 2.54 (1H), 2.38 (1H), 2.36 (6H), 2.30 (3H), 1.58 (2H), 1.54 (3H). |

-continued

| Example number | Compound Structure | Compound Name | Characterization |
|---|---|---|---|
| 206 | 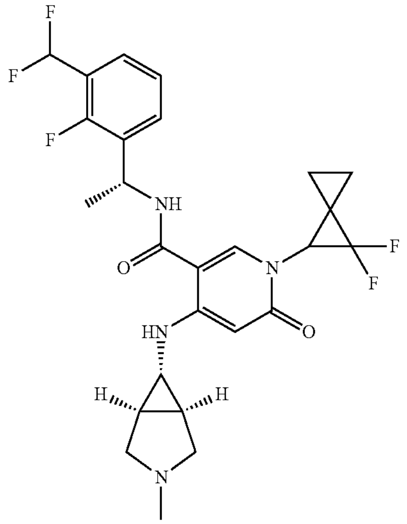 [SMILES: C[C@@H](NC(=O)c1cn(C2C(F)(F)C23CC3)c(=O)cc1N[C@H]1[C@@H]2CN(C)C[C@@H]21)c1cccc(C(F)F)c1F] | N-((R)-1-(3-(difluoromethyl)-2-fluorophenyl)ethyl)-1-(2,2-difluorospiro[2.2]pentan-1-yl)-4-(((1R,5S,6s)-3-methyl-3-azabicyclo[3.1.0]hexan-6-yl)amino)-6-oxo-1,6-dihydropyridine-3-carboxamide | MS obsd. (ESI$^+$): 523.3 [(M + H)$^+$]. $^1$H NMR (400 MHz, DMSO-d$_6$) δ 9.19 (1H), 8.26 (1H), 7.94 (1H), 7.69 (1H), 7.51 (1H), 7.35 (1H), 7.20 (1H), 5.38 (1H), 5.28 (1H), 4.22 (1H), 3.32 (1H), 3.01 (2H), 2.53 (2H), 2.22 (3H), 1.74 (1H), 1.62-1.44 (6H), 1.31 (2H). |
| 207 | 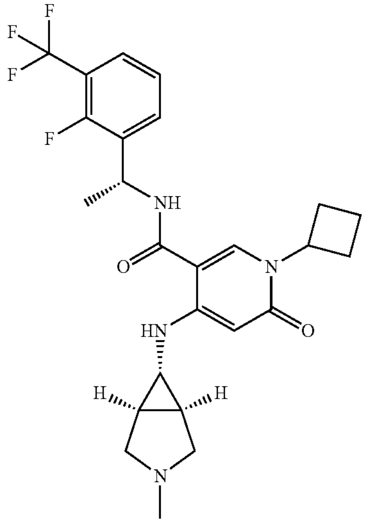 [SMILES: C[C@@H](NC(=O)c1cn(C2CCC2)c(=O)cc1N[C@H]1[C@@H]2CN(C)C[C@@H]21)c1cccc(C(F)(F)F)c1F] | 1-cyclobutyl-N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide | MS obsd. (ESI$^+$): 493.3 [(M + H)$^+$]. $^1$H NMR (400 MHz, DMSO-d$_6$) δ ppm 9.27 (1H), 8.31 (1H), 7.90 (2H), 7.66 (1H), 7.41 (1H), 5.35 (1H), 5.30 (1H), 5.00 (1H), 3.01 (2H), 2.53 (1H), 2.45 (3H), 2.22 (6H), 1.82-1.68 (2H), 1.51 (5H). |
| 208 | 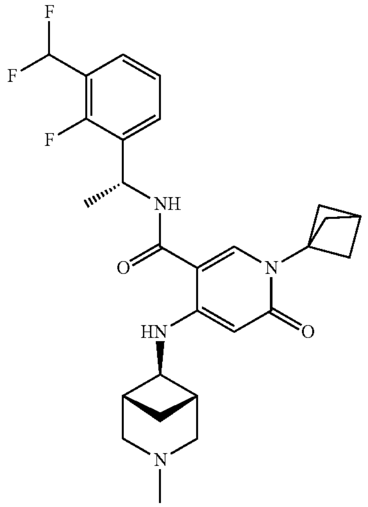 [SMILES: C[C@@H](NC(=O)c1cn(C23CC(C2)C3)c(=O)cc1N[C@@H]1[C@@H]2C[C@H]1CN(C)C2)c1cccc(C(F)F)c1F] | 1-(bicyclo[1.1.1]pentan-1-yl)-N-((R)-1-(3-(difluoromethyl)-2-fluorophenyl)ethyl)-4-(((1R,5S,6s)-3-methyl-3-azabicyclo[3.1.1]heptan-6-yl)amino)-6-oxo-1,6-dihydropyridine-3-carboxamide | MS obsd. (ESI$^+$): 501.4 [(M + H)$^+$]. $^1$H NMR (400 MHz, DMSO) δ 8.86 (1H), 8.12 (1H), 7.78 (1H), 7.62 (1H), 7.53 (1H), 7.36 (1H), 7.22 (1H), 5.30 (1H), 4.80 (1H), 3.17 (1H), 2.99 (2H), 2.82-2.67 (2H), 2.62 (1H), 2.29 (9H), 2.26 (2H), 2.08 (1H), 1.68 (1H), 1.48 (3H). |

-continued

| Example number | Compound Structure | Compound Name | Characterization |
|---|---|---|---|
| 209 | 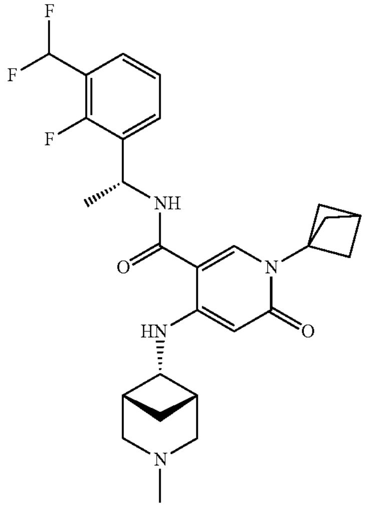 [SMILES: C[C@@H](NC(=O)c1cn(C23CC(C2)C3)c(=O)cc1N[C@H]1[C@@H]2C[C@H]1CN(C)C2)c1cccc(C(F)F)c1F] | 1-(bicyclo[1.1.1]pentan-1-yl)-N-((R)-1-(3-(difluoromethyl)-2-fluorophenyl)ethyl)-4-(((1R,5S,6r)-3-methyl-3-azabicyclo[3.1.1]heptan-6-yl)amino)-6-oxo-1,6-dihydropyridine-3-carboxamide | MS obsd. (ESI$^+$): 501.8 [(M + H)$^+$]. $^1$H NMR (400 MHz, MeOD) δ 7.89 (1H), 7.57 (1H), 7.51 (1H), 7.29 (1H), 7.00 (1H), 5.42 (1H), 5.36 (1H), 3.84 (1H), 3.56 (2H), 3.00 (2H), 2.75 (2H), 2.64 (4H), 2.39 (6H), 2.09 (1H), 1.80 (1H), 1.58 (3H). |
| 210, 211, 212, 213 | 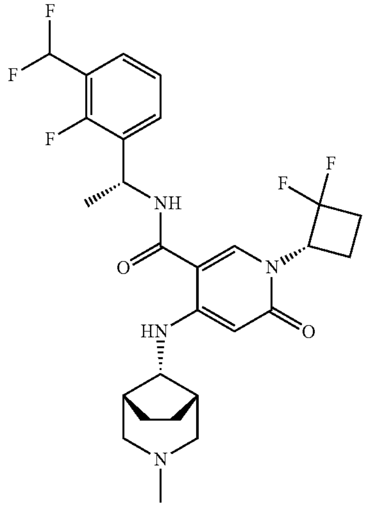 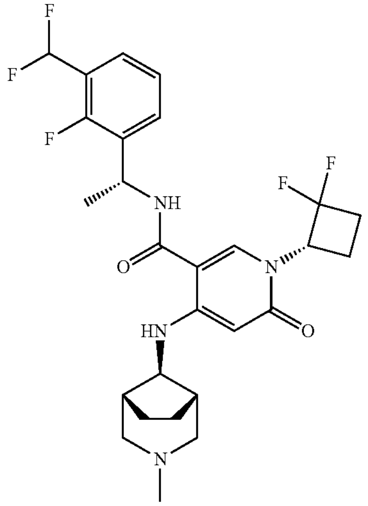 | 1-((S)-2,2-difluorocyclobutyl)-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide, 1-((S)-2,2-difluorocyclobutyl)-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide, 1-((R)-2,2-difluorocyclobutyl)-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide, and 1-((R)-2,2-difluorocyclobutyl)-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide | Example 210: MS obsd (ESI$^+$): 539.8 [M + H]$^+$. Analytical chiral UPCC: (Column: CHIRALPAK AS-3 4.6 * 100 mm 3 um, Flow rate: 3.0 mL/min, Cosolvent: EtOH(1% 7M NH3 in MeOH), Temp 40° C.) Retention time = 0.8 min Example 211: MS obsd (ESI+): 539.8 [M + H]$^+$. Analytical chiral UPCC: same conditions as example 210 Retention time = 1.0 min Example 212 MS obsd (ESI+): 539.8 [M + H]$^+$. Analytical chiral UPCC: same conditions as example 210 Retention time = 1.6 min Example 213: MS obsd (ESI+): 539.8 [M + H]$^+$. Analytical chiral UPCC: same conditions as example 210 Retention time = 3.4 min |

-continued
| Example number | Compound Structure | Compound Name | Characterization |
| --- | --- | --- | --- |
| | 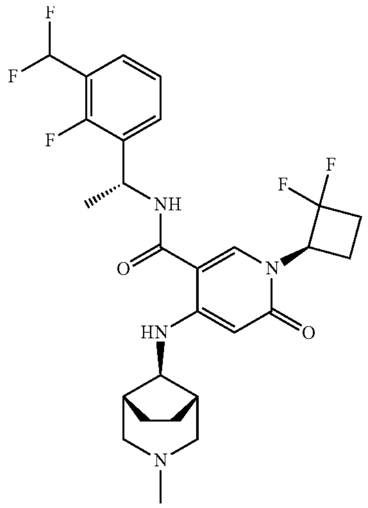 | | |
| | 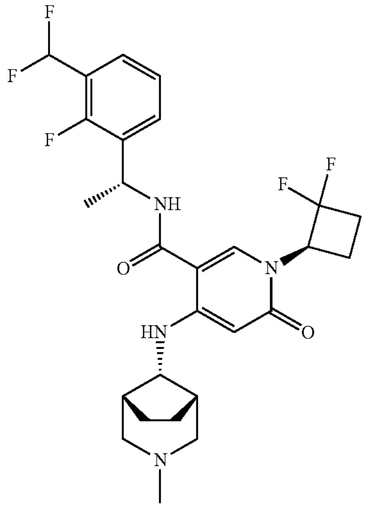 | | |

-continued

| Example number | Compound Structure | Compound Name | Characterization |
|---|---|---|---|
| 214 and 215 | 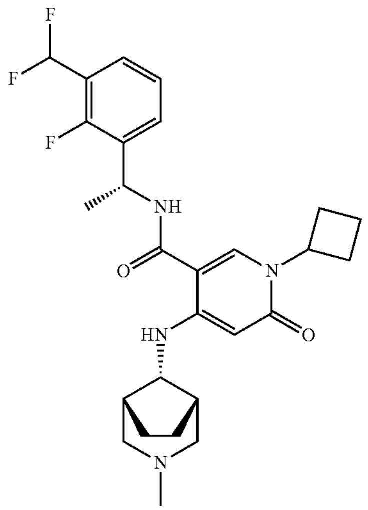 | 1-cyclobutyl-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide and 1-cyclobutyl-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide (diastereomers unassigned) | Example 214: MS obsd (ESI+): 503.3 $[M + H]^+$. $^1H$ NMR (400 MHz, $CD_3OD$) δ 8.06 (1H), 7.53 (2H), 7.28 (1H), 7.00 (1H), 5.47 (1H), 5.37 (1H), 4.99 (1H), 3.34 (1H), 2.83 (2H), 2.50-2.13 (11H), 1.88 (2H), 1.73 (4H), 1.57 (3H). Example 215: MS obsd (ESI+): 503.3 $[M + H]^+$. $^1H$ NMR (400 MHz, $CD_3OD$) δ 8.09 (1H), 7.59 (1H), 7.51 (1H), 7.29 (1H), 7.01 (1H), 5.46 (1H), 5.42 (1H), 4.98 (1H), 3.45 (1H), 2.55 (2H), 2.47-2.27 (6H), 2.27-2.10 (5H), 1.94-1.74 (6H), 1.59 (3H). |
| | 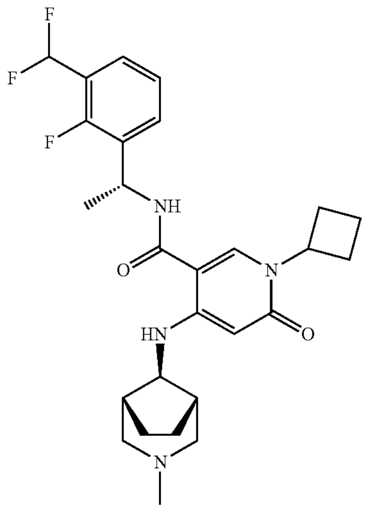 | | |
| 216 | 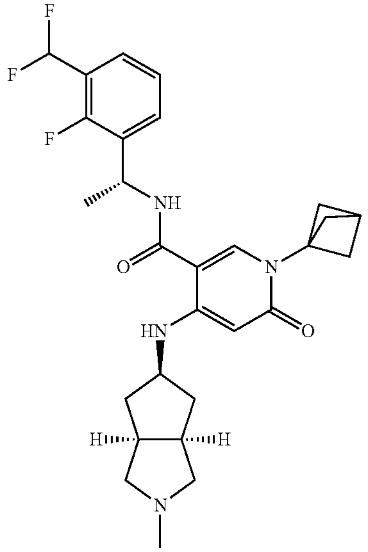 [SMILES: C[C@@H](NC(=O)c1cn(C23CC(C2)C3)c(=O)cc1N[C@@H]1C[C@@H]2CN(C)C[C@@H]2C1)c1cccc(C(F)F)c1F] | 1-(bicyclo[1.1.1]pentan-1-yl)-N-((R)-1-(3-(difluoromethyl)-2-fluorophenyl)ethyl)-4-(((3aR,5r,6aS)-2-methyloctahydrocyclopenta[c]pyrrol-5-yl)amino)-6-oxo-1,6-dihydropyridine-3-carboxamide | MS obsd (ESI+): 515.5 $[M + H]^+$. $^1H$ NMR (400 MHz, DMSO-$d_6$) δ: 8.85 (1H), 7.88 (1H), 7.71 (1H), 7.62 (1H), 7.52 (1H), 7.35 (1H), 7.21 (1H), 5.28 (1H), 5.17 (1H), 3.57 (1H), 2.65-2.51 (6H), 2.35-2.15 (12H), 1.46 (3H), 1.28-1.10 (2H). |

-continued

| Example number | Compound Structure | Compound Name | Characterization |
|---|---|---|---|
| 217 | 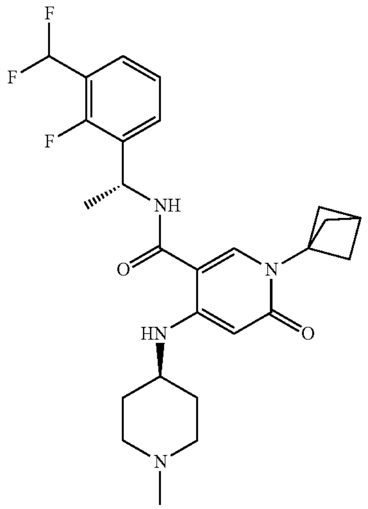 | (R)-1-(bicyclo[1.1.1]pentan-1-yl)-N-(1-(3-(difluoromethyl)-2-fluorophenyl)ethyl)-4-((1-methylpiperidin-4-yl)amino)-6-oxo-1,6-dihydropyridine-3-carboxamide | MS obsd (ESI+): 489.4 $[M + H]^+$. $^1H$ NMR (400 MHz, DMSO-$d_6$) δ 8.82 (1H), 7.73 (2H), 7.60 (1H), 7.53 (1H), 7.35 (1H), 7.21 (1H), 5.28 (1H), 5.14 (1H), 3.21 (2H), 2.61 (1H), 2.54 (1H), 2.28 (6H), 2.13 (3H), 2.06 (2H), 1.82 (2H), 1.47 (3H), 1.35 (2H). |
| 218 and 219 | 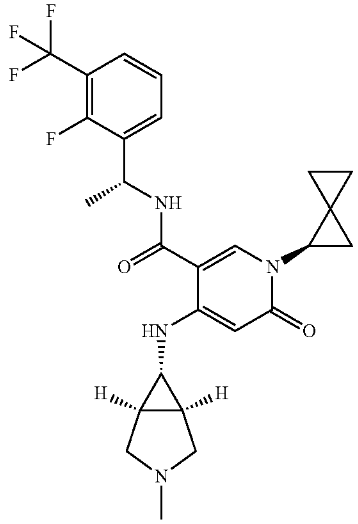 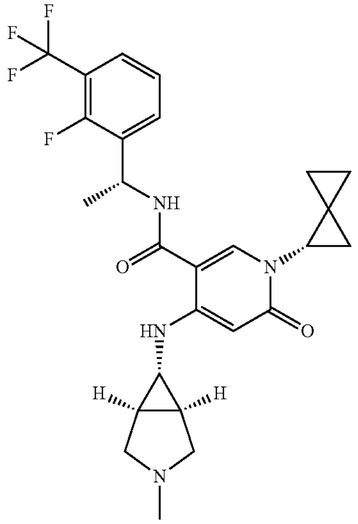 | N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide and N-((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide (diastereomers not assigned) | Example 218: MS obsd (ESI+): 505.3 $[M + H]^+$. Analytical chiral UPCC: (Column: CHIRALPAK AD-3 4.6 * 100 mm 3 um, Flow rate: 3.0 mL/min, Cosolvent: MeOH(0.2% 7M NH3 in MeOH), Temp 40° C.) Retention time = 0.7 min Example 219: MS obsd (ESI+): 505.3 $[M + H]^+$. Analytical chiral UPCC: (Column: CHIRALPAK AD-3 4.6 * 100 mm 3 um, Flow rate: 3.0 mL/min, Cosolvent: MeOH(0.2% 7M NH3 in MeOH), Temp 40° C.) Retention time = 1.4 min |

-continued

| Example number | Compound Structure | Compound Name | Characterization |
|---|---|---|---|
| 220 | 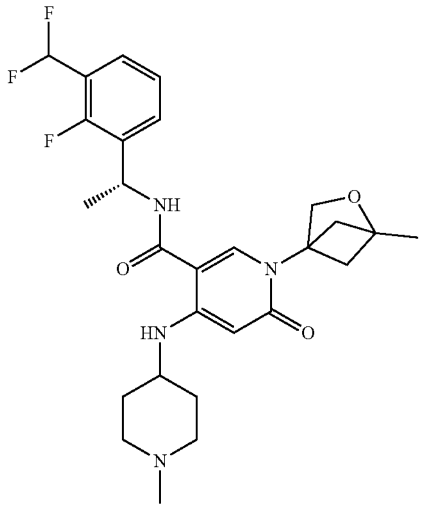 [SMILES: C[C@@H](NC(=O)c1cn(C23COC(C)(C2)C3)c(=O)cc1NC1CCN(C)CC1)c1cccc(C(F)F)c1F] | (R)-N-(1-(3-(difluoromethyl)-2-fluorophenyl)ethyl)-1-(1-methyl-2-oxabicyclo[2.1.1]hexan-4-yl)-4-((1-methylpiperidin-4-yl)amino)-6-oxo-1,6-dihydropyridine-3-carboxamide | MS obsd (ESI+): 519.2 [M + H]+ $^{1}$H NMR (400 MHz, DMSO-$d_6$) δ: 9.28-9.19 (2H), 8.61 (1H), 7.72-7.68 (1H), 7.58-7.54 (1H), 7.38-7.10 (2H), 6.70 (1H), 5.35 (1H), 5.26 (1H), 5.12 (2H), 3.61 (1H), 2.92 (2H), 2.59 (2H), 2.36 (2H), 2.21-2.06 (5H), 1.84 (2H), 1.56 (3H), 1.45 (5H). |
| 221 | 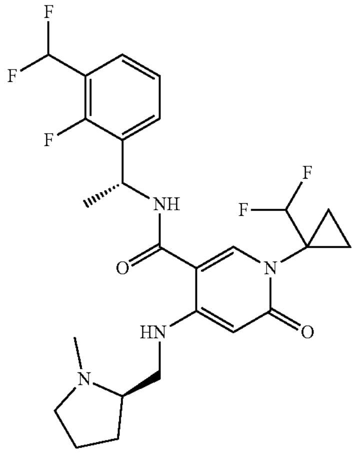 [SMILES: C[C@@H](NC(=O)c1cn(C2(C(F)F)CC2)c(=O)cc1NC[C@H]1CCCN1C)c1cccc(C(F)F)c1F] | N-((R)-1-(3-(difluoromethyl)-2-fluorophenyl)ethyl)-1-(1-(difluoromethyl) cyclopropyl)-4-((((R)-1-methylpyrrolidin-2-yl)methyl)amino)-6-oxo-1,6-dihydropyridine-3-carboxamide | MS obsd (ESI+): 513.5 [M + H]+. $^{1}$H NMR (400 MHz, DMSO-$d_6$) δ 8.77 (1H), 7.92 (1H), 7.85 (1H), 7.62-7.48 (2H), 7.36-7.06 (2H), 6.23 (1H), 5.28 (1H), 5.17 (s, 1H), 3.07-2.93 (2H), 2.88 (1H), 2.33 (1H), 2.21 (3H), 2.07 (1H), 1.76 (1H), 1.55-1.21 (10H). |
| 222 | 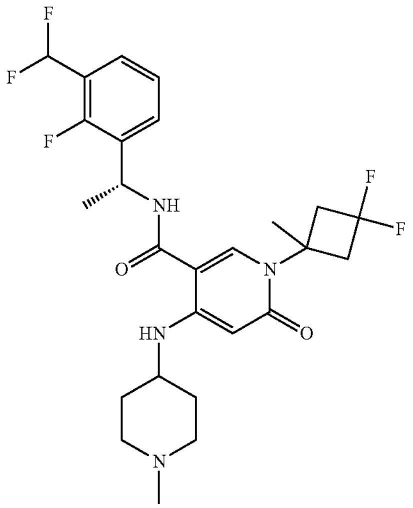 [SMILES: C[C@@H](NC(=O)c1cn(C2(C)CC(F)(F)C2)c(=O)cc1NC1CCN(C)CC1)c1cccc(C(F)F)c1F] | (R)-1-(3,3-difluoro-1-methylcyclobutyl)-N-(1-(3-(difluoromethyl)-2-fluorophenyl)ethyl)-4-((1-methylpiperidin-4-yl)amino)-6-oxo-1,6-dihydropyridine-3-carboxamide | MS obsd (ESI+): 527.4 [M + H]+. $^{1}$H NMR (400 MHz, DMSO-$d_6$) δ: 8.75 (1H), 7.82 (1H), 7.74 (1H), 7.64 (1H), 7.53 (1H), 7.35 (1H), 7.21 (1H), 5.28 (1H), 5.22 (1H), 3.27-3.12 (3H), 2.93 (2H), 2.78-2.60 (2H), 2.30-2.06 (5H), 1.79 (2H), 1.59 (3H), 1.48 (3H), 1.45-1.30 (2H). |

-continued

| Example number | Compound Structure | Compound Name | Characterization |
|---|---|---|---|
| 223 | 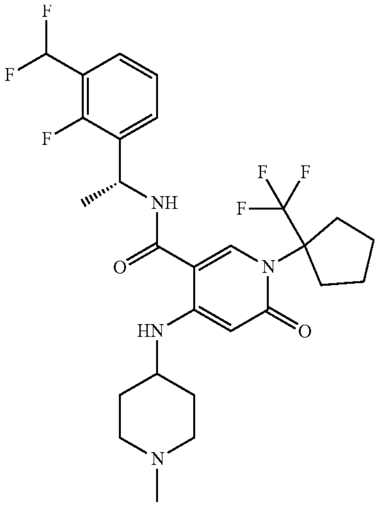 [SMILES: C[C@@H](NC(=O)c1cn(C2(C(F)(F)F)CCCC2)c(=O)cc1NC1CCN(C)CC1)c1cccc(C(F)F)c1F] | (R)-N-(1-(3-(difluoromethyl)-2-fluorophenyl)ethyl)-4-((1-methylpiperidin-4-yl)amino)-6-oxo-1-(1-(trifluoromethyl)cyclopentyl)-1,6-dihydropyridine-3-carboxamide | MS obsd (ESI+): 559.4 $[M + H]^+$. $^1H$ NMR (400 MHz, DMSO-$d_6$) δ: 8.88 (1H), 7.83 (1H), 7.64 (1H), 7.59 (1H), 7.52 (1H), 7.35 (1H), 7.21 (1H), 5.29 (1H), 5.18 (1H), 3.23 (2H), 3.17 (1H), 2.81 (2H), 2.13 (3H), 2.08 (2H), 2.04 (1H), 1.81 (3H), 1.75 (4H), 1.48 (3H), 1.41-1.30 (2H). |
| 224 | 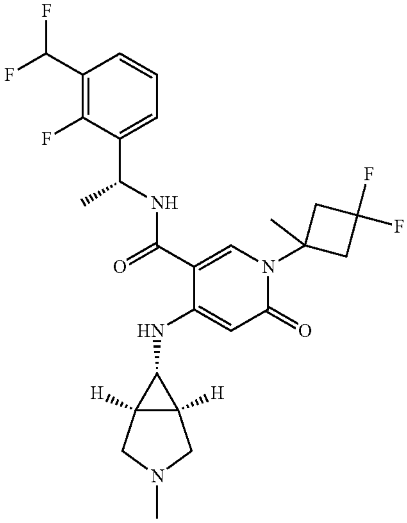 [SMILES: C[C@@H](NC(=O)c1cn(C2(C)CC(F)(F)C2)c(=O)cc1N[C@H]1[C@@H]2CN(C)C[C@@H]21)c1cccc(C(F)F)c1F] | 1-(3,3-difluoro-1-methylcyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+): 525.3 $[M + H]^+$. $^1H$ NMR (400 MHz, DMSO-$d_6$) δ: 8.73 (1H), 7.81 (1H), 7.69 (1H), 7.62 (1H), 7.52 (1H), 7.35 (1H), 7.21 (1H), 5.35 (1H), 5.25 (1H), 3.30-3.15 (2H), 3.05-2.87 (4H), 2.47 (1H), 2.40-2.24 (2H), 2.21 (3H), 1.60 (3H), 1.53-1.44 (5H). |
| 225 | 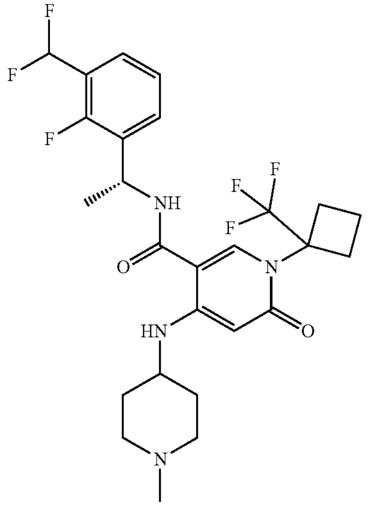 [SMILES: C[C@@H](NC(=O)c1cn(C2(C(F)(F)F)CCC2)c(=O)cc1NC1CCN(C)CC1)c1cccc(C(F)F)c1F] | (R)-N-(1-(3-(difluoromethyl)-2-fluorophenyl)ethyl)-4-((1-methylpiperidin-4-yl)amino)-6-oxo-1-(1-(trifluoromethyl) cyclobutyl)-1,6-dihydropyridine-3-carboxamide | MS obsd (ESI+): 545.4 $[M + H]^+$. $^1H$ NMR (400 MHz, DMSO-$d_6$) δ 8.85 (1H), 7.79 (1H), 7.66 (1H), 7.59 (1H), 7.53 (1H), 7.35 (1H), 7.21 (1H), 5.33-5.26 (1H), 5.17 (1H), 3.23 (1H), 2.90 (2H), 2.80-2.69 (2H), 2.54 (2H), 2.13 (3H), 2.10-1.82 (6H), 1.48 (3H), 1.39-1.32 (2H). |

-continued

| Example number | Compound Structure | Compound Name | Characterization |
|---|---|---|---|
| 226 | 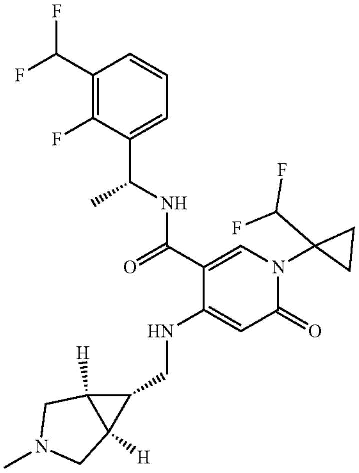 [SMILES: C[C@@H](NC(=O)c1cn(C2(C(F)F)CC2)c(=O)cc1NC[C@@H]1[C@H]2CN(C)C[C@@H]12)c1cccc(C(F)F)c1F] | N-((R)-1-(3-(difluoromethyl)-2-fluorophenyl)ethyl)-1-(1-(difluoromethyl)cyclopropyl)-4-((((1R,5S,6s)-3-methyl-3-azabicyclo[3.1.0]hexan-6-yl)methyl)amino)-6-oxo-1,6-dihydropyridine-3-carboxamide | MS obsd (ESI+): 525.5 $[M + H]^+$. $^1H$ NMR (400 MHz, DMSO-$d_6$) δ 8.81 (1H), 8.01 (1H), 7.97 (1H), 7.62 (1H), 7.53 (1H), 7.36 (1H), 7.22 (1H), 6.24 (1H), 5.31 (1H), 5.14 (1H), 2.94-2.74 (4H), 2.16 (5H), 1.49 (3H), 1.41-1.20 (m, 7H). |
| 227 and 228 | 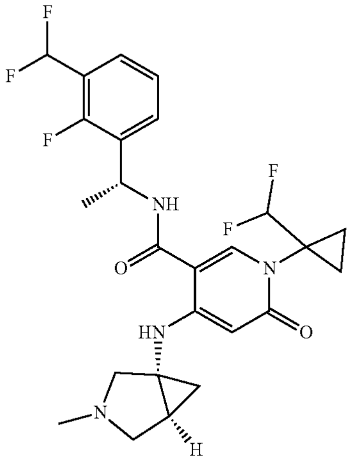 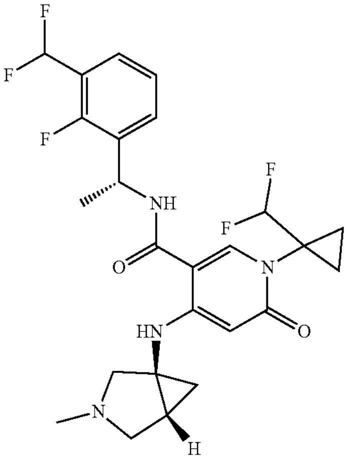 | N-((R)-1-(3-(difluoromethyl)-2-fluorophenyl)ethyl)-1-(1-(difluoromethyl)cyclopropyl)-4-(((1R,5S)-3-methyl-3-azabicyclo[3.1.0]hexan-1-yl)amino)-6-oxo-1,6-dihydropyridine-3-carboxamide and N-((R)-1-(3-(difluoromethyl)-2-fluorophenyl)ethyl)-1-(1-(difluoromethyl)cyclopropyl)-4-(((1S,5R)-3-methyl-3-azabicyclo[3.1.0]hexan-1-yl)amino)-6-oxo-1,6-dihydropyridine-3-carboxamide (unassigned diastereomers) | Example 227: MS obsd (ESI+): 511.3 $[M + H]^+$ Analytical chiral UPCC: (Column: CHIRALPAK IG-3 4.6 * 100 mm 3 um, Flow rate: 3.0 mL/min, Cosolvent: EtOH(1% 7M NH3 in MeOH), Temp 40° C.) Retention time = 1.6 min Example 228: MS obsd (ESI+): 511.3 $[M + H]^+$. Analytical chiral UPCC: (Column: CHIRALPAK IG-3 4.6 * 100 mm 3 um, Flow rate: 3.0 mL/min, Cosolvent: EtOH(1% 7M NH3 in MeOH), Temp 40° C.) Retention time = 2.3 min |

-continued

| Example number | Compound Structure | Compound Name | Characterization |
|---|---|---|---|
| 229 | 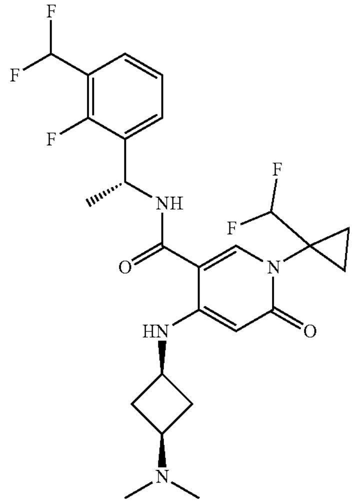 [SMILES: C[C@@H](NC(=O)c1cn(C2(C(F)F)CC2)c(=O)cc1N[C@H]1C[C@@H](N(C)C)C1)c1cccc(C(F)F)c1F] | N-((R)-1-(3-(difluoromethyl)-2-fluorophenyl)ethyl)-1-(1-(difluoromethyl) cyclopropyl)-4-(((1s,3S)-3-(dimethylamino) cyclobutyl)amino)-6-oxo-1,6-dihydropyridine-3-carboxamide | MS obsd (ESI+): 513.2 $[M + H]^+$. $^1H$ NMR (400 MHz, MeOD-$d_4$) δ: 8.02 (1H), 7.53 (2H), 7.28 (1H), 7.00 (1H), 6.14 (1H), 5.38 (1H), 5.31 (1H), 3.60 (1H), 2.68 (3H), 2.19 (6H), 1.72 (2H), 1.56 (3H), 1.44 (2H), 1.32 (2H). |
| 230 | 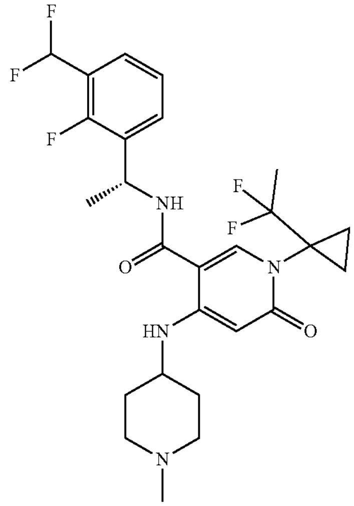 [SMILES: C[C@@H](NC(=O)c1cn(C2(C(C)(F)F)CC2)c(=O)cc1NC1CCN(C)CC1)c1cccc(C(F)F)c1F] | (R)-1-(1-(1,1-difluoroethyl)cyclopropyl)-N-(1-(3-(difluoromethyl)-2-fluorophenyl)ethyl)-4-((1-methylpiperidin-4-yl)amino)-6-oxo-1,6-dihydropyridine-3-carboxamide | MS obsd (ESI+): 527.2 $[M + H]^+$. $^1H$ NMR (400 MHz, DMSO-$d_6$) δ 8.81 (1H), 8.04 (1H), 7.94 (1H), 7.60 (1H), 7.53 (1H), 7.35 (1H), 7.21 (1H), 5.38-5.24 (1H), 5.20 (1H), 3.23 (1H), 2.57 (2H), 2.13 (3H), 2.05 (2H), 1.80 (2H), 1.60 (3H), 1.48 (3H), 1.42-1.27 (6H). |
| 231 | 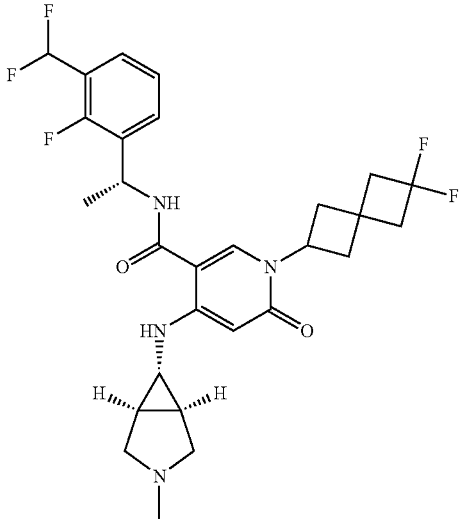 [SMILES: C[C@@H](NC(=O)c1cn(C2CC3(C2)CC(F)(F)C3)c(=O)cc1N[C@H]1[C@@H]2CN(C)C[C@@H]21)c1cccc(C(F)F)c1F] | N-((R)-1-(3-(difluoromethyl)-2-fluorophenyl)ethyl)-1-(6,6-difluorospiro[3.3 ]heptan-2-yl)-4-(((1R,5S,6s)-3-methyl-3-azabicyclo[3.1.0]hexan-6-yl)amino)-6-oxo-1,6-dihydropyridine-3-carboxamide | MS obsd (ESI+): 551.5 $[M + H]^+$. $^1H$ NMR (400 MHz, DMSO-$d_6$) δ ppm 8.76 (1H), 7.92 (1H), 7.74 (1H), 7.61 (1H), 7.52 (1H), 7.34 (1H), 7.20 (1H), 5.36 (1H), 5.27 (1H), 4.80 (1H), 2.99 (2H), 2.78 (2H), 2.65 (2H), 2.55 (3H), 2.46 (2H), 2.27 (2H), 2.19 (3H), 1.48 (5H). |

-continued

| Example number | Compound Structure | Compound Name | Characterization |
|---|---|---|---|
| 232 and 233 | 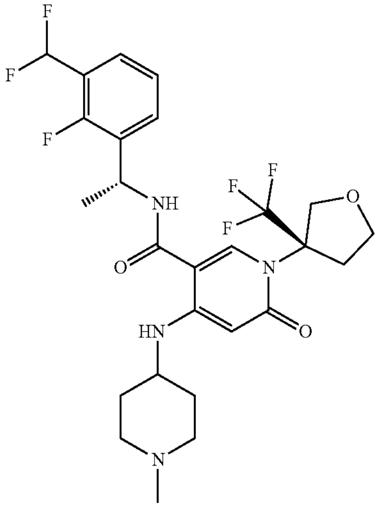 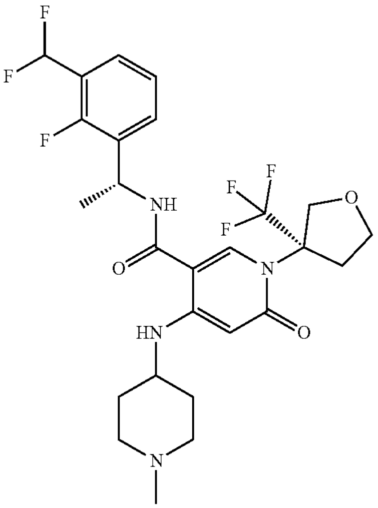 | N-((R)-1-(3-(difluoromethyl)-2-fluorophenyl)ethyl)-4-((1-methylpiperidin-4-yl)amino)-6-oxo-1-((S)-3-(trifluoromethyl) tetrahydrofuran-3-yl)-1,6-dihydropyridine-3-carboxamide and N-((R)-1-(3-(difluoromethyl)-2-fluorophenyl)ethyl)-4-((1-methylpiperidin-4-yl)amino)-6-oxo-1-((R)-3-(trifluoromethyl) tetrahydrofuran-3-yl)-1,6-dihydropyridine-3-carboxamide (unassigned diastereomers) | Example 232: MS obsd (ESI+): 561.3 $[M+H]^+$. Analytical chiral UPCC: (Column: YMC Cellulose-SC 4.6 * 100 mm 3 um, Flow rate: 3.0 mL/min, Cosolvent IPA(1% 7M NH3 in MeOH), Temp 40° C.) Retention time = 0.9 min Example 233: MS obsd (ESI+): 561.3 $[M+H]^+$. Analytical chiral UPCC: (Column: YMC Cellulose-SC 4.6 * 100 mm 3 um, Flow rate: 3.0 mL/min, Cosolvent IPA(1% 7M NH3 in MeOH), Temp 40° C.) Retention time = 1.4 min |

-continued

| Example number | Compound Structure | Compound Name | Characterization |
|---|---|---|---|
| 234 and 235 | 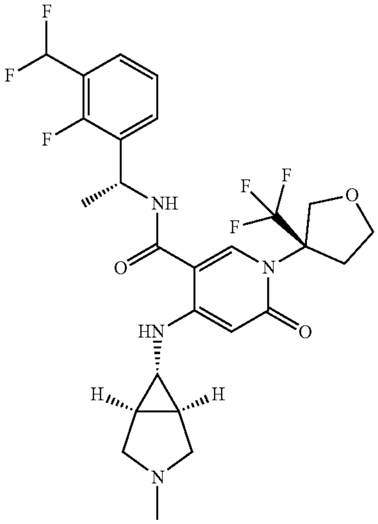 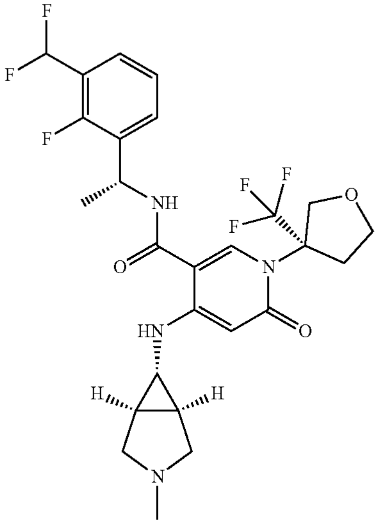 | N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-3-(trifluoromethyl) tetrahydrofuran-3-yl)-1,6-dihydropyridine-3-carboxamide and N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-3-(trifluoromethyl) tetrahydrofuran-3-yl)-1,6-dihydropyridine-3-carboxamide (diastereomers not assigned) | Example 234: MS obsd (ESI+): 559.3 $[M + H]^+$. Analytical chiral UPCC: (Column: CHIRALPAK OD-3 4.6 * 100 mm 3 um, Flow rate: 3.0 mL/min, Cosolvent: MeOH(0.2% 7M NH3 in MeOH), Temp 40° C.) Retention time = 1.5 min Example 235: MS obsd (ESI+): 559.3 $[M + H]^+$. Analytical chiral UPCC: (Column: CHIRALPAK OD-3 4.6 * 100 mm 3 um, Flow rate: 3.0 mL/min, Cosolvent: MeOH(0.2% 7M NH3 in MeOH), Temp 40° C.) Retention time = 2.1 min |

-continued

| Example number | Compound Structure | Compound Name | Characterization |
|---|---|---|---|
| 236, 237, 238, 239 | 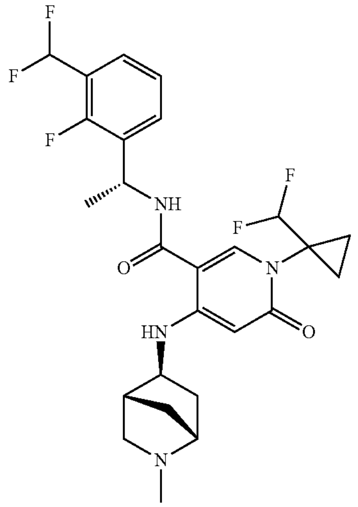 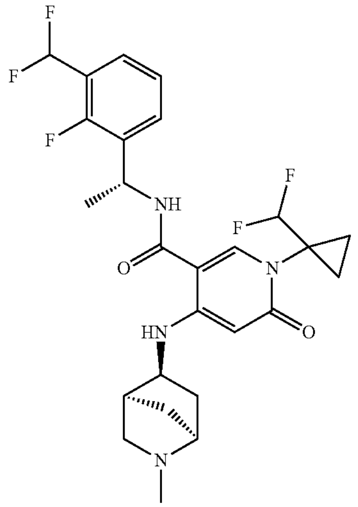 | N-((R)-1-(3-(difluoromethyl)-2-fluorophenyl)ethyl)-1-(1-(difluoromethyl)cyclopropyl)-4-(((1R,4R,5S)-2-methyl-2-azabicyclo[2.2.1]heptan-5-yl)amino)-6-oxo-1,6-dihydropyridine-3-carboxamide, N-((R)-1-(3-(difluoromethyl)-2-fluorophenyl)ethyl)-1-(1-(difluoromethyl) cyclopropyl)-4-(((1S,4S,5S)-2-methyl-2-azabicyclo[2.2.1]heptan-5-yl)amino)-6-oxo-1,6-dihydropyridine-3-carboxamide, N-((R)-1-(3-(difluoromethyl)-2-fluorophenyl)ethyl)-1-(1-(difluoromethyl) cyclopropyl)-4-(((1S,4S,5R)-2-methyl-2-azabicyclo[2.2.1]heptan-5-yl)amino)-6-oxo-1,6-dihydropyridine-3-carboxamide, and N-((R)-1-(3-(difluoromethyl)-2-fluorophenyl)ethyl)-1-(1-(difluoromethyl) cyclopropyl)-4-(((1R,4R,5R)-2-methyl-2-azabicyclo[2.2.1]heptan-5-yl)amino)-6-oxo-1,6-dihydropyridine-3-carboxamide (diastereomers not assigned) | Example 236: MS obsd (ESI+): 525.3 $[M + H]^+$. Analytical chiral UPCC: (Column: CHIRALPAK IG-3 4.6 * 100 mm 3 um, Flow rate: 3.0 mL/min, Cosolvent: EtOH(1% 7M NH3 in MeOH), Temp 40° C.) Retention time = 1.6 min Example 237: MS obsd (ESI+): 525.3 $[M + H]^+$. Analytical chiral UPCC: same conditions as example 236 Retention time = 1.8 min Example 238: MS obsd (ESI+): 525.5 $[M + H]^+$. Analytical chiral UPCC: same conditions as example 236 Retention time = 2.4 min Example 239: MS obsd (ESI+): 525.3 $[M + H]^+$. Analytical chiral UPCC: same conditions as example 236 Retention time = 3.1 min |

-continued
| Example number | Compound Structure | Compound Name | Characterization |
|---|---|---|---|
| | 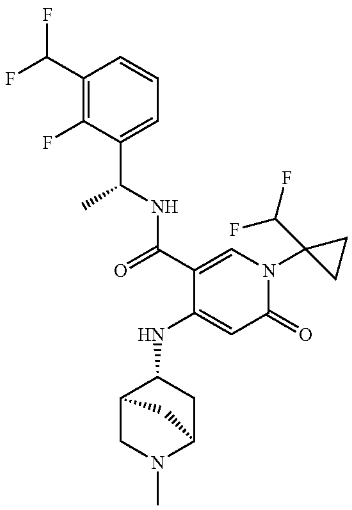 | | |
| | 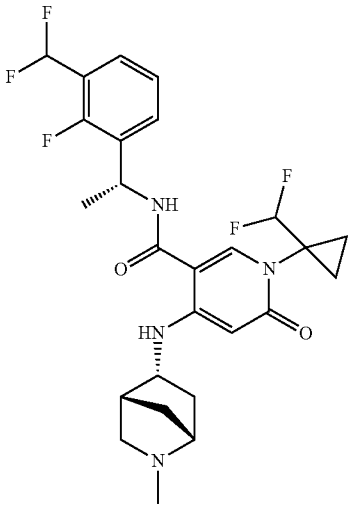 | | |
| 240 | 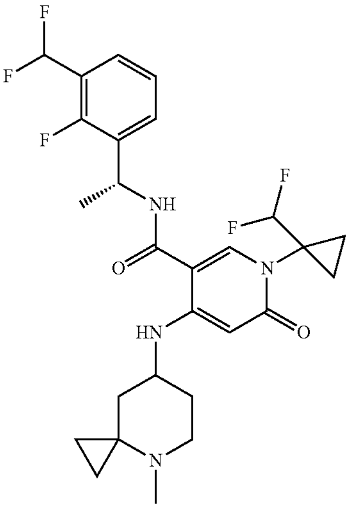 [SMILES: C[C@@H](NC(=O)c1cn(C2(C(F)F)CC2)c(=O)cc1NC1CCN(C)C2(CC2)C1)c1cccc(C(F)F)c1F] | N-((R)-1-(3-(difluoromethyl)-2-fluorophenyl)ethyl)-1-(1-(difluoromethyl) cyclopropyl)-4-((4-methyl-4-azaspiro[2.5]octan-7-yl)amino)-6-oxo-1,6-dihydropyridine-3-carboxamide | MS obsd (ESI+): 539.3 $[M + H]^+$. $^1H$ NMR (400 MHz, DMSO-$d_6$) δ ppm 8.80 (1H), 8.08 (1H), 8.03 (1H), 7.61 (1H), 7.53 (1H), 7.37-7.07 (2H), 6.23 (1H), 5.30 (1H), 5.18 (1H), 3.42 (1H), 2.86-2.68 (2H), 2.24 (3H), 1.68-1.59 (2H), 1.55-1.42 (4H), 1.38-1.15 (5H), 0.46 (2H), 0.32 (2H). |

-continued

| Example number | Compound Structure | Compound Name | Characterization |
|---|---|---|---|
| 241 | 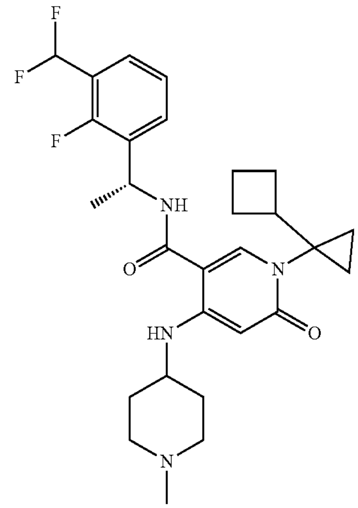 [SMILES: C[C@@H](NC(=O)c1cn(C2(C3CCC3)CC2)c(=O)cc1NC1CCN(C)CC1)c1cccc(C(F)F)c1F] | (R)-1-(1-cyclobutylcyclopropyl)-N-(1-(3-(difluoromethyl)-2-fluorophenyl)ethyl)-4-((1-methylpiperidin-4-yl)amino)-6-oxo-1,6-dihydropyridine-3-carboxamide | MS obsd (ESI+): 517.3 $[M + H]^+$. $^1H$ NMR (400 MHz, DMSO-$d_6$) δ: 8.71 (1H), 8.04 (1H), 7.89 (1H), 7.61 (1H), 7.52 (1H), 7.35 (1H), 7.21 (1H), 5.29 (1H), 5.16 (1H), 3.17 (1H), 2.85 (1H), 2.54 (2H), 2.12 (3H), 2.06 (2H), 1.87-1.56 (8H), 1.48 (3H), 1.39-1.26 (2H), 0.98 (4H) |
| 242 | 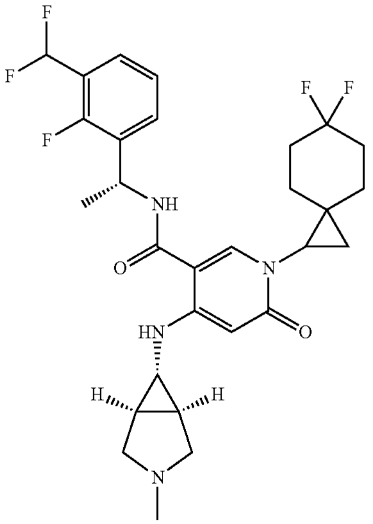 [SMILES: C[C@@H](NC(=O)c1cn(C2CC23CCC(F)(F)CC3)c(=O)cc1N[C@H]1[C@@H]2CN(C)C[C@@H]21)c1cccc(C(F)F)c1F] | N-((R)-1-(3-(difluoromethyl)-2-fluorophenyl)ethyl)-1-(6,6-difluorospiro[2.5]octan-1-yl)-4-(((1R,5S,6s)-3-methyl-3-azabicyclo[3.1.0]hexan-6-yl)amino)-6-oxo-1,6-dihydropyridine-3-carboxamide | MS obsd (ESI+): 565.4 $[M + H]^+$. $^1H$ NMR (400 MHz, DMSO-$d_6$) δ 8.77 (1H), 7.92 (1H), 7.87 (1H), 7.60 (1H), 7.52 (1H), 7.35 (1H), 7.20 (1H), 5.42 (1H), 5.25 (1H), 3.17 (1H), 3.01 (2H), 2.48 (2H), 2.27 (2H), 2.20 (3H), 1.98-1.31 (12H), 1.19 (1H), 1.01 (1H). |

-continued

| Example number | Compound Structure | Compound Name | Characterization |
|---|---|---|---|
| 243 and 244 | 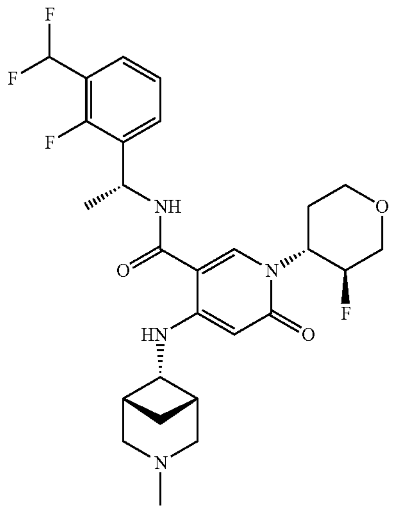 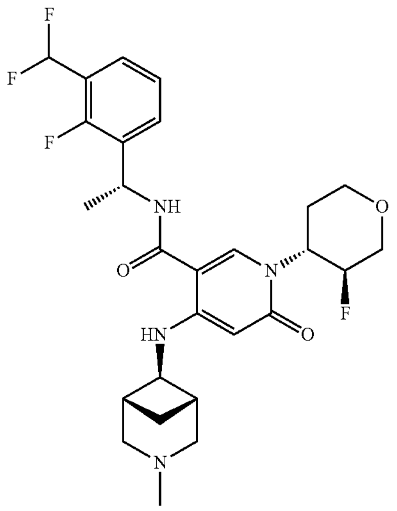 | N-((R)-1-(3-(difluoromethyl)-2-fluorophenyl)ethyl)-1-((3S,4R)-3-fluorotetrahydro-2H-pyran-4-yl)-4-(((1R,5S,6r)-3-methyl-3-azabicyclo[3.1.1]heptan-6-yl)amino)-6-oxo-1,6-dihydropyridine-3-carboxamide and N-((R)-1-(3-(difluoromethyl)-2-fluorophenyl)ethyl)-1-((3S,4R)-3-fluorotetrahydro-2H-pyran-4-yl)-4-(((1R,5S,6s)-3-methyl-3-azabicyclo[3.1.1]heptan-6-yl)amino)-6-oxo-1,6-dihydropyridine-3-carboxamide (diasteromers unassigned) | Example 243: MS obsd (ESI+): 537.3 $[M + H]^+$. Analytical chiral UPCC: (Column: CHIRALPAK AS-3 4.6 * 100 mm 3 um, Flow rate: 3.0 mL/min, Cosolvent: MeOH(0.2% 7M NH3 in MeOH), Temp 40° C.) Retention time = 0.7 min Example 244: MS obsd (ESI+): 537.3 $[M + H]^+$. Analytical chiral UPCC: (Column: CHIRALPAK AS-3 4.6 * 100 mm 3 um, Flow rate: 3.0 mL/min, Cosolvent: MeOH(0.2% 7M NH3 in MeOH), Temp 40° C.) Retention time = 1.2 min |

-continued

| Example number | Compound Structure | Compound Name | Characterization |
| --- | --- | --- | --- |
| 245 and 246 | 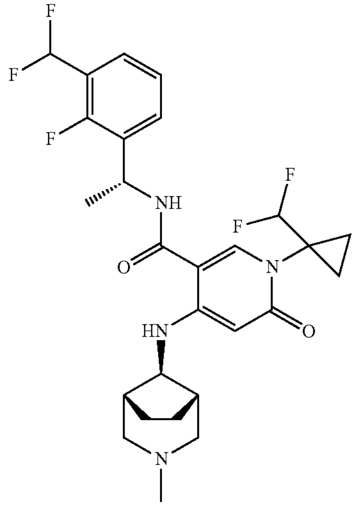 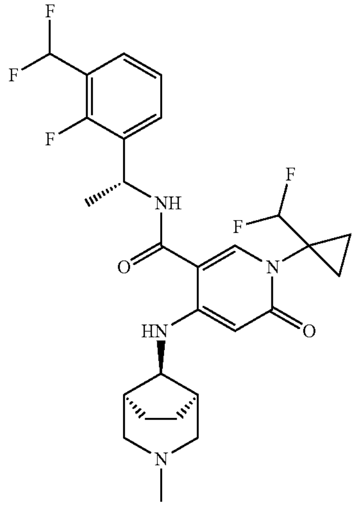 | N-((R)-1-(3-(difluoromethyl)-2-fluorophenyl)ethyl)-1-(1-(difluoromethyl) cyclopropyl)-4-(((1R,5S,8r)-3-methyl-3-azabicyclo[3.2.1]octan-8-yl)amino)-6-oxo-1,6-dihydropyridine-3-carboxamide and N-((R)-1-(3-(difluoromethyl)-2-fluorophenyl)ethyl)-1-(1-(difluoromethyl) cyclopropyl)-4-(((1R,5S,8s)-3-methyl-3-azabicyclo[3.2.1]octan-8-yl)amino)-6-oxo-1,6-dihydropyridine-3-carboxamide (diastereomers unassigned) | Example 245: MS obsd (ESI+): 539.2 [M + H]$^+$. $^1$H NMR (400 MHz, DMSO-$d_6$) δ: 8.84 (1H), 8.46 (1H) 8.03 (1H), 7.62 (1H), 7.53 (1H), 7.35 (1H), 7.21 (1H), 6.24 (1H), 5.34 (1H), 5.24 (1H), 3.35 (1H), 2.37 (2H), 2.14-2.05 (4H), 2.03 (3H), 1.67 (4H), 1.50 (3H), 1.34 (4H). Example 246: MS obsd (ESI+): 539.2 [M +H] $^1$H NMR (400 MHz, DMSO-$d_6$) δ: 8.81 (1H), 8.05 (1H), 7.99 (1H), 7.60 (1H), 7.53 (1H), 7.34 (1H), 7.22 (1H), 6.24 (1H), 5.29 (1H), 5.21 (1H), 3.20 (1H), 2.66-2.54 (2H), 2.21-2.03 (7H), 1.61 (2H), 1.49 (5H), 1.34 (4H). |
| 247 | 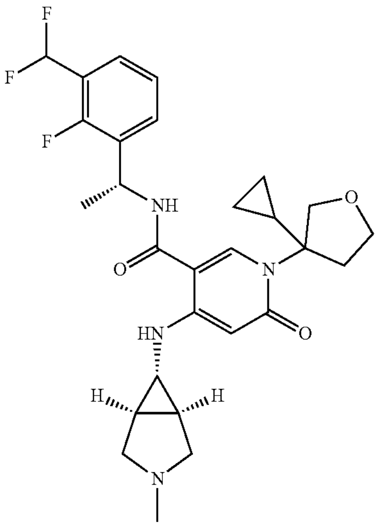 [SMILES: C[C@@H](NC(=O)c1cn(C2(C3CC3)CCOC2)c(=O)cc1N[C@H]1[C@@H]2CN(C)C[C@@H]21)c1cccc(C(F)F)c1F] | 1-(3-cyclopropyltetrahydrofuran-3-yl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide | MS obsd (ESI+): 531.4 [M + H]$^+$. $^1$H NMR (400 MHz, DMSO-$d_6$) δ: 8.75 (1H), 7.80 (1H), 7.67 (1H), 7.59 (1H), 7.52 (1H), 7.38-7.07 (2H), 5.34 (1H), 5.27 (1H), 4.27 (1H), 3.90-3.74 (3H), 2.99 (2H), 2.47 (1H), 2.39 (2H), 2.27 (2H), 2.19 (3H), 1.61-1.43 (6H), 0.62-0.37 (4H). |

-continued

| Example number | Compound Structure | Compound Name | Characterization |
|---|---|---|---|
| 248 and 249 | 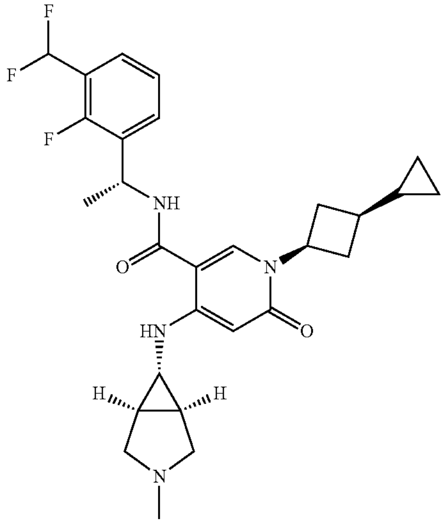 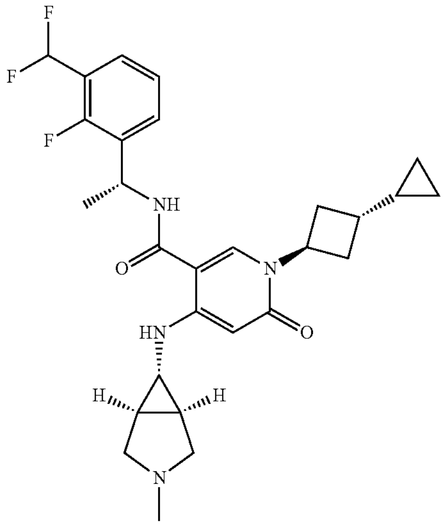 | 1-((1s,3S)-3-cyclopropylcyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide and 1-((1r,3R)-3-cyclopropylcyclobutyl)-N-((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (diastereomers unassigned) | Example 248: MS obsd (ESI+): 515.2 $[M + H]^+$. H NMR (400 MHz, DMSO-$d_6$) δ: 9.07 (1H), 8.22 (1H), 7.87 (1H), 7.71 (1H), 7.51 (1H), 7.34 (1H), 7.15 (1H), 5.35 (1H), 5.29 (1H), 5.12 (1H), 2.99 (2H), 2.57 (2H), 2.46 (1H), 2.26 (2H), 2.19 (3H), 2.07 (2H), 1.93 (1H), 1.57-1.42 (5H), 1.06 (1H), 0.49 (2H), 0.20-0.09 (2H). Example 249: MS obsd (ESI+): 515.2 $[M + H]^+$. $^1H$ NMR (400 MHz, DMSO-$d_6$) δ: 8.85 (1H), 7.91 (1H), 7.69 (1H), 7.63 (1H), 7.52 (1H), 7.35 (1H), 7.15 (1H), 5.35 (1H), 5.28 (1H), 4.65 (1H), 2.99 (2H), 2.46 (1H), 2.37 (2H), 2.27 (2H), 2.19 (3H), 2.05-1.91 (2H), 1.74 (1H), 1.48 (5H), 0.87 (1H), 0.41 (2H), 0.17-0.13 (2H). |

-continued

| Example number | Compound Structure | Compound Name | Characterization |
| --- | --- | --- | --- |
| 250 and 251 | 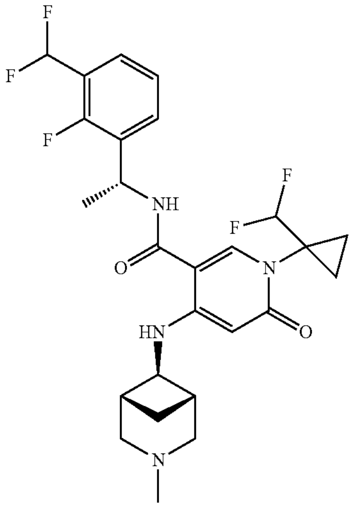 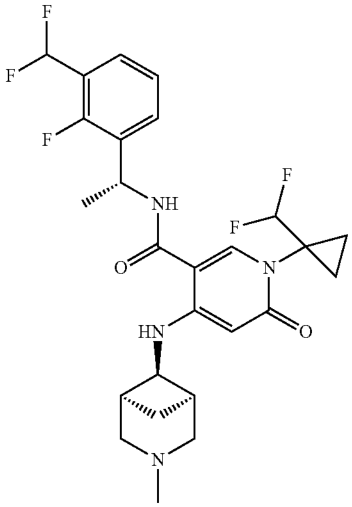 | N-((R)-1-(3-(difluoromethyl)-2-fluorophenyl)ethyl)-1-(1-(difluoromethyl) cyclopropyl)-4-(((1R,5S,6s)-3-methyl-3-azabicyclo[3.1.1]heptan-6-yl)amino)-6-oxo-1,6-dihydropyridine-3-carboxamide and N-((R)-1-(3-(difluoromethyl)-2-fluorophenyl)ethyl)-1-(1-(difluoromethyl) cyclopropyl)-4-(((1R,5S,6r)-3-methyl-3-azabicyclo[3.1.1]heptan-6-yl)amino)-6-oxo-1,6-dihydropyridine-3-carboxamide (diastereomers unassigned) | Example 250; MS obsd (ESI+): 525.5 $[M + H]^+$. $^1H$ NMR (400 MHz, DMSO-$d_6$) δ 8.83 (1H), 8.39 (1H), 8.09 (1H), 7.62 (1H), 7.53 (1H), 7.37 (1H), 7.21 (1H), 6.23 (1H), 5.33 (1H), 4.87 (1H), 3.17 (1H), 2.97 (2H), 2.72 (2H), 2.35-2.20 (5H), 2.07 (1H), 1.67 (1H), 1.49 (3H), 1.41-1.22 (4H). Example 251: MS obsd (ESI+): 525.5 [M +H] +. H NMR (400 MHz, DMSO-$d_6$) δ 8.80 (1H), 8.30 (1H), 7.98 (1H), 7.62 (1H), 7.52 (1H), 7.36 (1H), 7.21 (1H), 6.23 (1H), 5.38-5.27 (1H), 5.22 (1H), 3.61 (1H), 2.83 (2H), 2.40 (2H), 2.07 (3H), 1.70-1.58 (2H), 1.50 (3H), 1.33 (4H). |

-continued

| Example number | Compound Structure | Compound Name | Characterization |
|---|---|---|---|
| 252 and 253 | 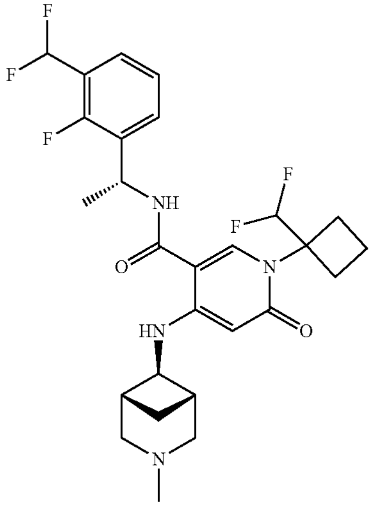 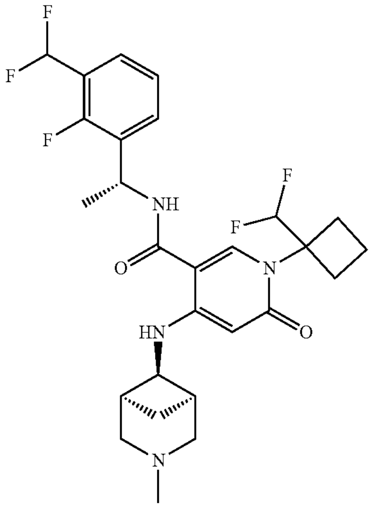 | N-((R)-1-(3-(difluoromethyl)-2-fluorophenyl)ethyl)-1-(1-(difluoromethyl) cyclobutyl)-4-(((1R,5S,6s)-3-methyl-3-azabicyclo[3.1.1]heptan-6-yl)amino)-6-oxo-1,6-dihydropyridine-3-carboxamide and N-((R)-1-(3-(difluoromethyl)-2-fluorophenyl)ethyl)-1-(1-(difluoromethyl) cyclobutyl)-4-(((1R,5S,6r)-3-methyl-3-azabicyclo[3.1.1]heptan-6-yl)amino)-6-oxo-1,6-dihydropyridine-3-carboxamide (diastereomers unassigned) | Example 252: MS obsd (ESI+): 539.2 $[M + H]^+$. $^1H$ NMR (400 MHz, DMSO-$d_6$) δ: 8.92 (1H), 8.28 (1H), 7.80 (1H), 7.62 (1H), 7.53 (1H), 7.36 (1H), 7.22 (1H), 6.36 (1H), 5.33 (1H), 4.85 (1H), 3.17 (1H), 2.99 (1H), 2.96 (1H), 2.71 (2H), 2.65 (4H), 2.31 (3H), 2.27 (2H), 2.07 (1H), 1.95-1.79 (2H), 1.68 (1H), 1.49 (3H). Example 253: MS obsd (ESI+): 539.2 $[M + H]^+$. $^1H$ NMR (400 MHz, DMSO-$d_6$) δ: 8.89 (1H), 8.20 (1H), 7.70 (1H), 7.62 (1H), 7.52 (1H), 7.35 (1H), 7.21 (1H), 6.35 (1H), 5.32 (1H), 5.21 (1H), 3.62 (1H), 2.91-2.78 (2H), 2.74-2.58 (4H), 2.45 (1H), 2.36 (1H), 2.08 (3H), 1.87 (2H), 1.64 (2H), 1.49 (3H). |

-continued

| Example number | Compound Structure | Compound Name | Characterization |
| --- | --- | --- | --- |
| 254 and 255 | 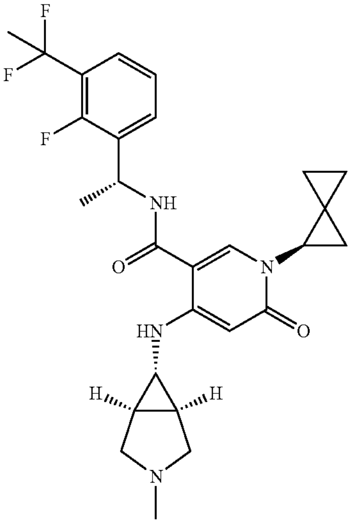 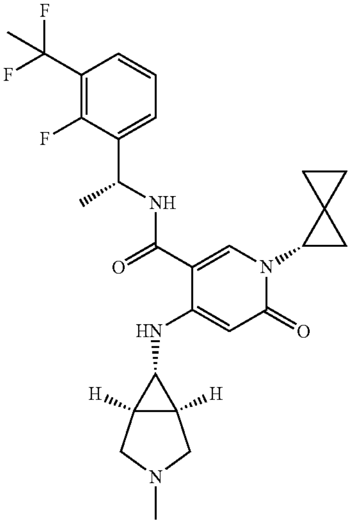 | N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide and N-((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide (diastereomers unassigned) | Example 254: MS obsd (ESI+): 501.4 $[M + H]^+$. Analytical chiral UPCC: (Column: CHIRALPAK AD-3 4.6 * 100 mm 3 um, Flow rate: 3.0 mL/min, Cosolvent: MeOH(0.2% 7M NH3 in MeOH), Temp 40° C.) Retention time = 0.7 min Example 255: MS obsd (ESI+): 501.4 $[M + H]^+$. Analytical chiral UPCC: (Column: CHIRALPAK AD-3 4.6 * 100 mm 3 um, Flow rate: 3.0 mL/min, Cosolvent: MeOH(0.2% 7M NH3 in MeOH), Temp 40° C.) Retention time = 1.6 min |

-continued

| Example number | Compound Structure | Compound Name | Characterization |
|---|---|---|---|
| 256 and 257 | 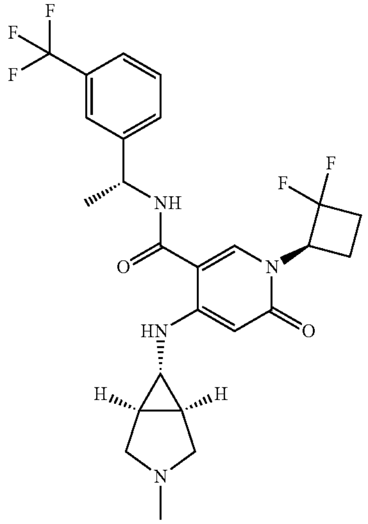 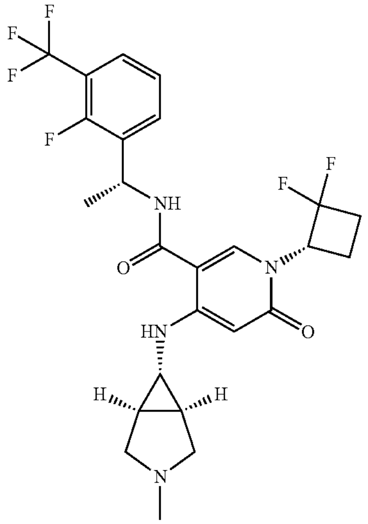 | 1-((R)-2,2-difluorocyclobutyl)-4-(((1R,5S,6s)-3-methyl-3-azabicyclo[3.1.0]hexan-6-yl)amino)-6-oxo-N-((R)-1-(3-(trifluoromethyl)phenyl)ethyl)-1,6-dihydropyridine-3-carboxamide and 1-((S)-2,2-difluorocyclobutyl)-4-(((1R,5S,6s)-3-methyl-3-azabicyclo[3.1.0]hexan-6-yl)amino)-6-oxo-N-((R)-1-(3-(trifluoromethyl)phenyl)ethyl)-1,6-dihydropyridine-3-carboxamide (diastereomers unassigned) | Example 256: MS obsd (ESI+): 511.2 $[M + H]^+$. Analytical chiral UPCC: (Column: CHIRALPAK-OD-3 4.6 * 100 mm 3 um, Flow rate: 3.0 mL/min, Cosolvent: MeOH(0.2% 7M NH3 in MeOH), Temp 40° C.) Retention time = 1.1 min Example 257: MS obsd (ESI+): 511.4 $[M + H]^+$. Analytical chiral UPCC: (Column: CHIRALPAK-OD-3 4.6 * 100 mm 3 um, Flow rate: 3.0 mL/min, Cosolvent: MeOH(0.2% 7M NH3 in MeOH), Temp 40° C.) Retention time = 1.8 min |

-continued

| Example number | Compound Structure | Compound Name | Characterization |
|---|---|---|---|
| 258 and 259 | 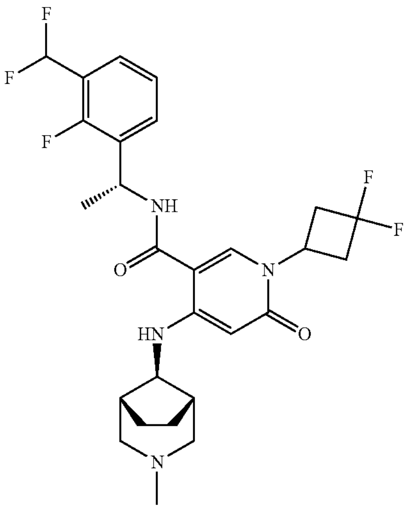 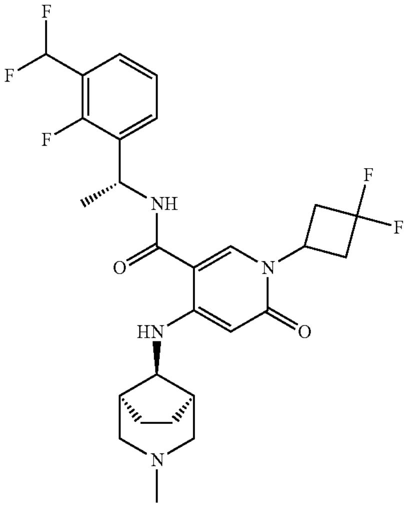 | 1-(3,3-difluorocyclobutyl)-N-((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide and 1-(3,3-difluorocyclobutyl)-N-((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide (diastereomers unassigned) | Example 258: MS obsd (ESI+): 539.3 $[M + H]^+$. Analytical chiral UPCC: (Column: Cellulose-SC 4.6 * 100 mm 3 um, Flow rate: 3.0 mL/min, Cosolvent: MeOH(0.2% 7M NH3 in MeOH), Temp 40° C.) Retention time = 1.8 min Example 259: MS obsd (ESI+): 539.5 $[M + H]^+$. Analytical chiral UPCC: (Column: Cellulose-SC 4.6 * 100 mm 3 um, Flow rate: 3.0 mL/min, Cosolvent: MeOH(0.2% 7M NH3 in MeOH), Temp 40° C.) Retention time = 1.3 min |

-continued

| Example number | Compound Structure | Compound Name | Characterization |
|---|---|---|---|
| 260 and 261 | 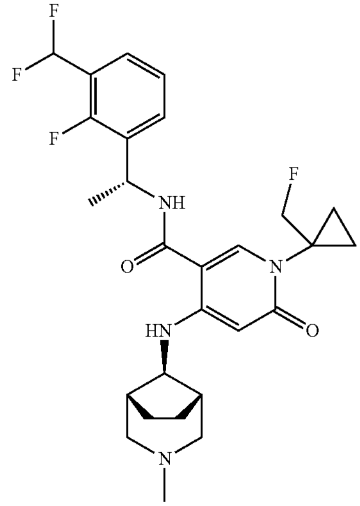 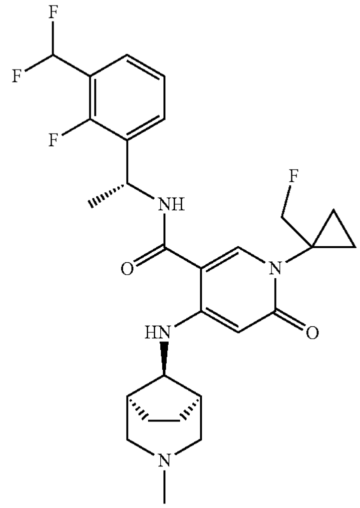 | N-((R)-1-(3-(difluoromethyl)-2-fluorophenyl)ethyl)-1-(1-(fluoromethyl) cyclopropyl)-4-(((1R,5S,8r)-3-methyl-3-azabicyclo[3.2.1]octan-8-yl)amino)-6-oxo-1,6-dihydropyridine-3-carboxamide and N-((R)-1-(3-(difluoromethyl)-2-fluorophenyl)ethyl)-1-(1-(fluoromethyl) cyclopropyl)-4-(((1R,5S,8s)-3-methyl-3-azabicyclo[3.2.1]octan-8-yl)amino)-6-oxo-1,6-dihydropyridine-3-carboxamide (diastereomers unassigned) | Example 260: MS obsd (ESI+): 521.3 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.0 min Example 261: MS obsd (ESH): 521.3 $[M + H]^+$. Analytical chiral UPCC: (Column: CHIRALPAK OZ-3 4.6 * 100 mm 3 um, Flow rate: 3.0 mL/min, Cosolvent: MeOH(0.2% 7M NH3 in MeOH), Temp 40° C.) Retention time = 1.4 min |

Example 262: (R)-1-(bicyclo[1.1.1]pentan-1-yl)-N-(1-(3-(difluoromethyl)-2-fluorophenyl)ethyl)-4-(((3-methoxybicyclo[1.1.1]pentan-1-yl)methyl)amino)-6-oxo-1,6-dihydropyridine-3-carboxamide

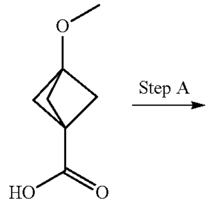

-continued

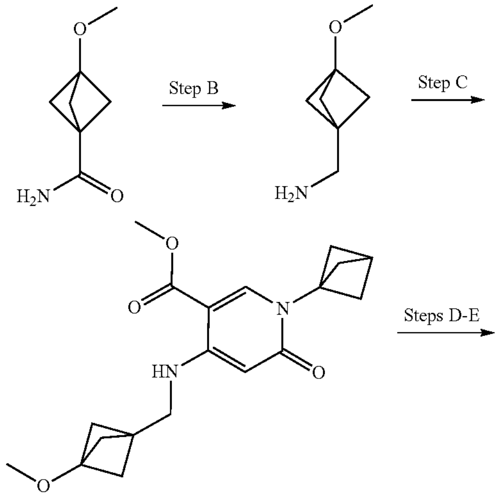

-continued

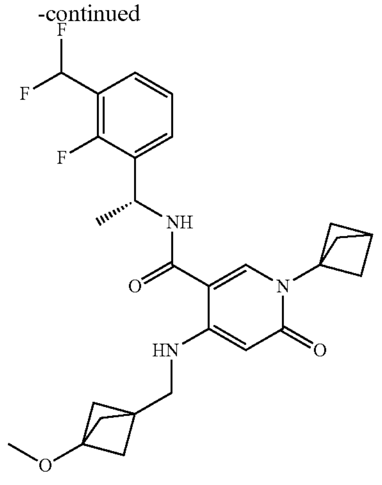

example 262

Step A: 3-Methoxybicyclo[1.1.1]pentane-1-carboxamide

A mixture of 3-methoxybicyclo[1.1.1]pentane-1-carboxylic acid (500 mg, 3.52 mmol) in $SOCl_2$ (5 mL) was heated to 50° C. and stirred for 2 hrs. Then the volatiles were removed in vacuo. To the residue was added ammonium hydroxide (5 mL) at 0° C. and the mixture was stirred for 1 h. The solvent was removed in vacuo to afford the crude target compound (391 mg, crude), which was used without further purification. MS obsd (ESI+): 142.3 $[M+H]^+$.

Step B: (3-Methoxybicyclo[1.1.1]pentan-1-yl)methanamine

A mixture of 3-methoxybicyclo[1.1.1]pentane-1-carboxamide (391 mg, crude) in 1M $BH_3$-THF (5 mL) was stirred for 16 hrs at rt. Then ice water (10 mL) was added into the mixture dropwise and stirred for 30 min. Then the mixture was extracted with DCM (3×40 mL). The combined organic layers were dried over $Na_2SO_4$ and concentrated in vacuo to afford the crude title compound (236 mg). MS obsd (ESI+): 128.3 $[M+H]^+$.

Step C: Methyl 1-(bicyclo[1.1.1]pentan-1-yl)-4-(((3-methoxybicyclo[1.1.1]pentan-1-yl)methyl)amino)-6-oxo-1,6-dihydropyridine-3-carboxylate To a mixture of (3-methoxy-1-bicyclo[1.1.1]pentanyl) methanamine (203 mg, crude) and methyl 1-(bicyclo[1.1.1]pentan-1-yl)-6-oxo-4-(((trifluoromethyl)sulfonyl)oxy)-1,6-dihydropyridine-3-carboxylate (451 mg, 1.23 mmol) in DMSO (2 mL) was added triethylamine (373 mg, 3.68 mmol). The mixture was stirred for 3 hrs at 80° C. The mixture was quenched with water and extracted with DCM (3×80 mL). The combined organic layers were washed with water (3×50 mL), dried over $Na_2SO_4$, filtered and concentrated. The residue was purified by silica gel chromatography (eluted with 0~5% MeOH in DCM) to afford the title compound (127 mg, 30% yield). MS obsd (ESI+): 345.3 $[M+H]^+$.

Steps D-E: (R)-1-(bicyclo[1.1.1]pentan-1-yl)-N-(1-(3-(difluoromethyl)-2-fluorophenyl)ethyl)-4-(((3-methoxybicyclo[1.1.1]pentan-1-yl)methyl)amino)-6-oxo-1,6-dihydropyridine-3-carboxamide (Example 263)

Steps D-E were performed according to analogous procedures described in example 62. MS obsd (ESI+): 502.4 $[M+H]^+$. $^1H$ NMR (400 MHz, DMSO-$d_6$) δ 8.84 (1H), 7.71 (1H), 7.67 (1H), 7.61 (1H), 7.53 (1H), 7.35 (1H), 7.21 (1H), 5.29 (1H), 5.12 (1H), 3.24 (2H), 3.15 (3H), 2.61 (1H), 2.29 (6H), 1.70 (6H), 1.47 (3H).

Example 263: N—((R)-1-(3-(difluoromethyl)-2-fluorophenyl)ethyl)-1-(1-(difluoromethyl)-2-oxabicyclo[2.1.1]hexan-4-yl)-4-(((1R,5S,6s)-3-methyl-3-azabicyclo[3.1.0]hexan-6-yl)amino)-6-oxo-1,6-dihydropyridine-3-carboxamide

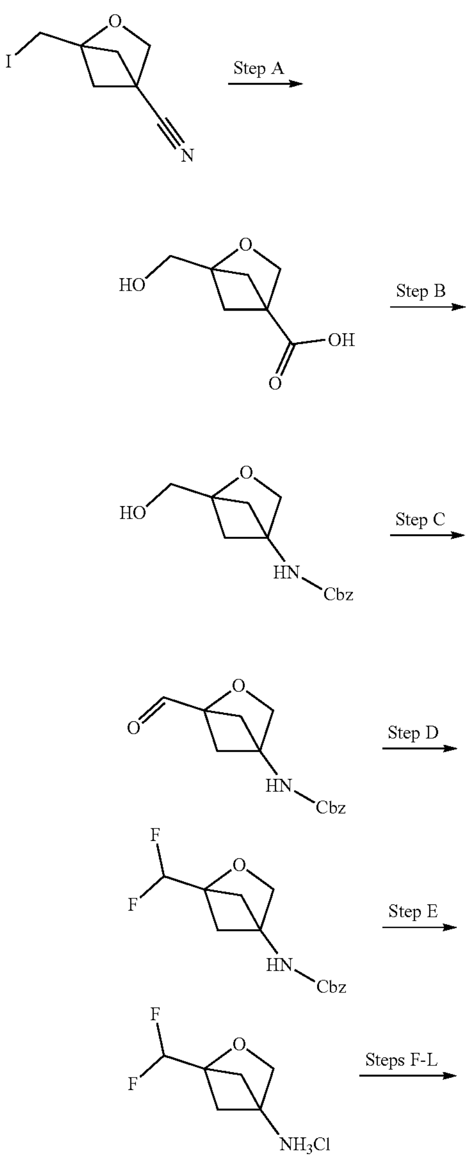

-continued

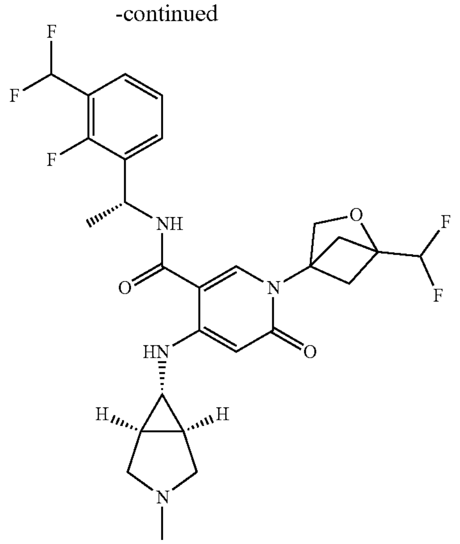

Example 263

Step A: 1-(hydroxymethyl)-2-oxabicyclo[2.1.1]hexane-4-carboxylic acid

To a solution of 1-(iodomethyl)-2-oxabicyclo[2.1.1]hexane-4-carbonitrile (3 g, 12.05 mmol, prepared according to the method of *Angew Chem.* 2020, 59, 7161-7167 in DMSO (30 mL) was added KOAc (1.77 g, 18.08 mmol). The mixture was vigorously stirred overnight at 90° C. The mixture was diluted with water (60 mL) and extracted with MTBE (3×200 mL). The combined organic layers were washed with brine, dried over anhydrous sodium sulfate. After filtration, the filtrate was concentrated under reduced pressure. The crude product was dissolved in THF (30 mL) and to the mixture was added LiOH (899 mg, 37.5 mmol) in $H_2O$ (5 mL) in portions at ambient temperature. The mixture was stirred overnight. The residue was diluted with water (50 mL), then adjusted to pH 5~6 with HCl (1M). The resulting solution was extracted with EA (3×40 mL). The organic layers were combined, washed with brine dried over $Na_2SO_4$, filtered and concentrated under reduced pressure. The residue was purified by silica gel column chromatography, (eluted with 0~100% EA/PE) to afford the title compound. GCMS (ES, m/z): 158.1 [M].

Step B: benzyl (1-(hydroxymethyl)-2-oxabicyclo[2.1.1]hexan-4-yl)carbamate

To a solution of 1-(hydroxymethyl)-2-oxabicyclo[2.1.1]hexane-4-carboxylic acid (1.58 g, 9.99 mmol) in anhydrous BnOH (16 mL), was added $(PhO)_2PON_3$ (4.12 g, 14.99 mmol) and $Et_3N$ (2.02 g, 19.98 mmol) under $N_2$ atmosphere and the mixture was stirred for 10 h at 80° C. After cooling down to rt, water (20 mL) was added and then adjusted to pH 6~7 with sodium bicarbonate. The solution was extracted with EA (3×40 mL). The organic layers were combined, washed with water, brine, dried over anhydrous $Na_2SO_4$ and concentrated under reduced pressure. The residue was purified by reverse-phase flash with the following conditions: C18, 120 g, 20~45 μm, 100 Å; mobile phase, $CH_3CN$:$H_2O$ (0.05% TFA)=20% increased to 70% in 40 min. Lyophilization afforded the title compound (600 mg, 22% yield) as a white solid. GCMS (ES, m/z): 263.3 [M].

Step C: benzyl (1-formyl-2-oxabicyclo[2.1.1]hexan-4-yl)carbamate

To a stirred mixture of benzyl (1-(hydroxymethyl)-2-oxabicyclo[2.1.1]hexan-4-yl)carbamate (3 g, 11.39 mmol) in DCM (40 mL) was added Dess-Martin Periodinane (9.67 g, 22.79 mmol) at r.t. The resulting mixture was stirred for 1 hr. The reaction mixture was quenched by water (50 ml). The resulting mixture was extracted with DCM (2×100 mL). The combined organic layers were washed with brine (100 mL), dried over anhydrous sodium sulfate. After filtration, the filtrate was concentrated under reduced pressure. The crude product was used in the next step directly without further purification (3.6 g, 13.78 mmol, Crude). MS obsd (ESI+): 262.1 $[M+H]^+$.

Step D: benzyl (1-(difluoromethyl)-2-oxabicyclo[2.1.1]hexan-4-yl)carbamate

To a stirred mixture of benzyl (1-formyl-2-oxabicyclo[2.1.1]hexan-4-yl)carbamate (3.6 g, crude) in DCM (50 mL) was added DAST (6.66 g, 41.34 mmol) at 0° C. The resulting mixture was stirred at r.t. for 16 h. The reaction mixture was quenched by water. The resulting mixture was extracted with DCM (2×200 mL). The combined organic layers were washed with brine (300 mL), dried over anhydrous sodium sulfate. After filtration, the filtrate was concentrated under reduced pressure. The reaction mixture was purified by reverse-phase flash with the following conditions: C18, 330 g, 20~45 μm, 100 Å; mobile phase, $CH_3CN$:$H_2O$ (0.05% $NH_4HCO_3$)=10% increased to 60% in 35 min. Lyophilization afforded the title compound (500 mg). MS obsd (ESI+): 284.1 $[M+H]^+$.

Step E: 1-(difluoromethyl)-2-oxabicyclo[2.1.1]hexan-4-amine hydrochloride

To a solution of benzyl (1-(difluoromethyl)-2-oxabicyclo[2.1.1]hexan-4-yl)carbamate (500 mg, 1.77 mmol) in EA (7 mL) and MeOH (7 mL) was added Pd/C (10%, 430 mg) in a pressure tank. The mixture was stirred at room temperature under 30 psi of hydrogen pressure for 16 h. The reaction mixture was filtered through a Celite pad and the filtrate concentrated under reduced pressure. The crude product was dissolved in MTBE (5 mL) and precipitated by the addition of HCl (0.5 mL, 2.0 mmol, 4M in dioxane). The precipitated solids were collected by filtration and washed with MTBE (5 mL) to afford the title compound (236.3 mg, 72% yield). MS obsd (ESI+): 150.2 $[M+H]^+$. $^{19}F$ NMR (376 MHz, DMSO-$d_6$) δ −128.55.

Steps F-L: N—((R)-1-(3-(difluoromethyl)-2-fluorophenyl)ethyl)-1-(1-(difluoromethyl)-2-oxabicyclo[2.1.1]hexan-4-yl)-4-(((1R,5S,6s)-3-methyl-3-azabicyclo[3.1.0]hexan-6-yl)amino)-6-oxo-1,6-dihydropyridine-3-carboxamide Steps F-L were performed according to analogous procedures described in Examples 92-154. MS obsd (ESI+): 553.2 $[M+H]^+$. $^1H$ NMR (400 MHz, $CD_3OD$) δ: 7.83 (1H), 7.58-7.47 (2H), 7.28 (1H), 6.99 (1H), 6.12 (1H), 5.64 (1H), 5.35 (1H), 4.02 (2H), 3.22 (2H), 2.70 (2H), 2.57 (1H), 2.48 (2H), 2.46-2.38 (3H), 2.36 (2H), 1.70 (2H), 1.54 (3H).

Example 264: 1-(1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide

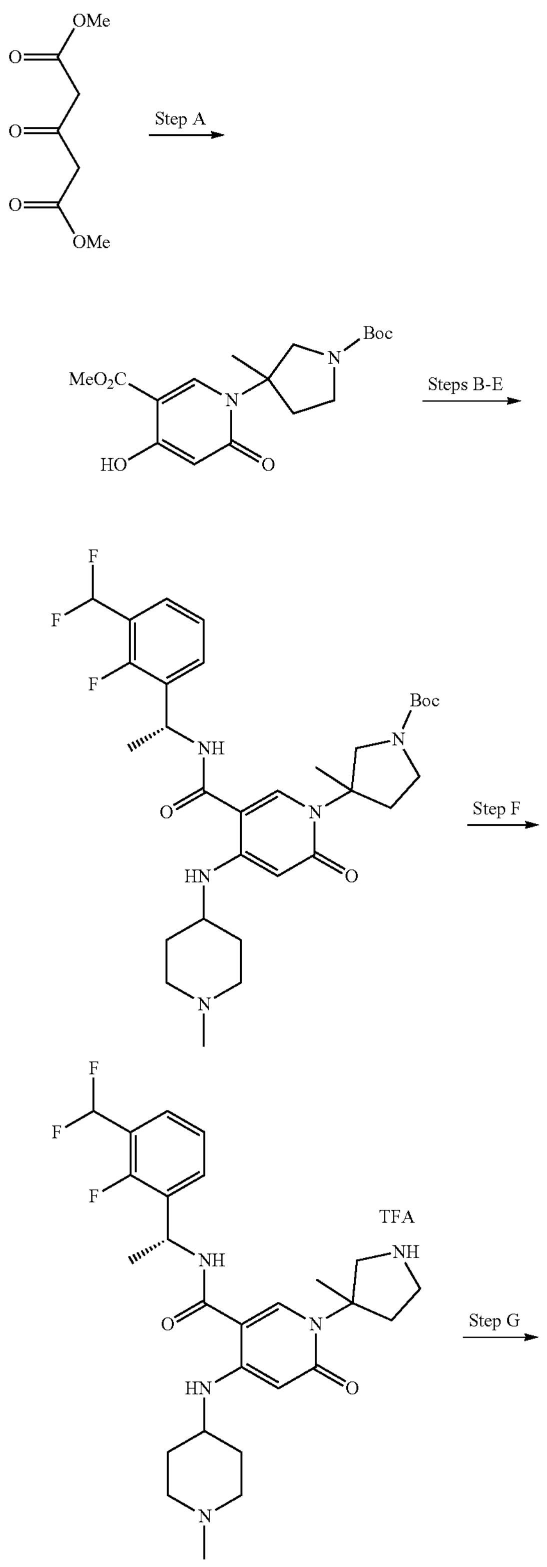

-continued

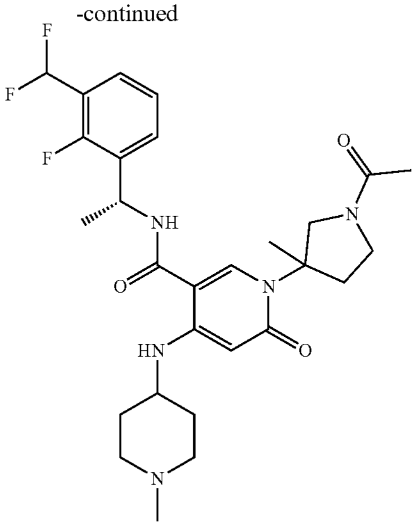

Example 264

Step A: methyl 1-(1-(tert-butoxycarbonyl)-3-methylpyrrolidin-3-yl)-4-hydroxy-6-oxo-1,6-dihydropyridine-3-carboxylate To a solution of dimethyl 3-oxopentanedioate (220 mg, 1.26 mmol) in methanol (10 mL) was added 1,1-dimethoxy-N,N-dimethyl-methanamine (181 mg, 1.52 mmol). The mixture was stirred at rt for 4 h. Then tert-butyl 3-amino-3-methyl-pyrrolidine-1-carboxylate (253 mg, 1.26 mmol) was added. The reaction was stirred for 16 h at rt. Sodium methoxide (136 mg, 2.52 mmol) was added and the mixture was stirred for 1 h at rt. The reaction was quenched with $H_2O$ (10 mL) and the mixture was adjusted to PH=3 using citric acid (aq). The mixture was extracted with DCM (3×15 mL) and the combined organic layers were dried over $Na_2SO_4$ and filtered. The solvent was removed in vacuo and the residue was purified by flash column chromatography (eluting with 0%-60%) to afford the title compound (320 mg, 72% yield). MS obsd. ($ESI^+$): 297.3 [$(M-tBu+H)^+$].

Steps B-E: tert-butyl 3-(5-(((R)-1-(3-(difluoromethyl)-2-fluorophenyl)ethyl)carbamoyl)-4-((1-methylpiperidin-4-yl)amino)-2-oxopyridin-1 (2H)-yl)-3-methylpyrrolidine-1-carboxylate Synthesized in an analogous manner to example 49 steps B-E. MS obsd (ESI+): 606.7 $[M+H]^+$.

Step F: N—((R)-1-(3-(difluoromethyl)-2-fluorophenyl)ethyl)-4-((1-methylpiperidin-4-yl)amino)-1-(3-methylpyrrolidin-3-yl)-6-oxo-1,6-dihydropyridine-3-carboxamide trifluoroacetate salt To a solution of tert-butyl 3-(5-(((R)-1-(3-(difluoromethyl)-2-fluorophenyl)ethyl)carbamoyl)-4-((1-methylpiperidin-4-yl)amino)-2-oxopyridin-1 (2H)-yl)-3-methylpyrrolidine-1-carboxylate (125 mg, 0.21 mmol) in DCM (3 mL) was added TFA (1 mL). The reaction was stirred for 1 h at rt. The solvent was removed in vacuo to afford the title compound (128 mg, crude). The crude product was used for the next step without further purification. MS obsd (ESI+): 506.6 $[M+H]^+$.

Step G: 1-(1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide To a solution of N—((R)-1-(3-(difluoromethyl)-2-fluorophenyl)ethyl)-4-((1-methylpiperidin-4-yl)amino)-1-(3-methylpyrrolidin-3-yl)-6-oxo-1,6-dihydropyridine-3-carboxamide trifluoroacetate salt (113 mg, 0.18 mmol) in DMF (5 mL) was added HATU (83 mg, 0.22 mmol, 1.2 eq.). The reaction was stirred for 1 h at rt. Then acetic acid (13 mg, 0.22 mmol) and DIPEA (70 mg, 0.55 mmol) were added and the reaction was stirred for 3 h at rt. The mixture was diluted with water and extracted into DCM (3x20 mL). The combined organic layers were dried over $Na_2SO_4$, filtered and concentrated. The residue was purified by flash column chromatography (eluting with 0-50% MeOH in DCM) followed by preparative HPLC (ACN/water/0.1% $NH_4HCO_3$) to afford the title compound (33 mg, 33% yield). MS obsd (ESI+): 548.5 $[M+H]^+$. $^1H$ NMR (400 MHz, DMSO-$d_6$) δ ppm 8.87-8.72 (1H), 87.84 (1H), 7.72-7.57 (2H), 7.53 (1H), 7.38-7.07 (2H), 5.34-5.24 (1H), 5.22 (1H), 4.39-4.21 (1H), 3.66-3.52 (2H), 3.45-3.24 (3H), 2.59 (2H), 2.38 (1H), 2.15 (5H), 1.95 (3H), 1.82 (2H), 1.55-1.44 (6H), 1.42-1.28 (2H).

Examples 265 and 266: 1-((S)-1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide (Example 265) and 1-((R)-1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide (Example 266) (Diastereomers Unassigned)

Example 265 and 266

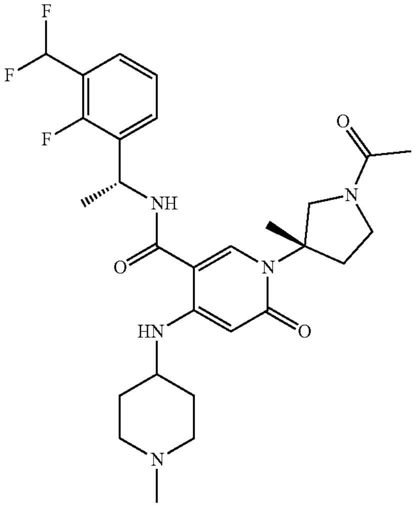

-continued

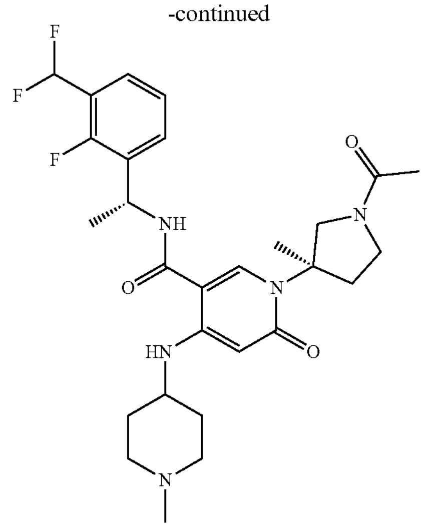

Example 264 was separated into individual diatereomers via chiral SFC: (Column: Daicel AS (25*250 mm, 10 um), mobile phase: CO2/EtOH [0.5% NH3 (7M in MeOH)]=85/15).

Example 265: MS obsd (ESI+): 548.5 $[M+H]^+$. Analytical chiral UPCC: (Column: CHIRALPAK AS-3 4.6*100 mm 3 um, Flow rate: 3.0 mL/min, Cosolvent:EtOH (1% 7M NH3 in MeOH), Temp 40° C.) Retention time=0.9 min Example 266: MS obsd (ESI+): 548.5 $[M+H]^+$. Analytical chiral UPCC: (Column: CHIRALPAK AS-3 4.6*100 mm 3 um, Flow rate: 3.0 mL/min, Cosolvent:EtOH (1% 7M NH3 in MeOH), Temp 40° C.) Retention time=2.0 min Example 267: N—((R)-1-(3-(difluoromethyl)-2-fluorophenyl)ethyl)-1-(1-(1-fluorocyclopropane-1-carbonyl)-3-methylpyrrolidin-3-yl)-4-((1-methylpiperidin-4-yl)amino)-6-oxo-1,6-dihydropyridine-3-carboxamide Example 267

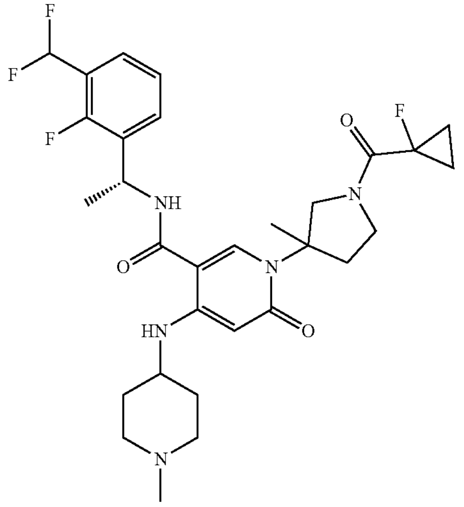

Example 267 was synthesized according to analogous procedures described in example 264. MS obsd (ESI+):

592.4 [M+H]+. $^1$H NMR (400 MHz, DMSO-d6, some protons obscured by solvent peak) δ ppm 8.80 (1H), 7.87 (1H), 7.67-7.60 (3H), 7.36-7.10 (2H), 5.34-5.18 (2H), 4.77-4.32 (1H), 3.92-3.46 (3H), 3.23 (1H), 2.13-2.07 (5H), 1.82 (2H), 1.62-1.42 (6H), 1.42-1.03 (6H).

Examples 268 and 269: N—((R)-1-(3-(difluoromethyl)-2-fluorophenyl)ethyl)-1-((S)-1-(1-fluorocyclopropane-1-carbonyl)-3-methylpyrrolidin-3-yl)-4-((1-methylpiperidin-4-yl)amino)-6-oxo-1,6-dihydropyridine-3-carboxamide (Example 268) and N—((R)-1-(3-(difluoromethyl)-2-fluorophenyl) ethyl)-1-((R)-1-(1-fluorocyclopropane-1-carbonyl)-3-methylpyrrolidin-3-yl)-4-((1-methylpiperidin-4-yl) amino)-6-oxo-1,6-dihydropyridine-3-carboxamide (Example 269) (Diastereomers not Assigned)

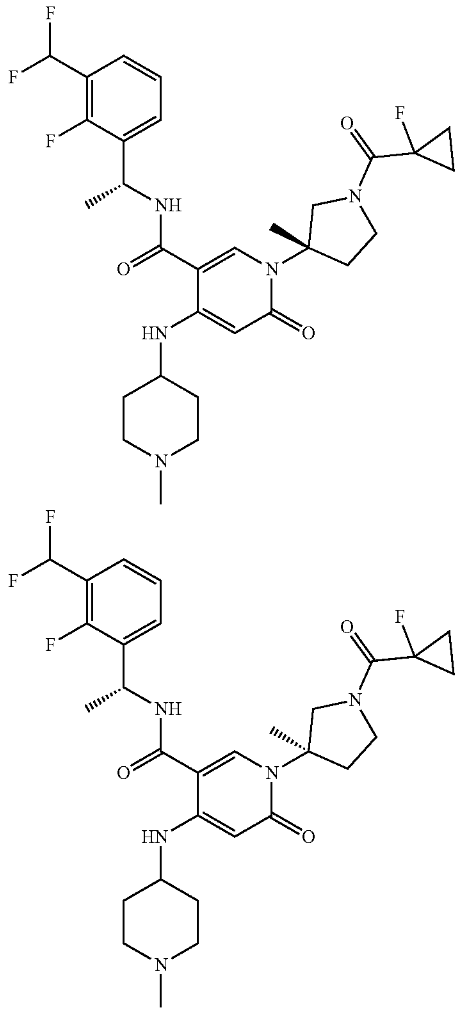

Examples 268 and 269

Example 267 was separated via Chiral-SFC (YMC Cellulose-SC (4.6*100 mm, 3 um) CO2/MeOH [0.2% $NH_3$ (7M in MeOH)]=65/35) to afford the individual diastereomers.

Example 268: MS obsd (ESI+): 592.5 [M+H]+. Analytical chiral UPCC: (Column: Cellulose-SC 4.6*100 mm 3 um, Flow rate: 3.0 mL/min, Cosolvent: MeOH (0.2% 7M NH3 in MeOH), Temp 40° C.) Retention time=2.0 min Example 269: MS obsd (ESI+): 592.5 [M+H]+. Analytical chiral UPCC: (Column: Cellulose-SC 4.6*100 mm 3 um, Flow rate: 3.0 mL/min, Cosolvent: MeOH (0.2% 7M NH3 in MeOH), Temp 40° C.) Retention time=4.3 min Example 270: 1-(1-(cyclopropanecarbonyl)-3-methylazetidin-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide

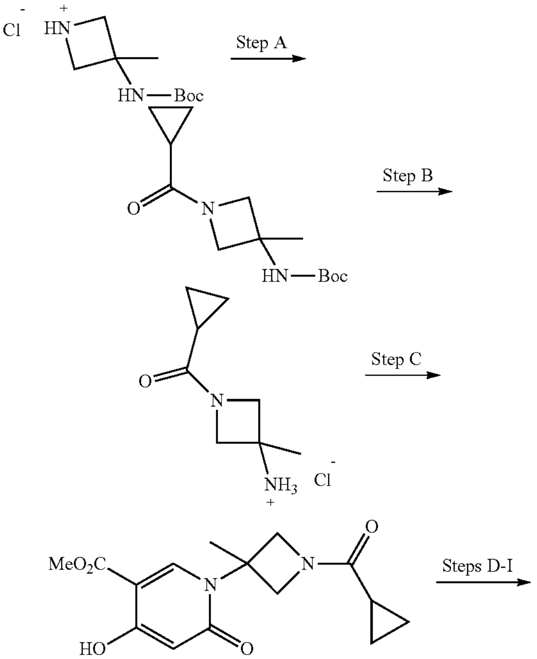

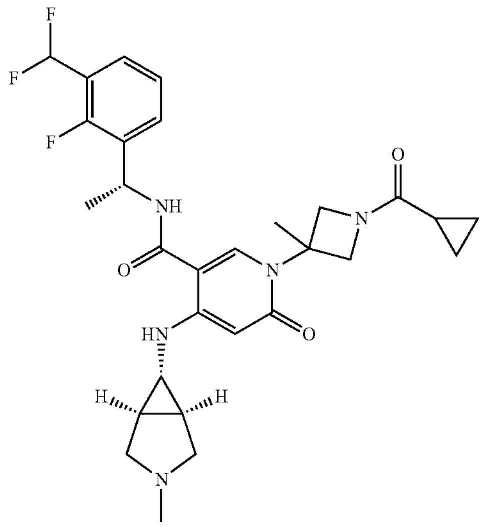

Example 270

Step A: Tert-butyl (1-(cyclopropanecarbonyl)-3-methylazetidin-3-yl)carbamate

To a solution of 3-((tert-butoxycarbonyl)amino)-3-methylazetidin-1-ium chloride (267 mg, 1.20 mmol) in DCM (8 mL) was added TEA (485 mg, 4.79 mmol) and cyclopropanecarbonyl chloride (125 mg, 1.20 mmol) at 0° C., then the mixture was stirred at rt for 3 hr. The mixture was poured into $NaHCO_3$ aq. (30 mL) at 0° C., then extracted with DCM (30 mL×3), the combined organic layers were dried over $Na_2SO_4$, filtered and concentrated. The residue was purified by column chromatography on silica gel (MeOH/DCM, 0-6%) to afford the title compound (288 mg, 94% yield). $^1H$ NMR (400 MHz, $CDCl_3$) δ: 4.86 (s, 1H), 4.25 (s, 2H), 3.96 (d, J=8.6 Hz, 2H), 1.58 (s, 3H), 1.46 (s, 9H), 1.39 (m, 1H), 1.01-0.93 (m, 2H), 0.80-0.71 (m, 2H).

Step B: 1-(cyclopropanecarbonyl)-3-methylazetidin-3-aminium chloride

Tert-butyl (1-(cyclopropanecarbonyl)-3-methylazetidin-3-yl)carbamate (288 mg, 1.13 mmol) was dissolved in HCl in dioxane (5 mL, 4 M). The mixture was stirred at rt for 1 h, after which the mixture was evaporated to afford the crude title compound (210 mg, 97% yield). $^1H$ NMR (400 MHz, DMSO-$d_6$) δ: 8.83 (s, 3H), 4.35 (d, J=9.2 Hz, 1H), 4.17 (d, J=9.2 Hz, 1H), 3.96 (d, J=10.2 Hz, 1H), 3.74 (d, J=10.2 Hz, 1H), 1.60-1.51 (m, 4H), 0.77-0.67 (m, 4H).

Step C: methyl 1-(1-(cyclopropanecarbonyl)-3-methylazetidin-3-yl)-4-hydroxy-6-oxo-1,6-dihydropyridine-3-carboxylate To a solution of dimethyl 3-oxopentanedioate (250 mg, 1.44 mmol) in methanol (5 mL) was added 1,1-dimethoxy-N,N-dimethyl-methanamine (257 mg, 2.15 mmol), and the mixture was stirred at rt for 6 h. Then, 1-(cyclopropanecarbonyl)-3-methylazetidin-3-aminium chloride (210 mg, 1.10 mmol) and TEA (265 mg, 2.62 mmol) were added. The mixture was stirred at rt for 16 hr, then the reaction mixture was concentrated and the residue was purified by column chromatography on silica gel (MeOH/DCM, 0-20%) to afford the title compound (123 mg, 30% yield). MS obsd (ESI+): 307.3 $[M+H]^+$.

Steps D-I: 1-(1-(cyclopropanecarbonyl)-3-methylazetidin-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide Steps D-I were performed according to analogous procedures described in examples 92-154. MS obsd (ESI+): 558.6 $[M+H]^+$. $^1H$ NMR (400 MHz, DMSO-$d_6$) δ: 8.74 (1H), 7.87 (1H), 7.81 (1H), 7.63 (1H), 7.52 (1H), 7.35 (1H), 7.21 (1H), 5.36 (1H), 5.26 (1H), 4.58 (1H), 4.40 (1H), 4.34 (1H), 3.92 (1H), 3.00 (2H), 2.48 (1H), 2.28 (2H), 2.20 (3H), 1.71 (3H), 1.59 (1H), 1.50 (2H), 1.47 (3H), 0.79-0.70 (3H), 0.66 (1H).

Examples 271-274: N—((R)-1-(3-(difluoromethyl)-2-fluorophenyl)ethyl)-4-(((1R,5S,6s)-3-methyl-3-azabicyclo[3.1.0]hexan-6-yl)amino)-1-((1S,2S)-2-methylcyclopropyl)-6-oxo-1,6-dihydropyridine-3-carboxamide (Example 271), N—((R)-1-(3-(difluoromethyl)-2-fluorophenyl)ethyl)-4-(((1R,5S,6s)-3-methyl-3-azabicyclo[3.1.0]hexan-6-yl)amino)-1-((1R,2R)-2-methylcyclopropyl)-6-oxo-1,6-dihydropyridine-3-carboxamide (Example 272), N—((R)-1-(3-(difluoromethyl)-2-fluorophenyl)ethyl)-4-(((1R,5S,6s)-3-methyl-3-azabicyclo[3.1.0]hexan-6-yl)amino)-1-((1S,2R)-2-methylcyclopropyl)-6-oxo-1,6-dihydropyridine-3-carboxamide (Example 273), N—((R)-1-(3-(difluoromethyl)-2-fluorophenyl)ethyl)-4-(((1R,5S,6s)-3-methyl-3-azabicyclo[3.1.0]hexan-6-yl)amino)-1-((1R,2S)-2-methylcyclopropyl)-6-oxo-1,6-dihydropyridine-3-carboxamide (Example 274) (Diastereomers not Assigned)

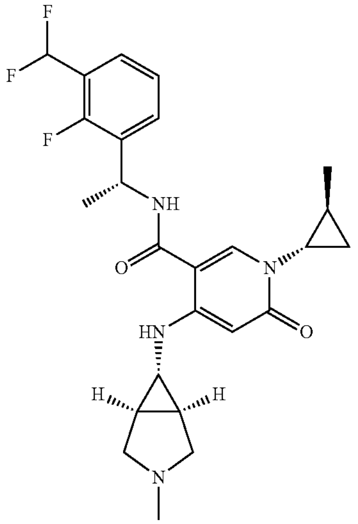

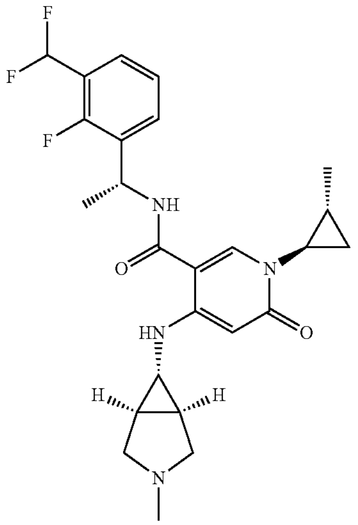

-continued

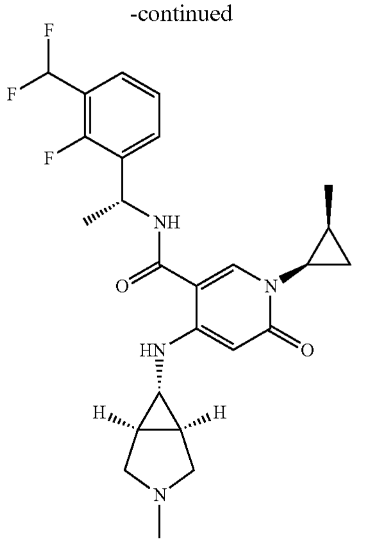

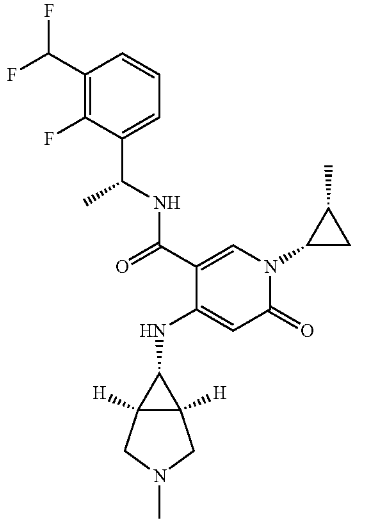 [SMILES: C[C@@H]1C[C@@H]1n1cc(C(=O)N[C@H](C)c2cccc(C(F)F)c2F)c(N[C@H]2[C@@H]3CN(C)C[C@@H]32)cc1=O]

Examples 271, 272, 273, 274

Examples 271-274 were synthesized according to analogous procedures described in examples 92-154. Diastereomers were first separated via chiral SFC (YMC Cellulose-SC (4.6*100 mm, 3 um) $CO_2$/EtOH [0.5% $NH_3$ (7M in MeOH)]=75/25) to afford 2 mixed fractions. The first eluting fraction was further separated by chiral SFC: (Regis (R,R)-Whelk-O1 (25*250 mm, 10 um) $CO_2$/EtOH [0.5% $NH_3$ (7M in MeOH)]=70/30) to afford 2 isomers.

Example 271: MS obsd (ESI+): 475.3 $[M+H]^+$. Analytical chiral UPCC: (Column: Regis (R,R)-Whelk-O1 4.6*100 mm 3 um, Flow rate: 3.0 mL/min, Cosolvent:EtOH (1% 7M NH3 in MeOH), Temp 40° C.) Retention time=1.7 min Example 272: MS obsd (ESI+): 475.3 $[M+H]^+$. Analytical chiral UPCC: (Column: Regis (R,R)-Whelk-O1 4.6*100 mm 3 um, Flow rate: 3.0 mL/min, Cosolvent:EtOH (1% 7M NH3 in MeOH), Temp 40° C.) Retention time=2.2 min The second eluting fraction from the initial purification was further separated by chiral SFC (Daicel OZ-3 (25*250 mm, 10 um) $CO_2$/MeOH [0.2% $NH_3$ (7M in MeOH)]=75/25) to afford 2 isomers.

Example 273: MS obsd (ESI+): 475.3 $[M+H]^+$. Analytical chiral UPCC: (Column: CHIRALPAK OZ-3 4.6*100 mm 3 um, Flow rate: 3.0 mL/min, Cosolvent: MeOH (0.2% 7M NH3 in MeOH), Temp 40° C.) Retention time=1.0 min Example 274: MS obsd (ESI+): 475.3 $[M+H]^+$. Analytical chiral UPCC: (Column: CHIRALPAK OZ-3 4.6*100 mm 3 um, Flow rate: 3.0 mL/min, Cosolvent: MeOH (0.2% 7M NH3 in MeOH), Temp 40° C.) Retention time=1.6 min Examples 275 and 276: N—((S)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Example 275) and N—((R)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Example 276) (Unassigned Stereoisomers)

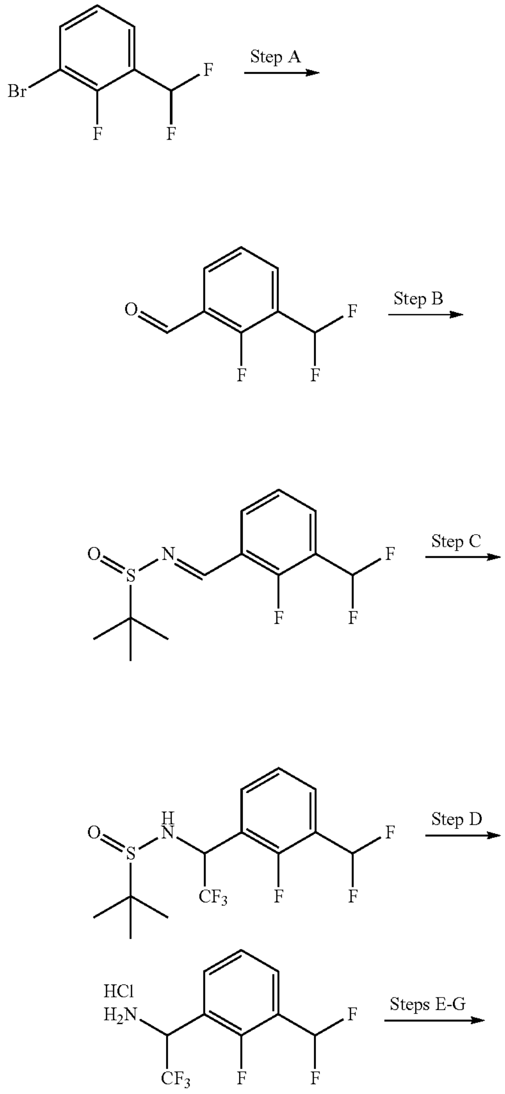

-continued

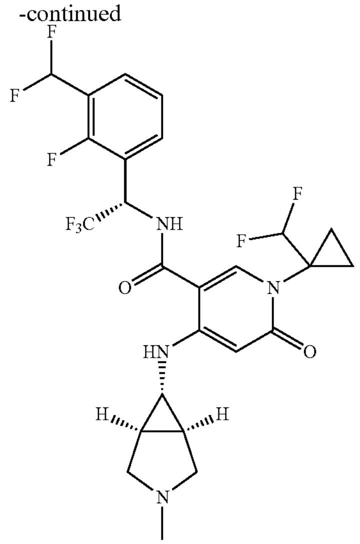

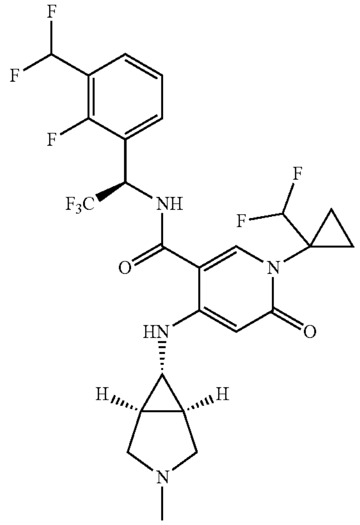

examples 275 and 276

Examples 275 and 276

Step A: 3-(difluoromethyl)-2-fluorobenzaldehyde 1-bromo-3-(difluoromethyl)-2-fluoro-benzene (2.0 g, 8.89 mmol) was dissolved in anhydrous THF (20 mL) and cooled to −78° C. n-Butyllithium (2.5 M, 3.73 mL) was added and the reaction stirred for 1 h. DMF (1.7 g, 23.73 mmol) was added to the solution. The reaction was stirred at −78° C. for 1 h and allowed to warm to room temperature for 1 hr. The reaction was quenched with saturated sodium bicarbonate and extracted with diethyl ether (50 mL×4). The combined organic layers were dried with sodium sulfate, filtered and concentrated. The residue was purified by flash chromatography (0-5% EtOAc in PE) to afford the title compound (1.2 g, 77% yield). $^1$H NMR (400 MHz, DMSO-$d_6$) δ: 10.26 (s, 1H), 8.00 (m, 2H), 7.55 (t, J=7.6 Hz, 1H), 7.32 (t, J=54.0 Hz, 1H).

Step B: N-(3-(difluoromethyl)-2-fluorobenzylidene)-2-methylpropane-2-sulfinamide To a solution of 3-(difluoromethyl)-2-fluorobenzaldehyde (1.2 g, 6.89 mmol) in THF (20 mL) was added 2-methylpropane-2-sulfinamide (1.0 g, 8.27 mmol) followed by $Ti(OEt)_4$ (3.2 g, 13.78 mmol) at rt. The reaction mixture was stirred at 60° C. for 3 hrs. The reaction mixture was concentrated and purified by flash chromatography (0-10% EA in PE) to afford the title compound (800 mg, 41% yield). MS obsd (ESI+): 278.3 $[M+H]^+$.

Step C: N-(1-(3-(difluoromethyl)-2-fluorophenyl)-2,2,2-trifluoroethyl)-2-methylpropane-2-sulfinamide To a solution of N-(3-(difluoromethyl)-2-fluorobenzylidene)-2-methylpropane-2-sulfinamide (800 mg, 2.88 mmol) and tetramethylammonium fluoride (1.1 g, 11.54 mmol) in anhydrous THF (10 mL) was added a solution of $TMSCF_3$ (6.5 g, 12.12 mmol) in THF (1 mL) dropwise at −35° C. The mixture was stirred at that temperature for 1 hr. The reaction mixture was quenched with saturated aqueous $NH_4Cl$ (60 mL) and extracted with ethyl acetate (3× 60 mL). The combined organic layers were dried over sodium sulfate, filtered and concentrated to afford the title compound (584 mg, 58% yield). MS obsd (ESI+): 348.1 $[M+H]^+$.

Step D: 1-(3-(difluoromethyl)-2-fluorophenyl)-2,2,2-trifluoroethan-1-amine hydrochloride A mixture of N-(1-(3-(difluoromethyl)-2-fluorophenyl)-2,2,2-trifluoroethyl)-2-methylpropane-2-sulfinamide (584 mg, 1.68 mmol) in HCl (5 mL, 4M in 1,4-dioxane) was stirred for 1 h at rt. The solvent was removed in vacuo. To the residue was added 20 mL ether and the mixture was stirred for 10 min and filtered to afford the title compound (470 mg, crude). MS obsd (ESI+): 244.0 $[M+H]^+$.

Steps E-G: N—((S)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide and N—((R)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide (Unassigned Stereoisomers)

Steps E-G were preformed according to analogous procedures described in Examples 92-154 steps E-G. Enantiomers were separated via chiral SFC: (column: Daicel AS (25*250 mm, 10 um)); Mobile phase: CO2/EtOH [0.5% NH3 (7M in MeOH)]=90/10).

Example 275: First eluting isomer. MS obsd (ESI+): 565.4 $[M+H]^+$. $^1$H NMR (400 MHz, DMSO-$d_6$) δ 9.48 (1H), 8.04 (1H), 7.94 (1H), 7.75 (1H), 7.64 (1H), 7.53 (1H), 7.28 (1H), 6.39-6.07 (2H), 5.39 (1H), 3.01 (2H), 2.51 (1H), 2.28 (2H), 2.20 (3H), 1.55 (2H), 1.41-1.22 (4H).

Example 276: Second eluting isomer. MS obsd (ESI+): 565.4 $[M+H]^+$.

The following compounds may be synthesized according to methods described for Examples 92-154 steps A-F

| Example number | Compound Structure | Compound Name | Characterization |
|---|---|---|---|
| 277 and 278 | 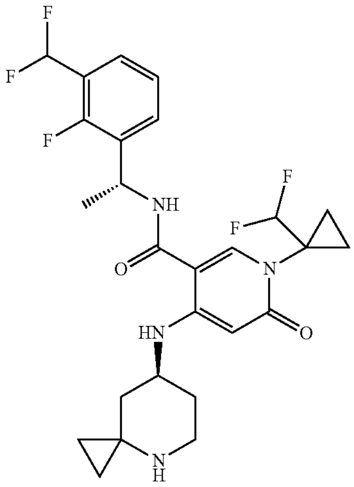 | 4-(((S)-4-azaspiro[2.5]octan-7-yl)amino)-N-((R)-1-(3-(difluoromethyl)-2-fluorophenyl)ethyl)-1-(1-(difluoromethyl) cyclopropyl)-6-oxo-1,6-dihydropyridine-3-carboxamide and 4-(((R)-4-azaspiro[2.5]octan-7-yl)amino)-N-((R)-1-(3-(difluoromethyl)-2-fluorophenyl)ethyl)-1-(1-(difluoromethyl) cyclopropyl)-6-oxo-1,6-dihydropyridine-3-carboxamide (diastereomers unassigned) | Example 277: MS obsd (ESI+): 525.2 [M + H]$^+$. Analytical chiral UPCC: (Column: YMC Cellulose-SC 4.6 * 100mm 3 um, Flow rate: 3.0 mL/min, Cosolvent: EtOH(1% 7M NH3 in MeOH), Temp 40° C.) Retention time = 1.4 min Example 278: MS obsd (ESI+): 525.2 [M + H]$^+$ Analytical chiral UPCC: (Column: YMC Cellulose-SC 4.6 * 100mm 3 um, Flow rate: 3.0 mL/min, Cosolvent: EtOH(1% 7M NH3 in MeOH), Temp 40 ° C.) Retention time = 1.7 min |
| | 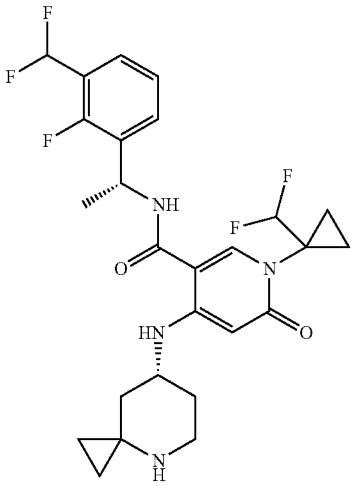 | | |
| 279 | 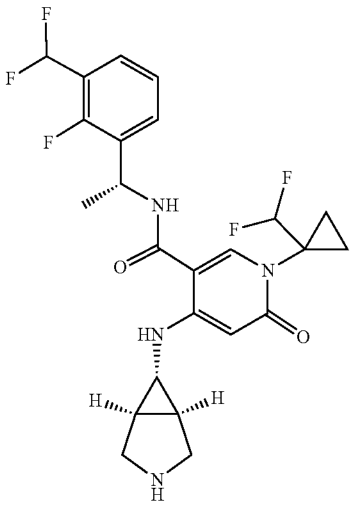 [SMILES: C[C@@H](NC(=O)c1cn(C2(C(F)F)CC2)c(=O)cc1N[C@H]1[C@@H]2CNC[C@@H]21)c1cccc(C(F)F)c1F] | 4-(((1R,5S,6s)-3-azabicyclo[3.1.0]hexan-6-yl)amino)-N-((R)-1-(3-(difluoromethyl)-2-fluorophenyl)ethyl)-1-(1-(difluoromethyl) cyclopropyl)-6-oxo-1,6-dihydropyridine-3-carboxamide | MS obsd (ESI+): 497.3 [M + H]$^+$. $^{1}$H NMR (400 MHZ, DMSO-d6) δ 8.81 (1H), 8.05 (1H), 7.95 (1H), 7.60 (1H), 7.52 (1H), 7.35 (1H), 7.21 (1H), 6.24 (1H), 5.37 (1H), 5.27 (1H), 2.96 (2H), 2.65 (2H), 2.18 (1H), 1.47 (5H), 1.39-1.22 (4H). |

-continued

| Example number | Compound Structure | Compound Name | Characterization |
|---|---|---|---|
| 280 and 281 | 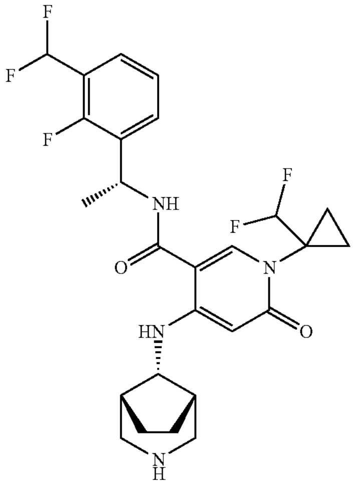 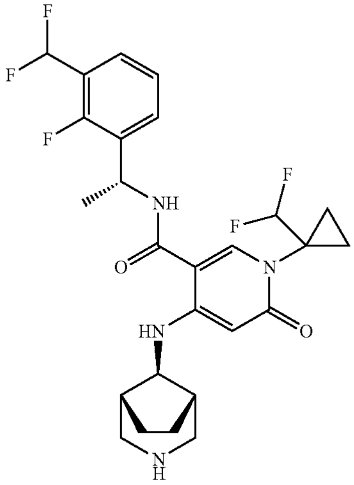 | 4-(((1R,5S,8r)-3-azabicyclo[3.2.1]octan-8-yl)amino)-N-((R)-1-(3-(difluoromethyl)-2-fluorophenyl)ethyl)-1-(1-(difluoromethyl) cyclopropyl)-6-oxo-1,6-dihydropyridine-3-carboxamide and 4-(((1R,5S,8s)-3-azabicyclo[3.2.1]octan-8-yl)amino)-N-((R)-1-(3-(difluoromethyl)-2-fluorophenyl)ethyl)-1-(1-(difluoromethyl) cyclopropyl)-6-oxo-1,6-dihydropyridine-3-carboxamide (diastereomers not assigned) | Example 280: MS obsd (ESI+): 525.5 [M + H]$^+$. $^1$H NMR (400 MHZ, DMSO-$d_6$) δ 8.86 (1H), 8.73 (1H), 8.10 (1H), 7.64 (1H), 7.54 (1H), 7.40-7.08 (2H), 6.25 (1H), 5.35 (1H), 5.21 (1H), 3.43 (1H), 2.73 (2H), 2.51 (1H), 2.38-2.27 (2H), 1.97 (2H), 1.77-1.63 (4H), 1.50 (3H), 1.35 (4H). Example 281: MS obsd (ESI+): 525.5 [M + H]$^+$. $^1$H NMR (400 MHZ, DMSO-$d_6$) 8 8.80 (1H), 8.04 (1H), 7.94 (1H), 7.60 (1H), 7.53 (1H), 7.38-7.08 (2H), 6.24 (1H), 5.30 (1H), 5.23 (1H), 3.29 (1H), 2.68 (2H), 2.58 (2H), 2.51 (1H), 2.04-1.95 (2H), 1.60-1.44 (7H), 1.34 (4H). |

Example 282: (R)—N-(1-(2-methyl-3-(trifluoromethyl)phenyl)ethyl)-6-oxo-4-(piperidin-4-ylamino)-1-(tetrahydro-2H-pyran-4-yl)-1,6-dihydropyridine-3-carboxamide

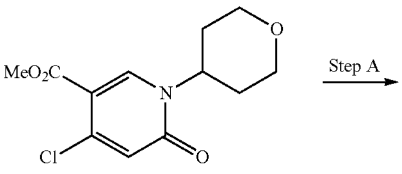

-continued

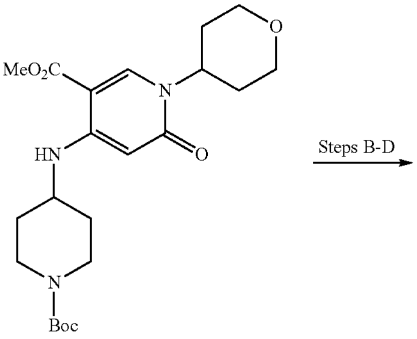

-continued

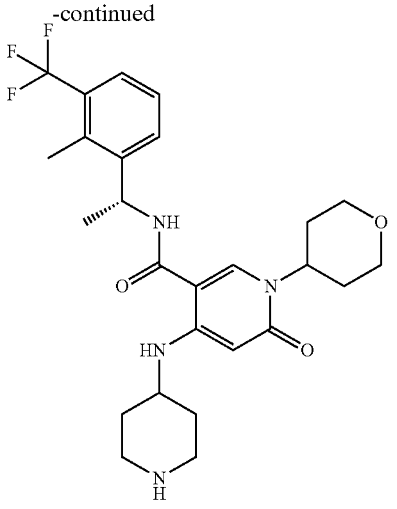

Example 282

Step A: methyl 4-((1-(tert-butoxycarbonyl)piperidin-4-yl)amino)-6-oxo-1-(tetrahydro-2H-pyran-4-yl)-1,6-dihydropyridine-3-carboxylate A mixture of methyl 4-chloro-6-oxo-1-tetrahydropyran-4-yl-pyridine-3-carboxylate (600 mg, 2.21 mmol), tert-butyl 4-aminopiperidine-1-carboxylate (531 mg, 2.65 mmol), XantPhos Pd G3 (209 mg, 0.22 mmol), and $Cs_2CO_3$ (2.33 g, 6.63 mmol) in dioxane (5 mL) was stirred at 110° C. for 5 h. The mixture was cooled to rt and filtered. The filtrate was concentrated and the residue was purified by silica gel chromatography (eluting with 5% MeOH in DCM) to afford the title compound (349 mg, 35% yield). MS obsd (ESI+): 436.3 $[M+H]^+$.

Steps B-D: (R)—N-(1-(2-methyl-3-(trifluoromethyl)phenyl)ethyl)-6-oxo-4-(piperidin-4-ylamino)-1-(tetrahydro-2H-pyran-4-yl)-1,6-dihydropyridine-3-carboxamide Steps B-D were preformed according to analogous procedures described in example 43 steps B-D. MS obsd (ESI+): 507.3 $[M+H]^+$. $^1H$ NMR (400 MHz, DMSO-$d_6$) δ 8.75 (1H), 8.12 (2H), 7.72 (1H), 7.58 (1H), 7.43 (1H), 5.32 (1H), 5.27 (1H), 4.86 (1H), 4.02 (2H), 3.47 (2H), 3.26 (1H), 2.83 (2H), 2.54 (1H), 2.46 (3H), 2.14-1.93 (3H), 1.78 (2H), 1.66 (2H), 1.45 (3H), 1.18 (2H).

Example 283: 4-((3,3-difluoro-1-methylpiperidin-4-yl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide

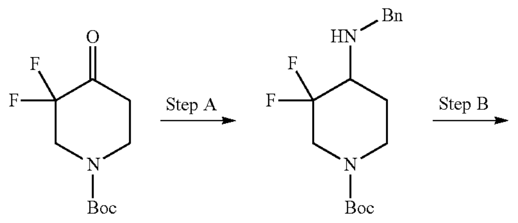

-continued

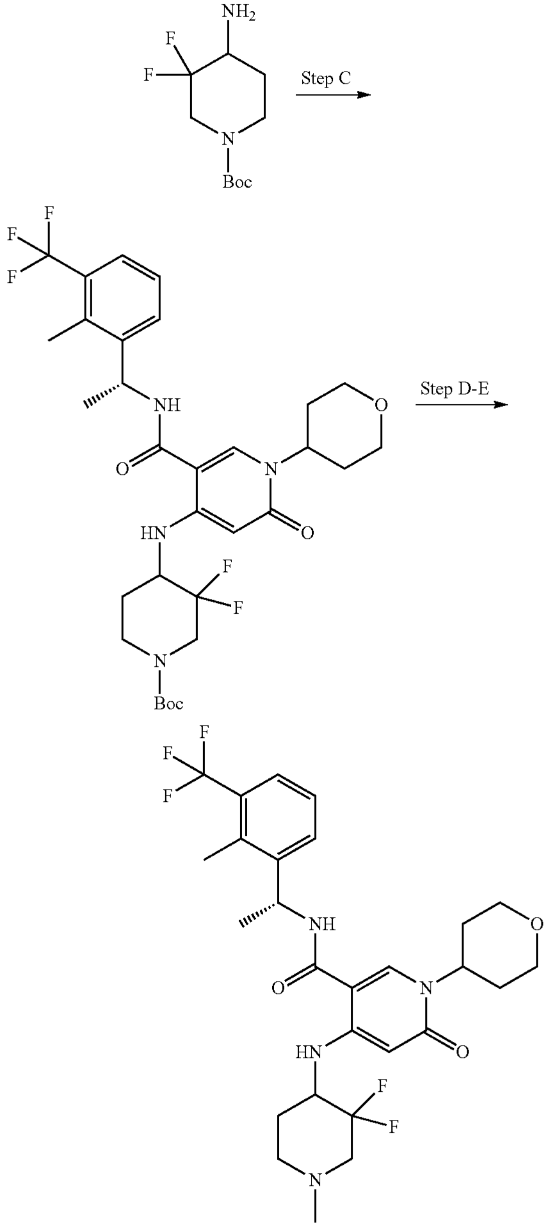

Example 283

Step A: tert-butyl 4-(benzylamino)-3,3-difluoropiperidine-1-carboxylate

Tert-butyl 3,3-difluoro-4-oxopiperidine-1-carboxylate (800 mg, 3.40 mmol) and benzylamine (729 mg, 6.80 mmol) were dissolved in DCM (30 mL) and sodium triacetoxyborohydride (3.60 g, 17.00 mmol) was added. The mixture was stirred at rt for 16 h. Then the mixture was quenched with saturated aqueous $NaHCO_3$ solution and extracted with DCM. The organic layers were combined, washed with brine, dried over $Na_2SO_4$, filtered and concentrated. The residue was purified by flash chromatography column (eluting with 10% to 30% EA in PE) to obtain the title compound (700 mg, 63% yield). MS obsd (ESI+): 327.4 $[M+H]^+$.

Step B: tert-butyl 4-amino-3,3-difluoropiperidine-1-carboxylate

Tert-butyl 4-(benzylamino)-3,3-difluoropiperidine-1-carboxylate (700 mg, 2.14 mmol) and and 10% Pd/C (260 mg) were dissolved in MeOH (20 mL). The mixture was purged with $H_2$ and stirred at rt for 16 h. The mixture was filtered and the solvent was removed under reduced pressure to obtain the target compound (500 mg, 98% yield). MS obsd (ESI+): 181.1, $[M\text{-t-Bu}]^+$.

Step C: tert-butyl 3,3-difluoro-4-((5-(((R)-1-(2-methyl-3-(trifluoromethyl)phenyl)ethyl)carbamoyl)-2-oxo-1-(tetrahydro-2H-pyran-4-yl)-1,2-dihydropyridin-4-yl)amino)piperidine-1-carboxylate (R)-4-chloro-N-(1-(2-methyl-3-(trifluoromethyl)phenyl)ethyl)-6-oxo-1-(tetrahydro-2H-pyran-4-yl)-1,6-dihydropyridine-3-carboxamide (100 mg, 0.22 mmol), tert-butyl 4-amino-3,3-difluoropiperidine-1-carboxylate (80 mg, 0.34 mmol), XantPhos-Pd-G3 (64 mg, 0.07 mmol) and cesium carbonate (147 mg, 0.45 mmol) were suspended in dioxane (1 mL). The mixture was stirred at 80° C. for 16 h. The reaction mixture was filtered and washed with EtOAc. The solution was concentrated under reduced pressure and the crude residue was purified by preparative TLC (MeOH/DCM=1/30) to afford the title compound (30 mg, 20% yield). MS obsd (ESI+): 643.8 $[M+H]^+$.

Steps D-E: 4-((3,3-difluoro-1-methylpiperidin-4-yl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide Steps D-E were preformed according to analogous procedures described in example 21, steps B-C. MS obsd (ESI+): 557.2 $[M+H]^+$. $^1H$ NMR (400 MHz, DMSO-$d_6$) δ: 8.79 (1H), 8.43 (1H), 8.15 (1H), 7.72 (1H), 7.59 (1H), 7.43 (1H), 5.54 (1H), 5.33 (1H), 4.86 (1H), 4.03 (2H), 3.93 (1H), 3.47 (2H), 2.99 (1H), 2.67 (1H), 2.46 (3H), 2.22 (3H), 2.10-1.87 (4H), 1.68 (2H), 1.46 (5H).

Example 284: (R)-4-((1-cyclopropylpiperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide Example 284

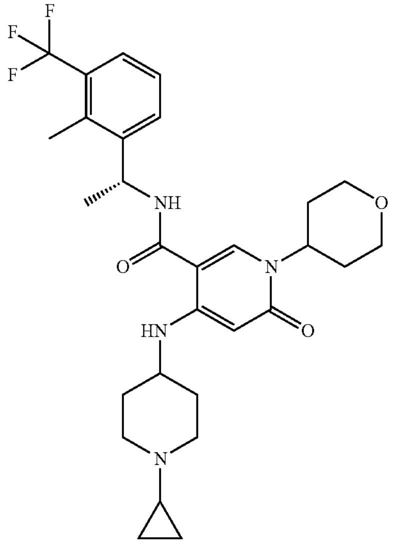

Example 284 was synthesized according to analogous procedures described in example 42. MS obsd (ESI+): 547.6 $[M+H]^+$. $^1H$ NMR (400 MHz, DMSO-$d_6$) δ 8.75 (1H), 8.12 (2H), 7.71 (1H), 7.58 (1H), 7.43 (1H), 5.32 (1H), 5.26 (1H), 4.93-4.77 (1H), 4.02 (2H), 3.47 (2H), 3.23 (1H), 2.74 (2H), 2.46 (3H), 2.33 (2H), 2.11-1.97 (2H), 1.81 (2H), 1.65 (2H), 1.55 (1H), 1.45 (3H), 1.34-1.18 (2H), 0.39 (2H), 0.30-0.20 (2H).

Example 285: 1-((1S,5S)-3-oxabicyclo[3.1.0]hexan-1-yl)-N—((R)-1-(3-(difluoromethyl)-2-fluorophenyl)ethyl)-4-((1-methylpiperidin-4-yl)amino)-6-oxo-1,6-dihydropyridine-3-carboxamide

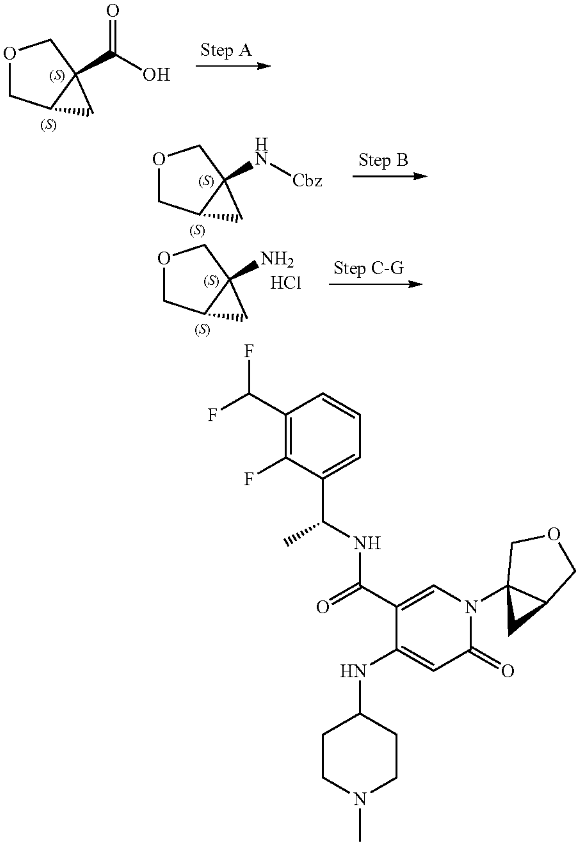

Example 285

Step A: benzyl ((1S,5S)-3-oxabicyclo[3.1.0]hexan-1-yl)carbamate

To a solution of (1S,5S)-3-oxabicyclo[3.1.0]hexane-1-carboxylic acid (2.6 g, 20.29 mmol) in $CCl_4$ (30 mL) was added $NEt_3$ (4.11 g, 40.59 mmol). The solution was heated to reflux and DPPA (7.40 g, 30.44 mmol) was added dropwise. The solution was heated at reflux for 2 h. After heating was stopped, BnOH (4.55 g, 101.46 mmol) was added in one portion. The mixture was left stirring for 10 h at 90° C. After cooling down to r.t., the reaction mixture was quenched with water (50 mL). The resulting mixture was extracted with ethyl acetate (3×500 mL). The organic layers were combined, dried over anhydrous sodium sulfate, filtered and concentrated. The crude product was purified by reverse-phase flash with the following conditions: C18, 120 g, 20~45 μm, 100 Å, mobile phase, $CH_3CN$:$H_2O$ (0.05% TFA)=20% increased to 70% in 40 min to afford the title compound (2.4 g, 50% yield). LCMS (ES, m/z): 234.10 $[M+H]^+$.

Step B: (1S,5S)-3-oxabicyclo[3.1.0]hexan-1-amine hydrochloride

To a solution of benzyl ((1S,5S)-3-oxabicyclo[3.1.0]hexan-1-yl)carbamate (2.6 g, 11.15 mmol, 1.0 eq.) in EtOAc (50 mL) and MeOH (10 mL) was added Pd/C (676 mg, 10% w/w). The flask was evacuated and flushed three times with nitrogen, followed by flushing with hydrogen. The mixture was stirred 3 h at 30° C. under $H_2$ atmosphere (10 atm.). After cooling down to r.t., the mixture was filtered through a Celite pad and concentrated under reduced pressure. The residue was dissolved in HCl (20 ml, 4M in dioxane) and concentrated again to afford the title compound (1.40 g, 91% yield. $^1$H NMR (400 MHz, DMSO-$d_6$) δ 9.10 (s, 3H), 3.85-3.80 (m, 1H), 3.74-3.70 (m, 2H), 3.64-3.55 (m, 1H), 1.96-1.90 (m, 1H), 1.28-1.25 (m, 1H), 0.72-0.65 (m, 1H). LCMS (ES, m/z): 100.15 $[M+H]^+$.

Steps C-G: 1-((1S,5S)-3-oxabicyclo[3.1.0]hexan-1-yl)-N—((R)-1-(3-(difluoromethyl)-2-fluorophenyl)ethyl)-4-((1-methylpiperidin-4-yl)amino)-6-oxo-1,6-dihydropyridine-3-carboxamide Steps C-G were preformed according to analogous procedures described in example 49 steps A-E, starting with (1S,5S)-3-oxabicyclo[3.1.0]hexan-1-amine hydrochloride. MS obsd (ESI+): 505.4 $[M+H]^+$. $^1$H NMR (400 MHz, DMSO-$d_6$) δ: 8.72 (1H), 8.10 (1H), 7.90 (1H), 7.63 (1H), 7.53 (1H), 7.37-7.08 (2H), 5.29 (1H), 5.20 (1H), 4.03 (1H), 3.87 (1H), 3.74 (2H), 3.23 (1H), 2.57 (2H), 2.12-2.00 (6H), 1.82 (2H), 1.48 (3H), 1.40-1.25 (3H), 1.03 (1H).

Example 286: (R)—N-(1-(3-(difluoromethyl)-2-fluorophenyl)ethyl)-1-(1-(difluoromethyl)cyclopropyl)-4-((1-(methyl-d3)piperidin-4-yl)amino)-6-oxo-1,6-dihydropyridine-3-carboxamide Example 286

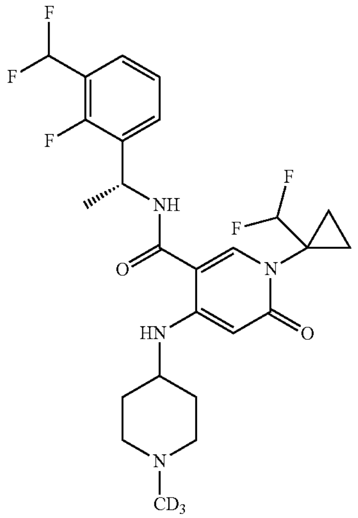

To a solution of (R)—N-(1-(3-(difluoromethyl)-2-fluorophenyl)ethyl)-1-(1-(difluoromethyl)cyclopropyl)-6-oxo-4-(piperidin-4-ylamino)-1,6-dihydropyridine-3-carboxamide hydrochloride (100 mg, 0.19 mmol) in acetonitrile (10.0 mL) was added $K_2CO_3$ (78 mg, 0.57 mmol) at rt. The reaction mixture was stirred for 20 min. To the reaction mixture was added trideuteriomethyl 4-methylbenzenesulfonate (39 mg, 0.21 mmol) at rt. The reaction mixture was stirred for 2 hrs at 80° C. After cooling to room temperature, the reaction was poured into water (10 mL) and extracted with DCM (20 mL*3). The combined organic layers were washed with brine, dried over anhydrous $Na_2SO_4$, filtered, and concentrated in vacuo. The residue was first purified by silica gel chromatography (eluting with 0 to 50% MeOH in DCM) followed by preparative HPLC (ACN/water/0.1% $NH_4HCO_3$) to obtain the title compound (12.6 mg, 13% yield) as a white solid. MS obsd (ESI+): 516.4 $[M+H]^+$. $^1$H NMR (400 MHz, DMSO-$d_6$) δ 8.80 (1H), 8.04 (1H), 8.02 (1H), 7.61 (1H), 7.53 (1H), 7.35 (1H), 7.21 (1H), 6.23 (1H), 5.28 (1H), 5.22 (1H), 3.23 (1H), 2.57 (2H), 2.07 (2H), 1.82 (2H), 1.48 (3H), 1.42-1.23 (6H).

Example 287: 1-((1S,5S)-3-oxabicyclo[3.1.0]hexan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide example 287

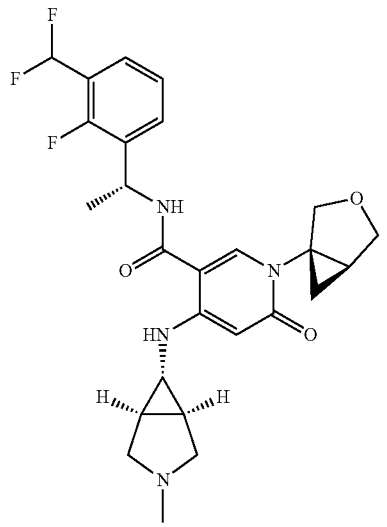

Example 287 was synthesized according to analogous procedures described in examples 92-154. MS obsd (ESI+): 503.4 $[M+H]^+$. $^1$H NMR (400 MHz, DMSO-$d_6$) δ 8.72 (1H), 8.11 (1H), 7.85 (1H), 7.61 (1H), 7.52 (1H), 7.34 (1H), 7.21 (1H), 5.34 (1H), 5.31-5.20 (1H), 4.03 (1H), 3.87 (1H), 3.75 (2H), 3.00 (2H), 2.47 (1H), 2.27 (2H), 2.20 (3H), 2.12-2.04 (1H), 1.49 (2H), 1.47 (3H), 1.35 (1H), 1.04 (1H).

Example 288: (R)—N-(1-(3-(difluoromethyl)-2-fluorophenyl)ethyl)-1-(1-(difluoromethyl)cyclopropyl)-4-((1-(1-methylcyclopropyl)piperidin-4-yl)amino)-6-oxo-1,6-dihydropyridine-3-carboxamide

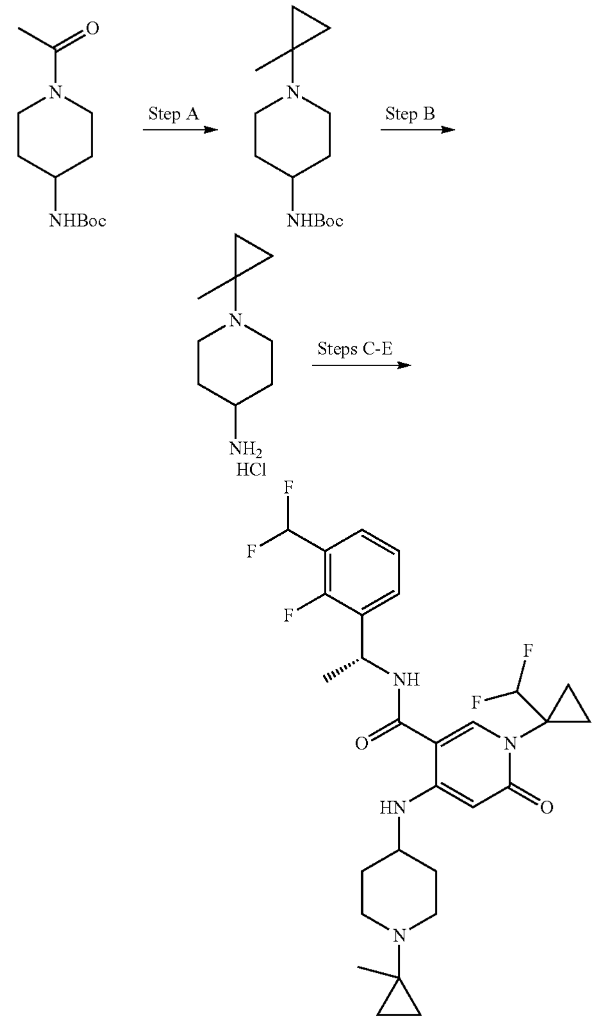

example 288

Step A: tert-butyl (1-(1-methylcyclopropyl)piperidin-4-yl)carbamate

To a solution tert-butyl N-(1-acetyl-4-piperidyl)carbamate (900 mg, 3.71 mmol) in THF (38 mL) was added Ti(iOPr)4 (5.28 g, 18.57 mmol) and stirred at r.t. for 5 minutes. Then ethylmagnesium bromide (1 M in THF, 37.1 mL) was added drop-wise and the mixture was stirred for another 16 h. The reaction mixture was poured into $NH_4Cl$ (sat., aq.), then extracted with EA (100 mL×3). The combined organic layers were washed with brine, dried over $Na_2SO_4$, filtered and concentrated. The crude product was purified by column chromatography (0-5% MeOH in DCM) to afford the title compound (200 mg, 21% yield). $^1H$ NMR (400 MHz, rotameric mixture in DMSO-$d_6$) δ 6.91-6.70 (1H), 3.24-3.06 (1H), 2.69 (2H), 2.39-2.21 (2H), 1.71-1.59 (2H), 1.43-1.31 (7H), 1.30-1.17 (4H), 0.98 (3H), 0.42-0.35 (2H), 0.31-0.23 (2H).

Step B: 1-(1-methylcyclopropyl)piperidin-4-amine hydrochloride

To a solution of tert-butyl (1-(1-methylcyclopropyl)piperidin-4-yl)carbamate (200 mg, 0.78 mmol) in 1,4-Dioxane (1 mL) was added HCl/1,4-dioxane (4 M, 1 mL). The mixture was stirred at room temperature for 1.5 h. The reaction mixture was concentrated under reduced pressure to afford the title compound (210 mg, crude). The crude product was used for the next step without further purification or analysis.

Steps C-E: (R)—N-(1-(3-(difluoromethyl)-2-fluorophenyl)ethyl)-1-(1-(difluoromethyl)cyclopropyl)-4-((1-(1-methylcyclopropyl)piperidin-4-yl)amino)-6-oxo-1,6-dihydropyridine-3-carboxamide Steps C-E were preformed according to analogous procedures described in example 49 steps C-E. MS obsd (ESI+): 553.3 $[M+H]^+$. $^1H$ NMR (400 MHz, DMSO-$d_6$) δ 8.79 (1H), 8.02 (2H), 7.60 (1H), 7.52 (1H), 7.35 (1H), 7.21 (1H), 6.24 (1H), 5.29 (1H), 5.21 (1H), 3.22 (1H), 2.70-2.58 (2H), 2.45 (2H), 1.80 (2H), 1.48 (3H), 1.37-1.17 (6H), 0.96 (3H), 0.44-0.37 (2H), 0.31-0.24 (2H).

Example 289: 1-((1S,5S)-3-oxabicyclo[3.1.0]hexan-1-yl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide example 289

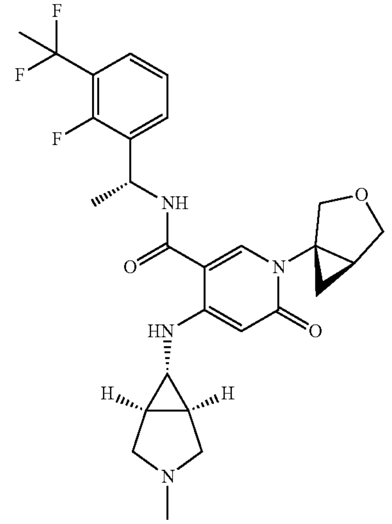

Example 289 was synthesized according to analogous procedures described in examples 92-154. MS obsd (ESI+): 517.2 $[M+H]^+$. $^1H$ NMR (400 MHz, DMSO-$d_6$) δ 8.75 (1H), 8.14 (1H), 7.93 (1H), 7.58 (1H), 7.46 (1H), 7.30 (1H), 5.37 (1H), 5.27 (1H), 4.03 (1H), 3.88 (1H), 3.75 (2H), 2.97 (2H), 2.10 (1H), 2.02 (3H), 1.79 (2H), 1.47 (3H), 1.35 (1H), 1.05 (1H).

Example 290: 1-((1S,5S)-3-oxabicyclo[3.1.0]hexan-1-yl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide example 290

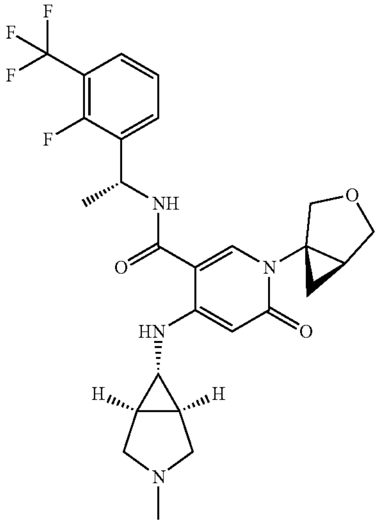

Example 290 was synthesized according to analogous procedures described in examples 92-154. MS obsd (ESI+): 521.3 $[M+H]^+$. $^1H$ NMR (400 MHz, $CDCl_3$) δ: 7.84 (1H), 7.76 (1H), 7.60 (1H), 7.53-7.41 (2H), 7.22 (1H), 5.57 (1H), 5.37-5.29 (1H), 4.15 (1H), 3.93 (1H), 3.83 (2H), 3.77-3.66 (2H), 3.14 (2H), 2.84 (1H), 2.75 (3H), 2.06 (1H), 1.89 (2H), 1.59 (3H), 1.23 (2H).

Examples 291 and 292: 1-((R)-3-cyclopropyltetrahydrofuran-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Example 291) and 1-((S)-3-cyclopropyltetrahydrofuran-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (Example 292) (Diastereomers not Assigned)

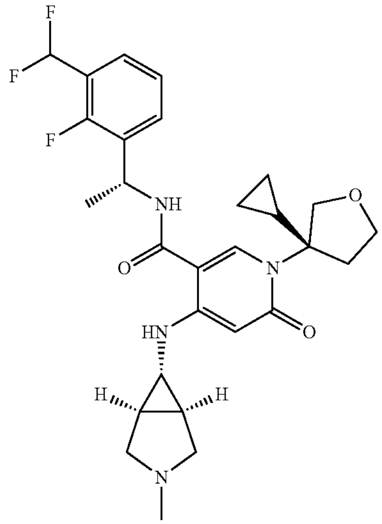

-continued

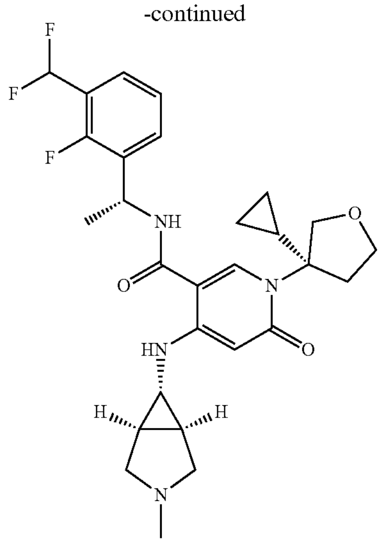

Examples 291 and 292

Example 247 was separated into individual diastereomers by chiral SFC SFC (Daicel OZ (25*250 mm, 10 um), $CO_2$/MeOH [0.2% $NH_3$ (7M in MeOH)]=70/30) to afford the title compounds.

Example 291: MS obsd (ESI+): 531.2 $[M+H]^+$. Analytical chiral UPCC: (Column: CHIRALPAK OZ-3 4.6*100 mm 3 um, Flow rate: 3.0 mL/min, Cosolvent: MeOH (0.2% 7M NH3 in MeOH), Temp 40° C.) Retention time=1.1 min Example 292: MS obsd (ESI+): 531.2 $[M+H]^+$. Analytical chiral UPCC: (Column: CHIRALPAK OZ-3 4.6*100 mm 3 um, Flow rate: 3.0 mL/min, Cosolvent: MeOH (0.2% 7M NH3 in MeOH), Temp 40° C.) Retention time=1.6 min Examples 293 and 294: N—((R)-1-(3-(difluoromethyl)-2-fluorophenyl)ethyl)-1-(1-(difluoromethyl)cyclopropyl)-4-(((1R,5S,8r)-3-(methyl-$d_3$)-3-azabicyclo[3.2.1]octan-8-yl)amino)-6-oxo-1,6-dihydropyridine-3-carboxamide (Example 293) and N—((R)-1-(3-(difluoromethyl)-2-fluorophenyl)ethyl)-1-(1-(difluoromethyl)cyclopropyl)-4-(((1R,5S,8s)-3-(methyl-d3)-3-azabicyclo[3.2.1]octan-8-yl)amino)-6-oxo-1,6-dihydropyridine-3-carboxamide (Example 294) (Diastereomers not Assigned)

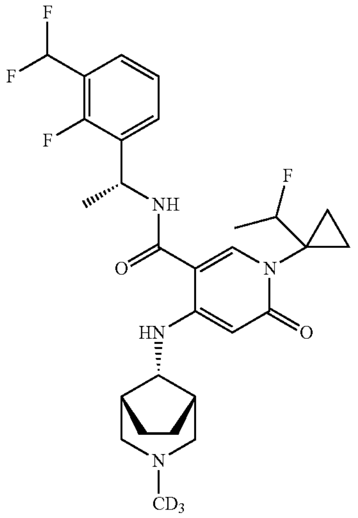

-continued

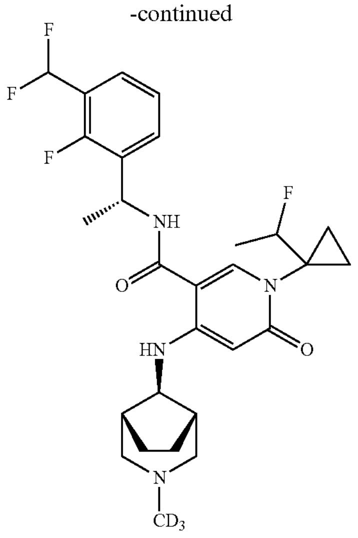

Example 293 and 294

Examples 293 and 294 were synthesized according to analogous procedures described in example 286. Individual diastereomers were separated by chiral SFC (Column: YMC Cellulose-SC (20*250 mm, 5 um), Mobile phase: CO2/MeOH [0.2% NH3 (7M in MeOH)]=75/25)

Example 293: First eluting isomer. MS obsd (ESI+): 542.2 $[M+H]^+$. $^1$H NMR (400 MHz, DMSO-d6) δ 8.81 (1H), 8.05 (1H), 7.99 (1H), 7.60 (1H), 7.53 (1H), 7.35 (1H), 7.21 (1H), 6.24 (1H), 5.33-5.26 (1H), 5.21 (1H), 3.20 (1H), 2.66-2.55 (2H), 2.13-2.05 (4H), 1.68-1.56 (2H), 1.52 (2H), 1.48 (3H), 1.38-1.23 (4H).

Example 294: Second eluting isomer. MS obsd (ESI+): 542.2 $[M+H]^+$. $^1$H NMR (400 MHz, DMSO-$d_6$) δ 8.84 (1H), 8.46 (1H), 8.03 (1H), 7.63 (1H), 7.53 (1H), 7.36 (1H), 7.21 (1H), 6.24 (1H), 5.34 (1H), 5.24 (1H), 3.35 (1H), 2.42-2.30 (2H), 2.12-2.05 (4H), 1.73-1.62 (4H), 1.50 (3H), 1.39-1.20 (4H).

Example 295: (R)-4-(((1-(2-methoxyethyl) azetidin-3-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide

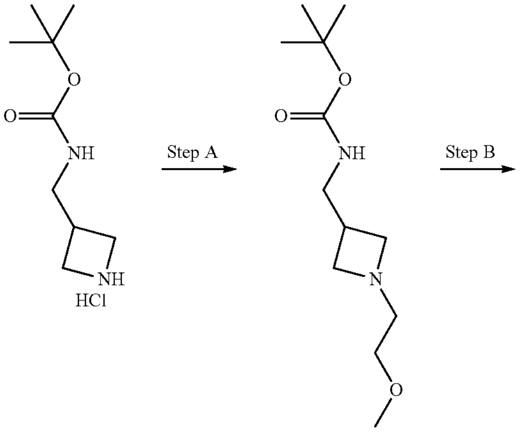

-continued

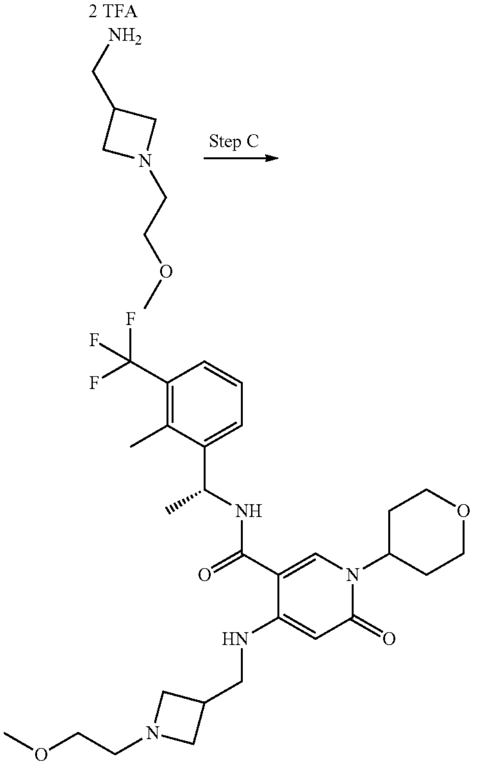

Example 295

Step A: tert-butyl ((1-(2-methoxyethyl) azetidin-3-yl)methyl)carbamate

A solution of tert-butyl N-(azetidin-1-ium-3-ylmethyl) carbamate; chloride (2.0 g, 8.98 mmol), 1-bromo-2-methoxy-ethane (1.5 g, 10.78 mmol), and DIPEA (2.9 g, 22.45 mmol) in DMF (20 mL) was stirred at r.t. under $N_2$ for 16 hr. The mixture was diluted with water (150 mL) and extracted with EA (70 mL×3). The organic layers were concentrated. The crude product was purified by flash chromatography (0-10% MeOH in DCM) to afford the title compound (523 mg, 23% yield) as a colorless oil. $^1$H NMR (400 MHz, DMSO-$d_6$) δ 6.98-6.84 (m, 1H), 3.38-3.26 (m, 4H), 3.21 (s, 3H), 3.12-2.98 (m, 4H), 2.65 (t, J=5.6 Hz, 2H), 2.49-2.39 (m, 1H), 1.37 (s, 9H).

Step B: (1-(2-methoxyethyl) azetidin-3-yl)methanamine trifluoroacetate salt

To a solution of tert-butyl ((1-(2-methoxyethyl) azetidin-3-yl)methyl)carbamate (485 mg, 1.99 mmol) in TFA (5 mL) and DCM (5 mL) was stirred at r.t. for 1 hr. The reaction was concentrated under vacuum to afford the title compound (995 mg, crude, 2 eq. TFA salt). $^1$H NMR (400 MHz, DMSO-$d_6$) δ 10.31-10.20 (brs, 1H), 7.99-7.90 (m, 3H), 4.21-4.04 (m, 2H), 4.03-3.82 (m, 2H), 3.54-3.46 (m, 2H), 3.41-3.32 (m, 2H), 3.27 (s, 3H), 3.24-3.15 (m, 1H), 3.12-2.90 (m, 2H).

Step C: (R)-4-(((1-(2-methoxyethyl) azetidin-3-yl) methyl)amino)-N-(1-(2-methyl-3-(trifluoromethyl) phenyl)ethyl)-6-oxo-1-(tetrahydro-2H-pyran-4-yl)-1,6-dihydropyridine-3-carboxamide To a solution of 4-chloro-N-[(1R)-1-[2-methyl-3-(trifluoromethyl)phenyl]ethyl]-6-oxo-1-tetrahydropyran-4-yl-pyridine-3-carboxamide (150 mg, 0.34 mmol) in DMSO (1 mL) was added (1-(2-methoxyethyl) azetidin-3-yl)methanamine trifluoroacetate salt (252 mg, crude) followed by $K_2CO_3$ (468 mg, 3.39 mmol). The mixture was stirred at 90° C. for 16 h. The reaction mixture was poured into water (40 mL) then extracted with EA (30 mL×3). The combined organic layers were washed with brine, dried over $Na_2SO_4$, filtered and concentrated under reduced pressure. The crude product was purified by column chromatography (0-25% MeOH in DCM) to afford the title compound (54.47 mg, 29% yield). MS obsd (ESI+): 551.7 $[M+H]^+$. $^1H$ NMR (400 MHz, DMSO-$d_6$) δ 8.80-8.72 (1H), 8.13 (1H), 8.09 (1H), 7.70 (1H), 7.58 (1H), 7.42 (1H), 5.37-5.27 (1H), 5.25 (1H), 4.92-4.79 (1H), 4.02 (2H), 3.47 (2H), 3.36 (2H), 3.26 (2H), 3.21-3.15 (5H), 3.01-2.89 (2H), 2.70-2.54 (3H), 2.46 (3H), 2.11-1.97 (2H), 1.65 (2H), 1.45 (3H).

Examples 296-299: N—((R)-1-(2-methyl-3-(trifluoromethyl)phenyl)ethyl)-4-(((1S,4R)-6-methyl-6-azaspiro[3.5]nonan-1-yl)amino)-6-oxo-1-(tetrahydro-2H-pyran-4-yl)-1,6-dihydropyridine-3-carboxamide (Example 296), N—((R)-1-(2-methyl-3-(trifluoromethyl)phenyl)ethyl)-4-(((1R,4S)-6-methyl-6-azaspiro[3.5]nonan-1-yl)amino)-6-oxo-1-(tetrahydro-2H-pyran-4-yl)-1,6-dihydropyridine-3-carboxamide (Example 297), N—((R)-1-(2-methyl-3-(trifluoromethyl)phenyl)ethyl)-4-(((1S,4S)-6-methyl-6-azaspiro[3.5]nonan-1-yl)amino)-6-oxo-1-(tetrahydro-2H-pyran-4-yl)-1,6-dihydropyridine-3-carboxamide (Example 298) and N—((R)-1-(2-methyl-3-(trifluoromethyl)phenyl)ethyl)-4-(((1R,4R)-6-methyl-6-azaspiro[3.5]nonan-1-yl)amino)-6-oxo-1-(tetrahydro-2H-pyran-4-yl)-1,6-dihydropyridine-3-carboxamide (Example 299) (Diastereomers not Assigned)

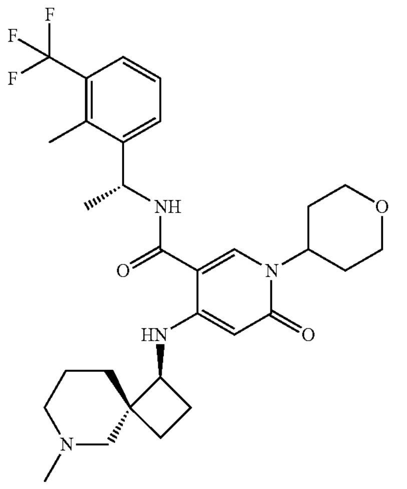

-continued

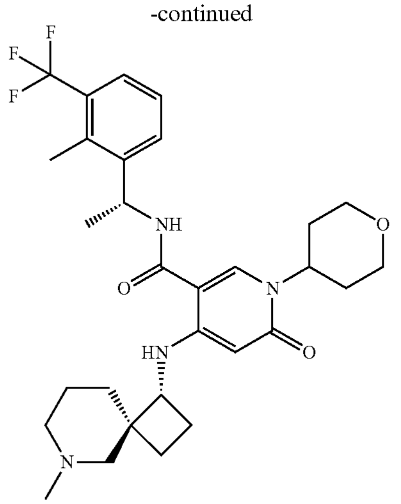

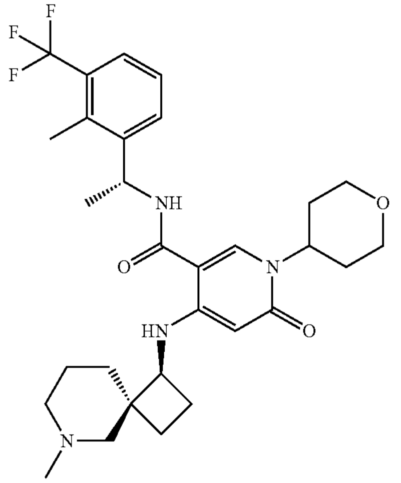

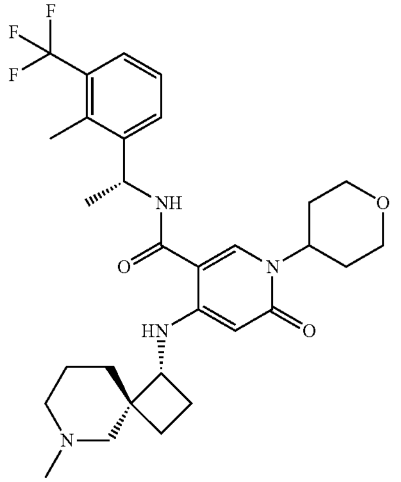 [SMILES: Cc1c([C@@H](C)NC(=O)c2cn(C3CCOCC3)c(=O)cc2N[C@@H]2CC[C@@]23CCCN(C)C3)cccc1C(F)(F)F]

Examples 296, 297, 298, 299

A diastereomeric mixture of N—((R)-1-(2-methyl-3-(trifluoromethyl)phenyl)ethyl)-4-((6-methyl-6-azaspiro[3.5]nonan-1-yl)amino)-6-oxo-1-(tetrahydro-2H-pyran-4-yl)-1,6-dihydropyridine-3-carboxamide was synthesized according to analogous procedures as described in example 21. The mixture was purified by silica gel chromatography (eluted with 0~20% MeOH in DCM) to afford two fractions.

The first eluting fraction was further purified by preparative HPLC (ACN/water/0.1% $NH_4HCO_3$) and then chiral SFC (Column: Regis (R,R)Whelk-O1, Co-Solvent: $CO_2$/MeOH [0.2% $NH_3$ (7M in MeOH)]=65/35) to afford examples 296 and 297.

Example 296: First eluting isomer from chiral separation. MS obsd (ESI+): 561.4 $[M+H]^+$. $^1$H NMR (400 MHz, DMSO-$d_6$, some protons obscured by solvent peak) δ: 8.73 (1H), 8.70 (1H), 7.96 (1H), 7.69 (1H), 7.56 (1H), 7.42 (1H), 5.28 (1H), 5.01 (s, 1H), 4.84 (1H), 4.01 (2H), 3.50-3.44 (3H), 2.27 (1H), 2.06-1.97 (4H), 1.89 (3H), 1.64 (2H), 1.61-1.48 (3H), 1.49-1.42 (6H), 1.35-1.23 (1H).

Example 297: Second eluting isomer from chiral separation. MS obsd (ESI+): 561.4 $[M+H]^+$. $^1$H NMR (400 MHz, DMSO-$d_6$, some protons obscured by solvent peak) δ: 8.67 (1H), 8.63 (1H), 7.91 (1H), 7.70 (1H), 7.57 (1H), 7.42 (1H), 5.29 (1H), 5.02 (1H), 4.83 (1H), 4.01 (2H), 3.46 (3H), 2.29 (1H), 2.05 (2H), 1.98 (5H), 1.70-1.59 (3H), 1.57-1.50 (2H), 1.45-1.40 (4H), 1.37-1.22 (3H).

The second eluting fraction from silica gel chromatography was further purified by chiral SFC (Column: Regis (R,R)Whelk-O1. Co-Solvent: $CO_2$/MeOH [0.2% $NH_3$ (7M in MeOH)]=65/35) to afford examples 298 and 299.

Example 298: First eluting isomer from chiral separation. MS obsd (ESI+): 561.5 $[M+H]^+$. $^1$H NMR (400 MHz, DMSO-$d_6$, some protons obscured by solvent peak) δ: 8.75 (1H), 8.38 (1H), 8.11 (1H), 7.71 (1H), 7.59 (1H), 7.43 (1H), 5.34 (1H), 5.21 (1H), 4.86 (1H), 4.02 (2H), 3.56 (1H), 3.47 (2H), 2.29-2.18 (1H), 2.10 (3H), 2.07-1.96 (3H), 1.78 (1H), 1.71-1.45 (10H), 1.11 (1H).

Example 299: Second eluting isomer from chiral separation. MS obsd (ESI+): 561.5 $[M+H]^+$. $^1$H NMR (400 MHz, DMSO-$d_6$, some protons obscured by solvent peak) δ: 8.73 (1H), 8.24 (1H), 8.07 (1H), 7.72 (1H), 7.59 (1H), 7.44 (1H), 5.34 (1H), 5.20 (1H), 4.90-4.78 (1H), 4.08-3.95 (2H), 3.55 (1H), 3.47 (2H), 2.30-2.21 (1H), 2.08 (3H), 2.05-1.95 (3H), 1.78-1.41 (12H), 1.05 (1H).

Example 300: N—((R)-1-(2-methyl-3-(trifluoromethyl)phenyl)ethyl)-6-oxo-1-(tetrahydro-2H-pyran-4-yl)-4-((5,6,7,8-tetrahydroimidazo[1,5-a]pyridin-8-yl)amino)-1,6-dihydropyridine-3-carboxamide example 300

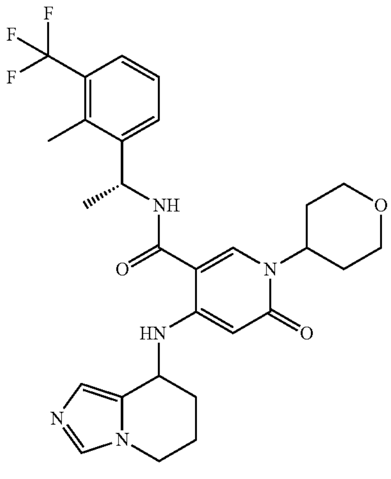

Example 300 was synthesized according to analogous procedures described in example 2. MS obsd (ESI+): 544.6 $[M+H]^+$. $^1$H NMR (400 MHz, DMSO-$d_6$, diastereomeric mixture) δ 8.83-8.73 (1H), 8.36 (1H), 8.14 (1H), 7.73-7.66 (1H), 7.60-7.52 (2H), 7.47-7.36 (1H), 6.69 (1H), 5.51 (1H), 5.34-5.21 (1H), 4.96-4.81 (1H), 4.77-4.66 (1H), 4.08-3.86 (4H), 3.49 (2H), 2.42 (3H), 2.16-1.99 (3H), 1.97-1.83 (2H), 1.68 (2H), 1.64-1.51 (1H), 1.44 (3H).

Example 301: 4-((((1r,4R)-4-(dimethylamino)cyclohexyl)methyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide example 301

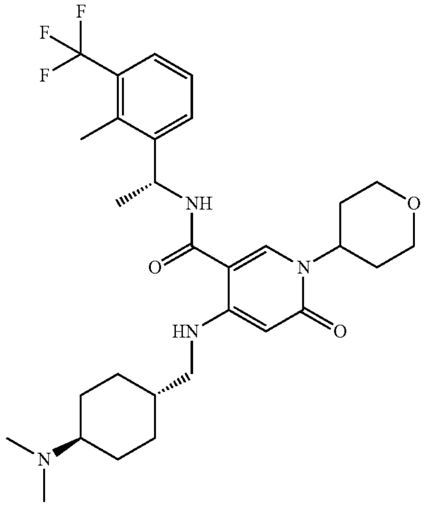

Example 301 was synthesized according to analogous procedures described in example 21 starting with tert-butyl ((1r,4r)-4-(aminomethyl)cyclohexyl)carbamate. MS obsd (ESI+): 563.6 $[M+H]^+$. $^1$H NMR (400 MHz, DMSO-$d_6$) δ 8.75 (1H), 8.10 (2H), 7.70 (1H), 7.58 (1H), 7.43 (1H), 5.37-5.28 (1H), 5.20 (1H), 4.85 (1H), 4.07-3.97 (2H), 3.51-3.47 (2H), 2.85 (2H), 2.46 (3H), 2.20 (7H), 2.11-1.96 (2H), 1.84-1.69 (4H), 1.69-1.61 (2H), 1.45 (4H), 1.23-1.08 (2H), 0.98-0.84 (2H).

Example 302: 4-((((1s,4S)-4-(dimethylamino)cyclohexyl)methyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide example 302

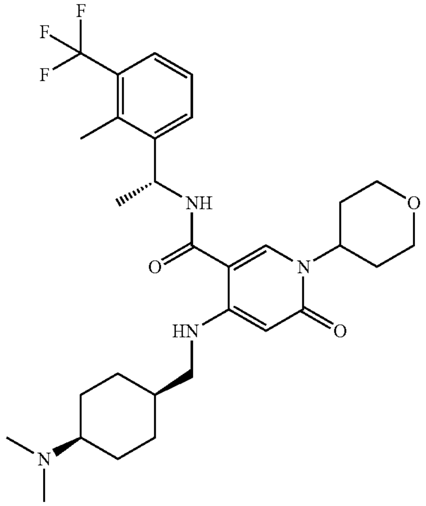

Example 302 was synthesized according to analogous procedures described in example 21 starting with tert-butyl ((1s,4s)-4-(aminomethyl)cyclohexyl)carbamate. MS obsd (ESI+): 563.6 $[M+H]^+$. $^1H$ NMR (400 MHz, DMSO-$d_6$) δ: 8.74 (1H), 8.09 (2H), 7.71 (1H), 7.59 (1H), 7.45 (1H), 5.36-5.29 (1H), 5.21 (1H), 4.86 (1H), 4.02 (2H), 3.50 (2H), 2.92 (2H), 2.46 (3H), 2.13 (6H), 2.08-2.02 (3H), 1.67 (5H), 1.46 (3H), 1.38 (6H).

Examples 303-306: N—((R)-1-(3-(difluoromethyl)-2-fluorophenyl)ethyl)-1-(1-(difluoromethyl)cyclopropyl)-4-(((7R,8aS)-octahydroindolizin-7-yl)amino)-6-oxo-1,6-dihydropyridine-3-carboxamide (Example 303), N—((R)-1-(3-(difluoromethyl)-2-fluorophenyl)ethyl)-1-(1-(difluoromethyl)cyclopropyl)-4-(((7S,8aR)-octahydroindolizin-7-yl)amino)-6-oxo-1,6-dihydropyridine-3-carboxamide (Example 304), N—((R)-1-(3-(difluoromethyl)-2-fluorophenyl)ethyl)-1-(1-(difluoromethyl)cyclopropyl)-4-(((7S,8aS)-octahydroindolizin-7-yl)amino)-6-oxo-1,6-dihydropyridine-3-carboxamide (Example 305), and N—((R)-1-(3-(difluoromethyl)-2-fluorophenyl)ethyl)-1-(1-(difluoromethyl)cyclopropyl)-4-(((7R,8aR)-octahydroindolizin-7-yl)amino)-6-oxo-1,6-dihydropyridine-3-carboxamide (Example 306) (Diastereomers not Assigned)

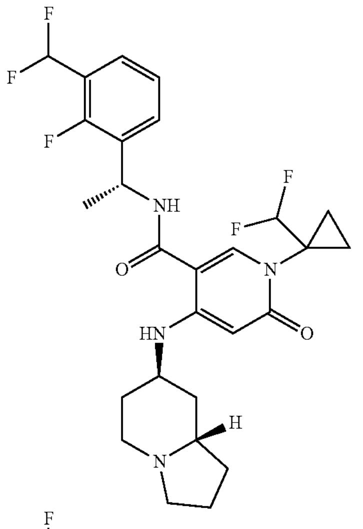

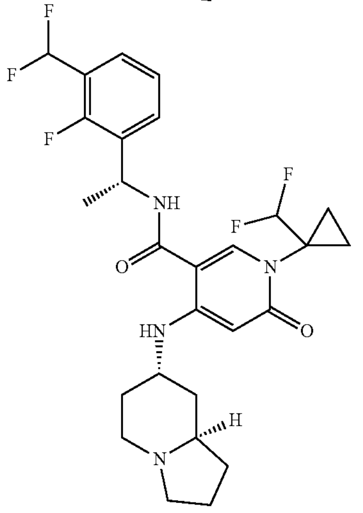

-continued

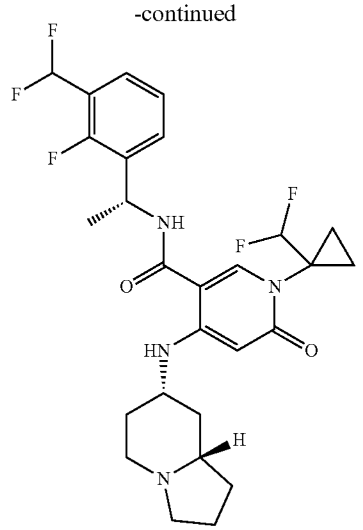

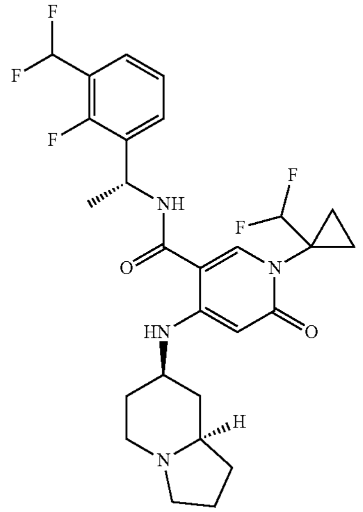 [SMILES: C[C@@H](NC(=O)c1cn(C2(C(F)F)CC2)c(=O)cc1N[C@@H]1CCN2CCC[C@@H]2C1)c1cccc(C(F)F)c1F]

Examples 303, 304, 305, 306

Examples 303-306 were synthesized according to analogous procedures described in example 49. The obtained mixture of 4 diastereomers was separated as follows: Initial purification by chiral SFC Daicel AS (25*250 mm, 10 um), $CO_2$/EtOH [0.5% $NH_3$ (7M in MeOH)]=85/15) afforded 2 fractions. The first eluting fraction was then further separated by chiral SFC (YMC Cellulose-SC (20*250 mm, 5 um), $CO_2$/EtOH [0.5% $NH_3$ (7M in MeOH)]=80/20) to obtain examples 303 and 304.

Example 303: First eluting fraction in second chiral purification. MS obsd (ESI+): 539.3 $[M+H]^+$. $^1H$ NMR (400 MHz, DMSO-$d_6$) δ: 8.81 (1H), 8.05 (1H), 8.00 (1H), 7.61 (1H), 7.53 (1H), 7.35 (1H), 7.21 (1H), 6.24 (1H), 5.29 (1H), 5.25 (1H), 3.24 (1H), 2.98 (1H), 2.90 (1H), 2.09-1.94 (3H), 1.94-1.83 (2H), 1.75 (1H), 1.70-1.55 (2H), 1.48 (3H), 1.39-1.18 (6H), 0.95 (1H).

Example 304: Second eluting fraction in second chiral purification. MS obsd (ESI+): 539.3 $[M+H]^+$. $^1H$ NMR (400 MHz, DMSO-$d_6$) δ: 8.81 (1H), 8.05 (1H), 8.00 (1H), 7.61 (1H), 7.53 (1H), 7.35 (1H), 7.21 (1H), 6.24 (1H), 5.29 (1H), 5.25 (1H), 3.24 (1H), 2.96 (1H), 2.89 (1H), 2.10-1.82 (5H), 1.77 (1H), 1.71-1.54 (2H), 1.48 (3H), 1.38-1.20 (6H), 0.97 (1H).

The second eluting fraction from the initial chiral SFC purification was then further separated by chiral SFC (YMC Cellulose-SC (20*250 mm, 5 um), $CO_2$/EtOH [0.5% $NH_3$ (7M in MeOH)]=80/20) to obtain examples 305 and 306.

Example 305: First eluting fraction in second chiral purification. MS obsd (ESI+): 539.3 $[M+H]^+$. $^1$H NMR (400 MHz, DMSO-$d_6$) δ: 8.80 (1H), 8.25 (1H), 8.02 (1H), 7.61 (1H), 7.53 (1H), 7.35 (1H), 7.21 (1H), 6.24 (1H), 5.31 (1H), 5.19 (1H), 3.68 (1H), 2.93-2.85 (1H), 2.85- 2.78 (1H), 1.98-1.87 (2H), 1.85-1.77 (1H), 1.77-1.52 (6H), 1.49 (3H), 1.38-1.13 (6H).

Example 306: Second eluting fraction in second chiral purification. MS obsd (ESI+): 539.3 $[M+H]^+$. $^1$H NMR (400 MHz, DMSO-$d_6$) δ: 8.81 (1H), 8.28 (1H), 8.04 (1H), 7.61 (1H), 7.53 (1H), 7.35 (1H), 7.21 (1H), 6.24 (1H), 5.32 (1H), 5.19 (1H), 3.69 (1H), 3.01-2.70 (2H), 2.03-1.52 (9H), 1.49 (3H), 1.41-1.11 (6H).

Examples 307 and 308: N—((R)-1-(3-(difluoromethyl)-2-fluorophenyl)ethyl)-1-((R)-2,2-dimethyltetrahydro-2H-pyran-4-yl)-4-((1-methylpiperidin-4-yl)amino)-6-oxo-1,6-dihydropyridine-3-carboxamide (Example 307) and N—((R)-1-(3-(difluoromethyl)-2-fluorophenyl)ethyl)-1-((S)-2,2-dimethyltetrahydro-2H-pyran-4-yl)-4-((1-methylpiperidin-4-yl)amino)-6-oxo-1,6-dihydropyridine-3-carboxamide (Example 308) (Diastereomers not Assigned)

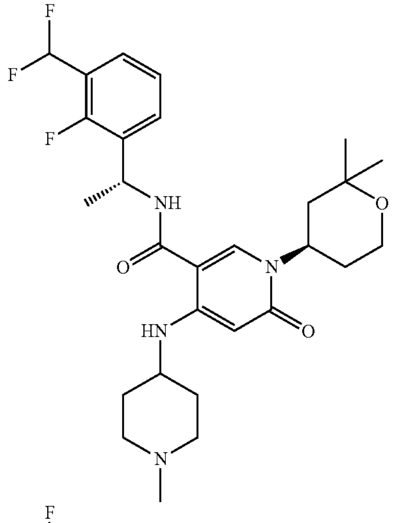

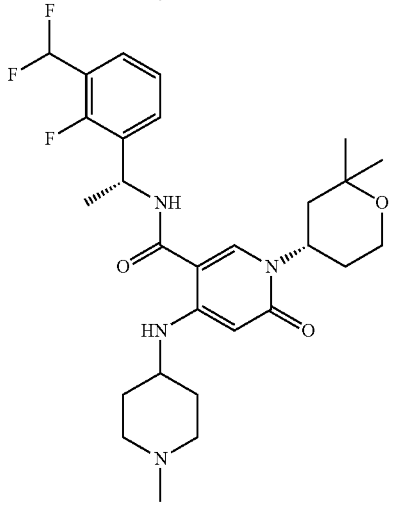

Example 307 and 308

Examples 307 and 308 were synthesized according to analogous procedures described in example 49. The diastereomeric mixture was separated via chiral SFC (Daicel AS (25*250 mm, 10 um), $CO_2$/EtOH [0.5% $NH_3$ (7M in MeOH)]=85/15).

Example 307: MS obsd (ESI+): 535.5 $[M+H]^+$. Analytical chiral UPCC: (Column: CHIRALPAK AS-3 4.6*100 mm 3 um, Flow rate: 3.0 mL/min, Cosolvent:EtOH (1% 7M NH3 in MeOH), Temp 40° C.) Retention time=1.4 min Example 308: MS obsd (ESI+): 535.5 $[M+H]^+$. Analytical chiral UPCC: (Column: CHIRALPAK AS-3 4.6*100 mm 3 um, Flow rate: 3.0 mL/min, Cosolvent:EtOH (1% 7M NH3 in MeOH), Temp 40° C.) Retention time=3.4 min Example 309 and 310: N—((R)-1-(3-(difluoromethyl)-2-fluorophenyl)ethyl)-1-((R)-2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide (Example 309) and N—((R)-1-(3-(difluoromethyl)-2-fluorophenyl)ethyl)-1-((S)-2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide (Example 310) (Diastereomers not Assigned)

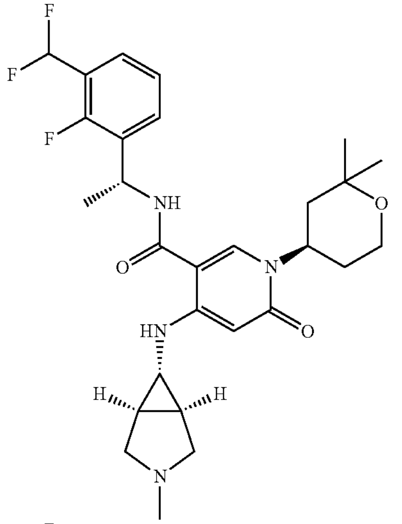

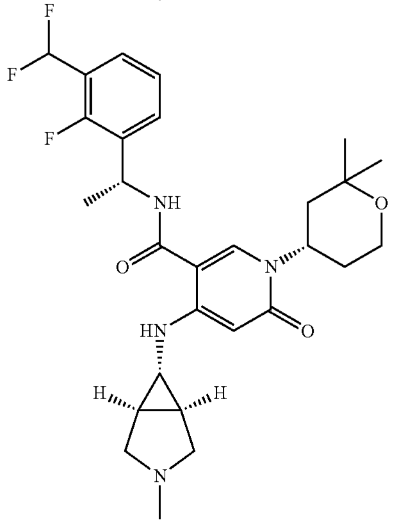

Example 309 and 310

Example 122 was separated into individual diastereomers via chiral SFC: Daicel AS-3 (4.6*100 mm 3 um)), $CO_2$/$CH_3OH$ [0.2% $NH_3$ (7M in $CH_3OH$)]=85/15)

Example 309: MS obsd (ESI+): 533.4 $[M+H]^+$. Analytical chiral UPCC: (Column: CHIRALPAK AS-3 4.6*100 mm 3 um, Flow rate: 3.0 mL/min, Cosolvent: MeOH (0.2% 7M NH3 in MeOH), Temp 40° C.) Retention time=1.0 min Example 310: MS obsd (ESI+): 533.4 $[M+H]^+$. Analytical chiral UPCC: (Column: CHIRALPAK AS-3 4.6*100 mm 3 um, Flow rate: 3.0 mL/min, Cosolvent: MeOH (0.2% 7M NH3 in MeOH), Temp 40° C.) Retention time=1.7 min Examples 311 and 312: N—((R)-1-(3-(difluoromethyl)-2-fluorophenyl)ethyl)-1-(1-(difluoromethyl)cyclopropyl)-4-(((S)-4-methyl-4-azaspiro[2.5]octan-7-yl)amino)-6-oxo-1,6-dihydropyridine-3-carboxamide (Example 311) and N—((R)-1-(3-(difluoromethyl)-2-fluorophenyl)ethyl)-1-(1-(difluoromethyl)cyclopropyl)-4-(((R)-4-methyl-4-azaspiro[2.5]octan-7-yl)amino)-6-oxo-1,6-dihydropyridine-3-carboxamide (Example 312) (Diastereomers Unassigned)

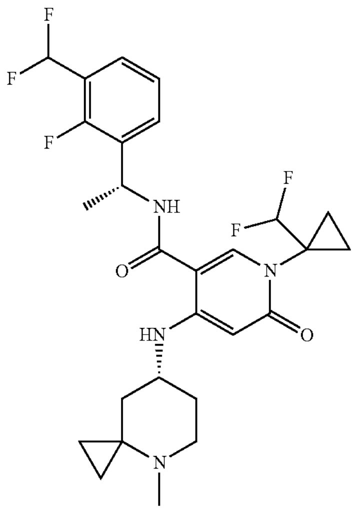

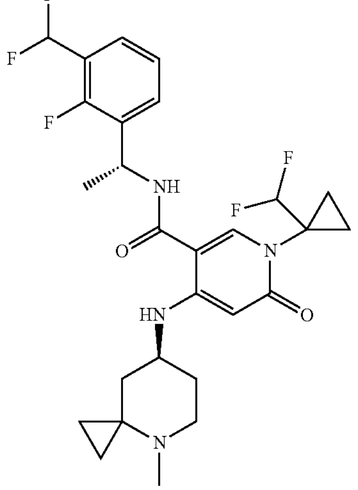

Examples 311 and 312

Example 240 was separated into individual diastereomers via chiral SFC (Column: YMC Cellulose-SC (20*250 mm, 5 um), Mobile phase: $CO_2$/MeOH [0.2% $NH_3$ (7M in MeOH)]=90/10).

Example 311: MS obsd (ESI+): 539.4 $[M+H]^+$. Analytical chiral UPCC: (Column: Cellulose-SC 4.6*100 mm 3 um, Flow rate: 3.0 mL/min, Cosolvent: MeOH (0.2% 7M NH3 in MeOH), Temp 40° C.) Retention time=1.1 min Example 312: MS obsd (ESI+): 539.4 $[M+H]^+$. Analytical chiral UPCC: (Column: Cellulose-SC 4.6*100 mm 3 um, Flow rate: 3.0 mL/min, Cosolvent: MeOH (0.2% 7M NH3 in MeOH), Temp 40° C.) Retention time=1.2 min Example 313: N—((R)-1-(3-(difluoromethyl)-2-fluorophenyl)ethyl)-1-(3-ethylbicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide

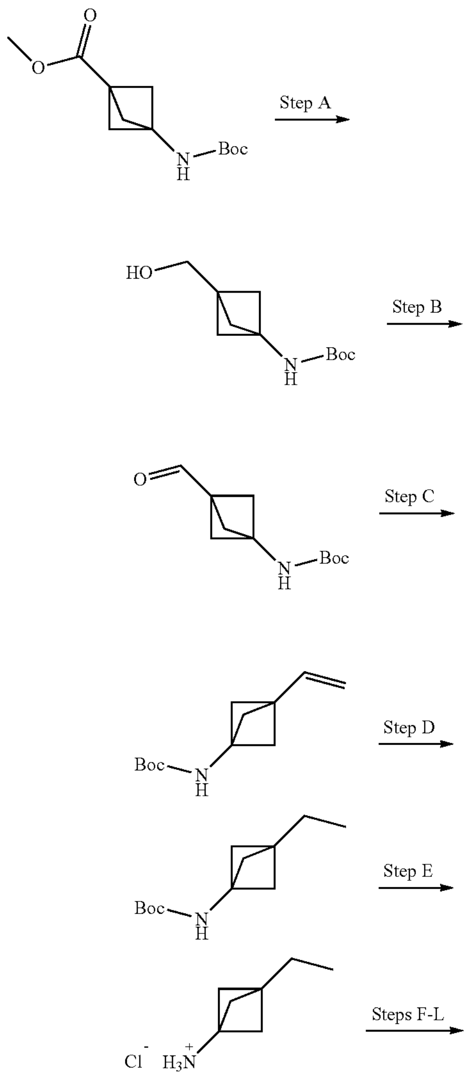

-continued

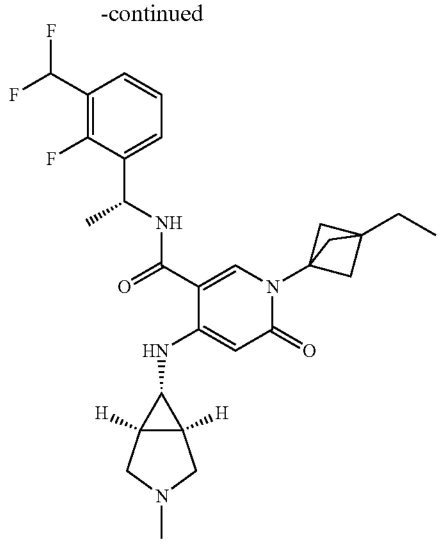

example 313

Step A: Tert-butyl (3-(hydroxymethyl) bicyclo[1.1.1]pentan-1-yl)carbamate

Methyl 3-(tert-butoxycarbonylamino) bicyclo[1.1.1]pentane-1-carboxylate (4.8 g, 19.89 mmol) was dissolved in THF (20 mL), and lithium borohydride (2 M in THF, 29.84 mL) was added at 0° C. The mixture was heated to 50° C. and stirred for 2 hrs. Cold water was poured into the mixture and the mixture was extracted with EA. The combined organic layers were washed with brine, dried with $Na_2SO_4$ and concentrated to obtain the title compound (4.0 g, 94% yield). $^1$H NMR (400 MHz, DMSO-$d_6$) δ: 7.38 (s, 1H), 4.44 (t, J=5.6 Hz, 1H), 3.43 (d, J=5.6 Hz, 2H), 1.73 (s, 6H), 1.37 (s, 9H).

Step B: Tert-butyl (3-formylbicyclo[1.1.1]pentan-1-yl)carbamate

Tert-butyl (3-(hydroxymethyl) bicyclo[1.1.1]pentan-1-yl) carbamate (3.5 g, 16.41 mmol) was dissolved in $CH_3CN$ (30 mL) and 2-Iodoxybenzoic acid (9.2 g, 32.82 mmol) was added. The mixture was stirred at 80° C. for 3 hrs. The reaction mixture was filtered and filtrate was concentrated. The crude residue was purified by flash chromatography column (eluted with EA/PE=10-20%) to obtain the title compound (2.8 g, 81% yield). $^1$H NMR (400 MHz, DMSO-$d_6$) δ:9.59 (s, 1H), 7.64 (s, 1H), 2.12 (s, 6H), 1.38 (s, 9H).

Step C: Tert-butyl (3-vinylbicyclo[1.1.1]pentan-1-yl)carbamate

Methyltriphenylphosphonium bromide (11.84 g, 33.14 mmol) was dissolved in THF (40 mL), and potassium tert-butoxide (3.72 g, 33.14 mmol) was added to the solution at 0° C. The reaction mixture was stirred at 0° C. for 30 min, then tert-butyl (3-formylbicyclo[1.1.1]pentan-1-yl)carbamate (2.8 g, 13.25 mmol) was added. The mixture was stirred at rt for 2 hrs. Cold water was poured into the reaction mixture, and the mixture was extracted with DCM. The combined organic layers were washed with bring and dried with $Na_2SO_4$. The solvent was removed under reduced pressure and the crude was purified by flash chromatography column (eluted with EA in PE (10-20%)) to obtain the title compound (2.4 g, 86% yield). $^1$H NMR (400 MHz, DMSO-$d_6$) δ: 7.59-7.15 (m, 1H), 6.01-5.89 (m, 1H), 5.03 (s, 1H), 4.99 (dd, J=7.6, 2.1 Hz, 1H), 1.90 (s, 6H), 1.37 (s, 9H).

Step D: Tert-butyl (3-ethylbicyclo[1.1.1]pentan-1-yl)carbamate

Tert-butyl (3-vinylbicyclo[1.1.1]pentan-1-yl)carbamate (200 mg, 0.96 mmol) and palladium on carbon (305 mg, 10% purity) were dissolved in $CH_3OH$ (5 mL). The mixture was purged with $H_2$ and stirred at rt for 16 hrs. The reaction mixture was filtered and the solvent was removed to obtain the title compound (190 mg, 94% yield). $^1$H NMR (400 MHz, DMSO-$d_6$) δ: 7.37 (s, 1H), 1.69 (s, 6H), 1.46 (q, J=7.4 Hz, 2H), 1.36 (s, 9H), 0.81 (t, J=7.4 Hz, 3H).

Step E: 3-ethylbicyclo[1.1.1]pentan-1-aminium chloride

Tert-butyl (3-ethylbicyclo[1.1.1]pentan-1-yl)carbamate (190 mg, 0.90 mmol) was dissolved in HCl (4M in Dioxane, 4 mL) and stirred at rt for 30 minutes. The reaction mixture was concentrated reduced pressure and the residue was triturated with petroleum ether and to obtain 3-ethylbicyclo [1.1.1]pentan-1-aminium chloride (120 mg, crude) as white solid. $^1$H NMR (400 MHz, DMSO-$d_6$) δ: 8.88 (s, 3H), 1.80 (s, 6H), 1.52 (q, J=7.4 Hz, 2H), 0.83 (t, J=7.4 Hz, 3H).

Steps F-L: N—((R)-1-(3-(difluoromethyl)-2-fluorophenyl)ethyl)-1-(3-ethylbicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide Steps F-L were preformed according to analogous procedures described in examples 92-154. MS obsd (ESI+): 515.5 $[M+H]^+$. $^1$H NMR (400 MHz, DMSO-$d_6$) δ: 8.80 (1H), 7.74 (1H), 7.68 (1H), 7.60 (1H), 7.52 (1H), 7.33 (1H), 7.14 (1H), 5.30 (1H), 5.24 (1H), 3.00 (1H), 2.98 (1H), 2.46 (1H), 2.26 (2H), 2.20 (3H), 2.12 (6H), 1.60 (2H), 1.58-1.46 (3H), 1.44 (4H), 0.88 (3H).

Biological Assays

SOS1-KRas(G12C) FRET Assay

Inhibition of the SOS1:KRAS interaction was measured using purified GST-tagged KRAS (res. 1-169, G12C, purified based on Hillig, et al., Proc Natl Acad Sci USA (2019); 116(7):2551-2560) and recombinant His10-SOS1 (res. 564-1049; purified based on Hillig, et al.). The final assay was performed at 20 uL with 0.5 nM SOS1 protein and 2.5 nM KRAS protein in a buffer of PBS, 0.1% BSA, 5 mM $MgCl_2$, 0.0025% Igepal, 100 mM KF, 5 mM DTT in a white 384 square well OptiPlate (PerkinElmer, Cat. 6007290). A 2×KRAS working solution was prepared in an assay buffer containing 5 nM GST-KRAS G12C and 2 nM anti-GST-Eu (K) (Cisbio, Cat. 61GSTKLA) and pre-incubated for 15 minutes at 25° C. Compounds were serially diluted in 100% DMSO from 2 mM (positive control, compound I-13, PCT Publ. No. WO2018/115380) or 20 mM and then diluted 1:20 in assay buffer before incubation with a solution of SOS1 protein mixed 1:5 with anti-6His-XL665 FRET donor (Cisbio, Cat. 61HISXL) for 15 minutes at 25° C. before addition of 2×KRAS working solution. The final DMSO concentration is 0.5%. Plates were incubated at RT for 2 hrs before the FRET signal was measured using Envision at emission 665 nm and 615 nm. FRET signal was converted to percentage of protein-protein interaction using the following equation:

$$\% \text{ Inhibition}=100\%-(C-N)/(P-N)*100\%$$

C: signal with compound treatment

P: signal for positive control (DMSO)

N: signal for negative control (no SOS1 added)

$IC_{50}$ and Hill coefficients were obtained using Graph Pad Prism (Graph Pad software, Inc, USA) with non-linear regression analysis.

TABLE A

| Example Number | SOS1-KRas(G12C) FRET $IC_{50}$ [uM] |
|---|---|
| 1 | 0.0274 |
| 2 | 0.0596 |
| 3 | 0.0412 |
| 4 | 0.0459 |
| 5 | 0.0355 |
| 6 | 0.0567 |
| 7 | 0.0534 |
| 8 | 0.0486 |
| 9 | 0.039 |
| 10 | 0.073 |
| 11 | 0.0376 |
| 12 | 0.705 |
| 13 | 0.155 |
| 14 | 0.225 |
| 15 | 0.847 |
| 16 | 0.0294 |
| 17 | 0.717 |
| 18 | 0.0778 |
| 19 | 0.347 |
| 20 | 0.0227 |
| 21 | 0.0537 |
| 22 | 0.0259 |
| 23 | 0.0471 |
| 24 | 0.04 |
| 25 | 0.0713 |
| 26 | 0.0271 |
| 27 | 0.0218 |
| 28 | 0.0592 |
| 29 | 0.0191 |
| 30 | 0.0363 |
| 31 | 0.0276 |
| 32 | 0.0582 |
| 33 | 0.018 |
| 34 | 0.0229 |
| 35 | 0.044 |
| 36 | 0.0308 |
| 37 | 0.0329 |
| 38 | 0.0458 |
| 39 | 0.0437 |
| 40 | 0.0118 |
| 41 | 0.0078 |
| 42 | 0.553 |
| 43 | 0.0757 |
| 44 | 0.0346 |
| 45 | 0.0379 |
| 46 | 0.0182 |
| 47 | 0.0045 |
| 48 | 0.0256 |
| 49 | 0.0135 |
| 50 | 0.0203 |
| 51 | 0.0185 |
| 52 | 0.0136 |
| 53 | 0.0156 |
| 54 | 0.0266 |
| 55 | 0.0236 |
| 56 | 0.0342 |
| 57 | 0.0282 |
| 58 | 0.0308 |
| 59 | 0.0315 |
| 60 | 0.0412 |
| 61 | 0.065 |
| 62 | 0.0201 |
| 63 | 0.0113 |

TABLE A-continued

| Example Number | SOS1-KRas(G12C) FRET $IC_{50}$ [uM] |
|---|---|
| 64 | 0.015 |
| 65 | 0.0504 |
| 66 | 0.0486 |
| 67 | 0.0106 |
| 68 | 0.0143 |
| 69 | 0.0174 |
| 70 | 0.0127 |
| 71 | 0.0219 |
| 72 | 0.0097 |
| 73 | 0.013 |
| 74 | 0.0046 |
| 75 | 0.0155 |
| 76 | 0.0125 |
| 77 | 0.0137 |
| 78 | 0.0009 |
| 79 | 0.0037 |
| 80 | 0.0167 |
| 81 | 0.174 |
| 82 | 0.0263 |
| 83 | 0.0257 |
| 84 | 0.0102 |
| 85 | 0.0261 |
| 86 | 0.0731 |
| 87 | 0.0617 |
| 88 | 0.0873 |
| 89 | 0.0229 |
| 90 | 0.0134 |
| 91 | 0.0139 |
| 92 | 0.0161 |
| 93 | 0.0232 |
| 94 | 0.0134 |
| 95 | 0.0216 |
| 96 | 0.0157 |
| 97 | 0.0167 |
| 98 | 0.0134 |
| 99 | 0.0648 |
| 100 | 0.0182 |
| 101 | 0.024 |
| 102 | 0.0121 |
| 103 | 0.0057 |
| 104 | 0.0454 |
| 105 | 0.013 |
| 106 | 0.0168 |
| 107 | 0.0084 |
| 108 | 0.147 |
| 109 | 0.0036 |
| 110 | 0.0238 |
| 111 | 0.0262 |
| 112 | 0.0136 |
| 113 | 0.0105 |
| 114 | 0.0211 |
| 115 | 0.0141 |
| 116 | 0.0267 |
| 117 | 0.0085 |
| 118 | 0.0166 |
| 119 | 0.0366 |
| 120 | 0.0357 |
| 121 | 0.0289 |
| 122 | 0.0174 |
| 123 | 0.0231 |
| 124 | 0.0314 |
| 125 | 0.0277 |
| 126 | 0.0044 |
| 127 | 0.0030 |
| 128 | 0.0082 |
| 129 | 0.025 |
| 130 | 0.0267 |
| 131 | 0.0221 |
| 132 | 0.0103 |
| 133 | 0.0232 |
| 134 | 0.0090 |
| 135 | 0.0521 |
| 136 | 0.006 |
| 137 | 0.0353 |
| 138 | 0.0197 |
| 139 | 0.0497 |
| 140 | 0.0152 |

TABLE A-continued

| Example Number | SOS1-KRas(G12C) FRET $IC_{50}$ [uM] |
|---|---|
| 141 | 0.0628 |
| 142 | 0.0049 |
| 143 | 0.0038 |
| 144 | 0.0040 |
| 145 | 0.0352 |
| 146 | 0.0054 |
| 147 | 0.045 |
| 148 | 0.0074 |
| 149 | 0.0616 |
| 150 | 0.0123 |
| 151 | 0.0473 |
| 152 | 0.0074 |
| 153 | 0.0584 |
| 154 | 0.0376 |
| 155 | 0.0212 |
| 156 | 0.0124 |
| 157 | 0.218 |
| 158 | 0.082 |
| 159 | 1.06 |
| 160 | 0.0214 |
| 161 | 0.024 |
| 162 | 0.0278 |
| 163 | 0.0293 |
| 164 | 0.0135 |
| 165 | 7.94 |
| 166 | 0.193 |
| 167 | >10 |
| 168 | 0.561 |
| 169 | 5.9 |
| 170 | 0.0409 |
| 171 | 1.25 |
| 172 | >10 |
| 173 | 1.18 |
| 174 | 1.18 |
| 175 | 0.013 |
| 176 | 0.109 |
| 177 | 0.0556 |
| 178 | >10 |
| 179 | 0.0707 |
| 180 | 0.113 |
| 181 | 0.0798 |
| 182 | 0.0338 |
| 183 | 0.0061 |
| 184 | 0.0558 |
| 185 | 0.0307 |
| 186 | 0.0275 |
| 187 | 0.0223 |
| 188 | 0.0413 |
| 189 | 0.0163 |
| 190 | 0.315 |
| 191 | 0.14 |
| 192 | 0.0129 |
| 193 | 0.151 |
| 194 | 0.0193 |
| 195 | 0.00544 |
| 196 | 0.0432 |
| 197 | 0.0317 |
| 198 | 0.00341 |
| 199 | 0.0101 |
| 200 | 0.0167 |
| 201 | 0.014 |
| 202 | 0.0195 |
| 203 | 0.0046 |
| 204 | 0.00361 |
| 205 | 0.0266 |
| 206 | 0.137 |
| 207 | 0.0093 |
| 208 | 0.013 |
| 209 | 0.0634 |
| 210 | 0.0043 |
| 211 | 0.0294 |
| 212 | 0.0382 |
| 213 | 0.149 |
| 214 | 0.0106 |
| 215 | 0.0682 |
| 216 | 0.0191 |
| 217 | 0.0074 |

TABLE A-continued

| Example Number | SOS1-KRas(G12C) FRET $IC_{50}$ [uM] |
|---|---|
| 218 | 0.0158 |
| 219 | 0.0269 |
| 220 | 0.0268 |
| 221 | 0.0382 |
| 222 | 0.0276 |
| 223 | 0.0141 |
| 224 | 0.0468 |
| 225 | 0.0139 |
| 226 | 0.0353 |
| 227 | 0.0619 |
| 228 | 0.0643 |
| 229 | 0.0227 |
| 230 | 0.0219 |
| 231 | 0.0102 |
| 232 | 0.0919 |
| 233 | 0.0048 |
| 234 | 0.0092 |
| 235 | 0.142 |
| 236 | 0.0453 |
| 237 | 0.0194 |
| 238 | 0.0293 |
| 239 | 0.0215 |
| 240 | 0.0135 |
| 241 | 0.029 |
| 242 | 0.0116 |
| 243 | 0.0063 |
| 244 | 0.0181 |
| 245 | 0.0442 |
| 246 | 0.0161 |
| 247 | 0.0137 |
| 248 | 0.0241 |
| 249 | 0.0165 |
| 250 | 0.0217 |
| 251 | 0.0341 |
| 252 | 0.017 |
| 253 | 0.0431 |
| 254 | 0.013 |
| 255 | 0.027 |
| 256 | 0.0139 |
| 257 | 0.0858 |
| 258 | 0.0763 |
| 259 | 0.0104 |
| 260 | 0.0124 |
| 261 | 0.0414 |
| 262 | 0.116 |
| 263 | 0.0149 |
| 264 | 0.0022 |
| 265 | 0.0278 |
| 266 | 0.0014 |
| 267 | 0.00244 |
| 268 | 0.0328 |
| 269 | 0.00121 |
| 270 | 0.00174 |
| 271 | 0.0369 |
| 272 | 0.0291 |
| 273 | 0.0157 |
| 274 | 0.0106 |
| 275 | 0.361 |
| 276 | >10 |
| 277 | 0.00946 |
| 278 | 0.0241 |
| 279 | 0.0373 |
| 280 | 0.0158 |
| 281 | 0.0184 |
| 282 | 0.0344 |
| 283 | 0.137 |
| 284 | 0.023 |
| 285 | 0.0047 |
| 286 | 0.0155 |
| 287 | 0.0099 |
| 288 | 0.0236 |
| 289 | 0.0133 |
| 290 | 0.0092 |
| 291 | 0.0755 |
| 292 | 0.0079 |
| 293 | 0.0192 |
| 294 | 0.0534 |

TABLE A-continued

| Example Number | SOS1-KRas(G12C) FRET $IC_{50}$ [uM] |
|---|---|
| 295 | 0.0536 |
| 296 | 0.252 |
| 297 | 0.0334 |
| 298 | 0.0881 |
| 299 | 0.0513 |
| 300 | 0.0208 |
| 301 | 0.0453 |
| 302 | 0.0315 |
| 303 | 0.0182 |
| 304 | 0.0257 |
| 305 | 0.0233 |
| 306 | 0.0417 |
| 307 | 0.0049 |
| 308 | 0.0179 |
| 309 | 0.0117 |
| 310 | 0.0372 |
| 311 | 0.0097 |
| 312 | 0.0356 |
| 313 | 0.0105 |

Surface Plasmon Resonance (SPR) SOS1 Binding Assay

Binding to SOS1 was measured using a SPR assay with purified recombinant human SOS1 substrate (res. 564-1049 with N-terminal Avi tag; purified and biotinylated based on Hillig, et al., Proc Natl Acad Sci USA (2019); 116 (7): 2551-2560). SPR measurements were performed on a Biacore 8K SPR instrument (GE Healthcare, Sweden). Assays were performed at 25° C. using Series S SA sensor chips pre-coated with streptavidin (GE Healthcare, Cat. BR100531). Biotinylated SOS1 diluted in sample buffer (20 mM Tris HCl, 150 mM NaCl, 1 mM DTT, 0.05% TWEEN 20, 1 mM $MgCl_2$, pH 8.0) was captured to one flow cell of the chip to about 3,000 resonance units (RU) using sample buffer supplemented with 5% DMSO as a running buffer. Serial dilutions of the assayed compounds in the running buffer at 100, 50 or 0.5 μM were injected for 60 s at a flow rate of 30 μL/min and association phases were recorded. Dissociation of the samples was monitored for 600 s. Data processing was performed using Biacore Insight Software (Biacore, GE Healthcare). Sensorgrams recorded on a SA flow cell without captured protein were subtracted from sensorgrams recorded on the SOS1 surface. Blank injections of running buffer were used for double referencing and solvent correction was applied to all sample sensorgrams to correct for buffer mismatches. $K_D$s were estimated using a kinetic or steady state, where applicable, fitting model describing a reversible equilibrium with 1:1 binding between SOS1 and the compound.

TABLE B

| Example Number | hSOSI $K_D$ (nM) |
|---|---|
| 1 | 6 |
| 2 | 27 |
| 3 | 16 |
| 4 | 16 |
| 5 | 20 |
| 6 | 30 |
| 7 | 20 |
| 8 | 12 |
| 9 | 17 |
| 10 | 74 |
| 12 | 245 |
| 13 | 91 |
| 14 | 103 |
| 16 | 23 |

TABLE B-continued

| Example Number | hSOSI $K_D$ (nM) |
|---|---|
| 20 | 10.4 |
| 21 | 17 |
| 24 | 27 |
| 25 | 45 |
| 26 | 11 |
| 29 | 11 |
| 42 | 186 |
| 45 | 21 |
| 47 | 2 |
| 48 | 7 |
| 49 | 3 |
| 50 | 8 |
| 51 | 8 |
| 52 | 6 |
| 55 | 12 |
| 61 | 34 |
| 63 | 7 |
| 64 | 9 |
| 65 | 48 |
| 66 | 34 |
| 69 | 13 |
| 70 | 4 |
| 72 | 3 |
| 74 | 2 |
| 79 | 2 |
| 80 | 8 |
| 81 | 96 |
| 82 | 17 |
| 83 | 20 |
| 84 | 9 |
| 85 | 12 |
| 86 | 29 |
| 87 | 84 |
| 88 | 96 |
| 89 | 12 |
| 90 | 9 |
| 91 | 12 |
| 92 | 9 |
| 93 | 13 |
| 94 | 7 |
| 95 | 12 |
| 96 | 9 |
| 97 | 7 |
| 98 | 6 |
| 99 | 30 |
| 100 | 10 |
| 101 | 11 |
| 102 | 8 |
| 103 | 3 |
| 104 | 24 |
| 105 | 9 |
| 106 | 19 |
| 107 | 3 |
| 108 | 343 |
| 109 | 2 |
| 110 | 12 |
| 111 | 17 |
| 112 | 6 |
| 113 | 6 |
| 114 | 13 |
| 115 | 6 |
| 116 | 11 |
| 117 | 6 |
| 118 | 11 |
| 119 | 23 |
| 120 | 24 |
| 121 | 21 |
| 122 | 9 |
| 123 | 15 |
| 124 | 13 |
| 125 | 13 |
| 126 | 2 |
| 127 | 3 |
| 128 | 3 |
| 129 | 8 |
| 130 | 23 |
| 131 | 17 |

TABLE B-continued

| Example Number | hSOSI $K_D$ (nM) |
|---|---|
| 132 | 8 |
| 133 | 11 |
| 134 | 5 |
| 135 | 31 |
| 136 | 3 |
| 137 | 27 |
| 138 | 12 |
| 139 | 25 |
| 140 | 7 |
| 141 | 33 |
| 142 | 4 |
| 143 | 3 |
| 144 | 3 |
| 145 | 37 |
| 146 | 9 |
| 147 | 73 |
| 148 | 6 |
| 149 | 56 |
| 151 | 12 |
| 152 | 4 |
| 153 | 25 |
| 154 | 23 |
| 155 | 11 |
| 156 | 3 |

What is claimed is:

1. A compound of Formula (I):

(I)

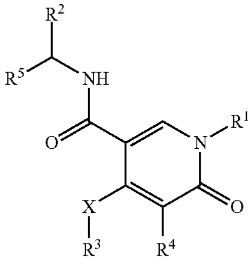

or a pharmaceutically acceptable salt thereof, wherein:

$R^1$ is a $C_1$-$C_6$ alkyl, 4 to 10-membered heterocyclyl or $C_3$-$C_{10}$ cycloalkyl, wherein each alkyl, heterocyclyl, and cycloalkyl is optionally substituted with one or more $R^a$;

$R^a$ is each independently $C_1$-$C_3$ alkyl, $C_1$-$C_3$ haloalkyl, $C_3$-$C_6$ cycloalkyl, halogen, —C(O)$C_1$-$C_3$ alkyl, or —C(O)—$C_3$-$C_6$ cycloalkyl, wherein each cycloalkyl is optionally substituted with one or more halogen;

$R^2$ is a $C_6$ aryl or 5 to 10-membered heteroaryl, wherein each aryl and heteroaryl is optionally substituted with one or more $R^b$;

$R^b$ is each independently halogen, $C_1$-$C_3$ haloalkyl, $C_1$-$C_3$ alkyl, or $C_3$ cycloalkyl;

$R^3$ is —H, 4 to 10-membered heterocyclyl, $C_1$-$C_6$ alkyl, $C_1$-$C_6$ alkylene-O—NH—C(NH)($NH_2$), $C_3$-$C_{10}$ cycloalkyl, $C_1$-$C_6$ alkylene-5 to 10-membered heteroaryl, $C_1$-$C_6$ alkylene-4 to 10-membered heterocyclyl, $C_1$-$C_6$ alkylene-($C_3$-$C_{10}$ cycloalkyl), or $C_3$-$C_{10}$ cycloalkyl, wherein each alkyl heterocyclyl, cycloalkyl, and heteroaryl is optionally substituted with one or more $R^c$;

$R^c$ is each independently $C_1$-$C_6$ alkyl, —OH, —O—($C_1$-$C_6$ alkyl), $C_1$-$C_6$ alkylene-O—$CH_3$, halogen, $C_1$-$C_6$ alkylene-5 to 10-membered heterocyclyl, —N($CH_3$)($CH_3$), $C_3$-$C_{10}$ cycloalkyl, $C_1$-$C_6$ haloalkyl, wherein each heterocyclyl, cycloalkyl, and alkyl is optionally substituted with one or more deuterium, $C_1$-$C_6$ alkyl, —OH, halogen, CN, or $C_1$-$C_6$ haloalkyl;

$R^4$ is H, —$CH_3$, —CN, -OMe, or halogen;

$R^5$ is $C_1$-$C_3$ alkyl or $C_1$-$C_3$ haloalkyl; and

X is NH or S.

2. The compound of claim 1, wherein $R^4$ is H.

3. The compound of claim 1, wherein $R^2$ is $C_6$ aryl, optionally substituted with one or more $R^b$.

4. The compound of claim 3, wherein $R^2$ is substituted with two $R^b$.

5. The compound of claim 4, wherein $R^2$ is is selected from

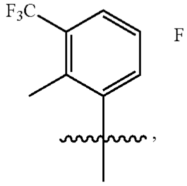

,

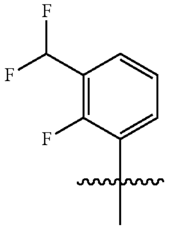

, and

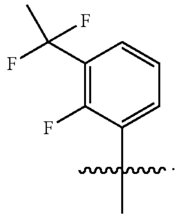

.

6. The compound of claim 1, wherein X is NH.

7. The compound of claim 1, wherein $R^5$ is $C_1$-$C_3$ alkyl.

8. The compound of claim 1, wherein $R^3$ is a 4 to 10-membered heterocyclyl optionally substituted with one or more $R^c$.

9. The compound of claim 8, wherein $R^3$ is a 4 to 6-membered heterocyclyl substituted with one $R^c$.

10. The compound of claim 9, wherein $R^c$ is —$CH_3$ or -$CD_3$.

11. The compound of claim 10, wherein $R^3$ is piperidinyl.

12. The compound of claim 1, wherein $R^1$ is a 4 to 10-membered heterocyclyl, optionally substituted with one or more $R^a$.

13. The compound of claim 12, wherein each $R^a$ is independently selected from $C_1$-$C_3$ alkyl, halogen, $C_1$-$C_3$ haloalkyl, and —C(O)$C_1$-$C_3$ alkyl.

14. The compound of claim 1, wherein in Formula (I)

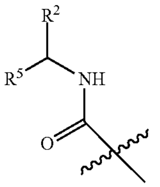

is

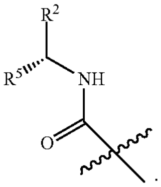

.

15. The compound of claim 1, wherein $R^1$ is a $C_3$-$C_{10}$ cycloalkyl, optionally substituted with one or more $R^a$.

16. The compound of claim 15, wherein $R^1$ is cyclopropyl, substituted with one $R^a$.

17. A compound selected from the group consisting of:

(R)—N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide;

(R)-4-((2-(dimethylamino)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((R)-1-methylpyrrolidin-3-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((S)-1-methylpyrrolidin-3-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((R)-1-methylpiperidin-3-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((S)-1-methylpiperidin-3-yl)amino)-6-oxo-1-(tetrahydro-2H-pyran-4-yl)-1,6-dihydropyridine-3-carboxamide;

4-(((1r,3R)-3-(dimethylamino)cyclobutyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

(R)—N-(1-(2-methyl-3-(trifluoromethyl)phenyl)ethyl)-4-(((1-methylazetidin-3-yl)methyl)amino)-6-oxo-1-(tetrahydro-2H-pyran-4-yl)-1,6-dihydropyridine-3-carboxamide;

(R)-4-((3-(dimethylamino) propyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

(R)-4-(((1-methyl-1H-imidazol-5-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

(R)—N-(1-(2-methyl-3-(trifluoromethyl)phenyl)ethyl)-6-oxo-4-(((tetrahydro-1H-pyrrolizin-7a (5H)-yl)methyl)amino)-1-(tetrahydro-2H-pyran-4-yl)-1,6-dihydropyridine-3-carboxamide;

(R)—N-(1-(2-methyl-3-(trifluoromethyl)phenyl)ethyl)-4-(methylamino)-6-oxo-1-(tetrahydro-2H-pyran-4-yl)-1,6-dihydropyridine-3-carboxamide;

4-(((1S,3S)-3-hydroxycyclopentyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

4-(((1R,3R)-3-hydroxycyclopentyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

(R)—N-(1-(2-methyl-3-(trifluoromethyl)phenyl)ethyl)-6-oxo-1-(tetrahydro-2H-pyran-4-yl)-4-((1-(2,2,2-trifluoroethyl)piperidin-4-yl)amino)-1,6-dihydropyridine-3-carboxamide;

(R)-4-((1-(2-fluoroethyl)piperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

(R)-5-bromo-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide;

(R)-5-methoxy-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide;

(R)-5-methyl-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide;

(R)-5-cyano-N-(1-(2-methyl-3-(trifluoromethyl)phenyl)ethyl)-4-((1-methylpiperidin-4-yl)amino)-6-oxo-1-(tetrahydro-2H-pyran-4-yl)-1,6-dihydropyridine-3-carboxamide;

(R)-4-((2-methyl-2-azaspiro[3.3]heptan-6-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,5S,6s)-3-methyl-3-azabicyclo[3.1.1]heptan-6-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,5S,6r)-3-methyl-3-azabicyclo[3.1.1]heptan-6-yl)amino)-6-oxo-1-(tetrahydro-2H-pyran-4-yl)-1,6-dihydropyridine-3-carboxamide;

4-(((3R,4R)-3-methoxy-1-methylpiperidin-4-yl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

4-(((3S,4S)-3-methoxy-1-methylpiperidin-4-yl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

(diastereomer of example 24, absolute stereochemistry arbitrarily assigned));

N—((R)-1-(2-methyl-3-(trifluoromethyl)phenyl)ethyl)-4-(((1R,5S,6s)-3-methyl-3-azabicyclo[3.1.0]hexan-6-yl)amino)-6-oxo-1-(tetrahydro-2H-pyran-4-yl)-1,6-dihydropyridine-3-carboxamide;

4-(((1s,3S)-3-(dimethylamino)cyclobutyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

(R)—N-(1-(2-methyl-3-(trifluoromethyl)phenyl)ethyl)-4-((1-methylazetidin-3-yl)amino)-6-oxo-1-(tetrahydro-2H-pyran-4-yl)-1,6-dihydropyridine-3-carboxamide;

(R)-4-(((3-methoxy-1-methylazetidin-3-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

(R)-4-(((3-fluoro-1-methylazetidin-3-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,5S,8s)-3-methyl-3-azabicyclo[3.2.1]octan-8-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((1R,5S,8r)-3-methyl-3-azabicyclo[3.2.1]octan-8-yl)amino)-6-oxo-1-(tetrahydro-2H-pyran-4-yl)-1,6-dihydropyridine-3-carboxamide (absolute stereochemistry is arbitrarily assigned);

(diastereomer of example 31, absolute stereochemistry is arbitrarily assigned);

N—((R)-1-(2-methyl-3-(trifluoromethyl)phenyl)ethyl)-4-(((S)-1-methylazepan-4-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((R)-1-methylazepan-4-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((S)-1-methylazepan-3-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((R)-1-methylazepan-3-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,2R,4S)-7-methyl-7-azabicyclo[2.2.1]heptan-2-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((1S,2S,4R)-7-methyl-7-azabicyclo[2.2.1]heptan-2-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((S)-4-methyl-4-azaspiro[2.5]octan-7-yl)amino)-6-oxo-1-(tetrahydro-2H-pyran-4-yl)-1,6-dihydropyridine-3-carboxamide (absolute stereochemistry is arbitrarily assigned);

N—((R)-1-(2-methyl-3-(trifluoromethyl)phenyl)ethyl)-4-(((R)-4-methyl-4-azaspiro[2.5]octan-7-yl)amino)-6-oxo-1-(tetrahydro-2H-pyran-4-yl)-1,6-dihydropyridine-3-carboxamide (absolute stereochemistry is arbitrarily assigned);

(R)—N-(1-(3-(difluoromethyl)-2-fluorophenyl)ethyl)-4-((1-methylpiperidin-4-yl)amino)-6-oxo-1-(tetrahydro-2H-pyran-4-yl)-1,6-dihydropyridine-3-carboxamide;

(R)—N-(1-(2-methyl-3-(trifluoromethyl)phenyl)ethyl)-6-oxo-1-(tetrahydro-2H-pyran-4-yl)-4-((tetrahydro-2H-pyran-4-yl)amino)-1,6-dihydropyridine-3-carboxamide;

(R)-4-(azetidin-3-ylamino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-6-oxo-4-(pyrrolidin-3-ylamino)-1-(tetrahydro-2H-pyran-4-yl)-1,6-dihydropyridine-3-carboxamide;

(R)-4-((1,4-dimethylpiperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

(R)-4-((2-(guanidinooxy)ethyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(3-(difluoromethyl)-2-fluorophenyl)ethyl)-4-((1-methylpiperidin-4-yl)amino)-1-((S)-3-methyltetrahydrofuran-3-yl)-6-oxo-1,6-dihydropyridine-3-carboxamide (absolute stereochemistry arbitrarily assigned);

N—((R)-1-(3-(difluoromethyl)-2-fluorophenyl)ethyl)-4-((1-methylpiperidin-4-yl)amino)-1-((R)-3-methyltetrahydrofuran-3-yl)-6-oxo-1,6-dihydropyridine-3-carboxamide (absolute stereochemistry arbitrarily assigned);

(R)—N-(1-(3-(difluoromethyl)-2-fluorophenyl)ethyl)-1-(1-(difluoromethyl)cyclopropyl)-4-((1-methylpiperidin-4-yl)amino)-6-oxo-1,6-dihydropyridine-3-carboxamide;

(R)-1-(1-(difluoromethyl)cyclopropyl)-N-(1-(2-methyl-3-(trifluoromethyl)phenyl)ethyl)-4-((1-methylpiperidin-4-yl)amino)-6-oxo-1,6-dihydropyridine-3-carboxamide;

(R)—N-(1-(3-(1,1-difluoroethyl)-2-fluorophenyl)ethyl)-1-(1-(difluoromethyl)cyclopropyl)-4-((1-methylpiperidin-4-yl)amino)-6-oxo-1,6-dihydropyridine-3-carboxamide;

(R)-1-(1-(difluoromethyl)cyclopropyl)-N-(1-(2-fluoro-3-(trifluoromethyl)phenyl)ethyl)-4-((1-methylpiperidin-4-yl)amino)-6-oxo-1,6-dihydropyridine-3-carboxamide;

(R)—N-(1-(3,3-difluoro-2,3-dihydrobenzofuran-7-yl)ethyl)-1-(1-(difluoromethyl)cyclopropyl)-4-((1-methylpiperidin-4-yl)amino)-6-oxo-1,6-dihydropyridine-3-carboxamide;

(R)-1-(1-(difluoromethyl)cyclopropyl)-N-(1-(3-fluorobenzofuran-7-yl)ethyl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6r)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6s)-3-(methyl-d3)-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6s)-3-ethyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6s)-3-isopropyl-3-azabicyclo[3.1.0]hexan-6-yl)amino)-6-oxo-1,6-dihydropyridine-3-carboxamide;

4-(((1R,5S,6s)-3-cyclopropyl-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-((2-(dimethylamino)ethyl)amino)-6-oxo-1,6-dihydropyridine-3-carboxamide;

(R)-4-((1-cyclopropylpiperidin-4-yl)amino)-N-(1-(3-(difluoromethyl)-2-fluorophenyl)ethyl)-1-(1-(difluoromethyl)cyclopropyl)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((3S,4R)-3-fluoro-1-methylpiperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3R,4S)-3-fluoro-1-methylpiperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3R,4R)-3-fluoro-1-methylpiperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3S,4S)-3-fluoro-1-methylpiperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3S,4R)-3-fluoro- 1-(methyl-d3)piperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3R,4S)-3-fluoro-1-(methyl-d3)piperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3S,4R)-3-fluoropiperidin-4-yl)amino)-6-oxo-1,6-dihydropyridine-3-carboxamide (absolute stereochemistry arbitrarily assigned);

N—((R)-1-(3-(difluoromethyl)-2-fluorophenyl)ethyl)-1-(1-(difluoromethyl)cyclopropyl)-4-(((3R,4S)-3-fluoropiperidin-4-yl)amino)-6-oxo-1,6-dihydropyridine-3-carboxamid (absolute stereochemistry arbitrarily assigned)e;

1-((1S,2R)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (absolute stereochemistry arbitrarily assigned);

1-((1R,2S)-[1,1'-bi(cyclopropan)]-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide (absolute stereochemistry arbitrarily assigned);

1-((1R,2S)-[1,1'-bi(cyclopropan)]-2-yl)-N—((R)-1-(3-(difluoromethyl)-2-fluorophenyl)ethyl)-4-((1-methylpiperidin-4-yl)amino)-6-oxo-1,6-dihydropyridine-3-carboxamide (absolute stereochemistry arbitrarily assigned);

1-((1S,2R)-[1,1'-bi(cyclopropan)]-2-yl)-N—((R)-1-(3-(difluoromethyl)-2-fluorophenyl)ethyl)-4-((1-methylpiperidin-4-yl)amino)-6-oxo-1,6-dihydropyridine-3-carboxamide (absolute stereochemistry arbitrarily assigned);

(R)—N-(1-(3-(difluoromethyl)-2-fluorophenyl)ethyl)-4-((1-methylpiperidin-4-yl)amino)-6-oxo-1-(1-(trifluoromethyl)cyclopropyl)-1,6-dihydropyridine-3-carboxamide;

(R)—N-(1-(3-(difluoromethyl)-2-fluorophenyl)ethyl)-1-(1-(difluoromethyl)cyclobutyl)-4-((1-methylpiperidin-4-yl)amino)-6-oxo-1,6-dihydropyridine-3-carboxamide;

(R)—N-(1-(3-(difluoromethyl)-2-fluorophenyl)ethyl)-1-(1-(fluoromethyl)cyclopropyl)-4-((1-methylpiperidin-4-yl)amino)-6-oxo-1,6-dihydropyridine-3-carboxamide;

(R)-1-(1-(cyclopropanecarbonyl)-3-methylazetidin-3-yl)-N-(1-(3-(difluoromethyl)-2-fluorophenyl)ethyl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((3S,4R)-3-fluorotetrahydro-2H-pyran-4-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((3R,4S)-3-fluorotetrahydro-2H-pyran-4-yl)-4-((1-methylpiperidin-4-yl)amino)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-((2-morpholinoethyl)amino)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-((1-(2-fluoroethyl)piperidin-4-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-(((R)-quinuclidin-3-yl)amino)-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-(((S)-quinuclidin-3-yl)amino)-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-((((S)-quinuclidin-2-yl)methyl)amino)-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-((((R)-quinuclidin-2-yl)methyl)amino)-1,6-dihydropyridine-3-carboxamide;

N—((R)-1-(3-(difluoromethyl)-2-fluorophenyl)ethyl)-1-(1-(difluoromethyl)cyclopropyl)-4-(((S)-1-(1-methyl-1H-imidazol-5-yl)ethyl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((R)-1-(1-methyl-1H-imidazol-5-yl)ethyl)amino)-6-oxo-1,6-dihydropyridine-3-carboxamide;

4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,6s)-3-(methyl-d3)-3-azabicyclo[3.1.0]hexan-6-yl)amino)-6-oxo-1,6-dihydropyridine-3-carboxamide;

1-((R)-2,2-difluorocyclopropyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-2,2-difluorocyclopropyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((R)-2,2-dimethylcyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((S)-2,2-dimethylcyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((1s,3S)-3-fluorocyclobutyl)-4-(((1R,5S,6s)-3-methyl-3-azabicyclo[3.1.0]hexan-6-yl)amino)-6-oxo-1,6-dihydropyridine-3-carboxamid;

N—((R)-1-(3-(difluoromethyl)-2-fluorophenyl)ethyl)-1-((1r,3R)-3-fluorocyclobutyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)

amino)-1-(3-methylbicyclo[1.1.1]pentan-1-yl)-6-oxo-1,6-dihydropyridine-3-carboxamide;

N—((R)-1-(3-(difluoromethyl)-2-fluorophenyl)ethyl)-1-isopropyl-4-(((1R,5S,6s)-3-methyl-3-azabicyclo[3.1.0]hexan-6-yl)amino)-6-oxo-1,6-dihydropyridine-3-carboxamide;

1-(3,3-difluorocyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-cyclopropyl-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(3-fluorobicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide;

1-((R)-2,2-difluorocyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-2,2-difluorocyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(3-(difluoromethyl) bicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(3-(trifluoromethyl) bicyclo[1.1.1]pentan-1-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(spiro[2.3]hexan-5-yl)-1,6-dihydropyridine-3-carboxamide;

1-(2-cyclopropylpropan-2-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1R,3R)-2,2-difluoro-3-methylcyclopropyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1S,3S)-2,2-difluoro-3-methylcyclopropyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((1S,2S)-2-(trifluoromethyl)cyclopropyl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((1R,2R)-2-(trifluoromethyl)cyclopropyl)-1,6-dihydropyridine-3-carboxamide;

N—((R)-1-(3-(difluoromethyl)-2-fluorophenyl)ethyl)-1-((1S,2S)-2-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((1R,2R)-2-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-spiro[2.3]hexan-1-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-spiro[2.3]hexan-1-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-(1-(trifluoromethyl)cyclopropyl)-1,6-dihydropyridine-3-carboxamide;

N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-(1-(trifluoromethyl)cyclopropyl)-1,6-dihydropyridine-3-carboxamide;

N—((R)-1-(3-(1,1-difluoroethyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide;

1-(4,4-difluorocyclohexyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((3aR,5r,6aS)-2-methyloctahydrocyclopenta[c]pyrrol-5-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((3aR,5s,6aS)-2-methyloctahydrocyclopenta[c]pyrrol-5-yl)amino)-6-oxo-1,6-dihydropyridine-3-carboxamide;

N—((R)-1-(3-(difluoromethyl)-2-fluorophenyl)ethyl)-1-(6,6-difluorospiro[3.3]heptan-2-yl)-4-(((3S,4R)-3-fluoro-1-methylpiperidin-4-yl)amino)-6-oxo-1,6-dihydropyridine-3-carboxamide;

N—((R)-1-(3-(difluoromethyl)-2-fluorophenyl)ethyl)-1-(6,6-difluorospiro[3.3]heptan-2-yl)-4-(((3R,4S)-3-fluoro-1-methylpiperidin-4-yl)amino)-6-oxo-1,6-dihydropyridine-3-carboxamide;

N—((R)-1-(3-(difluoromethyl)-2-fluorophenyl)ethyl)-1-((3S,4R)-3-fluorotetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((3R,4S)-3-fluorotetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide;

1-(1-(difluoromethyl)cyclopropyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclobutyl)-4-(((1R,5S,6s)-3-methyl-3-azabicyclo[3.1.0]hexan-6-yl)amino)-6-oxo-1,6-dihydropyridine-3-carboxamide;

1-(bicyclo[2.2.1]heptan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1s,3S)-3-(dimethylamino)cyclobutyl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(3-fluorobicyclo[1.1.1]pentan-1-yl)-4-(((1R,5S,8s)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(3-fluorobicyclo[1.1.1]pentan-1-yl)-4-(((1R,5S,8r)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1-(1-(trifluoromethyl)cyclopropyl)-1,6-dihydropyridine-3-carboxamide;

N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1-(1-(trifluoromethyl)cyclopropyl)-1,6-dihydropyridine-3-carboxamide;

1-cyclopropyl-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

1-cyclopropyl-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-4-(((3R,4S)-3-fluoro-1-methylpiperidin-4-yl)amino)-1-(3-fluorobicyclo[1.1.1]pentan-1-yl)-6-oxo-1,6-dihydropyridine-3-carboxamide;

N—((R)-1-(3-(difluoromethyl)-2-fluorophenyl)ethyl)-4-(((3S,4R)-3-fluoro-1-methylpiperidin-4-yl)amino)-1-(3-fluorobicyclo[1.1.1]pentan-1-yl)-6-oxo-1,6-dihydropyridine-3-carboxamide;

1-((S)-2,2-difluorocyclobutyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((R)-2,2-difluorocyclobutyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-2,2-difluorocyclobutyl)-N—((R)-1-(3-(difluoromethyl)-2-fluorophenyl)ethyl)-4-(((3-fluoro-1-methylazetidin-3-yl)methyl)amino)-6-oxo-1,6-dihydropyridine-3-carboxamide;

1-((R)-2,2-difluorocyclobutyl)-N—((R)-1-(3-(difluoromethyl)-2-fluorophenyl)ethyl)-4-(((3-fluoro-1-methylazetidin-3-yl)methyl)amino)-6-oxo-1,6-dihydropyridine-3-carboxamide;

1-((S)-2,2-difluorocyclobutyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((R)-2,2-difluorocyclobutyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-cyclobutyl-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((S)-3-methyltetrahydrofuran-3-yl)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((R)-3-methyltetrahydrofuran-3-yl)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((3S,4R)-3-methoxy-1-methylpiperidin-4-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((3R,4S)-3-methoxy-1-methylpiperidin-4-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-6-oxo-4-(((R)-quinuclidin-3-yl)amino)-1,6-dihydropyridine-3-carboxamide;

1-(bicyclo[1.1.1]pentan-1-yl)-N—((R)-1-(3-(difluoromethyl)-2-fluorophenyl)ethyl)-6-oxo-4-(((S)-quinuclidin-3-yl)amino)-1,6-dihydropyridine-3-carboxamide;

(R)—N-(1-(2-methyl-3-(trifluoromethyl)phenyl)ethyl)-6-oxo-4-(piperidin-4-ylthio)-1-(tetrahydro-2H-pyran-4-yl)-1,6-dihydropyridine-3-carboxamide;

N—((S)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)-2,2-difluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(trifluoromethyl)phenyl)ethyl)-1,6-dihydropyridine-3-carboxamide;

1-(bicyclo[1.1.1]pentan-1-yl)-4-(((1R,5S,6s)-3-methyl-3-azabicyclo[3.1.0]hexan-6-yl)amino)-6-oxo-N—((R)-1-(3-(pentafluoro-16-sulfaneyl)phenyl)ethyl)-1,6-dihydropyridine-3-carboxamide;

1-(bicyclo[1.1.1]pentan-1-yl)-N—((R)-1-(2-fluoro-3-(pentafluoro-16-sulfaneyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-cyclobutyl-4-(((1R,5S,6s)-3-methyl-3-azabicyclo[3.1.0]hexan-6-yl)amino)-6-oxo-N—((R)-1-(3-(pentafluoro-16-sulfaneyl)phenyl)ethyl)-1,6-dihydropyridine-3-carboxamide;

(R)-1-cyclobutyl-4-((1-methylpiperidin-4-yl)amino)-6-oxo-N-(1-(3-(pentafluoro-16-sulfaneyl)phenyl)ethyl)-1,6-dihydropyridine-3-carboxamide;

(R)-1-(1-(difluoromethyl)cyclopropyl)-N-(1-(2-fluoro-4-methoxy-3-(trifluoromethyl)phenyl)ethyl)-4-((1-methylpiperidin-4-yl)amino)-6-oxo-1,6-dihydropyridine-3-carboxamide;

(S)-1-(1-(difluoromethyl)cyclopropyl)-N-(1-(2-fluoro-4-methoxy-3-(trifluoromethyl)phenyl)ethyl)-4-((1-methylpiperidin-4-yl)amino)-6-oxo-1,6-dihydropyridine-3-carboxamide;

(R)-1-(1-(difluoromethyl)cyclopropyl)-N-(1-(4-fluoro-3-(trifluoromethyl)phenyl)ethyl)-4-((1-methylpiperidin-4-yl)amino)-6-oxo-1,6-dihydropyridine-3-carboxamide;

(S)-1-(1-(difluoromethyl)cyclopropyl)-N-(1-(4-fluoro-3-(trifluoromethyl)phenyl)ethyl)-4-((1-methylpiperidin-4-yl)amino)-6-oxo-1,6-dihydropyridine-3-carboxamide;

N-(1-(4-cyclopropyl-3-(trifluoromethyl)phenyl)ethyl)-1-(1-(difluoromethyl)cyclopropyl)-4-((1-methylpiperidin-4-yl)amino)-6-oxo-1,6-dihydropyridine-3-carboxamide;

N-(1-(2-chloro-3-(trifluoromethyl)phenyl)ethyl)-1-(1-(difluoromethyl)cyclopropyl)-4-((1-methylpiperidin-4-yl)amino)-6-oxo-1,6-dihydropyridine-3-carboxamide;

(R)-1-(1-(difluoromethyl)cyclopropyl)-N-(1-(2-methyl-6-(trifluoromethyl)pyridin-4-yl)ethyl)-4-((1-methylpiperidin-4-yl)amino)-6-oxo-1,6-dihydropyridine-3-carboxamide;

(S)-1-(1-(difluoromethyl)cyclopropyl)-N-(1-(2-methyl-6-(trifluoromethyl)pyridin-4-yl)ethyl)-4-((1-methylpiperidin-4-yl)amino)-6-oxo-1,6-dihydropyridine-3-carboxamide;

1-(1-(difluoromethyl)cyclopropyl)-N-(1-(4-methoxy-3-(trifluoromethyl)phenyl)ethyl)-4-((1-methylpiperidin-4-yl)amino)-6-oxo-1,6-dihydropyridine-3-carboxamide;

N—((R)-1-(3-(difluoro (pyridin-4-yl)methyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((S)-1-(3-(difluoro (pyridin-4-yl)methyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N-(1-(3-(difluoro (oxazol-4-yl)methyl)-2-fluorophenyl)ethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(2-chloro-3-cyanophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((S)-1-(2-chloro-3-cyanophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-cyano-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(2-chloro-3-(difluoromethoxy)phenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-cyano-2-methylphenyl)ethyl)-4-(((1R,5S,6s)-3-methyl-3-azabicyclo[3.1.0]hexan-6-yl)amino)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-(((3-hydroxybicyclo[1.1.1]pentan-1-yl)methyl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-(((S)-5,6,7,8-tetrahydroimidazo[1,5-a]pyridin-8-yl)amino)-1,6-dihydropyridine-3-carboxamide;

N—((R)-1-(3-(difluoromethyl)-2-fluorophenyl)ethyl)-1-(1-(difluoromethyl)cyclopropyl)-6-oxo-4-(((R)-5,6,7,8-tetrahydroimidazo[1,5-a]pyridin-8-yl)amino)-1,6-dihydropyridine-3-carboxamide;

(R)—N-(1-(3-(difluoromethyl)-2-fluorophenyl)ethyl)-1-(1-(difluoromethyl)cyclopropyl)-4-(((3-fluoro-1-methylazetidin-3-yl)methyl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((S)-4-fluoroquinuclidin-3-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((R)-4-fluoroquinuclidin-3-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-((((S)-1-methylpyrrolidin-2-yl)methyl)amino)-6-oxo-1,6-dihydropyridine-3-carboxamide;

(R)-4-((3-aminobicyclo[1.1.1]pentan-1-yl)amino)-1-(bicyclo[1.1.1]pentan-1-yl)-N-(1-(3-(difluoromethyl)-2-fluorophenyl)ethyl)-6-oxo-1,6-dihydropyridine-3-carboxamide;

(R)-4-amino-1-(bicyclo[1.1.1]pentan-1-yl)-N-(1-(3-(difluoromethyl)-2-fluorophenyl)ethyl)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-((1-(1-(hydroxymethyl)cyclopropyl)ethyl)amino)-6-oxo-1,6-dihydropyridine-3-carboxamide;

1-(2-oxabicyclo[2.1.1]hexan-4-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-cyano-2-methylphenyl)ethyl)-1-((1R,3R)-2,2-difluoro-3-methylcyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-cyano-2-methylphenyl)ethyl)-1-((1S,3S)-2,2-difluoro-3-methylcyclopropyl)-4-(((1R,5S,6s)-3-methyl-3-azabicyclo[3.1.0]hexan-6-yl)amino)-6-oxo-1,6-dihydropyridine-3-carboxamide;

1-((1R,3R)-2,2-difluoro-3-methylcyclopropyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1S,3S)-2,2-difluoro-3-methylcyclopropyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1R,3R)-2,2-difluoro-3-methylcyclopropyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((1S,3S)-2,2-difluoro-3-methylcyclopropyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((R)-2,2-difluorocyclopropyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-2,2-difluorocyclopropyl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((R)-2,2-difluorocyclopropyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-2,2-difluorocyclopropyl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((3R,4S)-3-fluoro-1-methylpiperidin-4-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((3S,4R)-3-fluoro-1-methylpiperidin-4-yl)amino)-6-oxo-1,6-dihydropyridine-3-carboxamide;

1-(bicyclo[1.1.1]pentan-1-yl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(2,2-difluorospiro[2.2]pentan-1-yl)-4-(((1R,5S,6s)-3-methyl-3-azabicyclo[3.1.0]hexan-6-yl)amino)-6-oxo-1,6-dihydropyridine-3-carboxamide;

1-cyclobutyl-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,6s)-3-methyl-3-azabicyclo[3.1.1]heptan-6-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((1R,5S,6r)-3-methyl-3-azabicyclo[3.1.1]heptan-6-yl)amino)-6-oxo-1,6-dihydropyridine-3-carboxamide;

1-((S)-2,2-difluorocyclobutyl)-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

1-((S)-2,2-difluorocyclobutyl)-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

1-((R)-2,2-difluorocyclobutyl)-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

1-((R)-2,2-difluorocyclobutyl)-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

1-cyclobutyl-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

1-cyclobutyl-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

1-(bicyclo[1.1.1]pentan-1-yl)-N—((R)-1-(3-(difluoromethyl)-2-fluorophenyl)ethyl)-4-(((3aR,5r,6aS)-2-methyloctahydrocyclopenta[c]pyrrol-5-yl)amino)-6-oxo-1,6-dihydropyridine-3-carboxamide;

(R)-1-(bicyclo[1.1.1]pentan-1-yl)-N-(1-(3-(difluoromethyl)-2-fluorophenyl)ethyl)-4-((1-methylpiperidin-4-yl)amino)-6-oxo-1,6-dihydropyridine-3-carboxamide;

N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide;

N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide;

(R)—N-(1-(3-(difluoromethyl)-2-fluorophenyl)ethyl)-1-(1-methyl-2-oxabicyclo[2.1.1]hexan-4-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-((((R)-1-methylpyrrolidin-2-yl)methyl)amino)-6-oxo-1,6-dihydropyridine-3-carboxamide;

(R)-1-(3,3-difluoro-1-methylcyclobutyl)-N-(1-(3-(difluoromethyl)-2-fluorophenyl)ethyl)-4-((1-methylpiperidin-4-yl)amino)-6-oxo-1,6-dihydropyridine-3-carboxamide;

(R)—N-(1-(3-(difluoromethyl)-2-fluorophenyl)ethyl)-4-((1-methylpiperidin-4-yl)amino)-6-oxo-1-(1-(trifluoromethyl)cyclopentyl)-1,6-dihydropyridine-3-carboxamide;

1-(3,3-difluoro-1-methylcyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

(R)—N-(1-(3-(difluoromethyl)-2-fluorophenyl)ethyl)-4-((1-methylpiperidin-4-yl)amino)-6-oxo-1-(1-(trifluoromethyl)cyclobutyl)-1,6-dihydropyridine-3-carboxamide;

N—((R)-1-(3-(difluoromethyl)-2-fluorophenyl)ethyl)-1-(1-(difluoromethyl)cyclopropyl)-4-(((((1R,5S,6s)-3-methyl-3-azabicyclo[3.1.0]hexan-6-yl)methyl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S)-3-methyl-3-azabicyclo[3.1.0]hexan-1-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1S,5R)-3-methyl-3-azabicyclo[3.1.0]hexan-1-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1s,3S)-3-(dimethylamino)cyclobutyl)amino)-6-oxo-1,6-dihydropyridine-3-carboxamide;

(R)-1-(1-(1,1-difluoroethyl)cyclopropyl)-N-(1-(3-(difluoromethyl)-2-fluorophenyl)ethyl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-(6,6-difluorospiro[3.3]heptan-2-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-((1-methylpiperidin-4-yl)amino)-6-oxo-1-((S)-3-(trifluoromethyl)tetrahydrofuran-3-yl)-1,6-dihydropyridine-3-carboxamide;

N—((R)-1-(3-(difluoromethyl)-2-fluorophenyl)ethyl)-4-((1-methylpiperidin-4-yl)amino)-6-oxo-1-((R)-3-(trifluoromethyl)tetrahydrofuran-3-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((S)-3-(trifluoromethyl)tetrahydrofuran-3-yl)-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1-((R)-3-(trifluoromethyl)tetrahydrofuran-3-yl)-1,6-dihydropyridine-3-carboxamide;

N—((R)-1-(3-(difluoromethyl)-2-fluorophenyl)ethyl)-1-(1-(difluoromethyl)cyclopropyl)-4-(((1R,4R,5S)-2-methyl-2-azabicyclo[2.2.1]heptan-5-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1S,4S,5S)-2-methyl-2-azabicyclo[2.2.1]heptan-5-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1S,4S,5R)-2-methyl-2-azabicyclo[2.2.1]heptan-5-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,4R,5R)-2-methyl-2-azabicyclo[2.2.1]heptan-5-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-((4-methyl-4-azaspiro[2.5]octan-7-yl)amino)-6-oxo-1,6-dihydropyridine-3-carboxamide;

(R)-1-(1-cyclobutylcyclopropyl)-N-(1-(3-(difluoromethyl)-2-fluorophenyl)ethyl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-(6,6-difluorospiro[2.5]octan-1-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((3S,4R)-3-fluorotetrahydro-2H-pyran-4-yl)-4-(((1R,5S,6r)-3-methyl-3-azabicyclo[3.1.1]heptan-6-yl)amino)-6-oxo-1,6-dihydropyridine-3-carboxamide;

N—((R)-1-(3-(difluoromethyl)-2-fluorophenyl)ethyl)-1-((3S,4R)-3-fluorotetrahydro-2H-pyran-4-yl)-4-(((1R,5S,6s)-3-methyl-3-azabicyclo[3.1.1]heptan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,8r)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,8s)-3-methyl-3-azabicyclo[3.2.1]octan-8-yl)amino)-6-oxo-1,6-dihydropyridine-3-carboxamide;

1-(3-cyclopropyltetrahydrofuran-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1s,3S)-3-cyclopropylcyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1r,3R)-3-cyclopropylcyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6s)-3-methyl-3-azabicyclo[3.1.1]heptan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,6r)-3-methyl-3-azabicyclo[3.1.1]heptan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclobutyl)-4-(((1R,5S,6s)-3-methyl-3-azabicyclo[3.1.1]heptan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclobutyl)-4-(((1R,5S,6r)-3-methyl-3-azabicyclo[3.1.1]heptan-6-yl)amino)-6-oxo-1,6-dihydropyridine-3-carboxamide;

N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1-((R)-spiro[2.2]pentan-1-yl)-1,6-dihydropyridine-3-carboxamide;

N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1-((S)-spiro[2.2]pentan-1-yl)-1,6-dihydropyridine-3-carboxamide;

1-((R)-2,2-difluorocyclobutyl)-4-(((1R,5S,6s)-3-methyl-3-azabicyclo[3.1.0]hexan-6-yl)amino)-6-oxo-N—((R)-1-(3-(trifluoromethyl)phenyl)ethyl)-1,6-dihydropyridine-3-carboxamide;

1-((S)-2,2-difluorocyclobutyl)-4-(((1R,5S,6s)-3-methyl-3-azabicyclo[3.1.0]hexan-6-yl)amino)-6-oxo-N—((R)-1-(3-(trifluoromethyl)phenyl)ethyl)-1,6-dihydropyridine-3-carboxamide;

1-(3,3-difluorocyclobutyl)-N—((R)-1-(3-(difluoromethyl)-2-fluorophenyl)ethyl)-4-(((1R,5S,8r)-3-methyl-3-azabicyclo[3.2.1]octan-8-yl)amino)-6-oxo-1,6-dihydropyridine-3-carboxamide;

1-(3,3-difluorocyclobutyl)-N—((R)-1-(3-(difluoromethyl)-2-fluorophenyl)ethyl)-4-(((1R,5S,8s)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(1-(fluoromethyl)cyclopropyl)-4-(((1R,5S,8r)-3-methyl-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(1-(fluoromethyl)cyclopropyl)-4-(((1R,5S,8s)-3-methyl-3-azabicyclo[3.2.1]octan-8-yl)amino)-6-oxo-1,6-dihydropyridine-3-carboxamide;

(R)-1-(bicyclo[1.1.1]pentan-1-yl)-N-(1-(3-(difluoromethyl)-2-fluorophenyl)ethyl)-4-(((3-methoxybicyclo[1.1.1]pentan-1-yl)methyl)amino)-6-oxo-1,6-dihydropyridine-3-carboxamide;

N—((R)-1-(3-(difluoromethyl)-2-fluorophenyl)ethyl)-1-(1-(difluoromethyl)-2-oxabicyclo[2.1.1]hexan-4-yl)-4-(((1R,5S,6s)-3-methyl-3-azabicyclo[3.1.0]hexan-6-yl)amino)-6-oxo-1,6-dihydropyridine-3-carboxamide;

1-(1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide;

1-((S)-1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide;

1-((R)-1-acetyl-3-methylpyrrolidin-3-yl)-N—((R)-1-(3-(difluoromethyl)-2-fluorophenyl)ethyl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-(1-(1-fluorocyclopropane-1-carbonyl)-3-methylpyrrolidin-3-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((S)-1-(1-fluorocyclopropane-1-carbonyl)-3-methylpyrrolidin-3-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((R)-1-(1-fluorocyclopropane-1-carbonyl)-3-methylpyrrolidin-3-yl)-4-((1-methylpiperidin-4-yl)amino)-6-oxo-1,6-dihydropyridine-3-carboxamide;

1-(1-(cyclopropanecarbonyl)-3-methylazetidin-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((1S,2S)-2-methylcyclopropyl)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((1R,2R)-2-methylcyclopropyl)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((1S,2R)-2-methylcyclopropyl)-6-oxo-1,6-dihydropyridine-3-carboxamide;

N—((R)-1-(3-(difluoromethyl)-2-fluorophenyl)ethyl)-4-(((1R,5S,6s)-3-methyl-3-azabicyclo[3.1.0]hexan-6-yl)amino)-1-((1R,2S)-2-methylcyclopropyl)-6-oxo-1,6-dihydropyridine-3-carboxamide;

N—((S)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)-2,2,2-trifluoroethyl)-1-(1-(difluoromethyl)cyclopropyl)-4-(((1R,5S,6s)-3-methyl-3-azabicyclo[3.1.0]hexan-6-yl)amino)-6-oxo-1,6-dihydropyridine-3-carboxamide;

4-(((S)-4-azaspiro[2.5]octan-7-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

4-(((R)-4-azaspiro[2.5]octan-7-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

4-(((1R,5S,6s)-3-azabicyclo[3.1.0]hexan-6-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

4-(((1R,5S,8r)-3-azabicyclo[3.2.1]octan-8-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

4-(((1R,5S,8s)-3-azabicyclo[3.2.1]octan-8-yl)amino)-N—((R)-1-(3-(difluoromethyl)-2-fluorophenyl)ethyl)-1-(1-(difluoromethyl)cyclopropyl)-6-oxo-1,6-dihydropyridine-3-carboxamide;

(R)—N-(1-(2-methyl-3-(trifluoromethyl)phenyl)ethyl)-6-oxo-4-(piperidin-4-ylamino)-1-(tetrahydro-2H-pyran-4-yl)-1,6-dihydropyridine-3-carboxamide;

4-((3,3-difluoro-1-methylpiperidin-4-yl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

(R)-4-((1-cyclopropylpiperidin-4-yl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

1-((1S,5S)-3-oxabicyclo[3.1.0]hexan-1-yl)-N—((R)-1-(3-(difluoromethyl)-2-fluorophenyl)ethyl)-4-((1-methylpiperidin-4-yl)amino)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-((1-(methyl-d3)piperidin-4-yl)amino)-6-oxo-1,6-dihydropyridine-3-carboxamide;

1-((1S,5S)-3-oxabicyclo[3.1.0]hexan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

(R)—N-(1-(3-(difluoromethyl)-2-fluorophenyl)ethyl)-1-(1-(difluoromethyl)cyclopropyl)-4-((1-(1-methylcyclopropyl)piperidin-4-yl)amino)-6-oxo-1,6-dihydropyridine-3-carboxamide;

1-((1S,5S)-3-oxabicyclo[3.1.0]hexan-1-yl)-N—((R)-1-(3-(1,1-difluoroethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((1S,5S)-3-oxabicyclo[3.1.0]hexan-1-yl)-N—((R)-1-(2-fluoro-3-(trifluoromethyl)phenyl)ethyl)-4-(((1R,5S,6s)-3-methyl-3-azabicyclo[3.1.0]hexan-6-yl)amino)-6-oxo-1,6-dihydropyridine-3-carboxamide;

1-((R)-3-cyclopropyltetrahydrofuran-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

1-((S)-3-cyclopropyltetrahydrofuran-3-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,8r)-3-(methyl-d3)-3-azabicyclo[3.2.1]octan-8-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((1R,5S,8s)-3-(methyl-d3)-3-azabicyclo[3.2.1]octan-8-yl)amino)-6-oxo-1,6-dihydropyridine-3-carboxamide;

(R)-4-(((1-(2-methoxyethyl) azetidin-3-yl)methyl)amino)-N-(1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1S,4R)-6-methyl-6-azaspiro[3.5]nonan-1-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,4S)-6-methyl-6-azaspiro[3.5]nonan-1-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1S,4S)-6-methyl-6-azaspiro[3.5]nonan-1-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-4-(((1R,4R)-6-methyl-6-azaspiro[3.5]nonan-1-yl)amino)-6-oxo-1-(tetrahydro-2H-pyran-4-yl)-1,6-dihydropyridine-3-carboxamide;

N—((R)-1-(2-methyl-3-(trifluoromethyl)phenyl)ethyl)-6-oxo-1-(tetrahydro-2H-pyran-4-yl)-4-((5,6,7,8-tetrahydroimidazo[1,5-a]pyridin-8-yl)amino)-1,6-dihydropyridine-3-carboxamide;

4-((((1r,4R)-4-(dimethylamino)cyclohexyl)methyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

4-((((1s,4S)-4-(dimethylamino)cyclohexyl)methyl)amino)-N—((R)-1-(2-methyl-3-(trifluoromethyl)phenyl)ethyl)-6-oxo-1-(tetrahydro-2H-pyran-4-yl)-1,6-dihydropyridine-3-carboxamide;

N—((R)-1-(3-(difluoromethyl)-2-fluorophenyl)ethyl)-1-(1-(difluoromethyl)cyclopropyl)-4-(((7R,8aS)-octahydroindolizin-7-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((7S,8aR)-octahydroindolizin-7-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((7S,8aS)-octahydroindolizin-7-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((7R,8aR)-octahydroindolizin-7-yl)amino)-6-oxo-1,6-dihydropyridine-3-carboxamide;

N—((R)-1-(3-(difluoromethyl)-2-fluorophenyl)ethyl)-1-((R)-2,2-dimethyltetrahydro-2H-pyran-4-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((S)-2,2-dimethyltetrahydro-2H-pyran-4-yl)-4-((1-methylpiperidin-4-yl)amino)-6-oxo-1,6-dihydropyridine-3-carboxamide;

N—((R)-1-(3-(difluoromethyl)-2-fluorophenyl)ethyl)-1-((R)-2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-((S)-2,2-dimethyltetrahydro-2H-pyran-4-yl)-4-(((1R,5S,6s)-3-methyl-3-azabicyclo[3.1.0]hexan-6-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((S)-4-methyl-4-azaspiro[2.5]octan-7-yl)amino)-6-oxo-1,6-dihydropyridine-3-carboxamide;

N—((R)-1-(3-(difluoromethyl)-2-fluorophenyl)ethyl)-1-(1-(difluoromethyl)cyclopropyl)-4-(((R)-4-methyl-4-azaspiro[2.5]octan-7-yl)amino)-6-oxo-1,6-dihydropyridine-3-carboxamide;

N—((R)-1-(3-(difluoromethyl)-2-fluorophenyl)ethyl)-1-(3-ethylbicyclo[1.1.1]pentan-1-yl)-4-(((1R,5S,6s)-3-methyl-3-azabicyclo[3.1.0]hexan-6-yl)amino)-6-oxo-1,6-dihydropyridine-3-carboxamide;

or a pharmaceutically acceptable salt thereof.

18. A pharmaceutical composition comprising a compound of claim 1, or a pharmaceutically acceptable salt thereof, and at least one pharmaceutically acceptable excipient.

19. The compound of claim 17, wherein the compound is:

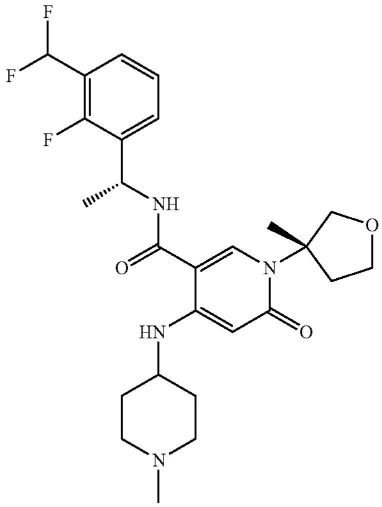 [SMILES: C[C@@H](NC(=O)c1cn([C@@]2(C)CCOC2)c(=O)cc1NC1CCN(C)CC1)c1cccc(C(F)F)c1F]

N—((R)-1-(3-(difluoromethyl)-2-fluorophenyl)ethyl)-4-((1-methylpiperidin-4-yl)amino)-1-((S)-3-methyltetrahydrofuran-3-yl)-6-oxo-1,6-dihydropyridine-3-carboxamide, or a pharmaceutically acceptable salt thereof.

20. The compound of claim 17, wherein the compound is:

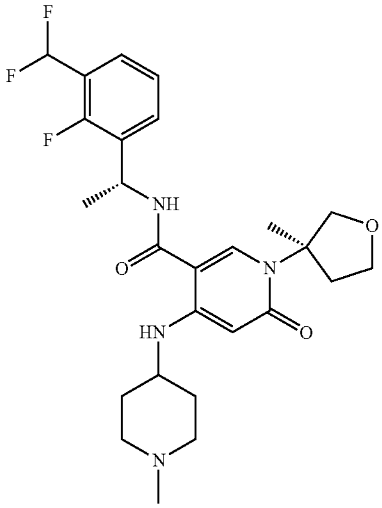 [SMILES: C[C@@H](NC(=O)c1cn([C@]2(C)CCOC2)c(=O)cc1NC1CCN(C)CC1)c1cccc(C(F)F)c1F]

N—((R)-1-(3-(difluoromethyl)-2-fluorophenyl)ethyl)-4-((1-methylpiperidin-4-yl)amino)-1-((R)-3-methyltetrahydrofuran-3-yl)-6-oxo-1,6-dihydropyridine-3-carboxamide, or a pharmaceutically acceptable salt thereof.

21. The compound of claim 17, wherein the compound is:

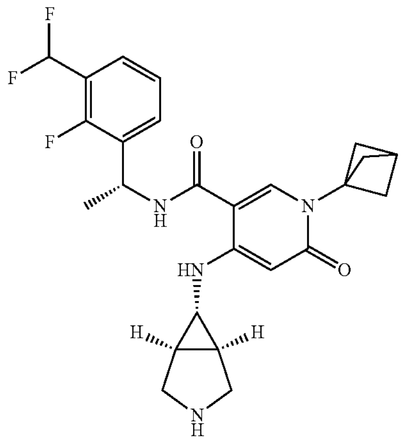 [SMILES: C[C@@H](NC(=O)c1cn(C23CC(C2)C3)c(=O)cc1N[C@H]1[C@@H]2CNC[C@@H]21)c1cccc(C(F)F)c1F]

4-(((1R,5S,6s)-3-azabicyclo[3.1.0]hexan-6-yl)amino)-1-(bicyclo[1.1.1]pentan-1-yl)-N—((R)-1-(3-(difluoromethyl)-2-fluorophenyl)ethyl)-6-oxo-1,6-dihydropyridine-3-carboxamide, or a pharmaceutically acceptable salt thereof.

22. The compound of claim 17, wherein the compound is:

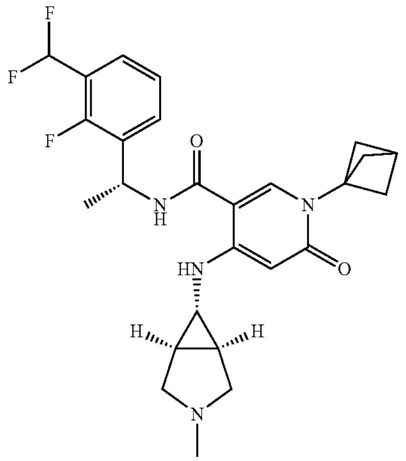 [SMILES: C[C@@H](NC(=O)c1cn(C23CC(C2)C3)c(=O)cc1N[C@H]1[C@@H]2CN(C)C[C@@H]21)c1cccc(C(F)F)c1F]

1-(bicyclo[1.1.1]pentan-1-yl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide, or a pharmaceutically acceptable salt thereof.

23. The compound of claim 17, wherein the compound is:

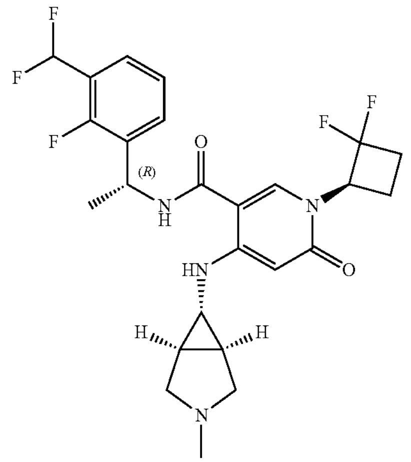

1-((R)-2,2-difluorocyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide, or a pharmaceutically acceptable salt thereof.

24. The compound of claim 17, wherein the compound is:

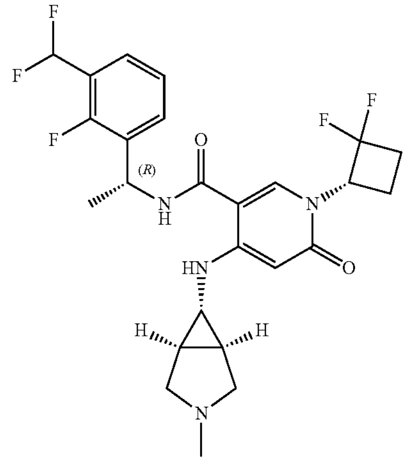

1-((S)-2,2-difluorocyclobutyl)-N—((R)-1-(3-(difluoromethyl)-2-fluorophenyl)ethyl)-4-(((1R,5S,6s)-3-methyl-3-azabicyclo[3.1.0]hexan-6-yl)amino)-6-oxo-1,6-dihydropyridine-3-carboxamide, or a pharmaceutically acceptable salt thereof.

25. A method for treating cancer in a subject in need thereof, comprising administering to the subject an effective amount of a compound of claim 1.

26. The method according to claim 25, wherein the cancer is a Ras pathway-associated cancer.

* * * * *